(12) United States Patent
Zhou et al.

(10) Patent No.: US 12,151,001 B2
(45) Date of Patent: Nov. 26, 2024

(54) OPTIMIZED EXPRESSION CASSETTES FOR GENE THERAPY

(71) Applicant: Tenaya Therapeutics, Inc., South San Francisco, CA (US)

(72) Inventors: Huanyu Zhou, San Mateo, CA (US); Christopher A. Reid, Walnut Creek, CA (US)

(73) Assignee: TENAYA THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 18/468,594

(22) Filed: Sep. 15, 2023

(65) Prior Publication Data

US 2024/0042060 A1    Feb. 8, 2024

Related U.S. Application Data

(63) Continuation of application No. PCT/US2022/073574, filed on Jul. 8, 2022.

(60) Provisional application No. 63/219,651, filed on Jul. 8, 2021.

(51) Int. Cl.
| | | |
|---|---|---|
| *C12N 15/85* | (2006.01) | |
| *A61K 48/00* | (2006.01) | |
| *C07K 14/47* | (2006.01) | |
| *C07K 14/705* | (2006.01) | |
| *C12N 15/86* | (2006.01) | |

(52) U.S. Cl.
CPC .......... *A61K 48/0058* (2013.01); *C07K 14/47* (2013.01); *C07K 14/4702* (2013.01); *C07K 14/705* (2013.01); *C12N 15/86* (2013.01); *C12N 2750/14143* (2013.01); *C12N 2750/14171* (2013.01); *C12N 2830/008* (2013.01); *C12N 2830/42* (2013.01); *C12N 2830/48* (2013.01); *C12N 2830/50* (2013.01)

(58) Field of Classification Search
CPC ........ C12N 15/79; C12N 15/85; C12N 15/86; C12N 15/8645; C12N 2750/14143; C12N 2830/008; C12N 2830/42; C12N 2830/48; C12N 2830/50; C07H 21/04
See application file for complete search history.

(56) References Cited

U.S. PATENT DOCUMENTS

| | | |
|---|---|---|
| 6,822,072 B1 | 11/2004 | Edwards et al. |
| 7,235,381 B2 | 6/2007 | Dumas Milne Edwards et al. |
| 10,570,183 B2 | 2/2020 | Olson et al. |
| 11,111,278 B2 | 9/2021 | Olson et al. |
| 2003/0175795 A1 | 9/2003 | Walker et al. |
| 2007/0036760 A1 | 2/2007 | Wilson et al. |
| 2012/0252882 A1 | 10/2012 | Chuah et al. |
| 2017/0298107 A1 | 10/2017 | Olson et al. |
| 2019/0160106 A1 | 5/2019 | Lefer et al. |
| 2020/0140502 A1 | 5/2020 | Olson et al. |
| 2021/0380650 A1 | 12/2021 | Olson et al. |
| 2023/0133924 A1 | 5/2023 | Zhou et al. |
| 2023/0241249 A1 | 8/2023 | Olson et al. |

FOREIGN PATENT DOCUMENTS

| | | |
|---|---|---|
| WO | WO 02/02765 A2 * | 1/2002 |
| WO | WO 2014/111458 A2 * | 7/2014 |
| WO | WO-2018156397 A1 | 8/2018 |
| WO | WO-2018170473 A1 | 9/2018 |
| WO | WO 2019/162356 A1 * | 8/2019 |
| WO | WO-2020014523 A1 | 1/2020 |
| WO | WO-2020047467 A2 | 3/2020 |
| WO | WO 2020/142479 A1 * | 7/2020 |
| WO | WO-2021163357 A2 | 8/2021 |
| WO | WO-2022032226 A1 | 2/2022 |
| WO | WO-2023283649 A1 | 1/2023 |

OTHER PUBLICATIONS

Rodino-Klapac et al., 2021 (US 20210128749 A1, effective filing date, Oct. 18, 2017).*
Voit et al., Mar. 25, 2021 (GeneSeq Accession No. BJD36636, computer printout, pp. 1-2).*
Bassel-Duby et al., 2017 (GeneSeq Accession No. BEM79203, computer printout, p. 1).*
Buckingham et al., 2001 (GeneSeq Accession No. AAF55512, computer printout, pp. 1-2).*
Tian et al., 2020 (GeneSeq Accession No. BHT59574, computer printout, p. 1).*
Haddad et al., 2016 (GenEmbl Accession No. AY191158, computer printout, pp. 1-2).*
Zhou et al., 2020 (GeneSeq Accession No. BHL25567, computer printout, pp. 1-2).*
Burns et al., 2020 (Geneseq Accession No. BHU54544, computer printout, pp. 1-2).*
Cabaniols et al., 2010 (Geneseq Accession No. AYA09574, computer printout, pp. 1-2).*
Bennett et al., 2009 (Geneseq Accession No. AXR77954, computer printout, p. 1).*

(Continued)

*Primary Examiner* — Shin Lin Chen
(74) *Attorney, Agent, or Firm* — COOLEY LLP

(57) ABSTRACT

In some aspects, cardiac-specific expression cassettes are provided herein. In some aspects, provided herein is an expression cassette comprising a polynucleotide sequence encoding a gene product for therapy of a heart disease, wherein the polynucleotide sequence is operably linked to promoter (e.g., a cardiac-specific promoter), and optionally an enhancer (e.g., a cardiac-specific enhancer). In some aspects, the disclosure provides recombinant adeno-associated virus (rAAV) virions, comprising a capsid protein and a viral genome comprising an expression cassette comprising a polynucleotide sequence encoding a therapeutic gene product, e.g., dwarf open reading frame (DWORF) polypeptide, operably linked to a promoter, the expression cassette flanked by inverted terminal repeats. The disclosure further provides pharmaceutical compositions and methods of treating or preventing heart disease.

26 Claims, 16 Drawing Sheets

Specification includes a Sequence Listing.

(56) References Cited

OTHER PUBLICATIONS

Wilson et al., 2005 (Geneseq Accession No. ADZ26973, computer printout, pp. 1-2).*

[Author Unknown] "A small protein plays a big role in heart muscle contraction," Science Daily, located at https://www.sciencedaily.com/releases/2016/01/160114212441.htm, published Jan. 16, 2016, 5 pages.

Bass-Stringer et. al., "Adeno-Associated Virus Gene Therapy: Translational Progress and Future Prospects in the Treatment of Heart Failure" Heart Lung Circ.Nov. 2018;27(11):1285-1300.

Bi et al., "Control of muscle formation by the fusogenic micropeptide myomixer," Science, 356(6335):323-327, 2017.

Expasy Translate Tool, accessed on Jan. 18, 2018, Swiss Institute for bioinformatics, 1 page.

Final Office Action for U.S. Appl. No. 17/392,137 dated Aug. 8, 2023, 14 pages.

Final Office Action issued in U.S. Appl. No. 15/491,057, dated Apr. 12, 2019, 7 pages.

International Preliminary Report on Patentability for International Application No. PCT/US2022/073574 dated Jan. 18, 2024, 8 pages.

International Search Report and Written Opinion for International Application No. PCT/US2022/073574 mailed Nov. 18, 2022, 15 pages.

International Search Report and written opinion for International Patent Application PCT/US2021/040428, mailed on Nov. 16, 2021, 12 pages.

Kranias., et al., "Modulation of cardiac contractility by the phospholamban/SERCA2a regulatome," Circ Res., 110: 1646-1660, 2012.

Lin., et al., "Cardiac-specific YAP activation improves cardiac function and survival in an experimental murine MI model," Circ Res., 115(3):354-363, 2014.

Makarewich., et al., "The DWORF micropeptide enhances contractility and prevents heart failure in a mouse model of dilated cardiomyopathy," Elife, 7:e38319, 2018, 23 pages.

Micheletti et al, "Istaroxime, a stimulator of sarcoplasmic reticulum calcium adenosine triphosphate isoform 2a activity, as a novel therapeutic approach to heart failure," American Journal of Cardiology, 99[suppl]:24A-32A, 2007.

Nelson et al., "A peptide encoded by a transcript annotated as long noncoding RNA enhances SERCA activity in muscle," Science, 351(6270):271-5, 2016.

Non-Final Office Action for U.S Appl. No. 17/392,137 dated Jan. 3, 2023, 7 pages.

Non-Final Office Action issued in U.S. Appl. No. 15/491,057, dated Feb. 22, 2018, 14 pages.

Non-Final Office Action issued in U.S. Appl. No. 16/743,831, mailed Dec. 10, 2020, 7 pages.

Olson, "New Insights into Muscle Development, Disease and Regeneration," located at https://professional.heart.org/idc/groups/ahamah-public/@wcm/@sop/@scon/documents/downloadable/ucm_475703.pdf, retrieved Oct. 4, 2017, 55 pages.

PCT International Preliminary Report on Patentability issued in International Application No. PCT/US2021/040428, mailed Jan. 19, 2023, 9 pages.

Penny., et al., "Randomized Clinical Trials of Gene Transfer for Heart Failure with Reduced Ejection Fraction," Hum Gene Ther., 28(5):378-384, 2017.

Prasad, K.-M. et al., "Robust Cardiomyocyte-Specific Gene Expression Following Systemic Injection of AAV: In Vivo Gene Delivery Follows a Poisson Distribution," Gene Ther., 18(1):43-52, Jan. 2011, 22 pages, doi:10.1038/gt.2010.105.

Restriction Requirement issued in U.S. Appl. No. 15/491,057, dated Sep. 21, 2018, 5 pages.

Restriction Requirement issued in U.S. Appl. No. 15/491,057, dated Aug. 31, 2017, 7 pages.

Restriction Requirement issued in U.S. Appl. No. 16/743,831, mailed Jul. 21, 2020, 7 pages.

Wang, C. et al., "Adeno-associated virus vector as a platform for gene therapy delivery," Nature Reviews Drug Discovery, 18:358-378 (2019).

* cited by examiner

HA-DWORF
SERCA2a

SEQUENCE LISTING

```
Sequence total quantity: 230
SEQ ID NO: 1            moltype = AA  length = 34
FEATURE                 Location/Qualifiers
source                  1..34
                        mol_type = protein
                        organism = Mus musculus
SEQUENCE: 1
MAEKESTSPH LMVPILLLVG WIVGCIIVIY IVFF                               34

SEQ ID NO: 2            moltype = DNA  length = 105
FEATURE                 Location/Qualifiers
source                  1..105
                        mol_type = other DNA
                        organism = Mus musculus
SEQUENCE: 2
atggctgaga aagagtcaac atcaccacac ctcatggttc ccattcttct cctggttgga  60
tggattgtag gctgcatcat cgttatttac attgtcttct tctaa                 105

SEQ ID NO: 3            moltype = AA  length = 35
FEATURE                 Location/Qualifiers
source                  1..35
                        mol_type = protein
                        organism = Homo sapiens
SEQUENCE: 3
MAEKAGSTFS HLLVPILLLI GWIVGCIIMI YVVFS                              35

SEQ ID NO: 4            moltype = DNA  length = 108
FEATURE                 Location/Qualifiers
source                  1..108
                        mol_type = other DNA
                        organism = Homo sapiens
SEQUENCE: 4
atggctgaaa aagcggggtc tacattttca caccttctgg ttcctattct tctcctgatt  60
ggctggattg tgggctgcat cataatgatt tatgttgtct tctcttag              108

SEQ ID NO: 5            moltype = AA  length = 35
FEATURE                 Location/Qualifiers
REGION                  1..35
                        note = Recombinant DWORF variant
source                  1..35
                        mol_type = protein
                        organism = synthetic construct
SEQUENCE: 5
MAEKAESTSP HLMVPILLLV GWIVGCIIVI YIVFF                              35

SEQ ID NO: 6            moltype = DNA  length = 108
FEATURE                 Location/Qualifiers
misc_feature            1..108
                        note = Recombinant DWORF variant
source                  1..108
```

```
                    mol_type = other DNA
                    organism = synthetic construct
SEQUENCE: 6
atggctgaga aagcagagtc aacatcacca cacctcatgg ttcccattct tctcctggtt    60
ggatggattg taggctgcat catcgttatt tacattgtct tcttctaa              108

SEQ ID NO: 7        moltype = AA   length = 34
FEATURE             Location/Qualifiers
REGION              1..34
                    note = Recombinant DWORF variant
source              1..34
                    mol_type = protein
                    organism = synthetic construct
SEQUENCE: 7
MAEKESTSPH LIVPILLLVG WIVGCIIVIY IVFF                                34

SEQ ID NO: 8        moltype = DNA   length = 105
FEATURE             Location/Qualifiers
misc_feature        1..105
                    note = Recombinant DWORF variant
source              1..105
                    mol_type = other DNA
                    organism = synthetic construct
SEQUENCE: 8
atggctgaga aagagtcaac atcaccacac ctcattgttc ccattcttct cctggttgga    60
tggattgtag gctgcatcat cgttatttac attgtcttct ctaa                   105

SEQ ID NO: 9        moltype = AA   length = 35
FEATURE             Location/Qualifiers
REGION              1..35
                    note = Recombinant DWORF variant
source              1..35
                    mol_type = protein
                    organism = synthetic construct
SEQUENCE: 9
MAEKAESTSP HLIVPILLLV GWIVGCIIVI YIVFF                               35

SEQ ID NO: 10       moltype = DNA   length = 108
FEATURE             Location/Qualifiers
misc_feature        1..108
                    note = Recombinant DWORF variant
source              1..108
                    mol_type = other DNA
                    organism = synthetic construct
SEQUENCE: 10
atggctgaga aagcagagtc aacatcacca cacctcattg ttcccattct tctcctggtt    60
ggatggattg taggctgcat catcgttatt tacattgtct tcttctaa              108

SEQ ID NO: 11       moltype = DNA   length = 413
FEATURE             Location/Qualifiers
misc_feature        1..413
                    note = Recombinant expression cassette or expression
                    cassette component
source              1..413
                    mol_type = other DNA
                    organism = synthetic construct
SEQUENCE: 11
gggataaaag cagtctgggc tttcacatga cagcatctgg ggctgcggca gagggtcggg    60
tccgaagcgc tgccttatca gcgtccccag ccctgggagg tgacagctgg ctggcttgtg   120
tcagcccctc gggcactcac gtatctccgt ccgacgggtt taaaatagca aaactctgag   180
gccacacaat agcttgggct tatatgggct cctgtggggg aagggggagc acggaggggg   240
ccggggccgc tgctgccaaa atagcagctc acaagtgttg cattcctctc tgggcgccgg   300
gcacattcct gctggctctg cccgccccgg ggtgggcgcc gggggaccct aaagcctct   360
gccccccaag gagcccttcc cagacagccg ccggcaccca ccgctccgtg gga          413

SEQ ID NO: 12       moltype = DNA   length = 600
FEATURE             Location/Qualifiers
misc_feature        1..600
                    note = Recombinant expression cassette or expression
                    cassette component
source              1..600
                    mol_type = other DNA
                    organism = synthetic construct
SEQUENCE: 12
gtcatggaga agacccacct tgcagatgtc tcactggggg ctggcagagc cggcaacctg    60
cctaaggctg ctcagtccat taggagccag tagcctggaa gatgtcttta ccccccagcat  120
cagttcaagt ggagcagcac ataactcttg ccctctgcct tccaagattc tggtgctgag   180
acttatggag tgtcttggag gttgccttct gcccccaac cctgctccca gctgccctc    240
ccaggcctgg gttgctggcc tctgctttat caggattctc aagagggaca gctggtttat   300
```

```
gttgcatgac tgttccctgc atatctgctc tggttttaaa tagcttatct gagcagctgg    360
aggaccacat gggcttatat ggcgtggggt acatgttcct gtagccttgt ccctggcacc    420
tgccaaaata gcagccaaca ccccccaccc ccaccgccat cccctgccc cacccgtccc     480
ctgtcgcaca ttcctccctc cgcagggctg gctcaccagg ccccagccca catgcctgct    540
taaagccctc tccatcctct gcctcaccca gtccccgctg agactgagca gacgcctcca    600

SEQ ID NO: 13            moltype = DNA  length = 1497
FEATURE                  Location/Qualifiers
misc_feature             1..1497
                         note = Recombinant expression cassette or expression
                          cassette component
source                   1..1497
                         mol_type = other DNA
                         organism = synthetic construct
SEQUENCE: 13
agaggaccct ttcaaggaca ttagtggtgg aggcagcata gtagctccca aggcagaggg     60
attgagagaa gagtttgagg actgggaagg cgggacacat gattgggtga tgggagaagg    120
gggcagagaa tagcgagatt gctttctttg cccacggaga aacagaggag tgtggatcat    180
gaatgggcaa gatctttaag tgccagggg ggtcatggag gaggggaggg cctgctccag     240
aggaggacca ttcctgcttc agagccaagc aggacctagg ctgtgaagat tcggagaaag    300
agatggaggg gagagtcagc tcagctgctt actggcttgc tttcctcctg tctctttcat    360
tttcataatc taccaaaccc tgcaatgggc cagccttgaa cagcaagtg catgtgcatg     420
gtcagacaca ggcaagcaag caagacccct aggcctgacc tatgcatctg caatctagta    480
ggtttagcag atcatagccc cgcactgctt gattttaaag ccgttagggg atgacctttg    540
acagtccgca tcacccctct cacacaacga gcgcctgttc aaggttcttg actggaagtt    600
ctaccttgta tctggcctcc tgtagcagtt tcagtccatt ccctgtgagg agggtgtgcc    660
acatggcttt gggggtcatg gagaagacc ccttgcaga tgtcctcact ggggctggca      720
gagccggcaa cctgcctaag gctgctcagt ccattaggag ccagtagcct ggaagatgtc    780
tttaccccca gcatcagttc aagtggagca gcacataact cttgccctct gccttccaag    840
attctggtgc tgagacttat ggagtgtctt ggaggttgcc ttctgccccc caaccctgct    900
cccagctggc cctcccaggc ctgggttgct ggcctctgct ttatcaggat tctcaagagg    960
gacagctggt ttatgttgca tgactgttcc ctgcatatct gctctggttt taaatagctt   1020
atctgagcag ctgaggacc acatgggctt atatggcgtg gggtacatgt tcctgtagcc   1080
ttgtccctgg cacctgccaa aatagcagcc aacacccccc accccaccg ccatccccct    1140
gccccacccg tccctgtcg cacattcctc cctccgcagg gctggctcac caggccccag    1200
cccacatgcc tgcttaaagc cctctccatc ctctgcctca cccagtcccc gctgagactg   1260
agcagacgcc tccaggatct gtcggcagct gctgttctga ggtaaggctc gggcagggct   1320
ctggggaaga ggagagcaga gaatggacgg ggagatgtga gggtcttggg ccctggcata   1380
tttacccaga gtcctggctgt gtccgcagaa gtccatggcc cctcctggtg gaggccacac   1440
ttcagaggac aggttgccag gtctgggctc caagattggt acaatagagc agagaga      1497

SEQ ID NO: 14            moltype = DNA  length = 130
FEATURE                  Location/Qualifiers
misc_feature             1..130
                         note = Recombinant expression cassette or expression
                          cassette component
source                   1..130
                         mol_type = other DNA
                         organism = synthetic construct
SEQUENCE: 14
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact   120
aggggttcct                                                           130

SEQ ID NO: 15            moltype = DNA  length = 130
FEATURE                  Location/Qualifiers
misc_feature             1..130
                         note = Recombinant expression cassette or expression
                          cassette component
source                   1..130
                         mol_type = other DNA
                         organism = synthetic construct
SEQUENCE: 15
aggaacccct agtgatggag ttggccactc cctctctgcg cgctcgctcg ctcactgagg     60
ccgggcgacc aaaggtcgcc cgacgcccgg gctttgcccg gcggcctca gtgagcgagc    120
gagcgcgcag                                                           130

SEQ ID NO: 16            moltype = AA   length = 735
FEATURE                  Location/Qualifiers
REGION                   1..735
                         note = Recombinant expression cassette or expression
                          cassette component
source                   1..735
                         mol_type = protein
                         organism = synthetic construct
SEQUENCE: 16
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
```

```
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRN                                                     735

SEQ ID NO: 17          moltype = DNA  length = 2209
FEATURE                Location/Qualifiers
misc_feature           1..2209
                       note = Recombinant expression cassette or expression
                       cassette component
source                 1..2209
                       mol_type = other DNA
                       organism = synthetic construct
SEQUENCE: 17
atggctgccg atggttatct tccagattgg ctcgaggaca accttagtga aggaattcgc    60
gagtggtggg ctttgaaacc tggagccccct caacccaagg caaatcaaca acatcaagac    120
aacgctcgag gtcttgtgct tccgggttac aaatacttg gacccggcaa cggactcgac    180
aagggggagc cggtcaacgc agcagacgcg cggccctcg agcacgacaa ggcctacgac    240
cagcagctca aggccggaga caacccgtac ctcaagtaca ccacgccga cgccgagttc    300
caggagcgac tcaaagaaga tacgtctttt ggggggaccc tcggcgcagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaagaga ctcaatttcg gtcagactgg cgacacagag    540
tcagtcccag acccctcaacc aatcggagaa cctcccgcag cccccctcag tgtgggatct    600
cttacaatgg cttcaggtgg tggcgcacca gtggcagaa ataacgaagg tgccgatgga    660
gtgggtagtt cctcgggaaa ttggcattgc gattccaat ggctggggga cagagtcatc    720
accaccagca cccgaacctg ggccctgccc acctacaaca atccactcta caagcaaatc    780
tccaacagca catctggagg atcttcaaat gacaacgcct acttcggcta cagcacccc    840
tggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagccgac gtttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtgccgg acccagcaac atggctgtcc agggaagaaa ctacataccc   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata   1680
accaacgaag agaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg gcaggacaga gatgtgtacc tgcaaggacc cattgggcc   1860
aaaattcctc acacggacgg caactttcac ccttctccgc tgatgggagg gtttggaatg   1920
aagcaccgc ctcctcagat cctcatcaaa acacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctgaaacc ggagatccag   2100
tacacttcca actattcaa gtctaataat gttgaatttg ctgttaatac tgaaggtgta   2160
tatagtgaac cccgccccat tggcaccaga tacctgactc gtaatctgt             2209

SEQ ID NO: 18          moltype = AA  length = 736
FEATURE                Location/Qualifiers
REGION                 1..736
                       note = Recombinant expression cassette or expression
                       cassette component
source                 1..736
                       mol_type = protein
                       organism = synthetic construct
SEQUENCE: 18
MAADGYLPDW LEDNLSEGIR EWWALKPGAP QPKANQQHQD NARGLVLPGY NYLGPGNGLD     60
RGEPVNRADE VAREHDISYN EQLEAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQANYGQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
```

```
YSEPRPIGTR YLTRNL                                                            736

SEQ ID NO: 19            moltype = AA   length = 736
FEATURE                  Location/Qualifiers
REGION                   1..736
                         note = Recombinant expression cassette or expression
                          cassette component
source                   1..736
                         mol_type = protein
                         organism = synthetic construct
SEQUENCE: 19
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQANYGQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 20            moltype = DNA  length = 1919
FEATURE                  Location/Qualifiers
misc_feature             1..1919
                         note = Recombinant expression cassette or expression
                          cassette component
source                   1..1919
                         mol_type = other DNA
                         organism = synthetic construct
SEQUENCE: 20
ctgcgcgctc gctcgctcac tgaggccgcc cgggcaaagc ccgggcgtcg ggcgaccttt   60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaaggtcat ggagaagacc caccttgcag atgtcctcac  240
tgggcctgcc agagccggca acctgcctaa ggctgctcag tccattagga gccagtaggc  300
tggaagatgt ctttaccccc agcatcagtt caagtggagc agcacataac tcttgccctc  360
tgccttccaa gattctggtg ctgagactta tggagtgtct tggaggttgc cttctgcccc  420
ccaaccctgc tcccagctgg ccctcccagg cctgggttgc tggcctctgc tttatcagga  480
ttctcaagag ggacagctgg tttatgttgc atgactgttc cctgcatatc tgctctgtgt  540
ttaaatagct tatctgagca gctggaggac cacatgggct tatatggcgt ggggtacatg  600
ttcctgtagc cttgtccctg gcacctgcca aaatagcagc caaaccccc caccccacc   660
gccatccccc tgcccaccc gtccctgtc gcacattcct ccctccgcag ggctggctca   720
ccaggcccca gcccacatgc ctgcttaaag ccctctccat cctctgcctc acccagtcct   780
cgctgagact gagcagacgc ctccagcggc cgcccgccac catggctgag aaagagtcaa   840
catcaccaca cctcatggtt cccattcttc tcctggttgg atggattgta ggctgcatca   900
tcgttattta cattgtcttc ttctaaaagc tttggatcca atcaacctct ggattacaaa   960
atttgtgaaa gattgactgg tattcttaac tatgttgctc cttttacgct atgtggataa  1020
gctgctttaa tgcctttgta tcatgctatt gcttcccgta tggctttcat tttctcctcc  1080
ttgtataaat cctggttgct gtctctttat gaggagttgt ggccgttgt caggcaacgt   1140
ggcgtggtgt gcactgtgtt tgctgacgca acccccactg gttggggcat tgccaccacc  1200
tgtcagctcc tttccgggac tttcgctttc ccctccgtc ttgccacggc ggaactcatc   1260
gccgctgcc ttgccgctg ctggacaggg gctcggctgt tgggcactgt caattccgtg   1320
gtgttgtcgg ggaaatcatc gtcctttcct tggctgctcg cctgtgttgc cacctggatt  1380
ctgcgcggga cgtcctctg ctacgtccct tcggccctca atccagcgga ccttccttcc  1440
cgcggcctgc tgccggctct gcggcctctt ccgcgtcttc gagatctgac tcgactgac  1500
cttctagttg ccagccatct gttgtttgcc cctccccgt gcttccttg accctggaag   1560
gtgccactcc cactgtcctt tcctaataaa atgaggaaat tgcatcgcat tgtctgagta   1620
ggtgtcattc tattctgggg ggtggggtgg gcaggacag caaggggag gattgggaag   1680
acaatagcag gcatgctggg gactcgagtt aaggggcgaat tccgattag gatcttccta   1740
gagcatggct acgtaagtaa gtagcatggc gggttaatca ttaactacaa ggaaccccta   1800
gtgatggagt tggccactcc ctctctgcgc gctcgctcgc tcactgaggc cgggcgacca   1860
aaggtcgccc gacgcccggg cttttgccgg cggccctcag tgagcgagcg agcgcgcag   1919

SEQ ID NO: 21            moltype = DNA  length = 3177
FEATURE                  Location/Qualifiers
misc_feature             1..3177
                         note = Recombinant expression cassette or expression
                          cassette component
source                   1..3177
                         mol_type = other DNA
                         organism = synthetic construct
SEQUENCE: 21
ctgcgcgctc gctcgctcac tgaggccgcc cgggcaaagc ccgggcgtcg ggcgaccttt   60
ggtcgcccgg cctcagtgag cgagcgagcg cgcagagagg gagtggccaa ctccatcact  120
aggggttcct tgtagttaat gattaacccg ccatgctact tatctacgta gccatgctct  180
```

```
aggaagatcg gaattcgccc ttaagagagg acccttcaa ggacattagt ggtggaggca    240
gcatagtagc tcccaaggca gagggattga gagaagagtt tgaggactgg gaaggcggga    300
cacatgattg ggtgatggga gaaggggggca gagaatagcg agattgcttt ctttgcccac    360
ggagaaacag aggagtgtgg atcatgaatg ggcaagatct ttaagtgcca ggggggggtca    420
tggaggaggg gagggcctgc tccagaggag gaccattcct gcttcagagc caagcaggac    480
ctaggctgtg aagattcgga gaaagagatg gaggggagag tcagctcagc tgcttactgg    540
cttgctttcc tcctgtctct ttcattttca taatctacca aaccctgcaa tgggccagcc    600
ttgaacatac aagtgcatgt gcatggtcag acacaggcaa gcaagcaaga cccctaggcc    660
tgacctatgc atctgcaatc tagtaggttt agcagatcat agccccgcac tgcttgattt    720
taaagccgtt aggggatgac ctttgacagt ccgcatcacc cctctcacac aacgagcgct    780
tgttcaaggt tcttgactgg aagttctacc ttgtatctgg cctcctgtag cagttttcagt    840
ccattccctg tgaggagggt gtgccacatg gctttggggg tcatgagaa gacccaccttt    900
gcagatgtcc tcactgggggc tggcagagcc ggcaacctgc ctaaggctgc tcagtccatt    960
aggagccagt agcctggaag atgtctttac ccccagcatc agttcaagtg gagcagcaca  1020
taactcttgc cctctgcctt ccaagattct ggtgctgaga cttatggagt gtcttggagg  1080
ttgccttctg cccccccaacc ctgctcccag ctggccctcc caggcctggg ttgctggcct  1140
ctgctttatc aggattctca agagggacag ctggtttatg ttgcatgact gttccctgca  1200
tatctgctct ggttttaaat agcttatctg agcagctgga ggaccacatg ggcttatatg  1260
gcgtggggta catgttcctg tagccttgtc cctggcacct gccaaaatag cagccaacac  1320
ccccacccc caccgccatc cccctgcccc accgtcccc tgtcgcacat tcctccctcc  1380
gcagggctgg ctcaccaggc cccagcccac atgcctgctt aaagccctct ccatcctctg  1440
cctcacccag tccccgctga gactgagcag acgcctcacg gatctgtcgg cagctgctgt  1500
tctgaggtaa ggctcgggca gggctctggg gaagaggaga gcagagaatg gacggggaga  1560
tgtgagggtc ttgggccctg gcatatttac ccagagtctg cctgtgtccg cagaagtcca  1620
tggcccctcc tggtggaggc cacacttcag aggacaggtt gccaggtctg ggctccaaga  1680
ttggtacaat agagcagaga gaggagtcgc tgcgacgctg ccttcgcccc gtgcccgct  1740
ccgccgccgc ctcgcgccgc ccgccccggc tctgactgac cgcgttactc ccacaggtga  1800
gcgggcggga cggcccttct cctccgggct gtaattagcg cttggtttaa tgacggcttg  1860
tttctttct gtggctgcgt gaaagccttg aggggctccg ggagctagag cctctgctaa  1920
ccatgttcat gccttcttct tttttcctaca gctcctgggc aacgtgctgg ttattgtgct  1980
gtctcatcat tttggcaaag aattcccaat cgataccaa tcgatacaga tctagcggcc  2040
gcgccgccac catggctgag aaagagtcaa catcaccaca cctcatggtt cccattcttc  2100
tcctggttgg atggattgta ggctgcatca tcgttattta cattgtcttc ttctaaccag  2160
aggttgattg gatccaagct ttggatccaa tggatccaat caacctctgg attacaaaat  2220
ttgtgaaaga ttgactggta ttcttaacta tgttgctcct tttacgctat gtggatacgc  2280
tgctttaatg cctttgtatc atgctattgc ttcccgtatg gctttcattt tctcctcctt  2340
gtataaatcc tggttgctgt ctctttatga ggagttgtgg cccgttgtca ggcaacgtgg  2400
cgtggtgtgc actgtgtttg ctgacgcaac ccccactggt tggggcattg ccaccacctg  2460
tcagctcctt tccgggactt tcgctttccc cctccccatt gccacggcgg aactcatcgc  2520
cgcctgcctt gcccgctgct ggacagggggc tcggctgttg ggcactgaca attccgtggt  2580
gttgtcgggg aaatcatcgt cctttccttg gctgctcgcc tgtgttgcca cctggattct  2640
gcgcgggacg tccttctgct acgtcccttc ggccctcaat ccagcggacc ttccttcccg  2700
cggcctgctg ccggctctgc ggcctcttcc gcgtcttcga gatctgcctc gactgtgcct  2760
tctagttgcc agccatctgt tgtttgcccc tcccccgtgc cttccttgac cctggaaggt  2820
gccactccca ctgtccttc ctaataaaat gaggaaattg catcgcattg tctgagtagg  2880
tgtcattcta ttctggggg ggggtgggg caggacagca aggggggagga ttgggaagac  2940
aatagcaggc atgctgggga ctcgagttaa gggcgaattc ccgattagga tcttcctaga  3000
gcatggctac gtagataagt agcatggcgg gttaatcatt aactacaagg aacccctagt  3060
gatggagttg gccactccct ctctgcgcgc tcgctcgctc actgaggccg ggcgaccaaa  3120
ggtcgcccga cgcccgggct ttgcccgggc ggcctcagtg agcgagcgag cgcgcag    3177
SEQ ID NO: 22         moltype = DNA  length = 1922
FEATURE               Location/Qualifiers
misc_feature          1..1922
                      note = Recombinant expression cassette or expression
                       cassette component
source                1..1922
                      mol_type = other DNA
                      organism = synthetic construct
SEQUENCE: 22
ctgcgcgctc gctcgctcac tgaggccgcc cgggcaaagc ccgggcgtcg ggcgaccttt      60
ggtcgcccgg cctcagtgag cgagcgagcg cgcagagagg gagtgccaa ctccatcact    120
aggggttcct tgtagttaat gattaacccg ccatgctact tatctacgta gccatgctct    180
aggaagatcg gaattcgccc ttaagtcat ggagaagacn cacctttgcag atgtctcac    240
tggggctggc agagcggca acctgcctaa ggctgctcag tccattagga gccagtagcc    300
tggaagatgt ctttaccccc agcatcagtt caagtggagc agcacataac tcttgccctc    360
tgccttccaa gattctggtg ctgagactta tggagtgtct tggaggttgc cttctgcccc    420
ccaaccctgc tcccagctgg ccctcccagg cctgggttgc tggcctctgc tttatcagga    480
ttctcaagag ggacagctgg tttatgttgc atgactgttc cctgcatatc tgctctgcat    540
ttaaatagct tatctgagca gctggaggac cacatgggct atatggcgt ggggtacatg    600
ttcctgtagc cttgtcctg gcacctgcca aaatagcagc caacacccc caccccacc    660
gccatccccc tgcccaccc gtccctgtc gcacattcct cctccgcag ggctggctca    720
ccaggcccca gcccacatgc ctgcttaaag ccctctccat cctctgcctc acccagtccc    780
cgctgagact gagcagacgc ctcaccggcc gccgccgac catggcagag aaggctgcaa    840
gcactttctc tcacctgctc gtgccgattt gctttttgat tgggtggata gttggctgta    900
tcataatgat ctacgttgtc ttttcataga agctttggat ccaatcaacc tctgattac    960
aaaatttgtg aaagattgac tggtattctt aactatgttg ctccttttac gctatggga   1020
tacgctgctt taatgccttt gtatcatgct attgcttccc gtatggcttt cattttctcc   1080
tccttgtata atcctggtt gctgtctctt tatgaggagt gtggcccgt tgtcaggcaa   1140
```

```
cgtggcgtgg tgtgcactgt gtttgctgac gcaaccccca ctggttgggg cattgccacc  1200
acctgtcagc tcctttccgg gactttcgct ttccccctcc ctattgccac ggcggaactc  1260
atcgccgcct gccttgcccg ctgctggaca ggggctcggc tgttgggcac tgacaattcc  1320
gtggtgttgt cggggaaatc atcgtccttt ccttggctgc tcgcctgtgt tgccacctgg  1380
attctgcgcg ggacgtcctt ctgctacgtc ccttcggcg tcaatccagc ggaccttcct  1440
tcccgcggcc tgctgccggc tctgcggcct cttccgcgtc ttcgagatct gcctcgactg  1500
tgccttctag ttgccagcca tctgttgttt gcccctcccc cgtgccttcc ttgaccctgg  1560
aaggtgccac tcccactgtc ctttcctaat aaaatgagga aattgcatcg cattgtctga  1620
gtaggtgtca ttctattctg gggggtgggg tggggcagga cagcaagggg gaggattggg  1680
aagacaatag caggcatgct ggggactcga gttaaggcg aattcccgat taggatcttc  1740
ctagagcatg gctacgtaga taagtagcat ggcgggttaa tcattaacta caaggaaccc  1800
ctagtgatgg agttggccac tccctctctg cgcgctcgct cgctcactga ggccgggcga  1860
ccaaaggtcg cccgacgccc gggctttgcc cggcggcct cagtgagcga gcgagcgcgc  1920
ag                                                                1922

SEQ ID NO: 23            moltype = DNA   length = 3180
FEATURE                  Location/Qualifiers
misc_feature             1..3180
                         note = Recombinant expression cassette or expression
                          cassette component
source                   1..3180
                         mol_type = other DNA
                         organism = synthetic construct
SEQUENCE: 23
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagagagg acccttttcaa ggacattagt ggtgaaggca  240
gcatagtagc tcccaaggca gagggattga gagaagagtt tgaggactgg gaaggcggga  300
cacatgattg ggtgatggga gaaggggca gagaatagcg agattgcttt ctttgcccac  360
ggagaaacag aggagtgtgg atcatgaatg ggcaagatct ttaagtgcca gggggggtca  420
tggaggaggg gagggcctgc tccagaggag gaccattcct gcttcagagc caagcaggac  480
ctaggctgtg aagattcgga gaaagagatg gaggggagag tcagctcagc tgcttactgg  540
cttgctttcc tcctgtctct ttcatttca taatctacca aaccctgcaa tgggccagcc  600
ttgaacatac aagtgcatgt gcatggtcag acacaggcaa gcaagcaaga ccctaggcc  660
tgacctatgc atctgcaatc tagtaggttt agcagatcat agccccgcac tgcttgattt  720
taaagccgtt aggggatgac ctttgacagt ccgcatcacc cctctcacac aacgagcgcc  780
tgttcaaggt tcttgactgg aagttctacc ttgtatctgg cctcctgtag cagtttcagt  840
ccattccctg tgaggagggt gtgccacatg gctttgggtt tcatggagaa gacccacctt  900
gcagatgtcc tcactggggc tggcagagcc ggcaacctgc taaggctgc tcagtccatt  960
aggagccagt agcctggaag atgtctttac ccccagcatc agttcaagtg gagcagcaca  1020
taactcttgc cctctgcctt ccaagattct ggtgctgaga cttatggagt gtcttggagg  1080
ttgcctttctg ccccccaacc ctgctcccag ctggccctcc caggcctggg ttgctggcct  1140
ctgctttatc aggattctca agagggacag ctggtttatg ttgcatgact gttccctgca  1200
tatctgctct ggttttaaat agcttatctg agcagctgga ggaccacatg gcttatatg   1260
gcgtggggta catgttcctg tagccttgtc cctggcacct gccaaaatag cagccaacac  1320
ccccaccccc caccgccatc ccctgcccc accgtcccc tgtcgcacat tcctccctcc  1380
gcagggctgg ctcaccaggc cccagcccac atgcctgctt aaagcccctct ccatcctctg  1440
cctcacccag tccccgctga gactgagcag acgcctccag gatctgtcgg cagctgctgt  1500
tctgaggtaa ggctcgggca gggctctggg gaagaggaga gcagagaatg gacggggaga  1560
tgtgagggtc ttgggccctg gcatatttac ccagagtctg cctgtgtccg cagaagtcca  1620
tggcccctcc tggtggaggc cacacttcag aggacaggtt gccaggtctg ggctccaaga  1680
ttggtacaat agagcagaga gaggagtcgc tgcgacgctg ccttcgcccc gtgcccgct   1740
ccgccgccgc ctcgcgccgc cgccccggc tctgactgac cgcgttactc ccacaggtga  1800
gcggggggga cggcccttct cctccgggct gtaattagcg cttggtttaa tgacggcttg  1860
tttctttttct gtggctgcgt gaaagccttg aggggctccg ggagctagag cctctgctaa  1920
ccatgttcat gccttcttct ttttcctaca gctcctgggc aacgtgctgg ttattgtgct  1980
gtctcatcat tttggcaaag aattcccaat cgatacccaa tcgatacaga tctagcggcc  2040
gcgccgccac catggcagag aaggctggaa gcactttctc tcacctgctc gtgccgattt  2100
tgcttttgat tgggtggata gttggctgta tcataatgat ctacgttgtc ttttcatagc  2160
cagaggttga ttggatccaa gctttggatc caatggatcc aatcaacctc tggattacaa  2220
aatttgtgaa agattgactg gtattcttaa ctatgttgct ccttttacgc tatgtggata  2280
cgctgcttta atgcctttgt atcatgctat tgcttcccgt atggctttca ttttctcctc  2340
cttgtataaa tcctggttgc tgtctcttta tgaggagttg tgcccgttg tcaggcaacg  2400
tggcgtggtg tgcactgtgt ttgctgacgc aaccccact ggttgggca ttgccaccac  2460
ctgtcagctc ctttccggga ctttcgcttt cccctcct attgccacgg cggaactcat  2520
cgccgcctgc cttgcccgct gctggacagg ggctcggctg ttgggcactg acaattccgt  2580
ggtgttgtcg gggaaatcat cgtccttttcc ttggctgctc gcctgtgttg ccacctggat  2640
tctgcgcgg acgtcctct gctacgtccc ttcggccctc aatccagcgg accttccttc  2700
ccgcggcctg ctgccggctc tgcggcctct tccgcgtctt cgagatctgc ctcgactgtg  2760
ccttctagtt gccagccatc tgttgtttgc cctccccg tgccttcctt gaccctggaa  2820
ggtgccactc ccactgtcct ttcctaataa aatgaggaaa ttgcatcgca ttgtctgagt  2880
aggtgtcatt ctattctggg ggtggggtg gggcaggaca gcaagggga ggattgggaa  2940
gacaatagca ggcatgctgg ggactcgagt taagggcgaa ttcccgatta ggatcttcct  3000
agagcatggc tacgtagata agtagcatgg cgggttaatc attaactaca aggaacccct  3060
agtgatggag ttggccactc cctctctgcg cgctcgctcg ctcactgagg ccgggcgacc  3120
aaaggtcgcc cgacgcccgg gctttgcccg gcggcctca gtgagcgagc gagcgcgcag  3180

SEQ ID NO: 24            moltype = DNA   length = 1684
```

```
FEATURE             Location/Qualifiers
misc_feature        1..1684
                    note = Recombinant expression cassette or expression
                       cassette component
source              1..1684
                    mol_type = other DNA
                    organism = synthetic construct
SEQUENCE: 24
ctgcgcgctc gctcgctcac tgaggccgcc cgggcaaagc ccgggcgtcg ggcgaccttt   60
ggtcgcccgg cctcagtgag cgagcgagcg cgcagagagg gagtggccaa ctccatcact  120
aggggttcct tgtagttaat gattaacccg ccatgctact tatctaccag ggtaatgggg  180
atcctctaga actatagcta gaattcgccc ttacgggccc cccctcgagg tcgggataaa  240
agcagtctgg gctttcacat gacagcatct ggggctgcgg cagagggtcg ggtccgaagc  300
gctgccttat cagcgtcccc agccctggga ggtgacagct ggctggcttg tgtcagcccc  360
tcgggcactc acgtatctcc gtccgacggg ttttaaaatag caaaactctg aggccacaca  420
atagcttggg cttatatggg ctcctgtggg ggaaggggga gcacggaggg ggccggggcc  480
gctgctgcca aaatagcagc tcacaagtgt tgcattcctc tctgggcgcc gggcacattc  540
ctgctggctc tgcccgcccc ggggtgggcg ccgggggggac cttaaagcct ctgcccccca  600
aggagcccctt cccagacagc cgccggcacc caccgctccg tgggacgatc cccgaagctc  660
tagagcttta ttgcggtagt ttatcacagt taaattgcta acgcagtcag tgcttctgac  720
acaacagtct cgaacttaag ctgcagaagt tggtcgtgag gcactgggca ggtaagtatc  780
aaggttacaa gacaggttta aggagaccaa tagaaactgg gctgtgtcga acagagaaga  840
ctcttgcgtt tctgataggc acctattggt cttactgaca tccactttgc ctttctctcc  900
acaggtgtcc actcccagtt caattacagc tcttaaggct agagtactta atacgactca  960
ctataggcta gccgccacca tggctgagaa agagtcaaca tcaccacacc tcatggttcc 1020
cattcttctc ctggttggat ggattgtagg ctgcatcatc gttatttaca ttgtcttctt 1080
ctaacggccg cgcggatcca gacatgataa gatacattga tgagtttgga caaaccacaa 1140
ctagaatgca gtgaaaaaaa tgctttattt gtgaaatttg tgatgctatt gctttatttg 1200
taaccattat aagctgcaat aaacaagtta acaacaacaa ttgcattcat tttatgtttc 1260
aggttcaggg ggaggtgtgg gaggttttt agtcgacccg aggcgcctcg aggacggggt 1320
gaactacgcc tgaggatccg atcttttttcc ctctgccaaa aattatgggg acatcatgaa 1380
gccccttgag catctgactt ctggctaata aaggaaattt attttcattg caatagtgtg 1440
ttggaatttt ttgtgtctct cactcggaag caattcgttg atctgaattt cgaccaccca 1500
taatacccat taccctggta gataagtagc atggcgggtt aatcattaac tacaaggaac 1560
ccctagtgat ggagttggcc actccctctc tgcgcgctcg ctcgctcact gaggccgggc 1620
gaccaaaggt cgcccgacgc ccgggctttg cccgggcggc ctcagtgagc gagcgagcgc 1680
gcag                                                             1684

SEQ ID NO: 25         moltype = DNA   length = 44
FEATURE               Location/Qualifiers
misc_feature          1..44
                      note = Recombinant expression cassette or expression
                         cassette component
source                1..44
                      mol_type = other DNA
                      organism = synthetic construct
SEQUENCE: 25
aaaaaaaaaa aaaaaaaaaa aaaaaaaaaa aaaaaaaaaa aaaa                   44

SEQ ID NO: 26         moltype = DNA   length = 540
FEATURE               Location/Qualifiers
misc_feature          1..540
                      note = Recombinant expression cassette or expression
                         cassette component
source                1..540
                      mol_type = other DNA
                      organism = synthetic construct
SEQUENCE: 26
tcaacctctg gattacaaaa tttgtgaaag attgactggt attcttaact atgttgctcc   60
ttttacgcta tgtggatacg ctgctttaat gcctttgtat catgctattg cttcccgtat  120
ggctttcatt ttctcctcct tgtataaatc ctggttgctg tctctttatg aggagttgtg  180
gcccgttgtc aggcaacgtg gcgtggtgtg cactgtgttt gctgacgcaa ccccccactgg  240
ttggggcatt gccaccacct gtcagctcct ttccgggact ttcgctttcc cctcccctat  300
tgccacggcg gaactcatcg ccgcctgcct gccgcgtgc tggacagggg ccctgcgtt  360
gggcactgac aattcgtgg tgttgtcggg gaaatcatcg tccttccctt ggctgctcgc  420
ctgtgttgcc acctcggatt ctgcgcggga cgtccttctg tacgtccctt cggccctcaa  480
tccagcggac cttccttccc gcggcctgct gccggtctg cggcctcttc cgcgtcttcg  540

SEQ ID NO: 27         moltype = DNA   length = 215
FEATURE               Location/Qualifiers
misc_feature          1..215
                      note = Recombinant expression cassette or expression
                         cassette component
source                1..215
                      mol_type = other DNA
                      organism = synthetic construct
SEQUENCE: 27
gcctcgactg tgccttctag ttgccagcca tctgttgttt gcccctcccc cgtgccttcc   60
ttgaccctgg aaggtgccac tcccactgtc ctttcctaat aaaatgagga aattgcatcg  120
```

```
cattgtctga gtaggtgtca ttctattctg gggggtgggg tggggcagga cagcaagggg    180
gaggattggg aagacaatag caggcatgct gggga                              215
```

```
SEQ ID NO: 28              moltype = DNA  length = 134
FEATURE                    Location/Qualifiers
misc_feature               1..134
                           note = Recombinant expression cassette or expression
                             cassette component
source                     1..134
                           mol_type = other DNA
                           organism = synthetic construct
SEQUENCE: 28
gatccagaca tgataagata cattgatgag tttggacaaa ccacaactag aatgcagtga    60
aaaaaatgct ttatttgtga aatttgtgat gctattgctt tatttgtaac cattataagc   120
tgcaataaac aagt                                                     134

SEQ ID NO: 29              moltype = AA  length = 736
FEATURE                    Location/Qualifiers
REGION                     1..736
                           note = Recombinant expression cassette or expression
                             cassette component
source                     1..736
                           mol_type = protein
                           organism = synthetic construct
SEQUENCE: 29
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN PQFSYEFENV   420
PFHSSYAHSQ SLDRLMNPLI DQYLYYLSKT ISQVNGRPRD LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 30              moltype = AA  length = 736
FEATURE                    Location/Qualifiers
REGION                     1..736
                           note = Recombinant expression cassette or expression
                             cassette component
source                     1..736
                           mol_type = protein
                           organism = synthetic construct
SEQUENCE: 30
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNLNSM LIWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 31              moltype = AA  length = 727
FEATURE                    Location/Qualifiers
REGION                     1..727
                           note = Recombinant expression cassette or expression
                             cassette component
source                     1..727
                           mol_type = protein
                           organism = synthetic construct
SEQUENCE: 31
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPFG LVEEGAKTAP TGKRIDDHFP KRKKARTEED SKPSTSSDAE AGPSGSQQLQ   180
IPAQPASSLG ADTMSAGGGG PLGDNNEGAD GVGSSSGNWH CDSQWLGDRV ITTSTRTWAL   240
PTYNNHLYKQ ISNSTSGGSS NDNAYFGYST PWGYFDFNRF HCHFSPRDWQ RLINNNWGFR   300
PKRLNFKLFN IQVKEVTDNN GVKTIANNLT STVQVFTDSD YQLPYVLGSA HEGCLPPFPA   360
DVFMIPQYGY LTLNDGSQAV GRSSFYCLEY FPSQMLRTGN NFQFSYEFEN VPFHSSYAHS   420
QSLDRLMNPL IDQYLYYLSK TIGYHKSGAA QLKFSVAGPS NMAVQGRNYI PGPSYRQQRV   480
```

```
STTVTQNNNS EFAWPGASSW ALNGRNSLMN PGPAMASHKE GEDRFFPLSG SLIFGKQGTG    540
RDNVDADKVM ITNEEEIKTT NPVATESYGQ VATNHQSAQA QAQTGWVQNQ GILPGMVWQD    600
RDVYLQGPIW AKIPHTDGNF HPSPLMGGFG MKHPPPQILI KNTPVPADPP TAFNKDKLNS    660
FITQYSTGQV SVEIEWELQK ENSKRWNPEI QYTSNYYKSN NVEFAVNTEG VYSEPRPIGT    720
RYLTRNL                                                              727

SEQ ID NO: 32          moltype = AA   length = 35
FEATURE                Location/Qualifiers
source                 1..35
                       mol_type = protein
                       organism = Homo sapiens
SEQUENCE: 32
MAEKAGSTFS HLLVPILLLI GWIVGCIIMI YVVFS                                35

SEQ ID NO: 33          moltype = DNA  length = 108
FEATURE                Location/Qualifiers
source                 1..108
                       mol_type = other DNA
                       organism = Homo sapiens
SEQUENCE: 33
atggcagaga aggctggaag cactttctct cacctgctcg tgccgatttt gcttttgatt    60
gggtggatag ttggctgtat cataatgatc tacgttgtct tttcatag                108

SEQ ID NO: 34          moltype = DNA  length = 2208
FEATURE                Location/Qualifiers
misc_feature           1..2208
                       note = Recombinant expression cassette or expression
                        cassette component
source                 1..2208
                       mol_type = other DNA
                       organism = synthetic construct
SEQUENCE: 34
atggccgccg acggctacct gcccgactgg ctggaggaca acctgagcga gggcatcagg     60
gagtggtggg ccctgaagcc cggcgccccc cagcccaagg ccaaccagca gcaccaggac    120
aacgccaggg gcctggtgct gccccggctac aactacctgg ccccggcaa cggcctggac    180
aggggcgagc ccgtgaacag ggccgacgag gtgccaggga gcacgacat cagctacaac    240
gagcagctgc aggccggcga caaccctac ctgaagtaca ccacgccga cgccgagttc    300
caggagaggc tgaaggagga caccagcttc ggcggcaacc tgggcagggc cgtgttccag    360
gccaagaaga ggctgctgga gccccctggc ctggtggagg aggccgccaa gaccgcccc    420
ggcaagaaga ggcccgtgga gcagagcccc caggagcccg acagcagcgc cggcatcggc    480
aagagcggcg cccagcccgc caagaagagg ctgaacttcg ccagaccgg cgacaccgag    540
agcgtgcccg acccccagcc catcggcgag ccccccgccg ccccccagcg cgtgggcagc    600
ctgaccatgg ccagcggcgg cggcgccccc gtggccgaca acaacgaggg cgccgacggc    660
gtgggcagca gcagcggcaa ctggcactgc gacagccagt ggctgggcga cagggtgatc    720
accaccagca ccaggacctg gccctgcc acctacaaca ccaccgta caagcagatc    780
agcaacagca ccagcggcgg cagcagcaac gacaacgcct acttcggcta cagcacccc    840
tggggctact tcgacttcaa caggttccac tgccacttca ctggcagagg             900
ctgatcaaca acaactgggg cttcaggccc aagaggctga acttcaagct gttcaacatc    960
caggtgaagg aggtgaccga caacaacggc gtgaagacca tcgccaacaa cctgaccagc   1020
accgtgcagg tgttcaccga cagcgactac cagctgccct acgtgctggg cagcgcccac   1080
gagggcgcc tgcccccctt ccccgccgac gtgttcatga tccccagta cggctacttc   1140
accctgaacg acggcagcca ggccgtgggc aggagcagct tctactgcct ggagtacttc   1200
cccagccaga tgctgaggac cggcaacaac ttccagttca gctacgagtt cgagaacgtg   1260
cccttccaca gcagctacgc ccacagccag agcctggaca gctgatgaa cccctgatc    1320
gaccagtacc tgtactacct gagcaagacc atcaacggca gccagaa ccagcagacc     1380
ctgaagttca gcgtggccgg ccccagcaac atggccgtgc agggcaggaa ctacatcccc   1440
ggccccagct acaggcagca gagggtgagc accaccgtga cccagaacaa caacagcgag   1500
ttcgcctggc ccgcgccag cagctgggcc ctgaacggca gaacagcct gatgaaccc    1560
ggccccgcca tggccagcca caaggagggc gaggacaggt tcttcccct gagcggcagc   1620
ctgatcttcg gcaagcaggg caccggcagg gacaacgtga acgccgacaa ggtgatgatc   1680
accaacgagg aggagatcaa gaccaccaac cccgtggcca ccgagagcta cggccaggtg   1740
gccaccaacc accaggccaa ctacggccag gcccagaccg gctgggtgca gaaccagggc   1800
atcctgcccg gcatggtgtg gcaggacagg gacgtgtacc tgcagggccc catctgggcc   1860
aagatccccc acaccgacgg caacttccac cccagcctgc tgatgggcgg cttcggcatg   1920
aagcacccc ccccccagat cctgatcaag aacaccccg tgcccgccga cccccccacc   1980
gccttcaaca ggacaagct gaacagcttc atcacccagt acagcaccgg ccaggtgagc   2040
gtggagatcg agtgggagct gcagaaggag aacagcaaga ggtggaaccc cgagatccag   2100
tacaccagca actactacaa gagcaacaac gtggagttcg ccgtgaacac cgagggcgtg   2160
tacagcgagc ccaggcccat cggcaccagg tacctgacca ggaacctg              2208

SEQ ID NO: 35          moltype = DNA  length = 2208
FEATURE                Location/Qualifiers
misc_feature           1..2208
                       note = Recombinant expression cassette or expression
                        cassette component
source                 1..2208
                       mol_type = other DNA
                       organism = synthetic construct
SEQUENCE: 35
```

```
atggccgccg acggctacct gcccgactgg ctggaggaca acctgagcga gggcatcagg    60
gagtggtggg ccctgaagcc cggcgccccc cagcccaagg ccaaccagca gcaccaggac   120
aacgccaggg gcctggtgct gcccggctac aagtacctgg gccccggcaa cggcctggac   180
aagggcgagc ccgtgaacgc cgccgacgcc gccgccctgg agcacgacaa ggcctacgac   240
cagcagctga aggccggcga caaccsctac ctgaagtaca accacgccga cgccgagttc   300
caggagaggc tgaaggagga caccagcttc ggcggcaacc tgggcagggc cgtgttccag   360
gccaagaaga ggctgctgga gccctgggc ctggtggagg aggccgccaa gaccgcccc    420
ggcaagaaga ggcccgtgga gcagagcccc caggagcccg acagcagcgc cggcatcggc   480
aagagcggcg cccagcccgc caagaagagg ctgaacttcg gccagaccgg cgacaccgag   540
agcgtgcccg accccagcc catcggcgag cccccgccg ccccagcgg cgtgggcagc    600
ctgaccatgg ccagcggcgg cggcgccccc gtggccgaca caacgagggc gccgacggc    660
gtgggcagca gcagcggcaa ctggcactgc gacagccagt ggctgggcga cagggtgatc   720
accaccagca ccaggacctg ggccctgccc acctacaaca ccacctgta caagcagatc   780
agcaacagca ccagcggcgg cagcagcaac gacaacgcct acttcggcta cagcaccccc   840
tggggctact tcgacttcaa caggttccac tgccacttca gccccaggga ctggcagagg   900
ctgatcaaca caactggggg cttcaggccc aagaggctga acttcaagct gttcaacatc   960
caggtgaagg aggtgaccga caacaacggc gtgaagacca tcgccaacaa cctgaccagc  1020
accgtgcagg tgttcaccga cagcgactac cagctgccct acgtgctggg cagcgcccac  1080
gagggctgcc tgcccccctt ccccgccgac gtgttcatga tcccccagta cggctacctg  1140
accctgaacg acggcagcca ggccgtgggc aggagcagct tctactgcct ggagtacttc  1200
cccagccaga tgctgaggac cggcaacaac ttccagttca gctacgagtt cgagaacgtg  1260
ccccttccaca gcagctacgc ccacagccag agcctggaca ggctgatgaa ccccctgatc  1320
gaccagtacc tgtactacct gagcaagacc atcaacggca gcggcagaa ccagcagacc   1380
ctgaagttca gcgtggccgg ccccagcaac atggccgtgc agggcaggaa ctacatcccc  1440
ggccccagct acaggcagca gagggtgagc accaccgtga cccagaacaa caacagcgag  1500
ttcgcctggc ccggcgccag cagctgggcc ctgaacggca ggaacagcct gatgaacccc  1560
ggccccgcca tggccagcca caaggagggc gaggacaggt tcttccccct gagcggcagc  1620
ctgatcttcg gcaagcaggg caccggcagg gacaacgtgg acgccgacaa ggtgatgatc  1680
accaacgagg aggagatcaa gaccaccaac cccgtggcca ccgagagcta cggccaggtg  1740
gccaccaacc accagccaa ctacggcag gcccagaccg gctgggtgca gaaccagggc   1800
atcctgcccg gcatggtgtg gcaggacagg gacgtgtacc tgcagggccc catctgggcc  1860
aagatccccc acaccgacgg caacttccac cccagccccc tgatgggcgg cttcggcatg  1920
aagcacccc ccccccagat cctgatcaag aacaccccg tgcccgccga ccccccacc   1980
gccttcaaca aggacaagct gaacagcttc atcacccagt acagcaccgg ccaggtgagc  2040
gtggagatcg agtgggagct gcagaaggag aacagcaga ggtgaaccc cgagatccag   2100
tacaccagca actactacaa gagcaacaac gtggagttcg ccgtgaacac cgagggcgtg  2160
tacagcgagc ccaggcccat cggcaccagg tacctgacca ggaacctg               2208
```

SEQ ID NO: 36        moltype = DNA  length = 2208
FEATURE               Location/Qualifiers
misc_feature       1..2208
                      note = Recombinant expression cassette or expression
                      cassette component
source                1..2208
                      mol_type = other DNA
                      organism = synthetic construct
SEQUENCE: 36

```
atggccgccg acggctacct gcccgactgg ctggaggaca acctgagcga gggcatcagg    60
gagtggtggg ccctgaagcc cggcgccccc cagcccaagg ccaaccagca gcaccaggac   120
aacgccaggg gcctggtgct gcccggctac aagtacctgg gccccggcaa cggcctggac   180
aagggcgagc ccgtgaacgc cgccgacgcc gccgccctgg agcacgacaa ggcctacgac   240
cagcagctga aggccggcga caaccctac ctgaagtaca accacgccga cgccgagttc    300
caggagaggc tgaaggagga caccagcttc ggcggcaacc tgggcagggc cgtgttccag   360
gccaagaaga ggctgctgga gccctgggc ctggtggagg aggccgccaa gaccgccccc   420
ggcaagaaga ggcccgtgga gcagagcccc caggagcccg acagcagcgc cggcatcggc   480
aagagcggcg cccagcccgc caagaagagg ctgaacttcg gccagaccgg cgacaccgag   540
agcgtgcccg accccagcc catcggcgag cccccgccg ccccagcgg cgtgggcagc    600
ctgaccatgg ccagcggcgg cggcgccccc gtggccgaca caacgagggc gccgacggc    660
gtgggcagca gcagcggcaa ctggcactgc gacagccagt ggctgggcga cagggtgatc   720
accaccagca ccaggacctg ggccctgccc acctacaaca ccacctgta caagcagatc    780
agcaacagca ccagcggcgg cagcagcaac gacaacgcct acttcggcta cagcaccccc   840
tggggctact tcgacttcaa caggttccac tgccacttca gccccaggga ctggcagagg   900
ctgatcaaca caactggggg cttcaggccc aagaggctga acttcaagct gttcaacatc   960
caggtgaagg aggtgaccga caacaacggc gtgaagacca tcgccaacaa cctgaccagc  1020
accgtgcagg tgttcaccga cagcgactac cagctgccct acgtgctggg cagcgcccac  1080
gagggctgcc tgcccccctt ccccgccgac gtgttcatga tcccccagta cggctacctg  1140
accctgaacg acggcagcca ggccgtgggc aggagcagct tctactgcct ggagtacttc  1200
cccagccaga tgctgaggac cggcaacaac ttccagttca gctacgagtt cgagaacgtg  1260
ccccttccaca gcagctacgc ccacagccag agcctggaca ggctgatgaa ccccctgatc  1320
gaccagtacc tgtactacct gagcaagacc atcagccagg tgaacggcag gcccaggac    1380
ctgaagttca gcgtggccgg ccccagcaac atggccgtgc agggcaggaa ctacatcccc  1440
ggccccagct acaggcagca gagggtgagc accaccgtga cccagaacaa caacagcgag  1500
ttcgcctggc ccggcgccag cagctgggcc ctgaacggca ggaacagcct gatgaacccc  1560
ggccccgcca tggccagcca caaggagggc gaggacaggt tcttccccct gagcggcagc  1620
ctgatcttcg gcaagcaggg caccggcagg gacaacgtgg acgccgacaa ggtgatgatc  1680
accaacgagg aggagatcaa gaccaccaac cccgtggcca ccgagagcta cggccaggtg  1740
gccaccaacc accagagcgc ccaggcccag gcccagaccg gctgggtgca gaaccagggc   1800
atcctgcccg gcatggtgtg gcaggacagg gacgtgtacc tgcagggccc catctgggcc  1860
aagatccccc acaccgacgg caacttccac cccagccccc tgatgggcgg cttcggcatg  1920
```

```
aagcacccc cccccagat cctgatcaag aacacccccg tgcccgccga ccccccacc      1980
gccttcaaca aggacaagct gaacagcttc atcacccagt acagcaccgg ccaggtgagc   2040
gtggagatcg agtgggagct gcagaaggag aacagcaaga ggtggaaccc cgagatccag   2100
tacaccagca actactacaa gagcaacaac gtggagttcg ccgtgaacac cgagggcgtg   2160
tacagcgagc ccaggcccat cggcaccagg tacctgacca ggaacctg                2208
```

```
SEQ ID NO: 37           moltype = DNA   length = 2208
FEATURE                 Location/Qualifiers
misc_feature            1..2208
                        note = Recombinant expression cassette or expression
                         cassette component
source                  1..2208
                        mol_type = other DNA
                        organism = synthetic construct
SEQUENCE: 37
atggccgccg acggctacct gcccgactgg ctggaggaca acctgagcga gggcatcagg   60
gagtggtggg ccctgaagcc cggcgccccc cagcccaagg ccaaccagca gcaccaggac   120
aacgccaggg gcctggtgct gcccggctac aagtacctgg gccccggcaa cggcctggac   180
aagggcgagc ccgtgaacgc cgccgacgcc gccgccctgg agcacgacaa ggcctacgac   240
cagcagctga aggccggcga caaccccctac ctgaagtaca accacgccga cgccgagttc   300
caggagaggc tgaaggagga caccagcttc ggcggcaacc tgggcagggc cgtgttccag   360
gccaagaaga ggctgctgga gcccctgggc ctggtgagga aggccgccaa gaccgcccgc   420
ggcaagaaga ggcccgtgga gcagagcccc caggagcccg acagcagcgc ggcatcggc    480
aagagcggcg cccagcccgc caagaagagg ctgaacttcg ccagaccggg cgacaccgag   540
agcgtgcccg accccagcc catcggcgag ccccgcccg ccccagcgg cgtgggcagc    600
ctgaccatgg ccagcggcgg cggcgccccc gtggccgaca acaacgaggg cgccgacgga   660
gtgggcagca gcgcggcaa ctggcactgc gacagccagt ggctgggcga cagggtgatc    720
accaccagca ccaggacctg gcccctgccc acctacaaca accacctgta caagcagatc    780
agcaacagca ccagcggcgg cagcagcaac gacaacgcct acttcggcta cagccaccccc   840
tgggctact tcgacttcaa caggttccac tgccacttca cctggcagagg                900
ctgatcaaca caactggggg cttcaggccc aagaggctga acttcaagct gttcaacatc    960
caggtgaagg aggtgaccga caacaacggc gtgaagacca tcgccaacaa cctgaccagc   1020
accgtgcagg tgttcaccga cagcgactac cagctgccct acgtgctggg cagcgcccac   1080
gagggctcc tgcccccctt cccgccgac gtgttcatga tcccccagta cggctacctg   1140
acctgaacg acggcagcca ggccgtgggc aggagcagct tctactgcct ggagtacttc    1200
cccagccaga tgctgaggac cggcaacaac ttccagttca gctacgagtt cgagaacgtg   1260
cccttccaca gcagctacgc ccacagccag agcctggaca ggctgatgaa ccccctgatc    1320
gaccagtacc tgtactacct gagcaagacc atcaacggca gcggcagaa ccagcagacc   1380
ctgaagttca gcgtggccgg cccccacaac atggccgtgc agggcaggaa ctacatcccc    1440
ggccccagct acaggcagca gagggtgagc accaccgtga cccagaacct gaacagcatg   1500
ctgatctggc cggcgccag cagctgggcc ctgaacggca ggaacagcct gatgaaccc    1560
ggccccgcca tggccagcca aaggagggc gaggacaggt cttcccct gagcggcagc    1620
ctgatcttcg gcaagcaggg caccggcagg gacaacgtga ggtgatgatc                1680
accaacgagg aggagatcaa gaccaccaac cccgtggcca ccgagagcta cggccaggtg    1740
gccaccaacc accagagcgc ccaggcccag gcccagaccg ctgggtgca gaaccagggc    1800
atcctgcccg gcatggtgtg gcaggacagg gacgtgtacc tgcaggggccc catctgggcc    1860
aagatccccc acaccgacgg caacttccac cccagccgtg gaccttcggcatg    1920
aagcacccc cccccagat cctgatcaag aacacccccg tgcccgccga ccccccacc      1980
gccttcaaca aggacaagct gaacagcttc atcacccagt acagcaccgg ccaggtgagc   2040
gtggagatcg agtgggagct gcagaaggag aacagcaaga ggtggaaccc cgagatccag   2100
tacaccagca actactacaa gagcaacaac gtggagttcg ccgtgaacac cgagggcgtg   2160
tacagcgagc ccaggcccat cggcaccagg tacctgacca ggaacctg                2208
```

```
SEQ ID NO: 38           moltype = DNA   length = 2181
FEATURE                 Location/Qualifiers
misc_feature            1..2181
                        note = Recombinant expression cassette or expression
                         cassette component
source                  1..2181
                        mol_type = other DNA
                        organism = synthetic construct
SEQUENCE: 38
atggccgccg acggctacct gcccgactgg ctggaggaca acctgagcga gggcatcagg   60
gagtggtggg ccctgaagcc cggcgccccc cagcccaagg ccaaccagca gcaccaggac   120
aacgccaggg gcctggtgct gcccggctac aagtacctgg gccccggcaa cggcctggac   180
aagggcgagc ccgtgaacgc cgccgacgcc gccgccctgg agcacgacaa ggcctacgac   240
cagcagctga aggccggcga caaccccctac ctgaagtaca accacgccga cgccgagttc   300
caggagaggc tgaaggagga caccagcttc ggcggcaacc tgggcagggc cgtgttccag   360
gccaagaaga ggctgctgga gcccctcggc ctggtgagga aggccgccaa gaccgcccgc   420
accggcaaga ggatcgacga ccacttcccg aagaggaaga aggccaggac cgaggaggac   480
agcaagccca gcaccagcag cgacgccgag gccggcccca gcgcagcca gcagctgcag   540
atccccgccc agcccgccag cagcctgggc gccgacacca tgagcgccgg cggcggcggc   600
cccctgggcg acaacaacga gggcgccgac ggcgtgggca gcagcggca actggcactgc   660
tgcgacagcc agtggctggg cgacaggtg atcaccacca gcacctggcc ctgggcgatc   720
cccacctaca caaccacct gtacaagcag atcagcaaca gcaccagcgg cggcagcagc   780
aacgacaacg cctacttcgg ctacagcacc cctgggggct acttcgactt caacaggttc   840
cactgccact tcagccccag ggactggcag aggctgatca caacaactg ggcttcagg    900
cccaagagg tgaacttcaa gctgttcaac atccaggtga aggaggtgac cgacaacaac   960
ggcgtgaaga ccatcgccaa caacctgacc agcaccgtgc aggtgttcac cgacagcgac   1020
```

```
taccagctgc cctacgtgct gggcagcgcc cacgagggct gcctgccccc cttcccgcc    1080
gacgtgttca tgatccccca gtacggctac ctgaccctga acgacggcag ccaggccgtg    1140
ggcaggagca gcttctactg cctggagtac ttccccagcc agatgctgag gaccggcaac    1200
aacttccagt tcagctacga gttcgagaac gtgcccttcc acagcagcta cgcccacagc    1260
cagagcctgg acaggctgat gaaccccctg atcgaccagt acctgtacta cctgagcaag    1320
accatcggct accacaagag cggcgccgcc cagctgaagt tcagcgtggc cggccccagc    1380
aacatggccg tgcagggcag gaactacatc cccggcccca gctacaggca gcagagggtg    1440
agcaccaccg tgacccagaa caacaacagc gagttcgcct ggcccggcgc cagcagctgg    1500
gccctgaacg gcaggaacag cctgatgaac cccgcccccg ccatggccag ccacaaggag    1560
ggcgaggaca ggttcttccc cctgagcggc agcctgatct tcggcaagca gggcaccggc    1620
agggacaacg tggacgccga caaggtgatg atcaccaacg aggaggagat caagaccacc    1680
aaccccgtgg ccaccgagag ctacggccag gtggccacca ccaccagag cgcccaggcc    1740
caggcccaga ccggctgggt gcagaaccag gcatcctgc ccggcatggt gtgccaggac    1800
agggacgtgt acctgcaggg ccccatctgg gccaagatcc ccacaccga cggcaacttc    1860
cacccccagc ccctgatggg cggcttcggc atgaagcacc cccccccca gatcctgatc    1920
aagaacaccc ccgtgcccgc cgaccccccc accgccttca caaggacaa gctgaacagc    1980
ttcatcaccc agtacagcac cggccaggtg agcgtggaga tcgagtggga gctgcagaag    2040
gagaacagca agaggtggaa ccccgagatc cagtacacca gcaactacta caaggagcaac    2100
aacgtggagt tcgccgtgaa caccgagggc gtgtacagcg agcccaggcc catcggcacc    2160
aggtacctga ccaggaacct g                                               2181

SEQ ID NO: 39          moltype = AA   length = 736
FEATURE                Location/Qualifiers
REGION                 1..736
                       note = Recombinant expression cassette or expression
                       cassette component
source                 1..736
                       mol_type = protein
                       organism = synthetic construct
SEQUENCE: 39
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ    120
AKKRVLEPFG LVEEGAKTAP GKKRPVEQSP QEPDSSSGIG KTGQQPAKKR LNFGQTGDSE    180
SVPDPQPLGE PPATPAAVGP TTMASGGGAP MADNNEGADG VGNASGNWHC DSTWLGDRVI    240
TTSTRTWALP TYNNHLYKQI SSASTGASND NHYFGYSTPW GYFDFNRPHC HFSPRDWQRL    300
INNNWGFRPK RLNFKLFNIQ VKEVTTNDGV TTIANNLTST VQVFSDSEYQ LPYVLGSAHQ    360
GCLPPFPADV FMIPQYGYLT LNNGSQAVGR SSFYCLEYFP SQMLRTGNNF TFSYTFEDVP    420
FHSSYAHSQS LDRLMNPLID QYLYYLNRTQ NQSGSAQNKD LLFSRGSPAG MSVQPKNWLP    480
GPCYRQQRVS KTKTDNNNSN FTWTGASKYN LNGRESIINP GTAMASHKDD KDKFFPMSGV    540
MIFGKESAGA SNTALDNVMI TDEEEIKATN PVATERFGTV AVNLQSSSTD PATGDVHVMG    600
ALPGMVWQDR DVYLQGPIWA KIPHTDGHFH PSPLMGGFGL KHPPPQILIK NTPVPANPPA    660
EFSATKFASF ITQYSTGQVS VEIEWELQKE NSKRWNPEVQ YTSNYAKSAN VDFTVDNNGL    720
YTEPRPIGTR YLTRPL                                                   736

SEQ ID NO: 40          moltype = DNA  length = 2208
FEATURE                Location/Qualifiers
misc_feature           1..2208
                       note = Recombinant expression cassette or expression
                       cassette component
source                 1..2208
                       mol_type = other DNA
                       organism = synthetic construct
SEQUENCE: 40
atggccgccg acggctacct gcccgactgg ctgaggaca acctgagcga gggcatcagg    60
gagtggtggg acctgaagcc cggcgccccc aagcccaagg ccaaccagca gaagcaggac    120
gacggcaggg gcctggtgct gcccggctac aagtacctgg gccccttcaa cggcctggac    180
aagggcgagc ccgtgaacgc cgccgacgcc gccgccctgg agcacgacaa ggcctacgac    240
cagcagctga aggccggcga caaccccctac ctgaggtaca accgccga cgccgagttc    300
caggagaggc tgcaggagga caccagcttc ggcggcaacc tgggcagggc cgtgttccag    360
gccaagaaga gggtgctgga gcccttcggc ctggtggagg agggcgccaa gaccgcccc    420
ggcaagaaga ggcccgtgga gcagagcccc caggagcccg acagcagcag cggcatcggc    480
aagaccggcc agcagcccgc caagaagagg ctgaacttcg gccagaccgg cgacagcgag    540
agcgtgcccg acccccagcc cctgggcgag cccccgcca ccccgccgc cgtgggcccc    600
accaccatgg ccagcggcgg cggcgccccc atggccgaca acaacgaggg cgccgaggac    660
gtgggcaacg ccagcggcaa ctggcactgc gacagcacct ggctgggcga cagggtgatc    720
accaccagca ccaggacctg ggccctgccc acctacaaca accctgta caagcagatc    780
agcagcgcca gcaccggcgc cagcaacgac aaccactact cggctacag cacccctgg    840
ggctactcg acttcaacag gttccactgc cacttcagcc caggactg gcagaggctg    900
atcaacaaca actgggggctt caggcccaag aggctgaact tcaagctgtt caacatccag    960
gtgaaggagg tgaccaccaa cgacggcgtg accaccatcc caacaacct gaccagcacc    1020
gtgcaggtgt tcagcgacag cgagtaccag ctgccctacg tgctgggcag cgccaccag    1080
ggctgcctgc cccccttccc cgccgacgtg ttcatgatcc ccagtacgg ctacctgacc    1140
ctgaacaacg gcagccaggc cgtgggcagg agcagcttct actgcctgga gtacttcccc    1200
agccagatgc tgaggaccgg caacaacttc accttcagct acaccttcga ggacgtgccc    1260
ttccacagca gctacgccca cagccagagc ctggacaggc tgatgaaccc cctgatcgac    1320
cagtacctgt actacctgaa caggacccag aaccagagcg gcagcgccca gaacaaggac    1380
ctgctgttca gcaggggcag cccgccggc atgagcgtgc agcccaagaa ctggctgccc    1440
ggcccctgct acaggcagca gagggtgagc aagaccaaga ccgacaacaa caacagcaac    1500
ttcacctgga ccggcgccag caagtacaac ctgaacggca gggagagcat catcaacccc    1560
```

```
ggcaccgcca tggccagcca caaggacgac aaggacaagt tcttccccat gagcggcgtg   1620
atgatcttcg gcaaggagag cgccggcgcc agcaacaccg ccctggacaa cgtgatgatc   1680
accgacgagg aggagatcaa ggccaccaac cccgtggcca ccgagaggtt cggcaccgtg   1740
gccgtgaacc tgcagagcag cagcaccgac cccgccaccg cgacgtgca cgtgatgggc    1800
gccctgcccg gcatggtgtg gcaggacagg gacgtgtacc tgcagggcc catctgggcc    1860
aagatccccc acaccgacgg ccacttccac cccagccccc tgatgggcgg cttcggcctg   1920
aagcaccccc cccccagat cctgatcaag aacacccccg tgcccgccaa ccccccgcc     1980
gagttcagcg ccaccaagtt cgccagcttc atcacccagt acagcaccgg ccaggtgagc   2040
gtggagatcg agtgggagct gcagaaggag aacagcaaga ggtggaaccc cgaggtgcag   2100
tacaccagca actacgccaa gagcgccaac gtggacttca ccgtggacaa caacggcctg   2160
tacaccgagc actaggccaa gagcggcacc agg tacctgacca ggcccctg            2208

SEQ ID NO: 41          moltype = AA   length = 724
FEATURE                Location/Qualifiers
REGION                 1..724
                       note = Recombinant expression cassette or expression
                        cassette component
source                 1..724
                       mol_type = protein
                       organism = synthetic construct
SEQUENCE: 41
MSFVDHPPDW LEEVGEGLRE FLGLEAGPPK PKPNQQHQDQ ARGLVLPGYN YLGPGNGLDR    60
GEPVNRADEV AREHDISYNE QLEAGDNPYL KYNHADAEFQ EKLADDTSFG GNLGKAVFQA   120
KKRVLEPFGL VEEGAKTAPT GKRIDDHFPK RKKARTEEDS KPSTSSDAEA GPSGSQQLQI   180
PAQPASSLGA DTMSAGGGGP LGDNNQGADG VGNASGDWHC DSTWMGDRVV TKSTRTWVLP   240
SYNNHQYREI KSGSVDGSNA NAYFGYSTPW GYFDFNRPFHS HWSPRDWQRL INNYWGFRPR   300
SLRVKIFNIQ VKEVTVQDST TTIANNLTST VQVFTDDDYQ LPYVVGNGTE GCLPAFPPQV   360
FTLPQYGYAT LNRDNTENPT ERSSFFCLEY FPSKMLRTGN NFEFTYNFEE VPFHSSFAPS   420
QNLFKLANPL VDQYLYRFVS TNNTGGVQFN KNLAGRYANT YKNWFPGPMG RTQGWNLGSG   480
VNRASVSAFA TTNRMELEGA SYQVPPQPNG MTNNLQGSNT YALENTMIFN SQPANPGTTA   540
TYLEGNMLIT SESETQPVNR VAYNVGGQMA TNNQSSTTAP ATGTYNLQEI VPGSVWMERD   600
VYLQGPIWAK IPETGAHFHP SPAMGGFGLK HPPPMMLIKN TPVPGNITSF SDVPVSSFIT   660
QYSTGQVTVE MEWELKKENS KRWNPEIQYT NNYNDPQFVD FAPDSTGEYR TTRPIGTRYL   720
TRPL                                                                724

SEQ ID NO: 42          moltype = DNA   length = 2172
FEATURE                Location/Qualifiers
misc_feature           1..2172
                       note = Recombinant expression cassette or expression
                        cassette component
source                 1..2172
                       mol_type = other DNA
                       organism = synthetic construct
SEQUENCE: 42
atgagcttcg tggaccaccc ccccgactgg ctggaggagg tgggcgaggg cctgagggag     60
ttcctgggcc tggaggccgg cccccccaag cccaagccca accagcagca ccaggaccag    120
gccagggccc tggtgctgcc cggctacaac tacctgggcc ccggcaacgg cctggacagg    180
ggcgagcccg tgaacagggc cgacgaggtg gccagggagc acgacatcag ctacaacgag    240
cagctggagg ccgcgacaa cccctacctg aagtacaacc acgccgacgc cgagttccag    300
gagaagctgc ccgacgacac cagcttcggc ggcaacctgg gcaaggccgt gttccaggcc    360
aagaagaggg tgctggagcc cttcggcctg gtggaggagg gcgccaagac cgcccccacc    420
ggcaagagga tcgacgacca cttccccaag aggaagaagg ccaggaccga ggaggacagc    480
aagcccagca ccagcagcga cgccgaggcc ggcccagcg gcagccagca gctgcagatc    540
cccgcccagc ccgccagcag cctgggcgcc gacaccatga gcgccggcgg cggcggcccc    600
ctgggcgaca acaacggg cgccgacggc gtgggcaacg ccagcggctg ctggcactgc     660
gacagcacct ggatgggcga cagggtggtg accaagagca ccaggacctg ggtgctgccc    720
agctacaaca accaccagta cagggagatc aagagcggca cgtggacgg cagcaacgcc    780
aacgcctact tcggctacag cacccccctg ggctacttcg acttcaacag gttccacagc    840
cactggagcc ccagggactg gcagaggctg atcaacaact actgggctt caggccccagg   900
agcctgaggg tgaagatctt caacatccag gtgaaggagg tgaccgtgca ggacagcacc    960
accaccatcg ccaacaacct gaccagcacc gtgcaggtgt tcaccgacga cgactaccag   1020
ctgccctacg tggtgggcaa cggcaccgag ggctgcctgc ccgccttccc ccccaggtg    1080
ttcaccctgc cccagtacgg ctacgccacc ctgaacaggg acaacaccga gaaccccacc   1140
gagaggagca gcttcttctg cctggagtac ttccccagca agatgctgag gaccggcaac   1200
aacttcgagt tcacctacaa cttcgaggag gtgcccttcc acagcagctt cgcccccagc   1260
cagaacctgt tcaagctggc caaccccctg gtgaccagt acctgtacag gttcgtgagc   1320
accaacaaca ccggcggcgt gcagttcaac aagaacctgg ccggcaggta cgccaacacc   1380
tacaagaact ggttcccggg cccccatggg caggacccagg ctggaacct gggcagcggc   1440
gtgaacaggg ccagcgtgag cgccttcgcc accaccaaca ggatggagct ggagggcgcc   1500
agctaccagg tgcccccccca gcccaacggc atgaccaaca acctgcaggg cagcaacacc   1560
tacgccctgg agaacaccat gatcttcaac agccagcccg ccaacccgg caccaccgcc   1620
acctacctgg agggcaacat gctgatcacc agcgagagcg agacccagcc cgtgaacagg   1680
gtggcctaca acgtgggcgg ccagatggcc accaacaacc agagcagcac caccgccccc   1740
gccaccggca cctacaacct gcaggagatc gtgcccggca gcgtgtggat ggagagggac   1800
gtgtacctgc agggccccat ctgggccaag atccccgaga ccggcgccca cttccacccc   1860
agccccgcca tgggcggctt cggcctgaag caccccccca ccatgatgct gatcaagaac   1920
acccccgtgc ccggcaacat caccagcttc agcgacgtgc ccgtgagcag cttcatcacc   1980
cagtacagca ccggccaggt gaccgtggag atggagtggg agctgaagaa ggagaacagc   2040
aagaggtgga accccgagat ccagtacacc aacaactaca acgaccccca gttcgtggac   2100
```

```
ttcgccccg    acagcaccgg    cgagtacagg    accaccaggc    ccatcggcac    caggtacctg    2160
accaggcccc   tg                                                                    2172

SEQ ID NO: 43          moltype = AA   length = 34
FEATURE                Location/Qualifiers
REGION                 1..34
                       note = Recombinant expression cassette or expression
                       cassette component
source                 1..34
                       mol_type = protein
                       organism = synthetic construct
SEQUENCE: 43
MAEKGSTFSH LLVPILLLIG WIVGCIIMIY VVFS                                               34

SEQ ID NO: 44          moltype = DNA   length = 102
FEATURE                Location/Qualifiers
misc_feature           1..102
                       note = Recombinant expression cassette or expression
                       cassette component
source                 1..102
                       mol_type = other DNA
                       organism = synthetic construct
SEQUENCE: 44
atggccgaga   agggcagcac    cttcagccac    ctgctggtgc    ccatcctgct    gctgatcggc    60
tggatcgtgg   gctgcatcat    catgatctac    gtggtgttca    gc                          102

SEQ ID NO: 45          moltype = DNA   length = 2322
FEATURE                Location/Qualifiers
misc_feature           1..2322
                       note = Recombinant expression cassette or expression
                       cassette component
source                 1..2322
                       mol_type = other DNA
                       organism = synthetic construct
SEQUENCE: 45
ctgcgcgctc   gctcgctcac    tgaggccgcc    cgggcaaagc    ccgggcgtcg    ggcgacctttt   60
ggtcgcccgg   cctcagtgag    cgagcgagcg    cgcagagagg    gagtgccaa     ctccatcact    120
aggggttcct   tgtagttaat    gattaacccg    ccatgctact    tatctacgta    gccatgtctc    180
aggaagatcg   gaattcgccc    ttaagaactg    gcctgcccga    gaccaaacgt    gcggaacgta    240
gttaagtgtt   agaggtagga    tttgaagcct    gtcgatcatt    ctgattctcc    ttttctctac    300
gtctgcttcc   tgtcaatggg    catcctcact    gtcaaatgca    gatggtacag    cagggcttgg    360
tctcagccaa   gcaggcctct    ccccagtctc    catggctcag    ctgtccagca    gtttcatccc    420
tagaccatcc   caaacatggt    tgagaagctc    tgagggggag    accagcact     gcccggcccc    480
tgaagataat   cagcagtcct    gctcagcata    tcaatccaag    cccactctag    acagagatgc    540
cggtgcccag   ttttctattt    ttaactggtg    tgaactgaag    gaaaagcaca    gcattagaag    600
tccaagcagt   catggagaag    acccaccttg    cagatgtcct    cactgggct     ggcagagccg    660
gcaacctgcc   taaggctgct    cagtccatta    ggagccagta    gcctggaaga    tgtctttacc    720
cccagcatca   gttcaagtgg    agcagcacat    aactcttgcc    ctctgccttc    caagattctg    780
gtgctgagac   ttatggagtg    tcttggaggt    tgccttctgc    ccccaaccc     tgctcccagc    840
tggccctccc   aggcctgggt    tgctggcctc    tgctttatca    ggattctcaa    gagggacagc    900
tggtttatgt   tgcatgactg    ttccctgcat    atctgctctg    gttttaaata    gcttatctga    960
gcagctggag   gaccacatgg    gcttatatgg    cgtggggtac    atgttcctgt    agccttgtcc    1020
ctggcacctg   ccaaaatagc    agccaacacc    cccaccccc     accgccatcc    ccctgcccca    1080
cccgtccct    gtcgcacatt    cctccctccg    cagggctggc    tcaccaggcc    ccagcccaca    1140
tgcctgctta   aagccctctc    catcctctgc    ctcacccagt    ccccgctgag    actgagcaga    1200
cgcctccagc   ggccgcccgc    caccatggct    gagaaagagt    caacatcacc    acacctcatg    1260
gttcccattc   ttctcctggt    tggatggatt    gtaggctgca    tcatcgttat    ttacattgtc    1320
ttcttctaaa   agctttggat    ccaatcaacc    tctggattac    aaaatttgtg    aaagattgac    1380
tggtattctt   aactatgttg    ctccttttac    gctatgtgga    tacgctgctt    taatgcctt     1440
gtatcatgct   attgcttccc    gtatggcttt    cattttctcc    tccttgtata    aatcctggtt    1500
gctgtctctt   tatgaggagt    tgtggcccgt    tgtcaggcaa    cgtggcgtgg    tgtgcactgt    1560
gtttgctgac   gcaacccca    ctggttgggg    cattgccacc    acctgtcagc    tcctttccgg    1620
gactttcgct   ttccccctcc    ctattgccac    ggcggaactc    atcgccgcct    gccttgcccg    1680
ctgctggaca   ggggctcggc    tgttgggcac    tgacaattcc    gtggtgttgt    cggggaaatc    1740
atcgtccttt   ccttggctgc    tcgcctgtgt    tgccacctgg    attctgcgcg    gacgtcttt     1800
ctgctacgtc   ccttcggccc    tcaatccagc    ggaccttcct    tcccgcggcc    tgctgccggc    1860
tctgcggcct   cttccgcgtc    ttcgagatct    gcctcgactg    tgccttctag    ttgccagcca    1920
tctgttgttt   gcccctcccc    cgtgccttcc    ttgaccctgg    aaggtgccac    tcccactgtc    1980
ctttcctaat   aaaatgagga    aattgcatcg    cattgtctga    gtaggtgtca    ttctattctg    2040
gggggtgggg   tggggcagga    cagcaagggg    gaggattggg    aagacaatag    caggcatgct    2100
ggggactcga   gttaagggcg    aattcccgat    taggatcttc    ctagagcatg    gctacgtaga    2160
taagtagcat   ggcgggttaa    tcattaacta    caaggaaccc    ctagtgatgg    agttggccac    2220
tccctctctg   cgcgctcgct    cgctcactga    ggccgggcga    ccaaaggtcg    cccgacgccc    2280
gggctttgcc   cgggcggcct    cagtgagcga    gcgagcgcgc    ag                          2322

SEQ ID NO: 46          moltype = DNA   length = 2513
FEATURE                Location/Qualifiers
misc_feature           1..2513
                       note = Recombinant expression cassette or expression
```

|  | cassette component |  |
|---|---|---|
| source | 1..2513 | |
| | mol_type = other DNA | |
| | organism = synthetic construct | |

SEQUENCE: 46

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattcgccc ttaagaactg gcctgcccga gaccaaacgt gcggaacgta   240
gttaagtgtt agaggtagga tttgaagcct gtcgatcatt ctgattctcc ttttctctac   300
gtctgcttcc tgtcaatggg catcctcact gtcaaatgca gatggtacag cagggcttgg   360
tctcagccag gcaggcctct ccccagtctc catggctcag ctgtccagca gtttcatccc   420
tagaccatcc caaacatggt tgagaagctc tgaggggagg acccagcact gcccggcccc   480
tgaagataat cagcagtcct gctcagcata tcaatccaag cccactctag acagagatgc   540
cggtgcccag ttttctattt ttaactggtg tgaactgaag gaaaagcaca gcattagaag   600
tccaagcacc ttcagattaa aaataactaa ggtaagggcc atgtgggtag gggaggtggt   660
gtgagacggt cctgtctctc ctctatctgc ccatcggccc tttggggagg aggaatgtgc   720
ccaaggacta aaaaaaggcc ctggaaccag aggggcgagg gcagcagacc tttcatgggc   780
aaacctcagg gctgctgtcg tcatggagaa gacccacctt gcagatgtcc tcactgggc    840
tggcagagcc ggcaacctgc ctaaggctgc tcagtccatt aggagccagt agcctggaag   900
atgtctttac ccccagcatc agttcaagtg agcagcacac taactcttgc cctctgcctt   960
ccaagattct ggtgctgaga cttatggagt gtcttggagg ttgccttctg ccccccaacc  1020
ctgctcccag ctggccctcc caggcctggg ttgctggcct ctgctttatc aggattctca  1080
agagggacag ctggtttatg ttgcatgact gttcccgca tatctgctct ggttttaaat  1140
agcttatctg agcagctgga ggaccacatg gcttatatg gcgtgggta catgttcctg  1200
tagccttgtc cctggcacct gccaaaatag cagccacac ccccaccccc caccgccatc  1260
cccctgcccc accgtcccc tgtcgcacat tcctccctcc gcagggctgg ctcaccaggc  1320
cccagcccac atgcctgctt aaagccctct ccatcctctg cctcacccag tccccgctga  1380
gactgagcag acgcctccag cggccgcccg ccaccatggc tgagaaagag tcaacatcac  1440
cacacctcat ggttcccatt cttctcctgg ttggatggat tgtaggctgc atcatcgtta  1500
tttacattgt cttcttctaa aagctttgga tccaatcaac ctctggatta caaaatttgt  1560
gaaagattga ctggtattct taactatgtt gctccttta cgctatgtgg atacgctgct  1620
ttaatgcctt tgtatcatgc tattgcttcc cgtatggctt tcatttttct ctccttgtat  1680
aaatcctggt tgctgtctct ttatgaggag ttgtggcccg ttgtcaggca acgtggcgtg  1740
gtgtgcactg tgtttgctga cgcaaccccc actggttggg gcattgccac cacctgtcag  1800
ctcctttccg ggactttcgc tttccccctc cctattgcca cggcggaact catcgccgcc  1860
tgccttgccc gctgctggac aggggctcgg ctgttgggca ctgacaattc cgtggtgttg  1920
tcggggaaat catcgtcctt tccttggctg ctcgcctgtg ttgccacctg gattctgcgc  1980
gggacgtcct tctgctacgt cccttcggcc ctcaatccag cggaccttcc ttcccgcggc  2040
ctgctgccgg ctctgcggcc tcttccgcgt cttcgagatc tgcctcgact gtgccttcta  2100
gttgccagcc atctgttgtt tgcccctccc cgtgccttcc ttgaccctg gaaggtgcca  2160
ctcccactgt ccttttcctaa taaaatgagg aaattgcatc gcattgtctg agtaggtgtc  2220
attctattct gggggtggg gtggggcagg acagcaaggg gaaggattgg gaagacaata  2280
gcaggcatgc tggggactcg agttaagggc gaattcccga ttaggatctt cctagagcat  2340
ggctacgtag ataagtagca tggcgggtta atcattaact acaaggaacc cctagtgatg  2400
gagttggcca ctccctctct gcgcgctcgc tcgctcactg aggccgggcg accaaaggtc  2460
gcccgacgcc cgggctttgc ccgggcggcc tcagtgagcg agcgagcgcg cag          2513
```

| SEQ ID NO: 47 | moltype = DNA length = 2110 |
|---|---|
| FEATURE | Location/Qualifiers |
| misc_feature | 1..2110 |
| | note = Recombinant expression cassette or expression cassette component |
| source | 1..2110 |
| | mol_type = other DNA |
| | organism = synthetic construct |

SEQUENCE: 47

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattcgccc ttaagccttc agattaaaaa taactaaggt aagggccatg   240
tgggtagggg aggtggtgtg agacggtcct gtctctcctc tatctgccca tcggcccttt   300
ggggaggagg aatgtgccca aggactaaaa aaggccctg gagccagagg ggcgagggca   360
gcagaccttt catgggcaaa cctcagggct gctgtgtca tggagaagac ccaccttgca   420
gatgtcctca ctgggctgg cagagccggc aacctgccta aggctgctca gtccattagg   480
agccagtagc ctggaagatg tctttacccc cagcatcagt tcaagtggag cagcacataa   540
ctcttgccct ctgccttcca agattctggt gctgagactt atggagtgtc ttggaggttg   600
ccttctgccc caaccctg ctcccagctg gccctccag gctgggttg ctggcctcat   660
ctttatcagg attctcaaga gggacagctg gtttatgttg catgactgtt ccctgcatat   720
ctgctctggt tttaaatagc ttatctgagc agctggagga ccacatggc ttatatggcg   780
tgggtacat gttcctgtag ccttgtccct ggcacctgcc aaaatagcag ccaacacccc   840
ccaccccac cgccatcccc ctgccccacc cgtccctgt cgcacattcc tcctccgca   900
gggctggctc accaggcccc agcccacatg cctgcttaaa gccctctcca tcctctgcct   960
cacccagtcc ccgctgagac tgagcagacg cctccagccg ccgccaatgg ctgagaaaga  1020
gaaagagtca acatcaccac acctcatggt tccattctt ctcctggttg atgaattg   1080
aggctgcatc atcgttattt acattgtctt ctttaaag ctttggatcc aatcaacctc  1140
tggattacaa aatttgtgaa agattgactg gtattcttaa ctatgttgct ccttttacgc  1200
tatgtggata cgctgcttta atgcctttgt atcatgctat tgcttcccgt atggctttca  1260
ttttctcctc cttgtataaa tcctggttgc tgtctcttta tgaggagttg tggcccgttg  1320
```

```
tcaggcaacg tggcgtggtg tgcactgtgt ttgctgacgc aacccccact ggttggggca    1380
ttgccaccac ctgtcagctc ctttccggga ctttcgcttt ccccctccct attgccacgg    1440
cggaactcat cgccgcctgc cttgcccgct gctggacagg ggctcggctg ttgggcactg    1500
acaattccgt ggtgttgtcg gggaaatcat cgtcctttcc ttggctgctc gcctgtgttg    1560
ccacctggat tctgcgcggg acgtccttct gctacgtccc ttcggccctc aatccagcgg    1620
accttccttc ccgcggcctg ctgccggctc tgcggcctct tccgcgtctt cgagatctgc    1680
ctcgactgtg ccttctagtt gccagccatc tgttgtttgc ccctccccg tgccttcctt     1740
gaccctggaa ggtgccactc ccactgtcct ttcctaataa aatgaggaaa ttgcatcgca    1800
ttgtctgagt aggtgtcatt ctattctggg gggtgggtg gggcaggaca gcaagggga     1860
ggattggaa gacaatagca ggcatgctgg ggactcgagt taagggcgaa ttcccgatta    1920
ggatcttcct agagcatggc tacgtagata agtagcatgg cgggttaatc attaactaca    1980
aggaacccct agtgatggag ttggccactc cctctctgcg cgctcgctcg ctcactgagg    2040
ccgggcgacc aaaggtcgcc cgacgcccgg gctttgcccg ggcggcctca gtgagcgagc    2100
gagcgcgcag                                                           2110

SEQ ID NO: 48           moltype = DNA  length = 2513
FEATURE                 Location/Qualifiers
misc_feature            1..2513
                        note = Recombinant expression cassette or expression
                        cassette component
source                  1..2513
                        mol_type = other DNA
                        organism = synthetic construct
SEQUENCE: 48
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagccttc agattaaaaa taactaaggt aagggccatg    240
tgggtagggg aggtggtgtg agacggtcct gtctctcctc tatctgccca tcggcccttt    300
ggggaggagg aatgtgccca aggactaaaa aaaggccctg gagccagagg ggcgagggca    360
gcagaccttt catgggcaaa cctcagggct gctgtcaact ggcctgcccg agaccaaacg    420
tgcggaacgt agttaagtgt tagaggtagg atttgaagcc tgtcgatcat tctgattctc    480
cttttctcta cgtctgcttc ctgtcaatgg gcatcctcac tgtcaaatgc agatggtaca    540
gcagggcttg gtctcagcca ggcaggcctc tccccagtct ccatggctca gctgtccagc    600
agtttcatcc ctagaccatc ccaaacatgt tgagaagct ctgaggggag gacccagcac     660
tgcccggccc ctgaagataa tcagcagtcc tgctcagcat atcaatccaa gcccactcta    720
gacagagatg ccggtgccca gttttctatt tttaactggt gtgaactgaa ggaaaagcac    780
agcattagaa gtcaagcag tcatggagaa gacccacctt gcagatgtcc tcactggggc     840
tggcagagcc ggcaacctgc ctaaggctgc tcagtccatt aggagccagt agctggaag    900
atgtctttac ccccagcatc agttcaagtg gagcagcaca taactcttgc cctctgcctt    960
ccaagattct ggtgctgaga cttatggagt gtcttggagg ttgcctttctg ccccccaacc   1020
ctgctcccag ctggccctcc caggcctggg ttgctggcct ctgctttatc aggattctca    1080
agagggacag ctggtttatg ttgcatgact gttccctgca tatctgctct ggttttaaat    1140
agcttatctg agcagctgga ggaccacatg gcttatatg gcgtggggta catgttcctg     1200
tagccttgtc cctggcacct gcaaaatag cagccaacac ccccccaccccc caccgccatc    1260
ccctgcccc accccgtcccc tgtcgcacat tcctccctcc gcagggctgg ctcaccaggc    1320
cccagccac atgcctgctt aaagcccctct ccatcctccg cctcaccccag tccccgctga    1380
gactgagcag acgcctccag cggccgcccg ccaccatggc tgagaaagag tcaacatcac    1440
cacacctcat ggttcccatt cttctcctgg ttggatggat tgtaggctgc atcatcgtta    1500
tttacattgt cttcttctaa aagctttgga tccaatcaac ctctggatta caaaatttgt    1560
gaaagattga ctggtattct taactatgtt gctccttta cgctatgtgg atacgctgct     1620
ttaatgcctt tgtatcatgc tattgcttcc cgtatggctt tcattttctc ctccttgtat    1680
aaatcctggt tgctgtctct ttatgaggag ttgtggcccg ttgtcaggca acgtggcgtg    1740
gtgtgcactg tgtttgctga cgcaaccccc actggttggg gcattgccac cacctgtcag    1800
ctccttccg ggactttcgc tttccccctc cctattgcca cggcggaact catcgccgcc     1860
tgccttgccc gctgctggac aggggctcgg ctgttgggca ctgacaattc cgtggtgttg    1920
tcggggaaat catcgtcctt tccttggctg ctcgcctgtg ttgccacctg gattctgcgc    1980
gggacgtcct tctgctacgt cccttcggcc ctcaatccag cggaccttcc ttcccgcggc    2040
ctgctgccgg ctctgcggcc tcttccgcgt cttcgagatc tgcctcgact gtgccttcta    2100
gttgccagcc atctgttgtt tgcccctccc ccgtgccttc cttgaccctg gaaggtgcca    2160
ctcccactgt cctttcctaa taaaatgagg aaattgcatc gcattgtctg agtaggtgtc    2220
attctattct gggggtggg gtggggcagg acagcaaggg ggaggattgg gaagacaata    2280
gcaggcatgc tggggactcg agttaagggc gaattcccga ttaggatctt cctagagcat    2340
ggctacgtag ataagtagca tggcgggtta atcattaact acaaggaacc ctagtgatgg    2400
gagttggcca ctccctctct gcgcgctcgc tcgctcactg aggccgggcg accaaaggtc    2460
gcccgacgcc cgggctttgc ccgggcggcc tcagtgagcg agcgagcgcg cag           2513

SEQ ID NO: 49           moltype = DNA  length = 2691
FEATURE                 Location/Qualifiers
misc_feature            1..2691
                        note = Recombinant expression cassette or expression
                        cassette component
source                  1..2691
                        mol_type = other DNA
                        organism = synthetic construct
SEQUENCE: 49
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact    120
agggggttcct tgtagttaat gattaacccg ccatgctact tatctacgta gccatgctct   180
```

```
aggaagatcg gaattcgccc ttaagccttc agattaaaaa taactaaggt aagggccatg   240
tgggtagggg aggtggtgtg agacggtcct gtctctcctc tatctgccca tcggcccttt   300
ggggaggagg aatgtgccca aggactaaaa aaaggccctg gagccagagg ggcgagggca   360
gcagaccttt catgggcaaa cctcaggggt gctgtcaact ggcctgcccg agaccaaacg   420
tgccgaacgt agttaagtgt tagaggtagg atttgaagcc tgtcgatcat tctgattctc   480
cttttctcta cgtctgcttc ctgtcaatgc gcatcctcac tgtcaaatgc agatggtaca   540
gcagggcttg gtctcagcca ggcaggcctc tccccagtct ccatggctca gctgtccagc   600
agtttcatcc ctagaccatc ccaaacatgg ttgagaagct ctgaggggag gacccagcac   660
tgcccggccc ctgaagataa tcagcagtcc tgctcagcat atcaatccaa gcccactcta   720
gacagagatg ccggtgccca gttttctatt tttaactggt gtgaactgaa ggaaaagcac   780
agcattagaa gtccaagcag tcatggagaa gacccacctt gcagatgtcc tcactgggc    840
tggcagagcc ggcaacctgc ctaaggctgc tcagtccatt aggagccagt agcctggaag   900
atgtctttac ccccagcatc agttcaagtg gagcagcaca taactcttgc cctctgcctt   960
ccaagattct ggtgctgaga cttatggagt gtcttggagg ttgccttctg ccccccaacc  1020
ctgctcccag ctggccctcc caggcctggg ttgctggcct ctgctttatc aggattctca  1080
agagggacag ctggtttatg ttgcatgact gttccctgca tatctgctct ggttttaaat  1140
agcttatctg agcagctgga ggaccacatg ggcttatatg gcgtgggta catgttcctg  1200
tagccttgtc cctggcacct gccaaaatag cagccaacac ccccaccccc caccgccatc  1260
ccctgcccc acccgtcccc tgtcgcacat tcctccctcc gcagggctgg ctcaccaggc  1320
cccagcccac atgcctgctt aaagccctct ccatcctctg cctcacccag tccccgctga  1380
gactgagcag acgcctccat aactggtaag taccgcctat agactctata ggcacacccc  1440
tttggctctt atgcatgctg acagactaac agactgttcc tttcctgggt cttttctgtt  1500
ggcctgtacg gaagtgttac ttctgctcta aaagctgcgg aattgtaccc cggccgatc   1560
caatcgatac agatctagcg gccgccgcc accatggctg agaaagagtc aacatcacca  1620
cacctcatgg ttcccattct tctcctggtt ggatggattg taggctgcat catcgttatt  1680
tacattgtct tcttctaaaa gctttggatc caatcaacct ctgattaca aaatttgtga   1740
aagattgact ggtattctta actatgttgc tcctttacg ctatgtggat acgctgcttt   1800
aatgcctttg tatcatgcta ttgcttcccg tatggctttc attttctcct ccttgtataa  1860
atcctggttg ctgtctcttt atgaggagtt gtggcccgtt gtcaggcaac gtggcgtggt  1920
gtgcactgtg tttgctgacg cacccccac tggttgggc attgccacca cctgtcagct  1980
cctttccggg actttcgctt tccccctccc tattgccacg gcggaactca tcgccgctg   2040
ccttgccccgc tgctggacag gggctcggct gttgggcact gacaattccg tggtgttgtc  2100
ggggaaatca tcgtcctttc cttggctgct cgcctgtgtt gccacctgga ttctgcgcgg  2160
gacgtccttc tcctacgtcc cttcggccct caatccagcg gaccttcctt cccgcggcct  2220
gctgccggct ctgcgggctc ttccggtct tcgagatctg cctcgactgt gccttctagt  2280
tgccagccat ctgttgtttg cccctccccc gtgccttcct tgaccctgga aggtgccact  2340
cccactgtcc tttcctaata aaatgaggaa attgcatcgc attgtctgag taggtgtcat  2400
tctattctgg ggggtgggt ggggcaggac agcaaggggg aggattggga agacaatagc   2460
aggcatgctg gggactcgag ttaagggcga attcccgatt aggatcttcc tagagcatgg  2520
ctacgtagat aagtagcatg gcgggttaat cattaactac aaggaacccc tagtgatgga  2580
gttggccact ccctctctgc gcgctcgctc gctcactgag gccgggcgac caaaggtcgc  2640
ccgacgcccg ggctttgccc gggcggcctc agtgagcgag cgagcgcgca g           2691
```

| SEQ ID NO: 50 | moltype = DNA   length = 2097 |
|---|---|
| FEATURE | Location/Qualifiers |
| misc_feature | 1..2097 |
| | note = Recombinant expression cassette or expression cassette component |
| source | 1..2097 |
| | mol_type = other DNA |
| | organism = synthetic construct |

SEQUENCE: 50
```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctgtaca gtcatgctct   180
aggaagatcg gaattcgccc ttaaggtcat ggagaagacc caccttgcag atgtcctcac   240
tggggctggc agagccggca acctgcctaa ggctgctcag tccattagga gccagtagcc   300
tggaagatgt ctttaccccc agcatcagtt caagtggagc agcacataac tcttgccctc   360
tgccttccaa gattctggtg ctgagactta tggagtgtct tggaggttgc cttctgcag    420
ccaaccctgc tcccagctgg ccctcccagg cctgggttgc tggcctctgc tttatcagga   480
ttctcaagag ggacagctgg tttatgttgc atgactgttc cctgcatatc tgctctggtt   540
ttaaatagct tatctgagca gctggaggac cacatgggct tatatggcgt ggggtacatg   600
ttcctgtagc cttgtcctg gcacctgcca aaatagcagc caacaccccc caccccccacc  660
gccatcccc tgccccaccc gtccctgtc gcacattccc tccgcggtcg gcctcca       720
ccaggcccca gcccacatgc ctgcttaaag ccctctccat cctctgcctc acccagtccc   780
cgctgagact gagcagacgc ctccataact ggtaagtacc gcctatagac tctataggca   840
caccccttg gctcttatgc atgctgacag actaacagac tgttcctttc tgggtctttt   900
tctgcaggcc tgtacggaag tgttacttct gctctaaaag ctgcggaatt gtacccgcgg   960
ccgatccaat cgatacagat ctagcggccg ccgccacca tggctgagaa agagtcaaca  1020
tcaccacacc tcatggttcc cattcttctc ctggttggat ggattgtagg ctgcatcatc  1080
gttatttaca ttgtcttctt ctaaaagctt tggatccaat caacctctgg attacaaaat  1140
ttgtgaaaga ttgactggta ttcttaacta tgttgctcct tttacgctat gtggatacgc  1200
tgctttaatg cctttgtatc atgctattgc ttcccgtatg gctttcattt tctcctcctt  1260
gtataaatcc tggttgctgt ctctttatga ggagttgtgg cccgttgtca ggcaacgtgg  1320
cgtggtgtgc actgtgtttg ctgacgcaac cccccactgg ttggggcattg ccaccacctg  1380
tcagctcctt tccgggactt tcgctttccc cctccctatt gccacggcgg aactcatcgc  1440
cgcctgcctt gcccgctgct ggacaggggc tcggctgttg ggcactgaca attccgtggt  1500
gttgtcgggg aaatcatcgt cctttccttg gctgctcgcc tgtgttgcca cctggattct  1560
gcgcgggacg tccttctgct acgtcccttc ggccctcaat ccagcggacc ttccttcccg  1620
```

```
cggcctgctg ccggctctgc ggcctcttcc gcgtcttcga gatctgcctc gactgtgcct   1680
tctagttgcc agccatctgt tgtttgcccc tccccgtgc cttccttgac cctggaaggt    1740
gccactccca ctgtcctttc ctaataaaat gaggaaattg catcgcattg tctgagtagg   1800
tgtcattcta ttctgggggg tggggtgggg caggacagca aggggagga ttgggaagac    1860
aatagcaggc atgctgggga ctcgagttaa gggcgaattc ccgattagga tcttcctaga   1920
gcatggctac gtagataagt agcatgcgcg gttaatcatt aactacaagg aacccctagt   1980
gatggagttg gccactccct ctctgcgcgc tcgctcgctc actgaggccg ggcgaccaaa   2040
ggtcgcccga cgcccgggct tgcccgggc ggcctcagtg agcgagcgag cgcgcag       2097
```

```
SEQ ID NO: 51          moltype = DNA   length = 2691
FEATURE                Location/Qualifiers
misc_feature           1..2691
                       note = Recombinant expression cassette or expression
                       cassette component
source                 1..2691
                       mol_type = other DNA
                       organism = synthetic construct
SEQUENCE: 51
ctgcgcgctc gctcgctcac tgaggccgcc cgggcaaagc ccgggcgtcg ggcgacccttt   60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattcgccc ttaagaactg gcctgcccga gaccaaacgt gcggaacgta   240
gttaagtgtt agaggtagga tttgaagcct gtcgatcatt ctgattctcc ttttctctac   300
gtctgcttcc tgtcaatggg catcctcact gtcaaatgca gatggtacag cagggcttgg   360
tctcagccag gcaggcctct ccccagtctc catggctcag ctgtccagca gtttcatccc   420
tagaccatcc caaacatggt tgagaagctc tgaggggagg acccagcact gcccagccca   480
tgaagataat cagcagtcct gctcagcata tcaatccaag cccactctag acagagatgc   540
cggtgcccag tttctatttt ttaactggtg tgaactgaag gaaaagcaca gcattagaag   600
tccaagcacc ttcagattaa aaataactaa ggtaagggcc atgtgggtag gggaggtggt   660
gtgagacggt cctgtctctc ctctatctgc ccatcgccc tttggggagg aggaatgtgc     720
ccaaggacta aaaaaaggcc ctggagccag aggggcgagg gcagcagacc tttcatgggc   780
aaacctcagg gctgctgtcg tcatggagaa gacccacctt gcagatgtcc tcactggggc   840
tggcagagcc ggcaacctgc ctaaggctgc tcagtccatt aggagccagt agcctggaag   900
atgtctttac ccccagcatc agttcaagtg gagcagcaca taactcttgc cctctgcctt   960
ccaagattct ggtgctgaga cttatggagt gtcttggagg ttgccttctg cccccaacc   1020
ctgctcccag ctggccctcc caggcctggg ttgctggcct ctgctttatc aggattctca   1080
agagggacag ctggtttatg ttgcatgact gttccctgca tatctgctct ggttttaaat   1140
agcttatctg agcagctgga ggaccacatg ggcttatatg gcgtgggta catgttcctg    1200
tagcctgtc cctggcacct gccaaaatag cagccacacc ccccacccc accgccatc     1260
cccctgcccc acccgtcccc tgtcgcacat tcctccctcc gcagggctgg ctcaccaggc   1320
cccagcccac atgcctgctt aaagccctct ccatctctg cctcacccag tccccgctga    1380
gactgagcag acgcctccat aactggtaag taccgcctat agactctata ggcacacccc   1440
tttggctctt atgcatgctg acagactaac agactgttcc tttctgggt cttttctgca    1500
ggcctgtacg gaagtgttac ttctgctcta aaagctgcgg aattgtaccc gcggccgatc   1560
caatcgatac agatctagcg gccgcccgcc accatggccg agaaggaatc taccagcccc   1620
cacctgatgg tgcctattct gctgctggtg ggctggatcg tcggctgcat catcgtgatc   1680
tacatcgtgt tcttctgaaa gctttggatc caatcaacct ctggattaca aaatttgtga   1740
aagattgact ggtattctta actatgttgc tccttttacg ctatgtggat acgctgcttt   1800
aatgcctttg tatcatgcta ttgcttcccg tatggctttc attttctcct ccttgtataa   1860
atcctggttg ctgtctcttt atgaggagtt gtggcccgtt gtcaggcaac gtggcgtggt   1920
gtgcactgtg tttgctgacg caaccccac tggttgggca attgccacca cctgtcagtc   1980
ccttccggg actttcgctt tccccctccc tattgccacg gcggaactca tcgccgcctg   2040
ccttgcccgc tgctggacag gggctcggct gttgggcact gacaattccg tggtgttgtc   2100
ggggaaatca tcgtcctttc cttggctgct cgcctgtgtt gccacctgga ttctgcgcgg   2160
gacgtcctc tgctacgtcc cttcggccct caatccagcg gaccttcctt ccgcggcct    2220
gctgccggct ctgcggcctc ttccgcgtct tcgagatctg cctcgactgt gccttctagt   2280
tgccagccat ctgttgtttg ccccctcccc gtgccttcct tgaccctgga aggtgccact   2340
cccactgtcc tttcctaata aaatgaggaa attgcatcgc attgtctgag taggtgtcat   2400
tctattctgg ggggtgggt ggggcaggac agcaagggg aggattggga agacaatagc    2460
aggcatgctg gggactcgag ttaagggcga attcccgatt ggatcttcc tagagcatgg   2520
ctacgtagat aagtagcatg gcgggttaat cattaactac aaggaacccc tagtgatgga   2580
gttggccact ccctctctgc gcgctcgctc gctcactgag gccgggcgac caaaggtcgc   2640
ccgacgcccg gctttgccc gggcggcctc agtgagcgag cgagcgcgca g             2691
```

```
SEQ ID NO: 52          moltype = DNA   length = 2500
FEATURE                Location/Qualifiers
misc_feature           1..2500
                       note = Recombinant expression cassette or expression
                       cassette component
source                 1..2500
                       mol_type = other DNA
                       organism = synthetic construct
SEQUENCE: 52
ctgcgcgctc gctcgctcac tgaggccgcc cgggcaaagc ccgggcgtcg ggcgacccttt   60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattcgccc ttaagaactg gcctgcccga gaccaaacgt gcggaacgta   240
gttaagtgtt agaggtagga tttgaagcct gtcgatcatt ctgattctcc ttttctctac   300
gtctgcttcc tgtcaatggg catcctcact gtcaaatgca gatggtacag cagggcttgg   360
```

```
tctcagccag gcaggcctct ccccagtctc catggctcag ctgtccagca gtttcatccc    420
tagaccatcc caaacatggt tgagaagctc tgagggagg acccagcact gcccggcccc     480
tgaagataat cagcagtcct gctcagcata tcaatccaag cccactctag acagagatgc    540
cggtgcccga ttttctattt ttaactggtg tgaactgaag gaaaagcaca gcattagaag    600
tccaagcagt catggagaag acccaccttg cagatgtcct cactggggct gcagagccg     660
gcaacctgcc taaggctgct cagtccatta ggagccagta gcctggaaga tgtctttacc    720
cccagcatca gttcaagtgg agcagcacat aactcttgcc ctctgccttc caagattctg    780
gtgctgagac ttatggagtg tcttggaggt tgccttctgc cccccaaccc tgctcccagc    840
tggccctccc aggcctgggt tgctggcctc tgctttatca ggattctcaa gagggacagg    900
tggtttatgt tgcatgactg ttccctgcat atctgctctg gttttaaata gcttatctga    960
gcagctggag gaccacatgg gcttatatgg cgtggggtac atgttcctgt agccttgtcc    1020
ctggcacctg ccaaaatagc agccaacacc ccccacccc accgcatcc ccctgcccca     1080
cccgtcccct gtcgcacatt cctccctccg cagggctggc tcaccaggcc cagcccaca    1140
tgcctgctta aagccctctc catcctctgc ctcacccgat ccccgctgag actgagcaga   1200
cgcctccata actggtaagt accgcctata gactctatag gcacacccct ttggctctta   1260
tgcatgctga cagactaaca gactgttcct ttcctgggtc ttttctgcag gcctgtacgg   1320
aagtgttact tctgctctaa aagctgcgga attgtacccg cggccgatcc aatcgataca   1380
gatctagcgg ccgccccgcca ccatggctga gaaagagtca acatcaccac acctcatggt   1440
tcccattctt ctcctggttg gatggattgt aggctgcatc atcgttattt acattgtctt   1500
cttctaaaaag ctttggatcc aatcaacctc tggattacaa aatttgtgaa agattgactg   1560
gtattcttaa ctatgttgct cctttacgc tatgtggata cgctgcttta atgcctttgt   1620
atcatgctat tgcttcccgt atggctttca ttttctcctc cttgtataaa tcctggttgc   1680
tgtctcttta tgaggagttg tggcccgttg tcaggcaacg tggcgtggtg tgcactgtgt   1740
ttgctgacgc aacccccact ggttggggca ttgccaccac ctgtcagctc ctttccggga   1800
cttcgcttt cccctccct attgccacgg cggaactcat cgccgcctgc cttgcccgct    1860
gctgacagg ggctcggctg ttgggcactg acaattcgct ggtgttgtcg gggaaatcat   1920
cgtcctttcc ttggctgctc gcctgtgttg ccacctggat tctgcgcggg acgtcttcc    1980
gctacgtccc ttcggccctc aatccagcgg accttccttc ccgcggcctg ctgccggctc   2040
tgcggcctct tccgcgtctt cgagatctgc ctcgactgtg ccttctagtt gccagccatc   2100
tgttgtttgc ccctccccg tgccttcctt gaccctggaa ggtgccactc ccactgtcct   2160
ttcctaataa aatgaggaaa ttgcatcgca ttgtctgagt aggtgtcatt ctattctggg   2220
gggtggggtg gggcaggaca gcaagggga ggattgggaa gacaatagca ggcatgctgg    2280
ggactcgagt taagggcgaa ttcccgatta ggatcttcct agagcatggc tacgtagata   2340
agtagcatgg cgggttaatc attaactaca aggaaccccc agtgatggag ttggccactc   2400
cctctctgcg cgctcgctcg ctcactgagg ccgggcgacc aaaggtcgcc cgacgcccgg   2460
gctttgcccg ggcggcctca gtgagcgagc gagcgcgcag                         2500
```

SEQ ID NO: 53              moltype = DNA  length = 2288
FEATURE                  Location/Qualifiers
misc_feature        1..2288
                       note = Recombinant expression cassette or expression
                       cassette component
source                1..2288
                       mol_type = other DNA
                       organism = synthetic construct
SEQUENCE: 53

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagccttc agattaaaaa taactaaggt aagggccatg    240
tgggtagggg aggtggtgtg agacggtcct gtctctcctc tatctgccca tcggccctt     300
ggggaggagg aatgtgccca aggactaaaa aaaggccctg gagccagagg ggcgagggca    360
gcagaccttt catgggcaaa cctcagggct gctgtcgtca tggagaagac ccaccttgca    420
gatgtcctca ctgggctgg cagagccggc aacctgccta aggctgctca gtccattagg    480
agccagtagc ctggaagatg tctttacccc cagcatcagt tcaagtggag cagcacataa    540
ctcttgccct ctgccttcca agattctggt gctgagactt atggagtgtc ttggaggttg    600
ccttctgccc cccaaccctg ctcccagctg gccctccag gcctgggttg ctggcctctg    660
ctttatcagg attctcaaga gggacagctg gtttatgttg catgactgtt ccctgcatat    720
ctgctctggt ttttaaatagc ttatctgagc agctggagga ccacatgggc ttatatggc    780
tggggtacat gttcctgtag ccttgtccct ggcacctgcc aaaatagcca acacccc      840
ccaccccac cgcatcccc ctgccccacc cgtccctgt cgcacattcc tccctccgca     900
gggctggctc accaggcccc agccacatg cctgcttaaa gccctctcca tcctctgcct    960
cacccagtcc ccgctgagac tgagcagacg cctccataac tggtaagtac cgcctataga   1020
ctctataggc acacccctt ggctcttatg catgctgaca gactaacaga ctgttccttt   1080
cctgggtctt ttctgcaggc ctgtacgaa gtgttacttc tgctctaaaa gctgcggaat   1140
tgtacccgcg gccgatccaa tcgatacaga tctagcggcc gccgccacc atggctgaga   1200
aagagtcaac atcaccacac tcatggttc cattcttct cctggttgga tggattgtag   1260
gctgcatcat cgttatttac attgtcttct ctaaaagctt tggatccaat caacctctg   1320
gattacaaaa tttgtgaaag attgactggt attcttaact atgttgctcc ttttacgcta   1380
tgtggatacg ctgctttaat gcctttgtat catgctattg cttcccgtat ggctttcatt   1440
ttctcctcct tgtataaatc ctggttgctg tctctttatg aggagttgtg gcccgttgtc   1500
aggcaacgtg gcgtggtgtg cactgtgttt gctgacgcaa ccccactgg ttggggcatt   1560
gccaccacct gtcagctcct ttccgggact ttcgctttcc ccctccctat tgccacggcg   1620
gaactcatcg ccgcctgcct tgcccgctgc tggacaggg gctcggctgt tgggcactga   1680
caattccgtgg tgttgtcggg gaaatcatcg tcctttcctt ggctgctcgc ctgtgttgcc   1740
acctggattc tgcgcgggac gtccttctgc tacgtccctt cggccctcaa tccagcggac   1800
cttccttccc gcggcctgct gccggctctg cggcctcttc cgcgtcttcg agatctgcct   1860
cgactgtgcc ttctagttgc cagccatctg ttgtttgccc ctccccgtgc cttccttga   1920
ccctggaagg tgccactccc actgtccttt cctaataaaa tgaggaaatt gcatcgcatt   1980
```

```
gtctgagtag gtgtcattct attctggggg gtggggtggg gcaggacagc aaggggggagg    2040
attgggaaga caatagcagg catgctgggg actcgagtta agggcgaatt cccgattagg    2100
atcttcctag agcatggcta cgtagataag tagcatggcg ggttaatcat taactacaag    2160
gaaccccctag tgatggagtt ggccactccc tctctgcgcg ctcgctcgct cactgaggcc    2220
gggcgaccaa aggtcgcccg acgcccgggc tttgcccggg cggcctcagt gagcgagcga    2280
gcgcgcag                                                               2288

SEQ ID NO: 54           moltype = DNA  length = 1919
FEATURE                 Location/Qualifiers
misc_feature            1..1919
                        note = Recombinant expression cassette or expression
                         cassette component
source                  1..1919
                        mol_type = other DNA
                        organism = synthetic construct
SEQUENCE: 54
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaaggtcat ggagaagacc caccttgcag atgtcctcac    240
tggggctggc agagccggca acctgcctaa ggctgctcag tccattagga gccagtagcc    300
tggaagatgt ctttacccc agcatcagtt caagtggagc agcacataac tcttgccctc    360
tgccttccaa gattctggtg ctgagactta tggagtgtct tggaggttgc cttctgcccc    420
ccaaccctgc tcccagctgg ccctcccagg cctgggttgc tggcctctgc tttatcagga    480
ttctcaagag ggacagctgg tttatgttgc atgactgttc cctgcatatc tgctctggtt    540
ttaaatagct tatctgagca gctgaggac cacatggcct tatatggcgt ggggtacatg    600
ttcctgtagc cttgtccctg gcacctgcca aaatagcagc caacaccccc caccccccacc    660
gccatccccc tgccccaccc gtccctgt gcacattcct ccctccgcag ggctggctca    720
ccaggcccca gcccacatgc ctgcttaaag ccctctccat cctctgcctc acccagtccc    780
cgctgagact gagcagacgc ctccagcggc cgcccgcca catggccgag aaggaatcta    840
ccagcccccca cctgatggtg cctattctgc tgctggtggg ctggatccgtc ggctgcatca    900
tcgtgatcta catcgtgttc ttctgaaagc tttggatcca atcaacctct ggattacaaa    960
atttgtgaaa gattgactgg tattcttaac tatgttgctc cttttacgct atgtggatac   1020
gctgctttaa tgcctttgta tcatgctatt gcttcccgta tggcttttcat tttctcctcc   1080
ttgtataaat cctggttgct gtctcttttat gaggagttgt ggccgttgt caggcaacgt    1140
ggcgtggtgt gcactgtgtt tgctgacgca accccactg gttggggcat tgccaccacc    1200
tgtcagctcc tttccgggac ttttcgcttc ccctccccta ttgccacggc ggaactcatc   1260
gccgcctgcc ttgcccgctg ctggacaggg gctcggctgt tgggcactga caattccgtg   1320
gtgttgtcgg ggaaatcatc gtcctttcct tggctgctcg cctgtgttgc cacctggatt   1380
ctgcgcggga cgtccttctg ctacgtccct tcgcccctca atccagcgga ccttccttcc   1440
cgcggcctgc tgccggctct gcggcctctt ccgcgtcttc gagatctgcc tcgactgtgc    1500
cttctagtta ccagccatct gttgtttgcc cctcccccgt gccttcctttg accctggaag   1560
gtgccactcc cactgtgcctt tcctaataaa atgaggaaat tgcatcgcat tgtctgagta   1620
ggtgtcattc tattctgggg ggtgggtggg gcaggacag caaggggggag gattgggaag   1680
acaatagcag gcatgctggg gactcgagtt aagggcgaat tcccgattag gatcttccta    1740
gagcatggct acgtagataa gtagcatggc gggttaatca ttaactacaa ggaaccccta   1800
tgatggagt tggccactcc ctctctgcgc gctcgctcgc tcactgaggc cgggcgacca   1860
aaggtcgccc gacgcccggg ctttgcccgg gcggcctcag tgagcgagcg agcgcgcag   1919

SEQ ID NO: 55           moltype = DNA  length = 3865
FEATURE                 Location/Qualifiers
misc_feature            1..3865
                        note = Recombinant expression cassette or expression
                         cassette component
source                  1..3865
                        mol_type = other DNA
                        organism = synthetic construct
SEQUENCE: 55
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagccttc agattaaaaa taactaaggt aagggcatg     240
tgggtagggg aggtggtgtg agacggtcct gtctctcctc tatctgccca tcggcccttt    300
ggggaggagg aatgtgccca aggactaaaa aaaggccctg aagccagagg ggcagggca    360
gcagaccttt catgggcaaa cctcagggct gctgtcgtca tggagaagac ccaccttgca    420
gatgtcctca ctggggctgg cagagccggc aacctgccta aggctgctca gtccattagg    480
agccagtagc ctggaagatg tctttacccc agcatcagt tcaagtggag cagcacataa    540
ctcttgccct ctgccttcca agattctggt gctgagactt atggagtgtc ttggaggttg    600
ccttctgccc cccaaccctg ctcccagctg gccctcccag gcctgggttg ctggcctctg    660
ctttatcagg attctcaaga gggacagctg gtttatgttg catgactgtt ccctgcatat    720
ctgctctggt tttaaatagc ttatctgagc agctggagga ccacatggcc ttatatggcg    780
tggggtacat gttcctgtag ccttgtccct ggcacctgcc aaaatagcag ccaacaccc    840
ccaccccccac cgcatcccc ctgccccacc gtccctgt gcacattcc tcctccgca      900
gggctggctc accaggccc agcccacatg cctgcttaaa gccctctcca tcctctgcct    960
cacccagtcc ccgctgagac tgagcagacg cctccataac tggtaagtac cgcctataga   1020
ctctataggc acacccctt ggctcttatg catgctgaca gactaacaga ctgttccttt   1080
cctgggtctt ttctgcaggc ctgtacgaa gtgttacttc tgctctaaaa gctgcggaat    1140
tgtacccgcg gccgatccaa tcgatacaga tctagcggcc gccgccacc atggctgaga    1200
aagagtcaac atcaccacac ctcatggttc ccattcttct cctggttgga tggattgtag   1260
```

```
gctgcatcat cgttatttac attgtcttct tctaaaagct ttggatccaa tcaacctctg  1320
gattacaaaa tttgtgaaag attgactggt attcttaact atgttgctcc ttttacgcta  1380
tgtggatacg ctgctttaat gcctttgtat catgctattg cttcccgtat ggctttcatt  1440
ttctcctcct tgtataaatc ctggttgctg tctctttatg aggagttgtg gcccgttgtc  1500
aggcaacgtg gcgtggtgtg cactgtgttt gctgacgcaa ccccccactgg ttggggcatt  1560
gccaccacct gtcagctcct ttccgggact ttcgctttcc ccctccctat tgccacggcg  1620
gaactcatcg ccgcctgcct tgcccgctgt ggacagggg ctcggctgtt gggcactgac  1680
aattccgtgg tgttgtcggg gaaatcatcg tcctttcctt ggctgctcgc ctgtgttgcc  1740
acctggattc tgcgcgggac gtccttctgc tacgtccctt cggccctcaa tccagcggac  1800
cttccttccc gcggcctgct gccggctctg cggcctcttc cgcgtcttcg agatctgcct  1860
cgactgtgcc ttctagttgc cagccatctg ttgtttgccc ctccccgtg ccttccttga  1920
ccctggaagg tgccactccc actgtccttt cctaataaaa tgaggaaatt gcatcgcatt  1980
gtctgagtag gtgtcattct attctggggg gtggggtggg gcaggacagc aaggggggagg  2040
attgggaaga caatagcagg catgctgggg actcgagtta agggcagcca gaagtcagat  2100
gctcaagggg cttcatgatg tccccataat ttttggcaga gggaaaaaga tcggatcctc  2160
aggcgtagtt caccccgtcc tcgaggccgc ccgggtcgac taaaaaaacct cccacacctc  2220
cccctgaacc tgaaacataa aatgaatgca attgttgttg ttaacttgtt tattgcagct  2280
tataatggtt acaaataaag caatagcatc acaaatttca caaataaagc attttttca  2340
ctgcattcta gttgtggttt gtccaaactc atcaatgtat cttatcatgt ctggatccgc  2400
gcggccgtca gaagaacacg atgtagatca cgatgatgca gccgacgatc cagcccacca  2460
gcagcagaat aggcaccatc aggtgggggc tggtagattc cttctcggcc atggtggcgg  2520
ctagcctata gtgagtcgta ttaagtactc tagccttaag agctgtaatt gaactgggag  2580
tggacacctg tggagagaaa ggcaaagtgg atgtcagtaa gaccaatagg tgcctatcag  2640
aaaacgaaga gtcttctctg tctcgacaag cccagtttct attggtctcc ttaaacctgt  2700
cttgtaacct tgatacttac ctgcccagtg cctcacgacc aacttctgca gcttaagttc  2760
gagactgttg tgtcagaagc aactgactgcg ttagcaattt aactgtgata aactaccgca  2820
ataaagctct agagcttcgg ggatcgtccc acgagcggt gggtgccggc ggctgtctgg  2880
gaagggctcc ttggggggca gaggctttaa ggtcccccg gcgcccaccc cggggcgggc  2940
agagccagca ggaatgtgcc cggcgcccag agaggaatgc aacacttgtg agctgctatt  3000
ttggcagcag cggcccggc cccctccgtg ctccccctc cccacagga gcccatataa  3060
gcccaagcta ttgtgtggcc tcagagtttt gctattttaa acccgtcgga cggagatacg  3120
tgagtgcccg aggggctgac acaagccagc cagctgtcac ctcccagggc tggggacgct  3180
gataaggcag cgcttcggac ccgacccctct gccgcagccc cagatgctgt catgtgaaag  3240
cccagactgc ttttatccct gcttggactt ctaatgctgt gcttttcctt cagttcacac  3300
cagttaaaaa tagaaaactg ggcaccggca tctctgtcta gagtgggctt ggattgtat  3360
gctgagcagg actgctgatt atcttcaggg gccgggcagt gctgggtcct ccctcagag  3420
cttctcaacc atgtttggga tggtctaggg atgaaactgc tggacagctg agccatggag  3480
actggggaga ggcctgcctg gctgagacca agccctgctg taccatctgc atttgacagt  3540
gaggatgccc attgacagga agcagacgta gagaaaagga gatcagaat gatcgacagg  3600
cttcaaatcc tacctctaac acttaactac gttccgcacg tttggtctcg ggcaggccag  3660
ttgaattccc gattaggatc ttcctagagc atggctacgt agataagtag catgcgcggt  3720
taatcattaa ctacaaggaa cccctagtga tggagttggc cactccctct ctgcgcgctc  3780
gctcgctcac tgaggccggg cgaccaaagg tcgcccgacg cccgggcttt gcccgggcgg  3840
cctcagtgag cgagcgagcg cgcag                                       3865

SEQ ID NO: 56           moltype = DNA  length = 3865
FEATURE                 Location/Qualifiers
misc_feature            1..3865
                        note = Recombinant expression cassette or expression
                        cassette component
source                  1..3865
                        mol_type = other DNA
                        organism = synthetic construct
SEQUENCE: 56
ctgcgcgctc gctcgctcac tgaggccgcc cgggcaaagc ccgggcgtcg ggcgaccttt   60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagccttc agattaaaaa taactaaggt aagggccatg  240
tgggtagggg aggtggtgtg agacggtcct gtctctcctc tatctgccca tcggccctt  300
ggggaggagg aatgtgccca aggactaaaa aaaggccctg gagccagagg ggcgagggca  360
gcagaccttt catgggcaaa cctcagggct gctgtcgtca tggagaagac ccaccttgca  420
gatgtcctca ctggggctgg cagagccggc aacctgccta aggctgctca gtccattagg  480
agccagtagc ctggaagatg tctttacccc cagcatcagt tcaagtggag cagcacataa  540
ctcttgccct ctgccttcca agattctggt gctgagactt atggagtgtc ttggaggttg  600
ccttctgccc cccaaccctg ctcccagctg gccctcccag gctgggttg ctggcctctg  660
cttatcagg attctcaaga gggacagctg gtttatgttg catgactgtt ccctgcatat  720
ctgctctggt tttaaatagc ttatctgagc agctggagga ccacatgggc ttatatggcg  780
tggggtacat gttcctgtag ccttgtccct ggcacctgcc aaaatagcag ccaacaccca  840
ccaccccac cgccatcccc ctgccccacc cgtccccgt cgcacattcc tccctctgcct  900
gggctggctc accaggcccc agccacatg cctgcttaaa gccctctcca tcctctgcct  960
cacccagtcc ccgctgagac tgagcagacg cctccataac tggtaagtac cgcctataga 1020
ctctataggc acaccccttt ggctcttatg catgctgaca gactaacaga ctgttccttt 1080
cctgggtctt ttctgcaggc ctgtacgaa gtgttacttc tgctctaaaa gctgcggaat 1140
tgtacccgcg ccgatccaa tcgatacaga tcagccgcc ggccgccaca atgcctgaga 1200
aagagtcaac atcaccacac ctcatggttc ccattcttct cctggttgga tggattgtag 1260
gctgcatcat cgttatttac attgtcttct tctaaaagct ttggatccaa tcaacctctg 1320
gattacaaaa tttgtgaaag attgactggt attcttaact atgttgctcc ttttacgcta 1380
tgtggatacg ctgctttaat gcctttgtat catgctattg cttcccgtat ggctttcatt 1440
ttctcctcct tgtataaatc ctggttgctg tctctttatg aggagttgtg gcccgttgtc 1500
```

| | | | | |
|---|---|---|---|---|
| aggcaacgtg | gcgtggtgtg | cactgtgttt | gctgacgcaa | ccccactgg ttggggcatt 1560 |
| gccaccacct | gtcagctcct | ttccgggact | ttcgctttcc | ccctcctat tgccacggcg 1620 |
| gaactcatcg | ccgcctgcct | tgcccgctgc | tggacagggg | ctcggctgtt gggcactgac 1680 |
| aattccgtgg | tgttgtcggg | gaaatcatcg | tcctttcctt | ggctgctcgc ctgtgttgcc 1740 |
| acctggattc | tgcgcgggac | gtccttctgc | tacgtccctt | cggccctcaa tccagcggac 1800 |
| cttccttccc | gcggcctgct | gccggctctg | cggcctcttc | cgcgtcttcg agatctgcct 1860 |
| cgactgtgcc | ttctagttgc | cagccatctg | ttgtttgccc | ctccccgtg ccttccttga 1920 |
| ccctggaagg | tgccactccc | actgtccttt | cctaataaaa | tgaggaaatt gcatcgcatt 1980 |
| gtctgagtag | gtgtcattct | attctggggg | gtggggtggg | gcaggacagc aaggggagg 2040 |
| attggaaga | caatagcagg | catgctgggg | actcgagtta | agggcagcca gaagtcagat 2100 |
| gctcaagggg | cttcatgatg | tccccataat | ttttggcaga | gggaaaaaga tcggatcctc 2160 |
| aggcgtagtt | caccccgtcc | tcgaggccgc | ccgggtcgac | taaaaaacct cccacacctc 2220 |
| cccctgaacc | tgaaacataa | aatgaatgca | attgttgttg | ttaaactggc ctgcccgaga 2280 |
| ccaaacgtgc | ggaacgtagt | taagtgttag | aggtaggatt | tgaagcctgt cgatcattct 2340 |
| gattctcctt | ttctctacgt | ctgcttcctg | tcaatgggca | tcctcactgt caaatgcaga 2400 |
| tggtacagca | gggcttggtc | tcagccaggc | aggcctctcc | ccagtctcca tggctcagct 2460 |
| gtccagcagt | ttcatcccta | gaccatccca | aacatggttg | agaagctctg aggggaggac 2520 |
| ccagcactgc | ccggccctg | aagataatca | gcagtcctgc | tcagcatatc aatccaagcc 2580 |
| cactctagac | agagatgccg | gtgcccagtt | ttctattttt | aactggtgtg aactgaagga 2640 |
| aaagcacagc | attagaagtc | caagcaggga | taaaagcagt | ctgggctttc acatgacagc 2700 |
| atctggggct | gcggcagagg | gtcgggtccg | aagcgctgcc | ttatcagcgt ccccagccct 2760 |
| gggaggtgac | agctggctgg | ctttgtgtcag | cccctcggtg | actcacgtat ctccgtccga 2820 |
| cgggtttaaa | atagcaaaac | tctgaggcca | cacaatagct | tgggcttata tgggctcctg 2880 |
| tgggggaagg | gggagcacgg | aggggccgg | ggccgctgct | gccaaaatag cagctcacaa 2940 |
| gtgttgcatt | cctctctggg | cgccgggcac | attcctgctg | gctctgcccg ccccggggtg 3000 |
| ggcgccgggg | ggaccttaaa | gcctctgccc | ccaaggagc | ccttcccaga cagccgccgg 3060 |
| cacccaccgc | tccgtgggac | gatccccgaa | gctctagagc | tttattgcgg tagtttatca 3120 |
| cagttaaatt | gctaacgcag | tcagtgcttc | tgacacaaca | gtctcgaact taagctgcag 3180 |
| aagttggtcg | tgaggcactg | gcaggtaag | tatcaaggtt | acaagacagg tttaaggaga 3240 |
| ccaatagaaa | ctgggcttgt | cgagacagag | aagactcttg | cgtttctgat aggcacctat 3300 |
| tggtcttact | gacatccact | ttgcctttct | ctccacaggt | gtccactccc agttcaatta 3360 |
| cagctcttaa | ggctagagta | cttaatacga | ctcactatag | gctagccgcc accatggccg 3420 |
| agaaggaatc | taccagcccc | cacctgatgg | tgccttattct | gctgctggtg ggctggatcg 3480 |
| tcggctgcat | catcgtgatc | tacatcgtgt | tcttctgacg | gccgcgcgga tccagacatg 3540 |
| ataagataca | ttgatgagtt | tggacaaacc | acaactgaca | tgcagtgaaa aaaatgcttt 3600 |
| atttgtgaaa | tttgtgatgc | tattgcttta | tttgtaacca | ttataagctg caataaacaa 3660 |
| gtgaattccc | gattaggatc | ttcctagagc | atggctacgt | agataagtag catggcgggt 3720 |
| taatcattaa | ctacaaggaa | ccccctagtga | tggagttggc | cactccctct ctgcgcgctc 3780 |
| gctcgctcac | tgaggccggg | cgaccaaagg | tcgcccgacg | cccgggcttt gcccgggcgg 3840 |
| cctcagtgag | cgagcgagcg | cgcag | | 3865 |

```
SEQ ID NO: 57           moltype = DNA  length = 3856
FEATURE                 Location/Qualifiers
misc_feature            1..3856
                        note = Recombinant expression cassette or expression
                         cassette component
source                  1..3856
                        mol_type = other DNA
                        organism = synthetic construct
SEQUENCE: 57
```

| | | | | |
|---|---|---|---|---|
| ctgcgcgctc | gctcgctcac | tgaggccgcc | cgggcaaagc | ccgggcgtcg ggcgaccttt 60 |
| ggtcgcccgg | cctcagtgag | cgagcgagcg | cgcagagagg | gagtggccaa ctccatcact 120 |
| aggggttcct | tgtagttaat | gattaacccg | ccatgctact | tatctacgta gccatgctct 180 |
| aggaagatcg | gaattctccc | cagcatgcct | gctattgtct | tcccaatcct ccccccttgct 240 |
| gtcctgcccc | accccaccc | ccagaataga | atgcaccta | ctcagacaat gcgatgcaat 300 |
| ttcctcattt | tattaggaaa | ggacagtggg | agtggcacct | tccagggtca aggaaggcac 360 |
| gggggagggg | caaacaacag | atggctgcca | actagaaggc | acagtcgagg cagatctcga 420 |
| agacgcggaa | gaggccgcag | agccggcagc | aggccgcggg | aaggaaggtc cgctggattg 480 |
| agggccgaag | ggacgtagca | gaaggacgtc | gaaggtggc | tccaggtggc aacacaggcg 540 |
| agcagccaag | gaaaggacga | tgatttcccc | gacaaccaca | cggaattgtc agtgcccaac 600 |
| agccgagccc | ctgtccagca | gcgggcaagg | caggcggcga | tgagttccgc cgtggcaata 660 |
| gggaggggga | aagcgaaagt | cccggaaagg | agctgacagg | tggtggcaat gcccaaccca 720 |
| gtgggggttg | cgtcagcaaa | cacagtgac | accacgccac | gttgcctgac aacgggccac 780 |
| aactcctcat | aaagagacag | caaccaggat | ttatacaagg | aaggaaaat gaaagccata 840 |
| cgggaagcaa | tagcatgata | caaaggcatt | aaagcagcgt | atccacatag cgtaaaagga 900 |
| gcaacatagt | taagaatacc | agtcaatctt | tcacaaattt | tgtaatccag aggttgattg 960 |
| gatccaaagc | ttttagaaga | agacaatgta | aataacgatg | atgcagccta caatccatcc 1020 |
| aaccaggaga | agaatgggaa | ccatgaggtg | tggtgatgtt | gactctttct cagccatggt 1080 |
| ggcgggtgac | cgctagatct | gtatcgattg | gatcggccgc | gggtacaatt ccgcagcttt 1140 |
| tagagcagaa | gtaacacttc | cgtacaggcc | tgcagaaaag | acccaggaaa ggaacagtct 1200 |
| gttagtctgt | cagcatgcat | aagagccaaa | gggtgtgcc | tatagagtct ataggcggta 1260 |
| cttaccagtt | atggaggcgt | ctgctcagtc | tcagcgggga | ctgggtgagg cagaggatgg 1320 |
| agagggcttt | aagcaggcat | gtgggctggg | gcctggtgag | ccagccctgc ggaggaagga 1380 |
| atgtgcgaca | ggggacgggt | ggggcagggg | gatggcgggg | gggtggggg gtgttggctg 1440 |
| ctatttttggc | aggtgccagg | gacaaggcta | caggaacatg | taccccacgc catataagcc 1500 |
| catgtggtcc | tccagctgct | cagataagct | atttaaaacc | agcagata tgcagggaac 1560 |
| agtcatgcaa | cataaaccag | ctgtccctct | tgagaatcct | gataaagcag aggccagcaa 1620 |
| cccaggcctg | ggagggccag | ctgggagcag | ggttgggggg | cagaaggcaa cctccaagac 1680 |
| actccataag | tctcagcacc | agaatcttgg | aaggcagagg | gcaagagtta tgtgctgctc 1740 |

```
cacttgaact gatgctgggg gtaaagacat cttccaggct actggctcct aatggactga   1800
gcagccttag gcaggttgcc ggctctgcca gccccagtga ggacatctgc aaggtgggtc   1860
ttctccatga cgacagcagc cctgaggttt gcccatgaaa ggtctgctgc cctcgcccct   1920
ctggctccag ggcctttttt tagtccttgg gcacattcct cctccccaaa gggccgatgg   1980
gcagatagag gagagacagg accgtctcac accacctccc ctacccacat ggcccttacc   2040
ttagttattt ttaatctgaa ggctcgagtt aagggcagcc agaagtcaga tgctcaaggg   2100
gcttcatgat gtccccataa ttttttggcag agggaaaaag atcggatcct caggcgtagt   2160
tcaccccgtc ctcgaggccg cccgggtcga ctaaaaaacc tcccacacct ccccctgaac   2220
ctgaaacata aaatgaatgc aattgttgtt gttaaactgg cctgcccgag accaaacgtg   2280
cggaacgtag ttaagtgtta gaggtaggat ttgaagcctg tcgatcattc tgattctcct   2340
tttctctacg tctgcttcct gtcaatgggc atcctcactg tcaaatgcag atggtacagc   2400
agggcttggt ctcagccagg caggcctctc cccagtctcc atggctcagc tgtccagcag   2460
tttcatccct agaccatccc aaacatggtt gagaagctct gaggggagga cccagcactg   2520
cccggcccct gaagataatc agcagtcctg ctcagcatat caatccaagc ccactctaga   2580
cagagatgcc ggtgcccagt tttctatttt taactggtgt gaactgaagg aaaagcacag   2640
cattagaagt ccaagcaggg ataaaagcag tctgggcttt cacatgacag catctggggc   2700
tgcggcagag ggtcgggtcc gaagcgctgc cttatcagcg tccccagccc tgggaggtga   2760
cagctggctg gcttgtgtca gcccctcggg cactcacgta tctccgtccg acgggtttaa   2820
aatagcaaaa ctctgaggcc acacaatagc ttgggcttat atgggctcct gtggggaag   2880
ggggagcacg gaggggccg gggccgctgc tgccaaaata gcagctcaca agtgttgcat   2940
tcctctctgg gcgccgggca cattcctgct ggctctgccc gccccgggt gggcgccggg   3000
gggaccttaa agcctctgcc cccaaggag cccttccag accgcgcg gcacccaccg      3060
ctccgtggga cgatccccga agctctagag ctttattgcg gtagtttatc acagttaaat   3120
tgctaacgca gtcagtgctt ctgacacaac agtctcgaac ttaagctgca gaagttggtc   3180
gtgaggcact gggcaggtaa gtatcaaggt tacaagacag gtttaaggag accaatagaa   3240
actgggcttg tcgagacaga gaagactctt gcgtttctga taggcaccta ttggtcttac   3300
tgacatccac tttgcctttc tctccacagg tgtccactcc cagttcaatt acagctctta   3360
aggctagagt acttaatacg actcactata ggctagccgc caccatggcc gagaaggaat   3420
ctaccagccc ccacctgatg gtgcctattc tgctgctggt gggctggatc gtcggctgca   3480
tcatcgtgat ctacatcgtg ttcttctgac ggccgcgcgg atccagacat gataagatac   3540
attgatgagt ttgacaaac cacaactaga atgcagtgaa aaaaatgctt tatttgtgaa   3600
atttgtgatg ctattgcttt аттттgтаасс attataagct gcaataaaca agtgaattcc   3660
cgattaggat cttcctagag catggctacg tagataagta gcatggcggg ttaatcatta   3720
actacaagga acccctagtg atggagttgg ccactccctc tctgcgcgct cgctcgctca   3780
ctgaggccgg gcgaccaaag gtcgcccgac gccggcттgcccgggcg gcctcagtga   3840
gcgagcgagc gcgcag                                                    3856

SEQ ID NO: 58         moltype = DNA   length = 3271
FEATURE               Location/Qualifiers
misc_feature          1..3271
                      note = Recombinant expression cassette or expression
                      cassette component
source                1..3271
                      mol_type = other DNA
                      organism = synthetic construct
SEQUENCE: 58
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaaggtcat ggagaagacc ccttgcag atgtcctcac     240
tgggctggc agagccggca acctgcctaa ggctgctcag tccattagga gccagtagct    300
tggaagatgt ctttaccccc agcatcagtt caagtggagc agcacataac tcttgccctc    360
tgccttccaa gattctggtg ctgagactta tggagtgtct tggaggttgc cttctgcccc    420
ccaaccctgc tcccagctgg ccctcccagg cctgggttgc tggcctctgc tttatcagga    480
ttctcaagag ggacagтcтgg tttatgttgc atgactgttc cctgcatatc tgctctggtt    540
ttaaatagct tatctgagca gctgaggac cacatgggct tatatggcgt gggtacatg     600
ttcctgtagc cttgtccctg gcacctgcca aatagcagc caacaccccc cacccccacc    660
gccatccccc tgccccaccc gtcccctgtc gcacattcct ccctccgcag ggctggctca    720
ccaggcccca gcccacatgc ctgcttaaag ccctctccat cctctgcctc acccagtcct    780
cgctgagact gagcagacgc ctccataact ggtaagtacc gcctatagac tctataggca    840
cacccctttg gctcttatgc atgctgacag actaacagac tgttcctttc ctgggtcttt    900
tctgcaggcc tgtacggaag tgttacttct gctctaaaag ctgcggaatt gtacccgcgg    960
ccgatccaat cgatacagat ctagcggccg cccgccacca tggctgagaa agagtcaaca   1020
tcaccacacc tcatggttcc сатtcтттcтc ctggttggat ggattgtagg ctgcatcatc   1080
gttatttaca ttgtcttctt ctaaaagctt tggatccaat caacctctgg attacaaaat   1140
ttgtgaaaga ttgactggta ttcttaacta tgttgctcct tttacgctat gtggatacgc   1200
tgctttaatg cctttgtatc atgctattgc ttcccgtatg gctttcattt tctcctcctt   1260
gtataaatcc tggttgctgt ctctttatga ggagttgtgg cccgttgtca ggcaacgtgg   1320
cgtggtgtgc actgtgtttg ctgacgcaac ccccactgtg gccccacctg ttccaccctg   1380
tcagctcctt tccgggactt tcgctttccc cctccctatt gccacggcgg aactcatcgc   1440
cgcctgcctt gcccgctgct ggacagggtc tggctgttg gcactgaca attccgtggt   1500
gttgtcgggg aaatcatcgt cctttccttg gctgctcgcc tgtgttgcca cctggattct   1560
gcgcgggacg tccttctgct acgtcccttc ggccctcaat ccagcggacc ttccttcccg   1620
cggcctgctg ggcgctctgc ggcctcttcc cgtctttgat gatctgcct тcтagтттgcc   1680
tctagttgcc agccatctgt tgtttgcccc tcccccgtgc cttccttgac cctggaaggt   1740
gccactccca ctgtcctttc ctaataaaat gaggaaattg catcgcattg tctgagtagg   1800
tgtcattcta ttctgggggg tggggtgggg caggacagca agggggagga ttgggaagac   1860
aataccaggc atgctgggga ctcgagttaa gggcагccag aagtcagatg ctcaaggggc   1920
ttcatgatgt ccccataatt tttggcagag gga aaaagat cggatcctca ggcgtagttc   1980
```

```
acccegtect cgaggecgec egggtegact aaaaaacete ccacaccice ccetgaacet 2040
gaaacataaa atgaatgcaa ttgttgttgt taacttgttt attgcagett ataatggtta 2100
caaataaagc aatagcatca caaatttcac aaataaagca tttttttcac tgcattctag 2160
ttgtggtttg tccaaactca tcaatgtatc ttatcatgtc tggatccgcg cggccgtcag 2220
aagaacacga tgtagatcac gatgatgcag ccgacgatcg agcccaccag cagcagaata 2280
ggcaccatca ggtgggggct ggtagattcc ttctcggcca tggtggcggc tagcctatag 2340
tgagtcgtat taagtactct agccttaaga gctgtaattg aactgggagt ggacacctgt 2400
ggagagaaag gcaagtggat tgtcagtaag accaataggt gcctatcaga aacgcaagag 2460
tcttctctgt ctcgacaagc ccagtttcta ttggtctcct taaacctgtc ttgtaacctt 2520
gatacttacc tgcccagtgc ctcacgacca acttctgcag cttaagttcg agactgttgt 2580
gtcagaagca ctgactgcgt tagcaattta actgtgataa actaccgcaa taaagctcta 2640
gagcttcggg gatcgtccca cggagcggtg ggtgccggcg gctgtctggg aagggctcct 2700
tgggggggcag aggcttaag gtccccccgg cgcccacccc gggcgggca gagccagcag 2760
gaatgctgcc ggcgcccaga gaggaatgca acacttggtg gctgctattt tggcagcagc 2820
ggccccggcc cctccgtgc tccccctccc cccacaggag cccatataag cccaagctat 2880
tgtgtgccct cagagtttg ctatttaaa cccgtcggac ggagatacgt gagtgcccga 2940
ggggctgaca caagccagcc agctgtcacc tccagggct ggggacgctg ataaggcagc 3000
gcttcggacc cgacccctcg ccgcagcccc agatgctgc atgtgaaagc ccagactgct 3060
tttatcccga attcccgatt aggatcttcc tagagcatgg ctacgtagat aagtagcatg 3120
gcgggttaat cattaactac aaggaacccc tagtgatgga gttggccact ccctctctgc 3180
gcgctcgctc gctcactgag gccgggcgac caaaggtcgc ccgacgcccg ggctttgccc 3240
gggcggcctc agtgagcgag cgagcgcgca g            3271

SEQ ID NO: 59            moltype = DNA  length = 3271
FEATURE                  Location/Qualifiers
misc_feature             1..3271
                         note = Recombinant expression cassette or expression
                         cassette component
source                   1..3271
                         mol_type = other DNA
                         organism = synthetic construct
SEQUENCE: 59
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc ttaaggtcat ggagaagatc cacctgcag atgtcctcac 240
tggggctggc agagccggca acctgcctaa ggctgctcag tccattagga gccagtagcc 300
tggaagatgt ctttacccc agcatcagtt caagtggagc agcacataac tcttgccctc 360
tgccttccaa gattctggtg ctgagactta tggagtgctt ggaggttgc cttctgcccc 420
ccaaccctgc tcccagctgg ccctcccagg cctgggttgc tggcctctgc tttatcagga 480
ttctcaagag ggacagctgg tttatgttgc atgactgttc cctgcatatc tgctctggtt 540
ttaaatagct tatctgagca gctggaggac cacatgggct tatatggcgt ggggtacatg 600
ttcctgtagc ctttgtccctg gcacctgcca aaatagcgac caacacccc cacccccacg 660
gccatccccc tgccccaccc gtccctgtc gcacattcct ccctccgcag gggctggctca 720
ccaggcccca gcccacatgc ctgcttaaag ccctctccat cctctgcctc acccagtccc 780
cgctgagact gagcagacgc ctccataact ggtaagtacc gcctatagac tctataggca 840
caccccttg gctcttatgc atgctgacag actaacagac tgttcctttc ctgggtcttt 900
tctgcaggcc tgtacggaag tgttacttct gctctaaaag ctgcggaatt gtacccgcgg 960
ccgatccaat cgatacagat ctagcggccg cccgccacca tggctgagaa agagtcaaca 1020
tcaccacacc tcatggttcc cattcttctc ctggttggat ggattgtagg ctgcatcatc 1080
gttatttaca ttgtcttctt ctaaaagctt tggatccaat caacctctgg attacaaaat 1140
ttgtgaaaga ttgactggta ttcttaacta tgttgctcct tttacgctat gtggatacgc 1200
tgctttaatg cctttgtatc atgctattgc ttccccgtatg gctttcattt tctcctcctt 1260
gtataaatcc tggttgctgt ctctttatga ggagttgtgg cccgttgtca ggcaacgtgg 1320
cgtggtgtgc actgtgtttg ctgacgcaac ccccactggt tgggcattg ccaccacctg 1380
tcagctcctt tccgggactt tcgctttccc cctccctatt gccacggcgg aactcatcgc 1440
cgcctgcctt gcccgctgct ggacagggc tcggctgttg ggcactgaca attccgtggt 1500
gttgtcgggg aaatcatcgt cctttccttg gctgctcgcc tgtgttgcca cctggattct 1560
gcgcgggacg tccttctgct acgtccctc ggccctcaat ccagcggacc ttccttcccg 1620
cggcctgctg ccggctctgc ggcctcttcc gcgtcttcga gatctgcctc gactgtgcct 1680
tctagttgcc agccatctgt tgtttgcccc tccccgtgc cttccttgac cctggaaggt 1740
gccactccca ctgtcctttc ctaataaaat gaggaaattg catcgcattg tctgagtagg 1800
tgtcattcta ttctggggg tggggtgggg caggacagca agggggagga ttgggaagac 1860
aatagcagge atgctgggga ctcgagttaa gggcagccag aagtcagatg ctcaagggga 1920
ttcatgatgt ccccataatt tttggcagag gaaaaagat cggatcctca ggcgtagttc 1980
acccccgtcct cgaggccgcc cgggtcgact aaaaaacctc ccacacctcc ccctgaacct 2040
gaaacataaa atgaatgcaa ttgttgttgt tagggataaa agcagtctgg ctttacatt 2100
gacagcatct ggggctgcgg cagagggtcg ggtccgaagc gctgccttat cagcgtcccc 2160
agccctgacc ggtgacagct ggctggcttg tgtcagcccc tcgggcactc acgtatctcc 2220
gtccgacggg tttaaaatag caaaactctg aggccacaca atagcttggg cttatatggg 2280
ctcctgtggg ggaaggggga gcacggaggg ggccggggcc gctgctgcca aaatagcagc 2340
tcacaagtgt tgcattcctc tctggcgcc gggcacattc ctgctggctc tgcccgcccc 2400
ggggtgggcg ccggggggac cttaaagcct tgccccca aggagccctt cccagacagc 2460
cgccggcacc caccgctccg tgggacgatc ccgaagctc acggcttta ttgcgtagt 2520
ttatcacagt taaattgcta acgcagtcag tgcttctgac acaacagtct cgaacttaag 2580
ctgcagaagt tggtcgtgag gcactgggca ggtaagtatc aaggttacaa acagggttta 2640
aggagaccaa tagaaactgg gcttgtcgag acagagaaga ctcttgcgtt tctgataggc 2700
acctattggt cttactgaca tccacttgc ctttctctcc acaggtgtcc actcccagtt 2760
caattacagc tcttaaggct agagtactta atacgactca ctataggcta gccgccacca 2820
```

```
tggccgagaa ggaatctacc agcccccacc tgatggtgcc tattctgctg ctggtgggct   2880
ggatcgtcgg ctgcatcatc gtgatctaca tcgtgttctt ctgacggccg cgcggatcca   2940
gacatgataa gatacattga tgagtttgga caaaccacaa ctagaatgca gtgaaaaaaa   3000
tgctttattt gtgaaatttg tgatgctatt gctttatttg taaccattat aagctgcaat   3060
aaacaagtga attcccgatt aggatcttcc tagagcatg ctacgtagat aagtagcatg   3120
gcgggttaat cattaactac aaggaacccc tagtgatgga gttggccact ccctctctgc   3180
gcgctcgctc gctcactgag gccgggcgac caaaggtcgc ccgacgcccg ggctttgccc   3240
gggcggcctc agtgagcgag cgagcgcgca g                                  3271

SEQ ID NO: 60           moltype = DNA   length = 3262
FEATURE                 Location/Qualifiers
misc_feature            1..3262
                        note = Recombinant expression cassette or expression
                         cassette component
source                  1..3262
                        mol_type = other DNA
                        organism = synthetic construct
SEQUENCE: 60
ctgcgcgctc gctcgctcac tgaggccgcc cgggcaaagc ccgggcgtcg ggcgacccttt   60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattctccc cagcatgcct gctattgtct tcccaatcct cccccttgct   240
gtcctgcccc accccacccc ccagaataga atgacaccta ctcagacaat gcgatgcaat   300
ttcctcattt tattaggaaa ggacagtggg agtggcacct tccagggtca aggaaggcac   360
gggggagggg caaacaacag atggctgcaa actagaaggc acagtcgagg cagatctcga   420
agacgcggaa gaggccgcag agccggcagc aggccgagca aaggaaggtc cgctggattg   480
agggccgaag gacgtagca gaaggacgtc ccgcgcagaa tccaggtggc aacacaggcg   540
agcagccaag gaaaggacga tgatttcccc gacaacacca cggaattgtc agtgcccaac   600
agccgagccc ctgtccagca gcgggcaagg caggcggcga tgagttccgc cgtggcaata   660
gggaggggga aagcgaaagt cccggaaagg agctgacagg tggtggcaat gccccaacca   720
gtgggggttg cgtcagcaaa cacagtgcac accacgccac gttgcctgac aacgggccac   780
aactcctcat aaaagacag caaccaggat ttatacaagg aggagaaaat gaaagccata   840
cgggaagcaa tagcatgata caaaggcatt aaagcagcgt atccacatag cgtaaaagga   900
gcaacatagt taagaattacc agtcaatctt tcacaaattt tgtaatccag aggttgattg   960
gatccaaagc ttttagaaga agacaatgta aataacgatg atgcagccta caatccatcc   1020
aaccaggaga agaatgggaa ccatgaggtg tggtgatgtt gactctttct cagccatggt   1080
ggcgggcggc cgctagatct gtatcgattg gatcggccgc gggtacaatt ccgcagcttt   1140
tagagcagaa gtaacacttc cgtacaggcc tgcagaaaag acccaggaaa ggaacagtct   1200
gttagtctgt cagcatgcat aagagccaaa ggggtggtgcc tatagagtct ataggcggta   1260
cttaccagtt atggaggcgt ctgctcagtc tcagcgggga ctgggtgagg cagaggatgg   1320
agagggcttt aagcaggcat gtgggctggg gcctggtgag ccagccctgc ggagggagga   1380
atgtgcgaca ggggacgggt ggggcagggg gatggcggtg ggggtggggg gtgttggctg   1440
ctatttttggc aggtgccagg gacaaggcta caggaacatg taccccacgc catataggcc   1500
catgtggtcc tccagctgct cagataagct attttaaaacc agagcagata tgcagggaac   1560
agtcatgcaa cataaaccag ctgtccctct tgagaatcct gataaagcag aggccagcaa   1620
cccaggcctg ggagggccag ctgggagcag ggttgggggg cagaaggcaa cctccaagac   1680
actccataag tctcagcacc agaatctttgg aaggcagagg gcaagagtta tgtgctgctc   1740
cacttgaact gatgctgggg gtaaagacat cttccaggct actggctcct aatggactga   1800
gcagccttag gcaggttgcc ggctctgcca gccccagtga ggacatctgc aaggtgggtc   1860
ttctccatga ccctcgagtt aagggcagcca gaagtcagat gctcaagggg cttcatgatg   1920
tccccataat tttggcaga gggaaaaaga tcggatcctg aggcgtagtt caccccgtcc   1980
tcgaggccgc ccgggtcgac taaaaaaacct cccacacctc ccctgaacc tgaaacataa   2040
aatgaatgca attgttgttg ttagggataa aagcagtctg ggctttcaca tgacagcatc   2100
tggggctgcg gcagagggtc gggtccgaag cgctgcctta tcagcgtccc cagccctggg   2160
aggtgacagc tggctggctt gtgtcagccc ctcgggcact cacgtatctc cgtccgacgg   2220
gtttaaaata gcaaaactct gaggccacac aatagcttgg gcttatatgg gctcctgtgt   2280
gggaaggggg agcacggagg gggccgggc cgctgctgcc aaaatagcag ctcacaagtg   2340
ttgcattcct ctctgggcgc cgggcacatt cctgctggct ctgcccgccc cggggtgggc   2400
gccggggga ccttaaagcc tctgcccccc aaggagccct tcccagacag cccgcggcac   2460
ccaccgctcc gtgggacgat cccgcgaagct ctagagcttt attgcggtag ttttatcacag   2520
ttaaaatcg ct aacgcagtca gtgcttctga cacaacagtc tcgaacttaa gctgcagaag   2580
ttggtcgtga ggcactgggc aggtaagtat caaggttaca agacaggttt aaggagacca   2640
atagaaactg ggcttgtcga gacagagaag actcttgcgt ttctgatagg cacctattgg   2700
tcttactgac atccactttg cctttctctc cacaggtgtc cactcccagt tcaattacag   2760
ctcttaaggc tagagtactt aatacgactc actataggct agccgccacc atggccgaga   2820
aggaatctac cagcccccac ctgatggtgc ctattctgct gctggtgggc tggatcgtcg   2880
gctgcatcat cgtgatctac atcgtgttct tctgacggcc gcgcggatcc agacatgata   2940
agatacattg atgagtttgg acaaaccaca actagaatgc agtgaaaaaa atgctttatt   3000
tgtgaaatttg tgatgctat tgctttattt gtaaccatta agctgcaa taaacaagtg   3060
aattcccgat taggatcttc ctagagcatg ctacgtaga taagtagcat ggcgggttaa   3120
tcattaacta caaggaaccc ctagtgatgg agttggccac ccctctctg cgcgctcgct   3180
cgctcactga ggccgggcga ccaaaggtcg cccgacgccc gggctttgcc cggcggcct   3240
cagtgagcga gcgagcgcgc ag                                            3262

SEQ ID NO: 61           moltype = DNA   length = 2325
FEATURE                 Location/Qualifiers
misc_feature            1..2325
                        note = Recombinant expression cassette or expression
                         cassette component
```

```
source                  1..2325
                        mol_type = other DNA
                        organism = synthetic construct
SEQUENCE: 61
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattcgccc ttaagaactg gcctgcccga gaccaaacgt gcggaacgta   240
gttaagtgtt agaggtagga tttgaagcct gtcgatcatt ctgattctcc ttttctctac   300
gtctgcttcc tgtcaatggg catcctcact gtcaaatgca gatggtacag cagggcttgg   360
tctcagccag gcaggcctct ccccagtctc catggctcag ctgtccagca gtttcatccc   420
tagaccatcc caaacatggt tgagaagctc tgagggagg acccagcact gcccggcccc    480
tgaagataat cagcagtcct gctcagcata tcaatccaag cccactctag acagagatgc   540
cggtgcccag ttttctattt ttaactggtg tgaactgaag gaaaagcaca gcattagaag   600
tccaagcagt catggagaag acccaccttg cagatgtcct cactggggct ggcagagcca   660
gcaacctgcc taaggctgct cagtccatta ggagccagta gcctgaagaa tgtctttacc   720
cccagcatca gttcaagtgg agcagcacat aactcttgcc ctctgccttc caagattctg   780
gtgctgagac ttatggagtg tcttggaggt tgccttctgc cccccaaccc tgctcccagc   840
tggccctccc aggcctgggt tgctggcctc tgctttatca ggattctcaa gagggacagc   900
tggtttatgt tgcatgactg ttccctgcat atctgctctg gttttaaata gcttatctga   960
gcagctggag gaccacatgg gcttatatgg cgtggggtac atgttcctgt agccttgtcc  1020
ctggcacctg ccaaaatagc agccaacacc cccaccccc accgccatcc ccctgcccca   1080
cccgtcccct gtcgcacatt cctccctccg cagggctggc tcaccaggcc ccagcccaca  1140
tgcctgctta agcccctctc catcctctgc ctcacccagt cccgctgag actgagcaga   1200
cgcctccagc ggccgccgc caccatggct gaaaaagcgg gtctacatt tcacaccttt    1260
ctggttccta ttcttctcct gattggctgg attgtgggct gcatcataat gatttatgtt   1320
gtcttctctt agaagctttg gatccaatca acctctggat tacaaaattt gtgaaagatt   1380
gactggtatt cttaactatg ttgctccttt tacgctatgt ggatacgctg ctttaatgcc   1440
tttgtatcat gctattgctt cccgtatggc tttcattttc tcctccttgt ataaatcctg   1500
gttgctgtct ctttatgagg agttgtggcc cgttgtcagg caacgtgggg tggtgtgcac  1560
tgtgtttgct gacgcaaccc ccactggttg gggcattgcc accacctgtc agctcctttc   1620
cgggactttc gctttccccc tccctattgc cacggcggaa ctcatcgccg cctgccttgc   1680
ccgctgctgg acaggggctc ggctgttggg cactgacaat tccgtggtgt tgtcggggaa  1740
atcatcgtcc tttccttggc tgctgcctg tgttgccacc tggattctgc gcgggacgtc   1800
cttctgctac gtcccttcgg ccctcaatcc agcggacctt ccttcccgcg gcctgctgcc  1860
ggctctgcgg cctcttccgc gtcttcgaga tctgcctcga ctgtgccttc tagttgccag  1920
ccatctgttg tttgccccctc cccgtgcct tccttgaccc tggaaggtgc cactcccact   1980
gtcctttcct aataaaatga ggaaattgca tcgcattgtc tgagtaggtg tcattctatt  2040
ctggggggtg gggtggggca ggacagcaag gggaggatt gggaagacaa tagcaggcat   2100
gctgggggact cgagttaagg gcgaattccc gattaggatc ttcctagagc atggctacgt  2160
agataagtag catggcgggt taatcattaa ctacaaggaa cccctagtga tggagttggc  2220
cactccctct ctgcgcgctc gctcgctcac tgaggccggg cgaccaaagg tcgcccgacg  2280
cccgggcttt gccgggcgg cctcagtgag cgagcgagcg cgcag                   2325

SEQ ID NO: 62            moltype = DNA   length = 3277
FEATURE                  Location/Qualifiers
misc_feature             1..3277
                         note = Recombinant expression cassette or expression
                         cassette component
source                   1..3277
                         mol_type = other DNA
                         organism = synthetic construct
SEQUENCE: 62
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattcgccc ttaaggtcat ggagaagacc caccttgcag atgtcctcac   240
tggggctggc agagccggca acctgcctaa ggctgctcag tccattagga gccagtagcc   300
tggaagatgt ctttaccccc agcatcagtt caagtggagc agcataac tcttgccctc    360
tgccttccaa gattctggtg ctgagactta tggagtgtct tggaggttgc cttctgcccc  420
ccaaccctgc tcccagctgg ccctcccagg cctgggttgc tggcctctgc tttatcagga   480
ttctcaagag ggacagctgg tttatgttgc atgactgttc cctgcatatc tgctctggtt   540
taaaatagct tatctgagca gctggaggac acatgggct tatatggcgt ggggtacatg   600
ttcctgtagc cttgtccctg gcacctgcca aaatagcaa caccccccac caccccccaa   660
gccatccccc tgccccaccc gtcccctgtc gcacattcct ccctccgcag ggctggctca   720
ccaggcccca gcccacatgc ctgcttaaag ccctctccat cctctgcctc acccagtccc   780
cgctgagact gagcagacgc tccataact ggtaagtacc gcctatagac tctataggca    840
cacccctttg gctcttatgc atgctgacag actaacagac tgttccttc ctgggtcttt    900
tctgcaggcc tgtacgaag tgttacttct gctctaaaag ctgcggaatt gtacccgcgg   960
ccgatccaat cgatacagat ctagcggccg cccgccacca tggctgaaaa agcggggtct  1020
acattttcac accttctggt tcctattctt ctcctgattg gctggattgt gggctgcatc  1080
ataatgattt atgttgtctt ctcttagaag ctttggatcc aatcaacctc tggattacaa  1140
aatttgtgaa agattgactg gtattcttaa ctatgttgct ccttttacgc tatgtggata  1200
cgctgcttta atgcctttgt atcatgctat tgcttcccgt atggctttca ttttctcctc  1260
cttgtataaa tcctggttgc tgtctcttta tgaggagttg tggcccgttg tcaggcaacg  1320
tggcgtggtg tgcactgtgt tgctgacgc aaccccact ggttgggca ttgccaccac    1380
ctgtcagctc ctttccggga ctttcgcttt ccccctccct attgccacgg cggaactcat  1440
cgccgcctgc cttgcccgct gctggacagg ggctcggctg ttgggcactg acaattccgt  1500
ggtgttgtcg gggaaatcat cgtcctttcc ttggctgctc gcctgtgttg ccacctggat  1560
```

```
tctgcgcggg acgtccttct gctacgtccc ttcggccctc aatccagcgg accttccttc  1620
ccgcggcctg ctgccggctc tgcggcctct tccgcgtctt cgagatctgc ctcgactgtg  1680
ccttctagtt gccagccatc tgttgtttgc ccctcccccg tgccttcctt gaccctggaa  1740
ggtgccactc ccactgtcct ttcctaataa aatgaggaaa ttgcatcgca ttgtctgagt  1800
aggtgtcatt ctattctggg gggtggggtg gggcaggaca gcaaggggga gggattgggaa  1860
gacaatagca ggcatgctgg ggactcgagt taagggcagc cagaagtcag atgctcaagg  1920
ggcttcatga tgtccccata attttttggca gagggaaaaa gatcggatcc tcaggcgtag  1980
ttcaccccgt cctcgaggcc gcccgggtcg actaaaaaac ctcccacacc tcccctgaa  2040
cctgaaacat aaaatgaatg caattgttgt tgttagggat aaaagcagtc tgggctttca  2100
catgacagca tctggggctg cggcagaggg tcgggtccga agcgctgcct tatcagcgtc  2160
cccagccctg ggaggtgaca gctggctggc ttgtgtcagc ccctcgggca ctcacgtatc  2220
tccgtccgac gggtttaaaa tagcaaaact ctgaggccac acaatagctt gggcttatat  2280
gggctcctgt gggggaaggg ggagcacgga ggggccggg gccgctgctg ccaaaatagc  2340
agctcacaag tgttgcattc ctctctgggc gccgggcaca ttcctgctgc ctctgcccgc  2400
cccggggtgg gcgccggggg gaccttaaag cctctgcccc ccaaggagcc cttcccagac  2460
agccgccggc acccaccgct ccgtgggacg atccccgaag ctctagagct ttattgcggt  2520
agtttatcac agttaaattg ctaacgcagt cagtgcttct gacacaacag tctcgaactt  2580
aagctgcaga agttggtcgt gaggcactgg gcaggtaagt atcaaggtta caagacaggt  2640
ttaaggagac caatagaaac tgggcttgtc gagacagaga agactcttgc gtttctgata  2700
ggcacctatt ggtcttactg acatccactt tgcctttctc tccacaggtg tccactccca  2760
gttcaattac agctcttaag gctagagtac ttaatacgac tcactatagg ctagccgcca  2820
ccatgccga gaaggccgga tctaccttca gccacctgct ggtccctatt ctgctgctga  2880
tcggctggat cgtgggctgc atcatcatga tctacgtggt gttcagctga cggccgcgcg  2940
gatccagaca tgataagata cattgatgag tttggacaaa ccacaactag aatgcagtga  3000
aaaaaatgct ttatttgtga aatttgtgat gctattgctt tatttgtaac cattataagc  3060
tgcaataaac aagtgaattc ccgattagga tcttcctaga gcatgcctac gtagataagt  3120
agcatggcgg gttaatcatt aactacaagg aaccccctagt gatggagttg gccactccct  3180
ctctgcgcgc tcgctcgctc actgaggccg ggcgaccaaa ggtcgcccga cgcccgggct  3240
tgcccgggc ggcctcagtg agcgagcgag cgcgcag                           3277
```

SEQ ID NO: 63          moltype = DNA   length = 3268
FEATURE                Location/Qualifiers
misc_feature           1..3268
                       note = Recombinant expression cassette or expression
                       cassette component
source                 1..3268
                       mol_type = other DNA
                       organism = synthetic construct
SEQUENCE: 63

```
ctgcgcgctc gctcgctcac tgaggccgcc cgggcaaagc ccgggcgtcg ggcgaccttt   60
ggtcgcccgg cctcagtgag cgagcgagcg cgcagagagg gagtgccaa ctccatcact   120
aggggttcct tgtagttaat gattaacccg ccatgctact tatctacgta gccatgctct  180
aggaagatcg gaattctccc cagcatgcct gctattgtct tcccaatcct cccccttgct  240
gtcctgcccc acccccaccccc ccagaataga atgacaccta ctcagacaat gcgatgcaat  300
ttcctcattt tattaggaaa ggacagtggg agtggcacct tccagggtca aggaaggcac   360
gggggagggg caaacaacag atggctgca actagaaggc acagtcgagg cagatctcga  420
agacgcggaa gaggccgcag agccggcagc aggccgcagg aaggaaggtc cgctggattg  480
agggccgaag ggacgtagca gaaggacgtc ccgcgcagaa tccaggtggc aacacaggcg  540
agcagccaag gaaaggacga tgattccccc gacaacacca cggaattgtc agtgcccaac  600
agccgagccc ctgtccagca gcgggcaagg caggcggcga tgagttccgc cgtggcaata  660
gggaggggaa aagcgaaagt cccggaaagg agctgacagg tggtggcaat gccccaacca  720
gtgggggttg cgtcagcaaa acagtgcac accacgccac gttgcctgac aacgggccac  780
aactcctcat aaagagacag caaccaggat ttatacaagg aggagaaaat gaaagccata  840
cgggaagcaa tagcatgata caaaggcatt aaagcagcgt atccacatag cgtaaaagga  900
gcaacatagt taagaatacc agtcaatctt tcacaaattt tgtaatccag aggttgattg  960
gatccaaagc ttctaagaga agacaacata aatcattatg atgcagccca caatccagcc  1020
aatcaggaga agaataggaa ccagaaggtg tgaaaatgta gacccgcttt ttcagccat   1080
ggtggcgggg ggccgctaga tctgtatcga ttggatcggc cgcgggtaca attccgcagc  1140
ttttagagca gaagtaacac ttccgtacag gcctgcagaa agacccaggg aaaggaacag  1200
tctgttagtc tgtcagcatg cataagagcc aaagggggtgt gcctatagga tctataggcg  1260
gtacttacca gttatggagg cgtctgctca gtctcagcgg ggactgggtg aggcagagga  1320
tggagagggc tttaagcagg catgtgggct ggggcctggt gagccagccc tgcggaggga  1380
ggaatgtgcg acaggggacg ggtggggcag ggggatggcg gtgggggtgg gggtgttgg   1440
ctgctatttt ggcaggtgcc agggacaagg ctacaggaag gtattacccca cgccatataa  1500
gcccatgtgg tcctccagct gctcagataa gctatttaaa accagagcag atatgcaggg  1560
aacagtcatg caacataaac cagctgtccc tcttgagaat cctgataaag cagaggccag  1620
caacccaggc ctgggagggc cagctgggag cagggttggg gggcagaagg caacctccaa  1680
gacactccat aagtctcagc accagaatct tggaaggcag agggcaagag ttatgtgctg  1740
ctccacttga actgatgctg ggggtaaaga catcttccag gctactggct cctaatggac  1800
tgagcagcct taggcaggtt gccggctctg ccagccccag tgaggacatc tgcaaggtgg  1860
gtcttctcca tgacctcgag ttaagggcag ccagaagtca gatgctcaag ggcttcatg   1920
atgtccccat aattttttggc agagggaaaa agatcggatc ctcaggcgta gttcaccccg  1980
tcctcgaggc cgcccgggtc gactaaaaaa cctcccacac ctcccctga acctgaaaca  2040
taaaatgaat gcaattgttg ttgttaggga taaaagcagt ctgggctttc acatgacagc  2100
atctggggct gcggcagagg gtcggtccg aagcgctgcc ttatcagcgt cccagccct   2160
ggaggtgac agctggctgg cttgtgtcag ccctcgggc actcacgtat ctccgtccga    2220
cgggtttaaa atagcaaaac tctgaggcca cacaatagct gggcttata tgggctcctg   2280
tgggggaagg gggagcacgg aggggccgg ggccgctgct gccaaaatag cagctcacaa   2340
gtgttgcatt cctctctggg cgccgggcac attcctgctg ctctgcccg ccccggggtg    2400
```

```
ggcgccgggg ggaccttaaa gcctctgccc cccaaggagc ccttcccaga cagccgccgg    2460
cacccaccgc tccgtgggac gatccccgaa gctctagagc tttattgcgg tagtttatca    2520
cagttaaatt gctaacgcag tcagtgcttc tgacacaaca gtctcgaact taagctgcag    2580
aagttggtcg tgaggcactg ggcaggtaag tatcaaggtt acaagacagg tttaaggaga    2640
ccaatagaaa ctgggcttgt cgagacagag aagactcttc cgtttctgat aggcacctat    2700
tggtcttact gacatccact ttgccttcct ctccacaggt gtccactccc agttcaatta    2760
cagctcttaa ggctagagta cttaatacga ctcactatag gctagccgcc accatggcca    2820
agaaggccgg atctaccttc agccacctgc tggtccctat tctgctgctg atcggctgga    2880
tcgtgggctg catcatcatg atctacgtgg tgttcagctg acggccgcgc ggatccagac    2940
atgataagat acattgatga gtttggacaa accacaacta gaatgcagtg aaaaaaatgc    3000
tttatttgtg aaatttgtga tgctattgct ttatttgtaa ccattataag ctgcaataaa    3060
caagtgaatt cccgattagg atcttcctag agcatggcta cgtagataag tagcatggcg    3120
ggttaatcat taactacaag gaaccctag tgatggagtt ggccactccc tctctgcgcg    3180
ctcgctcgct cactgaggcc gggcgaccaa aggtcgcccg acgcccgggc tttgcccggg    3240
cggcctcagt gagcgagcga gcgcgcag                                      3268

SEQ ID NO: 64           moltype = DNA   length = 2516
FEATURE                 Location/Qualifiers
misc_feature            1..2516
                        note = Recombinant expression cassette or expression
                         cassette component
source                  1..2516
                        mol_type = other DNA
                        organism = synthetic construct
SEQUENCE: 64
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagaactg gcctgcccga ccaaacgt gcggaacgta      240
gttaagtgtt agaggtagga tttgaagcct gtcgatcatt ctgattctcc tttctctac    300
gtctgcttcc tgtcaatggg catcctcact gtcaaatgca gatggtacag cagggcttgg   360
tctcagccag gcaggcctct ccccagtctc catggctcag ctgtccagca gtttcatccc    420
tagaccatcc caaacatggt tgagaagctc tgaggggagg acccagcact gcccggcccc    480
tgaagataat cagcagtcct gctcagcata tcaatccaag cccactctag acagagatgc    540
cggtgcccag ttttctattt ttaactggtg tgaactgaag gaaaagcaca gcattagaag    600
tccaagcacc ttcagattaa aaataactaa ggtaagggcc atgtgggtag gggaggtggt    660
gtgagacggt cctgtctctc ctctatctgc ccatcggccc tttggggagg aggaatgtgc    720
ccaaggacta aaaaaggcc ctggagccag aggggcgagg gcagcagacc tttcatgggc     780
aaacctcagg gctgctgtcg tcatggagaa gacccacctt gcagatgtcc tcactggggc    840
tggcagagcc ggcaacctgc ctaaggctgc tcagtccatt aggagccagt agcctgggaag  900
atgtctttac ccccagcatc agttcaagtg gagcagcaca taactcttgc cctctgcctt   960
ccaagattct ggtgctgaga cttatggagt gtcttggagg ttgccttctg ccccccaacc   1020
ctgctcccag ctggccctcc caggcctggg ttgctgcagc tgcttttatc aggattctca   1080
agagggacag ctggtttatg ttgcatgact gttccctgca tatctgctct ggttttaaat   1140
agcttatctg agcagctgga ggaccacatg ggcttatatg gcgtggggta catgttcctg   1200
tagccttgtc cctggcacct gccaaaatag cagccaacac cccccacccc caccgccatc   1260
ccctcgcccc acccgtcccc tgtcgcacat tcctccctcc gcagggctgg ctcaccaggc   1320
cccagcccac atgcctgctt aaagccctct ccatcctctg cctcacccag tcccgctga    1380
gactgagcag acgcctccag cggccgcccc ccaccatggc tgaaaaagcg gggtctacat   1440
tttcacacct tctggttcct attcttctcc tgattggctg gattgtgggc tgcatcataa   1500
tgatttatgt tgtcttctct tagaaagctt ggatccaatc aacctctgga ttacaaaatt   1560
tgtgaaagat tgactggtat tcttaactat gttgctcctt ttacgctatg tggatacgct   1620
gctttaatgc ctttgtatca tgctattgct tcccgtatgg ctttcatttt ctcctccttg   1680
tataaatcct ggttgctgtc tctttatgag gagttgtggc ccgttgtcag caacgtggcg   1740
gtggtgtgca ctgtgtttgc tgacgcaacc cccactggtt ggggcattgc caccacctgt   1800
cagctccttt ccgggacttt cgctttcccc ctccctattg ccacggcgga actcatcgcc   1860
gcctgccttg cccgctgctg acaggggctc ggctgttgg gcactgacaa ttccgtggtg    1920
ttgtcgggga aatcatcgtc ctttccttgg ctgctcgcct gtgttgccac ctggattctg   1980
cgcgggacgt ccttctgcta gtccccttcg gccctcaatc cagcggacct tccttcccgc   2040
ggcctgctgc cggctctgcg gcctcttccg cgtcttcgag atctgcctcg actgtgcctt   2100
ctagttgcca gccatctgtt gtttgcccct ccccgtgcc ttccttgacc ctggaaggtg    2160
ccactcccac tgtcctttcc taataaaatg aggaaattgc atcgcattgt ctgagtaggt   2220
gtcattctat tctgggggt ggggtgggc aggacagca ggggaggat tgggaagaca       2280
atagcaggca tgctgggac tcgagttaag ggcgaattc cgattaggat cttcctagga    2340
catggctacg tagataagta gcatggcggg ttaatcatta actacaagga acccctagtg   2400
atggagttgg ccactccctc tctgcgcgct cgctcgctca ctgaggccgg gcgaccaaag   2460
gtcgcccgac gcccgggctt tgcccgggcg gcctcagtga gcgagcgagc gcgcag       2516

SEQ ID NO: 65           moltype = DNA   length = 2113
FEATURE                 Location/Qualifiers
misc_feature            1..2113
                        note = Recombinant expression cassette or expression
                         cassette component
source                  1..2113
                        mol_type = other DNA
                        organism = synthetic construct
SEQUENCE: 65
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
```

```
aggggttcct tgtagttaat gattaacccg ccatgctact tatctacgta gccatgctct   180
aggaagatcg gaattcgccc ttaagccttc agattaaaaa taactaaggt aagggccatg   240
tgggtagggg aggtggtgtg agacggtcct gtctctcctc tatctgccca tcggccttt    300
ggggaggagg aatgtgccca aggactaaaa aaaggccctg gagccagagg ggcgagggca   360
gcagaccttt catgggcaaa cctcagggct gctgtcgtca tggagaagac ccaccttgca   420
gatgtcctca ctggggctgg cagagccggc aacctgccta aggctgctca gtccattagg   480
agccagtagc ctggaagatg tctttacccc cagcatcagt tcaagtggag cagcacataa   540
ctcttgccct ctgccttcca agattctggt gctgagactt atggagtgtc ttggaggttg   600
ccttctgccc cccaaccctg ctcccagctg gccctcccag gctgggttg ctggcctctg    660
ctttatcagg attctcaaga gggacagctg gtttatgttg catgactgtt ccctgcatat   720
ctgctctggt tttaaaatagc ttatctgagc agctggagga ccacatgggc ttatatggcg  780
tggggtacat gttcctgtag ccttgtccct ggcacctgcc aaaatagcag ccaacacccc   840
ccaccccac cgccatcccc ctgccccacc cgtccctgt cgcacattcc tccctccgca     900
gggctggctc accaggcccc agcccacatg cctgcttaaa gccctctcca tcctctgcct   960
cacccagtcc ccgctgagac tgagcagacg cctccagcgg ccgccgcca ccatgggctga  1020
aaaagcgggg tctacatttt cacaccttct ggttcctatt cttctcctga ttggctggat  1080
tgtgggctgc atcataatga tttatgttgt cttctcttag aagctttgga tccaatcaac  1140
ctctgatta caaaatttgt gaaagattga ctggtattct taactatgtt gctccttta    1200
cgctatgtgg atacgctgct taatgcctt tgtatcatgc tattgcttcc cgtatggctt   1260
tcattttctc ctccttgtat aaatcctggt tgctgtctct ttatgaggag ttgtggcccg  1320
ttgtcaggca acgtggcgtg gtgtgcactg tgtttgctga cgcaaccccc actggttggg  1380
gcattgccac cacctgtcag ctcctttccg ggactttgc tttccccctc cctattgcca   1440
cggcggaact catcgccgcc tgccttgccc gctgctggac agggggtcgg ctgttgggca  1500
ctgacaattc cgtggtgttg tcggggaaat catcgtcctt tccttggctg ctcgcctgtg  1560
ttgccacctg gattctgcgc gggacgtcct tctgctacgt cccttcggcc ctcaatccag  1620
cggaccttcc ttcccgcgg ctgctgccgg ctctgccgt tcttccgcgt cttcgagatc    1680
tgcctcgact gtgccttcta gttgccagcc atctgtttgtt tgcccctccc ccgtgccttc  1740
cttgaccctg gaaggtgcca ctcccactgt cctttcctaa taaaatgagg aaattgcatc   1800
gcattgtctg agtaggtgtc attctattct gggggtggg gtgggcagg acagcaaggg    1860
ggaggattgg gaagacaata gcaggcatgc tggggactcg agttaaggc gaattcccga   1920
ttaggatctt cctagagcat ggctacgtag ataagtagca tggcgggtta atcattaact  1980
acaaggaacc cctagtgatg gagttggcca ctccctctct gcgcgctcgc tcgctcactg   2040
aggccgggcg accaaaggtc gcccgacgcc cgggctttgc ccgggcggcc tcagtgagcg   2100
agcgagcgcg cag                                                      2113

SEQ ID NO: 66           moltype = DNA  length = 2516
FEATURE                 Location/Qualifiers
misc_feature            1..2516
                        note = Recombinant expression cassette or expression
                        cassette component
source                  1..2516
                        mol_type = other DNA
                        organism = synthetic construct
SEQUENCE: 66
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact  120
aggggttcct tgtagttaat gattaacccg ccatgctact tatctacgta gccatgctct   180
aggaagatcg gaattcgccc ttaagccttc agattaaaaa taactaaggt aagggccatg   240
tgggtagggg aggtggtgtg agacggtcct gtctctcctc tatctgccca tcggccttt    300
ggggaggagg aatgtgccca aggactaaaa aaaggccctg gagccagagg ggcgagggca   360
gcagaccttt catgggcaaa cctcagggct gctgtcgatc ggcctgcccg agaccaaacg   420
tgcggaacgt agttaagtgt tagaggtagg atttgaagcc tgtcgatcat tctgattctc   480
cttttctcta cgtctgcttc ctgtcaatgg gcatcctcac tgtcaaatgc agatggtaca   540
gcagggcttg gtctcagcca ggcaggcctc tccccagtct ccatggctca gctgtccagc   600
agtttcatcc ctagaccatc ccaaacatgg ttgagaagct ctgagggag gacccagcac   660
tgcccggccc ctgaagataa tcagcagtcc tgctcagcat atcaatccaa gcccactcta   720
gacagagatg ccggtgccca gttttctatt tttaactggt gtgaactgaa ggaaaagcac   780
agcattagaa gtccaagcag tcatggagaa gacccacctt gcagatgtcc tcactggggc   840
tggcagagcc ggcaacctgc ctaaggctgc tcagtccatt aggagccaagt agcctggaag   900
atgtctttac ccccagcatc agttcaagtg gagcagcaca taactcttgc cctctgcctt   960
ccaagattct ggtgctgaga cttatggagt gtcttggagg ttgccttctg ccccccaacc  1020
ctgctcccag ctgccctcc caggcctggg ttgctggcct ctgctttatc aggattctca   1080
agagggacag ctggtttatg ttgcatgact gttccctgca tatctgctct ggtttaaaat   1140
agcttatctg agcagctgga ggaccacatg gcttatatg gcgtggggta catgttcctg   1200
tagccttgtc cctggcacct gccaaaatag cagccaacac ccccacccc caccgccatc   1260
cccctgcccc acccgtcccc tgtcgcacat tcctccctcc gcagggctgg ctcaccaggc   1320
cccagcccac atgcctgctt aaagccctct ccatcctctg cctcacccag tccccgctga  1380
gactgagcag acgcctccag cggccgcccg ccaccatggc tgaaaaagcg gggtctacat   1440
tttcacacct tctggttcct attcttctcc tgattggctg gatcatcata   1500
tgatttatgt tgtcttctct tagaagcttt ggatccaatc aacctctgga ttacaaaatt   1560
tgtgaaagat tgactggtat tcttaactat gttgctcctt tacgctatg tggatacgct   1620
gctttaatgc ctttgtatca tgctattgct tcccgtatgg cttcatttt ctcctccttg   1680
tataaatcct ggttgctgtc tctttatgag gagttgtggc cgttgtcag gcaacgtggc   1740
gtggtgtgca ctgtgtttgc tgacgcaacc cccactggtt ggggcattgc caccacctgt   1800
cagctccttt ccgggacttt cgctttcccc ctccctattg ccacggcgga actcatcgcc   1860
gcctgccttg cccgctgctg acagggct cggcgttgg gcactgacaa ttccgtggtg     1920
ttgtcgggga aatcatcgtc ctttccttgg ctgctcgcct gtgttgccac ctggattctg   1980
cgcgggacgt ccttctgcta cgtcccttcg gccctcaatc cagcggacct tccttcccgc   2040
ggcctgctgc cggctctgcg gcctcttccg cgtcttcgag atctgcctcg actgtgcctt   2100
```

```
ctagttgcca gccatctgtt gtttgccct ccccgtgcc ttccttgacc ctggaaggtg    2160
ccactcccac tgtcctttcc taataaaatg aggaaattgc atcgcattgt ctgagtaggt    2220
gtcattctat tctgggggt ggggtggggc aggacagcaa gggggaggat tgggaagaca    2280
atagcaggca tgctggggac tcgagttaag ggcgaattcc cgattaggat cttcctagag    2340
catggctacg tagataagta gcatggcggg ttaatcatta actacaagga acccctagtg    2400
atggagttgg ccactccctc tctgcgcgct cgctcgctca ctgaggccgg gcgaccaaag    2460
gtcgcccgac gcccgggctt tgcccggggcg gcctcagtga gcgagcgagc gcgcag       2516

SEQ ID NO: 67            moltype = DNA   length = 2694
FEATURE                  Location/Qualifiers
misc_feature             1..2694
                         note = Recombinant expression cassette or expression
                          cassette component
source                   1..2694
                         mol_type = other DNA
                         organism = synthetic construct
SEQUENCE: 67
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact    120
agggggttcct tgtagttaat gattaacccg ccatgctact tatctacgta gccatgctct    180
aggaagatcg gaattcgccc ttaagccttc agattaaaaa taactaaggt aagggccatg    240
tgggtagggg aggtggtgtg agacggtcct gtctctcctc tatctgccca tcggcccttt    300
ggggaggagg aatgtgccca aggactaaaa aaaggccctg gagccagagg ggcgagggca    360
gcagaccttt catgggcaaa cctcagggct gctgtcaact ggcctgcccg agaccaaacg    420
tgcggaacgt agttaagtgt tagaggtagg atttgaagcc tgtcgatcat tctgattctc    480
cttttctcta cgtctgcttc ctgtcaatgg gcatcctcac tgtcaaatgc agatggtaca    540
gcagggcttg gtctcagcca ggcaggcctc tccccagtct ccatggctca gctgtccagc    600
agtttcatcc ctagaccatc ccaaacatgt tgagaagct ctgaggggag acccagcac     660
tgcccggccc ctgaagataa tcagcagtcc tgctcagcat atcaatccaa gcccactcta    720
gacagagatg ccggtgccca gttttctatt tttaactgct gtgaactgga ggaaaagcac    780
agcattagaa gtccaagcag tcatggagaa gacccacctt gcagatgtcc tcactgggc    840
tggcagagcc ggcaacctgc ctaaggctgc tcagtccatt aggagccagt agcctggaag    900
atgtctttac ccccagcatc agttcaagtg gagcagcaca taactcttgc cctctgcctt    960
ccaagattct ggtgctgaga cttatggagt gtcttggagg ttgcctttg ccccccaacc    1020
ctgctcccag ctgcccctcc caggcctggg ttgctggcct ctgctttatc aggattctca    1080
agagggacag ctggtttatg ttgcatgact gttccctgca tatctgctct ggttttaaat    1140
agcttatctg agcagctgga ggaccacatg ggcttatatg gcgtggggta catgttcctg    1200
tagccttgtc cctggcacct gccaaaatag cagccaacac ccccaccc caccgccatc      1260
cccctgcccc accgtcccc tgtcgcacat tcctccctcc gcagggctgg ctcaccaggc    1320
cccagcccac atgcctgctt aaagccctct ccatcctctg cctcacccag tccccgctga    1380
gactgagcag acgcctccat aactggtaag taccgcctat agactctata ggcacacccc    1440
tttggctctt atgcatgctg acagactaac agactgttcc tttcctgggt cttttctgca    1500
ggcctgtacg gaagtgttac ttctgctcta aaagctgcag aattgtaccc gcggccgatc    1560
caatcgatac agatctagcg gccgccgcc accatggctg aaaaagcggg gtctacttt     1620
tcacaccttc tggttcctat tcttctcctg attggctgga ttgtgggctg catcataatg    1680
atttatgttg tcttctctta gaagctttgg atccaatcaa cctctggatt acaaatttg    1740
tgaaagattg actggttttc ttaactatgt tgctcctttt acgctatgtg gatacgctgt    1800
tttaatgcct ttgtatcatg ctattgcttc ccgtatggct ttcatttct cctccttgta     1860
taaatcctgg ttgctgtctc tttatgagga gttgtggccc gttgtcaggc aacgtggcgt    1920
ggtgtgcact gtgtttgctg acgcaacccc cactggttgg ggcattgcca ccacctgtca    1980
gctccttcc gggactttcg cttccccct ccctattgcc acggcggaac tcatcgccgc     2040
ctgccttgcc cgctgctgga caggggctcg gctgttgggc actgacaatt ccgtggtgtt    2100
gtcggggaaa tcatcgtcct ttccttggct gtcgcctgt gttgccacct ggattctgcg    2160
cgggacgtcc ttctgctacg tcccttcggc cctcaatcca gcggaccttc cttcccgcgg    2220
cctgctgccg tctctgcggc ctcttccgcg tcttcgagat ctgcctcgac tgtgccttct    2280
agttgccagc catctgttgt ttgccctcc ccgtgcctt ccttgaccct ggaaggtgcc      2340
actcccactg tcctttccta ataaaatgag gaaattgcat cgcattgtct gagtaggtgt    2400
cattctattc tgggggtgg ggtggggcag gacagcaagg gggaggattg ggaagacaat     2460
agcaggcatg ctggggactc gagttaaggg cgaattcccg attaggatct tcctagagca    2520
tggctacgta gataagtagc atggcggtt aatcattaca caaggaaac ccctagtgat      2580
ggagttggcc actccctctc tgcgcgctcg ctcgctcact gaggccggc gaccaaaggt     2640
cgcccgacgc ccgggctttg cccggggcgg ctcagtgagc gagcgagcgc gcag          2694

SEQ ID NO: 68            moltype = DNA   length = 2100
FEATURE                  Location/Qualifiers
misc_feature             1..2100
                         note = Recombinant expression cassette or expression
                          cassette component
source                   1..2100
                         mol_type = other DNA
                         organism = synthetic construct
SEQUENCE: 68
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact    120
agggggttcct tgtagttaat gattaacccg ccatgctact tatctacgta gccatgctct    180
aggaagatcg gaattcgccc ttaaggtcat ggagaagacc caccttgcag atgtcctcac    240
tggggctggc agaccggca acctgcctaa ggctgctcag tccattagga gccagtagcc    300
tggaagatgt ctttaccccc agcatcagtt caagtggagc agcacataac tcttgccctc    360
tgccttccaa gattctggtg ctgagactta tggagtgtct tggaggttgc cttctgcccc    420
```

```
ccaaccctgc tcccagctgg ccctcccagg cctgggttgc tggcctctgc tttatcagga    480
ttctcaagag ggacagctgg tttatgttgc atgactgttc cctgcatatc tgctctggtt    540
ttaaatagct tatctgagca gctggaggac cacatgggct tatatggcgt ggggtacatg    600
ttcctgtagc cttgtccctg gcacctgcca aaatagcagc caacacccc caccccac      660
gccatcccc tgcccacc gtcccctgtc gcacattcct ccctccgcag ggctggctca      720
ccaggcccca gcccacatgc ctgcttaaag ccctctccat cctctgcctc acccagtccc    780
cgctgagact gagcagacgc ctccataact ggtaagtacc gcctatagac tctataggca    840
cacccctttg gctcttatgc atgctgacag actaacagac tgttcctttc ctgggtcttt    900
tctgcaggcc tgtacggaag tgttacttct gctctaaaag ctgcggaatt gtacccgcgg    960
ccgatccaat cgatacagat ctagcggccg cccgccacca tggctgaaaa agcggggtct   1020
acattttcac accttctggt tcctattctt ctcctgattg gctggattgt gggctgcatc   1080
ataatgattt atgttgtctt ctcttagaag ctttggatcc aatcaacctc tggattacaa   1140
aatttgtgaa agattgactg gtattcttaa ctatgttgct ccttttacgc tatgtggata   1200
cgctgcttta atgcctttgt atcatgctat tgctccgt atggctttca ttttctcctc     1260
cttgtataaa tcctggttgc tgtctcttta tgaggagttg tggcccgttg tcaggcaacg   1320
tggcgtggtg tgcactgtgt ttgctgacgc aaccccact ggttgggca ttgccaccac     1380
ctgtcagctc ctttccggga cttcgctttc cccctccct attgccacgg cggaactcat   1440
cgccgcctgc cttgcccgct gctggacagg ggctccggctg ttgggcactg acaattcgt   1500
ggtgttgtcg gggaaatcat cgtcccttcc ttggctgctc gcctgtgttg ccacctggat   1560
tctgcgcggg acgtccttct gctacgtccc ttcggccctc aatccagcgg accttccttc   1620
ccgcggcctg ctgccggctc tgcggcctct tccgcgtctt cgagatctgc ctcgactgtg   1680
ccttctagtt gccagccatc tgttgtttgc ccctccccg ctcttcctt gaccctggaa    1740
ggtgccactc ccactgtcct ttcctaataa aatgaggaaa ttgcatcgca ttgtctgagt   1800
aggtgtcatt ctattctggg gggtggggtg gggcaggaca gcaagggga ggattgggaa    1860
gacaatagca ggcatgctgg ggactcgagt taagggcgaa ttcccgatta ggatcttcct   1920
agagcatggc tacgtagata agtagcatgg cgggttaatc attaactaca aggaaccct    1980
agtgatggag ttggccactc cctctctgcg cgctcgctcg ctcactgagg ccgggcgacc   2040
aaaggtcgcc cgacgcccgg gctttgcccg ggcggcctca gtgagcgagc gagcgcgcag   2100

SEQ ID NO: 69         moltype = DNA   length = 2694
FEATURE               Location/Qualifiers
misc_feature          1..2694
                      note = Recombinant expression cassette or expression
                       cassette component
source                1..2694
                      mol_type = other DNA
                      organism = synthetic construct
SEQUENCE: 69
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagaactg gcctgcccga ccaaacgt gcggaacgta      240
gttaagtgtt agaggtagga tttgaagcct gtcgatcatt gtgattctcc ttttctctac    300
gtctgcttcc tgtcaatggg catcctcact gtcaaatgca gatggtacag cagggcttgg    360
tctcagccag gcaggcctct ccccagtctc catggctcag ctgtccagca gtttcatccc    420
tagaccatcc caaacatggt tgagaagctc tgaggggagg acccagcact gcccggcccc    480
tgaagataat cagcagtcct gctcagcata tcaatccaag cccactctag acagagatgc    540
cggtgcccag ttttctattt ttaactggtg tgaactgaag gaaaagcaca gcattagaag    600
tccaagcacc ttcagattaa aaataactaa ggtaagggcc atgtgggtag ggaggtggt    660
gtgagacggt cctgtctctc ctctatctgc ccatcggccc tttggggagg aggaatgtgc    720
ccaaggacta aaaaaaggcc ctggaaggcag aggggcaggg gcagcagacc tttcatgggc    780
aaacctcagg gctgctgtcg tcatggagaa gacccacctt gcagatgtcc tcactgggc     840
tggcagagcc ggcaacctgc ctaaggctgc tcagtccatt aggagccagt agcctggaag    900
atgtcttttac ccccagcatc agttcaagtg agcagcaca taactcttgc cctctgcctt    960
ccaagattct ggtgctgaga cttatggagt gtcttggaga ttgccttctg ccccccaacc   1020
ctgctcccag ctgccctcc caggcctggg ttgctggcct ctgctttatc aggattctca    1080
agagggacag ctggtttatg ttgcatgact gttcctgca tatctgctct ggttttaaat    1140
agcttatctg agcagctgga ggaccacatg ggcttatatg gcgtgggta catgttcctg    1200
tagccttgtc cctggcacct gccaaaatag cagccaacac cccacccc caccgccatc     1260
ccctgccc accgtcccc tgtcgcacat tccctccgca gggctgg ctcaccaggc         1320
cccagcccac atgcctgctt aaagccctct ccatcctctg cctcacccag tcccgctga    1380
gactgagcag acgcctccat aactggtaag taccgcctat agactctata ggcacacccc   1440
tttggctctt atgcatgctg acagactaac agactgttcc tttcctgggt cttttctgca   1500
ggcctgtacg gaagtgttac ttctgctcta aaagctgcgg aattgtaccc gcggccgatc    1560
caatcgatac agatctagcg gccgccgcc accatggctg aaaaagcggg gtctacatt     1620
tcacacccttc tggttcctat tcttctcctg attggctgga ttgtgggctg catcataatg   1680
atttatgttg tcttctctta gaagctttgg atccaatcaa cctctggatt acaaaatttg   1740
tgaaagattg actggtattc ttaactatgt tgctcctttt acgctatgtg gatacgctgc   1800
tttaatgcct ttgtatcatg ctattgcttc ccgtatggct ttcattttct cctccttgt    1860
taaatcctgg ttgctgtctc tttatgagga gttgtggccc gttgtcaggc aacgtggcgt   1920
ggtgtgcact gtgtttgctg acgcaacccc cactggttgg ggcattgcca ccacctgtca   1980
gctcctttcc gggactttcg ctttccccct cctattgcc acgcggaac tcatcgccgc     2040
ctgccttgcc cgctgctgga cagggctccg ctgttgggc actgacaatt ccgtggtgtt    2100
gtcggggaaa tcatcgtcct tccttggct gctcgcctgt gttgccacct ggattctgc     2160
cgggacgtcc ttctgctacg tcccttcggc cctcaatcca gcgaccttc cttcccgcgg    2220
cctgctgccg gtctctgcggc ctcttccgcg tcttcgagat ctgcctcgac tgtgccttct   2280
agttgccagc catctgttgt ttgcccctcc ccgtgcctt ccttgaccct ggaaggtgcc    2340
actcccactg tcctttccta ataaaatgag gaaattgcat cgcattgtct gagtaggtgt   2400
cattctattc tgggggtgg ggtggggcag acagcaagg ggaggattg ggaagacaat     2460
```

```
agcaggcatg ctgggactc gagttaaggg cgaattcccg attaggatct tcctagagca  2520
tggctacgta gataagtagc atggcgggtt aatcattaac tacaaggaac ccctagtgat  2580
ggagttggcc actccctctc tgcgcgctcg ctcgctcact gaggccgggc gaccaaaggt  2640
cgcccgacgc ccgggctttg cccggcggc ctcagtgagc gagcgagcgc gcag         2694
```

SEQ ID NO: 70          moltype = DNA   length = 2694
FEATURE                Location/Qualifiers
misc_feature           1..2694
                       note = Recombinant expression cassette or expression
                        cassette component
source                 1..2694
                       mol_type = other DNA
                       organism = synthetic construct
SEQUENCE: 70

```
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagaactg gcctgcccga gccaaacgt gcggaacgta  240
gttaagtgtt agaggtagga tttgaagcct gtcgatcatt ctgattctcc tttctctac  300
gtctgcttcc tgtcaatggg catcctcact gtcaaatgca gatggtacag cagggcttgg  360
tctcagccag gcaggcctct ccccagtctc catggctcag ctgtccagca gtttcatccc  420
tagaccatcc caaacatggt tgagaagctc tgaggggagg acccagcagt gcccggcccc  480
tgaagataat cagcagtcct gctcagcata tcaatccaag cccactctag acagagatgc  540
cggtgcccga ttttctattt ttaactggtg tgaactgaag gaaaagcaca gcattagaag  600
tccaagcacc ttcagattaa aaataactaa ggtaagggcc atgtgggtag gggaggtggt  660
gtgagacggt cctgtctctc ctctatctgc ccatcgtgcc tttgggggag aggaatgtgc  720
ccaaggacta aaaaaaggcc ctggagccag aggggcgagg gcagcagacc tttcatgggc  780
aaacctcagg gctgctgtcg tcatggagaa gacccacctt gcagatgtcc tcactgggc   840
tggcagagcc ggcaacctgc ctaaggctgc tcagtccatt aggagccagt agcctggaag  900
atgtctttac ccccagcatc agttcaagtg gagcagcaca taactcttgc cctctgcctt  960
ccaagattct ggtgctgaga cttatggagt gtcttggagg ttgccttctg cccccaacc  1020
ctgctcccag ctgccctcc caggcctggg ttgctggcct ctgctttatc aggattctca  1080
agagggacag ctggtttatg ttgcatgact gttccctgca tatctgctct ggttttaaat  1140
agcttatctg agcagctgga ggaccacatg ggcttatatg gcgtggggta catgttcctg  1200
tagccttgtc cctggcacct gccaaaatag cagccaacac cccccacccc caccgccatc  1260
ccctgcccc accgtccc tgtcgcacat tcctccctcc gcagggctgg ctcaccaggc  1320
cccagcccac atgcctgctt aaagccctct ccatcctctg cctcacccag tcccgctga   1380
gactgagcag acgcctccat aactggtaag taccgctat agactctata ggcacacccc  1440
tttggctctt atgcatgctg acagataac agactgttcc tttcctgggt cttttctgca  1500
ggcctgtacg gaagtgttac ttctgctcta aaagctgcgg aattgtaccc cgggccgatc  1560
caatcgatac agatctagcg gccgccgcc accatggctg aaaaagcggg gtctacattt  1620
tcacaccttc tggttcctat tcttctcctg attggctgga ttgtgggctg catcataatg  1680
atttatgttg tcttctctta gaagctttgg atccaatcaa cctctggatt acaaaatttg  1740
tgaaagattt actggtattc ttaactatgt tgctcctttt acgctatgtg gatacgctgc  1800
tttaatgcct ttgtatcatg ctattgcttc ccgtatggct ttcatttct cctccttgta  1860
taaatcctgg ttgctgtctc tttatgagga gttgtggccc gttgtcaggc aacgtggcgt  1920
ggtgtgcact gtgtttgctg acgcaacccc cactggttgg ggcattgcca ccacctgtca  1980
gctcctttcc gggactttcg ctttcccct cctattgcc acggcggaac tcatcgccgc  2040
ctgccttgcc cgctgctgga caggggctcg gctgttgggc actgacaatt ccgtggtgtt  2100
gtcggggaaa tcatcgtcct ttccttggct gctcgcctgt gttgccacct ggattctgcg  2160
cgggacgtcc ttctgctacg tcccttcggc cctcaatcca gcggaccttc cttcccgcgg  2220
cctgctgccg gctctgcggc ctcttccgcg tcttcgagat ctgcctcgac tgtgccttct  2280
agttgccagc catctgttgt ttgccccctc ccgtgcctt ccttgaccct ggaaggtgcc  2340
actcccactg tcctttccta ataaaatgag gaaattgcat cgcattgtct gagtaggtgt  2400
cattctattc tggggggtgg ggtggggcag gacagcaagg ggaggattg ggaagacaat  2460
agcaggcatg ctgggactc gagttaaggg cgaattcccg attaggatct tcctagagca  2520
tggctacgta gataagtagc atggcgggtt aatcattaac tacaaggaac ccctagtgat  2580
ggagttggcc actccctctc tgcgcgctcg ctcgctcact gaggccgggc gaccaaaggt  2640
cgcccgacgc ccgggctttg cccggcggc ctcagtgagc gagcgagcgc gcag         2694
```

SEQ ID NO: 71          moltype = DNA   length = 2291
FEATURE                Location/Qualifiers
misc_feature           1..2291
                       note = Recombinant expression cassette or expression
                        cassette component
source                 1..2291
                       mol_type = other DNA
                       organism = synthetic construct
SEQUENCE: 71

```
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagccttc agattaaaaa taactaaggt aagggccatg  240
tgggtagggg aggtggtgtg acgggtcct gtctctcctc tatctgccca tcgtgccca   300
ggggaggagg aatgtgccca aggactaaaa aaggccctg gagccagagg ggcgagggca  360
gcagaccttt catgggcaaa cctcaggct ctgtcgtca tggagaagac ccaccttgca  420
gatgtcctca ctgggctgg cagagccggc aacctgccta aggctgctca gtccattagg  480
agccagtagc ctggaagatg tctttacccc cagcatcagt tcaagtggag cagcacataa  540
ctcttgccct ctgccttcca agattctggt gctgagactt atggagtgtc ttggaggttg  600
```

-continued

```
cctcctgccc cccaaccctg ctcccagctg gccctcccag gcctggggttg ctggcctctg  660
ctttatcagg attctcaaga gggacagctg gtttatgttg catgactgtt ccctgcatat  720
ctgctctggt tttaaatagc ttatctgagc agctggagga ccacatgggc ttatatggcg  780
tggggtacat gttcctgtag ccttgtccct ggcacctgcc aaaatagcag ccaacacccc  840
ccaccccac cgccatcccc ctgccccacc cgtcccctgt cgcacattcc tccctccgca  900
gggctggctc accaggcccc agcccacatg cctgcttaaa gccctctcca tcctctgcct  960
cacccagtcc ccgctgagac tgagcagacg cctccataac tggtaagtac cgcctataga 1020
ctctataggc acacccttt ggctcttatg catgctgaca gactaacaga ctgttccttt 1080
cctgggtctt ttctgcaggc ctgtacggaa gtgttacttc tgctctaaaa gctgcggaat 1140
tgtaccccgcg gccgatccaa tcgatacaga tctagcggcc gcccgccacc atggctgaaa 1200
aagcggggtc tacatttttca cacccttctgg ttcctattct tctcctgatt ggctggattg 1260
tgggctgcat cataatgatt tatgttgtct tctcttagaa gctttggatc caatcaacct 1320
ctggattaca aaatttgtga aagattgact ggtattctta actatgttgc tccttttacg 1380
ctatgtggat acgctgcttt aatgcctttg tatcatgcta ttgcttccg tatggcttc 1440
attttctcct ccttgtataa atcctggttg ctgtctcttt atgaggagtt gtggcccgtt 1500
gtcaggcaac gtggcgtggt gtgcactgtg tttgctgacg caaccccccac tggttggggc 1560
attgccacca cctgtcagct cctttccggg actttcgctt tcccctccc tattgccacg 1620
gcggaactca tcgccgctg ccttgcccgc tgctggacag ggctcggctc gttgggcact 1680
gacaattccg tggtgttgtc gggaaatca tcgtcctttc cttggctgct cgcctgtgtt 1740
gccacctgga ttctgcgcgg gacgtccttc tgctacgtcc cttcggccct caatccagcg 1800
gaccttcctt cccgcggcct gctgccggct ctgcggcctc ttccgcgtct tcgagatctg 1860
cctcgactgt gcctttctagt tgccagccat ctgttgtttg ccctccccc gtgccttcct 1920
tgaccctgga aggtgccact cccactgtcc tttcctaata aaatgaggaa attgcatcgc 1980
attgtctgag taggtgtcat tctattctgg ggggtggggt ggggcaggac agcaaggggg 2040
aggattggga agacaaatag caggcatgct gggactcga ttaagggcga attcccgatt 2100
aggatcttcc tagagcatgg ctacgtagat aagtagcat gcgggttaat cattaactac 2160
aaggaaccccc tagtgatgga gttggccact ccctctctgc gcgctcgctc gctcactgag 2220
gccgggcgac caaaggtcgc ccgacgcccg ggctttgccc gggcggcctc agtgagcgag 2280
cgagcgcgca g                                                     2291
```

| SEQ ID NO: 72 | moltype = DNA   length = 1922 |
|---|---|
| FEATURE | Location/Qualifiers |
| misc_feature | 1..1922 |
| | note = Recombinant expression cassette or expression cassette component |
| source | 1..1922 |
| | mol_type = other DNA |
| | organism = synthetic construct |

SEQUENCE: 72
```
ctgcgcgctc gctcgctcac tgaggccgcc cgggcaaagc ccgggcgtcg gcgacctttt   60
ggtcgcccgg cctcagtgag cgagcgagcg cgcagagagg gagtgccaa ctccatcact  120
agggggttcct tgtagttaat gattaacccg ccatgctact tatctacgta gccatgctct  180
aggaagatcg gaattcgccc ttaaggtcat ggagaagacc caccttgcag atgtcctcac  240
tggggctggc agagccggca acctgcctaa ggctgctcag tccattagga gccagtagcc  300
tggaagatgt ctttaccccc agcatcagtt caagtggagc agcacataac tcttgccctc  360
tgccttccaa gattctggtg ctgagactta tggagtgtct tggaggttgc cttctgcccc  420
ccaaccctgc tcccagctgg ccctcccagg cctgggttgc tggcctctg ttttatcagga  480
ttctcaagag ggacagctgg tttatgttgc atgactgttc cctgcatatc tgctctggtt  540
ttaaatagct tatctgagca gctggaggac cacatgggct tatatggcgt ggggtacatg  600
ttcctgtagc cttgtccctg gcacctgcca aaatagcagc caacacccccc accccccacc  660
gccatccccc tgccccaccc gtccctgtc gcacattccc tccgcag gctggctcca  720
ccaggcccca gcccacatgc ctgcttaaag ccctctccat cctctgcctc acccagtccc  780
cgctgagact gagcagacgc ctccagcgg cgcccgccac catggccgag aaggccggat  840
ctaccttcag ccacctgctg gtcccttattc tgctgctgat cggctggatc gtgggctgca  900
tcatcatgat ctacgtggt ttcagctgaa agctttgat ccaatcaacc tctggattac  960
aaaatttgtg aaagattgac tggtattctt aactatgttg ctccttttac gctatgtgga 1020
tacgctgctt taatgccttt gtatcatgct attgcttccc gtatggcttt cattttctcc 1080
tccttgtata atcctggttg ctgtctctt tatgaggagt tgtggcccgt tgtcaggcaa 1140
cgtggcgtgg tgtgcactgt gtttgctgac gcaaccccca ctggttgggg cattgccacc 1200
acctgtcagc tccttttcgg gactttcgct ttcccctcc tattgccac ggcggaactc 1260
atcgccgcct gccttgcccg ctgctggaca ggggctcggc tgttgggcac tgacaattcc 1320
gtggtgttgt cggggaaatc atcgtccttt ccttggctgc tcgcctgtgt tgccacctgg 1380
attctgcgcg ggacgtcctt ctgctacgtc ccttcggccc tcaatccagc ggaccttcct 1440
tcccgcggcc tgctgccggc tctgcggcct ttccgcgtct tcgagatct gcctcgactg 1500
tgccttctag ttgccagcca tctgttgttt gccctccccc gtgccttcct tgaccctgga 1560
aggtgccac tcccactgtc ctttcctaat aaaatgagga aattgcatcg cattgtctga 1620
gtaggtgtca ttctattctg ggggtgggg tgggcagga cagcaagggg gaggattggg 1680
aagacaatag caggcatgct gggactcga gttaagggcga aattcccgat taggatcttc 1740
ctagagcatg gctacgtaga taagtagcat ggcgggttaa tcattaacta caaggaaccc 1800
ctagtgatgg agttggccac tccctctctg cgcgctcgct cgctcactga ggccgggcga 1860
ccaaaggtcg cccgacgccc gggctttgcc cgggcggcct cagtgagcga gcgagcgcgc 1920
ag                                                               1922
```

| SEQ ID NO: 73 | moltype = DNA   length = 3871 |
|---|---|
| FEATURE | Location/Qualifiers |
| misc_feature | 1..3871 |
| | note = Recombinant expression cassette or expression cassette component |
| source | 1..3871 |

```
                        mol_type = other DNA
                        organism = synthetic construct
SEQUENCE: 73
ctgcgcgctc gctcgctcac tgaggccgcc cgggcaaagc ccgggcgtcg ggcgaccttt   60
ggtcgccgg  cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagccttc agattaaaaa taactaaggt aagggccatg  240
tgggtagggg aggtggtgtg agacggtcct gtctctcctc tatctgccca tcggcccttt  300
ggggaggagg aatgtgccca aggactaaaa aaaggccctg gagccagagg ggcgagggca  360
gcagacccttt catgggcaaa cctcagggct gctgtcgtca tggagaagac ccaccttgca  420
gatgtcctca ctggggctgg cagagccggc aacctgccta aggctgctca gtccattagg  480
agccagtagc ctgaaagatg tctttacccc cagcatcagt tcaagtggag cagcacataa  540
ctcttgccct ctgccttcca agattctggt gctgagactt atggagtgtc ttggaggttg  600
ccttctgccc cccaaccctg ctcccagctg gccctcccag gcctgggttg ctggcctcga  660
ctttatcagg attctcaaga gggacagctg gtttatgttg catgactgtt ccctgcatat  720
ctgctctggt tttaaaatag cttatctgag cagctggagg accacatggg ttatatggcg  780
tggggtacat gttcctgtag ccttgtccct ggcacctgcc aaaatagcag ccaacacccc  840
ccaccccacc cgccatcccc ctgccccacc cgtccccctgt cgcacattcc tccctccgca  900
gggctggctc accaggcccc agcccacatg cctgcttaaa gccctctcca tcctctgcct  960
cacccagtcc ccgctgagac tgagcagacg cctccataac tggtaagtac cgcctataga 1020
ctctataggc acacccctttt ggctcttatg catgctgaca gactaacaga ctgttccttt 1080
cctgggtctt ttctgcaggc ctgtacggaa gtgttacttc tgtctaaaa gctgcggaat 1140
tgtacccgcg gccgatccaa tcgatacaga tctagcggcc gccgccacc atggctaaa  1200
aagcggggtc tacattttca caccttctgg ttcctattct tctcctgatt ggctggattg 1260
tgggctgcat cataatgatt tatgttgtct tctcttagaa gctttggatc caatcaacct 1320
ctggattaca aaatttgtga aagattgact tgtattctta actatgttgc tccttttacg 1380
ctatgtggat acgctgcttt aatgcctttg tatcatgcta ttgcttcccg tatggctttc 1440
attttctcct ccttgtataa atcctggttg ctgtctctttt atgaggagtt gtggcccgtt 1500
gtcaggcaac gtggcgtggt gtgcactgtg tttgctgacg caaccccac tggttggggc 1560
attgccacca cctgtcagct cctttccggg actttcgctt tcccccctccc tattgccacg 1620
gcggaactca tcgccgcctg ccttgcccgc tgctgacag gggctcggct gttgggcact 1680
gacaattccg tggtgttgtc ggggaaatca tcgtcctttc cttggctgct cgcctgtgtt 1740
gccacctgga ttctgcgcgg gacgtccttc tgctacgtcc cttcggccct caatccagcg 1800
gaccttcctt cccgcggcct gctgccggct ctgccgcctc ttccgcgtct tcgagatctg 1860
cctcgactgt gccttctagt tgccagccat ctgttgtttg ccctctcccc gtgccttcct 1920
tgaccctgga aggtgccact cccactgtcc tttcctaata aaatgaggaa attgcatcgc 1980
attgtctgag taggtgtcat tctattctgg ggggtggggt ggggcaggac agcaagggg  2040
aggattggga agacaaatagc aggcatgctg gggactcgag ttaagggcag ccagaagtca 2100
gatgctcaag gggcttcatg atgtccccat aattttttgc agaaggaaaa agatcggatc 2160
ctcaggcgta gttcaccccg tcctcgaggc cgcccgggtc gactaaaaaa cctcccacac 2220
ctcccccctga acctgaaaca taaaatgaat gcaattgttg ttgttaactt gtttattgca 2280
gcttataatg gttacaaata aagcaatagc atcacaaatt tcacaaataa agcatttttt 2340
tcactgcatt ctagttgtgg tttgtccaaa ctcatcaatg tatcttatca tgtctggatc 2400
cgcgcggccg tcagctgaac caccgtaga tcatgatgat gcagcccacg atccagccga 2460
tcagcagcag aatagggacc agcaggtggc tgaaggtaga tccggccttc tcggccatgg 2520
tggcggctag cctatagtga gtcgtattaa gtactctagc cttaagagct gtaattgaac 2580
tgggatgga  cacctgtgga gagaaaggca aagtggatgt cagtaagacc aataggtgcc 2640
tatcagaaac gcaagagtct tctctgtctc gacaagccca gttttctattg gtctccttaa 2700
acctgtcttg taaccttgat acttacctgc ccagtgcctc acgaccaact tctgcagctt 2760
aagttcgaga ctgttgtgtc agaagcactg actgcgttag caatttaact gtgataaact 2820
accgcaataa agctctagag cttcggggat cgtcccacgg agcggtgggt ccgggtgtca 2880
gtctgggaag ggctccttgg ggggcagagg ctttaaggtc ccccggcgc ccaccccggg 2940
gcgggcagag ccagcaggaa tgtgcccggc gcccagagag gaatgcaaca cttgtgagct 3000
gctattttgg cagcagcggc cccggccccc tccgtgctcc cccttccccc acaggagccc 3060
atataagccc aagctattgt gtggcctcag agttttgcta ttttaaaccc gtcggacgga 3120
gatacgtgag tgcccgaggg gctgacacaa gccagccagc tgtcacctcc caggggctggg 3180
gacgctgata aggcagcgct tcggacccga ccctctgccg cagccccaga tgctgtcatg 3240
tgaaagccca gactgctttt atccctgctt ggacttctaa tgctgtgctt ttccttcagt 3300
tcacaccagt taaaaataga aaactgggca ccggcatctc tgtctagagt gggcttggat 3360
tgatatgctc agcaggactg ctgattatct tcaggggccg gcagtgctg ggtcctcccc 3420
tcagagcttc tcaaccatgt ttgggatggt ctagggatga aactgctgga cagctgagcc 3480
atggagactg gggagaggcc tgcctggctg agaccaagcc ctgctgtacc atctgcattt 3540
gacagtgagg atgcccattg acaggaagca gacgtagaga aaaggagaat cagaatgatc 3600
gacaggcttc aaatcctacc tctaacactt aactacgttc gcacgtttg gtctcgggca 3660
ggccagttga attcccgatt aggatcttcc tagagcatgg ctacgtagat aagtagcatg 3720
gcgggtaat  cattaactac aaggaacccc tagtgatgga gttggccact ccctctctgc 3780
gcgctcgctc gctcactgag gccgggcgac caaaggtcgc ccgacgcccg gctttgccc  3840
gggcggcctc agtgagcgag cgagcgcgca g                                3871

SEQ ID NO: 74           moltype = DNA  length = 3871
FEATURE                 Location/Qualifiers
misc_feature            1..3871
                        note = Recombinant expression cassette or expression
                        cassette component
source                  1..3871
                        mol_type = other DNA
                        organism = synthetic construct
SEQUENCE: 74
ctgcgcgctc gctcgctcac tgaggccgcc cgggcaaagc ccgggcgtcg ggcgaccttt   60
```

```
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattcgccc ttaagccttc agattaaaaa taactaaggt aagggccatg  240
tgggtagggg aggtggtgtg agacggtcct gtctctcctc tatctgccca tcggcccttt  300
ggggaggagg aatgtgccca aggactaaaa aaaggccctg gagccagagg ggcgagggca  360
gcagaccttt catgggcaaa cctcagggct gctgtcgtca tggagaagac ccaccttgca  420
gatgtcctca ctggggctgg cagagccggc aacctgccta aggctgctca gtccattagg  480
agccagtagc ctgaagatgt tctttacccc cagcatcagt tcaagtggag cagcacataa  540
ctcttgccct ctgccttcca agattctggt gctgagactt atggagtgtc ttggaggttg  600
ccttctgccc cccaaccctg ctcccagctg gccctcccag gcctgggttg ctggcctctg  660
ctttatcagg attctcaaga gggacagctg gtttatgttg catgactgtt ccctgcatat  720
ctgctctggt tttaaatagc ttatctgagc agctggagga ccacatgggc ttatatggcg  780
tggggtacat gttcctgtag ccttgtccct ggcacctgcc aaaatagcag ccaacacccc  840
ccaccccccac cgccatcccc ctgccccacc cgtccccctgt cgcacattcc tccctccgca  900
gggctggctc accaggcccc agcccacatg cctgcttaaa gccctctcca tcctctgcct  960
cacccagtcc ccgctgagac tgagcagacg cctccataac tggtaagtac cgcctataga  1020
ctctataggc acacccccttt ggctcttatg catgctgaca gactaacaga ctgttccttt  1080
cctgggtctt ttctgcaggc ctgtacggaa gtgttacttc tgctctaaaa gctgcggaat  1140
tgtacccgcg gccgatccaa tcgatacaga tctagcggcc gccgccacc atggctaaa  1200
aagcgggggtc tacattttca caccttctgg ttcctattct tctcctgatt ggctggattg  1260
tgggctgcat cataatgatt tatgttgtct tctcttagaa gctttggatc caatcaacct  1320
ctggattaca aaatttgtga aagattgact ggtattctta actatgttgc tccttttacg  1380
ctatgtggat acgctgcttt aatgcctttg tatcatgcta ttgcttcccg tatggctttc  1440
atttttctcct ccttgtataa atcctggttg ctgtctctttt atgaggagtt gtggcccgtt  1500
gtcaggcaac gtgcgtggt gtgcactgtg tttgctgacg caacccccac tggttggggc  1560
attgccacca cctgtcagct cctttccggg actttcgctt tccccctccc tattgccacg  1620
gcggaactca tcgccgcctg ccttgcccgc tgctgacaga gggctcggtg gttgggcact  1680
gacaattccg tggtgttgtc ggggaaatca tcgtcctttc cttggctgct cgcctgtgtt  1740
gccacctgga ttctgcgcgg gacgtccttc tgctacgtcc cttcggccct caatccagcg  1800
gacctctctt cccgcggcct gctgccggct ctgcggcctc ttccgcgtct tcgagatctg  1860
cctcgactgt gccttctagt tgccagccat ctgttgtttg cccctccccc gtgccttcct  1920
tgaccctgga aggtgccact cccactgtcc tttcctaata aaatgaggaa attgcatcgc  1980
attgtctgag taggtgtcat tctattctgg ggggtgggggt ggggcaggac agcaaggggg  2040
aggattggga agacaatagc aggcatgctg gggactcgag ttaagggcag ccagaagtca  2100
gatgctcaag gggcttcatg atgtccccat aattttttgc agaggggaaaa agatcggatc  2160
ctcaggcgta gttcaccccg tcctcgaggc cgcccgggtc gactaaaaaa cctcccacac  2220
ctccccctga acctgaaaca taaaatgaat gcaattgttg ttgttaaact ggcctgcccg  2280
agaccaaacg tgcggaacgt agttaagtgt tagaggtagg atttgaagcc tgtcgatcat  2340
tctgattctc ctttttctcta cgtctcgttc ctgtcaatgg gcatcctcac tgtcaaatgc  2400
agatggtaca gcagggcttg gtctcagcca ggcaggcctc tccccagtct ccatggctca  2460
gctgtccagc agtttcatcc ctagaccatc ccaaacatgg ttgagaagct ctgagggag  2520
gacccagcac tgcccggccc ctgaagataa tcagcagtcc tgctcagcat atcaatccaa  2580
gccactcta gacagagatg ccggtgccca gttttctatt tttaactggt gtgaactgaa  2640
ggaaaagcac agcattagaa gtccaagcag ggataaaagc agtctgggct tcacatgac  2700
agcatctggg gctgcggcag agggtcgggt ccgaagcgct gccttatcag cgtccccagc  2760
cctgggaggt gacagctggc tggcttgtgt cagcccctcg ggcactcacg tatctccgtc  2820
cgacggtttt aaaatagcaa aactctgagg ccacacaata gcttgggctt atatgggctc  2880
ctgtgggga aggggagca cggagggggc cggggccgc gctgccaaaa tagcagctca  2940
caagtgttgc attcctctct gggcgccggg cacattcctg ctggctctgc ccgccccggg  3000
gtgggcgccg gggggaccctt aaagcctctg ccccccaagg agcccttccc agacagccgc  3060
cggcacccac cgctccgtgg gacgatcccc gaagctctag agtttattg cggtagttta  3120
tcacagttaa attgctaacg cagtcagtgc ttctgacaca acagtctcga acttaagctg  3180
cagaagttgg tcgtgaggca ctgggcaggt aagtatcaag gttacaagac aggtttaagg  3240
agaccaatag aaactgggct tgtcgagaca gagaagactc ttgcgtttct gataggcacc  3300
tattgtcttt actgacatcc actttgcctt tctctccaca ggtgtccact cccagttcaa  3360
ttacagctct taaggctaga gtacttaata cgactcacta taggctagcc gccaccatgg  3420
ccgagaaggc cggatctacc ttcgccacc tgctggtccc tattctgctg ctgatcggct  3480
ggatcgtggg ctgcatcatc atgatctacg tggtgttcag ctgacggccg cgcggatcca  3540
gacatgataa gatacattga tgagtttgga caaaccacaa ctagaatgca gtgaaaaaaa  3600
tgctttattt gtgaaatttg tgatgctatt gctttatttg taaccattat aagctgcaat  3660
aaacaagtga attcccgatt aggatcttcc tagagcatgg ctacgtagat aagtagcatg  3720
gcgggtaat cattaactac aaggaacccc tagtgatgga gttggccact ccctctctgc  3780
gcgctcgctc gctcactgag gccgggcgac caaaggtcgc ccgacgcccg gctttgccc  3840
gggcggcctc agtgagcgag cgagcgcgca g  3871
```

SEQ ID NO: 75 moltype = DNA length = 3862
FEATURE Location/Qualifiers
misc_feature 1..3862
  note = Recombinant expression cassette or expression cassette component
source 1..3862
  mol_type = other DNA
  organism = synthetic construct
SEQUENCE: 75

```
ctgcgcgctc gctcgctcac tgaggccgcc cgggcaaagc ccgggcgtcg gcgaccttt   60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatcg gaattctccc cagcatgcct gctattgtct tcccaatcct ccccttgct   240
gtcctgcccc accccacccc ccagaataga atgcacccta ctcagacaat gcgatgcaat  300
```

```
ttcctcattt tattaggaaa ggacagtggg agtggcacct tccagggtca aggaaggcac    360
gggggagggg caaacaacag atggctggca actagaaggc acagtcgagg cagatctcga    420
agacgcggaa gaggccgcag agccggcagc aggccgcggg aaggaaggtc cgctggattg    480
agggccgaag ggacgtagca gaaggacgtc ccgcgcagaa tccaggtggc aacacaggcg    540
agcagccaga gaaaggacga tgatttcccc gacaacacca cggaattgtc agtgccaac    600
agccgagccc ctgtccagca gcgggcaagg caggcggcga tgagttccgc cgtggcaata    660
gggagggga aagcgaaagt cccggaaagg agctgacagg tggtggcaat gccccaacca    720
gtggggggttg cgtcagcaaa cacagtgcac accacgccac gttgcctgac aacgggccac    780
aactcctcat aaagagacag caaccaggat ttatacaagg aggagaaaat gaaagccata    840
cgggaagcaa tagcatgata caaaggcatt aaagcagcgt atccacatag cgtaaaagga    900
gcaacatagt taagaatacc agtcaatctt tcacaaattt tgtaatccag aggttgattg    960
gatccaaagc ttctaagaga agacaacata aatcattatg atgcagccca caatccagcc   1020
aatcaggaga agaataggaa ccagaaggtg tgaaaatgta gaccccgctt tttcagccat   1080
ggtggcgggg ggccgctaga tctgtatcga ttggatcggc cgcgggtaca attccgcagc   1140
ttttagagca gaagtaacac ttccgtacag gcctgcagaa aagacccagg aaaggaacag   1200
tctgttagtc tgtcagcatg cataagagcc aaaggggtgt gcctatagag tctataggcg   1260
gtacttacca gttatggagg cgtctgctca gtctcagcgg ggactgggtg aggcagagga   1320
tggagagggc tttaagcagg catgtgggct ggggcctggt gagccagccc tgcggaggga   1380
ggaatgtgcg acaggggacg ggtggggcag ggggatggcg gtgggggtgg ggggtgttgg   1440
ctgctatttt ggcaggtgcc agggacaagg ctacaggaac atgtaccca cgccatataa   1500
gcccatgtgg tcctccagct gctcagataa gctatttaaa accagagcag atatgcaggg   1560
aacagtcatg caacataaac cagctgtccc tcttgagaat cctgataaag cagaggccag   1620
caacccaggc ctgggagggc cagctgggag cagggttggg gggcagaagg caacctccaa   1680
gacactccat aagtctcagc accagaatct tggaaggcag agggcaagag ttatgtgctg   1740
ctccacttga actgatgctg ggggtaaaga catcttccag gctactggct cctaatggac   1800
tgagcagcct taggcaggtt gccggctctg ccagccccag tgaggacatc tgcaaggtgg   1860
gtcttctcca tgacgacagc agccctgagg tttgccatg aaaggtctgc tgccctcgcc   1920
cctctggctc cagggccttt ttttagtcct tgggcacatt cctcctcccc aaagggccga   1980
tgggcagata gaggagagac aggaccgtct cacaccacct cccctaccca catggccctt   2040
accttagtta tttttaatct gaaggctcga gttaagggca gccagaagtc agatgctcaa   2100
ggggcttcat gatgtcccca taattttggg cagagggaaa aagatcggat cctcaggcgt   2160
agttcaccc gtcctcgagg ccgcccgggt cgactaaaaa acctcccaca cctcccctg   2220
aacctgaaac ataaaatgaa tgcaattgtt gttgttaaac tggcctgccc gagaccaaac   2280
gtgcggaacg tagttaagtg ttagaggtag gatttgaagc ctgtcgatca ttctgattct   2340
cctttttctct acgtctgctt cctgtcaatg ggcatcctca ctgtcaaatg cagatggtac   2400
agcagggctt ggtctcagcc aggcaggcct ctccccagtc tccatggctc agctgtccag   2460
cagtttcatc cctagaccat cccaaacatg gttgagaagc tctgagggga ggacccagca   2520
ctgcccggcc cctgaagata atcagcagtc ctgctcagca tatcaatcca agcccactct   2580
agacagagat gccggtgccc agttttctat ttttaactgg tgtgaactga aggaaaagca   2640
cagcattaga agtccaagca gggataaaag cagtctgggc tttcacatga cagcatctgg   2700
ggctgcggca gagggtcggg tccgaagcgc tgccttatca gcgtcccag ccctgggagg   2760
tgacagctgg ctggcttgtg tcagcccctc gggcactcac gtatctccgt ccgacgggtt   2820
taaaatagca aaactctgag gccacacaat agcttgggct tatatgggct cctgtgggga   2880
aaggggggagc acgaggggg ccggggccgc tgctgccaaa atagcagctc acaagtgttg   2940
cattcctctc tgggcgccgg gcacattcct gctggctctg cccgcccgg ggtgggcgcc   3000
gggggggacct taaagcctct gccccccaag gagcccttcc cagacagccg ccggcaccca   3060
ccgctccgtg ggacgatccc cgaagctcta gagctttatt cggtagttt atcacagtta   3120
aattgctaac gcagtcagtg cttctgacac aacagtctcg aacttaagct gcagaagttg   3180
gtcgtgaggc actgggcagg taagtatcaa ggttacaaga caggtttaag gagaccaata   3240
gaaactgggc ttgtcgagac agagaagact cttgcgtttc tgataggcac ctattggtct   3300
tactgacatc cactttgcct ttctctccac aggtgtccac tcccagttca attacagctc   3360
ttaaggctag agtacttaat acgactcact ataggctagc cgccaccatg gccgagaagg   3420
ccggatctac cttcagccac ctgctggtcc ctattctgct gctgatcggc tggatcgtgg   3480
gctgcatcat catgatctac gtggtgttca gctgacggcc gcgcggatcc agacatgata   3540
agatacattg atgagtttgg acaaaccaca actagaatgc agtgaaaaaa atgcttttatt  3600
tgtgaaattt gtgatgctat tgctttattt gtaaccatta taagctgcaa taaacaagtg   3660
aattcccgat taggatcttc ctagagcatg gctacgtaga taagtagcat ggcgggttaa   3720
tcattaacta caaggaaccc ctagtgatgg agttggccac tccctctctg cgcgctcgct   3780
cgctcactga ggccgggcga ccaaaggtcg cccgacgccc gggctttgcc cgggcggcct   3840
cagtgagcga gcgagcgcgc ag                                             3862

SEQ ID NO: 76          moltype = DNA  length = 105
FEATURE                Location/Qualifiers
misc_feature           1..105
                       note = Recombinant expression cassette or expression
                       cassette component
source                 1..105
                       mol_type = other DNA
                       organism = synthetic construct
SEQUENCE: 76
atggccgaga aggaatctac cagccccac ctgatggtgc ctattctgct gctggtgggc    60
tggatcgtcg gctgcatcat cgtgatctac atcgtgttct tctga                   105

SEQ ID NO: 77          moltype = DNA  length = 108
FEATURE                Location/Qualifiers
misc_feature           1..108
                       note = Recombinant expression cassette or expression
                       cassette component
source                 1..108
```

```
                            mol_type = other DNA
                            organism = synthetic construct
SEQUENCE: 77
atggccgaga aggccggatc taccttcagc cacctgctgg tccctattct gctgctgatc    60
ggctggatcg tgggctgcat catcatgatc tacgtggtgt tcagctga               108

SEQ ID NO: 78              moltype = DNA   length = 403
FEATURE                    Location/Qualifiers
misc_feature               1..403
                            note = Recombinant expression cassette or expression
                             cassette component
source                     1..403
                            mol_type = other DNA
                            organism = synthetic construct
SEQUENCE: 78
aactggcctg cccgagacca aacgtgcgga acgtagttaa gtgttagagg taggatttga    60
agcctgtcga tcattctgat tctccttttc tctacgtctg cttcctgtca atgggcatcc   120
tcactgtcaa atgcagatgg tacagcaggg cttggtctca gccaggcagg cctctcccca   180
gtctccatgg ctcagctgtc cagcagtttt atccctagac catcccaaac atggttgaga   240
agctctgagg ggaggaccca gcactgcccg gccctgaag ataatcagca gtcctgtca    300
gcatatcaat ccaagcccac tctagacaga gatgccggtg cccagttttc tatttttaac   360
tggtgtgaac tgaaggaaaa gcacagcatt agaagtccaa gca                    403

SEQ ID NO: 79              moltype = DNA   length = 191
FEATURE                    Location/Qualifiers
misc_feature               1..191
                            note = Recombinant expression cassette or expression
                             cassette component
source                     1..191
                            mol_type = other DNA
                            organism = synthetic construct
SEQUENCE: 79
ccttcagatt aaaaataact aaggtaaggg ccatgtgggt aggggaggtg gtgtgagacg    60
gtcctgtctc tcctctatct gcccatcggc cctttgggga ggaggaatgt gcccaaggac   120
taaaaaaagg ccctggagcc agaggggcga gggcagcaga cctttcatgg gcaaacctca   180
gggctgctgt c                                                       191

SEQ ID NO: 80              moltype = DNA   length = 96
FEATURE                    Location/Qualifiers
misc_feature               1..96
                            note = Recombinant expression cassette or expression
                             cassette component
source                     1..96
                            mol_type = other DNA
                            organism = synthetic construct
SEQUENCE: 80
gtaagtaccg cctatagact ctataggcac accccttttgg ctcttatgca tgctgacaga    60
ctaacagact gttcctttcc tgggtctttt ctgcag                             96

SEQ ID NO: 81              moltype = DNA   length = 133
FEATURE                    Location/Qualifiers
misc_feature               1..133
                            note = Recombinant expression cassette or expression
                             cassette component
source                     1..133
                            mol_type = other DNA
                            organism = synthetic construct
SEQUENCE: 81
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                     133

SEQ ID NO: 82              moltype =    length =
SEQUENCE: 82
000

SEQ ID NO: 83              moltype =    length =
SEQUENCE: 83
000

SEQ ID NO: 84              moltype =    length =
SEQUENCE: 84
000

SEQ ID NO: 85              moltype =    length =
SEQUENCE: 85
000

SEQ ID NO: 86              moltype =    length =
```

-continued

| | | |
|---|---|---|
| SEQUENCE: 86 000 | | |
| SEQ ID NO: 87 SEQUENCE: 87 000 | moltype = | length = |
| SEQ ID NO: 88 SEQUENCE: 88 000 | moltype = | length = |
| SEQ ID NO: 89 SEQUENCE: 89 000 | moltype = | length = |
| SEQ ID NO: 90 SEQUENCE: 90 000 | moltype = | length = |
| SEQ ID NO: 91 SEQUENCE: 91 000 | moltype = | length = |
| SEQ ID NO: 92 SEQUENCE: 92 000 | moltype = | length = |
| SEQ ID NO: 93 SEQUENCE: 93 000 | moltype = | length = |
| SEQ ID NO: 94 SEQUENCE: 94 000 | moltype = | length = |
| SEQ ID NO: 95 SEQUENCE: 95 000 | moltype = | length = |
| SEQ ID NO: 96 SEQUENCE: 96 000 | moltype = | length = |
| SEQ ID NO: 97 SEQUENCE: 97 000 | moltype = | length = |
| SEQ ID NO: 98 SEQUENCE: 98 000 | moltype = | length = |
| SEQ ID NO: 99 SEQUENCE: 99 000 | moltype = | length = |
| SEQ ID NO: 100 SEQUENCE: 100 000 | moltype = | length = |
| SEQ ID NO: 101 SEQUENCE: 101 000 | moltype = | length = |
| SEQ ID NO: 102 SEQUENCE: 102 000 | moltype = | length = |
| SEQ ID NO: 103 SEQUENCE: 103 000 | moltype = | length = |
| SEQ ID NO: 104 SEQUENCE: 104 000 | moltype = | length = |
| SEQ ID NO: 105 SEQUENCE: 105 000 | moltype = | length = |

| | | |
|---|---|---|
| SEQ ID NO: 106<br>SEQUENCE: 106<br>000 | moltype = | length = |
| SEQ ID NO: 107<br>SEQUENCE: 107<br>000 | moltype = | length = |
| SEQ ID NO: 108<br>SEQUENCE: 108<br>000 | moltype = | length = |
| SEQ ID NO: 109<br>SEQUENCE: 109<br>000 | moltype = | length = |
| SEQ ID NO: 110<br>SEQUENCE: 110<br>000 | moltype = | length = |
| SEQ ID NO: 111<br>SEQUENCE: 111<br>000 | moltype = | length = |
| SEQ ID NO: 112<br>SEQUENCE: 112<br>000 | moltype = | length = |
| SEQ ID NO: 113<br>SEQUENCE: 113<br>000 | moltype = | length = |
| SEQ ID NO: 114<br>SEQUENCE: 114<br>000 | moltype = | length = |
| SEQ ID NO: 115<br>SEQUENCE: 115<br>000 | moltype = | length = |
| SEQ ID NO: 116<br>SEQUENCE: 116<br>000 | moltype = | length = |
| SEQ ID NO: 117<br>SEQUENCE: 117<br>000 | moltype = | length = |
| SEQ ID NO: 118<br>SEQUENCE: 118<br>000 | moltype = | length = |
| SEQ ID NO: 119<br>SEQUENCE: 119<br>000 | moltype = | length = |
| SEQ ID NO: 120<br>SEQUENCE: 120<br>000 | moltype = | length = |
| SEQ ID NO: 121<br>SEQUENCE: 121<br>000 | moltype = | length = |
| SEQ ID NO: 122<br>SEQUENCE: 122<br>000 | moltype = | length = |
| SEQ ID NO: 123<br>SEQUENCE: 123<br>000 | moltype = | length = |
| SEQ ID NO: 124<br>SEQUENCE: 124<br>000 | moltype = | length = |
| SEQ ID NO: 125<br>SEQUENCE: 125<br>000 | moltype = | length = |

```
SEQ ID NO: 126          moltype =    length =
SEQUENCE: 126
000

SEQ ID NO: 127          moltype =    length =
SEQUENCE: 127
000

SEQ ID NO: 128          moltype =    length =
SEQUENCE: 128
000

SEQ ID NO: 129          moltype =    length =
SEQUENCE: 129
000

SEQ ID NO: 130          moltype =    length =
SEQUENCE: 130
000

SEQ ID NO: 131          moltype =    length =
SEQUENCE: 131
000

SEQ ID NO: 132          moltype =    length =
SEQUENCE: 132
000

SEQ ID NO: 133          moltype =    length =
SEQUENCE: 133
000

SEQ ID NO: 134          moltype =    length =
SEQUENCE: 134
000

SEQ ID NO: 135          moltype =    length =
SEQUENCE: 135
000

SEQ ID NO: 136          moltype =    length =
SEQUENCE: 136
000

SEQ ID NO: 137          moltype =    length =
SEQUENCE: 137
000

SEQ ID NO: 138          moltype =    length =
SEQUENCE: 138
000

SEQ ID NO: 139          moltype =    length =
SEQUENCE: 139
000

SEQ ID NO: 140          moltype =    length =
SEQUENCE: 140
000

SEQ ID NO: 141          moltype =    length =
SEQUENCE: 141
000

SEQ ID NO: 142          moltype =    length =
SEQUENCE: 142
000

SEQ ID NO: 143          moltype = AA  length = 736
FEATURE                 Location/Qualifiers
source                  1..736
                        mol_type = protein
                        note = Dependoparvovirus Adeno-associated virus serotype 9
                        organism = unidentified
SEQUENCE: 143
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
```

```
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 144          moltype = AA  length = 724
FEATURE                 Location/Qualifiers
source                  1..724
                        mol_type = protein
                        note = Dependoparvovirus Adeno-associated virus serotype 5
                        organism = unidentified
SEQUENCE: 144
MSFVDHPPDW LEEVGEGLRE FLGLEAGPPK PKPNQQHQDQ ARGLVLPGYN YLGPGNGLDR    60
GEPVNRADEV AREHDISYNE QLEAGDNPYL KYNHADAEFQ EKLADDTSFG GNLGKAVFQA   120
KKRVLEPFGL VEEGAKTAPT GKRIDDHFPK RKKARTEEDS KPSTSSDAEA GPSGSQQLQI   180
PAQPASSLGA DTMSAGGGGP LGDNNQGADG VGNASGDWHC DSTWMGDRVV TKSTRTWVLP   240
SYNNHQYREI KSGSVDGSNA NAYFGYSTPW GYFDFNRFHS HWSPRDWQRL INNYWGFRPR   300
SLRVKIFNIQ VKEVTVQDST TTIANNLTST QVFTDDDYQ LPYVVGNGTE GCLPAFPPQV    360
FTLPQYGYAT LNRDTENPT ERSSFFCLEY FPSKMLRTGN NFEFTYNFEE VPFHSSFAPS    420
QNLFKLANPL VDQYLYRFVS TNNTGGVQFN KNLAGRYANT YKNWFPGPMG RTQGWNLGSG   480
VNRASVSAFA TTNRMELEGA SYQVPPQPNG MTNNLQGSNT YALENTMIFN SQPANPGTTA   540
TYLEGNMLIT SESETQPVNR VAYNVGGQMA TNNQSSTTAP ATGTYNLQEI VPGSVWMERD   600
VYLQGPIWAK IPETGAHFHP SPAMGGFGLK HPPPMMLIKN TPVPGNITSF SDVPVSSFIT   660
QYSTGQVTVE MEWELKKENS KRWNPEIQYT NNYNDPQFVD FAPDSTGEYR TTRPIGTRYL   720
TRPL                                                               724

SEQ ID NO: 145          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 145
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT ISQVNGRPRD LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 146          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 146
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDSQAVG RSSFYCLEYF PSQMLRTGNN FQFSYEFENV    420
PFHSSYAHSQ SLDRLMNPLI DQYLYYLSKT IGYHKGAAQ LKFSVAGPSN MAVQGRNYIP    480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 147          moltype = AA  length = 736
FEATURE                 Location/Qualifiers
REGION                  1..736
```

```
                            note     = Recombinant AAV Capsid Protein
source                      1..736
                            mol_type = protein
                            organism = synthetic construct
SEQUENCE: 147
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVSYQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 148              moltype = AA   length = 736
FEATURE                     Location/Qualifiers
REGION                      1..736
                            note     = Recombinant AAV Capsid Protein
source                      1..736
                            mol_type = protein
                            organism = synthetic construct
SEQUENCE: 148
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSMVNQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 149              moltype = AA   length = 736
FEATURE                     Location/Qualifiers
REGION                      1..736
                            note     = Recombinant AAV Capsid Protein
source                      1..736
                            mol_type = protein
                            organism = synthetic construct
SEQUENCE: 149
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQANYGQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 150              moltype = AA   length = 736
FEATURE                     Location/Qualifiers
REGION                      1..736
                            note     = Recombinant AAV Capsid Protein
source                      1..736
                            mol_type = protein
                            organism = synthetic construct
SEQUENCE: 150
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
```

```
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNVGTQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 151          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 151
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IGYHKSGAAQ LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQNVSYQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 152          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 152
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNLNSM LIWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 153          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 153
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNQDAS LLWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 154          moltype = AA  length = 736
FEATURE                 Location/Qualifiers
REGION                  1..736
                        note = Recombinant AAV Capsid Protein
source                  1..736
                        mol_type = protein
                        organism = synthetic construct
```

```
SEQUENCE: 154
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNGMS FTWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 155          moltype = AA   length = 736
FEATURE                 Location/Qualifiers
REGION                  1..736
                        note = Recombinant AAV Capsid Protein
source                  1..736
                        mol_type = protein
                        organism = synthetic construct
SEQUENCE: 155
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGYHKSGAAQ LKFSVAGPSN MAVQGRNYIP   480
GPSYRQQRVS TTVTQNNSE FAWPGASSWA LNGRNSLMNP GPAMASHKEG EDRFFPLSGS   540
LIFGKQGTGR DNVDADKVMI TNEEEIKTTN PVATESYGQV ATNHQANYGQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 156          moltype = AA   length = 736
FEATURE                 Location/Qualifiers
REGION                  1..736
                        note = Recombinant AAV Capsid Protein
source                  1..736
                        mol_type = protein
                        organism = synthetic construct
SEQUENCE: 156
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGYHKSGAAQ LKFSVAGPSN MAVQGRNYIP   480
GPSYRQQRVS TTVTQNQDAS LLWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 157          moltype = AA   length = 736
FEATURE                 Location/Qualifiers
REGION                  1..736
                        note = Recombinant AAV Capsid Protein
source                  1..736
                        mol_type = protein
                        organism = synthetic construct
SEQUENCE: 157
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGYHKSGAAQ LKFSVAGPSN MAVQGRNYIP   480
GPSYRQQRVS TTVTQNNGMS FTWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
```

```
YSEPRPIGTR YLTRNL                                                          736

SEQ ID NO: 158            moltype = AA  length = 736
FEATURE                   Location/Qualifiers
REGION                    1..736
                          note = Recombinant AAV Capsid Protein
source                    1..736
                          mol_type = protein
                          organism = synthetic construct
SEQUENCE: 158
MAADGYLPDW LEDNLSEGIR EWWALKPGAP QPKANQQHQD NARGLVLPGY KYLGPGNGLD      60
KGEPVNAADA AALEHDKAYD QQLKAGDNPY LKYNHADAEF QERLKEDTSF GGNLGRAVFQ     120
AKKRLLEPLG LVEEAAKTAP GKKRPVEQSP QEPDSSAGIG KSGAQPAKKR LNFGQTGDTE     180
SVPDPQPIGE PPAAPSGVGS LTMASGGGAP VADNNEGADG VGSSSGNWHC DSQWLGDRVI     240
TTSTRTWALP TYNNHLYKQI SNSTSGGSSN DNAYFGYSTP WGYFDFNRFH CHFSPRDWQR     300
LINNNWGFRP KRLNFKLFNI QVKEVTDNNG VKTIANNLTS TVQVFTDSDY QLPYVLGSAH     360
EGCLPPPPAD VFMIPQYGYL TLNDGSQAVG RSSFYCLEYF PSQMLRTGNN FQFSYEFENV     420
PFHSSYAHSQ SLDRLMNPLI DQYLYYLSKT INGSGQNQQT LKFSVAGPSN MAVQGRNYIP     480
GPSYRQQRVS TTVTQNLNSM LIWPGASSWA LNGRNSLMNP GPAMASHKEG EDRFFPLSGS     540
LIFGKQGTGR DNVDADKVMI TNEEEIKTTN PVATESYGQV ATNHQANYGQ AQTGWVQNQG     600
ILPGMVWQDR DVYLQGPIWA KIPHTDGNFH PSPLMGGFGM KHPPPQILIK NTPVPADPPT     660
AFNKDKLNSF ITQYSTGQVS VEIEWELQKE NSKRWNPEIQ YTSNYYKSNN VEFAVNTEGV     720
YSEPRPIGTR YLTRNL                                                    736

SEQ ID NO: 159            moltype = AA  length = 726
FEATURE                   Location/Qualifiers
REGION                    1..726
                          note = Recombinant AAV Capsid Protein
source                    1..726
                          mol_type = protein
                          organism = synthetic construct
SEQUENCE: 159
MSFVDHPPDW LEEVGEGLRE FLGLEAGPPK PKPNQQHQDQ ARGLVLPGYN YLGPGNGLDR      60
GEPVNRADEV AREHDISYNE QLEAGDNPYL KYNHADAEFQ EKLADDTSFG GNLGKAVFQA     120
KKRVLEPFGL VEEGAKTAPT GKRIDDHFPK RKKARTEEDS KPSTSSDAEA GPSGSQQLQI     180
PAQPASSLGA DTMSAGGGGP LGDNNQGADG VGNASGDWHC DSTWMGDRVV TKSTRTWALP     240
TYNNHLYKQI SNSTSGGSSN DNAYFGYSTP WGYFDFNRFH CHFSPRDWQR LINNNWGFRP     300
KRLNFKLFNI QVKEVTDNNG VKTIANNLTS TVQVFTDSDY QLPYVLGSAH EGCLPPFPAD     360
VFMIPQYGYL TLNDGSQAVG RSSFYCLEYF PSQMLRTGNN FQFSYEFENV PFHSSYAHSQ     420
SLDRLMNPLI DQYLYYLSKT INGSGQNQQT LKFSVAGPSN MAVQGRNYIP GPSYRQQRVS     480
TTVTQNNNSE FAWPGASSWA LNGRNSLMNP GPAMASHKEG EDRFFPLSGS LIFGKQGTGR     540
DNVDADKVMI TNEEEIKTTN PVATESYGQV ATNHQSAQAQ AQTGWVQNQG ILPGMVWQDR     600
DVYLQGPIWA KIPHTDGNFH PSPLMGGFGM KHPPPQILIK NTPVPADPPT AFNKDKLNSF     660
ITQYSTGQVS VEIEWELQKE NSKRWNPEIQ YTNNYNDPQF VDFAPDSTGE YRTTRPIGTR     720
YLTRPL                                                               726

SEQ ID NO: 160            moltype = AA  length = 725
FEATURE                   Location/Qualifiers
REGION                    1..725
                          note = Recombinant AAV Capsid Protein
source                    1..725
                          mol_type = protein
                          organism = synthetic construct
SEQUENCE: 160
MAADGYLPDW LEDNLSEGIR EWWALKPGAP QPKANQQHQD NARGLVLPGY NYLGPGNGLD      60
RGEPVNRADE VAREHDISYN EQLEAGDNPY LKYNHADAEF QEKLADDTSF GGNLGKAVFQ     120
AKKRVLEPFG LVEEGAKTAP TGKRIDDHFP KRKKARTEED SKPSTSSDAE AGPSGSQQLQ     180
IPAQPASSLG ADTMSAGGGG PLGDNNQGAD GVGNASGDWH CDSTWMGDRV VTKSTRTWVL     240
PSYNNHQYRE IKSGSVDGSN ANAYFGYSTP WGYFDFNRFH SHWSPRDWQR LINNYWGFRP     300
RSLRVKIFNI QVKEVTVQDS TTTIANNLTS TVQVFTDDDY QLPYVVGNGT EGCLPAFPPQ     360
VFTLPQYGYA TLNRDNTENP TERSSFFCLE YFPSKMLRTG NNFEFTYNFE EVPFHSSFAP     420
SQNLFKLANP LVDQYLYRFV STNNTGGVQF NKNLAGRYAN TYKNWFPGPM GRTQGWNLGS     480
GVNRASVSAF ATTNRMELEG ASYQVPPQPN GMTNNLQGSN TYALENTMIF NSQPANPGTT     540
ATYLEGNMLI TSESETQPVN RVAYNVGGQM ATNNQSSTTA PATGTYNLQE IVPGSVWMER     600
DVYLQGPIWA KIPETGAHFH PSPAMGGFGL KHPPPMMLIK NTPVPGNITS FSDVPVSSFI     660
TQYSTGQVTV EMEWELKKEN SKRWNPEIQY TSNYYKSNNV EFAVNTEGVY SEPRPIGTRY     720
LTRNL                                                                725

SEQ ID NO: 161            moltype = AA  length = 725
FEATURE                   Location/Qualifiers
REGION                    1..725
                          note = Recombinant AAV Capsid Protein
source                    1..725
                          mol_type = protein
                          organism = synthetic construct
SEQUENCE: 161
MSFVDHPPDW LEEVGEGLRE FLGLEAGPPK PKPNQQHQDQ ARGLVLPGYN YLGPGNGLDR      60
GEPVNRADEV AREHDISYNE QLEAGDNPYL KYNHADAEFQ EKLADDTSFG GNLGKAVFQA     120
KKRVLEPFGL VEEAAKTAPT GKRIDDHFPK RKKARTEEDS KPSTSSDAEA GPSGSQQLQI     180
```

```
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTDNNGV KTIANNLTST VQVFTDSDYQ LPYVLGSAHE GCLPPFPADV  360
FMIPQYGYLT LNDGSQAVGR SSFYCLEYFP SQMLRTGNNF QFSYEFENVP FHSSYAHSQS  420
LDRLMNPLID QYLYYLSKTI NGSGQNQQTL KFSVAGPSNM AVQGRNYIPG PSYRQQRVST  480
TVTQNNNSEF AWPGASSWAL NGRNSLMNPG PAMASHKEGE DRFFPLSGSL IFGKQGTGRD  540
NVDADKVMIT NEEEIKTTNP VATESYGQVA TNHQSAQAQA QTGWVQNQGI LPGMVWQDRD  600
VYLQGPIWAK IPHTDGNFHP SPLMGGFGMK HPPPQILIKN TPVPADPPTA FNKDKLNSFI  660
TQYSTGQVSV EIEWELQKEN SKRWNPEIQY TSNYYKSNNV EFAVNTEGVY SEPRPIGTRY  720
LTRNL                                                             725

SEQ ID NO: 162           moltype = AA  length = 727
FEATURE                  Location/Qualifiers
REGION                   1..727
                         note = Recombinant AAV Capsid Protein
source                   1..727
                         mol_type = protein
                         organism = synthetic construct
SEQUENCE: 162
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QEKLADDTSF GGNLGKAVFQ  120
AKKRVSKEPFG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWLGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV SVEIEWELQK ENSKRWNPEI QYTSNYYKSN NVEFAVNTEG VYSEPRPIGT  720
RYLTRNL                                                           727

SEQ ID NO: 163           moltype = AA  length = 736
FEATURE                  Location/Qualifiers
REGION                   1..736
                         note = Recombinant AAV Capsid Protein
source                   1..736
                         mol_type = protein
                         organism = synthetic construct
SEQUENCE: 163
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVT VEMEWELKKE NSKRWNPEIQ YTNNYNDPQF VDFAPDSTGE  720
YRTTRPIGTR YLTRPL                                                 736

SEQ ID NO: 164           moltype = AA  length = 726
FEATURE                  Location/Qualifiers
REGION                   1..726
                         note = Recombinant AAV Capsid Protein
source                   1..726
                         mol_type = protein
                         organism = synthetic construct
SEQUENCE: 164
MSFVDHPPDW LEEVGEGLRE FLGLEAGPPK PKPNQQHQDQ ARGLVLPGYN YLGPGNGLDR   60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSFAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                            726

SEQ ID NO: 165           moltype = AA  length = 726
FEATURE                  Location/Qualifiers
```

```
REGION                      1..726
                            note = Recombinant AAV Capsid Protein
source                      1..726
                            mol_type = protein
                            organism = synthetic construct
SEQUENCE: 165
MSFVDHPPDW LEEVGEGLRE FLGLEAGPPK PKPNQQHQDQ ARGLVLPGYN YLGPGNGLDR   60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSQWLGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTSNYYKSNN VEFAVNTEGV YSEPRPIGTR  720
YLTRNL                                                            726

SEQ ID NO: 166              moltype = AA  length = 726
FEATURE                     Location/Qualifiers
REGION                      1..726
                            note = Recombinant AAV Capsid Protein
source                      1..726
                            mol_type = protein
                            organism = synthetic construct
SEQUENCE: 166
MSFVDHPPDW LEEVGEGLRE FLGLEAGPPK PKPNQQHQDQ ARGLVLPGYN YLGPGNGLDR   60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSQWLGDRVI TTSTRTWALP  240
TYNNHLYKQI SNSTSGGSSN DNAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
SLDRLMNPLI DQYLYYLSKT INGSGQNQQT LKFSVAGPSN MAVQGRNYIP GPSYRQQRVS  480
TTVTQNNNSE FAWPGASSWA LNGRNSLMNP GPAMASHKEG EDRFFPLSGS LIFGKQGTGR  540
DNVDADKVMI TNEEEIKTTN PVATESYGQV ATNHQSAQAQ AQTGWVQNQG ILPGMVWQDR  600
DVYLQGPIWA KIPHTDGNFH PSPLMGGFGM KHPPPQILIK NTPVPADPPT AFNKDKLNSF  660
ITQYSTGQVS VEIEWELQKE NSKRWNPEIQ YTNNYNDPQF VDFAPDSTGE YRTTRPIGTR  720
YLTRPL                                                            726

SEQ ID NO: 167              moltype = AA  length = 727
FEATURE                     Location/Qualifiers
REGION                      1..727
                            note = Recombinant AAV Capsid Protein
source                      1..727
                            mol_type = protein
                            organism = synthetic construct
SEQUENCE: 167
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWMGDRV ITTSTRTWAL  240
PTYNNHLYKQ ISNSTSGGSS NDNAYFGYST PWGYFDFNRF HCHFSPRDWQ RLINNNWGFR  300
PKRLNFKLFN IQVKEVTDNN GVKTIANNLT STVQVFTDSD YQLPYVLGSA HEGCLPPFPA  360
DVFMIPQYGY LTLNDGSQAV GRSSFYCLEY FPSQMLRTGN NFQFSYEFEN VPFHSSYAHS  420
QSLDRLMNPL IDQYLYYLSK TINGSGQNQQ TLKFSVAGPS NMAVQGRNYI PGPSYRQQRV  480
STTVTQNNNS EFAWPGASSW ALNGRNSLMN PGPAMASHKE GEDRFFPLSG SLIFGKQGTG  540
RDNVDADKVM ITNEEEIKTT NPVATESYGQ VATNHQSAQA QAQTGWVQNQ GILPGMVWQD  600
RDVYLQGPIW AKIPHTDGNF HPSPLMGGFG MKHPPPQILI KNTPVPADPP TAFNKDKLNS  660
FITQYSTGQV TVEMEWELKK ENSKRWNPEI QYTSNYYKSN NVEFAVNTEG VYSEPRPIGT  720
RYLTRNL                                                           727

SEQ ID NO: 168              moltype = AA  length = 726
FEATURE                     Location/Qualifiers
REGION                      1..726
                            note = Recombinant AAV Capsid Protein
source                      1..726
                            mol_type = protein
                            organism = synthetic construct
SEQUENCE: 168
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QEKLADDTSF GGNLGKAVFQ  120
AKKRVLEPFG LVEEGAKTAP TGKRIDDHFP KRKKARTEED SKPSTSSDAE AGPSGSQQLQ  180
IPAQPASSLG ADTMSAGGGG PLGDNNQGAD GVGNASGDWH CDSTWMGDRV VTKSTRTWVL  240
PSYNNHQYRE IKSGSVDGSN ANAYFGYSTP WGYFDFNRFH CHFSPRDWQR LINNNWGFRP  300
KRLNFKLFNI QVKEVTDNNG VKTIANNLTS TVQVFTDSDY QLPYVLGSAH EGCLPPFPAD  360
VFMIPQYGYL TLNDGSQAVG RSSFYCLEYF PSQMLRTGNN FQFSYEFENV PFHSSYAHSQ  420
```

-continued

```
SLDRLMNPLI DQYLYYLSKT INGSGQNQQT LKFSVAGPSN MAVQGRNYIP GPSYRQQRVS    480
TTVTQNNNSE FAWPGASSWA LNGRNSLMNP GPAMASHKEG EDRFFPLSGS LIFGKQGTGR    540
DNVDADKVMI TNEEEIKTTN PVATESYGQV ATNHQSAQAQ AQTGWVQNQG ILPGMVWQDR    600
DVYLQGPIWA KIPHTDGNFH PSPLMGGFGM KHPPPQILIK NTPVPADPPT AFNKDKLNSF    660
ITQYSTGQVS VEIEWELQKE NSKRWNPEIQ YTSNYYKSNN VEFAVNTEGV YSEPRPIGTR    720
YLTRNL                                                               726

SEQ ID NO: 169         moltype = AA  length = 726
FEATURE                Location/Qualifiers
REGION                 1..726
                       note = Recombinant AAV Capsid Protein
source                 1..726
                       mol_type = protein
                       organism = synthetic construct
SEQUENCE: 169
MSFVDHPPDW LEEVGEGLRE FLGLEAGPPK PKPNQQHQDQ ARGLVLPGYN YLGPGNGLDR     60
GEPVNRADEV AREHDISYNE QLEAGDNPYL KYNHADAEFQ EKLADDTSFG GNLGKAVFQA    120
KKRVLEPFGL VEEGAKTAPT GKRIDDHFPK RKKARTEEDS KPSTSSDAEA GPSGSQQLQI    180
PAQPASSLGA DTMSAGGGGP LGDNNQGADG VGNASGDWHC DSTWMGDRVV TKSTRTWALP    240
TYNNHLYKQI SNSTSGGSSN DNAYFGYSTP WGYFDFNRFH CHFSPRDWQR LINNNWGFRP    300
KRLNFKLFNI QVKEVTDNNG VKTIANNLTS TVQVFTDSDY QLPYVLGSAH EGCLPPFPAD    360
VFMIPQYGYL TLNDGSQAVG RSSFYCLEYF PSQMLRTGNN PPHSSYAHSQ                420
SLDRLMNPLI DQYLYYLSKT INGSGQNQQT LKFSVAGPSN MAVQGRNYIP GPSYRQQRVS    480
TTVTQNNNSE FAWPGASSWA LNGRNSLMNP GPAMASHKEG EDRFFPLSGS LIFGKQGTGR    540
DNVDADKVMI TNEEEIKTTN PVATESYGQV ATNHQSAQAQ AQTGWVQNQG ILPGMVWQDR    600
DVYLQGPIWA KIPHTDGNFH PSPLMGGFGM KHPPPQILIK NTPVPADPPT AFNKDKLNSF    660
ITQYSTGQVS VEIEWELQKE NSKRWNPEIQ YTSNYYKSNN VEFAVNTEGV YSEPRPIGTR    720
YLTRNL                                                               726

SEQ ID NO: 170         moltype = AA  length = 736
FEATURE                Location/Qualifiers
REGION                 1..736
                       note = Recombinant AAV Capsid Protein
source                 1..736
                       mol_type = protein
                       organism = synthetic construct
SEQUENCE: 170
MAADGYLPDW LEDNLSEGIR EWWALKPGAP QPKANQQHQD NARGLVLPGY NYLGPGNGLD     60
RGEPVNRADE VAREHDISYN EQLEAGDNPY LKYNHADAEF QERLKEDTSF GGNLGKAVFQ    120
AKKRVLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGNASGDWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSKMLRTGNN FQFSYEFENV    420
PPHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVT VEMEWELKKE NSKRWNPEIQ YTNNYNDPQF VDFAPDSTGE    720
YRTTRPIGTR YLTRNL                                                    736

SEQ ID NO: 171         moltype = AA  length = 735
FEATURE                Location/Qualifiers
REGION                 1..735
                       note = Recombinant AAV Capsid Protein
source                 1..735
                       mol_type = protein
                       organism = synthetic construct
SEQUENCE: 171
MSFVDHPPDW LEEVGEGLRE FLGLEAGPPK PKPNQQHQDQ ARGLVLPGYN YLGPGNGLDR     60
GEPVNAADAA ALEHDKAYDQ QLKAGDNPYL KYNHADAEFQ ERLKEDTSFG GNLGRAVFQA    120
KKRLLEPLGL VEEAAKTAPG KKRPVEQSPQ EPDSSAGIGK SGAQPAKKRL NFGQTGDTES    180
VPDPQPIGEP PAAPSGVGSL TMASGGGAPV ADNNEGADGV GSSGNWHCDS QWLGDRVITS    240
TSTRTWALPT YNNHLYKQIS NSTSGGSSND NAYFGYSTPW GYFDFNRFHC HFSPRDWQRL    300
INNNWGFRPK RLNFKLFNIQ VKEVTDNNGV KTIANNLTST VQVFTDSDYQ LPYVLGSAHE    360
GCLPPFPADV FMIPQYGYLT LNDGSQAVGR SSFYCLEYFP SQMLRTGNNF QFSYEFENVP    420
FHSSYAHSQS LDRLMNPLID QYLYYLSKTI NGSGQNQQTL KFSVAGPSNM AVQGRNYIPG    480
PSYRQQRVST TVTQNNNSEF AWPGASSWAL NGRNSLMNPG PAMASHKEGE DRFFPLSGSL    540
IFGKQGTGRD NVDADKVMIT NEEEIKTTNP VATESYGQVA TNHQSAQAQA QTGWVQNQGI    600
LPGMVWQDRD VYLQGPIWAK IPHTDGNFHP SPLMGGFGMK HPPPQILIKN TPVPADPPTA    660
FNKDKLNSFI TQYSTGQVSV EIEWELQKEN SKRWNPEIQY TNNYNDPQFV DFAPDSTGEY    720
RTTRPIGTRY LTRPL                                                     735

SEQ ID NO: 172         moltype = AA  length = 735
FEATURE                Location/Qualifiers
REGION                 1..735
                       note = Recombinant AAV Capsid Protein
source                 1..735
                       mol_type = protein
```

```
                       organism = synthetic construct
SEQUENCE: 172
MSFVDHPPDW LEEVGEGLRE FLGLEAGPPK PKPNQQHQDQ ARGLVLPGYN YLGPGNGLDR     60
GEPVNRADEV AREHDISYNE QLEAGDNPYL KYNHADAEFQ EKLADDTSFG GNLGKAVFQA    120
KKRVLEPLGL VEEAAKTAPG KKRPVEQSPQ EPDSSAGIGK SGAQPAKKRL NFGQTGDTES    180
VPDPQPIGEP PAAPSGVGSL TMASGGGAPV ADNNEGADGV GSSSGNWHCD SQWLGDRVIT    240
TSTRTWALPT YNNHLYKQIS NSTSGGSSND NAYFGYSTPW GYFDFNRFHC HFSPRDWQRL    300
INNNWGFRPK RLNFKLFNIQ VKEVTDNNGV KTIANNLTST VQVFTDSDYQ LPYVLGSAHE    360
GCLPPFPADV FMIPQYGYLT LNDGSQAVGR SSFYCLEYFP SQMLRTGNNF QFSYEFENVP    420
FHSSYAHSQS LDRLMNPLID QYLYYLSKTI NGSGQNQQTL KFSVAGPSNM AVQGRNYIPG    480
PSYRQQRVST TVTQNNNSEF AWPGASSWAL NGRNSLMNPG PAMASHKEGE DRFFPLSGSL    540
IFGKQGTGRD NVDADKVMIT NEEEIKTTNP VATESYGQVA TNHQSAQAQA QTGWVQNQGI    600
LPGMVWQDRD VYLQGPIWAK IPHTDGNFHP SPLMGGFGMK HPPPQILIKN TPVPADPPTA    660
FNKDKLNSFI TQYSTGQVSV EIEWELKKEN SKRWNPEIQY TSNYYKSNNV EFAVNTEGVY    720
SEPRPIGTRY LTRNL                                                     735

SEQ ID NO: 173          moltype = AA  length = 726
FEATURE                 Location/Qualifiers
REGION                  1..726
                        note = Recombinant AAV Capsid Protein
source                  1..726
                        mol_type = protein
                        organism = synthetic construct
SEQUENCE: 173
MSFVDHPPDW LEEVGEGLRE FLGLEAGPPK PKPNQQHQDQ ARGLVLPGYN YLGPGNGLDR     60
GEPVNRADEV AREHDISYNE QLEAGDNPYL KYNHADAEFQ EKLADDTSFG GNLGKAVFQA    120
KKRVLEPFGL VEEGAKTAPT GKRIDDHFPK RKKARTEEDS KPSTSSDAEA GPSGSQQLQI    180
PAQPASSLGA DTMSAGGGGP LGDNNQGADG VGNASGDWHC DSTWMGDRVV TKSTRTWALP    240
TYNNHLYKQI SNSTSGGSSN DNAYFGYSTP WGYFDFNRFH CHFSPRDWQR LINNNWGFRP    300
KRLNFKLFNI QVKEVTDNNG VKTIANNLTS TVQVFTDSDY QLPYVLGSAH EGCLPPFPAD    360
VFMIPQYGYL TLNDGSQAVG RSSFYCLEYF PSQMLRTGNN FQFSYEFENV PFHSSYAHSQ    420
SLDRLMNPLI DQYLYYLSKT INGSGQNQQT LKFSVAGPSN MAVQGRNYIP GPSYRQQRVS    480
TTVTQNNNSE FAWPGASSWA LNGRNSLMNP GPAMASHKEG EDRFFPLSGS LIFGKQGTGR    540
DNVDADKVMI TNEEEIKTTN PVATESYGQV ATNHQSAQAQ AQTGWVQNQG ILPGMVWQDR    600
DVYLQGPIWA KIPHTDGNFH PSPLMGGFGM KHPPPQILIK NTPVPADPPT AFNKDKLNSF    660
ITQYSTGQVS VEIEWELQKE NSKRWNPEIQ YTSNYYKSNN VEFAVNTEGV YSEPRPIGTR    720
YLTRNL                                                               726

SEQ ID NO: 174          moltype = AA  length = 726
FEATURE                 Location/Qualifiers
REGION                  1..726
                        note = Recombinant AAV Capsid Protein
source                  1..726
                        mol_type = protein
                        organism = synthetic construct
SEQUENCE: 174
MSFVDHPPDW LEEVGEGLRE FLGLEAGPPK PKPNQQHQDQ ARGLVLPGYN YLGPGNGLDR     60
GEPVNRADEV AREHDISYNE QLEAGDNPYL KYNHADAEFQ EKLADDTSFG GNLGKAVFQA    120
KKRVLEPFGL VEEGAKTAPT GKRIDDHFPK RKKARTEEDS KPSTSSDAEA GPSGSQQLQI    180
PAQPASSLGA DTMSAGGGAP VADNNEGADG VGSSSGNWHC DSQWLGDRVI TTSTRTWALP    240
TYNNHLYKQI SNSTSGGSSN DNAYFGYSTP WGYFDFNRFH CHFSPRDWQR LINNNWGFRP    300
KRLNFKLFNI QVKEVTDNNG VKTIANNLTS TVQVFTDSDY QLPYVLGSAH EGCLPPFPAD    360
VFMIPQYGYL TLNDGSQAVG RSSFYCLEYF PSQMLRTGNN FQFSYEFENV PFHSSYAHSQ    420
SLDRLMNPLI DQYLYYLSKT INGSGQNQQT LKFSVAGPSN MAVQGRNYIP GPSYRQQRVS    480
TTVTQNNNSE FAWPGASSWA LNGRNSLMNP GPAMASHKEG EDRFFPLSGS LIFGKQGTGR    540
DNVDADKVMI TNEEEIKTTN PVATESYGQV ATNHQSAQAQ AQTGWVQNQG ILPGMVWQDR    600
DVYLQGPIWA KIPHTDGNFH PSPLMGGFGM KHPPPQILIK NTPVPADPPT AFNKDKLNSF    660
ITQYSTGQVS VEIEWELQKE NSKRWNPEIQ YTSNYYKSNN VEFAVNTEGV YSEPRPIGTR    720
YLTRNL                                                               726

SEQ ID NO: 175          moltype = AA  length = 726
FEATURE                 Location/Qualifiers
REGION                  1..726
                        note = Recombinant AAV Capsid Protein
source                  1..726
                        mol_type = protein
                        organism = synthetic construct
SEQUENCE: 175
MSFVDHPPDW LEEVGEGLRE FLGLEAGPPK PKPNQQHQDQ ARGLVLPGYK YLGPGNGLDK     60
GEPVNAADAA ALEHDKAYDQ QLKAGDNPYL KYNHADAEFQ EKLADDTSFG GNLGKAVFQA    120
KKRVLEPFGL VEEGAKTAPT GKRIDDHFPK RKKARTEEDS KPSTSSDAEA GPSGSQQLQI    180
PAQPASSLGA DTMSAGGGAP VADNNEGADG VGSSSGNWHC DSQWLGDRVI TTSTRTWALP    240
TYNNHLYKQI SNSTSGGSSN DNAYFGYSTP WGYFDFNRFH CHFSPRDWQR LINNNWGFRP    300
KRLNFKLFNI QVKEVTDNNG VKTIANNLTS TVQVFTDSDY QLPYVLGSAH EGCLPPFPAD    360
VFMIPQYGYL TLNDGSQAVG RSSFYCLEYF PSQMLRTGNN FQFSYEFENV PFHSSYAHSQ    420
SLDRLMNPLI DQYLYYLSKT INGSGQNQQT LKFSVAGPSN MAVQGRNYIP GPSYRQQRVS    480
TTVTQNNNSE FAWPGASSWA LNGRNSLMNP GPAMASHKEG EDRFFPLSGS LIFGKQGTGR    540
DNVDADKVMI TNEEEIKTTN PVATESYGQV ATNHQSAQAQ AQTGWVQNQG ILPGMVWQDR    600
DVYLQGPIWA KIPHTDGNFH PSPLMGGFGM KHPPPQILIK NTPVPADPPT AFNKDKLNSF    660
```

```
ITQYSTGQVS VEIEWELQKE NSKRWNPEIQ YTSNYYKSNN VEFAVNTEGV YSEPRPIGTR    720
YLTRNL                                                               726

SEQ ID NO: 176          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 176
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ    120
AKKRLLEPFG LVEEGAKTAP TGKRIDDHFP KRKKARTEED SKPSTSSDAE AGPSGSQQLQ    180
IPAQPASSLG ADTMSAGGGG PLGDNNEGAD GVGSSSGNWH CDSQWLGDRV ITTSTRTWAL    240
PTYNNHLYKQ ISNSTSGGSS NDNAYFGYST PWGYFDFNRF HCHFSPRDWQ RLINNNWGFR    300
PKRLNFKLFN IQVKEVTDNN GVKTIANNLT STVQVFTDSD YQLPYVLGSA HEGCLPPFPA    360
DVFMIPQYGY LTLNDGSQAV GRSSFYCLEY FPSQMLRTGN NFQFSYEFEN VPFHSSYAHS    420
QSLDRLMNPL IDQYLYYLSK TINGSGQNQQ TLKFSVAGPS NMAVQGRNYI PGPSYRQQRV    480
STTVTQNNNS EFAWPGASSW ALNGRNSLMN PGPAMASHKE GEDRFFPLSG SLIFGKQGTG    540
RDNVDADKVM ITNEEEIKTT NPVATESYGQ VATNHQSAQA QAQTGWVQNQ GILPGMVWQD    600
RDVYLQGPIW AKIPHTDGNF HPSPLMGGFG MKHPPPQILI KNTPVPADPP TAFNKDKLNS    660
FITQYSTGQV SVEIEWELQK ENSKRWNPEI QYTSNYYKSN NVEFAVNTEG VYSEPRPIGT    720
RYLTRNL                                                              727

SEQ ID NO: 177          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 177
MAADGYLPDW LEDNLSEGIR EWWALKPGAP QPKANQQHQD NARGLVLPGY KYLGPGNGLD    60
KGEPVNAADA AALEHDKAYD QQLEAGDNPY LKYNHADAEF QEKLADDTSF GGNLGKAVFQ    120
AKKRVLEPFG LVEEGAKTAP TGKRIDDHFP KRKKARTEED SKPSTSSDAE AGPSGSQQLQ    180
IPAQPASSLG ADTMSAGGGG PLGDNNQGAD GVGNASGDWH CDSTWMGDRV VTTSTRTWAL    240
PTYNNHLYKQ ISNSTSGGSS NDNAYFGYST PWGYFDFNRF HCHFSPRDWQ RLINNNWGFR    300
PKRLNFKLFN IQVKEVTDNN GVKTIANNLT STVQVFTDSD YQLPYVLGSA HEGCLPPFPA    360
DVFMIPQYGY LTLNDGSQAV GRSSFYCLEY FPSQMLRTGN NFQFSYEFEN VPFHSSYAHS    420
QSLDRLMNPL IDQYLYYLSK TINGSGQNQQ TLKFSVAGPS NMAVQGRNYI PGPSYRQQRV    480
STTVTQNNNS EFAWPGASSW ALNGRNSLMN PGPAMASHKE GEDRFFPLSG SLIFGKQGTG    540
RDNVDADKVM ITNEEEIKTT NPVATESYGQ VATNHQSAQA QAQTGWVQNQ GILPGMVWQD    600
RDVYLQGPIW AKIPHTDGNF HPSPLMGGFG MKHPPPQILI KNTPVPADPP TAFNKDKLNS    660
FITQYSTGQV SVEIEWELQK ENSKRWNPEI QYTSNYYKSN NVEFAVNTEG VYSEPRPIGT    720
RYLTRNL                                                              727

SEQ ID NO: 178          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 178
MSFVDHPPDW LEEVGEGLRE FLGLEAGPPK PKPNQQHQDQ ARGLVLPGYN YLGPGNGLDR    60
GEPVNRADEV AREHDISYNE QLEAGDNPYL KYNHADAEFQ ERLKEDTSFG GNLGRAVFQA    120
KKRLLEPLGL VEEAAKTAPG KKRPVEQSPQ EPDSSAGIGK SGAQPAKKRL NFGQTGDTES    180
VPDPQPIGEP PAAPSGVGSL TMASGGGAPV ADNNEGADGG GSSSGNWHCD SQWLGDRVIT    240
TSTRTWALPT YNNHLYKQIS NSTSGGSSND NAYFGYSTPW GYFDFNRFHC HFSPRDWQRL    300
INNNWGRPKR LNFKLFNIQV KEVTDNNGVK TIANNLTSTV QVFTDSDYQ LPYVLGSAHE    360
GCLPPFPADV FMIPQYGYLT LNDGSQAVGR SSFYCLEYFP SQMLRTGNNF QFSYEFENVP    420
FHSSYAHSQS LDRLMNPLID QYLYYLSKTI NGSGQNQQTL KFSVAGPSNM AVQGRNYIPG    480
PSYRQQRVST TVTQNNNSEF AWPGASSWAL NGRNSLMNPG PAMASHKEGE DRFFPLSGSL    540
IFGKQGTGRD NVDADKVMIT NEEEIKTTNP VATESYGQVA TNHQSAQAQA QTGWVQNQGI    600
LPGMVWQDRD VYLQGPIWAK IPHTDGNFHP SPLMGGFGMK HPPPQILIKN TPVPADPPTA    660
FNKDKLNSFI TQYSTGQVSV EIEWELQKEN SKRWNPEIQY TSNYYKSNNV EFAVNTEGVY    720
SEPRPIGTRY LTRNL                                                     735

SEQ ID NO: 179          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 179
MAADGYLPDW LEDNLSEGIR EWWALKPGAP QPKANQQHQD NARGLVLPGY NYLGPGNGLD    60
RGEPVNRADE VAREHDISYN EQLEAGDNPY LKYNHADAEF QERLKEDTSF GGNLGRAVFQ    120
```

```
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 180          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 180
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QEKLADDTSF GGNLGKAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 181          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 181
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QEKLADDTSF GGNLGKAVFQ   120
AKKRVLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTGGSSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 182          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 182
MSFVDHPPDW LEEVGEGLRE FLGLEAGPPK PKPNQQHQDQ ARGLVLPGYN YLGPGNGLDR    60
GEPVNAADAA ALEHDKAYDQ QLKAGDNPYL KYNHADAEFQ ERLKEDTSFG GNLGRAVFQA   120
KKRLLEPLGL VEEAAKTAPG KKRPVEQSPQ EPDSSAGIGK SGAQPAKKRL NFGQTGDTES   180
VPDPQPIGEP PAAPSGVGSL TMASGGGAPV ADNNEGADGV GSSSGNWHCD SQWLGDRVIT   240
TSTRTWALPT YNNHLYKQIS NSTGGSSNDN AYFGYSTPW GYFDFNRFHC HFSPRDWQRL   300
INNNWGFRPK RLNFKLFNIQ VKEVTDNNGV KTIANNLTST VQVFTDSDYQ LPYVLGSAHE   360
GCLPPFPADV FMIPQYGYLT LNDGSQAVGR SSFYCLEYFP SQMLRTGNNF QFSYEFENVP   420
FHSSYAHSQS LDRLMNPLID QYLYYLSKTI NGSGQNQQTL KFSVAGPSNM AVQGRNYIPG   480
PSYRQQRVST TVTQNNNSEF AWPGASSWAL NGRNSLMNPG PAMASHKEGE DRFFPLSGSL   540
IFGKQGTGRD NVDADKVMIT NEEEIKTTNP VATESYGQVA TNHQSAQAQA QTGWVQNQGI   600
LPGMVWQDRD VYLQGPIWAK IPHTDGNFHP SPLMGGFGMK HPPPQILIKN TPVPADPPTA   660
FNKDKLNSFI TQYSTGQVSV EIEWELQKEN SKRWNPEIQY TNNYNDPQFV DFAPDSTGEY   720
RTTRPIGTRY LTRPL                                                   735

SEQ ID NO: 183          moltype = AA  length = 736
```

```
FEATURE                 Location/Qualifiers
REGION                  1..736
                        note = Recombinant AAV Capsid Protein
source                  1..736
                        mol_type = protein
                        organism = synthetic construct
SEQUENCE: 183
MAADGYLPDW LEDNLSEGIR EWWALKPGAP QPKANQQHQD NARGLVLPGY NYLGPGNGLD    60
RGEPVNRADE VAREHDISYN EQLEAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGYHKSGAAQ LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 184          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 184
MAADGYLPDW LEDNLSEGIR EWWALKPGAP QPKANQQHQD NARGLVLPGY NYLGPGNGLD    60
RGEPVNRADE VAREHDISYN EQLEAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQANYGQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 185          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 185
MAADGYLPDW LEDNLSEGIR EWWALKPGAP QPKANQQHQD NARGLVLPGY NYLGPGNGLD    60
RGEPVNRADE VAREHDISYN EQLEAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT IGYHKSGAAQ LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQNVSYQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                  736

SEQ ID NO: 186          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 186
MAADGYLPDW LEDNLSEGIR EWWALKPGAP QPKANQQHQD NARGLVLPGY NYLGPGNGLD    60
RGEPVNRADE VAREHDISYN EQLEAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
```

```
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNLNSM LIWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 187          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 187
MAADGYLPDW LEDNLSEGIR EWWALKPGAP QPKANQQHQD NARGLVLPGY NYLGPGNGLD     60
RGEPVNRADE VAREHDISYN EQLEAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT IGYHKSGAAQ LKFSVAGPSN MAVQGRNYIP    480
GPSYRQQRVS TTVTQNNSE FAWPGASSWA LNGRNSLMNP GPAMASHKEG EDRFFPLSGS    540
LIFGKQGTGR DNVDADKVMI TNEEEIKTTN PVATESYGQV ATNHQANYGQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 188          moltype = AA  length = 736
FEATURE                 Location/Qualifiers
REGION                  1..736
                        note = Recombinant AAV Capsid Protein
source                  1..736
                        mol_type = protein
                        organism = synthetic construct
SEQUENCE: 188
MAADGYLPDW LEDNLSEGIR EWWALKPGAP QPKANQQHQD NARGLVLPGY NYLGPGNGLD     60
RGEPVNRADE VAREHDISYN EQLEAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNLNSM LIWPGASSWA LNGRNSLMNP GPAMASHKEG EDRFFPLSGS    540
LIFGKQGTGR DNVDADKVMI TNEEEIKTTN PVATESYGQV ATNHQANYGQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 189          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 189
MSFVDHPPDW LEEVGEGLRE FLGLEAGPPK PKPNQQHQDQ ARGLVLPGYN YLGPGNGLDR     60
GEPVNRADEV AREHDISYNE QLEAGDNPYL KYNHADAEFQ EKLADDTSFG GNLGKAVFQA    120
KKRVLEPLGL VEEAAKTAPG KKRPVEQSPQ EPDSSAGIGK SGAQPAKKRL NFGQTGDTES    180
VPDPQPIGEP PAAPSGVGSL TMASGGGAPV ADNNEGADGV GSSSGNWHCD SQWLGDRVIT    240
TSTRTWALPT YNNHLYKQIS NSTSGGSSND NAYFGYSTPW GYFDFNRFHC HFSPRDWQRL    300
INNNWGFRPK RLNFKLFNIQ VKEVTDNNGV KTIANNLTST VQVFTDSDYQ LPYVLGSAHE    360
GCLPPFPADV FMIPQYGYLT LNDGSQAVGR SSFYCLEYFP SQMLRTGNNF QFSYEFENVP    420
FHSSYAHSQS LDRLMNPLID QYLYYLSKTI GYHKSGAAQK FSVAGPSNM AVQGRNYIPG    480
PSYRQQRVST TVTQNNSEF AWPGASSWAL NGRNSLMNPG PAMASHKEGE DRFFPLSGSL    540
IFGKQGTGRD NVDADKVMIT NEEEIKTTNP VATESYGQVA TNHQSAQAQA QTGWVQNQGI    600
LPGMVWQDRD VYLQGPIWAK IPHTDGNFHP SPLMGGFGMK HPPPQILIKN TPVPADPPTA    660
FNKDKLNSFI TQYSTGQVSV EIEWELKKEN SKRWNPEIQY TSNYYKSNNV EFAVNTEGVY    720
SEPRPIGTRY LTRNL                                                    735

SEQ ID NO: 190          moltype = AA  length = 735
FEATURE                 Location/Qualifiers
REGION                  1..735
                        note = Recombinant AAV Capsid Protein
source                  1..735
```

```
                        mol_type = protein
                        organism = synthetic construct
SEQUENCE: 190
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQANYGQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 191          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 191
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI GYHKSGAAQL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQNVSYQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 192          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 192
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNLNSML IWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELKKEN SKRWNPEIQY TSNYYKSNNV EFAVNTEGVY  720
SEPRPIGTRY LTRNL                                                  735

SEQ ID NO: 193          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 193
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPLGL VEEAAKTAPG KKRPVEQSPQ EPDSSAGIGK SGAQPAKKRL NFGQTGDTES  180
VPDPQPIGEP PAAPSGVGSL TMASGGGAPV ADNNEGADGV GSSSGNWHCD SQWLGDRVIT  240
TSTRTWALPT YNNHLYKQIS NSTSGGSSND NAYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI GYHKSGAAQL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQANYGQA QTGWVQNQGI  600
```

```
LPGMVWQDRD VYLQGPIWAK IPHTDGNFHP SPLMGGFGMK HPPPQILIKN TPVPADPPTA   660
FNKDKLNSFI TQYSTGQVSV EIEWELKKEN SKRWNPEIQY TSNYYKSNNV EFAVNTEGVY   720
SEPRPIGTRY LTRNL                                                    735

SEQ ID NO: 194          moltype = AA  length = 735
FEATURE                 Location/Qualifiers
REGION                  1..735
                        note = Recombinant AAV Capsid Protein
source                  1..735
                        mol_type = protein
                        organism = synthetic construct
SEQUENCE: 194
MSFVDHPPDW LEEVGEGLRE FLGLEAGPPK PKPNQQHQDQ ARGLVLPGYN YLGPGNGLDR    60
GEPVNRADEV AREHDISYNE QLEAGDNPYL KYNHADAEFQ EKLADDTSFG GNLGKAVFQA   120
KKRVLEPLGL VEEAAKTAPG KKRPVEQSPQ EPDSSAGIGK SGAQPAKKRL NFGQTGDTES   180
VPDPQPIGEP PAAPSGVGSL TMASGGGAPV ADNNEGADGV GSSSGNWHCD SQWLGDRVIT   240
TSTRTWALPT YNNHLYKQIS NSTSGGSSND NAYFGYSTPW GYFDFNRPHC HFSPRDWQRL   300
INNNWGFRPK RLNFKLFNIQ VKEVTDNNGV KTIANNLTST VQVFTDSDYQ LPYVLGSAHE   360
GCLPPFPADV FMIPQYGYLT LNDGSQAVGR SSFYCLEYFP SQMLRTGNNF QFSYEFENVP   420
FHSSYAHSQS LDRLMNPLID QYLYYLSKTI NGSGQNQQTL KFSVAGPSNM AVQGRNYIPG   480
PSYRQQRVST TVTQNLNSML IWPGASSWAL NGRNSLMNPG PAMASHKEGE DRFFPLSGSL   540
IFGKQGTGRD NVDADKVMIT NEEEIKTTNP VATESYGQVA QTGWVQNQGI               600
LPGMVWQDRD VYLQGPIWAK IPHTDGNFHP SPLMGGFGMK HPPPQILIKN TPVPADPPTA   660
FNKDKLNSFI TQYSTGQVSV EIEWELKKEN SKRWNPEIQY TSNYYKSNNV EFAVNTEGVY   720
SEPRPIGTRY LTRNL                                                    735

SEQ ID NO: 195          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 195
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPFG LVEEGAKTAP TGKRIDDHFP KRKKARTEED SKPSTSSDAE AGPSGSQQLQ   180
IPAQPASSLG ADTMSAGGGG PLGDNNEGAD GVGSSSGNWH CDSQWLGDRV ITTSTRTWAL   240
PTYNNHLYKQ ISNSTSGGSS NDNAYFGYST PWGYFDFNRF HCHFSPRDWQ RLINNNWGFR   300
PKRLNFKLFN IQVKEVTDNN GVKTIANNLT STVQVFTDSD YQLPYVLGSA HEGCLPPFPA   360
DVFMIPQYGY LTLNDGSQAV GRSSFYCLEY FPSQMLRTGN NFQFSYEFEN VPFHSSYAHS   420
QSLDRLMNPL IDQYLYYLSK TIGYHKSGAA QLKFSVAGPS NMAVQGRNYI PGPSYRQQRV   480
STTVTQNNNS EFAWPGASSW ALNGRNSLMN PGPAMASHKE GEDRFFPLSG SLIFGKQGTG   540
RDNVADKVM ITNEEEIKTT NPVATESYGQ VATNHQSAQA QAQTGWVQNQ GILPGMVWQD   600
RDVYLQGPIW AKIPHTDGNF HPSPLMGGFG MKHPPPQILI KNTPVADPP TAFNKDKLNS   660
FITQYSTGQV SVEIEWELQK ENSKRWNPEI QYTSNYYKSN NVEFAVNTEG VYSEPRPIGT   720
RYLTRNL                                                             727

SEQ ID NO: 196          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 196
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPFG LVEEGAKTAP TGKRIDDHFP KRKKARTEED SKPSTSSDAE AGPSGSQQLQ   180
IPAQPASSLG ADTMSAGGGG PLGDNNEGAD GVGSSSGNWH CDSQWLGDRV ITTSTRTWAL   240
PTYNNHLYKQ ISNSTSGGSS NDNAYFGYST PWGYFDFNRF HCHFSPRDWQ RLINNNWGFR   300
PKRLNFKLFN IQVKEVTDNN GVKTIANNLT STVQVFTDSD YQLPYVLGSA HEGCLPPFPA   360
DVFMIPQYGY LTLNDGSQAV GRSSFYCLEY FPSQMLRTGN NFQFSYEFEN VPFHSSYAHS   420
QSLDRLMNPL IDQYLYYLSK TINGSGQNQQ TLKFSVAGPS NMAVQGRNYI PGPSYRQQRV   480
STTVTQNNNS EFAWPGASSW ALNGRNSLMN PGPAMASHKE GEDRFFPLSG SLIFGKQGTG   540
RDNVADKVM ITNEEEIKTT NPVATESYGQ VATNHQSAQA QAQTGWVQNQ GILPGMVWQD   600
RDVYLQGPIW AKIPHTDGNF HPSPLMGGFG MKHPPPQILI KNTPVADPP TAFNKDKLNS   660
FITQYSTGQV SVEIEWELQK ENSKRWNPEI QYTSNYYKSN NVEFAVNTEG VYSEPRPIGT   720
RYLTRNL                                                             727

SEQ ID NO: 197          moltype = AA  length = 727
FEATURE                 Location/Qualifiers
REGION                  1..727
                        note = Recombinant AAV Capsid Protein
source                  1..727
                        mol_type = protein
                        organism = synthetic construct
SEQUENCE: 197
MAADGYLPDW LEDNLSEGIR EWWALKPGAP QPKANQQHQD NARGLVLPGY KYLGPGNGLD    60
```

```
KGEPVNAADA AALEHDKAYD QQLKAGDNPY LKYNHADAEF QERLKEDTSF GGNLGRAVFQ   120
AKKRLLEPFG LVEEGAKTAP TGKRIDDHFP KRKKARTEED SKPSTSSDAE AGPSGSQQLQ   180
IPAQPASSLG ADTMSAGGGG PLGDNNEGAD GVGSSSGNWH CDSQWLGDRV ITTSTRTWAL   240
PTYNNHLYKQ ISNSTSGGSS NDNAYFGYST PWGYFDFNRF HCHFSPRDWQ RLINNNWGFR   300
PKRLNFKLFN IQVKEVTDNN GVKTIANNLT STVQVFTDSD YQLPYVLGSA HEGCLPPFPA   360
DVFMIPQYGY LTLNDGSQAV GRSSFYCLEY FPSQMLRTGN NFQFSYEFEN VPFHSSYAHS   420
QSLDRLMNPL IDQYLYYLSK TIGYHKSGAA QLKFSVAGPS NMAVQGRNYI PGPSYRQQRV   480
STTVTQNNNS EFAWPGASSW ALNGRNSLMN PGPAMASHKE GEDRFFPLSG SLIFGKQGTG   540
RDNVDADKVM ITNEEEIKTT NPVATESYGQ VATNHQNVSY QAQTGWVQNQ GILPGMVWQD   600
RDVYLQGPIW AKIPHTDGNF HPSPLMGGFG MKHPPPQILI KNTPVPADPP TAFNKDKLNS   660
FITQYSTGQV SVEIEWELQK ENSKRWNPEI QYTSNYYKSN NVEFAVNTEG VYSEPRPIGT   720
RYLTRNL                                                              727

SEQ ID NO: 198           moltype = AA   length = 727
FEATURE                  Location/Qualifiers
REGION                   1..727
                         note = Recombinant AAV Capsid Protein
source                   1..727
                         mol_type = protein
                         organism = synthetic construct
SEQUENCE: 198
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPFG LVEEGAKTAP TGKRIDDHFP KRKKARTEED SKPSTSSDAE AGPSGSQQLQ   180
IPAQPASSLG ADTMSAGGGG PLGDNNEGAD GVGSSSGNWH CDSQWLGDRV ITTSTRTWAL   240
PTYNNHLYKQ ISNSTSGGSS NDNAYFGYST PWGYFDFNRF HCHFSPRDWQ RLINNNWGFR   300
PKRLNFKLFN IQVKEVTDNN GVKTIANNLT STVQVFTDSD YQLPYVLGSA HEGCLPPFPA   360
DVFMIPQYGY LTLNDGSQAV GRSSFYCLEY FPSQMLRTGN NFQFSYEFEN VPFHSSYAHS   420
QSLDRLMNPL IDQYLYYLSK TINGSGQNQQ TLKFSVAGPS NMAVQGRNYI PGPSYRQQRV   480
STTVTQNNNS MLIWPGASSW ALNGRNSLMN PGPAMASHKE GEDRFFPLSG SLIFGKQGTG   540
RDNVDADKVM ITNEEEIKTT NPVATESYGQ VATNHQSAQA QAQTGWVQNQ GILPGMVWQD   600
RDVYLQGPIW AKIPHTDGNF HPSPLMGGFG MKHPPPQILI KNTPVPADPP TAFNKDKLNS   660
FITQYSTGQV SVEIEWELQK ENSKRWNPEI QYTSNYYKSN NVEFAVNTEG VYSEPRPIGT   720
RYLTRNL                                                              727

SEQ ID NO: 199           moltype = AA   length = 727
FEATURE                  Location/Qualifiers
REGION                   1..727
                         note = Recombinant AAV Capsid Protein
source                   1..727
                         mol_type = protein
                         organism = synthetic construct
SEQUENCE: 199
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPFG LVEEGAKTAP TGKRIDDHFP KRKKARTEED SKPSTSSDAE AGPSGSQQLQ   180
IPAQPASSLG ADTMSAGGGG PLGDNNEGAD GVGSSSGNWH CDSQWLGDRV ITTSTRTWAL   240
PTYNNHLYKQ ISNSTSGGSS NDNAYFGYST PWGYFDFNRF HCHFSPRDWQ RLINNNWGFR   300
PKRLNFKLFN IQVKEVTDNN GVKTIANNLT STVQVFTDSD YQLPYVLGSA HEGCLPPFPA   360
DVFMIPQYGY LTLNDGSQAV GRSSFYCLEY FPSQMLRTGN NFQFSYEFEN VPFHSSYAHS   420
QSLDRLMNPL IDQYLYYLSK TIGYHKSGAA QLKFSVAGPS NMAVQGRNYI PGPSYRQQRV   480
STTVTQNNNS EFAWPGASSW ALNGRNSLMN PGPAMASHKE GEDRFFPLSG SLIFGKQGTG   540
RDNVDADKVM ITNEEEIKTT NPVATESYGQ VATNHQANYG QAQTGWVQNQ GILPGMVWQD   600
RDVYLQGPIW AKIPHTDGNF HPSPLMGGFG MKHPPPQILI KNTPVPADPP TAFNKDKLNS   660
FITQYSTGQV SVEIEWELQK ENSKRWNPEI QYTSNYYKSN NVEFAVNTEG VYSEPRPIGT   720
RYLTRNL                                                              727

SEQ ID NO: 200           moltype = AA   length = 727
FEATURE                  Location/Qualifiers
REGION                   1..727
                         note = Recombinant AAV Capsid Protein
source                   1..727
                         mol_type = protein
                         organism = synthetic construct
SEQUENCE: 200
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPFG LVEEGAKTAP TGKRIDDHFP KRKKARTEED SKPSTSSDAE AGPSGSQQLQ   180
IPAQPASSLG ADTMSAGGGG PLGDNNEGAD GVGSSSGNWH CDSQWLGDRV ITTSTRTWAL   240
PTYNNHLYKQ ISNSTSGGSS NDNAYFGYST PWGYFDFNRF HCHFSPRDWQ RLINNNWGFR   300
PKRLNFKLFN IQVKEVTDNN GVKTIANNLT STVQVFTDSD YQLPYVLGSA HEGCLPPFPA   360
DVFMIPQYGY LTLNDGSQAV GRSSFYCLEY FPSQMLRTGN NFQFSYEFEN VPFHSSYAHS   420
QSLDRLMNPL IDQYLYYLSK TINGSGQNQQ TLKFSVAGPS NMAVQGRNYI PGPSYRQQRV   480
STTVTQNLNS MLIWPGASSW ALNGRNSLMN PGPAMASHKE GEDRFFPLSG SLIFGKQGTG   540
RDNVDADKVM ITNEEEIKTT NPVATESYGQ VATNHQANYG QAQTGWVQNQ GILPGMVWQD   600
RDVYLQGPIW AKIPHTDGNF HPSPLMGGFG MKHPPPQILI KNTPVPADPP TAFNKDKLNS   660
FITQYSTGQV SVEIEWELQK ENSKRWNPEI QYTSNYYKSN NVEFAVNTEG VYSEPRPIGT   720
RYLTRNL                                                              727
```

```
SEQ ID NO: 201          moltype = DNA   length = 2091
FEATURE                 Location/Qualifiers
source                  1..2091
                        mol_type = other DNA
                        organism = Homo sapiens
SEQUENCE: 201
atgagtgggg gccgcttcga ctttgatgat ggagggcgt actgcggggg ctggagggg    60
ggaaaggccc atgggcatgg actgtgcaca ggccccaagg gccagggcga atactctggc   120
tcctggaact ttggctttga ggtggcaggt gtctacacct ggcccagcgg aaacacctttt  180
gagggatact ggagccaggg caaacggcat gggctgggca tagagaccaa ggggcgctgg   240
ctctacaagg gcgagtggac acatggcttc aagggacgct acggaatccg gcagagctca   300
agcagcggtg ccaagtatga gggcacctgg aacaatggcc tgcaagacgg ctatggcacc   360
gagacctatg ctgatggagg gacgtaccaa ggccagttca ccaacggcat gcgccatggc   420
tacggagtac gccagagcgt gccctacggg atggccgtgg tggtgcgctc gccgctgcgc   480
acgtcgctgt cgtccctgcg cagcgagcac agcaacggca cggtggcccc ggactctccc   540
gcctcgccgg cctccgacgg ccccgcgctg ccctcgcccg ccatcccgcg tggcggcttc   600
gcgctcagcc tcctggccaa tgccgaggcg gccgcgcggg cgcccaaggg cggcggcctc   660
ttccagcggg gcgcgctgct gggcaagctg cggcgcgcag agtcgcgcac gtccgtgggt   720
agccagcgca gccgtgtcag cttccttaag agcgacctca gctcgggcgc cagcgacgcc   780
gcgtccaccg ccagcctggg agaggccgcc gagggcgccg acgaggccgc accccttcgag  840
gccgatatcg acgccaccac caccgagacc tacatgggcg agtggaagaa cgacaaacgc   900
tcgggcttcg gcgtgagcga acgctccagt ggcctccgct agggggcgct gtggctggac   960
aacctgcgcc acggctatgg ctgcaccacg ctgcccgacg gccaccgcga ggagggcaag  1020
taccgccaca acgtgctggt caaggacacc aagcgccga tgctgcagct caagagcaac  1080
aaggtccgcc agaaagtgga gcacagtgtg gagggtgccc agcgcgccgc tgctatcgcg  1140
cgccagaagg ccgagattgc cgcctccagc acaagccagg ccaagtgagg ca agctgaggca 1200
gcggaacagg ccgccctggc tgccaaccag gagtccaaca ttgctcgcac tttggccagg  1260
gagctggctc cggacttcta ccagccaggt ccggaatatc agaagcgccg gctgctgcag  1320
gagatcctgg agaactcgga gagcctgctg gagccccccg accggggcgc cggcgcagcg  1380
ggcctcccac agccgccccg cgagagcccg cagctgcacg agcgtgaagc ccctcggccc  1440
gagggtggct cccccgtcac cggccgggacg ccccccgcagc ccaagcggcc caggccagc   1500
gtgtccaagg acggcctgct gagcccaggc gcctggaacg gcgagcccag cggtgagggc  1560
agccggtcag tcactccgtc cgagggcgcg ggccgccgca gccccgcgcg tccagccacc  1620
gagcgcatgg ccatcgaggc tctgcaggca ccgcctgcgc cgtcgcggga gccggaggtg  1680
gcgctttacc agggctacca cagctatgct gtgcgcaccc cgccgccga gccccaccc    1740
tttgaggacc agcccgagcc cgaggtctcc gggtccgagt ccgcgccctc gtccccggcc  1800
accgcccccg tgcaggcccc cacgctccga ggccccgagc ctgcacgcga gacccccgcc  1860
aagctggagc ccaagcccat catccccaaa gccgagccca gggccaaggc ccgcaagact  1920
gaggctgagg gctgaccaa ggcggggccc aagaagaggc gcggaaaga ggccgcactg   1980
gcggcagagc ggaggtggga ggtggaagag gtccccaaca ccatcctcat ctgcatggtg  2040
atcctgctga acatcggcct ggccatcctc tttgttcacc tctgacctg a            2091

SEQ ID NO: 202          moltype = AA  length = 696
FEATURE                 Location/Qualifiers
source                  1..696
                        mol_type = protein
                        organism = Homo sapiens
SEQUENCE: 202
MSGGRFDFDD GGAYCGGWEG GKAHGHGLCT GPKGQGEYSG SWNFGFEVAG VYTWPSGNTF    60
EGYWSQGKRH GLGIETKGRW LYKGEWTHGF KGRYGIRQSS SSGAKYEGTW NNGLQDGYGT   120
ETYADGGTYQ GQFTNGMRHG YGVRQSVPYG MAVVVRSPLR TSLSSLRSEH SNGTVAPDSP   180
ASPASDGPAL PSPAIPRGGF ALSLLANAEA AARAPKGGGL FQRGALLGKL RRAESRTSVG   240
SQRSRVSFLK SDLSSGASDA ASTASLGEAA EGADEAAPFE ADIDATTTET YMGEWKNDKR   300
SGFGVSERSS GLRYEGEWLD NLRHGYGCTT LPDGHREEGK YRHNVLVKDT KRRMLQLKSN   360
KVRQKVEHSV EGAQRAAAIA RQKAEIAASR TSHAKAKAEA AEQAALAANQ ESNIARTLAR   420
ELAPDFYQPG PEYQKRRLLQ EILENSESLL EPPDRGAGAA GLPQPPRESP QLHERETPRP   480
EGGSPSPAGT PPQPKRPRPG VSKDGLLSPG AWNGEPSGEG SRSVTPSEGA GRRSPARPAT   540
ERMAIEALQA PPAPSREPEV ALYQGYHSYA VRTTPPEPPP FEDQPEPEVS GSESAPSSPA   600
TAPLQAPTLR GPEPARETPA KLEPKPIIPK AEPRAKARKT EARGLTKAGA KKKARKEAAL   660
AAEAEVEVEE VPNTILICMV ILLNIGLAIL FVHLLT                             696

SEQ ID NO: 203          moltype = DNA  length = 1728
FEATURE                 Location/Qualifiers
source                  1..1728
                        mol_type = other DNA
                        organism = Homo sapiens
SEQUENCE: 203
atgagcgccg ccaccactc gcccatgatg caggtggcgt ccggcaacgg tgaccgcgac    60
cctttgcccc ccggatggga gatcaagatc gacccgtggc ccggctggcc cttcttcgtg   120
gaccacaaca gccgcaccac tacgtggaac gacccgcgcg tgccctctga gggccccaag   180
gagactccat cctctgccaa tggccttcc cgggagggct ctaggctgcc gcctgctagg   240
gaaggccacc ctgtgtaccc ccagctccga ccaggctaca ttcccattcc tgtgctccat   300
gaaggcgctg agaaccggca ggtgcaccct ttccatgtct atcccagcc tgggatgcag   360
cgattccgaa ctgaggcggc agcagcggct cctcagaggt ccagtgtcacc tctgcgggga   420
atgccagaaa ccactcagcc agataaacag tgtggacagg tggcagcggc ggcggcagcc   480
cagcccccag cctccacgg acctgagcgg tccagtctc cagctgcctc tgactgctca   540
tcctcatcct cctcggccag cctgccttcc tccggcagga gcagcctggg cagtcaccag   600
ctcccgcggg ggtacatctc cattccggtg atacacgagc agaacgttac ccggccagca   660
gcccagcct ccttccacca agcccagaag acgcactacc cagcgcagca gggggagtac   720
```

```
cagacccacc agcctgtgta ccacaagatc caggggagcc actgggagcc ccggcccctg    780
cgggcggcat ccccgttcag gtcatctgtc cagggtgcat cgagccggga gggctcacca    840
gccaggagca gcacgccact ccactccccc tcgcccatcc gtgtgcacac cgtggtcgac    900
aggcctcagc agcccatgac ccatcgagaa actgcacctg tttcccagcc tgaaaacaaa    960
ccagaaagta agccaggccc agttggacca gaactccctc ctggacacat cccaattcaa    1020
gtgatccgca aagaggtgga ttctaaacct gtttcccaga agcccccacc tccctctgag    1080
aagtagagg tgaaagttcc ccctgctcca gttccttgtc ctcctcccag ccctggccct    1140
tctgctgtcc cctcttcccc caagagtgtg gctacagaag agagggcagc ccccagcact    1200
gcccctgcag aagctacacc tccaaaacca ggagaagccg aggctccccc aaaacatcca    1260
ggagtgctga aagtggaagc catcctggag aaggtacagg ggctggagca ggctgtagac    1320
aactttgaag gcaagaagac tgacaaaaag tacctgatga tcgaagagta tttgaccaaa    1380
gagctgctgg ccctggattc agtggacccc gagggacgag ccgatgtgcg tcaggccagg    1440
agagacggtg tcaggaaggt tcagaccatc ttggaaaaac ttgaacagaa agccattgat    1500
gtcccaggtc aagtccaggt ctatgaactc cagcccagca accttgaagc agatcagcca    1560
ctgcaggcaa tcatggagat gggtgccgtg gcagcagaca agggcaagaa aaatgctgga    1620
aatgcagaag atccccacac agaaacccag cagccagaag ccacagcagc agcgacttca    1680
aaccccagca gcatgacaga cacccctggt aacccagcag caccgtag              1728

SEQ ID NO: 204        moltype = AA  length = 575
FEATURE               Location/Qualifiers
source                1..575
                      mol_type = protein
                      organism = Homo sapiens
SEQUENCE: 204
MSAATHSPMM QVASGNGDRD PLPPGWEIKI DPQTGWPFFV DHNSRTTTWN DPRVPSEGPK     60
ETPSSANGPS REGSRLPPAR EGHPVYPQLR PGYIPIPVLH EGAENRQVHP FHVYPQPGMQ    120
RFRTEAAAAA PQRSQSPLRG MPETTQPDKQ CGQVAAAAAA QPPASHGPER SQSPAASDCS    180
SSSSSSASLPS SGRSSLGSHQ LPRGYISIPV IHEQNVTRPA AQPSFHQAQK THYPAQQGEY    240
QTHQPVYHKI QGDDWEPRPL RAASPFRSSV QGASSREGSP ARSSTPLHSP SPIRVHTVVD    300
RPQQPMTHRE TAPVSQPENK PESKPGPVGP ELPPGHIPIQ VIRKEVDSKP VSQKPPPPSE    360
KVEVKVPPAP VPCPPPSPGP SAVPSSPKSV ATEERAAPST APAEATPPKP GEAEAPPKHP    420
GVLKVEAILE KVQGLEQAVD NFEGKKTDKK YLMIEEYLTK ELLALDSVDP EGRADVRQAR    480
RDGVRKVQTI LEKLEQKAID VPGQVQVYEL QPSNLEADQP LQAIMEMGAV AADKGKKNAG    540
NAEDPHTETQ QPEATAAATS NPSSMTDTPG NPAAP                              575

SEQ ID NO: 205        moltype = DNA  length = 528
FEATURE               Location/Qualifiers
source                1..528
                      mol_type = other DNA
                      organism = Homo sapiens
SEQUENCE: 205
atggacatcg ccatccacca cccctggatc cgccgcccct ctttcctttt ccactccccc     60
agccgcctct ttgaccagtt cttcggagag cacctgttgg agtctgatct tttcccgacg    120
tctacttccc tgagtccctt ctaccttcgg ccaccctcct tcctgcgggc acccagctgg    180
tttgacactg gactctcaga gatgcgcctg gagaaggaca ggttctctgt caacctggat    240
gtgaagcact tctccccaga ggaactcaaa gttaaggtgt tgggagatgt gattgaggtg    300
catggaaaac atgaagagcg ccaggatgaa catggtttca tctccaggga gttccacagg    360
aaataccgga tcccagctga tgtagaccct ctcaccatta cttcatccct gtcatctgat    420
ggggtcctca ctgtgaatgg accaaggaaa caggtctctg gccctgagcg caccattccc    480
atcacccgtg aagagaagcc tgctgtcacc gcagccccca gaaatag                528

SEQ ID NO: 206        moltype = AA  length = 175
FEATURE               Location/Qualifiers
source                1..175
                      mol_type = protein
                      organism = Homo sapiens
SEQUENCE: 206
MDIAIHHPWI RRPFFPFHSP SRLFDQFFGE HLLESDLFPT STSLSPFYLR PPSFLRAPSW     60
FDTGLSEMRL EKDRFSVNLD VKHFSPEELK VKVLGDVIEV HGKHEERQDE HGFISREFHR    120
KYRIPADVDP LTITSSLSSD GVLTVNGPRK QVSGPERTIP ITREEKPAVT AAPKK         175

SEQ ID NO: 207        moltype = DNA  length = 1995
FEATURE               Location/Qualifiers
source                1..1995
                      mol_type = other DNA
                      organism = Homo sapiens
SEQUENCE: 207
atggagaccc cgtcccagcg gcgcgcgcacc cgcagcgggg cgcaggccag ctccactccg     60
ctgtcgccca cccgcatcac ccggctgcag gagaaggagg acctgcagga gctcaatgat    120
cgcttggcgg tctacatcga ccgtgtgcgc tcgctggaaa cggagaacgc agggctcgcg    180
cttcgcatca ccgagtctga gaggtggtc agccgcgagg tgtccggcat caaggccgcc    240
tacgaggccg agctcgggga tgcccgcaag acccttgact cagtagccaa ggagcgcgcc    300
cgcctgcagc tggagctgag caaagtgcgt gaggagttta aggagctgaa agcgcgcaat    360
accaagaagg agggtgacct gatacgtgct caggctcggc tgaaggacct ggagctctg    420
ctgaactcca aggaggccgc actgagcact gctctcagtg agaagcgcac gctggagggc    480
gagctgcatg atctgcgggg ccaggtgcc aagcttgagg cagccctagg tgaggccaag    540
aagcaacttc aggatgagat gctgcggcgg gtggatgctg agaacaggct gcagaccatg    600
aaggaggaac tggacttcca gaagaacatc tacagtgagg agctgcgtga gaccaagcgc    660
cgtcatgaga cccgactggt ggagattgac aatgggaagc agcgtgagtt tgagagcggg    720
```

```
ctggcggatg cgctgcagga actgcgggcc cagcatgagg accaggtgga gcagtataag   780
aaggagctgg agaagactta ttctgccaag ctggacaatg ccaggcagtc tgctgagagg   840
aacagcaacc tggtgggggc tgcccacgag gagctgcagc agtcgcgcat ccgcatcgac   900
agcctctctg cccagctcag ccagctccag aagcagctgg cagccaagga ggcgaagctt   960
cgagacctgg aggactcact ggcccgtgag cgggacacca gccggcggct gctggcggaa  1020
aaggagcggg agatgccga gatgcgggca aggatgcagc agcagctgga cgagtaccag  1080
gagcttctgg acatcaagct ggccctggac atggagatcc acgcctaccg caagctcttg  1140
gagggcgagg aggagaggct acgcctgtcc cccagccta cctcgcagcg cagccgtggc  1200
cgtgcttcct ctcactcatc ccagacacag ggtggggca gcgtcaccaa gcgcaagcga  1260
ctggagtcca ctgagagccg cagcagcttc tcacagcacg cacgcactag cggggcgctg  1320
gccgtggagg aggtggatga ggagggcaag tttgtccggc tgcgcaacaa gtccaatgag  1380
gaccagtcca tgggcaattg gcagatcaag cgccagaatg gagatgatcc cttgctgact  1440
taccggttcc caccaaagtt caccctgaag gctgggcagg tggtgacgat ctgggctgca  1500
ggagctgggg ccacccacag cccccctacc gacctggtgt ggaaggcaca gaacacctgg  1560
ggctgcggga acagcctgcg tacggctctc atcaactcca ctggggaaga agtggccatg  1620
cgcaagctgg tgcgctcagt gactgtggtt gaggacgacg aggatgagga tgagatgac  1680
ctgctccatc accaccacgg ctcccactgc agcagctcgg ggaccccgc tgagtacaac  1740
ctgcgctcgc gcaccgtgct gtgcgggacc tgcgggcagc ctgccgacaa ggcatctgcc  1800
agcggctcag gagcccaggt gggcggaccc atctcctctg gctcttctgc ctccagtgtc  1860
acggtcactc gcagctaccg cagtgtgggg gcagtgggg gtggcagctt cggggacaat  1920
ctggtcaccc gctcctacct cctgggcaac tccagccccc gaaccagag ccccagaac  1980
tgcagcatca tgtaa                                                  1995

SEQ ID NO: 208          moltype = AA  length = 664
FEATURE                 Location/Qualifiers
source                  1..664
                        mol_type = protein
                        organism = Homo sapiens
SEQUENCE: 208
METPSQRRAT RSGAQASSTP LSPTRITRLQ EKEDLQELND RLAVYIDRVR SLETENAGLR   60
LRITESEEVV SREVSGIKAA YEAELGDARK TLDSVAKERA RLQLELSKVR EEFKELKARN  120
TKKEGDLIAA QARLKDLEAL LNSKEAALST ALSEKRTLEG ELHDLRGQVA KLEAALGEAK  180
KQLQDEMLRR VDAENRLQTM KEELDFQKNI YSEELRETKR RHETRLVEID NGKQREFESR  240
LADALRELRA QHEDVEQYK KELEKTYSAK LDNARQSAER NSNLVGAAHE ELQQSRIRID  300
SLSAQLSQLQ KQLAAKEAKL RDLEDSLARE RDTSRRLLAE KEREMAEMRA RMQQQLDEYQ  360
ELLDIKLALD MEIHAYRKLL EGEEERLRLS PSPTSQRSRG RASSHSSQTQ GGGSVTKKRK  420
LESTESRSSF SQHARTSGRV AVEEVDEEGK FVRLRNKSNE DQSMGNWQIK RQNGDDPLLT  480
YRFPPKFTLK AGQVVTIWAA GAGATHSPPT DLVWKAQNTW GCGNSLRTAL INSTGEEVAM  540
RKLVRSVTVV EDDEDEDGDD LLHHHGSHC SSSGDPAEYN LRSRTVLCGT CGQPADKASA  600
SGSGAQVGGP ISSGSSASSV TVTRSYRSVG GSGGGSFGDN LVTRSYLLGN SSPRTQSPQN  660
CSIM                                                              664

SEQ ID NO: 209          moltype = DNA  length = 1719
FEATURE                 Location/Qualifiers
source                  1..1719
                        mol_type = other DNA
                        organism = Homo sapiens
SEQUENCE: 209
atggagaccc cgtcccagcg gcgcgccacc cgcagcgggg cgcaggccag ctccactccg   60
ctgtcgccca cccgcatcac ccggctgcag gagaaggagg acctgcagga gctcaatgat  120
cgcttggcgg tctacatcga ccgtgtgcgc tcgctgggaaa cggagaacgc agggctgcgg  180
cttcgcatca ccgagtctga agaggtggtc agccgcgagg tgtccggcat caaggccgcc  240
tacgaggccg agctcgggga tgcccgcaag acccttgact cagtagccaa ggagcgcgcc  300
cgcctgcagc tggagctgag caaagtgcgt gaggagttta aggagctgaa agcgcgcaat  360
accaagaagg agggtgacct gatagctgct caggctcggc tgaaggacct ggaggctctg  420
ctgaactcca aggaggccgc actgagcact gctctcagtg agaagcgcac gctggagggc  480
gagctgcatg atctgcgggg ccaggtggcc aagcttgagg cagccctagg tgaggccaag  540
aagcaacttc aggatgagat gctgcggcgg gtggatgctg agaacaggct gcagaccatg  600
aaggaggaac tggacttcca gaaaacatc tacagtgagg agctgcgtga gaccaagcgc  660
cgtcatgaga cccgactggt ggagattgac aatgggaagc agcgtgagtt tgagagccgt  720
ctggcggatg cgctgcagga actgcgggcc cagcatgagg accaggtgga gcagtataag  780
aaggagctgg agaagactta ttctgccaag ctggacaatg ccaggcagtc tgctgagagg  840
aacagcaacc tggtgggggc tgcccacgag gagctgcagc agtcgcgcat ccgcatcgac  900
agcctctctg cccagctcag ccagctccag aagcagctgg cagccaagga ggcgaagctt  960
cgagacctgg aggactcact ggcccgtgag cgggacacca gccggcggct gctggcggaa 1020
aaggagcggg agatgccga gatgcgggca aggatgcagc agcagctgga cgagtaccag 1080
gagcttctgg acatcaagct ggccctggac atggagatcc acgcctaccg caagctcttg 1140
gagggcgagg aggagaggct acgcctgtcc cccagccta cctcgcagcg cagccgtggc 1200
cgtgcttcct ctcactcatc ccagacacag ggtggggca gcgtcaccaa aagcgcaag 1260
ctggagtcca ctgagagccg cagcagcttc tcacagcacg cacgcactag cggggcgctg 1320
gccgtggagg aggtggatga ggagggcaag tttgtccggc tgcgcaacaa gtccaatgag 1380
gaccagtcca tgggcaattg gcagatcaag cgccagaatg gagatgatcc cttgctgact 1440
taccggttcc caccaaagtt caccctgaag gctgggcagg tggtgacgat ctgggctgca 1500
ggagctgggg ccacccacag cccccctacc gacctggtgt ggaaggcaca gaacacctgg 1560
ggctgcggga acagcctgcg tacggctctc atcaactcca ctggggaaga agtggccatg 1620
cgcaagctgg tgcgctcagt gactgtggtt gaggacgacg aggatgagga tgagatgac 1680
ctgctccatc accaccacgt gagtggtagc cgccgctga                        1719

SEQ ID NO: 210          moltype = AA  length = 572
```

```
FEATURE                 Location/Qualifiers
source                  1..572
                        mol_type = protein
                        organism = Homo sapiens
SEQUENCE: 210
METPSQRRAT RSGAQASSTP LSPTRITRLQ EKEDLQELND RLAVYIDRVR SLETENAGLR    60
LRITESEEVV SREVSGIKAA YEAELGDARK TLDSVAKERA RLQLELSKVR EEFKELKARN   120
TKKEGDLIAA QARLKDLEAL LNSKEAALST ALSEKRTLEG ELHDLRGQVA KLEAALGEAK   180
KQLQDEMLRR VDAENRLQTM KEELDFQKNI YSEELRETKR RHETRLVEID NGKQREFESR   240
LADALQELRA QHEDQVEQYK KELEKTYSAK LDNARQSAER NSNLVGAAHE ELQQSRIRID   300
SLSAQLSQLQ KQLAAKEAKL RDLEDSLARE RDTSRRLLAE KEREMAEMRA RMQQQLDEYQ   360
ELLDIKLALD MEIHAYRKLL EGEEERLRLS PSPTSQRSRG RASSHSSQTQ GGGSVTKKRK   420
LESTESRSSF SQHARTSGRV AVEEVDEEGK FVRLRNKSNE DQSMGNWQIK RQNGDDPLLT   480
YRFPPKFTLK AGQVVTIWAA GAGATHSPPT DLVWKAQNTW GCGNSLRTAL INSTGEEVAM   540
RKLVRSVTVV EDDEDEDGDD LLHHHHVSGS RR                                 572

SEQ ID NO: 211          moltype = DNA  length = 633
FEATURE                 Location/Qualifiers
source                  1..633
                        mol_type = other DNA
                        organism = Homo sapiens
SEQUENCE: 211
atggcggatg ggagcagcga tgcggctagg gaacctcgcc ctgcaccagc cccaatcaga    60
cgccgctcct ccaactaccg cgcttatgcc acggagccgc acgccaagaa aaaatctaag   120
atctccgcct cgagaaaatt gcagctgaag actctgctgc tgcagattgc aaagcaagag   180
ctggagcgag aggcggagga gaagcggggc agagaagagg gcgctctgag cacccgctgc   240
cagccgctgg agttggccgg gctgggcttc gcggagctga aggacttgtg ccgacagctc   300
cacgcccgtg tggacaaggt ggatgaagag agatacgaca tagaggcaaa agtcaccaag   360
aacatcacgg agattgcaga tctgactcag aagatctttg accttcgagg caagtttaag   420
cggccccacc tgcggagagt gaggatctct gcagatgcag gctgctgggg   480
gcccgggcta aggagtccct ggacctgcgg gccccacctca agcaggtgaa gaaggaggac   540
accgagaagg aaaaccggga ggtgggagac tggcgcaaga acatcgatgc actgagtgga   600
atggagggcc gcaagaaaaa gtttgagagc tga                                 633

SEQ ID NO: 212          moltype = AA  length = 210
FEATURE                 Location/Qualifiers
source                  1..210
                        mol_type = protein
                        organism = Homo sapiens
SEQUENCE: 212
MADGSSDAAR EPRPAPAPIR RRSSNYRAYA TEPHAKKKSK ISASRKLQLK TLLLQIAKQE    60
LEREAEERRG EKGRALSTRC QPLELAGLGF AELQDLCRQL HARVDKVDEE RYDIEAKVTK   120
NITEIADLTQ KIFDLRGKFK RPTLRRVRIS ADAMMQALLG ARAKESLDLR AHLKQVKKED   180
TEKENREVGD WRKNIDALSG MEGRKKKFES                                    210

SEQ ID NO: 213          moltype = DNA  length = 1233
FEATURE                 Location/Qualifiers
source                  1..1233
                        mol_type = other DNA
                        organism = Homo sapiens
SEQUENCE: 213
atggtgtgct tccgcctctt cccggttccg ggctcagggc tcgttctggt ctgcctagtc    60
ctgggagctg tgcggtctta tgcattggaa cttaatttga cagattcaga aaatgccact   120
tgcctttatg caaaatggca gatgaatttc acagtacgct atgaaactac aaataaaact   180
tataaaactg taaccatttc agaccatggc actgtgacat ataatggaag cattgtgggg   240
gatgatcaga atggtcccaa aatagcagtg cagttcggac ctggctttttc ctggattgca   300
aattttacca aggcagcatc tacttattca attgacagcg tctcattttc ctacaacact   360
ggtgataaca caacatttcc tgatgctgaa gataaaggaa ttcttactgt tgatgaactt   420
ttggccatca gaattccatt gaatgacctt tttagatgca atagtttatc aactttggaa   480
aagaatgatg ttgtccaaca ctactgggat gttcttgtac aagcttttgt ccaaaatgtc   540
acagtgagca caaatgagtt cctgtgtgat aaagacaaaa cttcaacagt ggcacccacc   600
atacacacca ctgtgccatc tcctactaca cacctactc caaaggaaaa accagaagct   660
ggaacctatt cagttaataa tggcaatgat acttgtctgc tggctaccat ggggctgcag   720
ctgaacatca ctcaggataa ggttgcttca gttattaaca tcaaccccaa tacaactcac   780
tccacaggca gctgccgttc tcacactgct ctacttagac tcaatagcag caccattaag   840
tatctagact ttgtctttgc tgtgaaaaat gaaaaccgat tttatctgaa ggaagtgaac   900
atcagcatgt atttggttaa tggctccgtt ttcagcattg caaataacaa tctcagctac   960
tgggatgccc cctgggaaag ttcttatatg tgcaacaaag agcagactgt ttcagtgtct  1020
ggagcatttc agataaatac ctttgatcta agggttcagc aatgtgacac acaagga     1080
aagtattcta cagctcaaga ctgcagtgca gatgacgaca acttccttgt gcccatagcc  1140
gtgggagctg cctggcagg agtacttatt ctagtgttgc tggcttattt tattggtctc  1200
aagcaccatc atgctggata tgagcaattt tag                                1233

SEQ ID NO: 214          moltype = AA  length = 410
FEATURE                 Location/Qualifiers
source                  1..410
                        mol_type = protein
                        organism = Homo sapiens
SEQUENCE: 214
```

```
MVCFRLFPVP GSGLVLVCLV LGAVRSYALE LNLTDSENAT CLYAKWQMNF TVRYETTNKT    60
YKTVTISDHG TVTYNGSICG DDQNGPKIAV QFGPGFSWIA NFTKAASTYS IDSVSFSYNT   120
GDNTTFPDAE DKGILTVDEL LAIRIPLNDL FRCNSLSTLE KNDVVQHYWD VLVQAFVQNG   180
TVSTNEFLCD KDKTSTVAPT IHTTVPSPTT TPTPKEKPEA GTYSVNNGND TCLLATMGLQ   240
LNITQDKVAS VININPNTTH STGSCRSHTA LLRLNSSTIK YLDFVFAVKN ENRFYLKEVN   300
ISMYLVNGSV FSIANNNLSY WDAPLGSSYM CNKEQTVSVS GAFQINTFDL RVQPFNVTQG   360
KYSTAQDCSA DDDNFLVPIA VGAALAGVLI LVLLAYFIGL KHHHAGYEQF             410

SEQ ID NO: 215          moltype = DNA   length = 1233
FEATURE                 Location/Qualifiers
source                  1..1233
                        mol_type = other DNA
                        organism = Homo sapiens
SEQUENCE: 215
atggtgtgct tccgcctctt cccggttccg ggctcagggc tcgttctggt ctgcctagtc    60
ctgggagctg tgcggtctta tgcattggaa cttaatttga cagattcaga aaatgccact   120
tgcctttatg caaaatggca gatgaatttc acagtacgct atgaaactac aaataaaact   180
tataaaactg taaccatttc agaccatggc actgtgacat ataatggaag catttgtggg   240
gatgatcaga atggtcccaa aatagcagtg cagttcggac ctggcttttc ctggattgcg   300
aattttacca aggcagcatc tacttattca attgacagcg tctcattttc ctacaacact   360
ggtgataaca caacatttcc tgatgctgaa gataaaggaa ttcttactgt tgatgaactt   420
ttggccatca gaattccatt gaatgacctt tttagatgca atagtttatc aacttttgaa   480
aagaatgatg ttgtccaaca ctactgggat gttcttgtac aagcttttgt ccaaaatggc   540
acagtgagca aaatgagtt cctgtgtgat aaagacaaaa cttaacagt ggcacccacc   600
atacacacca ctgtgccatc tcctactaca cacctactc caaggaaaa accagaagct    660
ggaacctatt cagttaataa tggcaatgat acttgtctgc ttgctaccat ggggctgcag   720
ctgaacatca ctcaggataa ggttgcttca gttattaaca tcaaccccaa tacaactcac   780
tccacaggca gctgccgttc tcacactgct ctacttagac tcaatagcag caccattaag   840
tatctagact ttgtctttgc tgtgaaaaat gaaaaccgat tttatctgaa ggaagtgaac   900
atcagcatgt atttggttaa tggctccgtt ttcagcattg caaataacaa tctcagctac   960
tgggatgccc ccctgggaag ttcttatatg tgcaacaaag agcagactgt ttcagtgtct  1020
ggagcatttc agataaatac ctttgatcta agggttcagc ctttcaatgt gacacaagga  1080
aagtattcta cagcccaaga tgttcgctg atgatgaca ccattctaat cccaattata  1140
gttggtgctg gtctttcagg cttgattatc gttatagtaa ttgcttacgt aattggcaga  1200
agaaaaagtt atgctggata tcagactctg taa                               1233

SEQ ID NO: 216          moltype = AA   length = 410
FEATURE                 Location/Qualifiers
source                  1..410
                        mol_type = protein
                        organism = Homo sapiens
SEQUENCE: 216
MVCFRLFPVP GSGLVLVCLV LGAVRSYALE LNLTDSENAT CLYAKWQMNF TVRYETTNKT    60
YKTVTISDHG TVTYNGSICG DDQNGPKIAV QFGPGFSWIA NFTKAASTYS IDSVSFSYNT   120
GDNTTFPDAE DKGILTVDEL LAIRIPLNDL FRCNSLSTLE KNDVVQHYWD VLVQAFVQNG   180
TVSTNEFLCD KDKTSTVAPT IHTTVPSPTT TPTPKEKPEA GTYSVNNGND TCLLATMGLQ   240
LNITQDKVAS VININPNTTH STGSCRSHTA LLRLNSSTIK YLDFVFAVKN ENRFYLKEVN   300
ISMYLVNGSV FSIANNNLSY WDAPLGSSYM CNKEQTVSVS GAFQINTFDL RVQPFNVTQG   360
KYSTAQECSL DDDTILIPII VGAGLSGLII VIVIAYVIGR RKSYAGYQTL             410

SEQ ID NO: 217          moltype = DNA   length = 1236
FEATURE                 Location/Qualifiers
source                  1..1236
                        mol_type = other DNA
                        organism = Homo sapiens
SEQUENCE: 217
atggtgtgct tccgcctctt cccggttccg ggctcagggc tcgttctggt ctgcctagtc    60
ctgggagctg tgcggtctta tgcattggaa cttaatttga cagattcaga aaatgccact   120
tgcctttatg caaaatggca gatgaatttc acagtacgct atgaaactac aaataaaact   180
tataaaactg taaccatttc agaccatggc actgtgacat ataatggaag catttgtggg   240
gatgatcaga atggtcccaa aatagcagtg cagttcggac ctggcttttc ctggattgcg   300
aattttacca aggcagcatc tacttattca attgacagcg tctcattttc ctacaacact   360
ggtgataaca caacatttcc tgatgctgaa gataaaggaa ttcttactgt tgatgaactt   420
ttggccatca gaattccatt gaatgacctt tttagatgca atagtttatc aacttttgaa   480
aagaatgatg ttgtccaaca ctactgggat gttcttgtac aagcttttgt ccaaaatggc   540
acagtgagca aaatgagtt cctgtgtgat aaagacaaaa cttaacagt ggcacccacc   600
atacacacca ctgtgccatc tcctactaca cacctactc caaggaaaa accagaagct    660
ggaacctatt cagttaataa tggcaatgat acttgtctgc tggctaccat ggggctgcag   720
ctgaacatca ctcaggataa ggttgcttca gttattaaca tcaaccccaa tacaactcac   780
tccacaggca gctgccgttc tcacactgct ctacttagac tcaatagcag caccattaag   840
tatctagact ttgtctttgc tgtgaaaaat gaaaaccgat tttatctgaa ggaagtgaac   900
atcagcatgt atttggttaa tggctccgtt ttcagcattg caaataacaa tctcagctac   960
tgggatgccc ccctgggaag ttcttatatg tgcaacaaag agcagactgt ttcagtgtct  1020
ggagcatttc agataaatac ctttgatcta agggttcagc ctttcaatgt gacacaagga  1080
aagtattcta cagctgaaga tgttctgct gactctgacc tcaactttct tattcctgtt  1140
gcagtggggtg tggccttggg cttccttata attgttgtct ttatctctta tgattggaa  1200
agaaggaaaa gtcgtactgg ttatcagtct gtgtaa                            1236

SEQ ID NO: 218          moltype = AA   length = 411
```

```
FEATURE              Location/Qualifiers
source               1..411
                     mol_type = protein
                     organism = Homo sapiens
SEQUENCE: 218
MVCFRLFPVP GSGLVLVCLV LGAVRSYALE LNLTDSENAT CLYAKWQMNF TVRYETTNKT   60
YKTVTISDHG TVTYNGSICG DDQNGPKIAV QFGPGFSWIA NFTKAASTYS IDSVSFSYNT  120
GDNTTFPDAE DKGILTVDEL LAIRIPLNDL FRCNSLSTLE KNDVVQHYWD VLVQAFVQNG  180
TVSTNEFLCD KDKTSTVAPT IHTTVPSPTT TPTPKEKPEA GTYSVNNGND TCLLATMGLQ  240
LNITQDKVAS VININPNTTH STGSCRSHTA LLRLNSSTIK YLDFVFAVKN ENRFYLKEVN  300
ISMYLVNGSV FSIANNNLSY WDAPLGSSYM CNKEQTVSVS GAFQINTFDL RVQPFNVTQG  360
KYSTAEECSA DSDLNFLIPV AVGVALGFLI IVVFISYMIG RRKSRTGYQS V           411

SEQ ID NO: 219       moltype = DNA   length = 8616
FEATURE              Location/Qualifiers
source               1..8616
                     mol_type = other DNA
                     organism = Homo sapiens
SEQUENCE: 219
atgagctgca acggaggctc ccacccgcgg atcaacactc tgggccgcat gatccgcgcc   60
gagtctggcc cggacctgcg ctacgaggtg accagcggcg gcggggcac cagcaggatg   120
tactattctc ggcgcggcgt gatcaccgac cagaactgca acggctactg tcaaaccggc   180
acgatgtcca ggcaccagaa ccagaacacc atccaggagc tgctgcagaa ctgctccgac   240
tgcttgatgc gagcagagct catcgtgcag cctgaattga agtatggaga tggaatacaa   300
ctgactcgga gtcgagaatt ggatgagtgt tttgcccagg ccaatgacca aatggaaatc   360
ctcgacagct tgatcagaga gatgcgacag atgggcacgc cctgtgatgc ttaccagaaa   420
aggcttcttc agctccaaga gcaaatgcga gcccctttata aagccatcag tgtccctcga   480
gtccgcaggg ccagctccaa gggtggtgga ggctacactt gtcagagtgg ctctggctgg   540
gatgagttca ccaaacatgt caccagtgaa tgtttgggt ggatgaggca gcaaaggggcg   600
gagatggaca tggtggcctg gggtgtggac ctggcctcaa tggagcagca cattaacagc   660
caccggggca tccacaactc catcggcgac tatcgctggc agctggacaa aatcaaagcc   720
gacctgcgcg agaaatctgc gatctaccag ttggaggagg agtatgaaaa cctgctgaaa   780
gcgtcctttg agaggatgga tcacctgcga cagctgcaga acatcattca ggccacgtcc   840
agggaagatca tgtggatcaa tgactgcgag gaggaggac tgctgtacga ctggagcgac   900
aagaacacca acatcgctca gaaacaggag gccttctcca tacgcatgag tcaactggtg   960
gttaaagaaa aagagctcaa taagctgaaa caagaaagtg accaacttgt cctcaatcag  1020
catccagctt cagacaaaat tgaggcctat atggacactc tgcagacgca gtggagttgg  1080
attcttcaga tcaccaagtg cattgatgtt catctgaaag aaaatgctgc ctactttcag  1140
tttttttgaag aggcgcagtc tactgaagca tacctgaagg ggctccagga tcccatcagg  1200
aagaagtacc cctgcgacaa gaacatgccc ctgcagcacc tgctggaaca gatcaaggag  1260
ctggagaaaa acgagagaa atccttgaa tacaagcgtc aggtgcagaa cttggtaaac  1320
aagtctaaga agattgtaca gctgaagcct cgtaacccag actacagaag caataaaccc  1380
attattctca gagctctctg tgactacaaa caagatcaga aaatcgtgcaa taaggggggat  1440
gagtgtatcc tgaaggacaa caacgagcgc agcaagtggt acgtgacggg cccgggaggc  1500
gttgacatgc ttgttccctc tgtgggggctg atcatccctc ctccgaaccc actggccgtg  1560
gacctctctt gcaagattga gcagtactac gaagccatct ggctctgtg aaccagctc   1620
tacatcaaca tgaagagcct ggtgtcctgg cactactgca tgattgacta agagaagatc  1680
agggccatga caatcgccaa gctgaaaaca atgcggcagg aagattacat gaagacgata  1740
gccgaccttg agttacatta ccaagagttc atcagaaata gccaaggctc agagatgttt  1800
ggagatgatg acaagcggaa aatacagtct cagttcaccg atgcccagaa gcattaccag  1860
accctgtca ttcagctccc tggctatccc cagcaccaga cagtgaccac aactgaaatc  1920
actcatcatg gaacctgcca agatgtcaac cataataaag taattgaaac caacagagaa  1980
aatgacaagc aagaaacatg gatgctgatg gagctgcaga agattcgcag cagatagag  2040
cactgcgagg gcaggatgac tctcaaaaac ctccctctag cagaccaggg atcttctcac  2100
cacatcacag tgaaaattaa cgagcttaag agtgtgcaga atgattcaca agcaattgct  2160
gaggttctca accagcttaa agatatgctt gccaacttca gaggttctga aaagtactgc  2220
tatttacaga atgaagtatt tggactattt cagaaactgg aaaatatcaa tggtgttaca  2280
gatggctact aaatagcctt atgcacagta aggcactgc tccaggctat tctccaaaca  2340
gaagacatgt taaaggttta tgaagcaagg ctcactgagg aggaaactgt ctgcctggca  2400
ctggataaag tggaagctta ccgctgtgga ctgaagaaaa taaaaatga cttgaacttg  2460
aagaagtcgt tgttgccac tatgaagaca gaactacaga agcccagca gatccactct  2520
cagacttcac agcagtatcc actttatgat ctggacttgg gcaagttcgg tgaaaaagtc  2580
acacagctga cagaccgctg gcaaaggata gataaacaga tcgactttag gttatgggac  2640
ctggagaaac aaatcaagca attgcagaat tatcgtgata actatcaggc tttctgcaag  2700
tggctctatg atgctaaacg ccgccaggat tccttagaat ccatgaaatt tggagattcc  2760
aacacagtca tgcggttttt gaatgagcag aagaacttgc acagtgaaat atctggcaaa  2820
cgagacaaat cagaggaagt acaaaaaatt gctgaacttt cgccaattc aattaaggat  2880
tatgagctcc agctggcctc atacacctca ggactggaaa ctctgctgaa catacctatc  2940
aagaggacca tgattcagtc cccttctggg gtgattctgc aagaggctgc agatgttcat  3000
gctcggtaca ttgaactact tacaagatct tggagactatt acaggttctt aagtgagatg  3060
ctgaagagtt tggaagatct gaagctgaaa atacccaaga tcgaagtttt ggaagaggag  3120
ctcagactgg cccgagatgc caactcggaa aactgtaata gaacaaatt cctgatcag  3180
aacctgcaga aataccaggc agagtgttcc cagttcaaaa cgaagcttgc gagcctggag  3240
gagctgaaga gacaggctga gctgatggga agtcggtca acaaaatct gacaagaagtgo  3300
tacggccaaa taaagaaact caatgagaag atcacccgac tgacttatga gattgaagat  3360
gaaagagaa gaagaaatc tgtggaagac agatttgacc aacagaagaa tgactatgac  3420
caactgcaga aagcaaggca atgtgaaaag gagaacttg ttggcagaa attagagtct  3480
gagaagcca tcaaggagaa ggagtacgag attgaaaggt tgaggttct actgcaggaa  3540
gaaggcaccc ggaagagaga atatgaaaat gagctggcaa aggtaagaaa ccactataat  3600
```

```
gaggagatga gtaatttaag gaacaagtat gaaacagaga ttaacattac gaagaccacc  3660
atcaaggaga tatccatgca aaaagaggat gattccaaaa atcttagaaa ccagcttgat  3720
agactttcaa gggaaaatcg agatctgaag gatgaaattg tcaggctcaa tgacagcatc  3780
ttgcaggcca ctgagcagcg aaggcgagct gaagaaaacg cccttcagca aaaggcctgt  3840
ggctctgaga taatgcagaa gaagcagcat ctggagatga aactgaagca ggtcatgcag  3900
cagcgctctg aggacaatgc ccggcacaag cagtccctgg aggaggctgc caagaccatt  3960
caggacaaaa ataaggagat cgagagactc aaagctgagt ttcaggagga ggccaagcgc  4020
cgctgggaat atgaaaatga actgagtaag gtaagaaaca attatgatga ggagatcatt  4080
agcttaaaaa atcagtttga gaccgagatc aacatcacca agaccaccat ccaccagctc  4140
accatgcaga aggaagagga taccagtggc taccgggctc agatagacaa tctcacccga  4200
gaaaacagga gcttatctga agaaataaag aggctgaaga acactctaac ccagaccaca  4260
gagaatctca ggagggtgga agaagacatc aacagcaaa aaggccactgg ctctgaggtg  4320
tctcagagga aacagcagct ggaggttgag ctgagacaag tcactcagat gcgaacagag  4380
gagagcgtaa gatataagca atctctttgat gatgctgcca aaaccatcca ggataaaaac  4440
aaggagatag aaaggttaaa acaactgatc gacaaagaaa caaatgaccg gaaatgcctg  4500
gaagatgaaa acgcgagatt acaaagggtc cagtatgacc tgcagaaagc aaacagtagt  4560
gcgacggaga caataaacaa actgaaggtt caggagcaag aactgacacg cctgaggatc  4620
gactatgaaa gggtttccca ggagaggact gtgaaggacc aggatatcac gcggttccag  4680
aactctctga aagagctgca gctgcagaag cagaaggtgg aagaggagct gaatcggctg  4740
aagaggaccg cgtcagaaga ctcctgcaag aggaagaagc tggaggaaga gctgaaggc  4800
atgaggaggt cgctgaagga gcaagccatc aaaatcacca acctgaccca gcagctggag  4860
caggcatcca ttgttaagaa gaggagtgag gatgacctcc ggcagcagag ggacgtgctg  4920
gatgccacc tgagggaaaa gcagaggacc aggaagagc tgaggaggct ctcttctgag  4980
gtcgaggccc tgaggcggca gttactccag gaacaggaaa gtgtcaaaca agctcacttg  5040
aggaatgagc atttccagaa ggcgatgaa gataaaagca gaagcttaaa tgaaagcaaa  5100
atagaaattg agaggctgca gtctctcaca gagaacctga ccaaggagca cttgatgtta  5160
gaagaagaac tgcggaacct gaggctggag tacgatgacc tgaggagagg acgaagcgaa  5220
gcggacagtg ataaaaatgc aaccatcttg gaactaagga gccagctgca gatcagcaac  5280
aaccggaccc tggaactgca ggggctgatt aatgatttac agagagagag ggaaaatttg  5340
agacaggaaa ttgagaaatt ccaaaagcag gctttagagg catctaatag gattcaggaa  5400
tcaaagaatc agtgtactca ggtggtacga gaaagagaga gccttctggt gaaaatcaaa  5460
gtcctggagc aagacaaggc aaggctgcag aggctggagg atgagctgaa tcgtgcaaaa  5520
tcaactctag aggcagaaac cagggtgaaa cagcgcctgg agtgtgagaa acagcaaatt  5580
cagaatgacc tgaatcagtg gaagactcaa tattcccgca aggaggaggc tattaggaag  5640
atagaatcgg aaaagaaaa gagtgagaga gagaagaaca gtcttaggag tgagatcgaa  5700
agactccaag cagagatcaa gagaattgaa gagaggtgca ggcgtaagct ggaggattct  5760
accagggaga cacagtcaca gttagaaaca gaacgctccc gatatcagag ggagattgat  5820
aaaactcagac agcgcccata tgggtcccat cgagagaccc agactgagtg tgagtggacc  5880
gttgacacct ccaagctggt gtttgatggg ctgaggaaga aggtgacagc aatgcagctc  5940
tatgagtgtc agctgatcga caaaacaacc ttggacaaac tattgaaggg gaagaagtca  6000
gtggaagaag ttgcttctga aatccagcca ttccttcggg gtgcaggatc tatcgctgga  6060
gcatctgctt ctcctaagga aaaatactct ttggtagagg ccaagagaaa gaattaatc  6120
agcccagaat ccacagtcat gcttctggag gcccaggcag ctacaggtgg tataattgat  6180
ccccatcgga atgagaagct gactgtcgac agtgccatag ctcggacct cattgacttc  6240
gatgaccgtc agcagatata tgcagcagaa aaagctatca ctggttttga tgatccattt  6300
tcaggcaaga cagtatctgt ttcagaagcc atcaagaaaa atttgattga tagagaaacc  6360
ggaatgcgcc tgctggaagc ccagattgct tcaggggtg tagtagaccc tgtgaacagt  6420
gtcttttgc caaaagatgt cgccttggcc cgggggctga ttgatagaga tttgtatcga  6480
tccctgaatg atcccgaga tagtcagaaa aactttgtgg atccagtcac caaaaagaag  6540
gtcagttacg tgcagctgaa ggaacggtgc agaatcgaac cacatactgg tctgctcttg  6600
ctttcagtac agaagagaag catgtccttc caaggaatca gcaacctgt gaccgtcact  6660
gagctagtag attctggat attgagaccg tccactgtca atgaactgga atctggtcag  6720
atttcttatg acgaggttgg tgagagaatt aaggacttcc tccagggttc aagctgcata  6780
gcaggcatat acaatgagac cacaaaacag aagcttggca tttatgaggc catgaaaatt  6840
ggcttagtcc gacctggtac tgctctggag ttgctgaaga cccaagcagc tactggcttt  6900
atagtggatc ctgttagcaa cttgaggtta ccagtggagg aagcctacaa gagaggtctg  6960
gtgggcattg agttcaaaga gaagcctcct tctcagaaac gagctgtcac tgggtataat  7020
gatcctgaaa caggaaacat catctctttg ttccaagcca tgaataagga actcatcgaa  7080
aagggccacg gtattcgctt attagaagca cagatccgga ccggggggat cattgaccca  7140
aaggagagcc atcgtttacc agttgacata gcatataaga ggggctattt caatgaggaa  7200
ctcagtgaga ttctctcaga tccaagtgat gataccaaag gatttttga ccccaacact  7260
gaagaaaatc ttacctatct gcaactaaaa gaaagatgca ttaaggatga ggaaacaggg  7320
ctctgtcttc tgcctctgaa agaaaagaag aaacaggtgc agacatcaca aaagaatacc  7380
ctcaggaggc gtagagtggt catagttgac ccagaaacca ataaagaaat gtctgtcaag  7440
gaggcctaca gaagggcct aattgattat gaaaccttca agaactgtg tgagcaggaa  7500
tgtgaatggg aagaaataac catcacggga tcagatggct ccaccaggt ggtcctggta  7560
gatagaaaga caggcagtca gtatgatatt caagatgcta ttgacaaggg ccttgttgac  7620
aggaagttct ttgatcagta ccgatccggc agcctcagcc tcactcaatt tgctgacatg  7680
atctccttga aaaatggtgt cggcaccagc agcagcatgg cgatggtgat cagcgatgat  7740
gttttagcca gctcccgaca tgaatcagta agtaagattt ccaccatatc cagcgtcagg  7800
aatttaacca taaggagcag ctctttttca gacaccctgg aagaatcgag ccccattgca  7860
gccatctttg acacagaaaa cctggagaaa atctccatta cagaaggtat agagcggggc  7920
atcgttgaca gcatcacggg tcagaggctt ctggaggctc aggcctgcac aggtggcatc  7980
atccacccaa ccacgggcca gaagctgtca cttcaggacg cagtctccca gggtgtgatt  8040
gaccaagaca tggccaccag gctgaagcct gctcagaaag ccttcatagg cttcgagggt  8100
gtgaaggaaa agaagaagat gtcagcagca gaggcagtga agaaaaaatg gctcccgtat  8160
gaggctggca ggcgcttcct ggagttccag tacctcacgg gaggtcttgt tgacccgaa  8220
gtgcatggga ggataagcac cgaagaagcc atccggaagg ggttcataga tggccgcgcc  8280
gcacagaggc tgcaagacac cagcagctat gccaaaatcc tgacctgccc caaaaccaaa  8340
```

```
ttaaaaatat cctataagga tgccataaat cgctccatgg tagaagatat cactgggctg  8400
cgccttctgg aagccgcctc cgtgtcgtcc aagggcttac ccagcccctta caacatgtct  8460
tcggctccgg ggtcccgctc cggctcccgc tcgggatctc gctccggatc tcgctccggg  8520
tcccgcagtg ggtcccggag aggaagcttt gacgccacag ggaattcttc ctactcttat  8580
tcctactcat ttagcagtag ttctattggg cactag                            8616

SEQ ID NO: 220          moltype = AA   length = 2871
FEATURE                 Location/Qualifiers
source                  1..2871
                        mol_type = protein
                        organism = Homo sapiens
SEQUENCE: 220
MSCNGGSHPR INTLGRMIRA ESGPDLRYEV TSGGGGTSRM YYSRRGVITD QNSDGYCQTG    60
TMSRHQNQNT IQELLQNCSD CLMRAELIVQ PELKYGDGIQ LTRSRELDEC FAQANDQMEI   120
LDSLIREMRQ MGQPCDAYQK RLLQLQEQMR ALYKAISVPR VRRASSKGGG GYTCQSGSGW   180
DEFTKHVTSE CLGWMRQQRA EMDMVAWGVD LASVEQHINS HRGIHNSIGD YRWQLDKIKA   240
DLREKSAIYQ LEEEYENLLK ASFERMDHLR QLQNIIQATS REIMWINDCE EEELLYDWSD   300
KNTNIAQKQE AFSIRMSQLE VKEKELNKLK QESDQLVLNQ HPASDKIEAY MDTLQTQWSW   360
ILQITKCIDV HLKENAAYFQ FFEEAQSTEA YLKGLQDSIR KKYPCDKNMP LQHLLEQIKE   420
LEKEREKILE YKRQVQNLVN KSKKIVQLKP RNPDYRSNKP IILRALCDYK QDQKIVHKGD   480
ECILKDNNER SKWYVTGPGG VDMLVPSVGL IIPPPNPLAV DLSCKIEQYY EAILALWNQL   540
YINMKSLVSW HYCMIDIEKI RAMTIAKLKT MRQEDYMKTI ADLELHYQEF IRNSQGSEMF   600
GDDDKRKIQS QFTDAQKHYQ TLVIQLPGYP QHQTVTTTEI THHGTCQDVN HNKVIETNRE   660
NDKQETWMLM ELQKIRRQIE HCEGRMTLKN LPLADQGSSH HITVKINELK SVQNDSQAIA   720
EVLNQLKDML ANFRGSEKYC YLQNEVFGLF QKLENINGVT DGYLNSLCTV RALLQAILQT   780
EDMLKVYEAR LTEEETVCLD LDKVEAYRCG LKKIKNDLNL KSLLATMKT ELQKAQQIHS   840
QTSQQYPLYD LDLGKFGEKV TQLTDRWQRI DKQIDFRLWD LEKQIKQLRN YRDNYQAFCK   900
WLYDAKRRQD SLESMKFGDS NTVMRFLNEQ KNLHSEISGK RDKSEEVQKI AELCANSIKD   960
YELQLASYTS GLETLLNIPI KRTMIQSPSG VILQEAADVH ARYIELLTRS GDYYRFLSEM  1020
LKSLEDLKLK NTKIEVLEEE LRLARDANSE NCNKNKFLDQ NLQKYQAECS QFKAKLASLE  1080
ELKRQAELDG KSAKQNLDKC YGGIKELNEK ITRLTYEIED EKRRKSVED RFDQQKNDYD  1140
QLQKARQCEK ENLGWQKLES EKAIKEKEYE IERLRVLLQE EGTRKREYEN ELAKVRNHYN  1200
EEMSNLRNKY ETEINITKTT IKEISMQKED DSKNLRNQLD RLSRENRDLK DEIVRLNDSI  1260
LQATEQRRRA EENALQQKAC GSEIMQKKQH LEIELKQVMQ QRSEDNARHK QSLEEAAKTI  1320
QDKNKEIERL KAEFQEEAKR RWEYENELSK VRNNYDEEII SLKNQFETEI NITKTTIHQL  1380
TMQKEEDTSG YRAQIDNLTR ENRSLSEEIK RLKNTLTQTT ENLRRVEEDI QQQKATGSEV  1440
SQRKQQLEVE LRQVTQMRTE ESVRYKQSLD DAAKTIQDKN KEIERLQKLI DKETNDRKCL  1500
EDENARLQRV QYDLQKANSS ATETINKLKV QEQELTRLRI DYERVSQERT VKDQDITRFQ  1560
NSLKELQLQK QKVEEELNRL KRTASEDSCK RKKLEEELEG MRRSLKEQAI KITNLTQQLE  1620
QASIVKKRSE DDLRQQRDVL DGHLREKQRT QEELRRLSSE VEALRRQLLQ EQESVKQAHL  1680
RNEHFQKAIE DKSRSLNESK IEIERLQSLT ENLTKEHLML EEELRNLRLE YDDLRRGRSE  1740
ADSDKNATIL ELRSQLQISN NRTLELQGLI NDLQRERENL RQEIEKFQKQ ALEASNRIQE  1800
SKNQCTQVVQ ERESLLVKIK VLEQDKARLQ RLEDELNRAK STLEAETRVK QRLECEKQQI  1860
QNDLNQWKTQ YSRKEEAIRK IESEREKSER EKNSLRSEIE RLQAEIKRIE ERCRRKLEDS  1920
TRETQSQLET ERSRYQREID KLRRPYGSH RETQTECEWT VDTSKLVFDG LRKKVTAMQL  1980
YECQLIDKTT LDKLLKGKKS VEEVASEIQP FLRGAGSIAG ASASPKEKYS LVEAKRKKLI  2040
SPESTVMLLE AQAATGGIID PHRNEKLTVD SAIARDLIDF DDRQQIYAAE KAITGFDDPF  2100
SGKTVSVSEA IKKNLIDRET GMRLLEAQIA SGGVVDPVNS VFLPKDVALA RGLIDRDLYR  2160
SLNDPRDSQK NFVDPVTKKK VSYVQLKERC RIEPHTGLLL LSVQKRSMSF QGIRQPVTVT  2220
ELVDSGILRP STVNELESGQ ISYDEVGERI KDFLQGSSCI AGIYNETTKQ KLGIYEAMKI  2280
GLVRPGTALE LLEAQAATGF IVDPVSNLRL PVEEAYKRGL VGIEFKEKLL SAERAVTGYN  2340
DPETGNIISL FQAMNKELIE KGHGIRLLEA QIATGGIIDP KESHRLPVDI AYKRGYFNEE  2400
LSEILSDPSD DTKGFFDPNT EENLTYLQLK ERCIKDEETG LCLLPLKEKK KQVQTSQKNT  2460
LRKRRVVIVD PETNKEMSVQ EAYKKGLIDY ETFKELCEQE CEWEEITITG SDGSTRVVLV  2520
DRKTGSQYDI QDAIDKGLVD RKFFDQYRSG SLSLTQFADM ISLKNGVGTS SSMGSGVSDD  2580
VFSSSRHESV SKISTISSVR NLTIRSSSFS DTLEESSPIA AIFDTENLEK ISITEGIERG  2640
IVDSITQRL LEAQACTGGI IHPTTGQKLS LQDAVSQGVI DQDMATRLKP AQKAFIGFEG  2700
VKGKKKMSAA EAVKEKWLPY EAGQRFLEFQ YLTGGLVDPE VHGRISTEEA IRKGFIDGRA  2760
AQRLQDTSSY AKILTCPKTK LKISYKDAIN RSMVEDITGL RLLEAASVSS KGLPSPYNMS  2820
SAPGSRSGSR SGSRSGSRSG SRSGSRRGSF DATGNSSYSY SYSFSSSIG H             2871

SEQ ID NO: 221          moltype = DNA   length = 6819
FEATURE                 Location/Qualifiers
source                  1..6819
                        mol_type = other DNA
                        organism = Homo sapiens
SEQUENCE: 221
atgagctgca acggaggctc ccacccgcgg atcaacactc tgggccgcat gatccgcgcc    60
gagtctgcc cggaacctgcg ctacgaggtg accagcggcg gcgggggcac cagcaggatg   120
tactattctc ggcgcggcgt gatcaccgac cagaactcgg acggctactg tcaaaccggc   180
acgatgtcca ggcaccagaa ccagaacacc atccaggagc tgctcagaa ctgctccgac   240
tgcttgatgc gagcagagct catcgtgcag cctgaattga gtatggaga tggaatacaa   300
ctgactcgga gtcgagaatt ggatgagtgt tttgcccagg ccaatgacca aatggaaatc   360
ctcgacagga tgatcagaga gatgcggcag atgggccagc cctgtgatgc ttaccagaaa   420
aggcttcttc agctccaaga gcaaatgcga gcccttttata aagccatcag tgtccctcga   480
gtccgcaggg ccagctccaa gggtggtgga ggctacactt gtcagagtgg ctctggctgg   540
gatgagttca ccaaacatgt caccagtgaa tgtttgggt ggatgaggca gcaaggggcg   600
gagatggaca tggtggcctg gggtgtggac ctggcctcag tggagcagca cattaacagc   660
caccgggca tccacaactc catcggcgac tatcgctggc agctggacaa aatcaaagcc   720
```

```
gacctgcgcg agaaatctgc gatctaccag ttggaggagg agtatgaaaa cctgctgaaa    780
gcgtcctttg agaggatgga tcacctgcga cagctgcaga acatcattca ggccacgtcc    840
agggagatca tgtggatcaa tgactgcgag gaggaggagc tgctgtacga ctggagcgac    900
aagaacacca acatcgctca gaaacaggag gccttctcca tacgcatgag tcaactgaaa    960
gttaaagaaa aagagctcaa taagctgaaa caagaaagtg accaacttgt cctcaatcag   1020
catccagctt cagacaaaat tgaggcctat atggacactc tgcagacgca gtggagttga   1080
attcttcaga tcaccaagtg cattgatgtt catctgaaag aaaatgctgc ctactttcag   1140
ttttttgaag aggcgcagtc tactgaagca tacctgaagg ggctccagga ctccatcagg   1200
aagaagtacc cctgcgacaa gaacatgccc ctgcagcacc tgctgaaaca gatcaaggag   1260
ctggagaaag aacgagagaa aatccttgaa tacaagcgtc aggtgcagaa cttggtaaac   1320
aagtctaaga agattgtaca gctgaagcct cgtaacccag actacagaag caataaaccc   1380
attattctca gagctctctg tgactacaaa caagatcaga aaatcgtgca taggggggat   1440
gagtgtatcc tgaaggacaa caacgagcgc agcaagtggt acgtgacggg cccgggaggc   1500
gttgacatgc ttgttccctc tgtggggctg atcatccctc ctccgaaccc actgccggtg   1560
gacctctctt gcaagattga gcagtactac gaagccatct tggctctgtg gaaccagctc   1620
tacatcaaca tgaagagcct ggtgtcctgg cactactgca tgattgacat agagaagatc   1680
agggccatga caatcgccaa gctgaaaaca atgcggcagg aagattacat gaagacgata   1740
gccgaccttg agttacatta ccaagagttc atcagaaata gccaaggctc agagatgttt   1800
ggagatgatg acaagcggaa aatacagtct cagttcaccg atgcccagaa gcattaccag   1860
accctggtca ttcagctccc tggctatccc cagcaccaga cagtgaccac aactgaaatc   1920
actcatcatg gaacctgcca agatgtcaac cataataaag taattgaaac caacagagaa   1980
aatgcaaagc aagaaacatg gatgctgatg gagctgcaga agattcgcag cgcagatagag   2040
cactgcgagg gcaggatgac tctcaaaaac ctccctctag cagaccaggg atcttctcac   2100
cacatcacag tgaaaattaa cgagcttaag agtgtgcaga atgattcaca agcaattgct   2160
gaggttctca accagcttaa agatatgctt gccaacttca gaggttctga aaagtactgc   2220
tatttacaga atgaagtatt tggactattt cagaaactgg aaaatatcaa tggtgttaca   2280
gatggctact taaatagctt atgcacagta agggcactgc tccaggctat tctccaaaca   2340
gaagacatgt taaaggttta tgaagccagg ctcactgagg aggaaactgt ctgcctggac   2400
ctggataaag tggaagctta ccgctgtgga ctgaagaaaa taaaaaatga cttgaacttg   2460
aagaagtcgt tgttggccac tatgaagaca gaactacaga aagcccagca gatccactct   2520
cagacttcac agcagtatcc actttatgat ctggacttgg gcaagttcgg tgaaaaagtc   2580
acacagctga cagaccgctg gcaaaggata gataaacaga tcgactttag gttatgggac   2640
ctggagaaac aaatcaagca attgaggaat tatcgtgata actatcaggc tttctgcaag   2700
tggctctatg atgctaaacg ccgccaggat tccttagaat ccatgaaatt tggagattcc   2760
aacacagtca tgcggttttt gaatgacgag aagaacttgc acagtgaaat atctggcaaa   2820
cgagacaaat cagaggaagt acaaaaaatt gctgaacttt cgccaattc aattaaggat   2880
tatgagctcc agctggcctc atacacctca ggactgaaaa ctctgctgaa catacctatc   2940
aagaggacca tgattcagtc cccttctggg gtgattctgc aagaggctgc agatgttcat   3000
gctcggtaca ttgaactact tacaagatct ggagactatt acaggtttct aagtgagatg   3060
ctgaagagtt tggaagatct gaagctgaaa aataccaaga tcgaagtttt ggaagaggag   3120
ctcagactgg cccgagatgc caactcggaa aactgtaata agaacaaatt cctggatcag   3180
aacctgcaga aataccaggc agagtgttcc cagttcaaag cgaagcttgc gagcctggag   3240
gagctgaaga gacaggctga gctgatggg aagtcggcta agcaaaatct agacaagtgc   3300
tacgccaaaa taaagaact caatgagaag atccacccgac tgacttatga gattgaagat   3360
gaaaagagaa gaagaaaatc tgtggaagac agatttgacc aacagaagaa tgactatgac   3420
caactgcaga aagcaaggca atgtgaaaag gagaaccttg gttggcagaa attagagtct   3480
gagaaagcca tcaaggagaa gggagtacga attgaaaggt tgggggttct actgcaggaa   3540
gaaggcaccc ggaagagaga atatgaaaat gagctggcaa aggcatctaa taggattcag   3600
gaatcaaaga atcagtgtac tcaggtggta caggaaagag agagccttct ggtgaaaatc   3660
aaagtcctgg agcaagacaa ggcaaggctg cagaggctgg aggatgagct gaatcgtgca   3720
aaatcaactc tagaggcaga aaccagggtg aaacagcgcc tggagtgtga gaaacagcaa   3780
attcagaatg acctgaatca gtggaagact caatattccc gcaaggagga ggctattagg   3840
aagatagaat cggaaagaga aaagagtgag agagagaaga cagtcttag gagtgagatc   3900
gaaagactcc aagcagagat caagagaatt gaagagaggt gcaggcgtaa gctggaggat   3960
tctaccaggg agacacagtc acagttagaa acagaaccgt cccgatatca gagggagatt   4020
gataaactca gacagcgccc atatgggtcc catcgagaga cccagactga gtgtgagtgg   4080
accgttgaca cctccaagct ggtgtttgat gggctgagga agaaggtgac agcaatgcag   4140
ctctatgagt gtcagctgat cgacaaaaca accttggaca aactattgaa ggggaagaag   4200
tcagtggaag aagttgcttc tgaaatccag ccattcctc ggggtgcagg atctatcgat   4260
ggagcatctg cttcctcctaa ggaaaatac tctttggtag aggccaagag aaagaaatta   4320
atcagcccag aatccacagt catgcttctg gaggcccagg cagctacagg tggtataatt   4380
gatccccatc ggaatgagaa gctgactgtc gacagtgcca tagctcggga cctcattgac   4440
ttcgatgacc gtcagcagat atatgcagca gaaaaagcta tcactggttt tgatgatcca   4500
ttttcaggca agacagtatc tgtttcagaa gccatcaaga aaatttgat tgatagagaa   4560
accggaatgc gcctgctgga agccagatt gcttcagggg gtgtagtaga ccctgtgaac   4620
agtgtctttt tgccaaagaa tgtcgccttg gcccggggc tgattgatag agatttgtat   4680
cgatccctga atgatcccg agatagtcag aaaaactttg tggatccagt caccaaaaag   4740
aaggtcagtt acgtgcagct gaaggaacgg tgcagaatcg aaccacatac tggtctgctc   4800
ttgctttcag tacaaggag aagcatgtcc ttccaaggaa tcagacaacc tgtgaccgtc   4860
actgagctag tagattctgg tatattgaga ccgtccactg tcaatgaact ggaatctggt   4920
cagatttctt atgacgaggt tggtgagaga attaaggact tcctccaggg ttcaagctgc   4980
atagcaggca tatacaatga gaccacaaaa cagaagcttg gcattatga ggccatgaaa   5040
attggcttag tccgacctgg tactgctctg gagttgctga agcccaagc agctactggc   5100
tttatagtga tcctcgttag caacttgagg ttaccagttg aggaagccta caagagaggt   5160
ctggtgggca ttgagttcaa agagaagctc ctgtctgcag aacgagctgt cactgggtat   5220
aatgatcctg aaacaggaaa catcatctct tgttccaag ccatgaataa ggaactcatc   5280
gaaaagggcc acggtattcg cttattgaaa gcacagatcg caaccggggg gatcattgac   5340
ccaaaggaga gccatcgttt accagttgac atagcatata gaggggcta tttcaatgag   5400
gaactcagtg agattctctc agatccaagt gatgatacca aaggattttt tgaccccaac   5460
```

-continued

```
actgaagaaa atcttaccta tctgcaacta aaagaaagat gcattaagga tgaggaaaca    5520
gggctctgtc ttctgcctct gaaagaaaag aagaaacagg tgcagacatc acaaaagaat    5580
accctcagga agcgtagagt ggtcatagtt gacccagaaa ccaataaaga aatgtctgtt    5640
caggaggcct acaagaaggg cctaattgat tatgaaacct tcaaagaact gtgtgagcag    5700
gaatgtgaat gggaagaaat aaccatcacg ggatcagatg gctccaccag ggtggtcctg    5760
gtagatagaa agacaggcag tcagtatgat attcaagatg ctattgacaa gggccttgtt    5820
gacaggaagt tctttgatca gtaccgatcc ggcagcctca gcctcactca atttgctgac    5880
atgatctcct tgaaaaatgg tgtcggcacc agcagcagca tgggcagtgg tgtcagcgat    5940
gatgtttttta gcagctcccg acatgaatca gtaagtaagt tttccaccat atccagcgtc    6000
aggaatttaa ccataaggag cagctctttt tcagacaccc tggaagaatc gagccccatt    6060
gcagccatct ttgacacaga aaacctggag aaaatctcca ttacagaagg tatagagcgg    6120
ggcatcgttg acagcatcac gggtcagagg cttctggagg ctcaggcctg cacaggtggc    6180
atcatccacc caaccacggg ccagaagctg tcacttcagg acgcagtctc ccagggtgtg    6240
attgaccaag acatggccac caggctgaag cctgctcaga aagccttcat aggcttcgag    6300
ggtgtgaagg gaaagaagaa gatgtcagca gcagaggcag tgaaagaaaa atggctcccg    6360
tatgaggctg ccagcgcttc ctggagttc cagtacctca cggaggtct tgttacccg    6420
gaagtgcatg ggaggataag caccgaagaa gccatccgga aggggttcat agatggccgc    6480
gccgcacaga ggctgcaaga caccagcagc tatgccaaaa tcctgacctg ccccaaaacc    6540
aaattaaaaa tatcctataa ggatgccata aatcgctcca tggtagaaga tatcactggg    6600
ctgcgccttc tggaagccgc ctccgtgtcg tccaagggct tacccagccc ttacaacatg    6660
tcttcggctc cgggggtcccg ctccggctcc cgctcgggat ctcgctccgg atctcgctcc    6720
gggtcccgca gtgggtcccg gagagggaagc tttgacgcca cagggaattc ttcctactct    6780
tattcctact catttagcag tagttctatt gggcactag                           6819
```

SEQ ID NO: 222         moltype = AA  length = 2272
FEATURE                Location/Qualifiers
source                 1..2272
                       mol_type = protein
                       organism = Homo sapiens
SEQUENCE: 222
```
MSCNGGSHPR INTLGRMIRA ESGPDLRYEV TSGGGGTSRM YYSRRGVITD QNSDGYCQTG      60
TMSRHQNQNT IQELLQNCSD CLMRAELIVQ PELKYGDGIQ LTRSRELDEC FAQANDQMEI    120
LDSLIREMRQ MGQPCDAYQK RLLQLQEQMR ALYKAISVPR VRRASSKGGG GYTCQSGSGW    180
DEFTKHVTSE CLGWMRQQRA EMDMVAWGVD LASVEQHINS HRGIHNSIGD YRWQLDKIKA    240
DLREKSAIYQ LEEEYENLLK ASFERMDHLR QLQNIIQATS REIMWINDCE EEELLYDWSD    300
KNTNIAQKQE AFSIRMSQLE VKEKELNKLK QESDQLVLNQ HPASDKIEAY MDTLQTQWSW    360
ILQITKCIDV HLKENAAYFQ FFEEAQSTEA YLKGLQDSIR KKYPCDKNMP LQHLLEQIKE    420
LEKEREKILE YKRQVQNLVN KSKKIVQLKP RNPDYRSNKP IILRALCDYK QDQKIVHKGD    480
ECILKDNNER SKWYVTGPGG VDMLVPSVGL IIPPPNPLAV DLSCKIEQYY EAILALWNQL    540
YINMKSLVSW HYCMIDIEKI RAMTIAKLKT MRQEDYMKTI ADLELHYQEF IRNSQGSEMF    600
GDDDKRKIQS QFTDAQKHYQ TLVIQLPGYP QHQTVTTTEI THHGTCQDVN HNKVIETNRE    660
NDKQETWMLM ELQKIRRQIE HCEGRMTLKN LPLADQGSSH HITVKINELK SVQONDSQAIA    720
EVLNQLKDML ANFRGSEKYC YLQNEVFGLF QKLENINGVT DGYLNSLCTV RALLQAILQT    780
EDMLKVYEAR LTEEETVCLD LDKVEAYRCG LKKIKNDLNL KKSLLATMKT ELQKAQQIHS    840
QTSQQYPLYD LDLGKFGEKV TQLTDRWQRI DKQIDFRLWD LEKQIKQLRN YRDNYQAFCK    900
WLYDAKRRQD SLESMKFGDS NTVMRFLNEQ KNLHSEISGK RDKSEEVQKI AELCANSIKD    960
YELQLASYTS GLETLLNIPI KRTMIQSPSG VILQEAADVK ARYIELLTRS GDYYRFLSEM   1020
LKSLEDLKLK NTKIEVLEEE LRLARDANSE NCNKNKFLDQ NLQKYQAECS QFKAKLASLE   1080
ELKRQAELDG KSAKQNLDKC YGQIKELNEK ITRLTYEIED EKRRRKSVED RFDQQKNDYD   1140
QLQKARQCEK ENLGWQKLES EKAIKEKEYE IERLRVLLQE EGTRKREYEN ELAKASNRIQ   1200
ESKNQCTQVV QERESLLVKI KVLEQDKARL QRLEDELNRA KSTLEAETRV KQRLECEKQQ   1260
IQNDLNQWKT QYSRKEEAIR KIESEREKSE REKNSLRSEI ERLQAEIKRI EERCRRKLED   1320
STRETQSQLE TERSRYQREI DKLRQRPYGS HRETQTECEW TVDTSKLVFD GLRKKVTAMQ   1380
LYECQLIDKT TLDKLLKGKK SVEEVASEIQ PFLRGAGSIA GASASPKEKY SLVEAKRKKL   1440
ISPESTVMLL EAQAATGGII DPHRNEKLTV DSAIARDLID FDDRQQIYAA EKAITGFDDP   1500
FSGKTVSVSE AIKKNLIDRE TGMRLLEAQI ASGGVVDPVN SVFLPKDVAL ARGLIDRDLY   1560
RSLNDPRDSQ KNFVDPVTKK KVSYVQLKER CRIEPHTGLL LLSVQKRSMS FQGIRQPVTV   1620
TELVDSGILR PSTVNELESG QISYDEVGER IKDFLQGSSC IAGIYNETTK QKLGIYEAMK   1680
IGLVRPGTAL ELLEAQAATG FIVDPVSNLR LPVEEAYKRG LVGIEFKEKL LSAERAVTGY   1740
NDPETGNIIS LFQAMNKELI EKGHGIRLLE AQIATGGIID PKESHRLPVD IAYKRGYFNE   1800
ELSEILSDPS DDTKGFFDPN TEENLTYLQL KERCIKDEET GLCLLPLKEK KKQVQTSQKN   1860
TLRKRRVVIV DPETNKEMSV QEAYKKGLID YETFKELCEQ ECEWEEITIT GSDGSTRVVL   1920
VDRKTGSQYD IQDAIDKGLV DRKFFDQYRS GSLSLTQFAD MISLKNGVGT SSSMGSGVSD   1980
DVFSSSRHES VSKISTISSV RNLTIRSSSF SDTLEESSPI AAIFDTENLE KISITEGIER   2040
GIVDSITGQR LLEAQACTGG IIHPTTGQKL SLQDAVSQGV IDQDMATRLK PAQKAFIGFE   2100
GVKGKKKMSA AEAVKEKWLP YEAGQRFLEF QYLTGGLVDP EVHGRISTEE AIRKGFIDGR   2160
AAQRLQDTSS YAKILTCPKT KLKISYKDAI NRSMVEDITG LRLLEAASVS SKGLPSPYNM   2220
SSAPGSRSGS RSGSRSGSRS GSRSGSRRGS FDATGNSSYS YSYSFSSSSI GH           2272
```

SEQ ID NO: 223         moltype = DNA  length = 3357
FEATURE                Location/Qualifiers
source                 1..3357
                       mol_type = other DNA
                       organism = Homo sapiens
SEQUENCE: 223
```
atggcgcgga gcccgggacg cgcgtacgcc ctgctgcttc tcctgatctg ctttaacgtt     60
ggaagtggac ttcacttaca ggtcttaagc acaagaaatg aaaataagct gcttcctaaa    120
catcctcatt tagtgcggca aaagcgcgcc tggatcaccg ccccgtggc tcttcggag    180
ggagaggatc tgtccaagaa gaatccaatt gccaagatac attctgatct tgcagaagaa    240
```

```
agaggactca aaaattactta caaatacact ggaaaaggga ttacagaacc acctttttggt    300
atatttgtct ttaacaaaga tactggagaa ctgaatgtta ccagcattct tgatcgagaa    360
gaaacaccat tttttctgct aacaggttac gctttggatg caagaggaaa caatgtagag    420
aaaccccttag agctacgcat taaggttctt gatatcaatg acaacgaacc agtgttcaca    480
caggatgtct ttgttgggtc tgttgaagag ttgagtgcag cacatactct tgtgatgaaa    540
atcaatgcaa cagatgcaga tgagcccaat accctgaatt cgaaaatttc ctatagaatc    600
gtatctctgg agcctgctta tcctccagtt ttcacctaa ataaagatac aggagagatt     660
tatacaacca gtgttacctt ggacagagag gaacacagca gctacacttt gacagtagaa    720
gcaagagatg gcaatggaga agttacagac aaacctgtaa aacaagctca agttcagatt    780
cgtattttgg atgtcaatga caatatacct gtagtagaaa ataaagtgct tgaagggatg    840
gttgaagaaa atcaagtcaa cgtagaagtt acgcgcataa aagtgttcga tgcagatgaa    900
ataggttctg ataattggct ggcaaatttt acatttgcat caggaaatga aggaggttat    960
ttccacatag aaacagatgc tcaaactaac gaaggaattt gtgacccttat taaggaagta   1020
gattatgaag aaatgaagaa tcttgacttc agtgttattg tcgctaataa agcagctttt    1080
cacaagtcga ttaggagtaa atacaagcct acacccattc ccatcaaggt caaagtgaaa    1140
aatgtgaaaa aaggcattca ttttaaaagc agcgtcatct caatttatgt tagcgagagc    1200
atggatagat caagcaaagg ccaaataatt ggaaattttc aagcttttga tgaggacact    1260
ggactaccag cccatgcaag atatgtaaaa ttagaagata gagataattg gatctctgtg    1320
gattctgtca catctgaaat taaacttgca aaacttcctg attttgaatc tagatatgtt    1380
caaaatggca catacactgt aaagattgtg gccatatcag aagattatcc tagaaaaacc    1440
atcactggca cagtccttat caatgttgaa gacatcaacg acaactgtcc cacactgata    1500
gagcctgtgc agacaatctg tcacgatgca gagtatgtga atgttactgc agaggacctg    1560
gatggacacc caaacagtgg ccctttcagt ttctccgtca ttgacaaacc acctggcatg    1620
gcagaaaaat ggaaaatagc acgccaagaa agtaccagtg tgctgctgca acaaagtgag    1680
aaaaagcttg ggagaagtga aattcagttc ctgatttcag acaatcaggg ttttagttgt    1740
cctgaaaagc aggtccttac actcacagtt tgtgagtgtc tgcatggcag cggctgcaga    1800
gaagcacagc atgactccta tgtgggcctg gacccgcag caattgcgct catgattttg    1860
gcctttctgc tcctgctatt ggtaccactt ttactgctga tgtgccattg cggaaagggc    1920
gccaaaggct ttacccccat acctggcacc atagagatgc tgcatccttg gaataatgaa    1980
ggagccacc ctgaagacaa ggtgtgcca tcatttctgc cagtgatca aggggggcagt    2040
ctagtaggaa gaaatggagt aggaggtatg gccaaggaag ccacgatgaa aggaagtagc    2100
tctgcttcca ttgtcaaagg gcaacatgag atgtccgaga tggatggaag gtgggaagaa    2160
cacagaagcc tgctttctgg tagagctacc cagtttacag gggccacagg cgctatcatg    2220
accactgaaa ccacgaagac cgcaagggcc acaggggctt ccagagacat ggccggagct    2280
caggcagctg ctgttgcact gaacgaagaa ttcttaagaa attatttcac tgataaagcg    2340
gcctcttaca ctgaggaaga tgaaaatcac acagccaaag attgccttct ggtttattct    2400
caggaagaaa ctgaatcgct gaatgcttct attggttgtt gcagttttat tgaaggagag    2460
ctagatgacc gcttcttaga tgatttggga cttaaattca agacactagc tgaagtttgc    2520
ctgggtcaaa aaatagatat aaataaggaa attgagcaga gacaaaaacc tgccacagaa    2580
acaagtatga acacagcttc acattcactc tgtgagcaaa ctatggttaa ttcagagaat    2640
acctactcct ctggcagtag cttcccagtt ccaaaatctt tgcaagaagc caatgcgag    2700
aaagtaactc aggaaatagt cactgaaaga tctgtgtctt ctaggcaggc gcaaaaggta    2760
gctacacctc ttcctgaccc aatggcttct agaaatgtga tagcaacaga aacttcctac    2820
gtcacagggt ccactatgcc accaaccact gtgatcctgg gtcctagcca gccacagagc    2880
cttattgtga cagagagggt gtatgctcca gcttctacct tggtagatca gccttatgct    2940
aatgaaggta cagttgtggt cactgaaaga gtaatacagc ctcatggggg tggatcgaat    3000
cctctggaag gcactcagca tcttcaagat gtaccttacg tcatggtgag ggaaagagag    3060
agcttccttg cccccagctc aggtgtgcag cctactctgg ccatgcctaa tatagcagta    3120
ggacagaatg tgacagtgac agaaagagtt ctagcacctg cttccactct gcaatccagt    3180
taccagattc ccactgaaaa ttctatgacg gctaggaaca ccacggtgtc tggagctgga    3240
gtccctggcc ctctgccaga ttttggttta gaggaatctg gtcattctaa ttctaccata    3300
accacatctt ccaccagagt taccaagcat agcactgtac agcattctta ctcctaa       3357
```

SEQ ID NO: 224        moltype = AA  length = 1118
FEATURE               Location/Qualifiers
source                1..1118
                       mol_type = protein
                       organism = Homo sapiens

```
SEQUENCE: 224
MARSPGRAYA LLLLLICFNV GSGLHLQVLS TRNENKLLPK HPHLVRQKRA WITAPVALRE      60
GEDLSKKNPI AKIHSDLAEE RGLKITYKYT GKGITEPPFG IFVFNKDTGE LNVTSILDRE     120
ETPFFLLTGY ALDARGNNVE KPLELRIKVL DINDNEPVFT QDVFVGSVEE LSAAHTLVMK     180
INATDADEPN TLNSKISYRI VSLEPAYPPV FYLNKDTGEI YTTSVTLDRE EHSSYTLTVE     240
ARDGNGEVTD KPVKQAQVQI RILDVNDNIP VVENKVLEGM VEENQVNVEV TRIKVFDADE     300
IGSDNWLANF TFASGNEGGY FHIETDAQTN EGIVTLIKEV DYEEMKNLDF SVIVANKAAF     360
HKSIRSKYKP TPIPIKVKVK NVKEGIHFKS SVISIYVSES MDRSSKGQII GNFQAFDEDT     420
GLPAHARYVK LEDRDNWISV DSVTSEIKLA KLPDFESRYV QNGTYTVKIV AISEDYPRKT     480
ITGTVLINVE DINDNCPTLI EPVQTICHDA EYVNVTAEDL DGHPNSGPFS FSVIDKPPGM     540
AEKWKIARQE STSVLLQQSE KKLGRSEIQF LISDNQGFSC PEKQVLTLTV CECLHGSGCR     600
EAQHDSYVGL GPAAIALMIL AFLLLLLVPL LLLMCHCGKG AKGFTPIPGT IEMLHPWNNE     660
GAPPEDKVVP SFLPVDQGGS LVGRNGVGGM AKEATMKGSS SASIVKGQHE MSEMDGRWEE     720
HRSLLSGRAT QFTGATGAIM TTETTKTARA TGASRDMAGA QAAVALNEE FLRNYFTDKA      780
ASYTEEDENH TAKDCLLVYS QEETESLNAS IGCCSFIEGE LDDRFLDDLG LKFKTLAEVC     840
LGQKIDINKE IEQRQKPATE TSMNTASHSL CEQTMVNSEN TYSSGSSFPV PKSLQEANAE     900
KVTQEIVTER SVSSRQAQKV ATPLPDPMAS RNVIATETSY VTGSTMPPTT VILGPSQPQS     960
LIVTERVYAP ASTLVDQPYA NEGTVVVTER VIQPHGGGSN PLEGTQHLQD VPYVMVRERE    1020
SFLAPSSGVQ PTLAMPNIAV GQNVTVTERV LAPASTLQSS YQIPTENSMT ARNTTVSGAG    1080
VPGPLPDFGL EESGHSNSTI TTSSTRVTKH STVQHSYS                            1118
```

| SEQ ID NO: 225 | moltype = DNA   length = 2238 |
|---|---|
| FEATURE | Location/Qualifiers |
| source | 1..2238 |
| | mol_type = other DNA |
| | organism = Homo sapiens |

SEQUENCE: 225

| | | | | | | |
|---|---|---|---|---|---|---|
| atggaggtga | tgaacctgat | ggagcagcct | atcaaggtga | ctgagtggca | gcagacatac | 60 |
| acctacgact | cgggtatcca | ctcgggcgcc | aacacctgcg | tgccctccgt | cagcagcaag | 120 |
| ggcatcatgg | aggaggatga | ggcctgcggg | cgccagtaca | cgctcaagaa | aaccaccact | 180 |
| tacacccagg | gggtgccccc | cagccaaggt | gatctggagt | accagatgtc | cacaacagcc | 240 |
| agggccaaac | gggtgcggga | ggccatgtgc | cctggtgtgt | caggcgagga | cagctcgctt | 300 |
| ctgctggcca | cccaggtgga | ggggcaggcc | accaacctgc | agcgactggc | cgagccgtcc | 360 |
| cagctgctca | agtcggccat | tgtgcatctc | atcaactacc | aggacgatgc | cgagctggcc | 420 |
| actcgcgccc | tgcccgagct | caccaaactg | ctcaacgacg | aggaccccgt | ggtggtcacc | 480 |
| aaggcggcca | tgattgtgaa | ccagctgtcg | aagaaggagg | cgtcgcggcg | ggccctgatg | 540 |
| ggctcgcccc | agctggtggc | cgctgtcgtg | cgtaccatgc | agaataccag | cgacctggac | 600 |
| acagcccgct | gcaccaccag | catcctgcac | aacctctccc | accacggga | ggggctgctc | 660 |
| gccatcttca | agtcgggtgg | catccctgct | ctggtccgca | tgctcagctc | ccctgtgagg | 720 |
| tcggtcctgt | tctatgccat | caccacgctg | cacaacctgc | tcctgtacca | ggagggcgcc | 780 |
| aagatggccg | tgcgcctggc | cgacgggctg | caaaagatgg | tgcccctgct | caacaagaac | 840 |
| aaccccaagt | tcctggccat | caccaccgac | tgcctgcagc | tcctggccta | cggcaaccag | 900 |
| gagagcaagc | tgatcatcct | ggccaatggg | gggcccaag | ccctcgtgca | gatcatgcgt | 960 |
| aactacagtt | atgaaaagct | gctctggacc | accagtcgtg | tgctcaaggt | gctatccgtg | 1020 |
| tgtcccagca | ataagcctgc | cattgtggag | gctggtggga | tgcaggccct | gggcaagcac | 1080 |
| ctgaccagca | acagccccg | cctggtgcag | aactgcctgt | ggaccctgcg | caacctctca | 1140 |
| gatgtggcca | ccaagcagga | ggggctggag | agtgtgctga | agattctggt | gaatcagctg | 1200 |
| agtgtggatg | acgtcaacgt | cctcacctgt | gccacgggca | cactctccaa | cctgacatgc | 1260 |
| aacaacagca | gaacaagac | gctggtgaca | cagaacagcg | gtgtggaggc | tctcatccat | 1320 |
| gccatcctgc | gtgctggtga | caaggacgac | atcacgagc | ctgccgtctg | cgctctgcgc | 1380 |
| cacctcacta | gccgccaccc | tgaggccgaa | atggccaga | actctgtgcg | tctcaactat | 1440 |
| ggcatcccag | ccatcgtgaa | gctgctcaac | cagcccaacc | agtggccact | ggtcaaggca | 1500 |
| accatcggct | tgatcaggaa | tctggccctg | tgcccagcca | accatgcccc | gctgcaggag | 1560 |
| gcagcggtca | tccccgcct | cgtccaactg | ctggtgaagg | cccaccagga | tgcccagcgc | 1620 |
| cacgtagctg | caggcacaca | gcagccctac | acggatggtg | tgaggatgga | ggagattgtg | 1680 |
| gagggctgca | ccggagcact | gcacatcctc | gcccggaccc | ccatgaaccg | catggagatc | 1740 |
| ttccggctca | acaccattcc | cctgtttgtg | cagctcctgt | actcgtcggt | ggagaacatc | 1800 |
| cagcgcgtgg | ctgccggggt | gctgtgtgag | ctggcccagg | acaaggaggc | ggccgacgcc | 1860 |
| attgatgcag | aggggcctc | ggccccactc | atggagttgc | tgcactcccg | caacgagggc | 1920 |
| actgccacct | acgctgctgc | cgtcctgttc | cgcatctccg | aggacaagaa | cccagactac | 1980 |
| cggaagcgcg | tgtccgtgga | gctcaccaac | tccctcttca | agcatgaccc | ggctgcctgg | 2040 |
| gaggctgccc | agagcatgat | tcccatcaat | gagccctatg | gagatgacat | ggatgccacc | 2100 |
| taccgcccca | tgtactccag | cgatgtgccc | cttgacccgc | tggagatgca | catggacatg | 2160 |
| gatggagact | acccccatcga | cacctacagc | gacggcctca | ggccccgta | ccccactgca | 2220 |
| gaccacatgc | tggcctag | | | | | 2238 |

| SEQ ID NO: 226 | moltype = AA   length = 745 |
|---|---|
| FEATURE | Location/Qualifiers |
| source | 1..745 |
| | mol_type = protein |
| | organism = Homo sapiens |

SEQUENCE: 226

| | | | | | | |
|---|---|---|---|---|---|---|
| MEVMNLMEQP | IKVTEWQQTY | TYDSGIHSGA | NTCVPSVSSK | GIMEEDEACG | RQYTLKKTTT | 60 |
| YTQGVPPSQG | DLEYQMSTTA | RAKRVREAMC | PGVSGEDSSL | LLATQVEGQA | TNLQRLAEPS | 120 |
| QLLKSAIVHL | INYQDDAELA | TRALPELTKL | LNDEDPVVVT | KAAMIVNQLS | KKEASRRALM | 180 |
| GSPQLVAAVV | RTMQNTSDLD | TARCTTSILH | NLSHHREGLL | AIFKSGGIPA | LVRMLSSPVE | 240 |
| SVLFYAITTL | HNLLLYQEGA | KMAVRLADGL | QKMVPLLNKN | NPKFLAITTD | CLQLLAYGNQ | 300 |
| ESKLIILANG | GPQALVQIMR | NYSYEKLLWT | TSRVLKVLSV | CPSNKPAIVE | AGGMQALGKH | 360 |
| LTSNSPRLVQ | NCLWTLRNLS | DVATKQEGLE | SVLKILVNQL | SVDDVNVLTC | ATGTLSNLTC | 420 |
| NNSKNKTLVT | QNSGVEALIH | AILRAGDKDD | ITEPAVCALR | HLTSRHPEAE | MAQNSVRLNY | 480 |
| GIPAIVKLLN | QPNQWPLVKA | TIGLIRNLAL | CPANHAPLQE | AAVIPRLVQL | LVKAHQDAQR | 540 |
| HVAAGTQQPY | TDGVRMEEIV | EGCTGALHIL | ARDPMNRMEI | FRLNTIPLFV | QLLYSSVENI | 600 |
| QRVAAGVLCE | LAQDKEAADA | IDAEGASAPL | MELLHSRNEG | TATYAAAVLF | RISEDKNPDY | 660 |
| RKRVSVELTN | SLFKHDPAAW | EAAQSMIPIN | EPYGDDMDAT | YRPMYSSDVP | LDPLEMHMDM | 720 |
| DGDYPIDTYS | DGLRPPYPTA | DHMLA | | | | 745 |

| SEQ ID NO: 227 | moltype = DNA   length = 1716 |
|---|---|
| FEATURE | Location/Qualifiers |
| source | 1..1716 |
| | mol_type = other DNA |
| | organism = Homo sapiens |

SEQUENCE: 227

| | | | | | | |
|---|---|---|---|---|---|---|
| atgagtgggg | gccgcttcga | ctttgatgat | ggaggggcgt | actgcggggg | ctgggagggg | 60 |
| ggaaaggccc | atgggcatgg | actgtgcaca | ggccccaagg | ccagggcga | atactctggc | 120 |
| tcctggaact | ttggctttga | ggttgcaggt | gtctacacct | ggccccagcg | aaacaccttt | 180 |
| gaggatact | ggagccaggg | caaacgcat | gggctgggca | tagagaccaa | ggggcgctgg | 240 |
| ctctacaagg | gcgagtggac | acatggcttc | aagggacgct | acggaatccg | gcagagctca | 300 |
| agcagcggtg | ccaagtatga | gggcacctgg | aacaatggcc | tgcaagacgg | ctatggcacc | 360 |
| gagacctatg | ctgatggagg | gacgtaccaa | ggccagttcc | caacggcat | cgccatggcc | 420 |
| tacgagtac | ccagagcgt | gccctacggg | atggccgtgg | tggtgcgctc | gccgctgcgc | 480 |

```
acgtcgctgt cgtccctgcg cagcgagcac agcaacggca cggtggcccc ggactctccc   540
gcctcgccgg cctccgacgg ccccgcgctg ccctcgcccg ccatcccgcg tggcggcttc   600
gcgctcagcc tcctggccaa tgccgaggcg gccgcgcggg cgcccaaggg cggcggcctc   660
ttccagcggg gcgcgctgct gggcaagctg cggcgcgcag agtcgcgcac gtccgtgggt   720
agccaggcga gccgtgtcag cttccttaag agcgacctca gctcgggcgc cagcgacgcc   780
gcgtccaccg ccagcctggg agaggccgcc gagggcgccg acgaggccgc acccttcgag   840
gccgatatcg acgccaccac caccgagacc tacatgggcg agtggaagaa cgacaaacgc   900
tcgggcttcg gcgtgagcga acgctccagt ggcctccgct acgagggcga gtggctggac   960
aacctgcgcc acgctatgg ctgcaccacg ctgcccgacg gccaccgcga ggagggcaag  1020
taccgccaca acgtgctggt caaggacacc aagcgccgca tgctgcagct caagagcaac  1080
aaggtccgcc agaaagtgga gcacagtgtg gagggtgccc agcgcgccgc tgctatcgcg  1140
cgccagaagg ccgagattgc cgcctccagg acaagccacg ccaaggccaa agctgaggca  1200
gcggaacagg ccgccctggc tgccaaccag gagtccaaca ttgctcgcac tttggccagg  1260
gagctggctc cggacttcta ccagccaggt ccggaatatc agaagcgccg gctgctgcag  1320
gagatcctgg agaactcgga gagcctgctg gagcccccg accggggcgc cggcgcagcg  1380
ggcctcccac agccgccccg cgagagcccg cagctgcacg agcgtgagac ccctcggccc  1440
gagggtggct ccccgtcacc ggccgggacg ccccgcagc caagcggcc caggcccggg  1500
gtgtccaagg acggcctgct gagcccaggc gcctggaacg gcgagccag cggtgagggc  1560
agccggtcag tcactccgtc cgagggcgcg ggccgccgca gccccgcgcg tccagccacc  1620
gagcgcatgg ccatcgaggc tctgcaggca ccgcctgcgc cgtcgcggga gccggaggtg  1680
gcgctttacc agggctacca cagctatgct gtgcgc                             1716

SEQ ID NO: 228         moltype = AA  length = 572
FEATURE                Location/Qualifiers
source                 1..572
                       mol_type = protein
                       organism = Homo sapiens
SEQUENCE: 228
MSGGRFDFDD GGAYCGGWEG GKAHGHGLCT GPKGQGEYSG SWNFGFEVAG VYTWPSGNTF    60
EGYWSQGKRH GLGIETKGRW LYKGEWTHGF KGRYGIRQSS SSGAKYEGTW NNGLQDGYGT   120
ETYADGGTYQ GQFTNGMRHG YGVRQSVPYG MAVVVRSPLR TSLSSLRSEH SNGTVAPDSP   180
ASPASDGPAL PSPAIPRGGF ALSLLANAEA AARAPKGGGL FQRGALLGKL RRAESRTSVG   240
SQRSRVSFLK SDLSSGASDA ASTASLGEAA EGADEAAPFE ADIDATTTET YMGEWKNDKR   300
SGFGVSERSS GLRYEGEWLD NLRHGYGCTT LPDGHREEGK YRHNVLVKDT KRRMLQLKSN   360
KVRQKVEHSV EGAQRAAAIA RQKAEIAASR TSHAKAKAEA AEQAALAANQ ESNIARTLAR   420
ELAPDFYQPG PEYQKRRLLQ EILENSESLL EPPDRGAGAA GLPQPPRESP QLHERETPRP   480
EGGSPSPAGT PPQPKRPRPG VSKDGLLSPG AWNGEPSGEG SRSVTPSEGA GRRSPARPAT   540
ERMAIEALQA PPAPSREPEV ALYQGYHSYA VR                                 572

SEQ ID NO: 229         moltype = DNA  length = 159
FEATURE                Location/Qualifiers
source                 1..159
                       mol_type = other DNA
                       organism = Homo sapiens
SEQUENCE: 229
atggagaaag tccaatacct cactcgctca gctataagaa gagcctcaac cattgaaatg    60
cctcaacaag cacgtcaaaa gctacagaat ctatttatca atttctgtct catcttaata   120
tgtctcttgc tgatctgtat catcgtgatg cttctctga                           159

SEQ ID NO: 230         moltype = AA  length = 52
FEATURE                Location/Qualifiers
source                 1..52
                       mol_type = protein
                       organism = Homo sapiens
SEQUENCE: 230
MEKVQYLTRS AIRRASTIEM PQQARQKLQN LFINFCLILI CLLLICIIVM LL            52
```

OPTIMIZED EXPRESSION CASSETTES FOR GENE THERAPY

CROSS-REFERENCE TO RELATED APPLICATION

This application is a continuation of International Patent Application No. PCT/US2022/073574, filed on Jul. 8, 2022, which claims the benefit of U.S. Provisional Patent Application No. 63/219,651, filed on Jul. 8, 2021, the contents of each of which are incorporated by reference herein in their entireties.

FIELD OF THE INVENTION

This invention relates generally to gene therapies, e.g., optimized gene expression cassettes, recombinant adeno-associated virus (AAV) virions, and methods for treating and preventing heart disease using the same.

REFERENCE TO AN ELECTRONIC SEQUENCE LISTING

The contents sequence of the electronic listing (TENA_021_03US_SubSeqList_ST26.xml; Size: 430,577 bytes; and Date of Creation: Sep. 21, 2023), submitted in XML format via the USPTO Patent Center, are herein incorporated by reference in their entirety.

BACKGROUND

Cardiomyopathy is responsible for about half of cardiac-related deaths. It is estimated that about 1 in 250 to 1 in 10,000 adults are affected by some form of cardiomyopathy (McKenna et al. *Circ Res.* 121:722-730 (2017)). Despite major efforts in screening, diagnostics, and therapeutic strategies, the prevalence of cardiomyopathies and incidence of cardiomyopathy-related deaths remains high (Brieler et al. *Am Fam Physician.* 96:640-646 (2017)).

Cardiomyopathy refers to a collection of conditions of the heart that occur when its ability to pump blood is reduced. Reduction in proper functioning, such as a contractile dysfunction, of the heart muscle can lead to myocardial infarction, heart failure, blood clots, valve problems, and cardiac arrest. Cardiomyopathies can be separated into primary and secondary categories that result in varied phenotypes (McKenna et al. *Circ Res.* 121:722-730 (2017)). Primary cardiomyopathies can be genetic, acquired, or mixed in etiology. Genetic cardiomyopathies are inherited and include arrhythmogenic right ventricular dysplasia, hypertrophic, ion channel disorders, left ventricular compaction, and mitochondrial myopathies. Acquired cardiomyopathies are due primarily to non-secondary, non-genetic causes that lead to cardiac complications and include myocarditis, peripartum, tachycardia-induced cardiomyopathy, and stress-induced cardiomyopathy. Cardiomyopathies with mixed etiology are caused by a combination of non-genetic and genetic factors, and include dilated cardiomyopathy and restrictive cardiomyopathy. Secondary cardiomyopathies refer to heart disease resulting from an extra cardiovascular cause. The underlying causes of secondary cardiomyopathies can be endocrine, infection, exposure to toxins, autoimmune related, nutritional, and/or neuromuscular.

Cardiomyocytes play a central role cardiomyopathy. Cardiomyocytes, also called cardiac muscle cells, cardiac myocytes, or myocardiocytes, are cardiac cells that make up the heart muscle and are responsible for the contractile function that allows the heart to act as a pump. There are many mechanisms that reduce cardiomyocytes' ability to function properly (Dadson et al. *Clin Sci* (Lond) 131:1375-1392 (2017)). In arrhythmogenic right ventricular cardiomyopathy, progressive replacement of cardiomyocytes with fibrotic tissue results in the electrical isolation of cardiomyocytes and atrophy of the ventricular myocardium, the major structure responsible for contractile function in the heart. In mitochondrial cardiomyopathy, a deficiency in ATP production has a direct effect on contractile function in cardiomyocytes that have a high metabolic demand. Cardiomyopathies also emerge as a result of abnormal contractile function resulting from loss of normal $Ca^{2+}$ ion-release, uptake, and sequestration processes due to loss of activity in regulatory enzymes, such as sarco/endoplasmic reticulum calcium ATPase (SERCA) (Lennon et al. *Int J Mol Med.* 7:131-41 (2001)).

Treatment strategies for cardiomyopathy are needed.

Gene therapy approaches for the treatment of heart disease often employ vectors configured to transduce cardiac cells and to express a transgene in a cardiac tissue-specific manner. Adeno-associated virus (AAV) vectors, cardiac-specific promoters, or both in combination, may be used to deliver a polynucleotide encoding a gene product (e.g., a therapeutic protein) to heart tissue and thereby express the gene product in that tissue to treat the heart disease.

However, achieving high expression of gene products remains challenging, especially in cardiac cells.

Given these challenges, there remains a need in the art for improved gene therapy vectors, especially for heart disease.

SUMMARY

In some aspects, the present invention relates generally to vectors for delivery of a polynucleotide encoding a dwarf open reading frame (DWORF) or another transgene to cardiac cells, e.g., cardiomyocytes. Disclosed herein are recombinant adeno-associated virus virions (rAAV virions), including expression cassettes and capsid proteins, that effectively deliver DWORF polynucleotides into cardiac cells, along with related compositions and methods. In any aspects described herein where DWORF transgene is referenced, DWORF can be substituted by a reference to another transgene expression of which in cardiac cells is desired. In some embodiments, where AAV-based expression vectors and virions are referenced, the disclosure also contemplates use of other viral and non-viral vectors for delivery of transgenes. In particular, any viral and non-viral vectors that can be used for delivery of transgenes into cardiac cells are provided herein.

In some aspects, provided herein is an expression cassette comprising a polynucleotide sequence comprising:
i) one or more promoters, optionally wherein the one or more promoters are cardiac-specific promoters; and
ii) one or more copies of a transgene, optionally wherein the transgene encodes a polypeptide for treating or preventing a heart disease or alleviating symptoms associated with a heart disease;
wherein in addition to elements (i) and (ii), the expression cassette comprises one or more of the following:
iii) one or more enhancers, optionally wherein the one or more enhancers are cardiac-specific enhancers;
iv) the one or more copies of a transgene is at least two copies of the transgene;
v) the polynucleotide sequence comprises one or more introns; and/or vi) at least one copy of the one or more copies of the transgene is codon-optimized.

In some embodiments of the expression cassette described above, in addition to elements (i) and (ii), the expression cassette comprises one, two, three or all four of elements (iii), (iv), (v) and (vi) (any combination of elements (iii), (iv), (v) and (vi) can be used). In some embodiments of the expression cassette described above, in addition to elements (i) and (ii), the expression cassette comprises one or more enhancers, wherein the one or more enhancers are cardiac-specific enhancers, and/or the polynucleotide sequence comprises one or more introns. In some embodiments of the expression cassette described above, in addition to elements (i) and (ii), the expression cassette comprises one or more enhancers, wherein the one or more enhancers are cardiac-specific enhancers, and the polynucleotide sequence comprises one or more introns. In some embodiments, the one or more introns improve, or can improve, the efficiency of transgene expression. In some embodiments of the expression cassette described above, in addition to elements (i) and (ii), the expression cassette comprises two copies of the transgene, wherein the two copies are not identical, optionally wherein first copy is codon-optimized and second copy is not codon-optimized nucleotide sequence encoding the transgene. In some embodiments of the expression cassette described above, in addition to elements (i) and (ii), the expression cassette comprises two copies of the transgene, wherein the two copies are not identical to each other, optionally wherein first copy is codon-optimized and second copy is not codon-optimized nucleotide sequence encoding the transgene, and further the polynucleotide sequence comprises one or more introns. In some embodiments of the expression cassette described above, in addition to elements (i) and (ii), the expression cassette comprises two copies of the transgene, wherein the two copies are not identical to each other, optionally wherein first copy is codon-optimized and second copy is not codon-optimized nucleotide sequence encoding the transgene, and further the polynucleotide sequence comprises one or more introns, and further the polynucleotide sequence comprises one or more enhancers (e.g., wherein the one or more enhancers are cardiac-specific enhancers). In some embodiments, the one or more introns improve, or can improve, the efficiency of transgene expression. In some embodiments where two copies of the transgene are used, two copies of the promoters are also used.

In some embodiments of the expression cassette, the polynucleotide sequence comprises one or more promoters, wherein the one or more promoters are cardiac-specific enhancers. In some embodiments of the expression cassette, at least one promoter is a cardiac-specific promoter, or all of the promoters are cardiac-specific promoters. In some embodiments of the expression cassette, the polynucleotide sequence comprises a single promoter. In some embodiments of the expression cassette, the polynucleotide sequence comprises two promoters. In some embodiments of the expression cassette, at least one promoter of the one or more promoters is a chicken cTnT promoter. In some embodiments, the chicken cTnT promoter shares at least 90%, 95%, 96%, 97%, 98%, or 99% identity to SEQ ID NO: 11. In some embodiments, the chicken cTnT promoter comprises SEQ ID NO: 11. In some embodiments of the expression cassette, at least one promoter of the one or more promoters is a human cTnT promoter. In some embodiments, the human cTnT promoter shares at least 90%, 95%, 96%, 97%, 98%, or 99% identity to SEQ ID NO: 12 or SEQ ID NO: 13. In some embodiments, the human cTnT promoter comprises SEQ ID NO: 12 or SEQ ID NO: 13. In some embodiments, the expression cassette comprises a chicken cTnT promoter and a human cTnT promoter.

In some embodiments of the expression cassette, the polynucleotide sequence comprises one or more copies of a transgene, wherein the transgene encodes a polypeptide for treating or preventing a heart disease or alleviating symptoms associated with a heart disease.

In some embodiments of the expression cassette, one or more copies of a transgene is at least two copies of the transgene. In some embodiments of the expression cassette, one or more copies of a transgene is two copies of the transgene. In some embodiments, one or more copies of a transgene is at least two copies of the transgene, and wherein the polynucleotide sequence comprises at least two promoters each operably linked to the at least two copies of the transgene. In some embodiments, one or more copies of a transgene is two copies of the transgene, and wherein the polynucleotide sequence comprises two promoters each operably linked to the two copies of the transgene. In some embodiments of the expression cassette comprising two copies of the transgene, the two "copies" are not identical. While not being bound by any theory, using two nucleic acid sequences encoding a polypeptide that are not identical may prevent DNA recombination within the vector. In some embodiments, the expression cassette comprises one copy of the transgene that has the original DNA sequence encoding a polypeptide and one copy of the transgene that has a codon optimized DNA sequence encoding the polypeptide. In some embodiments of the expression cassette comprising two copies of the transgene, the first copy of the transgene is sufficiently different from the second copy of the transgene to prevent DNA recombination.

In some embodiments of the expression cassette, the polynucleotide sequence comprises one or more enhancers, optionally wherein the one or more enhancers are cardiac-specific enhancers. In some embodiments of the expression cassette, the polynucleotide sequence comprises two or more enhancers (e.g., 2, 3, or 4 enhancers). In some embodiments of the expression cassette, one or more enhancers are cardiac-specific enhancers (e.g., at least one enhancer is a cardiac-specific enhancer, or 2, 3, or 4, or all of the enhancers are cardiac-specific enhancers). In some embodiments of the expression cassette, the polynucleotide sequence comprises one enhancer. In some embodiments of the expression cassette, the polynucleotide sequence comprises no enhancers. In some embodiments, the one or more cardiac-specific enhancers are selected from a ACTC1 enhancer and a αMHC enhancer. In some embodiments, the ACTC1 enhancer shares at least 90%, 95%, 96%, 97%, 98%, or 99% identity to SEQ ID NO: 78. In some embodiments, the ACTC1 enhancer comprises SEQ ID NO: 78. In some embodiments, the αMHC enhancer shares at least 90%, 95%, 96%, 97%, 98%, or 99% identity to SEQ ID NO: 79. In some embodiments, the αMHC enhancer comprises SEQ ID NO: 79. In some embodiments, the expression cassette comprises an αMHC enhancer and an ACTC1 enhancer. In some embodiments of the expression cassette, the enhancer sequence comprises an αMHC enhancer followed by an ACTC1 enhancer. In some embodiments of the expression cassette, the enhancer sequence comprises an ACTC1 enhancer followed by an αMHC enhancer.

In some embodiments of the expression cassette, the polynucleotide sequence comprises one or more introns. In some embodiments of the expression cassette, the polynucleotide sequence comprises one intron. In some embodiments of the expression cassette, the polynucleotide sequence comprises two introns. In some embodiments of the expression cassette, the polynucleotide sequence comprises more than two introns. In some embodiments of the expression cassette, one or more introns are the same. In some embodiments of the expression cassette, one or more introns are different from each other. In some embodiments, the expression cassette comprises an intron and the intron is selected from a CMV intron and a chimeric intron. In some embodiments, the CMV intron shares at least 90%, 95%, 96%, 97%, 98%, or 99% identity to SEQ ID NO: 80. In some embodiments, the CMV intron comprises SEQ ID NO: 80. In some embodiments, the chimeric intron shares at least 90%, 95%, 96%, 97%, 98%, or 99% identity to SEQ ID NO: 81. In some embodiments, the chimeric intron comprises SEQ ID NO: 81. In some embodiments, the expression cassette comprises a CMV intron and a chimeric intron. In some embodiments, the expression cassette does not comprise an intron (e.g., does not comprise a CMV intron or a chimeric intron).

In some embodiments of the expression cassette, at least one copy of the one or more copies of the transgene is codon-optimized (e.g., codon-optimized for optimum human expression). In some embodiments of the expression cassette, two copies of the transgene are codon-optimized. In some embodiments of the expression cassette, first copy of the transgene is codon-optimized and second copy of the transgene is not codon optimized (e.g., original DNA sequence) or is otherwise different from the first copy. In some embodiments of the expression cassette, the first copy of the transgene is sufficiently different from the second copy of the transgene to prevent DNA recombination.

In some embodiments, the expression cassette further comprises one or more (e.g., two) post-transcriptional regulatory elements ("PTRE"). In some embodiments, the expression cassette further comprises one or more (e.g., two) WPRE sequences. In some embodiments, the expression cassette comprises one WPRE sequence. In some embodiments, the WPRE sequence shares at least 90%, 95%, 96%, 97%, 98%, or 99% identity to SEQ ID NO: 26. In some embodiments, the WPRE sequence comprises SEQ ID NO: 26. In some embodiments, the expression cassette does not comprise a WPRE sequence.

In some embodiments, the expression cassette further comprises one or more polyadenylation sequences ("p(A)"). In some embodiments, the expression cassette comprises one polyadenylation sequence. In some embodiments, the expression cassette comprises two polyadenylation sequences. In some embodiments, the polyadenylation sequence is selected from a BGH polyadenylation sequence and a SV40 polyadenylation sequence. In some embodiments, the BGH polyadenylation sequence shares at least 90%, 95%, 96%, 97%, 98%, or 99% identity to SEQ ID NO: 27. In some embodiments, the BGH polyadenylation sequence comprises SEQ ID NO: 27. In some embodiments, the SV40 polyadenylation sequence shares at least 90%, 95%, 96%, 97%, 98%, or 99% identity to SEQ ID NO: 28. In some embodiments, the SV40 polyadenylation sequence comprises SEQ ID NO: 28. In some embodiments, the expression cassette comprises a BGH polyadenylation sequence and a SV40 polyadenylation sequence.

In some embodiments, the expression cassette comprises 5' to 3' arrangement of elements selected from any one of the following:
  (i) 5'-promoter-intron-transgene-PTRE-p(A)-3';
  (ii) 5'-promoter-transgene-PTRE-p(A)-promoter-transgene-PTRE-p(A);
  (iii) 5'-enhancer-promoter-transgene-PTRE-p(A)-3';
  (iv) 5'-enhancer-promoter-intron-transgene-PTRE-p(A)-3';
  (v) 5'-enhancer-enhancer-promoter-transgene-PTRE-p(A)-3';
  (vi) 5'-enhancer-enhancer-promoter-intron-transgene-PTRE-p(A)-3';
  (vii) 5'-enhancer-promoter-intron-transgene-PTRE-p(A)-p(A)-transgene-intron-promoter-enhancer-3';
  (viii) 5'-enhancer-promoter-intron-transgene-PTRE-p(A)-enhancer-promoter-intron-transgene-p(A)-3';
  (ix) 5'-p(A)-PTRE-transgene-intron-promoter-enhancer-enhancer-promoter-intron-transgene-p(A)-3';
  (x) 5'-promoter-intron-transgene-PTRE-p(A)-p(A)-transgene-intron-promoter-3';
  (xi) 5'-promoter-intron-transgene-PTRE-p(A)-promoter-intron-transgene-p(A)-3'; and
  (xii) 5'-p(A)-PTRE-transgene-intron-promoter-promoter-intron-transgene-p(A)-3'.

In some embodiments of the expression cassette, the transgene has an increased expression level compared to an expression cassette comprising a polynucleotide having an arrangement of elements from 5' to 3' comprising: 5'-promoter-transgene-WPRE-p(A)-3'. In some embodiments, the increased expression level is between about 1.5-fold and about 150-fold. In some embodiments, the increased expression level is at least 2 fold, at least 5 fold, at least 10 fold, at least 25 fold, at least 50 fold, at least 75 fold, or at least 100 fold.

In some embodiments, the expression cassette is flanked by ITRs. In some embodiments, the ITRs share at least 90%, 95%, 96%, 97%, 98%, or 99% identity to one or more of SEQ ID NO: 14 and SEQ ID NO: 15. In some embodiments, the ITRs comprise one or more of SEQ ID NO: 14 and SEQ ID NO: 15.

In some embodiments, the expression cassette comprises from about 1.9 kb to about 3.7 kb. In some embodiments, the expression cassette comprises from about 2.5 kb to about 3.7 kb, optionally from about 2.8 kb to about 3.6 kb.

In some embodiments, the transgene in the expression cassette encodes a polypeptide useful in the treatment of a heart disease or disorder, optionally when a wild type copy of the gene is introduced to a subject. In some embodiments, the transgene in the expression cassette encodes a polypeptide which is associated with a heart disease (e.g., where loss of function mutations in the gene encoding the polypeptide are associated with heart disease).

In some embodiments, the transgene in the expression cassette encodes a polypeptide selected from: DWORF, JPH2, BAG3, CRYAB, Lamin A isoform of LMNA, Lamin C isoform of LMNA, TNNI3, PLN, LAMP2a, LAMP2b, LAMP2c, DPI isoform of DSP, DPII isoform of DSP, DSG2, and JUP. In some embodiments, the expression cassette comprises a transgene which shares at least 75%, 80%, 90%, 95%, 96%, 97%, 98%, 99% or 100% sequence identity to SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, or SEQ ID NO:229. In some embodiments, the polypeptide shares at least 75%, 80%, 90%, 95%, 96%, 97%, 98%, 99% or 100% sequence identity to SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, or SEQ ID NO:230.

In some embodiments, the transgene in the expression cassette encodes a DWORF polypeptide. In some embodiments, the transgene shares at least 75%, 80%, 90%, 95%, 96%, 97%, 98%, 99% or 100% sequence identity to SEQ ID NO:2, SEQ ID NO:4, SEQ ID NO:6, SEQ ID NO:8, SEQ ID NO:10, SEQ ID NO:33, SEQ ID NO:44, SEQ ID NO:76, or SEQ ID NO:77. In some embodiments, the polypeptide shares at least 75%, 80%, 90%, 95%, 96%, 97%, 98%, 99% or 100% sequence identity to SEQ ID NO:1, SEQ ID NO:3, SEQ ID NO:5, SEQ ID NO:7, SEQ ID NO:9, SEQ ID NO:32, or SEQ ID NO:43.

In some embodiments, the expression cassette comprises a 5' to 3' arrangement of elements selected from any one of the following:
(i) 5'-human or chicken TnT promoter-chimeric intron-transgene-WPRE-p(A)-3';
(ii) 5'-first human or chicken TnT promoter-first copy of transgene-WPRE-p(A)-second human or chicken TnT promoter—second copy of transgene-WPRE-p(A), optionally where the first and second promoter sequences and the first and second copies of the transgene are in the same forward orientation;
(iii) 5'-human TnT promoter-CMV intron-transgene-WPRE-bGHpA-3';
(iv) 5'-ACTC1e enhancer-cardiac-human TnT promoter-transgene-WPRE-bGHpA-3';
(v) 5'-αMHCe enhancer-human TnT promoter-transgene-WPRE-bGHpA-3';
(vi) 5'-ACTC1e enhancer-human TnT promoter-CMV intron-transgene-WPRE-bGHpA-3';
(vii) 5'-αMHCe enhancer-human TnT promoter-CMV intron-transgene-WPRE-bGHpA-3';
(viii) 5'-ACTC1e enhancer-αMHCe enhancer-human TnT promoter-transgene-WPRE-bGHpA-3';
(ix) 5'-αMHCe enhancer-ACTC1e enhancer-human TnT promoter-transgene-WPRE-bGHpA-3';
(x) 5'-ACTC1e enhancer-αMHCe enhancer-human TnT promoter-CMV intron-transgene-WPRE-bGHpA-3';
(xi) 5'-αMHCe enhancer-ACTC1e enhancer-human TnT promoter-CMV intron-transgene-WPRE-bGHpA-3';
(xii) 5'-human TnT promoter-transgene with a codon-optimized polynucleotide sequence-WPRE-bGHpA-3';
(xiii) 5'-αMHCe enhancer-human TnT promoter-CMV intron-first transgene-WPRE-bGHpA-SV40pA-second transgene (e.g., with a codon-optimized polynucleotide sequence)-chimeric intron-chicken TnT promoter—ACTC1e enhancer-3', optionally wherein the first transgene and the human TnT promoter are in a forward orientation, and the second transgene and the chicken TnT promoter are in a reverse orientation;
(xiv) 5'-αMHCe enhancer-human TnT promoter-CMV intron-first transgene-WPRE-bGHpA-ACTC1e enhancer-chicken TnT promoter-chimeric intron-second transgene (e.g., with a codon-optimized polynucleotide sequence)-SV40pA-3', optionally wherein the first transgene, the human TnT promoter, the second transgene and the chicken TnT promoter are in a forward orientation;
(xv) 5'-bGHpA-WPRE-first transgene-CMV intron-human TnT promoter-αMHCe enhancer-ACTC1e enhancer-chicken TnT promoter-chimeric intron-second transgene (e.g., with a codon-optimized polynucleotide sequence)-SV40pA-3', optionally wherein the first transgene and the human TnT promoter are in a reverse orientation, and the second transgene and the chicken TnT promoter are in a forward orientation;
(xvi) 5'-human TnT promoter-CMV intron-first transgene-WPRE-bGHpA-pSV40pA-second transgene (e.g., with a codon-optimized polynucleotide sequence)-chimeric intron-chicken TnT promoter-3', optionally wherein the first transgene and the human TnT promoter are in a forward orientation, and the second transgene and the chicken TnT promoter are in a reverse orientation; and
(xvii) 5'-huma TnT promoter-CMV intron-first transgene-WPRE-bGHpA-chicken TnT promoter-chimeric intron-second transgene (e.g., with a codon-optimized polynucleotide sequence)-SV40pA-3', optionally wherein the first transgene, the human TnT promoter, the second transgene and the chicken TnT promoter are in a forward orientation; and (xix) 5'-bGHpA-WPRE-first transgene-CMV intron-human TnT promoter-chicken TnT promoter-chimeric intron-second transgene (e.g., with a codon-optimized polynucleotide sequence)-SV40pA-3', optionally wherein the first transgene and the human TnT promoter are in a reverse orientation, and the second transgene and the chicken TnT promoter are in a forward orientation.

In some embodiments, the expression cassette comprises 5' to 3' arrangement of elements selected from any one of the following:
(i) 5'-ACTC1e enhancer-αMHCe enhancer-human TnT promoter-CMV intron-transgene-WPRE-bGHpA-3';
(ii) 5'-αMHCe enhancer-ACTC1e enhancer-human TnT promoter-CMV intron-transgene-WPRE-bGHpA-3';
(iii) 5'-αMHCe enhancer-human TnT promoter-CMV intron-first transgene-WPRE-bGHpA-SV40pA-second transgene (e.g., with a codon-optimized polynucleotide sequence)-chimeric intron-chicken TnT promoter—ACTC1e enhancer-3', optionally wherein the first transgene and the human TnT promoter are in a forward orientation, and the second transgene and the chicken TnT promoter are in a reverse orientation;
(iv) 5'-αMHCe enhancer-human TnT promoter-CMV intron-first transgene-WPRE-bGHpA-ACTC1e enhancer-chicken TnT promoter-chimeric intron-second transgene (e.g., with a codon-optimized polynucleotide sequence)-SV40pA-3', optionally wherein the first transgene, the human TnT promoter, the second transgene and the chicken TnT promoter are in a forward orientation;
(v) 5'-bGHpA-WPRE-first transgene-CMV intron-human TnT promoter-αMHCe enhancer-ACTC1e enhancer-chicken TnT promoter-chimeric intron-second transgene (e.g., with a codon-optimized polynucleotide sequence)-SV40pA-3', optionally wherein the first transgene and the human TnT promoter are in a reverse orientation, and the second transgene and the chicken TnT promoter are in a forward orientation;
(vi) 5'-human TnT promoter-CMV intron-first transgene-WPRE-bGHpA-pSV40pA-second transgene (e.g., with a codon-optimized polynucleotide sequence)-chimeric intron-chicken TnT promoter-3', optionally wherein the first transgene and the human TnT promoter are in a forward orientation, and the second transgene and the chicken TnT promoter are in a reverse orientation;
(vii) 5'-huma TnT promoter-CMV intron-first transgene-WPRE-bGHpA-chicken TnT promoter-chimeric intron-second transgene (e.g., with a codon-optimized polynucleotide sequence)-SV40pA-3', optionally wherein the first transgene, the human TnT promoter, the second transgene and the chicken TnT promoter are in a forward orientation; and (viii) 5'-bGHpA-WPRE-first transgene-CMV intron-human TnT promoter-chicken TnT promoter-chimeric intron-second transgene (e.g., with a codon-optimized polynucleotide sequence)-SV40pA-3', optionally wherein the first transgene and the human TnT promoter are in a reverse orientation, and the second transgene and the chicken TnT promoter are in a forward orientation.

In some embodiments, the expression cassette is a recombinant expression cassette.

In some aspects, provided herein is a recombinant vector comprising any of the expression cassettes described herein. In some embodiments, the vector is a viral vector. In some embodiments, the vector is a non-viral vector.

In some aspects, provided herein is a recombinant adeno-associated virus (rAAV) virion, comprising a capsid protein and a viral genome comprising any of the expression cassettes described herein, wherein the expression cassette is flanked by inverted terminal repeats (ITRs). In some embodiments, the ITRs share at least 90%, 95%, 96%, 97%, 98%, or 99% identity to one or more of SEQ ID NO: 14 and SEQ ID NO: 15. In some embodiments, the ITRs share at least 90%, 95%, 96%, 97%, 98%, or 99% identity to one or more of SEQ ID NO: 14 and SEQ ID NO: 15. In some embodiments, the capsid protein shares at least 98%, at least 99%, or 100% identity to an AAV9 capsid protein (SEQ ID NO: 143). In some embodiments, the capsid protein shares at least 98%, at least 99%, or 100% identity to an AAV5 capsid protein (SEQ ID NO: 144). In some embodiments, the capsid protein is a chimeric capsid protein. In some embodiments, the capsid protein is an AAV5/AAV9 chimeric capsid protein. In some embodiments, the capsid protein is selected from any one of SEQ ID NOs: 145-200.

In some aspects, provided herein is a pharmaceutical composition comprising any of the vectors described herein or any of the rAAV virions described herein, and a pharmaceutically acceptable carrier.

In some aspects, provided herein is a kit comprises any of the pharmaceutical compositions described herein, or any components of such pharmaceutical compositions (e.g., a vector or an rAAV virion).

In some aspects, provided herein is a method of increasing expression of a polypeptide in a cardiac cell or cardiac tissue comprising contacting a cell with any vector described herein, any rAAV virion described herein, or any pharmaceutical composition described herein. In some embodiments, the cardiac cell is a cardiomyocyte. In some embodiments, the cardiac tissue is heart tissue. In some embodiments, the polypeptide expression is increased between about 1.5-fold and 150-fold. In some embodiments, the polypeptide expression is increased at least 2 fold, at least 5 fold, at least 10 fold, at least 25 fold, at least 50 fold, at least 75 fold, or at least 100 fold. In some embodiments, the contacting is in vitro. In some embodiments, the contacting is in vivo.

In some aspects, provided herein is a method of increasing polypeptide expression in a subject comprising administering to the subject any vector described herein, any rAAV virion described herein, or any pharmaceutical composition described herein. In some embodiments, the subject is a mammal. In some embodiments, the subject is a human. In some embodiments, following administering, the polypeptide expression is increased in the heart of the subject. In some embodiments, the subject being treated has a heart disease or is at risk of a heart disease. In some embodiments, the subject being treated has borderline or reduced ejection fraction. In some embodiments, the subject being treated has normal ejection fraction. In some embodiments, wherein the subject being treated has a genetic mutation associated with a heart disease (e.g., a mutation in a PLN gene). In some embodiments, the subject has a low or undetectable level of expression of the polypeptide encoded by the transgene, compared to a healthy subject.

In some aspects, provided herein is a method of treating or preventing a heart disease or disorder in a subject in need thereof comprising administering to the subject any vector described herein, any rAAV virion described herein, or any pharmaceutical composition described herein. In some embodiments, the subject being treated has a heart disease or disorder. In some embodiments, the subject being treated is a risk of developing a heart disease or disorder. In some embodiments, the heart disease or disorder is cardiomyopathy. In some embodiments, the cardiomyopathy is dilated cardiomyopathy. In some embodiments, the heart disease or disorder is myocardial infarction. In some embodiments, the myocardial infarction is chronic myocardial infarction. In some embodiments, the subject has an inherited risk allele for a heart disease or disorder. In some embodiments, the subject has an inherited risk allele for a heart disease or disorder due to a genetic mutation. In some embodiments, the subject has an inherited risk allele for a heart disease or disorder due to a genetic mutation in a PLN gene (for example, one or more mutations in the PLN gene described herein or known in the art). In some embodiments, the heart disease or disorder is with reduced ejection fraction (HFrEF). In some embodiments, the heart disease of disorder is with preserved ejection fraction (HFpEF). In some embodiments, the method leads to expression of the polypeptide encoded by the transgene in the heart of the subject. In some embodiments, the method leads to expression of the polypeptide encoded by the transgene in cardiomyocytes of the subject. In some embodiments, the method causes no detectable expression of the polypeptide encoded by the transgene in the muscles of the subject except the heart, in the liver of the subject, and/or in the cardiac fibroblasts of the subject. In some embodiments, the method improves one or more measures of cardiac function, optionally fraction shortening and/or left ventricular internal dimension (LVID). In some embodiments, the improvement in cardiac function is observed at or later than week 2, week 4, week 6, week 8, week 10, week 12, week 14, week 16, week 18, week 20, week 22, and/or week 24, after the administering. In some embodiments, the administering is systemic administration. In some embodiments, the systemic administration is selected from intravenous or intracoronary injection. In some embodiments, when an rAAV virion is administered, it is administered as a unit dose. In some embodiments, the unit dose comprises about $3 \times 10^{14}$ vg/kg or less, about $2 \times 10^{14}$ vg/kg or less, about $1 \times 10^{14}$ vg/kg or less, about $9 \times 10^{13}$ vg/kg or less, about $8 \times 10^{13}$ vg/kg or less, about $7 \times 10^{13}$ vg/kg or less, about $6 \times 10^{13}$ vg/kg or less, about $5 \times 10^{13}$ vg/kg or less, about $4 \times 10^{13}$ vg/kg or less, about $3 \times 10^{13}$ vg/kg or less, about $2 \times 10^{13}$ vg/kg or less, or about $1 \times 10^{13}$ vg/kg or less. In some embodiments, the subject being treated is a mammal. In some embodiments, the subject being treated is a human.

In one aspect, the disclosure provides a recombinant adeno-associated virus (rAAV) virion, comprising a capsid protein and a viral genome comprising an expression cassette comprising a polynucleotide sequence encoding a dwarf open reading frame (DWORF) polypeptide operatively linked to a promoter, the expression cassette flanked by inverted terminal repeats.

In some embodiments, the DWORF polypeptide shares at least 90%, 95%, 96%, 97%, 98%, or 99% identity to a sequence selected from SEQ ID NOs: 1, 3, 4, 7, 9, 23, and 43. In some embodiments, the DWORF polypeptide is selected from SEQ ID NOs: 1, 3, 4, 7, 9, 23, and 43.

In some embodiments, the promoter is a chicken cTnT promoter. In some embodiments, the chicken cTnT promoter shares at least 90%, 95%, 96%, 97%, 98%, or 99% identity to SEQ ID NO: 11. In some embodiments, the chicken cTnT promoter comprises SEQ ID NO: 11. In some embodiments, the promoter is a human cTnT promoter. In some embodiments, the human cTnT promoter shares at least 90%, 95%, 96%, 97%, 98%, or 99% identity to SEQ ID NO: 12 or SEQ ID NO: 13. In some embodiments, the human cTnT promoter comprises SEQ ID NO: 12 or SEQ ID NO: 13.

In some embodiments, the expression cassette further comprises one or more enhancers. In some embodiments, the enhancer the one or more enhancers are selected from a ACTC1 cardiac enhancer and a αMHC enhancer. In some embodiments, the ACTC1 cardiac enhancer shares at least 90%, 95%, 96%, 97%, 98%, or 99% identity to SEQ ID NO: 78. In some embodiments, the ACTC1 cardiac enhancer comprises SEQ ID NO: 78. In some embodiments, the αMHC enhancer shares at least 90%, 95%, 96%, 97%, 98%, or 99% identity to SEQ ID NO: 79. In some embodiments, the αMHC enhancer comprises SEQ ID NO: 79.

In some embodiments, the expression cassette further comprises an intron. In some embodiments, the intron is selected from a CMV intron and a chimeric intron. In some embodiments, the CMV intron shares at least 90%, 95%, 96%, 97%, 98%, or 99% identity to SEQ ID NO: 80. In some embodiments, the CMV intron comprises SEQ ID NO: 80. In some embodiments, the chimeric intron shares at least 90%, 95%, 96%, 97%, 98%, or 99% identity to SEQ ID NO: 81. In some embodiments, the chimeric intron comprises SEQ ID NO: 81.

In some embodiments, the expression cassette further comprises a WPRE sequence. In some embodiments, the WPRE sequence shares at least 90%, 95%, 96%, 97%, 98%, or 99% identity to SEQ ID NO: 26. In some embodiments, the WPRE sequence comprises SEQ ID NO: 26.

In some embodiments, the expression cassette further comprises a polyadenylation sequence. In some embodiments, the polyadenylation sequence is selected from a BGH polyadenylation sequence and a SV40 polyadenylation sequence. In some embodiments, the BGH polyadenylation sequence shares at least 90%, 95%, 96%, 97%, 98%, or 99% identity to SEQ ID NO: 27. In some embodiments, the BGH polyadenylation sequence comprises SEQ ID NO: 27. In some embodiments, the SV40 polyadenylation sequence shares at least 90%, 95%, 96%, 97%, 98%, or 99% identity to SEQ ID NO: 28. In some embodiments, the SV40 polyadenylation sequence comprises SEQ ID NO: 28.

In some embodiments, the expression cassette is flanked by ITRs. In some embodiments, the ITRs share at least 90%, 95%, 96%, 97%, 98%, or 99% identity to one or more of SEQ ID NO: 14 and SEQ ID NO: 15. In some embodiments, the ITRs comprise one or more of SEQ ID NO: 14 and SEQ ID NO: 15.

In some embodiments, the expression cassette comprises a single promoter. In some embodiments, the expression cassette comprises two promoters. In some embodiments, the expression cassette comprises a single copy a sequence encoding the DWORF polypeptide. In some embodiments, the expression cassette comprises two copies of a sequence encoding the DWORF polypeptide. In some embodiments, where the expression cassette comprises two copies of a sequence encoding the DWORF polypeptide, the two "copies" are not identical. While not being bound by any theory, using two nucleic acid sequences encoding a polypeptide that are not identical may prevent DNA recombination within the vector. In some embodiments, the expression cassette comprises one copy that has the original DNA sequence encoding the DWORF polypeptide and one copy that has a codon optimized DNA sequence encoding the DWORF polypeptide. In some embodiments, the expression cassette comprises two copies of a sequence encoding the DWORF polypeptide, wherein one copy is codon-optimized and one copy is not codon optimized. In some embodiments, the expression cassette comprises one, two, three, or four enhancers. In some embodiments, the expression cassette comprises one or two introns. In some embodiments, the expression cassette comprises one or two WPRE sequences. In some embodiments, the expression cassette comprises one or two polyadenylation sequences.

In some embodiments, the expression cassette comprises about 3.2 kb, about, about 3.3 kb, about 3.4 kb, about 3.5 kb, about 3.6 kb, about 3.7 kb, or less. In some embodiments, the expression cassette comprises about 1.9 kb, about 2.1 kb, about 2.2 kb, about 2.3 kb, about 2.4 kb, about 2.5 kb, about 2.6 kb, about 2.7 kb, about 2.8 kb, about 2.9 kb, about 3.0 kb, about 3.1 kb, about 3.2 kb, or more.

In some embodiments, the expression cassette comprises a polynucleotide sequence that shares at least 75%, 80%, 90%, 95%, 96%, 97%, 98%, 99%, or 100% identity to any one of SEQ ID NOs: 20-24 or SEQ ID NOs: 45-75. In some embodiments, wherein the expression cassette comprises any one of SEQ ID NOs: 20-24 or SEQ ID NOs: 45-75. In some embodiments, the expression cassette comprises a polynucleotide sequence that shares at least 75%, 80%, 90%, 95%, 96%, 97%, 98%, or 99% identity to SEQ ID NO: 61. In some embodiments, the expression cassette comprises SEQ ID NO: 61. In some embodiments, the expression cassette comprises a polynucleotide sequence that shares at least 75%, 80%, 90%, 95%, 96%, 97%, 98%, or 99% identity to SEQ ID NO: 62. In some embodiments, the expression cassette comprises SEQ ID NO: 62. In some embodiments, the expression cassette comprises a polynucleotide sequence that shares at least 75%, 80%, 90%, 95%, 96%, 97%, 98%, or 99% identity to SEQ ID NO: 63. In some embodiments, the expression cassette comprises SEQ ID NO: 63.

In some embodiments, the capsid protein shares at least 98%, at least 99%, or 100% identity to an AAV9 capsid protein (SEQ ID NO: 143). In some embodiments, the capsid protein shares at least 98%, at least 99%, or 100% identity to an AAV5 capsid protein (SEQ ID NO: 144). In some embodiments, the capsid protein is a chimeric capsid protein. In some embodiments, the capsid protein is an AAV5/AAV9 chimeric capsid protein. In some embodiments, the capsid protein is selected from any one of SEQ ID NOs: 145-200.

In one aspect, the disclosure provides an expression cassette comprising polynucleotide sequence encoding a dwarf open reading frame (DWORF) polypeptide operatively linked to a promoter. In some embodiments, the DWORF polypeptide shares at least 75%, 80%, 90%, 95%, 96%, 97%, 98%, or 99% identity to SEQ ID NOs: 1, 3, 4, 7, 9, 23, and 43. In some embodiments, the DWORF polypeptide is selected from SEQ ID NOs: 1, 3, 4, 7, 9, 23, and 43.

In some embodiments, the promoter is a chicken cTnT promoter. In some embodiments, the chicken cTnT promoter shares at least 90%, 95%, 96%, 97%, 98%, or 99% identity to SEQ ID NO: 11. In some embodiments, the chicken cTnT promoter comprises SEQ ID NO: 11. In some embodiments, the promoter is a human cTnT promoter. In some embodiments, the human cTnT promoter shares at least 90%, 95%, 96%, 97%, 98%, or 99% identity to SEQ ID NO: 12 or SEQ ID NO: 13. In some embodiments, the human cTnT promoter comprises SEQ ID NO: 12 or SEQ ID NO: 13.

In some embodiments, the expression cassette further comprises one or more enhancers. In some embodiments, the enhancer the one or more enhancers are selected from a ACTC1 cardiac enhancer and a αMHC enhancer. In some embodiments, the ACTC1 cardiac enhancer shares at least 90%, 95%, 96%, 97%, 98%, or 99% identity to SEQ ID NO: 78. In some embodiments, the ACTC1 cardiac enhancer comprises SEQ ID NO: 78. In some embodiments, the αMHC enhancer shares at least 90%, 95%, 96%, 97%, 98%, or 99% identity to SEQ ID NO: 79. In some embodiments, the αMHC enhancer comprises SEQ ID NO: 79.

In some embodiments, the expression cassette further comprises an intron. In some embodiments, the intron is selected from a CMV intron and a chimeric intron. In some embodiments, the CMV intron shares at least 90%, 95%, 96%, 97%, 98%, or 99% identity to SEQ ID NO: 80. In some embodiments, the CMV intron comprises SEQ ID NO: 80. In some embodiments, the chimeric intron shares at least 90%, 95%, 96%, 97%, 98%, or 99% identity to SEQ ID NO: 81. In some embodiments, the chimeric intron comprises SEQ ID NO: 81.

In some embodiments, the expression cassette further comprises a WPRE sequence. In some embodiments, the WPRE sequence shares at least 90%, 95%, 96%, 97%, 98%, or 99% identity to SEQ ID NO: 26. In some embodiments, the WPRE sequence comprises SEQ ID NO: 26.

In some embodiments, the expression cassette further comprises a polyadenylation sequence. In some embodiments, the polyadenylation sequence is selected from a BGH polyadenylation sequence and a SV40 polyadenylation sequence. In some embodiments, the BGH polyadenylation sequence shares at least 90%, 95%, 96%, 97%, 98%, or 99% identity to SEQ ID NO: 27. In some embodiments, the BGH polyadenylation sequence comprises SEQ ID NO: 27. In some embodiments, the SV40 polyadenylation sequence shares at least 90%, 95%, 96%, 97%, 98%, or 99% identity to SEQ ID NO: 28. In some embodiments, the SV40 polyadenylation sequence comprises SEQ ID NO: 28.

In some embodiments, the expression cassette is flanked by ITRs. In some embodiments, the ITRs share at least 90%, 95%, 96%, 97%, 98%, or 99% identity to one or more of SEQ ID NO: 14 and SEQ ID NO: 15. In some embodiments, the ITRs comprise one or more of SEQ ID NO: 14 and SEQ ID NO: 15.

In some embodiments, the expression cassette comprises a single promoter. In some embodiments, the expression cassette comprises two promoters. In some embodiments, the expression cassette comprises a single copy a sequence encoding the DWORF polypeptide. In some embodiments, the expression cassette comprises two copies of a sequence encoding the DWORF polypeptide. In some embodiments, the expression cassette comprises one, two, three, or four enhancers. In some embodiments, the expression cassette comprises one or two introns. In some embodiments, the expression cassette comprises one or two WPRE sequences. In some embodiments, the expression cassette comprises one or two polyadenylation sequences.

In some embodiments, the expression cassette comprises about 3.2 kb, about, about 3.3 kb, about 3.4 kb, about 3.5 kb, about 3.6 kb, about 3.7 kb, or less. In some embodiments, the expression cassette comprises about 1.9 kb, about 2.1 kb, about 2.2 kb, about 2.3 kb, about 2.4 kb, about 2.5 kb, about 2.6 kb, about 2.7 kb, about 2.8 kb, about 2.9 kb, about 3.0 kb, about 3.1 kb, about 3.2 kb, or more.

In some embodiments, the expression cassette comprises a polynucleotide sequence that shares at least 75%, 80%, 90%, 95%, 96%, 97%, 98%, 99%, or 100% identity to any one of SEQ ID NOs: 20-24 or SEQ ID NOs: 45-75. In some embodiments, the expression cassette comprises any one of SEQ ID NOs: 20-24 or SEQ ID NOs: 45-75. In some embodiments, the expression cassette comprises a polynucleotide sequence that shares at least 75%, 80%, 90%, 95%, 96%, 97%, 98%, or 99% identity to SEQ ID NO: 61. In some embodiments, the expression cassette comprises SEQ ID NO: 61. In some embodiments, the expression cassette comprises a polynucleotide sequence that shares at least 75%, 80%, 90%, 95%, 96%, 97%, 98%, or 99% identity to SEQ ID NO: 62. In some embodiments, the expression cassette comprises SEQ ID NO: 62. In some embodiments, the expression cassette comprises a polynucleotide sequence that shares at least 75%, 80%, 90%, 95%, 96%, 97%, 98%, or 99% identity to SEQ ID NO: 63. In some embodiments, the expression cassette comprises SEQ ID NO: 63.

In some embodiments, the expression cassette comprises a 5' inverted terminal repeat and a 3' inverted terminal repeat.

In one aspect, the disclosure provides a pharmaceutical composition comprising the rAAV virion disclosed herein and an pharmaceutically acceptable diluent. In another aspect, the disclosure provides a kit comprising a pharmaceutical composition provided herein.

In one aspect, the disclosure provides a method of increasing DWORF expression in a cell comprising contacting a cell with the rAAV virion disclosed herein or the pharmaceutical composition disclosed herein. In some embodiments, the cell is a cardiac cell. In some embodiments, the cardiac cell is a cardiomyocyte. In some embodiments, DWORF expression is increased between about 1.5-fold and 150-fold. In some embodiments, the contacting is in vitro. In some embodiments, the contacting is in vivo.

In one aspect, the disclosure provides a method of increasing DWORF expression in a tissue comprising contacting the tissue with the rAAV virion disclosed herein or the pharmaceutical composition disclosed herein. In some embodiments, the tissue is cardiac tissue. In some embodiments, DWORF expression is increased between about 1.5-fold and 150-fold. In some embodiments, the contacting is in vitro. In some embodiments, the contacting is in vivo.

In one aspect, the disclosure provides a method of increasing DWORF expression in an organ comprising contacting the organ with the rAAV virion disclosed herein or the pharmaceutical composition disclosed herein. In some embodiments, DWORF expression is increased between about 1.5-fold and 150-fold.

In some embodiments, the organ is a heart. In some embodiments, the heart is diseased or is at risk of heart disease. In some embodiments, the heart has reduced or borderline ejection fraction. In some embodiments, the heart has a normal ejection fraction.

In some embodiments, the heart comprises a genetic mutation associated with a heart disease. In some embodiments, the genetic mutation is a PLN mutation. In some embodiments, the heart has low or undetectable DWORF expression compared to a healthy heart. In some embodiments, the contacting is in vitro. In some embodiments, the contacting is in vivo.

In one aspect, the disclosure provides a method of increasing DWORF expression in a subject comprising administering to the subject the rAAV virion disclosed herein or the pharmaceutical composition disclosed herein. In some embodiments, the subject is an animal. In some embodiments, the subject is a human. In some embodiments, DWORF expression is increased in the heart of the subject. In some embodiments, the subject has a heart disease or is at risk of a heart disease. In some embodiments, the subject has borderline or reduced ejection fraction. In some embodiments, the subject has normal ejection fraction. In some embodiments, the subject has a genetic mutation associated with a heart disease. In some embodiments, the genetic mutation is a PLN mutation. In some embodiments, the subject has a low or undetectable level of DWORF expression compared to a healthy subject.

In one aspect, the disclosure provides a method of treating a heart disease or disorder in a subject in need thereof comprising administering to the subject the rAAV virion disclosed herein or the pharmaceutical composition disclosed herein.

In some embodiments, the subject has a heart disease or disorder. In some embodiments, the subject is a risk of developing a heart disease or disorder. In some embodiments, the heart disease or disorder is cardiomyopathy. In some embodiments, the heart disease or disorder is dilated cardiomyopathy. In some embodiments, the heart disease or disorder is myocardial infarction. In some embodiments, the heart disease or disorder is chronic myocardial infarction. In some embodiments, the heart disease or disorder is acute myocardial infarction.

In some embodiments, the subject has an inherited risk allele for a heart disease or disorder. In some embodiments, the inherited risk allele comprises a mutation to the PLN gene. In some embodiments, the mutation to the PLN gene is a PLN promoter mutation. In some embodiments, the mutation to the PLN gene is a PLNL39stop mutation. In some embodiments, the mutation to the PLN gene is a RC9 mutation. In some embodiments, the mutation to the PLN gene is a R9L mutation. In some embodiments, the mutation to the PLN gene is a PLN gene duplication. In some embodiments, the mutation to the PLN gene is a R14del mutation.

In some embodiments, the heart disease or disorder is with reduced ejection fraction (HFrEF). In some embodiments, the heart disease of disorder is with preserved ejection fraction (HFpEF).

In some embodiments, the method causes expression of the DWORF polypeptide in the heart of the subject. In some embodiments, the method causes expression of the DWORF polypeptide in cardiomyocytes.

In some embodiments, the method causes no detectable expression of the DWORF polypeptide in the muscles of the subject except the heart. In some embodiments, the method causes no detectable expression of the DWORF polypeptide in the liver of the subject. In some embodiments, the method causes no detectable expression of the DWORF polypeptide in cardiac fibroblasts.

In some embodiments, the method improves one or more measures of cardiac function, optionally fraction shortening and/or left ventricular internal dimension (LVID). In some embodiments, the improvement in cardiac function is observed at weeks 2 through week 16. In some embodiments, the method reduces cardiac remodeling. In some embodiments, the method counteracts a decrease in DWORF expression in subjects suffering from or at risk of a heart disease.

In some embodiments, the rAAV virion is administered by systemic administration. In some embodiments, the systemic administration is selected from intravenous or intracoronary injection.

In some embodiments, the rAAV is administered as a unit dose. In some embodiments, the unit dose comprises about $3 \times 10^{14}$ vg/kg or less, about $2 \times 10^{14}$ vg/kg or less, about $1 \times 10^{14}$ vg/kg or less, about $9 \times 10^{13}$ vg/kg or less, about $8 \times 10^{13}$ vg/kg or less, about $7 \times 10^{13}$ vg/kg or less, about $6 \times 10^{13}$ vg/kg or less, about $5 \times 10^{13}$ vg/kg or less, about $4 \times 10^{13}$ vg/kg or less, about $3 \times 10^{13}$ vg/kg or less, about $2 \times 10^{13}$ vg/kg or less, or about $1 \times 10^{13}$ vg/kg or less.

In one aspect, the disclosure provides a method of alleviating one or more symptoms of a heart disease or disorder in a subject in need thereof comprising administering the rAAV virion disclosed herein or the pharmaceutical composition disclosed herein.

In one aspect, the disclosure provides a method of improving one or more symptoms of a heart disease or disorder in a subject in need thereof comprising administering the rAAV virion disclosed herein or the pharmaceutical composition disclosed herein.

In one aspect, the disclosure provides a method of preventing one or more symptoms of a heart disease or disorder in a subject in need thereof comprising administering the rAAV virion disclosed herein or the pharmaceutical composition disclosed herein.

In one aspect, the disclosure provides an expression cassette comprising a polynucleotide comprising a 5' to 3' arrangement of elements, wherein the elements comprise: i) one or more promoters; ii) optionally one or more enhancers; iii) optionally one or more introns; iv) one or more transgenes; v) optionally one or more WPRE sequences; and vi) optionally one or more polyadenylation sequences, p(A). In some embodiments, the 5' to 3' arrangement of elements is selected from: i) 5'-promoter-intron-transgene-WPRE-p(A)-3'; ii) 5'-enhancer-promoter-transgene-WPRE-p(A)-3'; iii) 5'-enhancer-enhancer-promoter-transgene-WPRE-p(A)-3'; iv) 5'-enhancer-enhancer-promoter-intron-transgene-WPRE-p(A)-3'; v) 5'-enhancer-enhancer-promoter-intron-transgene-WPRE-p(A)-3'; vi) 5'-enhancer-promoter-intron-transgene-WPRE-p(A)-p(A)-transgene-intron-promoter-enhancer-3'; vii) 5'-enhancer-promoter-intron-transgene-WPRE-p(A)-enhancer-promoter-intron-transgene-p(A)-3'; viii) 5'-p(A)-WPRE-transgene-intron-promoter-enhancer-promoter-intron-transgene-p(A)-3'; ix) 5'-promoter-intron-transgene-WPRE-p(A)-p(A)-transgene-intron-promoter-3'; x) 5'-promoter-intron-transgene-WPRE-p(A)-promoter-intron-transgene-p(A)-3'; and xi) 5'-p(A)-WPRE-transgene-intron-promoter-promoter-intron-transgene-p(A)-3'. In some embodiments, the transgene has an increased expression level compared to a second expression cassette comprising a polynucleotide having an arrangement of elements from 5' to 3' comprising: 5'-promoter-transgene-WPRE-p(A)-3'. In some embodiments, the increased expression level is between about 1.5-fold and about 150-fold compared to the second expression cassette.

In one aspect, the disclosure provides a recombinant adeno-associated virus (rAAV) virion, comprising a capsid protein and a viral genome comprising an expression cassette of any one of disclosed herein, the expression cassette flanked by inverted terminal repeats. In some embodiments, the expression cassette comprises a transgene, wherein the transgene encodes a polypeptide use for treating or a preventing a heart disease, or alleviating symptoms associated with a heart disease. In some embodiments, the capsid protein is selected from any one of SEQ ID NOs: 145-200.

BRIEF DESCRIPTIONS OF DRAWINGS

Figure 11A:
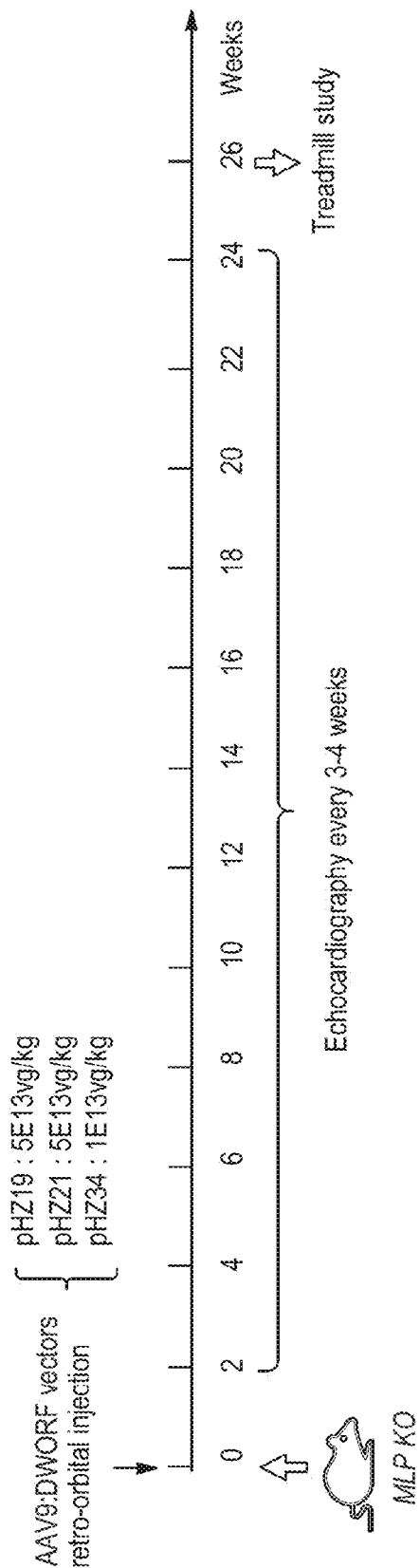
FIG. 11A is a schematic diagram of DWORF gene therapy efficacy study in the MLP-KO DCM mouse model.
Figure 11B:
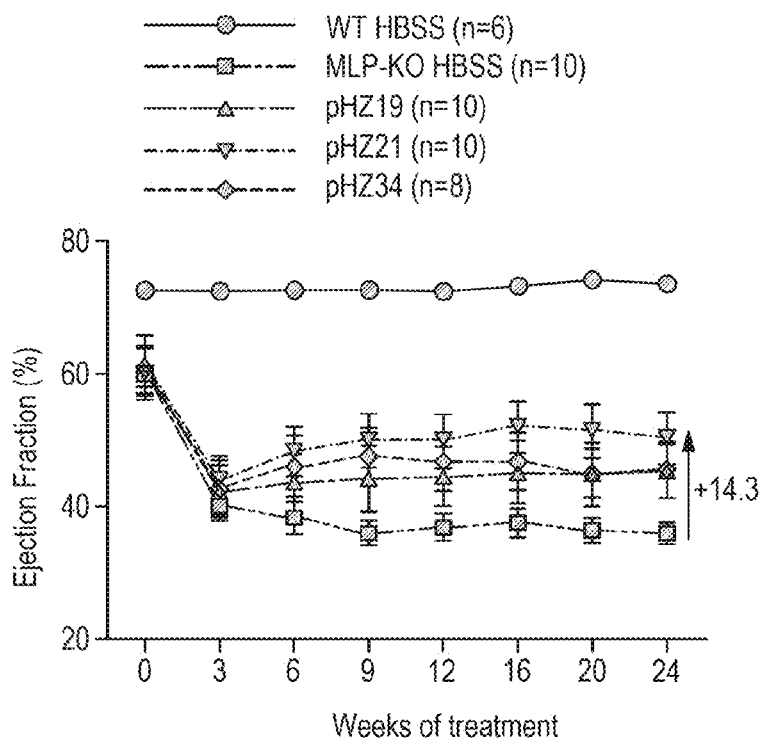
Figure 11C:
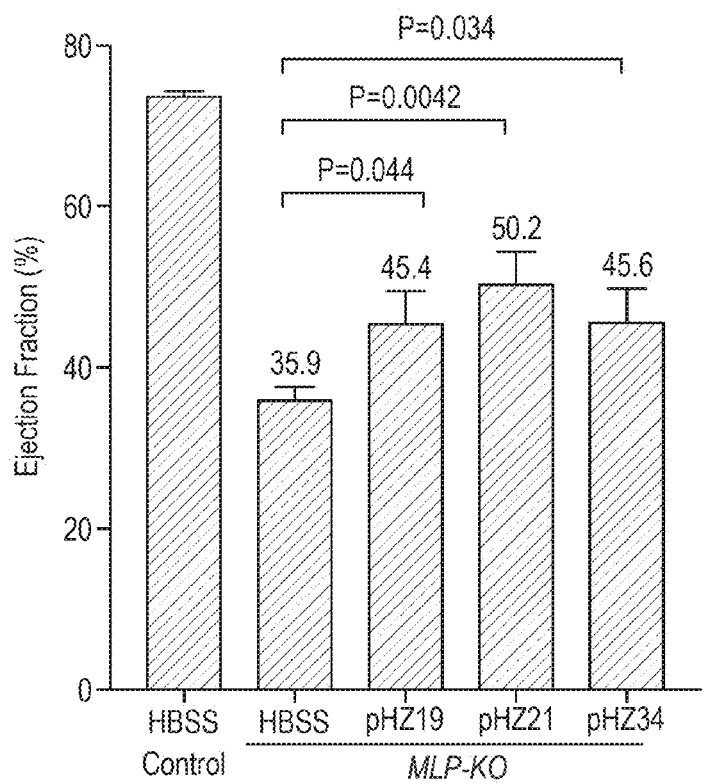

FIGS. 11B and 11C demonstrate that AAV9:DWORF constructs containing novel promoters improve the ejection fraction relative to a saline control in the MLP-KO DCM mouse model.

Figure 11D:
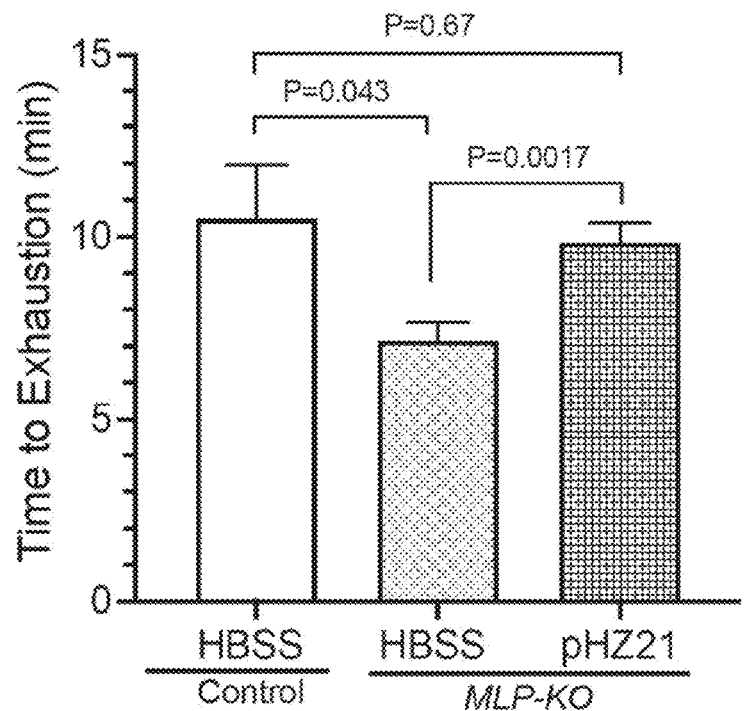
Figure 11E:
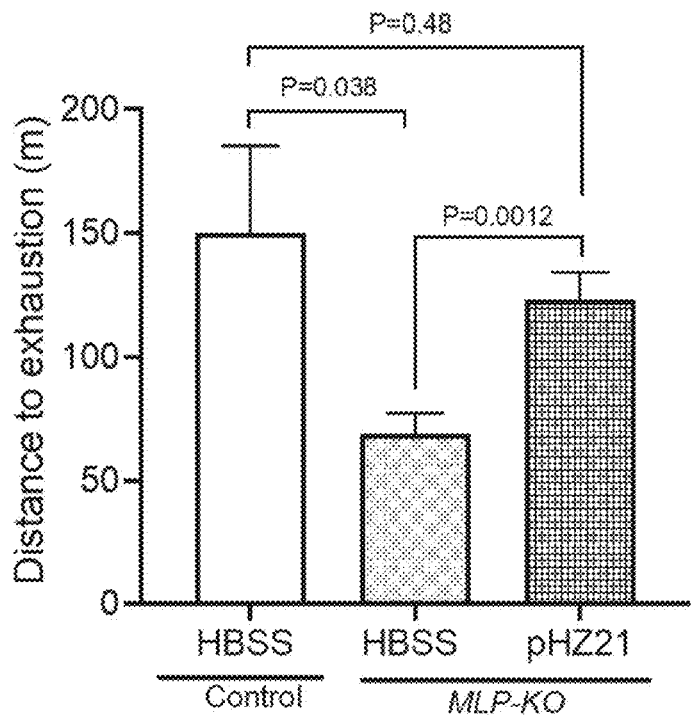

FIGS. 11D and 11E demonstrate that AAV9:DWORF constructs improved exercise capacity, including running distance and time to exhaustion, in the MLP-KO DCM mouse model 26 weeks post-treatment.

Figure 12A:
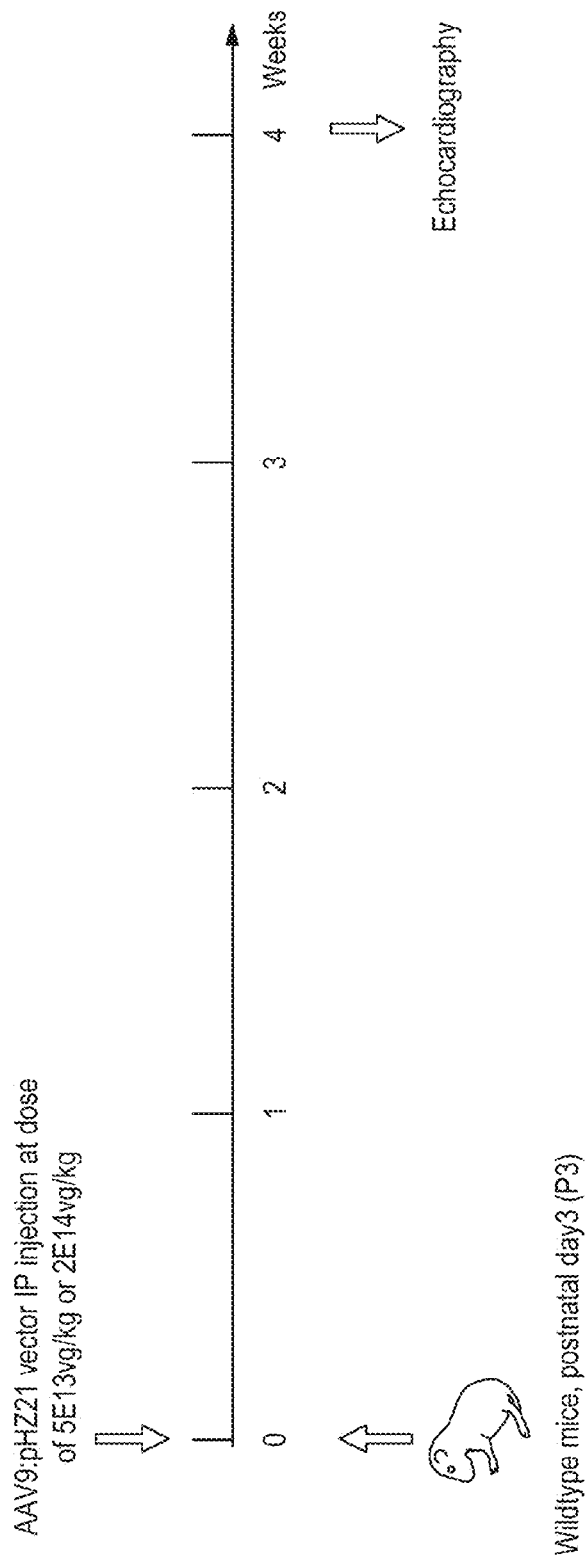

FIG. 12A is a schematic diagram of detailing DWORF gene therapy tolerability study in naïve mice.

Figure 12B:
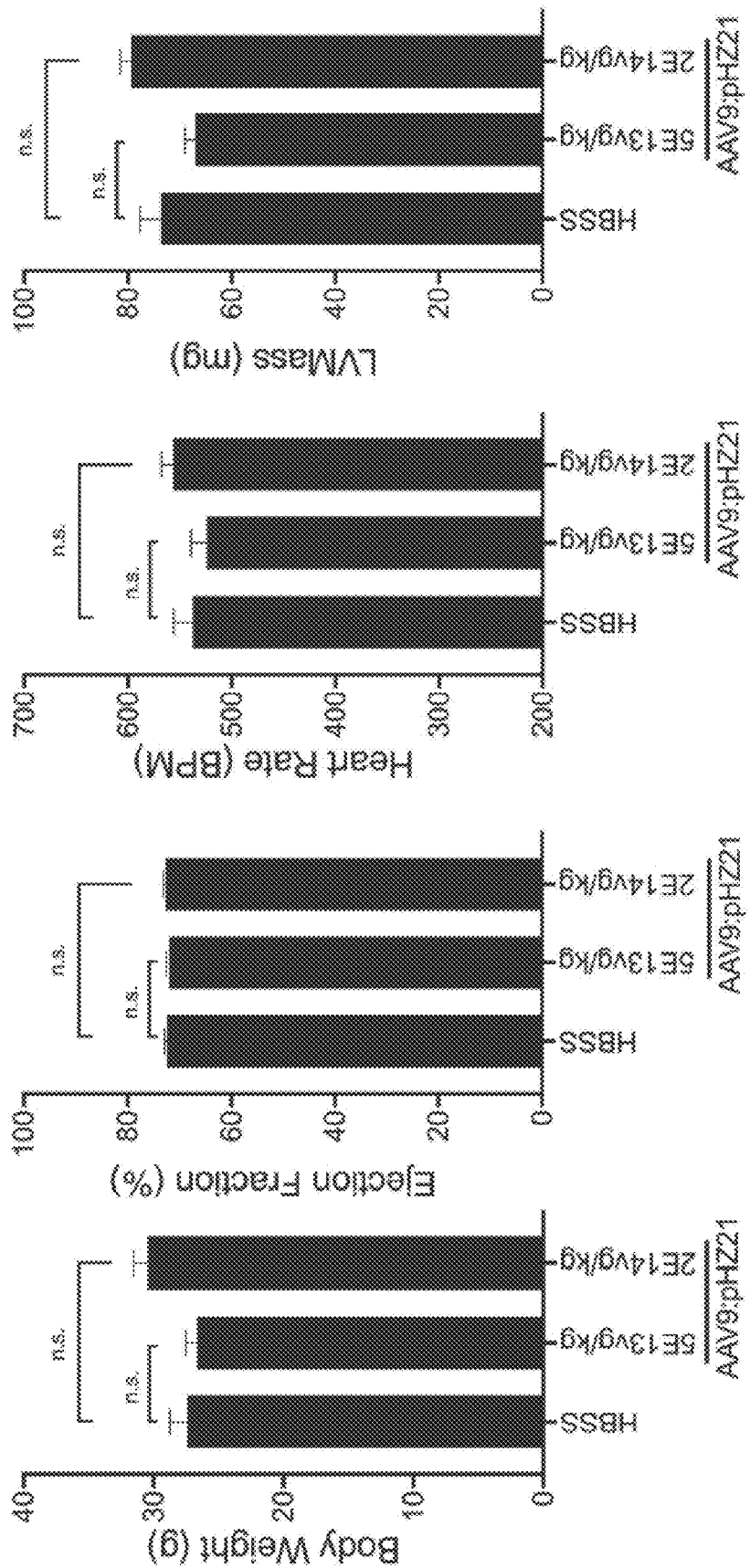

FIG. 12B demonstrates that AAV9:pHZ21 is well tolerated in naïve mice up to $2\times10^{14}$ vg/kg dose with no difference in body weight, ejection fraction, heart rate, and left ventricular mass (LV mass).

DETAILED DESCRIPTION

In some aspects, described herein are optimized gene therapy expression cassettes, and their use in the treatment of heart disease. In some aspects, described herein are gene therapy expression cassettes that are able to mediate high expression of transgenes. In some embodiments, described herein are cardiac-specific gene therapy expression cassettes that are able to mediate significantly higher expression of a transgene than can be achieved using a cTnT promoter alone (e.g., a chicken cTnT promoter alone and/or a human cTnT promoter alone) or using the expression cassette depicted in FIG. 7A. In some aspects, described herein are gene therapy expression cassettes that allow to lower the viral load while achieving desired expression of a transgene. In some aspects, described herein are gene therapy expression cassettes that allow to achieve durable expression of a transgene. In some embodiments, described herein are gene therapy expression cassettes that allow to achieve expression of a transgene for at least, or more than, 12 weeks, 16 weeks, 18 weeks, 20 weeks, 22 weeks, 24 weeks, or 26 weeks, after administration of a gene therapy expression cassette comprising the transgene to a subject. In some embodiments, described herein are gene therapy expression cassettes that allow to achieve expression of a transgene for at least, or more than, 24 weeks or at least 6 months after administration of a gene therapy expression cassette comprising the transgene to a subject. In some aspects, administration of a gene therapy expression cassette described herein to a subject results in one or more improvements in cardiac function (e.g., an improvement in ejection fraction or an improvement in exercise capacity). In some embodiments, administration of a gene therapy expression cassette described herein to a subject results in a durable improvement in cardiac function (e.g., a durable improvement in ejection fraction or a durable improvement in exercise capacity). In some embodiments, administration of a gene therapy expression cassette described herein to a subject results in one or more improvements in cardiac function for at least, or more than, 12 weeks, 16 weeks, 18 weeks, 20 weeks, 22 weeks, 24 weeks, or 26 weeks after the administration. In some embodiments, administration of a gene therapy expression cassette described herein to a subject results in one or more improvements in cardiac function for at least, or more than, 24 weeks or at least 6 months after the administration. In some embodiments, a gene therapy expression cassette described herein allows for cardiac cell-specific expression of a transgene (e.g., cardiomyocyte-specific expression of a transgene).

In some aspects, the present disclosure provides a viral or a non-viral vector comprising an expression cassette encoding a gene product, and methods of use thereof. In some embodiments, the expression cassettes described herein comprise a polynucleotide encoding a gene product operably linked to a cardiac cell-specific promoter and/or enhancer (such as any combination of cardiac cell-specific promoters and enhancers described herein, in any orientation as described herein). In some embodiments, the expression cassettes described herein comprise two copies of a polynucleotide encoding a gene product and a cardiac cell-specific promoter (such as any combination of such sequences, in any orientation as described herein). In some embodiments, the expression cassettes described herein comprise a polynucleotide encoding a gene product operably linked to a cardiac cell-specific promoter and/or enhancer (such as one promoter, or any combination of cardiac cell-specific promoters and enhancers described herein, in any orientation as described herein), a WPRE sequence, and/or one or two copies of a polyA sequence (such as any combination of such sequences, in any orientation as described herein). In some embodiments, the expression cassettes described herein comprise a polynucleotide encoding a gene product operably linked to a cardiac cell-specific promoter and/or an intron. In some embodiments, the expression cassettes described herein comprise one or two copies of a polynucleotide encoding a gene product, one or two copies of a cardiac cell-specific promoter, one, two or more copies of a cardiac-specific enhancer, and/or one or more intron sequences (such as any combination of such sequences, in any orientation as described herein). In some embodiments, the expression cassettes described herein comprise one or two copies of a polynucleotide encoding a gene product, one or two copies of a cardiac cell-specific promoter, one, two or more copies of a cardiac-specific enhancer, one or more intron sequences (such as any combination of such sequences, in any orientation as described herein). a WPRE sequence, and one or two copies of a polyA sequence (such as any combination of such sequences, in any orientation as described herein). In some embodiments, the vectors comprising the expression cassettes described herein may, for example, transduce cardiac cells. In some embodiments, targeted cardiac cells express the gene product, e.g., provide a high level of expression of the gene product. In some aspects, the present disclosure provides pharmaceutical compositions comprising the vectors described herein. In some aspects, the disclosure provides methods for treating a subject diagnosed with or at risk of a heart disease (e.g., cardiomyopathy) using the vectors and pharmaceutical compositions of the disclosure.

In some aspects, the present disclosure provides recombinant adeno-associated virus (rAAV) virions as a vector for the expression cassette described herein.

Abnormal calcium handling is a universal characteristic of cardiomyopathy, and reduced sarco/endoplasmic reticulum calcium ATPase (SERCA) activity plays a central role in both the initiation and progression of the disease. SERCA is a calcium pump that promotes the uptake, maintenance, and cycling of $Ca^{2+}$ ions in cardiac cells, such as cardiomyocytes. SERCA activity is regulated by an inhibitory peptide, phospholamban. There is significant interest in increasing the activity of SERCA by increasing the abundance of a polypeptide called Dwarf Open Reading Frame (DWORF) that enhances SERCA activity through its direct displacement of the SERCA inhibitory peptide phospholamban. Contacting SERCA with DWORF is a strategy for increasing SERCA activity in a cell.

In some aspects, the present disclosure provides recombinant adeno-associated virus (rAAV) virions comprising a polynucleotide encoding a DWORF polypeptide, or a functional variant thereof, and methods of use thereof. In some embodiments, the rAAV virions described herein comprise a polynucleotide encoding a DWORF polypeptide, or a functional variant thereof, operably linked to a cardiac cell-specific promoter and/or enhancer (such as any combination of cardiac cell-specific promoters and enhancers described herein, in any orientation as described herein). In some embodiments, the rAAV virions described herein comprise one or two copies of a polynucleotide encoding a DWORF polypeptide, or a functional variant thereof, a WPRE sequence, and one or two copies of a polyA sequence (such as any combination of such sequences, in any orientation as described herein). In some embodiments, the rAAV virions described herein comprise a polynucleotide encoding a DWORF polypeptide operably linked to a cardiac cell-specific promoter and/or an intron. In some embodiments, the rAAV virions described herein comprise one or two copies of a polynucleotide encoding DWORF, one or two copies of a cardiac cell-specific promoter, one, two or more copies of a cardiac-specific enhancer, and/or one or more intron sequences (such as any combination of such sequences, in any orientation as described herein). In some embodiments, the rAAV virions described herein comprise one or two copies of a polynucleotide encoding DWORF, one or two copies of a cardiac cell-specific promoter, one, two or more copies of a cardiac-specific enhancer, one or more intron sequences (such as any combination of such sequences, in any orientation as described herein). a WPRE sequence, and one or two copies of a polyA sequence (such as any combination of such sequences, in any orientation as described herein). In some embodiments, the rAAV virions described herein may, for example, transduce cardiac cells with a polynucleotide with a sequence encoding DWORF polypeptide operatively linked to a cardiac cell-specific promoter region into the host cell genome. In some embodiments, targeted cardiac cells express the DWORF polypeptide and may have increased SERCA activity. Also provided in the disclosure are pharmaceutical compositions comprising the rAAV virions described herein. In an aspect, the disclosure provides methods for treating a subject diagnosed with or at risk of cardiomyopathy using the rAAV virions and pharmaceutical compositions of the disclosure.

Terminology

Unless the context indicates otherwise, the features of the invention can be used in any combination. Any feature or combination of features set forth can be excluded or omitted. Certain features of the invention, which are described in separate embodiments may also be provided in combination in a single embodiment. Features of the invention, which are described in a single embodiment may also be provided separately or in any suitable sub-combination.

Generally, technical and scientific terms used herein have the same meaning as commonly understood by one of ordinary skill in the art to which this invention belongs. The detailed description is divided into sections only for the reader's convenience and disclosure found in any section may be combined with that in another section.

The practice of the present disclosure will employ, unless otherwise indicated, conventional techniques of tissue culture, immunology, molecular biology, cell biology and recombinant DNA, which are within the skill of the art. See, e.g., Sambrook and Russell eds. (2001) Molecular Cloning: A Laboratory Manual, $3^{rd}$ edition; Ausubel et al. eds. (2007) Current Protocols in Molecular Biology; Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (2002) Cold Spring Harbor Laboratory Press; Sohail (2004) Gene Silencing by RNA Interference: Technology and Application (CRC Press); and Sell (2013) Stem Cells Handbook.

The conjunction "and/or" means both "and" and "or," and lists joined by "and/or" encompasses all possible combinations of one or more of the listed items.

As used herein, the term "about," when used to modify a numeric value, indicates that deviations of up to 10% above and below the numeric value remain within the intended meaning of the recited value.

"AAV" is an abbreviation for adeno-associated virus. The term covers all subtypes of AAV, except where a subtype is indicated, and to both naturally occurring and recombinant forms. The abbreviation "rAAV" refers to recombinant adeno-associated virus. "AAV" includes AAV or any subtype. "AAV5" refers to AAV subtype 5. "AAV9" refers to AAV subtype 9. The genomic sequences of various serotypes of AAV, as well as the sequences of the native inverted terminal repeats (ITRs), Rep proteins, and capsid subunits may be found in the literature or in public databases such as GenBank. See, e.g., GenBank Accession Numbers NC_002077 (AAV1), AF063497 (AAV1), NC_001401 (AAV2), AF043303 (AAV2), NC_001729 (AAV3), NC_001829 (AAV4), U89790 (AAV4), NC_006152 (AAV5), AF513851 (AAV7), AF513852 (AAV8), NC_006261 (AAV8), and AY530579 (AAV9). Publications describing AAV include Srivistava et al. (1983) J. Virol. 45:555; Chiorini et al. (1998) J. Virol. 71:6823; Chiorini et al. (1999) J. Virol. 73:1309; Bantel-Schaal et al. (1999) J. Virol. 73:939; Xiao et al. (1999) J. Virol. 73:3994; Muramatsu et al. (1996) Virol. 221:208; Shade et al. (1986) J Virol. 58:921; Gao et al. (2002) Proc. Nat. Acad. Sci. USA 99: 11854; Moris et al. (2004) Virology 33:375-383; Int'l Pat. Publ Nos. WO2018/222503A1, WO2012/145601A2, WO2000/028061A2, WO1999/61601A2, and WO1998/11244A2; U.S. patent application Ser. Nos. 15/782,980 and 15/433,322; and U.S. Pat. Nos. 10,036,016, 9,790,472, 9,737,618, 9,434,928, 9,233,131, 8,906,675, 7,790,449, 7,906,111, 7,718,424, 7,259,151, 7,198,951, 7,105,345, 6,962,815, 6,984,517, and 6,156,303.

An "rAAV virion" refers to a viral particle including at least one viral capsid protein (e.g. VP1) and an encapsidated rAAV vector (or fragment thereof).

An "infectious" virion or viral particle is one that comprises a competently assembled viral capsid and is capable of delivering a polynucleotide component into a cell for which the virion is tropic.

"Packaging" refers to a series of intracellular events that result in the assembly of an rAAV virion including encapsidation of the rAAV vector. AAV "rep" and "cap" genes refer to polynucleotide sequences encoding replication and encapsidation proteins of adeno-associated virus. AAV rep and cap are referred to herein as AAV "packaging genes." Packaging requires either a helper virus itself or, more commonly in recombinant systems, helper virus function supplied by a helper-free system (i.e. one or more helper plasmids). A "helper virus" for AAV refers to a virus that allows AAV (e.g. wild-type AAV) to be replicated and packaged by a mammalian cell. The helper viruses may be an adenovirus, herpesvirus or poxvirus, such as vaccinia.

The term "inverted terminal repeats" or "ITRs" as used herein refers to AAV viral cis-elements named so because of their symmetry. These elements are essential for efficient multiplication of an AAV genome. In some embodiments, the minimal elements indispensable for ITR function are a Rep-binding site and a terminal resolution site plus a variable palindromic sequence allowing for hairpin formation.

The terms "parental capsid" or "parental sequence" refer to a reference sequence from which a particle capsid or sequence is derived. Unless otherwise specified, parental sequence refers to the sequence of the wild-type capsid protein of the same serotype as the engineered capsid protein.

"Recombinant," as applied to a polynucleotide means that the polynucleotide is distinct from a polynucleotide found in nature (e.g., the polynucleotide is the product of various combinations of cloning, restriction or ligation steps, and other procedures, or the polynucleotide is assembled from synthetic oligonucleotides. A "recombinant" protein is a protein produced from a recombinant polypeptide. A recombinant virion is a virion that comprises a recombinant polynucleotide and/or a recombinant protein, e.g. a recombinant capsid protein.

As used herein, the term "percent sequence identity," and the term "identity" when it is used to refer to % sequence identity, with respect to a reference nucleic acid or amino acid sequence is the percentage of nucleic acid bases or amino acid residues in a candidate sequence that are identical with the nucleic acid bases or amino acid residues in the reference sequence, respectively, after aligning the sequences and introducing gaps, if necessary, to achieve the maximum percent sequence identity. Methods of sequence alignment are well known in the art. Sequences can be aligned using various computer programs, such BLAST, available at ncbi.nlm.nih.gov. Alignments can be made using publicly available computer software such as BLASTp, BLASTn, BLAST-2, ALIGN or MegAlign Pro (DNASTAR) software. Other techniques for alignment are described in Methods in Enzymology, vol. 266: Computer Methods for Macromolecular Sequence Analysis (1996); and Meth. Mol. Biol. 70: 173-187 (1997); J. Mol. Biol. 48: 44. Skill artisans are capable of choosing an appropriate alignment method depending on various factors including sequence length, divergence, and the presence of absence of insertions or deletions with respect to the reference sequence.

The terms "operably linked" and "operatively linked" refer to a nucleic acid sequence placed into a functional relationship with another nucleic acid sequence. These terms, as used herein, have a meaning commonly known in the art. For example, a promoter is operably linked to a gene when that promoter is placed in a location that permits that promoter to initiate transcription of that gene. An enhancer is operably linked to a gene when that enhancer, when bound by an appropriate transcription factor, can regulate (e.g., enhance) expression of that gene.

"Treatment," "treating," and "treat" are defined as acting upon a disease, disorder, or condition with an agent to reduce or ameliorate harmful or any other undesired effects of the disease, disorder, or condition and/or its symptoms.

As used herein the term "effective amount" and the like in reference to an amount of a composition refers to an amount that is sufficient to induce a desired physiologic outcome (e.g., treatment of a disease). An effective amount can be administered in one or more administrations, applications or dosages. Such delivery is dependent on a number of variables including the time period which the individual dosage unit is to be used, the bioavailability of the composition, the route of administration, etc. It is understood, however, that specific amounts of the compositions (e.g., rAAV virions) for any particular subject depends upon a variety of factors including the activity of the specific agent employed, the age, body weight, general health, sex, and diet of the subject, the time of administration, the rate of excretion, the composition combination, severity of the particular disease being treated and form of administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "individual," "subject," and "patient" are used interchangeably herein, and refer to a mammal, including, but not limited to, human and non-human primates (e.g., simians); mammalian sport animals (e.g., horses); mammalian farm animals (e.g., sheep, goats, etc.); mammalian pets (e.g., dogs, cats, etc.); and rodents (e.g., mice, rats, etc.).

As used herein, the term "cardiomyopathy" refers to any disease or dysfunction that affects myocardium directly. The etiology of the disease or disorder may be, for example, inflammatory, metabolic, toxic, infiltrative, fibroplastic, hematological, genetic, or unknown in origin. Two fundamental forms are recognized (1) a primary type, consisting of heart muscle disease of unknown cause; and (2) a secondary type, consisting of myocardial disease of known cause or associated with a disease involving other organ systems. "Specific cardiomyopathy" refers to heart diseases associated with certain systemic or cardiac disorders; examples include hypertensive and metabolic cardiomyopathy. The cardiomyopathies include dilated cardiomyopathy (DCM), a disorder in which left and/or right ventricular systolic pump function is impaired, leading to progressive cardiac enlargement; hypertrophic cardiomyopathy, characterized by left ventricular hypertrophy without obvious causes such as hypertension or aortic stenosis; and restrictive cardiomyopathy, characterized by abnormal diastolic function and excessively rigid ventricular walls that impede ventricular filling. Cardiomyopathies also include left ventricular non-compaction, arrhythmogenic right ventricular cardiomyopathy, and arrhythmogenic right ventricular dysplasia.

"Heart failure" refers to the pathological state in which an abnormality of cardiac function is responsible for failure of the heart to pump blood at a rate commensurate with the requirements of the metabolizing tissues and/or allows the heart to do so only from an abnormally elevated diastolic volume. Heart failure includes systolic and diastolic failure. Patients with heart failure are classified into those with low cardiac output (typically secondary to ischemic heart disease, hypertension, dilated cardiomyopathy, and/or valvular or pericardial disease) and those with elevated cardiac output (typically due to hyperthyroidism, anemia, pregnancy, arteriovenous fistulas, beriberi, and Paget's disease). Heart failure includes heart failure with reduced ejection fraction (HFrEF) and heart failure with preserved ejection fraction (HFpEF).

The term "therapeutic gene" as used herein refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that partially or wholly correct a genetic deficiency in a cell or mammal.

As used herein the term "cardiac cell" refers to any cell present in the heart that provides a cardiac function, such as heart contraction or blood supply, or otherwise serves to maintain the structure of the heart. Cardiac cells as used herein encompass cells that exist in the epicardium, myocardium or endocardium of the heart. Cardiac cells also include, for example, cardiac muscle cells or cardiomyocytes, and cells of the cardiac vasculatures, such as cells of a coronary artery or vein. Other non-limiting examples of cardiac cells include epithelial cells, endothelial cells, fibroblasts, cardiac stem or progenitor cells, cardiac conducting cells and cardiac pacemaking cells that constitute the cardiac muscle, blood vessels and cardiac cell supporting structure. Cardiac cells may be derived from stem cells, including, for example, embryonic stem cells or induced pluripotent stem cells.

Expression Cassettes

Expression Cassette Overview

The vectors of the disclosure may comprise any expression cassette described herein. In some aspects, the rAAV virions of the disclosure comprise a viral genome comprising an expression cassette as shown in FIG. 1, FIGS. 7A-7C, or variations thereof. The expression cassette may comprise a polynucleotide encoding any gene product described herein, or functional variant thereof, optionally operatively linked to a promoter, optionally an intron, optionally a polyadenylation (poly(A)) signal, optionally a woodchuck hepatitis virus post-transcriptional element (WPRE), and optionally a transcription termination signal. The expression cassette may be flanked by inverted terminal repeats (ITRs). These components provide the function of expressing the transgene after a host cell is targeted by, e.g., the rAAV virion. The promoter sequence, when present, controls expression of the polynucleotide encoding a gene product.

The expression cassette may comprise a polynucleotide encoding a DWORF polypeptide, or functional variant thereof, optionally operably linked to a promoter, optionally an intron, optionally a polyadenylation (poly(A)) signal, optionally a woodchuck hepatitis virus post-transcriptional element (WPRE), and optionally a transcription termination signal. The promoter sequence, when present, controls expression of the polynucleotide encoding the DWORF polypeptide, or functional variant thereof. The promoter sequence can be a cardiac cell-specific promoter. The promoter sequence can be further operably linked to an enhancer, such as any cardiac cell-specific enhancer described herein.

In any constructs shown in FIG. 1 and FIGS. 7A-7C, DWORF nucleotide sequence can be replaced by a nucleotide sequence encoding another gene product or polypeptide, such as any gene product or polypeptide described herein (e.g., see the description of transgenes and gene products encoded by such transgenes below). Accordingly, in some embodiments, provided herein is any expression cassette shown in FIG. 1 and FIGS. 7A-7C wherein the DWORF nucleotide sequence is replaced by a nucleotide sequence encoding another gene product or polypeptide.

Also, in any expression cassettes shown in Table 1, DWORF nucleotide sequence can be replaced by a nucleotide sequence encoding another gene product or polypeptide, such as any gene product or polypeptide described herein (e.g., see the description of transgenes and gene products encoded by such transgenes below). Further, in any expression cassette shown in Table 1, the ITR sequences can be omitted. Accordingly, in some embodiments, provided herein is any expression cassette shown in Table 1 wherein the DWORF nucleotide sequence is replaced by a nucleotide sequence encoding another gene product or polypeptide, and/or wherein the specified ITR sequence is not present.

Transgenes

In some embodiments, the expression cassette of the disclosure comprises a transgene. Transgenes can include nucleotide sequences encoding any polypeptide for use in treating or preventing a heart disease or disorder, or alleviating symptoms therefrom. The promoters, enhancers and combinations thereof described herein are operably linked to a transgene encoding a product. A transgene can be a gene or nucleotide sequence that encodes a product, or functional fragment thereof. A product can be, for example, a polypeptide or a non-coding nucleotide. By non-coding nucleotide, it is meant that the sequence transcribed from the transgene or nucleotide sequence is not translated into a polypeptide. In some embodiments, the product encoded by the transgene or nucleotide operably linked to an enhancer described herein is a non-coding polynucleotide. A non-coding polynucleotide can be an RNA, such as for example a microRNA (miRNA or mIR), short hairpin RNA (shRNA), long non-coding RNA (lnRNA), and/or a short interfering RNA (siRNA). In some embodiments, the transgene encodes a product natively expressed by a cardiac cell, e.g., a cardiomyocyte. In some embodiments, the transgene encodes a product natively expressed in a cell type other than a cardiac cell. Without limitation, cell types other than cardiac fibroblasts can be from any multicellular organism, single-celled organism, or microorganism.

In some embodiments, the transgene encodes a polypeptide. In some embodiments, the transgene encodes a non-coding polynucleotide such as, for example, a microRNA (miRNA or mIR).

In some embodiments, the transgene comprises a sequence encoding a product selected from cadherins, connexins, Cx43, growth factors such as fibroblast growth factor (FGF)-2 and transforming growth factor-β, cytokines such as interleukin (IL)-1β and the IL-6 family, leukemia inhibitory factor, cardiotrophin-1, cardiogenic transcription factors, insulin-like growth factor, GATA4, MEF2C, TBX5, ESRRG, MESP1, MYOCD, ZFPM2, HAND2, miR-1, miR-133, Oct4, Sox2, Klf4, c-Myc, SRF, SMARCD3, Nkx2-5, Akt, PKB, Baf60c, BMP4, miR-208, and miR-499.

In some embodiments, the transgene encodes a functional cardiac protein. In some embodiments, the gene product is a genome-editing endonuclease (optionally with a guide RNA, single-guide RNA, and/or repair template) that replaces or repairs a non-functional cardiac protein into a functional cardiac protein. Functional cardiac proteins include, but are not limited to cardiac troponin T; a cardiac sarcomeric protein; β-myosin heavy chain; myosin ventricular essential light chain 1; myosin ventricular regulatory light chain 2; cardiac a-actin; a-tropomyosin; cardiac troponin I; cardiac myosin binding protein C; four-and-a-half LIM protein 1; titin; 5'-AMP-activated protein kinase subunit gamma-2; troponin I type 3, myosin light chain 2, actin alpha cardiac muscle 1; cardiac LIM protein; caveolin 3 (CAV3); galactosidase alpha (GLA); lysosomal-associated membrane protein 2 (LAMP2); mitochondrial transfer RNA glycine (MTTG); mitochondrial transfer RNA isoleucine (MTTI); mitochondrial transfer RNA lysine (MTTK); mitochondrial transfer RNA glutamine (MTTQ); myosin light chain 3 (MYL3); troponin C (TNNC1); transthyretin (TTR); sarcoendoplasmic reticulum calcium-ATPase 2a (SERCA2a); stromal-derived factor-1 (SDF-1); adenylate cyclase-6 (AC6); beta-ARKct (β-adrenergic receptor kinase C terminus); fibroblast growth factor (FGF); platelet-derived growth factor (PDGF); vascular endothelial growth factor (VEGF); hepatocyte growth factor; hypoxia inducible growth factor; thymosin beta 4 (TMSB4X); nitric oxide synthase-3 (NOS3); unocartin 3 (UCN3); melusin; apolipoprotein-E (ApoE); superoxide dismutase (SOD); and S100A1 (a small calcium binding protein; see, e.g., Ritterhoff and Most (2012) *Gene Ther.* 19:613; Kraus et al. (2009) *Mol. Cell. Cardiol.* 47:445).

In some embodiments, the transgene can treat or prevent coronary heart disease. In some embodiments, the transgene comprises a sequence encoding a product selected from vascular endothelial growth factor (VEGF), a VEGF isoform, VEGF-A, VEGF-B, VEGF-C, VEGF-D, VEGF-D$^{dNdC}$, VEGF-A$_{1164}$, VEGF-A$_{165}$, VEGF-A$_{121}$, VEGF-2, placenta growth factor (PIGF), fibroblast growth factor 4 (FGF-4), human growth factor (HGF), human granulocyte colony-stimulating factor (hGCSF), and hypoxia inducible factor 1α (HIF-1α).

In some embodiments, the transgene can treat or prevent heart failure. In some embodiments, the transgene can treat or prevent chronic heart failure. In some embodiments, the transgene comprises a sequence encoding a product selected from SERCA2a, stromal cell-derived factor-1 (SDF-1), adenylyl cyclase type 6, S100A1, miRNA-17-92, miR-302-367, anti-miR-29a, anti-miR-30a, antimiR-141, cyclin A2, cyclin-dependent kinase 2, Tbx20, miRNA-590, miRNA-199, anti-sense oligonucleotide against Lp(a), interfering RNA against PCSK9, anti-sense oligonucleotide against apolipoprotein C-III, lipoprotein lipase$^{S447X}$, anti-sense oligonucleotide against apolipoprotein B, anti-sense oligonucleotide against c-myc, and E2F oligonucleotide decoy.

In some embodiments, the transgene encodes a gene product whose expression complements a defect in a gene responsible for a genetic disorder. The disclosure polynucleotides encoding one or more of the following—e.g., for use, without limitation, in the disorder indicated in parentheses, or for other disorders caused by each: TAZ (Barth syndrome); FXN (Freidrich's Ataxia); CASQ2 (CPVT); FBN1 (Marfan); RAF1 and SOS1s (Noonan); SCN5A (Brugada); KCNQ1 and KCNH2s (Long QT Syndrome); DMPK (Myotonic Dystrophy 1); LMNA (Limb Girdle Dystrophy Type 1B); JUP (Naxos); TGFBR2 (Loeys-Dietz); EMD (X-Linked EDMD); and ELN (SV Aortic Stenosis). In some embodiments, a polynucleotide encodes one or more of: cardiac troponin T (TNNT2); BAG family molecular chaperone regulator 3 (BAG3); myosin heavy chain (MYH7); tropomyosin 1 (TPM1); myosin binding protein C (MYBPC3); 5'-AMP-activated protein kinase subunit gamma-2 (PRKAG2); troponin I type 3 (TNNI3); titin (TTN); myosin, light chain 2 (MYL2); actin, alpha cardiac muscle 1 (ACTC1); potassium voltage-gated channel, KQT-like subfamily, member 1 (KCNQ1); myocyte enhancer factor 2c (MEF2C); and cardiac LIM protein (CSRP3).

In some embodiments, the transgene comprises a nucleotide sequence encoding a protein selected from DWORF, junctophilin (e.g., JPH2), BAG family molecular chaperone regulator 3 (BAG3), phospholamban (PLN), alpha-crystallin B chain (CRYAB), LMNA (such as Lamin A and Lamin C isoforms), troponin I type 3 (TNNI3), lysosomal-associated membrane protein 2 (LAMP2, such as LAMP2a, LAMP2b and LAMP2c isoforms), desmoplakin (DSP, such as DPI and DPII isoforms), desmoglein 2 (DSG2), and junction plakoglobin (JUP). In some embodiments, the transgene comprises a nucleotide sequence encoding a human protein. In some embodiments, the transgene comprises a human nucleotide sequence (a human DNA sequence). In some embodiments, the transgene comprises a DNA sequence that has been codon-optimized. In some embodiments, the transgene comprises a nucleotide sequence encoding a wild-type protein, or a functionally active fragment thereof.

In some embodiments, the transgene comprises a polynucleotide sequence encoding a DWORF polypeptide.

In some embodiments, the transgene comprises a polynucleotide sequence encoding a junctophilin 2 (JPH2) polypeptide. In some embodiments, the transgene comprises a polynucleotide sequence encoding a full-length JPH2 polypeptide. In some embodiments, the transgene comprises a polynucleotide sequence encoding an N-terminal fragment of the JPH2 polypeptide. In some embodiments, the transgene comprises a polynucleotide sequence encoding an N-terminal fragment of the JPH2 polypeptide, which retains the JPH2 activity.

In some embodiments, the transgene comprises a polynucleotide sequence encoding a BAG3 polypeptide.

In some embodiments, the transgene comprises a polynucleotide sequence encoding a CRYAB polypeptide.

In some embodiments, the transgene comprises a polynucleotide sequence encoding a LMNA polypeptide. In some embodiments, the transgene comprises a polynucleotide sequence encoding the LaminA isoform of LMNA. In some embodiments, the transgene comprises a polynucleotide sequence encoding the LaminC isoform of LMNA.

In some embodiments, the transgene comprises a polynucleotide sequence encoding a TNNI3 polypeptide.

In some embodiments, the transgene comprises a polynucleotide sequence encoding a PLN polypeptide.

In some embodiments, the transgene comprises a polynucleotide sequence encoding a LAMP2 polypeptide. In some embodiments, the transgene comprises a polynucleotide sequence encoding the LAMP2a isoform. In some embodiments, the transgene comprises a polynucleotide sequence encoding the LAMP2b isoform. In some embodiments, the transgene comprises a polynucleotide sequence encoding the LAMP2c isoform.

In some embodiments, the transgene comprises a polynucleotide sequence encoding a DSP polypeptide. In some embodiments, the transgene comprises a polynucleotide sequence encoding the DPI isoform of DSP. In some embodiments, the transgene comprises a polynucleotide sequence encoding the DPII isoform of DSP.

In some embodiments, the transgene comprises a polynucleotide sequence encoding a DSG2 polypeptide.

In some embodiments, the transgene comprises a polynucleotide sequence encoding a JUP polypeptide.

It is appreciated that the transgenes described herein are non-limiting and transgenes useful for treating a heart disease may be discovered for use in the expression cassettes described herein.

DWORF Transgene

In some embodiments, the expression cassette of the present disclosure comprises a polynucleotide sequence encoding a DWORF polypeptide. In some embodiments, the expression cassette provides increased expression of a DWORF polypeptide in cardiac cell. In some embodiments, the cardiac cell is a cardiomyocyte. In some embodiments, expression of the DWORF polypeptide may be increased 5%, 10%, 15%, 20%, or 25% compared to expression of the DWORF polypeptide factor in an untreated subject. In some embodiments, expression of the DWORF polypeptide may be increased 1-fold, 2-fold, 3-fold, 4-fold, or 5-fold compared to expression of the DWORF polypeptide in an untreated subject. In some embodiments, the DWORF polypeptide may be expressed at any detectable level in the cardiac cell, whereas the DWORF polypeptide may not be expressed, or expressed at undetectable levels, in an untreated subject. Put another way, the cardiac cell to which the rAAV virion is administered may express a DWORF polypeptide in higher abundance than in a cardiac cell that has only endogenous (i.e., native) expression of the DWORF polypeptide.

DWORF polypeptide is an endogenous enhancer of SERCA calcium pump activity, a desirable drug target for regulation of cardiac contractility. DWORF is also an unusually small protein, which makes it a good candidate for delivery to a target cell or tissue by rAAV virions. Because DWORF is an endogenous protein, expression of DWORF in humans would not be immunogenic, allowing for long-term dosing and expression. The structural features of DWORF polypeptides are as follows. First, the polypeptides may have 5 to 35 consecutive residues of the Dwarf Open Reading Frame (DWORF), located on chromosome 3 of a mammalian species, including mouse and human (Nelson et al. *Science*. 351: 271-275 (2016); U.S. Pat. No. 10,570,183). Thus, the term "a peptide having no more than X consecutive residues," even when including the term "comprising," cannot be understood to comprise a greater number of consecutive residues. In general, the peptides will be 35 residues or less, again, comprising no more than 20 consecutive residues of DWORF. The overall length may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 residues. Ranges of peptide length of 5-34/35 residues, 6-34/35 residues, 7-50 residues, 7-25, residues, 5-20 residues, 6-20 residues, 7-20 residues, and 7-15 residues are contemplated. The number of consecutive DWORF residues may be 5, 6, 7, 8, 9, 10, 11, 12, 13, 14, 15, 16, 17, 18, 19 or 20. Ranges of consecutive residues of 5-20 residues, 5-20 residues, 6-20 residues, 7-20 residues and 5-15 residues, 5-15, residues, 6-15 residues or 7-15 residues are contemplated. Illustrative DWORF sequences can be found in Table 2a.

In some embodiments, DWORF polypeptide is human DWORF polypeptide. In some embodiments, the expression cassette comprises a single polynucleotide sequence encoding a dwarf open reading frame (DWORF) polypeptide. In some embodiments, the polynucleotide sequence encoding DWORF is codon optimized. In some embodiments, the DWORF polypeptide comprises a polypeptide sequence that shares at least 9500 identity to SEQ ID NO: 1, SEQ ID NO: 3, SEQ ID NO: 5, SEQ ID NO: 7, or SEQ ID NO: 9. In some embodiments, the DWORF polypeptide comprises a polypeptide sequence that shares at least 9800 identity to SEQ ID NO: 1, SEQ ID NO: 3, SEQ ID NO: 5, SEQ ID NO: 7, or SEQ ID NO: 9. In some embodiments, the DWORF polypeptide comprises the polypeptide sequence of SEQ ID NO: 1, SEQ ID NO: 3, SEQ ID NO: 5, SEQ ID NO: 7, or SEQ ID NO: 9.

sequence may be increased 1-fold, 2-fold, 3-fold, 4-fold, or 5-fold compared to expression in an untreated subject. In some embodiments, the polypeptide encoded by the polynucleotide sequence may be expressed at any detectable level in the cardiac cell, whereas it may not be expressed, or expressed at undetectable levels, in an untreated subject. In some embodiments, the cardiac cell to which a vector described herein is administered may express a polypeptide encoded by the polynucleotide sequence in higher abundance than in a cardiac cell that has only endogenous (i.e., native) expression of the polypeptide.

TABLE 2a

Illustrative DWORF Sequences

| DWORF Variant | DWORF Polypeptide | Nucleotide (Open Reading Frame) |
|---|---|---|
| Mouse Variant | MAEKESTSPHLMVPILLLVGWIVGCIIVI YIVFF (SEQ ID NO: 1) | ATGGCTGAGAAAGAGTCAACATCACCACACCTCATGGTTCC CATTCTTCTCCTGGTTGGATGGATTGTAGGCTGCATCATCG TTATTTACATTGTCTTCTTCTAA (SEQ ID NO: 2) |
| Human Variant | MAEKAGSTFSHLLVPILLLIGWIVGCIIM IYVVFS (SEQ ID NO: 3) | ATGGCTGAAAAGCGGGGTCTACATTTTCACACCTTCTGGT TCCTATTCTTCTCCTGATTGGCTGGATTGTGGGCTGCATCA TAATGATTTATGTTGTCTTCTCTTAG (SEQ ID NO: 4) |
| Artificial | MAEKAESTSPHLMVPILLLVGWIVGCIIV IYIVFF (SEQ ID NO: 5) | ATGGCTGAGAAAGCAGAGTCAACATCACCACACCTCATGGT TCCCATTCTTCTCCTGGTTGGATGGATTGTAGGCTGCATCA TCGTTATTTACATTGTCTTCTTCTAA (SEQ ID NO: 6) |
| Artificial | MAEKESTSPHLIVPILLLVGWIVGCIIVI YIVFF (SEQ ID NO: 7) | ATGGCTGAGAAAGAGTCAACATCACCACACCTCATTGTTCC CATTCTTCTCCTGGTTGGATGGATTGTAGGCTGCATCATCG TTATTTACATTGTCTTCTTCTAA (SEQ ID NO: 8) |
| Artificial | MAEKAESTSPHLIVPILLLVGWIVGCIIV IYIVFF (SEQ ID NO: 9) | ATGGCTGAGAAAGCAGAGTCAACATCACCACACCTCATTGT TCCCATTCTTCTCCTGGTTGGATGGATTGTAGGCTGCATCA TCGTTATTTACATTGTCTTCTTCTAA (SEQ ID NO: 10) |
| Human Variant | MAEKESTSPHLMVPILLLVGWIVGCIIVI YIVFF (SEQ ID NO: 32) | ATGGCAGAGAAGGCTGGAAGCACTTTCTCTCACCTGCTCGT GCCGATTTTGCTTTTGATTGGGTGGATAGTTGGCTGTATCA TAATGATCTACGTTGTCTTTTCATAG (SEQ ID NO: 33) |
| Human Variant | MAEKGSTFSHLLVPILLLIGWIVGCIIMI YVVFS (SEQ ID NO: 43) | ATGGCCGAGAAGGGCAGCACCTTCAGCCACCTGCTGGTGCC CATCCTGCTGCTGATCGGCTGGATCGTGGGCTGCATCATCA TGATCTACGTGGTGTTCAGC (SEQ ID NO: 44) |
| Codon Optimized Mouse DWORF | MAEKESTSPHLMVPILLLVGWIVGCIIVI YIVFF (SEQ ID NO: 1) | ATGGCCGAGAAGGAATCTACCAGCCCCCACCTGATGGTGCC TATTCTGCTGCTGGTGGGCTGGATCGTCGGCTGCATCATCG TGATCTACATCGTGTTCTTCTGA (SEQ ID NO: 76) |
| Codon Optimized Human DWORF | MAEKAGSTFSHLLVPILLLIGWIVGCIIM IYVVFS (SEQ ID NO: 3) | ATGGCCGAGAAGGCCGGATCTACCTTCAGCCACCTGCTGGT CCCTATTCTGCTGCTGATCGGCTGGATCGTGGGCTGCATCA TCATGATCTACGTGGTGTTCAGCTGA (SEQ ID NO: 77) |

Other Exemplary Transgenes

In some embodiments, the expression cassette of the present disclosure comprises a polynucleotide sequence encoding another gene product (not DWORF), for example, a polypeptide selected from JPH2, BAG3, CRYAB, LMNA (e.g., Lamin A or Lamin C isoform), TNNI3, PLN, LAMP2 (e.g., LAMP2a, LAMP2b or LAMP2c isoform), DSP (e.g., DPI or DPII isoform), desmoglein 2 (DSG2), and junction plakoglobin (JUP). In some embodiments, the expression cassette provides increased expression of the gene product in a cardiac cell. In some embodiments, the cardiac cell is a cardiomyocyte. In some embodiments, expression of the polypeptide encoded by the polynucleotide sequence may be increased 5%, 10%, 15%, 20%, or 25% compared to expression in an untreated subject. In some embodiments, expression of the polypeptide encoded by the polynucleotide In some embodiments, the polypeptide is a human polypeptide. In some embodiments, the polynucleotide sequence encoding the polypeptide is codon optimized. In some embodiments, the expression cassette comprises a single polynucleotide sequence encoding a polypeptide. In some embodiments, the expression cassette comprises two polynucleotide sequences encoding a polypeptide. In some embodiments, the expression cassette comprises two polynucleotide sequences encoding a polypeptide, wherein at least one of the sequences is codon-optimized.

In some embodiments, a polynucleotide sequence encodes JPH2, e.g., human JPH2. In some embodiments, a polynucleotide sequence has at least 75%, 80%, 85%, 90%, 95%, 98%, 99% or 100% sequence identity to SEQ ID NO:201. In some embodiments, a polynucleotide sequence is a codon-optimized sequence encoding JPH2, e.g., human JPH2. In some embodiments, the gene product or polypeptide expressed using any expression construct described herein is JPH2, e.g., human JPH2. In some embodiments, the JPH2 polypeptide has at least 75%, 80%, 85%, 90%, 95%, 98%, 99% or 100% sequence identity to SEQ ID NO:202.

In some embodiments, a polynucleotide sequence encodes an N-terminal fragment of JPH2, e.g., human JPH2. In some embodiments, a polynucleotide sequence of an N-terminal fragment of JPH2 has at least 75%, 80%, 85%, 90%, 95%, 98%, 99% or 100% sequence identity to SEQ ID NO:227. In some embodiments, a polynucleotide sequence is a codon-optimized sequence encoding an N-terminal fragment of JPH2, e.g., human JPH2. In some embodiments, the gene product or polypeptide expressed using any expression construct described herein is an N-terminal fragment of JPH2, e.g., human JPH2. In some embodiments, the N-terminal fragment of JPH2 polypeptide has at least 75%, 80%, 85%, 90%, 95%, 98%, 99% or 100% sequence identity to SEQ ID NO:228. The human sequences of an N-terminal fragment of JPH2 correspond to the mouse JPH2 N-terminal peptide with amino acids 1-565, generated by a Calpain cleavage (see Guo et al., 2018, Science 362, doi: 10.1126/science.aan3303).

In some embodiments, a polynucleotide sequence encodes BAG3, e.g., human BAG3. In some embodiments, a polynucleotide sequence has at least 75%, 80%, 85%, 90%, 95%, 98%, 99% or 100% sequence identity to SEQ ID NO:203. In some embodiments, a polynucleotide sequence is a codon-optimized sequence encoding BAG3, e.g., human BAG3. In some embodiments, the gene product or polypeptide expressed using any expression construct described herein is BAG3, e.g., human BAG3. In some embodiments, the BAG3 polypeptide has at least 75%, 80%, 85%, 90%, 95%, 98%, 99% or 100% sequence identity to SEQ ID NO:204.

In some embodiments, a polynucleotide sequence encodes CRYAB, e.g., human CRYAB. In some embodiments, a polynucleotide sequence has at least 75%, 80%, 85%, 90%, 95%, 98%, 99% or 100% sequence identity to SEQ ID NO:205. In some embodiments, a polynucleotide sequence is a codon-optimized sequence encoding CRYAB, e.g., human CRYAB. In some embodiments, the gene product or polypeptide expressed using any expression construct described herein is CRYAB, e.g., human CRYAB. In some embodiments, the CRYAB polypeptide has at least 75%, 80%, 85%, 90%, 95%, 98%, 99% or 100% sequence identity to SEQ ID NO:206.

In some embodiments, a polynucleotide sequence encodes LMNA, e.g., human LMNA. In some embodiments, a polynucleotide sequence encodes Lamin A isoform of LMNA, e.g., human Lamin A. In some embodiments, a polynucleotide sequence has at least 75%, 80%, 85%, 90%, 95%, 98%, 99% or 100% sequence identity to SEQ ID NO:207. In some embodiments, a polynucleotide sequence encodes Lamin C isoform of LMNA, e.g., human Lamin C. In some embodiments, a polynucleotide sequence has at least 75%, 80%, 85%, 90%, 95%, 98%, 99% or 100% sequence identity to SEQ ID NO:209. In some embodiments, a polynucleotide sequence is a codon-optimized sequence encoding an LMNA polypeptide. In some embodiments, a polynucleotide sequence is a codon-optimized sequence encoding Lamin A or Lamin C, e.g., human Lamin A or Lamin C. In some embodiments, the gene product or polypeptide expressed using any expression construct described herein is LMNA, e.g., human LMNA. In some embodiments, the gene product or polypeptide expressed using any expression construct described herein is Lamin A isoform of LMNA, e.g., human. In some embodiments, the Lamin A polypeptide has at least 75%, 80%, 85%, 90%, 95%, 98%, 99% or 100% sequence identity to SEQ ID NO:208. In some embodiments, the gene product or polypeptide expressed using any expression construct described herein is Lamin C isoform of LMNA, e.g., human. In some embodiments, the Lamin C polypeptide has at least 75%, 80%, 85%, 90%, 95%, 98%, 99% or 100% sequence identity to SEQ ID NO:210.

In some embodiments, a polynucleotide sequence encodes TNNI3, e.g., human TNNI3. In some embodiments, a polynucleotide sequence has at least 75%, 80%, 85%, 90%, 95%, 98%, 99% or 100% sequence identity to SEQ ID NO:211. In some embodiments, a polynucleotide sequence is a codon-optimized sequence encoding TNNI3, e.g., human TNNI3. In some embodiments, the gene product or polypeptide expressed using any expression construct described herein is TNNI3, e.g., human TNNI3. In some embodiments, the TNNI3 polypeptide has at least 75%, 80%, 85%, 90%, 95%, 98%, 99% or 100% sequence identity to SEQ ID NO:212.

In some embodiments, a polynucleotide sequence encodes PLN, e.g., human PLN. In some embodiments, a polynucleotide sequence has at least 75%, 80%, 85%, 90%, 95%, 98%, 99% or 100% sequence identity to SEQ ID NO:229. In some embodiments, a polynucleotide sequence is a codon-optimized sequence encoding PLN, e.g., human PLN. In some embodiments, the gene product or polypeptide expressed using any expression construct described herein is PLN, e.g., human PLN. In some embodiments, the PLN polypeptide has at least 75%, 80%, 85%, 90%, 95%, 98%, 99% or 100% sequence identity to SEQ ID NO:230.

In some embodiments, a polynucleotide sequence encodes LAMP2, e.g., human LAMP2. In some embodiments, a polynucleotide sequence encodes LAMP2a isoform of LAMP2, e.g., human LAMP2a. In some embodiments, a polynucleotide sequence has at least 75%, 80%, 85%, 90%, 95%, 98%, 99% or 100% sequence identity to SEQ ID NO:213. In some embodiments, a polynucleotide sequence encodes LAMP2b isoform of LAMP, e.g., human LAMP2b. In some embodiments, a polynucleotide sequence has at least 75%, 80%, 85%, 90%, 95%, 98%, 99% or 100% sequence identity to SEQ ID NO:215. In some embodiments, a polynucleotide sequence encodes LAMP2c isoform of LAMP, e.g., human LAMP2c. In some embodiments, a polynucleotide sequence has at least 75%, 80%, 85%, 90%, 95%, 98%, 99% or 100% sequence identity to SEQ ID NO:217. In some embodiments, a polynucleotide sequence is a codon-optimized sequence encoding LAMP2, e.g., human LAMP2. In some embodiments, a polynucleotide sequence is a codon-optimized sequence encoding LAMP2a, LAMP2b or LAMP2c. In some embodiments, the gene product or polypeptide expressed using any expression construct described herein is a LAMP2 polypeptide, e.g., human LAMP2. In some embodiments, the gene product or polypeptide expressed using any expression construct described herein is LAMP2a isoform of LAMP2, e.g., human. In some embodiments, the LAMP2a polypeptide has at least 75%, 80%, 85%, 90%, 95%, 98%, 99% or 100% sequence identity to SEQ ID NO:214. In some embodiments, the gene product or polypeptide expressed using any expression construct described herein is LAMP2b isoform of LAMP2, e.g., human. In some embodiments, the LAMP2b polypeptide has at least 75%, 80%, 85%, 90%, 95%, 98%, 99% or 100% sequence identity to SEQ ID NO:216. In some embodiments, the gene product or polypeptide expressed using any expression construct described herein is LAMP2c isoform of LAMP2, e.g., human. In some embodiments, the LAMP2c polypeptide has at least 75%, 80%, 85%, 90%, 95%, 98%, 99% or 100% sequence identity to SEQ ID NO:218.

In some embodiments, a polynucleotide sequence encodes DSP, e.g., human DSP. In some embodiments, a polynucleotide sequence encodes DPI isoform of DSP, e.g., human DPI. In some embodiments, a polynucleotide sequence has at least 75%, 80%, 85%, 90%, 95%, 98%, 99% or 100% sequence identity to SEQ ID NO:219. In some embodiments, a polynucleotide sequence encodes DPII isoform of DSP, e.g., human DPII. In some embodiments, a polynucleotide sequence has at least 75%, 80%, 85%, 90%, 95%, 98%, 99% or 100% sequence identity to SEQ ID NO:221. In some embodiments, a polynucleotide sequence is a codon-optimized sequence encoding a DSP polypeptide. In some embodiments, a polynucleotide sequence is a codon-optimized sequence encoding DPI or DPII, e.g., human DPI or DPII. In some embodiments, the gene product or polypeptide expressed using any expression construct described herein is DSP, e.g., human DSP. In some embodiments, the gene product or polypeptide expressed using any expression construct described herein is DPI isoform of DSP, e.g., human. In some embodiments, the DPI polypeptide has at least 75%, 80%, 85%, 90%, 95%, 98%, 99% or 100% sequence identity to SEQ ID NO:220. In some embodiments, the gene product or polypeptide expressed using any expression construct described herein is DPII isoform of DSP, e.g., human. In some embodiments, the DPII polypeptide has at least 75%, 80%, 85%, 90%, 95%, 98%, 99% or 100% sequence identity to SEQ ID NO:222.

In some embodiments, a polynucleotide sequence encodes DSG2, e.g., human DSG2. In some embodiments, a polynucleotide sequence has at least 75%, 80%, 85%, 90%, 95%, 98%, 99% or 100% sequence identity to SEQ ID NO:223. In some embodiments, a polynucleotide sequence is a codon-optimized sequence encoding DSG2, e.g., human DSG2. In some embodiments, the gene product or polypeptide expressed using any expression construct described herein is DSG2, e.g., human DSG2. In some embodiments, the DSG2 polypeptide has at least 75%, 80%, 85%, 90%, 95%, 98%, 99% or 100% sequence identity to SEQ ID NO:224.

In some embodiments, a polynucleotide sequence encodes JUP, e.g., human JUP. In some embodiments, a polynucleotide sequence has at least 75%, 80%, 85%, 90%, 95%, 98%, 99% or 100% sequence identity to SEQ ID NO:225. In some embodiments, a polynucleotide sequence is a codon-optimized sequence encoding JUP, e.g., human JUP. In some embodiments, the gene product or polypeptide expressed using any expression construct described herein is JUP, e.g., human JUP. In some embodiments, the JUP polypeptide has at least 75%, 80%, 85%, 90%, 95%, 98%, 99% or 100% sequence identity to SEQ ID NO:226.

In some embodiments, any other polynucleotide sequence described herein can be used in any expression construct described herein. In some embodiments, such polynucleotide sequence encodes any gene product or polypeptide described herein. The polynucleotide sequence can be sequence-optimized (such as for expression in a human). In some embodiments, the sequence encodes a human polypeptide. The sequences of the polynucleotides and polypeptides described herein are known in the art. Sequences that have at least 75%, 80%, 85%, 90%, 95%, 98%, 99% or 100% sequence identity to such sequence are also contemplated herein. Illustrative sequences can be found in Table 2b.

TABLE 2b

Illustrative Gene product Sequences

| Transgene | Polypeptide | Nucleotide (Open Reading Frame) |
|---|---|---|
| Human JPH2 (the N-terminal part of the sequence that, in some instances, can be used on its own, as an alternative to the full-length JPH2, is shown in bold) | MSGGRFDFDDGGAYCGGWEG GKAHGHGLCTGPKGQGEYSGS WNFGFEVAGVYTWPSGNTFEG YWSQGKRHGLGIETKGRWLYK GEWTHGFKGRYGIRQSSSSGAK YEGTWNNGLQDGYGTETYADG GTYQGQFTNGMRHGYGVRQSV PYGMAVVVRSPLRTSLSSLRSE HSNGTVAPDSPASPASDGPALPS PAIPRGGFALSLLANAEAAARAP KGGGLFQRGALLGKLRRAESR TSVGSQRSRVSFLKSDLSSGASD AASTASLGEAAEGADEAAPFEA DIDATTTETYMGEWKNDKRSG FGVSERSSGLRYEGEWLDNLRH GYGCTTLPDGHREEGKYRHNV LVKDTKRRMLQLKSNKVRQKV EHSVEGAQRAAAIARQKAEIAA SRTSHAKAKAEAAEQAALAAN QESNIARTLARELAPDFYQPGPE YQKRRLLQEILENSESLLEPPDR GAGAAGLPQPPRESPQLHERET PRPEGGSPSPAGTPPQPKRPRPG VSKDGLLSPGAWNGEPSGEGSR SVTPSEGAGRRSPARPATERMAI EALQAPPAPSREPEVALYQGYH SYAVRTTPPEPPPFEDQPEPEVSGS ESAPSSPATAPLQAPTLRGPEPAR ETPAKLEPKPIIPKAEPRAKARKTE ARGLTKAGAKKKARKEAALAAE AEVEVEEVPNTILICMVILLNIGLA ILFVHLLT (SEQ ID NO: 202) | ATGAGTGGGGCCGCTTCGACTTTGATGATG GAGGGGCGTACTGCGGGGGCTGGGAGGGG GGAAAGGCCCATGGGCATGGACTGTGCACA GGCCCCAAGGGCCAGGGCGAATACTCTGGC TCCTGGAACTTTGGCTTTGAGGTGGCAGGTG TCTACACCTGGCCCAGCGGAAACACCTTTGA GGGATACTGGGCACAGGGCAAACGGCATGG GCTGGGCATAGAGACCAAGGGGCGCTGGCT CTACAAGGGCGAGTGGACACATGGCTTCAA GGGACGCTACGGAATCCGGCAGAGCTCAAG CAGCGGTGCCAAGTATGAGGGCACCTGGAA CAATGGCCTGCAAGACGGCTATGGCACCGA GACCTATGCTGATGGAGGGACGTACCAAGG CCAGTTCACCAACGGCATGCGCCATGGCTAC GGAGTACGCCAGAGCGTGCCCTACGGGATG GCCGTGGTGGTGCGCTCGCCGCTGCGCACG TCGCTGTCGTCCCTGCGCAGCGAGCACAGC AACGGCACGGTGGCCCCGGACTCTCCCGCC TCGCCGGCCTCCGACGGCCCCGCGCTGCCC TCGCCCGCCATCCCGCGTGGCGGCTTCGCG CTCAGCCTCCTGGCCAATGCCGAGGCGGCC GCGCGGGCGCCCAAGGGCGGCGGCCTCTTC CAGCGGGGCGCGCTGCTGGGCAAGCTGCGG CGCGCAG AGTCGCGCACGTCCGTGGGTAGCCAGCGCA GCCGTGTCAGCTTCCTTAAGAGCGACCTCAG CTCGGGCGCCAGCGACGCCGCGTCCACCGC CAGCCTGGGAGGGCCGCCGAGGGCGCCGA CGAGGCCGCACCCTTCGAGGCCGATATCGA CGCCACCACCACCGAGACCTACATGGGCGA GTGGAAGAACGACAAACGCTCGGGCTTCGG CGTGAGCGAACGCTCCAGTGGCCTCCGCTA CGAGGGCGAGTGGCTGGACAACCTGCGCCA |

TABLE 2b-continued

Illustrative Gene product Sequences

| Transgene | Polypeptide | Nucleotide (Open Reading Frame) |
|---|---|---|
| | | CGGCTATGGCTGCACCACGCTGCCCGACGG<br>CCACCGCGAGGAGGGCAAGTACCGCCACAA<br>CGTGCTGGTCAAGGACACCAAGCGCCGCAT<br>GCTGCAGCTCAAGAGCAACAAGGTCCGCCA<br>GAAAGTGGAGCACAGTGTGGAGGGTGCCCA<br>GCGCGCCGCTGCTATCGCGCGCCAGAAGGC<br>CGAGATTGCCGCCTCCAGGACAAGCCACGC<br>CAAGGCCAAAGCTGAGGCAGCGGAACAGGC<br>CGCCCTGGCTGCCAACCAGGAGTCCAACATT<br>GCTCGCACTTTGGCCAGGGAGCTGGCTCCG<br>GACTTCTACCAGCCAGGTCCGGAATATCAGA<br>AGCGCCGGCTGCTGCAGGAGATCCTGGAGA<br>ACTCGGAGAGCCTGCTGGAGCCCCCCGACC<br>GGGGCGCCGGCGCAGCGGGCCTCCCACAGC<br>CGCCCCGCGAGAGCCCGCAGCTGCACGAGC<br>GTGAGACCCCTCGGCCCGAGGGTGGCTCCC<br>CGTCACCGGCCGGGACGCCCCCGCAGCCCA<br>AGCGGCCCAGGCCCGGGGTGTCCAAGGACG<br>GCCTGCTGAGCCCAGGCGCCTGGAACGGCG<br>AGCCAGCGGTGAGGGCAGCCGGTCAGTCA<br>CTCCGTCCGAGGGCGCGGGCCGCCGCAGCC<br>CCGCGCGTCCAGCCACCGAGCGCATGGCCA<br>TCGAGGCTCTGCAGGCACCGCCTGCGCCGT<br>CGCGGGAGCCGGAGGTGGCGCTTTACCAGG<br>GCTACCACAGCTATGCTGTGCGCACCACGCC<br>GCCCGAGCCCCACCCTTTGAGGACCAGCCCG<br>AGCCCGAGGTCTCCGGGTCCGAGTCCGCGCCT<br>CGTCCCCGGCACCGCCCCGCTGCAGGCCCCCA<br>CGCTCCGAGGCCCCGAGCCTGCACGCGAGACC<br>CCCGCCAAGCTGGAGCCCAAGCCCATCATCCCC<br>AAAGCCGAGCCCAGGGCCAAGGCCCGCAAGAC<br>TGAGGCTCGAGGGCTGACCAAGGCGGGGGCCA<br>AGAAGAAGGCGCGGAAGGAGGCCGCACTGGC<br>GGCAGAGGCGGAGGTGGAGGTGGAAGAGGTCC<br>CCAACACCATCCTCATCTGCATGGTGATCCTGC<br>TGAACATCGGCCTGGCCATCCTCTTTGTTCACC<br>TCCTGACCTGA (SEQ ID NO: 201) |
| Human<br>BAG3 | MSAATHSPMMQVASGNGDRDPL<br>PPGWEIKIDPQTGWPFFVDHNSRT<br>TTWNDPRVPSEGPKETPSSANGPS<br>REGSRLPPAREGHPVYPQLRPGYI<br>PIPVLHEGAENRQVHPFHVYPQPG<br>MQRFRTEAAAAAPQRSQSPLRGM<br>PETTQPDKQCGQVAAAAAQPPA<br>SHGPERSQSPAASDCSSSSSSASLP<br>SSGRSSLGSHQLPRGYISIPVIHEQ<br>NVTRPAAQPSFHQAQKTHYPAQQ<br>GEYQTHQPVYHKIQGDDWEPRPL<br>RAASPFRSSVQGASSREGSPARSS<br>TPLHSPSPIRVHTVVDRPQQPMTH<br>RETAPVSQPENKPESKPGPVGPEL<br>PPGHIPIQVIRKEVDSKPVSQKPPP<br>PSEKVEVKVPPAPVPCPPPSPGPS<br>AVPSSPKSVATEERAAPSTAPAEA<br>TPPKPGEAEAPPKHPGVLKVEAIL<br>EKVQGLEQAVDNFEGKKTDKKY<br>LMIEEYLTKELLALDSVDPEGRA<br>DVRQARRDGVRKVQTILEKLEQK<br>AIDVPGQVQVYELQPSNLEADQP<br>LQAIMEMGAVAADKGKKNAGN<br>AEDPHTETQQPEATAAATSNPSS<br>MTDTPGNPAAP (SEQ ID NO: 204) | ATGAGCGCCGCCACCCACTCGCCCATGATGCA<br>GGTGGCGTCCGGCAACGGTGACCGCGACCCTTT<br>GCCCCCCGGATGGGAGATCAAGATCGACCCGC<br>AGACCGGCTGGCCCTTCTTCGTGGACCACAACA<br>GCCGCACCACTACGTGGAACGACCCGCGCGTG<br>CCCTCTGAGGGCCCCAAGGAGACTCCATCCTCT<br>GCCAATGGCCCTTCCCGGGAGGGCTCTAGGCTG<br>CCGCCTGCTAGGGAAGGCCACCCTGTGTACCCC<br>CAGCTCCGACCAGGCTACATTCCCATTCCTGTG<br>CTCCATGAAGGCGCTGAGAACCGGCAGGTGCA<br>CCCTTTCCATGTCTATCCCCAGCCTGGGATGCA<br>GCGATTCCGAACTGAGGCGGCAGCAGCGGCTC<br>CTCAGAGGTCCCAGTCACCTCTGCGGGGCATGC<br>CAGAAACCACTCAGCCAGATAAACAGTGTGGA<br>CAGGTGGCAGCGGCGGCGGCAGCCCAGCCCCC<br>AGCCTCCCACGGACCTGAGCGGTCCCAGTCTCC<br>AGCTGCCTCTGACTGCTCATCCTCATCCTCCTC<br>GGCCAGCCTGCCTTCCTCCGGCAGGAGCAGCCT<br>GGGCAGTCACCAGCTCCCGCGGGGTACATCT<br>CCATTCCGGTGATACACGAGCAGAACGTTACCC<br>GGCCAGCAGCCCAGCCCTCCTTCCACCAAGCCC<br>AGAAGACGCACTACCCAGCGCAGCAGGGGGAG<br>TACCAGACCCACCAGCCTGTGTACCACAAGATC<br>CAGGGGGATGACTGGGAGCCCCGGCCCCTGCG<br>GGCGGCATCCCCGTTCAGGTCATCTGTCCAGGG<br>TGCATCGAGCCGGGAGGGCTCACCAGCCAGGA<br>GCAGCACGCCACTCCACTCCCCCTCGCCCATCC<br>GTGTGCACACCGTGGTCGACAGGCCTCAGCAG<br>CCCATGACCCATCGAGAAACTGCACCTGTTTCC<br>CAGCCTGAAAACAAACCAGAAAGTAAGCCAGG<br>CCCAGTTGGACCAGAACTCCCTC<br>CTGGACACATCCCAATTCAAGTGATCCGCAAA<br>GAGGTGGATTCTAAACCTGTTTCCCAGAAGCCC<br>CCACCTCCCTCTGAGAAGGTAGAGGTGAAAGT<br>TCCCCCTGCTCCAGTTCCTTGTCCTCCTCCCAGC<br>CCTGGCCCTTCTGCTGTCCCCTCTTCCCCCAAG<br>AGTGTGGCTACAGAAGAGAGGGCAGCCCCCAG<br>CACTGCCCCTGCAGAAGCTACACCTCCAAAACC |

TABLE 2b-continued

Illustrative Gene product Sequences

| Transgene | Polypeptide | Nucleotide (Open Reading Frame) |
|---|---|---|
| | | AGGAGAAGCCGAGGCTCCCCCAAAACATCCAG GAGTGCTGAAAGTGGAAGCCATCCTGGAGAAG GTACAGGGGCTGGAGCAGGCTGTAGACAACTT TGAAGGCAAGAAGACTGACAAAAAG TACCTGATGATCGAAGAGTATTTGACCAAAGA GCTGCTGGCCCTGGATTCAGTGGACCCCGAGG GACGAGCCGATGTGCGTCAGGCCAGGAGAGAC GGTGTCAGGAAGGTTCAGACCATCTTGGAAAA ACTTGAACAGAAAGCCATTGATGTCCCAGGTC AAGTCCAGGTCTATGAACTCCAGCCCAGCAAC CTTGAAGCAGATCAGCCACTGCAGGCAATCAT GGAGATGGGTGCCGTGGCAGCAGACAAGGGCA AGAAAAATGCTGGAAATGCAGAAGATCCCCAC ACAGAAACCCAGCAGCCAGAAGCCACAGCAGC AGCGACTTCAAACCCCAGCAGCATGACAGACA CCCCTGGTAACCCAGCAGCACCGTAG (SEQ ID NO: 203) |
| Human CRYAB | MDIAIHHPWIRRPFFPFHSPSRLFD QFFGEHLLESDLFPTSTSLSPFYLR PPSFLRAPSWFDTGLSEMRLEKDR FSVNLDVKHFSPEELKVKVLGDVI EVHGKHEERQDEHGFISREFHRK YRIPADVDPLTITSSLSSDGVLTVN GPRKQVSGPERTIPITREEKPAVT AAPKK (SEQ ID NO: 206) | ATGGACATCGCCATCCACCACCCCTGGATCCGC CGCCCCTTCTTTCCTTTCCACTCCCCCAGCCGCC TCTTTGACCAGTTCTTCGGAGAGCACCTGTTGG AGTCTGATCTTTTCCCGACGTCTACTTCCCTGA GTCCCTTCTACCTTCGGCCACCCTCCTTCCTGCG GGCACCCAGCTGGTTTGACACTGGACTCTCAGA GATGCGCCTGGAGAAGGACAGGTTCTCTGTCA ACCTGGATGTGAAGCACTTCTCCCCAGAGGAA CTCAAAGTTAAGGTGTTGGGAGATGTGATTGA GGTGCATGGAAAACATGAAGAGCGCCAGGATG AACATGGTTTCATCTCCAGGGAGTTCCACAGGA AATACCGGATCCCAGCTGATGTAGACCCTCTCA CCATTACTTCATCCCTGTCATCTGATGGGGTCC TCACTGTGAATGGACCAAGGAAACAGGTCTCT GGCCCTGAGCGCACCATTCCCATCACCCGTGAA GAGAAGCCTGCTGTCACCGCAGCCCCCAAGAA ATAG (SEQ ID NO: 205) |
| Human LMNA LaminA | METPSQRRATRSGAQASSTPLSPT RITRLQEKEDLQELNDRLAVYIDR VRSLETENAGLRLRITESEEVVSR EVSGIKAAYEAELGDARKTLDSV AKERARLQLELSKVREEFKELKA RNTKKEGDLIAAQARLKDLEALL NSKEAALSTALSEKRTLEGELHDL RGQVAKLEAALGEAKKQLQDEM LRRVDAENRLQTMKEELDFQKNI YSEELRETKRRHETRLVEIDNGKQ REFESRLADALQELRAQHEDQVE QYKKELEKTYSAKLDNARQSAER NSNLVGAAHEELQQSRIRIDSLSA QLSQLQKQLAAKEAKLRDLEDSL ARERDTSRRLLAEKEREMAEMRA RMQQQLDEYQELLDIKLALDMEI HAYRKLLEGEEERLRLSPSPTSQR SRGRASSHSSQTQGGGSVTKKRK LESTESRSSFSQHARTSGRVAVEE VDEEGKFVRLRNKSNEDQSMGN WQIKRQNGDDPLLTYRFPPKFTL KAGQVVTIWAAGAGATHSPPTDL VWKAQNTWGCGNSLRTALINST GEEVAMRKLVRSVTVVEDDEDE DGDDLLHHHHGSHCSSSGDPAEY NLRSRTVLCGTCGQPADKASASG SGAQVGGPISSGSSASSVTVTRSY RSVGGSGGGSFGDNLVTRSYLLG NSSPRTQSPQNCSIM (SEQ ID NO: 208) | ATGGAGACCCCGTCCCAGCGGCGCGCCACCCG CAGCGGGGCGCAGGCCAGCTCCACTCCGCTGT CGCCCACCCGCATCACCCGGCTGCAGGAGAAG GAGGACCTGCAGGAGCTCAATGATCGCTTGGC GGTCTACATCGACCGTGTGCGCTCGCTGGAAAC GGAGAACGCAGGGCTGCGCCTTCGCATCACCG AGTCTGAAGAGGTGGTCAGCCGCGAGGTGTCC GGCATCAAGGCCGCCTACGAGGCCGAGCTCGG GGATGCCCGCAAGACCCTTGACTCAGTAGCCA AGGAGCGCGCCCGCCTGCAGCTGGAGCTGAGC AAAGTGCGTGAGGAGTTTAAGGAGCTGAA AGCGCGCAATACCAAGAAGGAGGGTGACCTGA TAGCTGCTCAGGCTCGGCTGAAGGACCTGGAG GCTCTGCTGAACTCCAAGGAGGCCGCACTGAG CACTGCTCTCAGTGAGAAGCGCACGCTGGAGG GCGAGCTGCATGATCTGCGGGGCCAGGTGGCC AAGCTTGAGGCAGCCCTAGGTGAGGCCAAGAA GCAACTTCAGGATGAGATGCTGCGGCGGGTGG ATGCTGAGAACAGGCTGCAGACCATGAAGGAG GAACTGGACTTCCAGAAGAACATCTACAGTGA GGAGCTGCGTGAGACCAAGCGCCGTCATGAGA CCCGACTGGTGGAGATTGACAATGGGAAGCAG CGTGAGTTTGAGAGCCGCCTGGCCGATGCGCT GCAGGAACTGCGGGCCCAGCATGAGGACCAGG TGGAGCAGTATAAGAAGGAGCTGGAGAAGACT TATTCTGCCAAGCTGGACAATGCCAGGCAGTCT GCTGAGAGGAACAGCAACCTGGTGGGGGCTGC CCACGAGGAGCTGCAGCAGTCGCGCATCCGCA TCGACAGCCTCTCTGCCCAGCTCAGCCAGCTCC AGAAGCAGCTGGCAGCCAAGGAGGCGAAGCTT CGAGACCTGGAGGACTCACTGGCCCGTGAGCG GGACACCAGCCGGCGGCTGCTGGCGGAAAAGG AGCGGGAGATGGCCGAGATGCGGGCAAGGATG CAGCAGCAGCTGGACGAGTACCAGGAGCTTCT GGACATCAAGCT GGCCCTGGACATGGAGATCCACGCCTACCGCA AGCTCTTGGAGGGCGAGGAGGAGAGGCTACGC CTGTCCCCCAGCCCTACCTCGCAGCGCAGCCGT GGCCGTGCTTCCTCTCACTCATCCCAGACACAG GGTGGGGGCAGCGTCACCAAAAAGCGCAAACT |

TABLE 2b-continued

Illustrative Gene product Sequences

| Transgene | Polypeptide | Nucleotide (Open Reading Frame) |
|---|---|---|
| | | GGAGTCCACTGAGAGCCGCAGCAGCTTCTCAC<br>AGCACGCACGCACTAGCGGGCGCGTGGCCGTG<br>GAGGAGGTGGATGAGGAGGGCAAGTTTGTCCG<br>GCTGCGCAACAAGTCCAATGAGGACCAGTCCA<br>TGGGCAATTGGCAGATCAAGCGCCAGAATGGA<br>GATGATCCCTTGCTGACTTACCGGTTCC<br>CACCAAAGTTCACCCTGAAGGCTGGGCAGGTG<br>GTGACGATCTGGGCTGCAGGAGCTGGGGCCAC<br>CCACAGCCCCCTACCGACCTGGTGTGGAAGG<br>CACAGAACACCTGGGGCTGCGGGAACAGCCTG<br>CGTACGGCTCTCATCAACTCCACTGGGGAAGA<br>AGTGGCCATGCGCAAGCTGGTGCGCTCAGTGA<br>CTGTGGTTGAGGACGACGAGGATGAGGATGGA<br>GATGACCTGCTCCATCACCACCACGGCTCCCAC<br>TGCAGCAGCTCGGGGGACCCCGCTGAGTACAA<br>CCTGCGCTCGCGCACCGTGCTGTGCGGGACCTG<br>CGGGCAGCCTGCCGACAAGGCATCTGCCAGCG<br>GCTCAGGAGCCCAGGTGGGCGGACCCATCTCC<br>TCTGGCTCTTCTGCCTCCAGTGTCACGGTCACT<br>CGCAGCTACCGCAGTGTGGGGGGCAGTGGGGG<br>TGGCAGCTTCGGGGACAATCTGGTCACCCGCTC<br>CTACCTCCTGGGCAACTCCAGCCCCCGAACCCA<br>GAGCCCCAGAACTGCAGCATCATGTAA (SEQ<br>ID NO: 207) |
| Human<br>LMNA<br>LaminC | METPSQRRATRSGAQASSTPLSPT<br>RITRLQEKEDLQELNDRLAVYIDR<br>VRSLETENAGLRLRITESEEVVSR<br>EVSGIKAAYEAELGDARKTLDSV<br>AKERARLQLELSKVREEFKELKA<br>RNTKKEGDLIAAQARLKDLEALL<br>NSKEAALSTALSEKRTLEGELHDL<br>RGQVAKLEAALGEAKKQLQDEM<br>LRRVDAENRLQTMKEELDFQKNI<br>YSEELRETKRRHETRLVEIDNGKQ<br>REFESRLADALQELRAQHEDQVE<br>QYKKELEKTYSAKLDNARQSAER<br>NSNLVGAAHEELQQSRIRIDSLSA<br>QLSQLQKQLAAKEAKLRDLEDSL<br>ARERDTSRRLLAEKEREMAEMRA<br>RMQQQLDEYQELLDIKLALDMEI<br>HAYRKLLEGEEERLRLSPSPTSQR<br>SRGRASSHSSQTQGGGSVTKKRK<br>LESTESRSSFSQHARTSGRVAVEE<br>VDEEGKFVRLRNKSNEDQSMGN<br>WQIKRQNGDDPLLTYRFPPKFTL<br>KAGQVVTIWAAGAGATHSPPTDL<br>VWKAQNTWGCGNSLRTALINST<br>GEEVAMRKLVRSVTVVEDDEDE<br>DGDDLLHHHHVSGSRR(SEQ ID<br>NO: 210) | ATGGAGACCCCGTCCCAGCGGCGCGCCACCCG<br>CAGCGGGGCGCAGGCCAGCTCCACTCCGCTGT<br>CGCCCACCCGCATCACCCGGCTGCAGGAGAAG<br>GAGGACCTGCAGGAGCTCAATGATCGCTTGGC<br>GGTCTACATCGACCGTGTGCGCTCGCTGGAAAC<br>GGAGAACGCAGGGCTGCGCCTTCGCATCACCG<br>AGTCTGAAGAGGTGGTCAGCCGCGAGGTGTCC<br>GGCATCAAGGCCGCCTACGAGGCCGAGCTCGG<br>GGATGCCCGCAAGACCCTTGACTCAGTAGCCA<br>AGGAGCGCGCCCGCCTGCAGCTGGAGCTGAGC<br>AAAGTGCGTGAGGAGTTTAAGGAGCTGAA<br>AGCGCGCAATACCAAGAAGGAGGGTGACCTGA<br>TAGCTGCTCAGGCTCGGCTGAAGGACCTGGAG<br>GCTCTGCTGAACTCCAAGGAGGCCGCACTGAG<br>CACTGCTCTCAGTGAGAAGCGCACGCTGGAGG<br>GCGAGCTGCATGATCTGCGGGGCCAGGTGGCC<br>AAGCTTGAGGCGCCCTAGGTGAGGCCAAGAA<br>GCAACTTCAGGATGAGATGCTGCGGCGGGTGG<br>ATGCTGAGAACAGGCTGCAGACCATGAAGGAG<br>GAACTGGACTTCCAGAAGAACATCTACAGTGA<br>GGAGCTGCGTGAACCAAGCGCCGTCATGAGA<br>CCCGACTGGTGGAGATTGACAATGGGAAGCAG<br>CGTGAGTTTGAGAGCCGGCTGGCGGATGCGCT<br>GCAGGAACTGCGGGCCCAGCATGAGGACCAGG<br>TGGAGCAGTATAAGAAGGAGCTGGAGAAGACT<br>TATTCTGCCAAGCTGGACAATGCCAGGCAGTCT<br>GCTGAGAGGAACAGCAACCTGGTGGGGGCTGC<br>CCACGAGGAGCTGCAGCAGTCGCGCATCCGCA<br>TCGACAGCCTCTCTGCCCAGCTCAGCCAGCTCC<br>AGAAGCAGCTGGCAGCCAAGGAGGCGAAGCTT<br>CGAGACCTGGAGGACTCACTGGCCCGTGAGCG<br>GGACACCAGCCGGCGGCTGCTGGCGGAAAAGG<br>AGCGGGAGATGGCCGAGATGCGGGCCAAGGATG<br>CAGCAGCAGCTGGACGAGTACCAGGAGCTTCT<br>GGACATCAAGCTGGCCCTGGACATGGAGATCC<br>ACGCCTACCGCAAGCTCTTGGAGGGCGAGGAG<br>GAGAGGCTACGCCTGTCCCCCAGCCCTACCTCG<br>CAGCGCAGCCGTGGCCGTGCTTCCTCTCACTCA<br>TCCCAGACACAGGGTGGGGGCAGCGTCACCAA<br>AAAGCGCAAACTGGAGTCCACTGAGAGCCGCA<br>GCAGCTTCTCACAGCACGCACGCACTAGCGGG<br>CGCGTGGCCGTGGAGGAGGTGGATGAGGAGGG<br>CAAGTTTGTCCGGCTGCGCAACAAGTCCAATGA<br>GGACCAGTCCATGGGCAATTGGCAGATCAAGC<br>GCCAGAATGGAGATGATCCCTTGCTGACTTACC<br>GGTTCC<br>CACCAAAGTTCACCCTGAAGGCTGGGCAGGTG<br>GTGACGATCTGGGCTGCAGGAGCTGGGGCCAC<br>CCACAGCCCCCTACCGACCTGGTGTGGAAGG<br>CACAGAACACCTGGGGCTGCGGGAACAGCCTG<br>CGTACGGCTCTCATCAACTCCACTGGGGAAGA |

TABLE 2b-continued

Illustrative Gene product Sequences

| Transgene | Polypeptide | Nucleotide (Open Reading Frame) |
|---|---|---|
| | | AGTGGCCATGCGCAAGCTGGTGCGCTCAGTGA<br>CTGTGGTTGAGGACGACGAGGATGAGGATGGA<br>GATGACCTGCTCCATCACCACCACGTGAGTGGT<br>AGCCGCCGCTGA (SEQ ID NO: 209) |
| Human<br>TNNI3 | MADGSSDAAREPRPAPAPIRRRSS<br>NYRAYATEPHAKKKSKISASRKL<br>QLKTLLLQIAKQELEREAEERRGE<br>KGRALSTRCQPLELAGLGFAELQ<br>DLCRQLHARVDKVDEERYDIEAK<br>VTKNITEIADLTQKIFDLRGKFKR<br>PTLRRVRISADAMMQALLGARAK<br>ESLDLRAHLKQVKKEDTEKENRE<br>VGDWRKNIDALSGMEGRKKKFE<br>S (SEQ ID NO: 212) | ATGGCGGATGGGAGCAGCGATGCGGCTAGGGA<br>ACCTCGCCCTGCACCAGCCCCAATCAGACGCCG<br>CTCCTCCAACTACCGCGCTTATGCCACGGAGCC<br>GCACGCCAAGAAAAAATCTAAGATCTCCGCCT<br>CGAGAAAATTGCAGCTGAAGACTCTGCTGCTG<br>CAGATTGCAAAGCAAGAGCTGGAGCGAGAGGC<br>GGAGGAGCGGCGCGGAGAGAAGGGGCGCGCT<br>CTGAGCACCCGCTGCCAGCCGCTGGAGTTGGCC<br>GGGCTGGGCTTCGCGGAGCTGCAGGACTTGTG<br>CCGACAGCTCCACGCCCGTGTGGACAAGGTGG<br>ATGAAGAGAGATACGACATAGAGGCAAAAGTC<br>ACCAAGAACATCACGGAGATTGCAGATCTGAC<br>TCAGAAGATCTTTGACCTTCGAGGCAAGTTTAA<br>GCGGCCCACCCTGCGGAGAGTGAGGATCTCTG<br>CAGATGCCATGATGCAGGCGCTGCTGGGGGCC<br>CGGGCTAAGGAGTCCCTGGACCTGCGGGCCCA<br>CCTCAAGCAGGTGAAGAAGGAGGACACCGAGA<br>AGGAAAACCGGGAGGTGGGAGACTGGCGCAA<br>GAACATCGATGCACTGAGTGGAATGGAGGGCC<br>GCAAGAAAAAGTTTGAGAGCTGA<br>(SEQ ID NO: 211) |
| Human<br>LAMP2a | MVCFRLFPVPGSGLVLVCLVLGA<br>VRSYALELNLTDSENATCLYAKW<br>QMNFTVRYETTNKTYKTVTISDH<br>GTVTYNGSICGDDQNGPKIAVQF<br>GPGFSWIANFTKAASTYSIDSVSF<br>SYNTGDNTTFPDAEDKGILTVDEL<br>LAIRIPLNDLFRCNSLSTLEKNDV<br>VQHYWDVLVQAFVQNGTVSTNE<br>FLCDKDKTSTVAPTIHTTVPSPTT<br>TPTPKEKPEAGTYSVNNGNDTCL<br>LATMGLQLNITQDKVASVININPN<br>TTHSTGSCRSHTALLRLNSSTIKY<br>LDFVFAVKNENRFYLKEVNISMY<br>LVNGSVFSIANNNLSYWDAPLGS<br>SYMCNKEQTVSVSGAFQINTFDL<br>RVQPFNVTQGKYSTAQDCSADD<br>DNFLVPIAVGAALAGVLILVLLAY<br>FIGLKHHHAGYEQF<br>(SEQ ID NO: 214) | ATGGTGTGCTTCCGCCTCTTCCCGGTTCCGGGC<br>TCAGGGCTCGTTCTGGTCTGCCTAGTCCTGGGA<br>GCTGTGCGGTCTTATGCATTGGAACTTAATTTG<br>ACAGATTCAGAAAATGCCACTTGCCTTTATGCA<br>AAATGGCAGATGAATTTCACAGTACGCTATGA<br>AACTACAAATAAAACTTATAAAACTGTAACCA<br>TTTCAGACCATGGCACTGTGACATATAATGGAA<br>GCATTTGTGGGGATGATCAGAATGGTCCCAAA<br>ATAGCAGTGCAGTTCGGACCTGGCTTTTCCTGG<br>ATTGCGAATTTTACCAAGGCAGCATCTACTTAT<br>TCAATTGACAGTGTCTCATTTTCCTACAACACT<br>GGTGATAACACAACATTTCCTGATGCTGAAGAT<br>AAAGGAATTCTTACTGTTGATGAACTTTTGGCC<br>ATCAGAATTCCATTGAATGACCTTTTTAGATGC<br>AATAGTTTATCAACTTTGGAAAAGAATGATGTT<br>GTCCAACACTACTGGGATGTTCTTGTACAAGCT<br>TTTGTCCAAAATGGCACAGTGAGCACAAATGA<br>GTTCCTGTGTGATAAAGACAAAACTTCAACAGT<br>GGCACCCACCATACACACCACTGTGCCATCTCC<br>TACTACAACACCTACTCCAAAGGAAAAACCAG<br>AAGCTGGAACCTATTCAGTTAATAATGGCAATG<br>ATACTTGTCTGCTGGCTACCATGGGGCTGCAGC<br>TGAACATCACTCAGGATAAGGTTGCTTCAGTTA<br>TTAACATCAACCCCAATACAACTCACTCCACAG<br>GCAGCTGCCGTTCTCACACTGCTCTACTTAGAC<br>TCAATAGCAGCACCATTAAGTATCTAGACTTTG<br>TCTTTGCTGTGAAAAATGAAAACCGATTTTATC<br>TGAAGGAAGTGAACATCAGCATGTATTTGGTTA<br>ATGGCTCCGTTTTCAGCATTGCAAATAACAATC<br>TCAGCTACTGGGATGCCCCCCTGGGAAGTTCTT<br>ATATGTGCAACAAAGAGCAGACTGTTTCAGTGT<br>CTGGAGCATTTCAGATAAATACCTTTGATCTAA<br>GGGTTCAGCCTTTCAATGTGACACAAGGAAAG<br>TATTCTACAGCTCAAGACTGCAGTGCAGATGAC<br>GACAACTTCCTTGTGCCCATAGCGGTGGGAGCT<br>GCCTTGGCAGGAGTACTTATTCTAGTGTTGCTG<br>GCTTATTTTATTGGTCTCAAGCACCATCATGCT<br>GGATATGAGCAATTTTAG (SEQ ID NO: 213) |
| Human<br>LAMP2b | MVCFRLFPVPGSGLVLVCLVLGA<br>VRSYALELNLTDSENATCLYAKW<br>QMNFTVRYETTNKTYKTVTISDH<br>GTVTYNGSICGDDQNGPKIAVQF<br>GPGFSWIANFTKAASTYSIDSVSF<br>SYNTGDNTTFPDAEDKGILTVDEL<br>LAIRIPLNDLFRCNSLSTLEKNDV<br>VQHYWDVLVQAFVQNGTVSTNE<br>FLCDKDKTSTVAPTIHTTVPSPTT<br>TPTPKEKPEAGTYSVNNGNDTCL | ATGGTGTGCTTCCGCCTCTTCCCGGTTCCGGGC<br>TCAGGGCTCGTTCTGGTCTGCCTAGTCCTGGGA<br>GCTGTGCGGTCTTATGCATTGGAACTTAATTTG<br>ACAGATTCAGAAAATGCCACTTGCCTTTATGCA<br>AAATGGCAGATGAATTTCACAGTACGCTATGA<br>AACTACAAATAAAACTTATAAAACTGTAACCA<br>TTTCAGACCATGGCACTGTGACATATAATGAA<br>GCATTTGTGGGGATGATCAGAATGGTCCCAAA<br>ATAGCAGTGCAGTTCGGACCTGGCTTTTCCTGG<br>ATTGCGAATTTTACCAAGGCAGCATCTACTTAT |

TABLE 2b-continued

Illustrative Gene product Sequences

| Transgene | Polypeptide | Nucleotide (Open Reading Frame) |
|---|---|---|
| | LATMGLQLNITQDKVASVININPN TTHSTGSCRSHTALLRLNSSTIKY LDFVFAVKNENRFYLKEVNISMY LVNGSVFSIANNNLSYWDAPLGS SYMCNKEQTVSVSGAFQINTFDL RVQPFNVTQGKYSTAQECSLDDD TILIPIIVGAGLSGLIIVIVIAYVIGR RKSYAGYQTL (SEQ ID NO: 216) | TCAATTGACAGCGTCTCATTTTCCTACAACACT GGTGATAACACAACATTTCCTGATGCTGAAGAT AAAGGAATTCTTACTGTTGATGAACTTTTGGCC ATCAGAATTCCATTGAATGACCTTTTTAGATGC AATAGTTTATCAACTTTGGAAAAGAATGATGTT GTCCAACACTACTGGGATGTTCTTGTACAAGCT TTTGTCCAAAATGGCACAGTGAGCACAAATGA GTTCCTGTGTGATAAAGACAAAACTTCAACAGT GGCACCCACCATACACACCACTGTGCCATCTCC TACTACAACACCTACTCCAAAGGAAAAACCAG AAGCTGGAACCTATTCAGTTAATAATGGCAATG ATACTTGTCTGCTGGCTACCATGGGGCTGCAGC TGAACATCACTCAGGATAAGGTTGCTTCAGTTA TTAACATCAACCCCAATACAACTCACTCCACAG GCAGCTGCCGTTCTCACACTGCTCTACTTAGAC TCAATAGCAGCACCATTAAGTATCTAGACTTTG TCTTTGCTGTGAAAAATGAAAACCGATTTTATC TGAAGGAAGTGAACATCAGCATGTATTTGGTTA ATGGCTCCGTTTTCAGCATTGCAAATAACAATC TCAGCTACTGGGATGCCCCCCTGGGAAGTTCTT ATATGTGCAACAAAGAGCAGACTGTTTCAGTGT CTGGAGCATTTCAGATAAATACCTTTGATCTAA GGGTTCAGCCTTTCAATGTGACACAAGGAAAG TATTCTACAGCCCAAGAGTGTTCGCTGGATGAT GACACCATTCTAATCCCAATTATAGTTGGTGCT GGTCTTTCAGGCTTGATTATCGTTATAGTGATT GCTTACGTAATTGGCAGA AGAAAAAGTTATGCTGGATATCAGACTCTGTA A (SEQ ID NO: 215) |
| Human LAMP2c | MVCFRLFPVPGSGLVLVCLVLGA VRSYALELNLTDSENATCLYAKW QMNFTVRYETTNKTYKTVTISDH GTVTYNGSICGDDQNGPKIAVQF GPGFSWIANFTKAASTYSIDSVSF SYNTGDNTTFPDAEDKGILTVDEL LAIRIPLNDLFRCNSLSTLEKNDV VQHYWDVLVQAFVQNGTVSTNE FLCDKDKTSTVAPTIHTTVPSPTT TPTPKEKPEAGTYSVNNGNDTCL LATMGLQLNITQDKVASVININPN TTHSTGSCRSHTALLRLNSSTIKY LDFVFAVKNENRFYLKEVNISMY LVNGSVFSIANNNLSYWDAPLGS SYMCNKEQTVSVSGAFQINTFDL RVQPFNVTQGKYSTAEECSADSD LNFLIPVAVGVALGFLIIVVFISYM IGRRKSRTGYQSV (SEQ ID NO: 218) | ATGGTGTGCTTCCGCCTCTTCCCGGTTCCGGGC TCAGGGCTCGTTCTGGTCTGCCTAGTCCTGGGA GCTGTGCGGTCTTATGCATTGGAACTTAATTTG ACAGATTCAGAAAATGCCACTTGCCTTTATGCA AAATGGCAGATGAATTTCACAGTACGCTATGA AACTACAAATAAAACTTATAAAACTGTAACCA TTTCAGACCATGGCACTGTGACATATAATGGAA GCATTTGTGGGGATGATCAGAATGGTCCCAAA ATAGCAGTGCAGTTCGGACCTGGCTTTTCCTGG ATTGCGAATTTTACCAAGGCAGCATCTACTTAT TCAATTGACAGCGTCTCATTTTCCTACAACACT GGTGATAACACAACATTTCCTGATGCTGAAGAT AAAGGAATTCTTACTGTTGATGAACTTTTGGCC ATCAGAATTCCATTGAATGACCTTTTTAGATGC AATAGTTTATCAACTTTGGAAAAGAATGATGTT GTCCAACACTACTGGGATGTTCTTGTACAAGCT TTTGTCCAAAATGGCACAGTGAGCACAAATGA GTTCCTGTGTGATAAAGACAAAACTTCAACAGT GGCACCCACCATACACACCACTGTGCCATCTCC TACTACAACACCTACTCCAAAGGAAAAACCAG AAGCTGGAACCTATTCAGTTAATAATGGCAATG ATACTTGTCTGCTGGCTACCATGGGGCTGCAGC TGAACATCACTCAGGATAAGGTTGCTTCAGTTA TTAACATCAACCCCAATACAACTCACTCCACAG GCAGCTGCCGTTCTCACACTGCTCTACTTAGAC TCAATAGCAGCACCATTAAGTATCTAGACTTTG TCTTTGCTGTGAAAAATGAAAACCGATTTTATC TGAAGGAAGTGAACATCAGCATGTATTTGGTTA ATGGCTCCGTTTTCAGCATTGCAAATAACAATC TCAGCTACTGGGATGCCCCCCTGGGAAGTTCTT ATATGTGCAACAAAGAGCAGACTGTTTCAGTGT CTGGAGCATTTCAGATAAATACCTTTGATCTAA GGGTTCAGCCTTTCAATGTGACACAAGGAAAG TATTCTACAGCTGAAGAATGTTCTGCTGACTCT GACCTCAACTTTCTTATTCCTGTTGCAGTGGGT GTGGCCTTGGGCTTCCTTATAATTGTTGTCTTTA TCTCTTATATGATTGGAAGAAGGAAAAGTCGTA CTGGTTATCAGTCTGTGTAA (SEQ ID NO: 217) |
| Human DSP_DPI | MSCNGGSHPRINTLGRMIRAESGP DLRYEVTSGGGGTSRMYYSRRG VITDQNSDGYCQTGTMSRHQNQ NTIQELLQNCSDCLMRAELIVQPE LKYGDGIQLTRSRELDECFAQAN DQMEILDSLIREMRQMGQPCDAY QKRLLQLQEQMRALYKAISVPRV | ATGAGCTGCAACGGAGGCTCCCACCCGCGGAT CAACACTCTGGGCCGCATGATCCGCGCCGAGT TCGGGCCCGGACCTGCGCTACGAGGTGACCAGCG GCGGCGGGGGCACCAGCAGGATGTACTATTCT CGGCGCGGCGTGATCACCGACCAGAACTCGGA CGGCTACTGTCAAACCGGCACGATGTCCAGGC ACCAGAACCAGAACACCATCCAGGAGCTGCTG |

TABLE 2b-continued

Illustrative Gene product Sequences

| Transgene | Polypeptide | Nucleotide (Open Reading Frame) |
|---|---|---|
| | RRASSKGGGGYTCQSGSGWDEFT<br>KHVTSECLGWMRQQRAEMDMV<br>AWGVDLASVEQHINSHRGIHNSI<br>GDYRWQLDKIKADLREKSAIYQL<br>EEEYENLLKASFERMDHLRQLQN<br>IIQATSREIMWINDCEEEELLYDW<br>SDKNTNIAQKQEAFSIRMSQLEVK<br>EKELNKLKQESDQLVLNQHPASD<br>KIEAYMDTLQTQWSW<br>ILQITKCIDVHLKENAAYFQFFEE<br>AQSTEAYLKGLQDSIRKKYPCDK<br>NMPLQHLLEQIKELEKEREKILEY<br>KRQVQNLVNKSKKIVQLKPRNPD<br>YRSNKPIILRALCDYKQDQKIVHK<br>GDECILKDNNERSKWYVTGPGGV<br>DMLVPSVGLIIPPPNPLAVDLSCKI<br>EQYYEAILALWNQLYINMKSLVS<br>WHYCMIDIEKIRAMTIAKLKTMR<br>QEDYMKTIADLELHYQEFIRNSQ<br>GSEMFGDDDKRKIQSQFTDAQKH<br>YQTLVIQLPGYPQHQTVTTTEITH<br>HGTCQDVNHNKVIETNRENDKQE<br>TWMLMELQKIRRQIEHCEGRMTL<br>KNLPLADQGSSHHITVKINELKSV<br>QNDSQAIAEVLNQLKDMLANFRG<br>SEKYCYLQNEVFGLFQKLENING<br>VTDGYLNSLCTVRALLQAILQTE<br>DMLKVYEARLTEEETVCLDLDKV<br>EAYRCGLKKIKNDLNLKKSLLAT<br>MKTELQKAQQIHS<br>QTSQQYPLYDLDLGKFGEKVTQL<br>TDRWQRIDKQIDFRLWDLEKQIK<br>QLRNYRDNYQAFCKWLYDAKRR<br>QDSLESMKFGDSNTVMRFLNEQK<br>NLHSEISGKRDKSEEVQKIAELCA<br>NSIKDYELQLASYTSGLETLLNIPI<br>KRTMIQSPSGVILQEAADVHARYI<br>ELLTRSGDYYRFLSEMLKSLEDL<br>KLKNTKIEVLEEERLARDANSEN<br>CNKNKFLDQNLQKYQAECSQFK<br>AKLASLEELKRQAELDGKSAKQN<br>LDKCYGQIKELNEKITRLTYEIED<br>EKRRRKSVEDRFDQQKNDYDQL<br>QKARQCEKENLGWQKLESEKAIK<br>EKEYEIERLVLLQEEGTRKREYE<br>NELAKVRNHYNEEMSNLENKYE<br>TEINITKTTIKEISMQKEDDSKNLR<br>NQLDRLSRENRDLKDEIVRLNDSI<br>LQATEQRRRAEENALQQKACGSE<br>IMQKKQHLEIELKQVMQQRSEDN<br>ARHKQSLEEAAKTIQDKNKEIERL<br>KAEFQEEAKRRWEYENELSKVRN<br>NYDEEIISLKNQFETEINITKTTIHQ<br>LTMQKEEDTSGYRAQIDNLTREN<br>RSLEEIKRLKNTLTQTTENLRRV<br>EEDIQQQKATGSEVSQRKQQLEV<br>ELRQVTQMRTEESVRYKQSLDDA<br>AKTIQDKNKEIERLKQLIDKETND<br>RKCLEDENARLQRVQYDLQKAN<br>SSATETINKLKVQEQELTRLRIDY<br>ERVSQERTVKDQDITRFQNSLKEL<br>QLQKQKVEEELNRLKRTASEDSC<br>KRKKLEEELEGMRRSLKEQAIKIT<br>NLTQQLEQASIVKKRSEDDLRQQ<br>RDVLDGHLREKQRTQEELRRLSS<br>EVEALRRQLLQEQESVKQAHLRN<br>EHFQKAIEDKSRSLNESKIEIERLQ<br>SLTENLTKEHLMLEEEELRNLRLEY<br>DDLRRGRSEADSDKNATILELRSQ<br>LQISNNRTLELQGLINDLQREREN<br>LRQEIEKFQKQALEASNRIQESKN<br>QCTQVVQERESLLVKIKVLEQDK<br>ARLQRLEDELNRAKSTLEAETRV<br>KQRLECEKQQIQNDLNQWKTQY<br>SRKEEAIRKIESEREKSEREKNSLR<br>SEIERLQAEIKRIEERCRRKLEDST | CAGAACTGCTCCGACTGCTTGATGCGAGCAGA<br>GCTCATCGTGCAGCCTGAATTGAAGTATGGAG<br>ATGGAATACAACTGACTCGGAGTCGAGAATTG<br>GATGAGTGTTTTGCCCAGGCCAATGACCA<br>AATGGAAATCCTCGACAGCTTGATCAGAGAGA<br>TGCGGCAGATGGGCCAGCCCTGTGATGCTTACC<br>AGAAAAGGCTTCTTCAGCTCCAAGAGCAAATG<br>CGAGCCCTTTATAAAGCCATCAGTGTCCCTCGA<br>GTCCGCAGGGCCAGCTCCAAGGGTGGTGGAGG<br>CTACACTTGTCAGAGTGGCTCTGGCTGGGATGA<br>GTTCACCAAACATGTCACCAGTGAATGTTTGGG<br>GTGGATGAGGCAGCAAAGGGCGGAGATGGACA<br>TGGCTGGCCTGGGGTGTGGACCTGGCCTCAGTGG<br>AGCAGCACATTAACAGCCACCGGGGCATCCAC<br>AACTCCATCGGCGACTATCGCTGGC<br>AGCTGGACAAAATCAAAGCCGACCTGCGCGAG<br>AAATCTGCGATCTACCAGTTGGAGGAGGAGTA<br>TGAAAACCTGCTGAAAGCGTCCTTTGAGAGGA<br>TGGATCACCTGCGACAGCTGCAGAACATCATTC<br>AGGCCACGTCCAGGGAGATCATGTGGATCAAT<br>GACTGCGAGGAGGAGGAGCTGCTGTACGACTG<br>GAGCGACAAGAACACCAACATCGCTCAGAAAC<br>AGGAGGCCTTCTCCATACGCATGAGTCAACTGG<br>AAGTTAAAGAAAAAGAGCTCAATAAGCTGAAA<br>CAAGAAAGTGACCAACTTGTCCTCAATCAGCAT<br>CCAGCTTCAGACAAAATTGAGGCCTATATGGA<br>CACTCTGCAGACGCAGTGGAGTTGGATTCTTCA<br>GATCACCAAGTGCATTGATGTTCATCTGAAAGA<br>AAATGCTGCCTACTTTCAGTTTTTTGAAGAGGC<br>AGTCTACTGAAGCATACCTGAAGGGGCTCC<br>AGGACTCCATCAGGAAGAAGTACCCCTGCGAC<br>AAGAACATGCCCCTGCAGCACCTGCTGGAACA<br>GATCAAGGAGCTGGAGAAAGAACGAGAGAAA<br>ATCCTTGAATACAAGCGTCAGGTGCAGAACTTG<br>GTAAACAAGTCTAAGAAGATTGTACAGCTGAA<br>GCCTCGTAACCCAGACTACAGAAGCAATAAAC<br>CCATTATTCTCAGAGCTCTCTG<br>TGACTACAAACAAGATCAGAAAATCGTGCATA<br>AGGGGGATGAGTGTATCCTGAAGGACAACAAC<br>GAGCGCAGCAAGTGGTACGTGACGGGCCCGGG<br>AGGCGTTGACATGCTTGTTCCCTCTGTGGGGCT<br>GATCATCCCTCCTCCGAACCCACTGGCCGTGGA<br>CCTCTCTTGCAAGATTGAGCAGTACTACGAAGC<br>CATCTTGGCTCTGTGGAACCAGCTCTACATCAA<br>CATGAAGAGCCTGGTGTCCTGGCACTACTGCAT<br>GATTGACATAGAGAAGATCAGGGCCATGACAA<br>TCGCCAAGCTGAAAACAATGCGGCAGGAAGAT<br>TACATGAAGACGATAGCCGACCTTGAGTTACAT<br>TACCAAGAGTTCATCAGAAATAGCCAAGGCTC<br>AGAGATGTTTGGAGATGATGACAAGCGGAAAA<br>TACAGTCTCAGTTCACCGATGCCCAGAAGCATT<br>ACCAGACCCTGGTCATTCAGCTCCCTGGCTATC<br>CCCAGCACCAGACAGTGACCACAACTGAAATCC<br>ACTCATCATGGAACCTGCCAAGATGTCAACCAT<br>AATAAAGTAATTGAAACCAACAGAGAAAATGA<br>CAAGCAAGAAACATGGATGCTGATGGAGCTGC<br>AGAAGATTCGCAGGCAGATAGAGCACTGCGAG<br>GGCAGGATGACTCTCAAAAACCTCCCTCTAGCA<br>GACCAGGGATCTTCTCACCACATCACAGTGAA<br>AATTAACGAGCTTAAGAGTGTGCAGAATGATT<br>CACAAGCAATTGCTGAGGTTCTCAACCAGCTTA<br>AAGATATGCTTGCCAACTTCAGAGGTTCTGAAA<br>AGTACTGCTATTTACAGAATGAAGTATTTGGAC<br>TATTTCAGAAACTGGAAAATATCAATGGTGTTA<br>CAGATGGCTACTTAAATAGCTTATGCACAGTAA<br>GGGCACTGCTCCAGGCTATTCTCCAAACAGAA<br>GACATGTTAAAGGTTTATGAAGCCAGGCTCACT<br>GAGGAGGAAACTGTCTGCCTGGACCTGGATAA<br>AGTGGAAGCTTACCGCTGTGGACTGAAGAAAA<br>TAAAAAATGA<br>CTTGAACTTGAAGAAGTCGTTGTTGGCCACTAT<br>GAAGACAGAACTACAGAAAGCCCAGCAGATCC<br>ACTCTCAGACTTCACAGCAGTATCCACTTTATG<br>ATCTGGACTTGGGCAAGTTCGGTGAAAAAGTC<br>ACACAGCTGACAGACCGCTGGCAAAGGATAGA<br>TAAACAGATCGACTTTAGGTTATGGGACCTGGA |

TABLE 2b-continued

Illustrative Gene product Sequences

| Transgene | Polypeptide | Nucleotide (Open Reading Frame) |
|---|---|---|
| | RETQSQLETERSRYQREIDKLRQR PYGSHRETQTECEWTVDTSKLVF DGLRKKVTAMQLYECQLIDKTTL DKLLKGKKSVEEVASEIQPFLRGA GSIAGASASPKEKYSLVEAKRKK LISPESTVMLLEAQAATGGIIDPHR NEKLTVDSAIARDLIDFDDRQQIY AAEKAITGFDDPFSGKTVSVSEAI KKNLIDRETGMRLLEAQIASGGV VDPVNSVFLPKDVALARGLIDRD LYR SLNDPRDSQKNFVDPVTKKKVSY VQLKERCRIEPHTGLLLLSVQKRS MSFQGIRQPVTVTELVDSGILRPS TVNELESGQISYDEVGERIKDFLQ GSSCIAGIYNETTKQKLGIYEAMKI GLVRPGTALELLEAQAATGFIVDP VSNLRLPVEEAYKRGLVGIEFKEK LLSAERAVTGYNDPETGNIISLFQ AMNKELIEKGHGIRLLEAQIATGG IIDPKESHRLPVDIAYKRGYFNEEL SEILSDPSDDTKGFFDPNTEENLT YLQLKERCIKDEETGLCLLPLKEK KKQVQTSQKNTLRKRRVVIVDPE TNKEMSVQEAYKKGLIDYETFKE LCEQECEWEEITITGSDGSTRVVL VDRKTGSQYDIQDAIDKGLVDRK FFDQYRSGSLSLTQFADMISLKNG VGTSSSMGSGVSDDVFSSSRHESV SKISTISSVRNLTIRSSSFSDTLEES SPIAAIFDTENLEKISITEGIERGIV DSITGQRLLEAQACTGGIIHPTTG QKLSLQDAVSQGVIDQDMATRLK PAQKAFIGFEGVKGKKKMSAAEA VKEKWLPYEAGQRFLEFQYLTGG LVDPEVHGRISTEEAIRKGFIDGR AAQRLQDTSSYAKILTCPKTKLKI SYKDAINRSMVEDITGLRLLEAAS VSSKGLPSPYNMSSAPGSRSGSRS GSRSGSRSGSRSGSRRGSFDATGN SSYSYSYSFSSSSIGH (SEQ ID NO: 220) | GAAACAAATCAAGCAATTGAGGAATTATCGTG ATAACTATCAGGCTTTCTGCAAGTGGCTCTATG ATGCTAAACGCCGCCAGGATTCCTTAGAATCCA TGAAATTTGGAGATTCCAACACAGTCATGCGGT TTTTGAATGAGCAGAAGAACTTGC ACAGTGAAATATCTGGCAAACGAGACAAATCA GAGGAAGTACAAAAAATTGCTGAACTTTGCGC CAATTCAATTAAGGATTATGAGCTCCAGCTGGC CTCATACACCTCAGGACTGGAAACTCTGCTGAA CATACCTATCAAGAGGACCATGATTCAGTCCCC TTCTGGGGTGATTCTGCAAGAGGCTGCAGATGT TCATGCTCGGTACATTGAACTACTTACAAGATC TGGAGACTATTACAGGTTCTTAAGTGAGATGCT GAAGAGTTTGGAAGATCTGAAGCTGAAAAATA CCAAGATCGAAGTTTTGGAAGAGGAGCTCAGA CTGGCCCGAGATGCCAACTCGGAAAACTGTAA TAAGAACAAATTCCTGGATCAGAACCTGCAGA AATACCAGGCAGAGTGTTCCCAGTTCAAAGCG AAGCTTGCGAGCCTGGAGGAGCTGAAGAGACA GGCTGAGCTGGATGGGAAGTCGGCTAAGCAAA ATCTAGACAAGTGCTACGGCCAAATAAAAGAA CTCAATGAGAAGATCACCCGACTGACTTATGA GATTGAAGATGAAAAGAGAAGAAGAAATCTG TGGAAGACAGATTTGACCAACAGAAGAATGAC TATGACCAACTGCAGAAAGCAAGGCAATGTGA AAAGGAGAACCTTGGTTGGCAGAAATTAGAGT CTGAGAAAGCCATCAAGGAGAAGGAGTACGAG ATTGAAAGGTTGAGGGTTCTACTGCAGGAAGA AGGCACCC GGAAGAGAGAATATGAAAATGAGCTGGCAAAG GTAAGAAACCACTATAATGAGGAGATGAGTAA TTTAAGGAACAAGTATGAAACAGAGATTAACA TTACGAAGACCACCATCAAGGAGATATCCATG CAAAAAGAGGATGCCAAAAATCTTAGAA CCAGCTTGATAGACTTTCAAGGGAAAATCGAG ATCTGAAGGATGAAATTGTCAGGCTCAATGAC AGCATCTTGCAGGCCACTGAGCAGCGAAGGCG AGCTGAAGAAAACGCCCTTCAGCAAAAGGCCT GTGGCTCTGAGATAATCAGAAGAAGCAGCAT CTGGAGATAGAACTGAAGCAGGTCATGCAGCA GCGCTCTGAGGACAATGCCCGGCACAAGCAGT CCCTGGAGGAGGCTGCCAAGACCATTCAGGAC AAAAATAAGGAGATCGAGAGACTCAAAGCTGA GTTTCAGGAGGAGGCCAAGCGCCGCTGGGAAT ATGAAAATGAACTGAGTAAGGTAAGAAACAAT TATGATGAGGAGATCATTAGCTTAAAAAATCA GTTTGAGACCGAGATCAACATCACCAAGACCA CCATCCACCAGCTCACCATGCAGAAGGAAGAG GATACCAGTGGCTACCGGGCTCAGATAGACAA TCTCACCCGAGAAAACAGGAGCTTATCTGAAG AAATAAAGAGGCTGAAGAACACTCTAACCCAG ACCACAGAGAATCTCAGGAGGGTGGAAGAAGA CATCCAACAGCAAAAGGCCACTGGCTCTGAGG TGTCTCAGAGGGAAACAGCAGCTGGAGGTTGAG CTGAGACAAGTCACTCAGATGCGAACAGAGGA GAGCGTAAGATATAAGCAATCTCTTGATGATGC TGCCAAAACCATCCAGGATAAAAACAAGGAGA TAGAAAGGTTAAAACAACTGATCGACAAAGAA ACAAATGACCGGAAATGCCTGGAAGATGAAAA CGCGAGATTACAAAGGGTCCAGTATGACCTGC AGAAAGCAAACAGTAGTGCGACGGAGACAATA AACAAACTGAAGGTTCAGGAGCAAGAACTGAC ACGCCTGAGGATCGACTATGAAAGGGTTTCCC AGGAGAGGACTGTGAAGGACCAGGATATCACG CGGTTCCAGAACTCTCTGAAAGAGCTGCAGCTG CAGAAGCAGAAGGTGGAAGAGGAGCTGAATCG GCTGAAGAGGACCGCGTCAGAAGACTCCTGCA AGAGGAAGAAGCTGGAGGAAGAGCTGGAAGG CATGAGGAGGTCGCTGAAGGAGCAAGCCATCA AAATCACCAACCTGACCCAGCAGCTGGAGCAG GCATCCATTGTTAAGAAGAGGAGTGAGGATGA CCTCCGGCAGCAGAGGGACGTGCTGGATGGCC ACCTGAGGGAAAGCAGAGGACCCAGGAAGA GCTGAGGAGGCTCTCTTCTGAGGTCGAGGCCCT GAGGCGGCAGTTACTCCAGGAACAGGAAAGTG TCAAACAAGCTCACTTGAGGAATGAGCATTTCC |

TABLE 2b-continued

Illustrative Gene product Sequences

| Transgene | Polypeptide | Nucleotide (Open Reading Frame) |
|---|---|---|
| | | AGAAGGCGATAGAAGATAAAAGCAGAAGCTTA |
| | | AATGAAAGCAAAATAGAAATTGAGAGGCTGCA |
| | | GTCTCTCACAGAGAACCTGACCAAGGAGCA |
| | | CTTGATGTTAGAAGAAGAACTGCGGAACCTGA |
| | | GGCTGGAGTACGATGACCTGAGGAGAGGACGA |
| | | AGCGAAGCGGACAGTGATAAAAATGCAACCAT |
| | | CTTGGAACTAAGGAGCCAGCTGCAGATCAGCA |
| | | ACAACCGGACCCTGGAACTGCAGGGGCTGATT |
| | | AATGATTTACAGAGAGAGGGAAAATTTGAG |
| | | ACAGGAAATTGAGAAATTCCAAAAGCAGGCTT |
| | | TAGAGGCATCTAATAGGATTCAGGAATCAAAG |
| | | AATCAGTGTACTCAGGTGGTACAGGAAAGAGA |
| | | GAGCCTTCTGGTGAAAATCAAAGTCCTGGAGC |
| | | AAGACAAGGCAAGGCTGCAGAGGCTGGAGGAT |
| | | GAGCTGAATCGTGCAAAATCAACTCTAGAGGC |
| | | AGAAACCAGGGTGAAACAGCGCCTGGAGTGTG |
| | | AGAAACAGCAAATTCAGAATGACCTGAATCAG |
| | | TGGAAGACTCAATATTCCCGCAAGGAGGAGGC |
| | | TATTAGGAAGATAGAATCGGAAAGAGAAAAGA |
| | | GTGAGAGAGAGAAGAACAGTCTTAGGAGTGAG |
| | | ATCGAAAGACTCCAAGCAGAGATCAAGAGAAT |
| | | TGAAGAGAGGTGCAGGCGTAAGCTGGAGGATT |
| | | CTACCAGGGAGACACAGTCACAGTTAGAAACA |
| | | GAACGCTCCCGATATCAGAGGGAGATTGATAA |
| | | ACTCAGACAGCGCCCATATGGGTCCCATCGAG |
| | | AGACCCAGACTGAGTGTGAGTGGACCGTTGAC |
| | | ACCTCCAAGCTGGTGTTTGATGGGCTGAGGAA |
| | | GAAGGTGACAGCAATGCAGCTCTATGAGTGTC |
| | | AGCTGATCGACAAAACAACCTTGGACAAACTA |
| | | TTGAAGGGGAAGAAGTCAGTGGAAGAAGTTGC |
| | | TTCTGAAATCCAGCCATTCCTTCGGGGTGCAGG |
| | | ATCTATCGCTGGAGCATCTGCTTCTCCTAAGGA |
| | | AAAATACTCTTTGGTAGAGGCCAAGAGAAAGA |
| | | AATTAATCAGCCCAGAATCCACAGTCATGCTTC |
| | | TGGAGGCCCAGGCAGCTACAGGTGGTATAATT |
| | | GATCCCCATCGGAATGAGAAGCTGACTGTCGA |
| | | CAGTGCCATAGCTCGGGACCTCATTGACTTCGA |
| | | TGACCGTCAGCAGATATATGCAGCAGAAAAAG |
| | | CTATCACTGGTTTTGATGATCCATTTTCAGGCA |
| | | AGACAGTATCTGTTTCAGAAGCCATCAAGAAA |
| | | AATTTGATTGATAGAGAAACCGGAATGCGCCT |
| | | GCTGGAAGCCCAGATTGCTTCAGGGGGTGTAG |
| | | TAGACCCTGTGAACAGTGTCTTTTTGCCAAAAG |
| | | ATGTCGCCTTGGCCCGGGGGCTGATTGATAGAG |
| | | ATTTGTATCGATCCCTGAATGATCCCCGAGATA |
| | | GTCAGAAAAACTTTGTGGATCCAGTCACCAAA |
| | | AAGAAGGTCAGTTACGTGCAGCTGAAGGAACG |
| | | GTGCAGAATCGAACCACATACTGGTCTGCTCTTG |
| | | CTTTCAGTACAGAAGAGAAGCATGTCCTTCCAA |
| | | GGAATCAGACAACCTGTGACCGTCACTGAGCT |
| | | AGTAGATTCTGGTATATTGAGACCGTCCACTGT |
| | | CAATGAACTGGAATCTGGTCAGATTTCTTATGA |
| | | CGAGGTTGGTGAGAGAATTAAGGACTTCCTCC |
| | | AGGGTTCAAGCTGCATAGCAGGCATATACAAT |
| | | GAGACCACAAAACAGAAGCTTGGCATTTATGA |
| | | GGCCATGAAAATTGGCTTAGTCCGACCTGGTAC |
| | | TGCTCTGGAGTTGCTGGAAGCCCAAGCAGCTAC |
| | | TGGCTTTATAGTGGATCCTGTTAGCAACTTGAG |
| | | GTTACCAGTGGAGGAAGCCTACAAGAGAGGTC |
| | | TGGTGGGCATTGAGTTCAAAGAGAAGCTCCTGT |
| | | CTGCAGAACGAGCTGTCACTGGGTATAATGATC |
| | | CTGAAACAGGAAACATCATCTCTTTGTTCCAAG |
| | | CCATGAATAAGGAACTCATCGAAAAGGGCCAC |
| | | GGTATTCGCTTATTAGAAGCACAGATCGCAACC |
| | | GGGGGGATCATTGACCCAAAGGAGAGCCATCG |
| | | TTTACCAGTTGACATAGCATATAAGAGGGGCTA |
| | | TTTCAATGAGGAACTCAGTGAGATTCTCTCAGA |
| | | TCCAAGTGATGATACCAAAGGATTTTTTGACCC |
| | | CAACACTGAAGAAAATCTTACCTATCTGCAACT |
| | | AAAAGAAAGATGCATTAAGGATGAGGAAACAG |
| | | GGCTCTGTCTTCTGCCTCTGAAAGAAAAGAAGA |
| | | AACAGGTGCAGACATCACAAAAGAATACCCTC |
| | | AGGAAGCGTAGAGTGGTCATAGTTGACCCAGA |
| | | AACCAATAAAGAAATGTCTGTTCAGGAGGCCT |
| | | ACAAGAAGGGCCTAATTGATTATGAAACCTTC |
| | | AAAGAACTGTGTGAGCAGGAATGTGAATGGGA |

TABLE 2b-continued

Illustrative Gene product Sequences

| Transgene | Polypeptide | Nucleotide (Open Reading Frame) |
|---|---|---|
| | | AGAAATAACCATCACGGGATCAGATGGCTCCA<br>CCAGGGTGGTCCTGGTAGATAGAAAGACAGGC<br>AGTCAGTATGATATTCAAGATGCTATTGACAAG<br>GGCCTTGTTGACAGGAAGTTCTTTGATCAGTAC<br>CGATCCGGCAGCCTCAGCCTCACTCAATTTGCT<br>GACATGATCTCCTTGAAAAATGGTGTCGGCACC<br>AGCAGCAGCATGGGCAGTGGTGTCAGCGATGA<br>TGTTTTTAGCAGCTCCCGACATGAATCAGTAAG<br>TAAGATTTCCACCATATCCAGCGTCAGGAATTT<br>AACCATAAGGAGCAGCTCTTTTTCAGACACCCT<br>GGAAGAATCGAGCCCCATTGCAGCCATCTTTGA<br>CACAGAAAACCTGGAGAAAATCTCCATTACAG<br>AAGGTATAGAGCGGGGCATCGTTGACAGCATC<br>ACGGGTCAGAGGCTT<br>CTGGAGGCTCAGGCCTGCACAGGTGGCATCAT<br>CCACCCAACCACGGGCCAGAAGCTGTCACTTC<br>AGGACGCAGTCTCCCAGGGTGTGATTGACCAA<br>GACATGGCCACCAGGCTGAAGCCTGCTCAGAA<br>AGCCTTCATAGGCTTCGAGGGTGTGAAGGGAA<br>AGAAGAAGATGTCAGCAGCAGAGGCAGTGAAA<br>GAAAAATGGCTCCCGTATGAGGCTGGCCAGCG<br>CTTCCTGGAGTTCCAGTACCTCACGGGAGGTCT<br>TGTTGACCCGGAAGTGCATGGGAGGATAAGCA<br>CCGAAGAAGCCATCCGGAAGGGGTTCATAGAT<br>GGCCGCCGCACACAGAGGCTGCAAGACACCAG<br>CAGCTATGCCAAAATCCTGACCTGCCCCAAAAC<br>CAAATTAAAAATATCCTATAAGGATGCCATAA<br>ATCGCTCCATGGTAGAAGATATCACTGGGCTGC<br>GCCTTCTGGAAGCCGCCTCCGTGTCGTCCAAGG<br>GCTTACCCAGCCCTTACAACATGTCTTCGGCTC<br>CGGGGTCCCGCTCCGGCTCCCGCTCGGGATCTC<br>GCTCCGGATCTCGCTCCGGGTCCCGCAGTGGGT<br>CCCGGAGAGGAAGCTTTGACGCCACAGGGAAT<br>TCTTCCTACTCTTATTCCTACTCATTTAGCAGTA<br>GTTCTATTGGGCACTAG (SEQ ID NO: 219) |
| Human DSP<br>DPII<br>isoform | MSCNGGSHPRINTLGRMIRAESGP<br>DLRYEVTSGGGGTSRMYYSRRG<br>VITDQNSDGYCQTGTMSRHQNQ<br>NTIQELLQNCSDCLMRAELIVQPE<br>LKYGDGIQLTRSRELDECFAQAN<br>DQMEILDSLIREMRQMGQPCDAY<br>QKRLLQLQEQMRALYKAISVPRV<br>RRASSKGGGGYTCQSGSGWDEFT<br>KHVTSECLGWMRQQRAEMDMV<br>AWGVDLASVEQHINSHRGIHNSI<br>GDYRWQLDKIKADLREKSAIYQL<br>EEEYENLLKASFERMDHLRQLQN<br>IIQATSREIMWINDCEEEELLYDW<br>SDKNTNIAQKQEAFSIRMSQLEVK<br>EKELNKLKQESDQLVLNQHPASD<br>KIEAYMDTLQTQWSW<br>ILQITKCIDVHLKENAAYFQFFEE<br>AQSTEAYLKGLQDSIRKKYPCDK<br>NMPLQHLLEQIKELEKEREKILEY<br>KRQVQNLVNKSKKIVQLKPRNPD<br>YRSNKPIILRALCDYKQDQKIVHK<br>GDECILKDNNERSKWYVTGPGGV<br>DMLVPSVGLIIPPPNPLAVDLSCKI<br>EQYYEAILALWNQLYINMKSLVS<br>WHYCMIDIEKIRAMTIAKLKTMR<br>QEDYMKTIADLELHYQEFIRNSQ<br>GSEMFGDDDKRKIQSQFTDAQKH<br>YQTLVIQLPGYPQHQTVTTTEITH<br>HGTCQDVNHNKVIETNRENDKQE<br>TWMLMELQKIRRQIEHCEGRMTL<br>KNLPLADQGSSHHITVKINELKSV<br>QNDSQAIAEVLNQLKDMLANFRG<br>SEKYCYLQNEVFGLFQKLENING<br>VTDGYLNSLCTVRALLQAILQTE<br>DMLKVYEARLTEEETVCLDLDKV<br>EAYRCGLKKIKNDLNLKKSLLAT<br>MKTELQKAQQIHS<br>QTSQQYPLYDLDLGKFGEKVTQL<br>TDRWQRIDKQIDFRLWDLEKQIK<br>QLRNYRDNYQAFCKWLYDAKRR | ATGAGCTGCAACGGAGGCTCCCACCCGCGGAT<br>CAACACTCTGGGCCGCATGATCCGCGCCGAGTC<br>TGGCCCGGACCTGCGCTACGAGGTGACCAGCG<br>GCGGCGGGGGCACCAGCAGGATGTACTATTCT<br>CGGCGCGGCGTGATCACCGACCAGAACTCGGA<br>CGGCTACTGTCAAACCGGCACGATGTCCAGAC<br>ACCAGAACCAGAACACCATCCAGGAGCTGCTG<br>CAGAACTGCTCCGACTGCTTGATGCGAGCAGA<br>GCTCATCGTGCAGCCTGAATTGAAGTATGGAG<br>ATGGAATACAACTGACTCGGAGTCGAGAATTG<br>GATGAGTGTTTTGCCCAGGCCAATGACCAAATG<br>GAAATCCTCGACAGCTTGATCAGAGAGATGCG<br>GCAGATGGGCCAGCCCTGTGATGCTTACCAGA<br>AAAGGCTTCTTCAGCTCCAAGAGCAAATGCGA<br>GCCCTTTATAAAGCCATCAGTGTCCCTCGAGTC<br>CGCAGGGCCAGCTCCAAGGGTGGTGGAGGCTA<br>CACTTGTCAGAGTGGCTCTGGCTGGGATGAGTT<br>CACCAAACATGTCACCAGTGAATGTTTGGGGTG<br>GATGAGGCAGCAAAGGGCGGAGATGGACATGG<br>TGGCCTGGGGTGTGGACCTGGCCTCAGTGGAG<br>CAGCACATTAACAGCCACCGGGGCATCCACAA<br>CTCCATCGGCGACTATCGCTGGC<br>AGCTGGACAAAATCAAAGCCGACCTGCGCGAG<br>AAATCTGCGATCTACCAGTTGGAGGAGGAGTA<br>TGAAAACCTGCTGAAAGCGTCCTTTGAGAGGA<br>TGGATCACCTGCGACAGCTGCAGAACATCATTC<br>AGGCCACGTCCAGGGAGATCATGTGGATCAAT<br>GACTGCGAGGAGGAGGAGCTGCTGTACGACTG<br>GAGCGACAAGAACACCAACATCGCTCAGAAAC<br>AGGAGGCCTTCTCCATACGCATGAGTCAACTGG<br>AAGTTAAAGAAAAAGGCTCAATAAGCTGAAA<br>CAAGAAAGTGACCAACTTGTCCTCAATCAGCAT<br>CCAGCTTCAGACAAAATTGAGGCCTATATGGA<br>CACTCTGCAGACGCAGTGGAGTTGGATTCTTCA<br>GATCACCAAGTGCATTGATGTTCATCTGAAAGA<br>AAATGCTGCCTACTTTCAGTTTTTTGAAGAGGC<br>GCAGTCTACTGAAGCATACCTGAAGGGGCTCC<br>AGGACTCCATCAGGAAGAAGTACCCCTGCGAC<br>AAGAACATGCCCCTGCAGCACCTGCTGGAACA<br>GATCAAGGAGCTGGAGAAAGAACGAGAGAAA |

TABLE 2b-continued

Illustrative Gene product Sequences

| Transgene | Polypeptide | Nucleotide (Open Reading Frame) |
|---|---|---|
| | QDSLESMKFGDSNTVMRFLNEQK<br>NLHSEISGKRDKSEEVQKIAELCA<br>NSIKDYELQLASYTSGLETLLNIPI<br>KRTMIQSPSGVILQEAADVHARYI<br>ELLTRSGDYYRELSEMLKSLEDL<br>KLKNTKIEVLEEELRLARDANSEN<br>CNKNKFLDQNLQKYQAECSQFK<br>AKLASLEELKRQAELDGKSAKQN<br>LDKCYGQIKELNEKITRLTYEIED<br>EKRRRKSVEDRFDQQKNDYDQL<br>QKARQCEKENLGWQKLESEKAIK<br>EKEYEIERLRVLLQEEGTRKREYE<br>NELAKASNRIQESKNQCTQVVQE<br>RESLLVKIKVLEQDKARLQRLED<br>ELNRAKSTLEAETRVKQRLECEKQQ<br>IQNDLNQWKTQYSRKEEAIRKIES<br>EREKSEREKNSLRSEIERLQAEIKR<br>IEERCRRKLED<br>STRETQSQLETERSRYQREIDKLR<br>QRPYGSHRETQTECEWTVDTSKL<br>VFDGLRKKVTAMQLYECQLIDKT<br>TLDKLLKGKKSVEEVASEIQPFLR<br>GAGSIAGASASPKEKYSLVEAKR<br>KKLISPESTVMLLEAQAATGGIID<br>PHRNEKLTVDSAIARDLIDFDDRQ<br>QIYAAEKAITGFDDPFSGKTVSVS<br>EAIKKNLIDRETGMRLLEAQIASG<br>GVVDPVNSVFLPKDVALARGLID<br>RDLYRSLNDPRDSQKNFVDPVTK<br>KKVSYVQLKERVRIEPHTGLLLLS<br>VQKRSMSFQGIRQPVTVTELVDS<br>GILRPSTVNELESGQISYDEVGERI<br>KDFLQGSSCIAGIYNETTKQKLGI<br>YEAMKIGLVRPGTALELLEAQAA<br>TGFIVDPVSNLRLPVEEAYKRGLV<br>GIEFKEKLLSAERAVTGYNDPETG<br>NIISLFQAMNKELIEKGHGIRLLEA<br>QIATGGIIDPKESHRLPVDIAYKRG<br>YFNEELSEILSDPSDDTKGFFDPNT<br>EENLTYLQLKERCIKDEETGLCLL<br>PLKEKKKQVQTSQKNTLRKRRVV<br>IVDPETNKEMSVQEAYKKGLIDY<br>ETFKELCEQECEWEEITITGSDST<br>RVVLVDRKTGSQYDIQDAIDKGL<br>VDRKFFDQYRSGSLSLTQFADMIS<br>LKNGVGTSSSMGSGVSDDVFSSS<br>RHESVSKISTISSVRNLTIRSSSFSD<br>TLEESSPIAAIFDTENLEKISITEGIE<br>RGIVDSITGQRLLEAQACTGGIIHP<br>TTGQKLSLQDAVSQGVIDQDMAT<br>RLKPAQKAFIGFEGVKGKKKMSA<br>AEAVKEKWLPYEAGQRFLEFQYL<br>TGGLVDPEVHGRISTEEAIRKGFI<br>DGRAAQRLQDTSSAKILTCPKT<br>KLKISYKDAINRSMVEDITGLRLL<br>EAASVSSKGLPSPYNMSSAPGSRS<br>GSRSGSRSGSRSGSRSGSRRGSFD<br>ATGNSSYSYSYSFSSSSIGH<br>(SEQ ID NO: 222) | ATCCTTGAATACAAGCGTCAGGTGCAGAACTTG<br>GTAAACAAGTCTAAGAAGATTGTACAGCTGAA<br>GCCTCGTAACCCAGACTACAGAAGCAATAAAC<br>CCATTATTCTCAGAGCTCTCTG<br>TGACTACAAACAAGATCAGAAAATCGTGCATA<br>AGGGGGATGAGTGTATCCTGAAGGACAACAAC<br>GAGCGCAGCAAGTGGTACGTGACGGGCCCGGG<br>AGGCGTTGACATGCTTGTTCCCTCTGTGGGGCT<br>GATCATCCCTCCTCCGAACCCACTGGCCGTGGA<br>CCTCTCTTGCAAGATTGAGCAGTACTACGAAGC<br>CATCTTGGCTCTGTGGAACCAGCTCTACATCAA<br>CATGAAGAGCCTGGTGTCCTGGCACTACTGCAT<br>GATTGACATAGAGAAGATCAGGGCCATGACAA<br>TCGCCAAGCTGAAAACAATGCGGCAGGAAGAT<br>TACATGAAGACGATAGCCGACCTTGAGTTACAT<br>TACCAAGAGTTCATCAGAAATAGCCAAGGCTC<br>AGAGATGTTTGGAGATGATGACAAGCGGAAAA<br>TACAGTCTCAGTTCACCGATGCCCAGAAGCATT<br>ACCAGACCCTGGTCATTCAGCTCCCTGGCTATC<br>CCCAGCACCAGACAGTGACCACAACTGAAATC<br>ACTCATCATGGAACCTGCCAAGATGTCAACCAT<br>AATAAAGTAATTGAAACCAACAGAGAAAATGA<br>CAAGCAAGAAACATGGATGCTGATGGAGCTGC<br>AGAAGATTCGCAGGCAGATAGAGCACTGCGAG<br>GGCAGGATGACTCTCAAAAACCTCCCTCTAGCA<br>GACCAGGGATCTTCTCACCACATCACAGTGAA<br>AATTAACGAGCTTAAGAGTGTGCAGAATGATT<br>CACAAGCAATTGCTGAGGTTCTCAACCAGCTTA<br>AAGATATGCTTGCCAACTTCAGAGGTTCTGAAA<br>AGTACTGCTATTTACAGAATGAAGTATTTGGAC<br>TATTTCAGAAACTGGAAAATATCAATGGTGTTA<br>CAGATGGCTACTTAAATAGCTTATGCACAGTAA<br>GGGCACTGCTCCAGGCTATTCTCCAAACAGAA<br>GACATGTTAAAGGTTTATGAAGCCAGGCTCACT<br>GAGGAGGAAACTGTCTGCCTGGACCTGGATAA<br>AGTGGAAGCTTACCGCTGTGGACTGAAGAAAA<br>TAAAAAATGA (SEQ ID NO: 221)<br>CTTGAACTTGAAGAAGTCGTTGTTGGCCACTAT<br>GAAGACAGAACTACAGAAAGCCCAGCAGATCC<br>ACTCTCAGACTTCACAGCAGTATCCACTTTATG<br>ATCTGGACTTGGGCAAGTTCGGTGAAAAAGTC<br>ACACAGCTGACAGACCGCTGGCAAAGGATAGA<br>TAAACAGATCGACTTTAGGTTATGGGACCTGGA<br>GAAACAAATCAAGCAATTGAGGAATTATCGTG<br>ATAACTATCAGGCTTTCTGCAAGTGGCTCTATG<br>ATGCTAAACGCCGCCAGGATTCCTTAGAATCCA<br>TGAAATTTGGAGATTCCAACACAGTCATGCGGT<br>TTTTGAATGAGCAGAAGAACTTGC<br>ACAGTGAAATATCTGGCAAACGAGACAAATCA<br>GAGGAAGTACAAAAAATTGCTGAACTTTGCGC<br>CAATTCAATTAAGGATTATGAGCTCCAGCTGGC<br>CTCATACACCTCAGGACTGGAAACTCTGCTGAA<br>CATACCTATCAAGAGGACCATGATTCAGTCCCC<br>TTCTGGGGTGATTCTGCAAGAGGCTGCAGATGT<br>TCATGCTCGGTACATTGAACTACTTACAAGATC<br>TGGAGACTATTACAGGTTCTTAAGTGAGATGCT<br>GAAGAGTTTGGAAGATCTGAAGCTGAAAAATA<br>CCAAGATCGAAGTTTTGGAAGAGGAGCTCAGA<br>CTGGCCCGAGATGCCAACTCGGAA<br>AACTGTAATAAGAACAAATTCCTGGATCAGAA<br>CCTGCAGAAATACCAGGCAGAGTGTTCCCAGTT<br>CAAAGCGAAGCTTGCGAGCCTGGAGGAGCTGA<br>AGAGACAGGCTGAGCTGGATGGGAAGTCGGCT<br>AAGCAAAATCTAGACAAGTGCTACGGCCAAAT<br>AAAAGAACTCAATGAGAAGATCACCCGACTGA<br>CTTATGAGATTGAAGATGAAAAGAGAAGAAGA<br>AAATCTGTGGAAGACAGATTTGACCAACAGAA<br>GAATGACTATGACCAACTGCAGAAAGCAAGGC<br>AATGTGAAAAGGAGAACCTTGGTTGGCAGAAA<br>TTAGAGTCTGAGAAAGCCATCAAGGAGAAGGA<br>GTACGAGATTGAAAGGTTGAGGGTTCTACTGC<br>AGGAAGAAGGCACCC<br>GGAAGAGAGAATATGAAAATGAGCTGGCAAAG<br>GCATCTAATAGGATTCAGGAATCAAAGAATCA<br>GTGTACTCAGGTGGTACAGGAAAGAGAGAGCC<br>TTCTGGTGAAAATCAAAGTCCTGGAGCAAGAC |

TABLE 2b-continued

Illustrative Gene product Sequences

| Transgene | Polypeptide | Nucleotide (Open Reading Frame) |
|---|---|---|
| | | AAGGCAAGGCTGCAGAGGCTGGAGGATGAGCT |
| | | GAATCGTGCAAAATCAACTCTAGAGGCAGAAA |
| | | CCAGGGTGAAACAGCGCCTGGAGTGTGAGAAA |
| | | CAGCAAATTCAGAATGACCTGAATCAGTGGAA |
| | | GACTCAATATTCCCGCAAGGAGGAGGCTATTA |
| | | GGAAGATAGAATCGGAAAGAGAAAAGAGTGA |
| | | GAGAGAGAAGAACAGTCTTAGGAGTGAGATCG |
| | | AAAGACTCCAAGCAGAGATCAAGAGAATTGAA |
| | | GAGAGGTGCAGGCGTAAGCTGGAGGATTCTAC |
| | | CAGGGAGACACAGTCACAGTTAGAAACAGAACGC |
| | | TCCCGATATCAGAGGGAGATTGATAAACTCAGA |
| | | CAGCGCCCATATGGGTCCCATCGAGAGACCCA |
| | | GACTGAGTGTGAGTGGACCGTTGACACCTCCA |
| | | AGCTGGTGTTTGATGGGCTGAGGAAGAAGGTG |
| | | ACAGCAATGCAGCTCTATGAGTGTCAGCTGATC |
| | | GACAAAACAACCTTGGACAAACTATTGAAGGG |
| | | GAAGAAGTCAGTGGAAGAAGTTGCTTCTGAAA |
| | | TCCAGCCATTCCTTCGGGGTGCAGGATCTATCG |
| | | CTGGAGCATCTGCTTCTCCTAAGGAAAAATACT |
| | | CTTTGGTAGAGGCCAAGAGAAAGAAATTAATC |
| | | AGCCCAGAATCCACAGTCATGCTTCTGGAGGCC |
| | | CAGGCAGCTACAGGTGGTATAATTGATCCCCAT |
| | | CGGAATGAGAAGCTGACTGTCGACAGTGCCAT |
| | | AGCTCGGGACCTCATTGACTTCGATGACCGTCA |
| | | GCAGATATATGCAGCAGAAAAAGCTATCACTG |
| | | GTTTTGATGATCCATTTTCAGGCAAGACAGTAT |
| | | CTGTTTCAGAAGCCATCAAGAAAAATTTGATTG |
| | | ATAGAGAAACCGGAATGCGCCTGCTGGAAGCC |
| | | CAGATTGCTTCAGGGGGTGTAGTAGACCCTGTG |
| | | AACAGTGTCTTTTTGCCAAAAGATGTCGCCTTG |
| | | GCCCGGGGGCTGATTGATAGAGATTTGTATCGA |
| | | TCCCTGAATGATCCCCGAGATAGTCAGAAAAA |
| | | CTTTGTGGATCCAGTCACCAAAAAGAAGGTCA |
| | | GTTACGTGCAGCTGAAGGAACGGTGCAGAATC |
| | | GAACCACATACTGGTCTGCTCTTGCTTTCAGTA |
| | | CAGAAGAGAAGCATGTCCTTCCAAGGAATCAG |
| | | ACAACCTGTGACCGTCACTGAGCTAGTAGATTC |
| | | TGGTATATTGAGACCGTCCACTGTCAATGAACT |
| | | GGAATCTGGTCAGATTTCTTATGACGAGGTTGG |
| | | TGAGAGAATTAAGGACTTCCTCCAGGGTTCAA |
| | | GCTGCATAGCAGGCATATACAATGAGACCACA |
| | | AAACAGAAGCTTGGCATTTATGAGGCCATGAA |
| | | AATTGGCTTAGTCCGACCTGGTACTGCTCTGGA |
| | | GTTGCTGGAAGCCCAAGCAGCTACTGGCTTTAT |
| | | AGTGGATCCTGTTAGCAACTTGAGGTTACCAGT |
| | | GGAGGAAGCCTACAAGAGAGGTCTGGTGGGCA |
| | | TTGAGTTCAAAGAGAAGCTCCTGTCTGCAGAAC |
| | | GAGCTGTCACTGGGTATAATGATCCTGAAACA |
| | | GGAAACATCATCTCTTTGTTCCAAGCCATGAAT |
| | | AAGGAACTCATCGAAAAGGGCCACGGTATTCG |
| | | CTTATTAGAAGCACAGATCGCAACCGGGGGGA |
| | | TCATTGACCCAAAGGAGAGCCATCGTTTACCAG |
| | | TTGACATAGCATATAAGAGGGGCTATTTCAATGA |
| | | GGAACTCAGTGAGATTCTCTCAGATCCAAGTGAT |
| | | GATACCAAAGGATTTTTTGACCCCAACACTGAA |
| | | GAAAATCTTACCTATCTGCAACTAAAAGAAAG |
| | | ATGCATTAAGGATGAGGAAACAGGGCTCTGTC |
| | | TTCTGCCTCTGAAAGAAAAGAAGAAACAGGTG |
| | | CAGACATCACAAAAGAATACCCTCAGGAAGCG |
| | | TAGAGTGGTCATAGTTGACCCAGAAACCAATA |
| | | AAGAAATGTCTGTTCAGGAGGCCTACAAGAAG |
| | | GGCCTAATTGATTATGAAACCTTCAAAGAACTG |
| | | TGTGAGCAGGAATGTGAATGGGAAGAAATAAC |
| | | CATCACGGGATCAGATGGCTCCACCAGGGTGG |
| | | TCCTGGTAGATAGAAAGACAGGCAGTCAGTAT |
| | | GATATTCAAGATGCTATTGACAAGGGCCTTGTT |
| | | GACAGGAAGTTCTTTGATCAGTACCGATCCGGC |
| | | AGCCTCAGCCTCACTCAATTTGCTGACATGATC |
| | | TCCTTGAAAAATGGTGTCGGCACCAGCAGCAG |
| | | CATGGGCAGTGGTGTCAGCGATGATGTTTTTAG |
| | | CAGCTCCCGACATGAATCAGTAAGTAAGATTTC |
| | | CACCATATCCAGCGTCAGGAATTTAACCATAAG |
| | | GAGCAGCTCTTTTTCAGACACCCTGGAAGAATC |
| | | GAGCCCCATTGCAGCCATCTTTGACACAGAAA |
| | | ACCTGGAGAAAATCTCCA |
| | | TTACAGAAGGTATAGAGCGGGGCATCGTTGAC |

TABLE 2b-continued

Illustrative Gene product Sequences

| Transgene | Polypeptide | Nucleotide (Open Reading Frame) |
|---|---|---|
| | | AGCATCACGGGTCAGAGGCTTCTGGAGGCTCA<br>GGCCTGCACAGGTGGCATCATCCACCCAACCA<br>CGGGGCCAGAAGCTGTCACTTCAGGACGCAGTC<br>TCCCAGGGTGTGATTGACCAAGACATGGCCAC<br>CAGGCTGAAGCCTGCTCAGAAAGCCTTCATAG<br>GCTTCGAGGGTGTGAAGGGAAAGAAGAAGATG<br>TCAGCAGCAGAGGCAGTGAAAGAAAAATGGCT<br>CCCGTATGAGGCTGGCCAGCGCTTCCTGGAGTT<br>CCAGTACCTCACGGGAGGTCTTGTTGACCCGGA<br>AGTGCATGGGAGGATAAGCACCGAAGAAGCCA<br>TCCGGAAGGGGTTCATAGATGGCCGCGCCGCA<br>CAGAGGCTGCAAGACACCAGCAGCTATGCCAA<br>AATCCTGACCTGCCCCAAAACCAAATTAAAAA<br>TATCCTATAAGGATGCCATAAATCGCTCCATGG<br>TAGAAGATATCACTGGGCTGCGCCTTCTGGAAG<br>CCGCCTCCGTGTCGTCCAAGGGCTTACCCAGCC<br>CTTACAACATGTCTTCGGCTCCGGGGTCCCGCT<br>CCGGCTCCCGCTCGGGATCTCGCTCCGGATCTC<br>GCTCCGGGTCCCGCAGTGGGTCCCGGAGAGGA<br>AGCTTTGACGCCACAGGGAATTCTTCCTACTCT<br>TATTCCTACTCATTTAGCAGTAGTTCTATTGGG<br>CACTAG (SEQ ID NO: 221) |
| Human<br>DSG2 | MARSPGRAYALLLLLICFNVGSG<br>LHLQVLSTRNENKLLPKHPHLVR<br>QKRAWITAPVALREGEDLSKKNP<br>IAKIHSDLAEERGLKITYKYTGKG<br>ITEPPFGIFVFNKDTGELNVTSILD<br>REETPFFLLTGYALDARGNNVEK<br>PLELRIKVLDINDNEPVFTQDVFV<br>GSVEELSAAHTLVMKINATDADE<br>PNTLNSKISYRIVSLEPAYPPVFYL<br>NKDTGEIYTTSVTLDREEHSSYTL<br>TVEARDGNGEVTDKPVKQAQVQI<br>RILDVDNDNIPVVENKVLEGMVEE<br>NQVNVEVTRIKVFDADEIGSDNW<br>LANFTFASGNEGGYFHIETDAQT<br>NEGIVTLIKEVDYEEMKNLDFSVI<br>VANKAAFHKSIRSKYKPTPIPIKV<br>KVKNVKEGIHFKSSVISIYVSESM<br>DRSSKGQIIGNFQAFDEDTGLPAH<br>ARYVKLEDRDNWISVDSVTSEIK<br>LAKLPDFESRYVQNGTYTVKIVAI<br>SEDYPRKTITGTVLINVEDINDNC<br>PTLIEPVQTICHDAEYVNVTAEDL<br>DGHPNSGPFSFSVIDKPPGMAEK<br>WKIARQESTSVLLQQSEKKLGRS<br>EIQFLISDNQGFSCPEKQVLTLTVC<br>ECLHGSGCREAQHDSYVGLGPAA<br>IALMILAFLLLLLVPLLLLMCHCG<br>KGAKGFTPIPGTIEMLHPWNNEG<br>APPEDKVVPSFLPVDQGGSLVGR<br>NGVGGMAKEATMKGSSSASIVK<br>GQHEMSEMDGRWEEHRSLLSGR<br>ATQFTGATGAIMTTETTKTARAT<br>GASRDMAGAQAAAVALNEEFLR<br>NYFTDKAASYTEEDENHTAKDCL<br>LVYSQEETESLNASIGCCSFIEGEL<br>DDRFLDDLGLKFKTLAEVCLGQK<br>IDINKEIEQRQKPATETSMNTASH<br>SLCEQTMVNSENTYSSGSSFPVPK<br>SLQEANAEKVTQEIVTERSVSSRQ<br>AQKVATPLPDPMASRNVIATETS<br>YVTGSTMPPTTVILGPSQPQSLIVT<br>ERVYAPASTLVDQPYANEGTVVV<br>TERVIQPHGGGSNPLEGTQHLQD<br>VPYVMRERESFLAPSSGVQPTL<br>AMPNIAVGQNVTVTERVLAPAST<br>LQSSYQIPTENSMTARNTTVSGAG<br>VPGPLPDFGLEESGHSNSTITTSST<br>RVTKHSTVQHSYS<br>(SEQ ID NO: 224) | ATGGCGCGGAGCCCGGGACGCGCGTACGCCCT<br>GCTGCTTCTCCTGATCTGCTTTAACGTTGGAAG<br>TGGACTTCACTTACAGGTCTTAAGCACAAGAAA<br>TGAAAATAAGCTGCTTCCTAAACATCCTCATTT<br>AGTGCGGCAAAAGCGCGCCTGGATCACCGCCC<br>CCGTGGCTCTTCGGGAGGGAGAGGATCTGTCC<br>AAGAAGAATCCAATTGCCAAGATACATTCTGA<br>TCTTGCAGAAGAAAGAGGACTCAAAATTACTT<br>ACAAATACACTGGAAAAGGGATTACAGAGCCA<br>CCTTTTGGTATATTTGTCTTTAACAAAGATACT<br>GGAGAACTGAATGTTACCAGCATTCTTGATCGA<br>GAAGAAACACCATTTTTTCTGCTAACAGGTTAC<br>GCTTTGGATGCAAGAGGAAACAATGTAGAGAA<br>ACCCTTAGAGCTACGCATTAAGGTTCTTGATAT<br>CAATGACAACGAACCAGTGTTCACACAGGATG<br>TCTTTGTTGGGTCTGTTGAAGAGTTGAGTGCAG<br>CACATACTCTTGTGATGAAAATCAATGCAACAG<br>ATGCAGATGAGCCCAATACCCTGAATTCGAAA<br>ATTTCCTATAGAATCGTATCTCTGGAGCCTGCT<br>TATCCTCCAGTGTTCTACCTAAATAAAGATACA<br>GGAGAGATTTATACAACCAGTGTTACCTTGGAC<br>AGAGAGGAACACAGCAGCTACACTTTGACAGT<br>AGAAGCAAGAGATGGCAATGGAGAAGTTACAG<br>ACAAACCTGTAAAACAAGCTCAAGTTCAGATT<br>CGTATTTTGGATGTCAATGACAATATACCTGTA<br>GTAGAAAATAAAGTGCTTGAAGGGATGGTTGA<br>AGAAAATCAAGTCAACGTAGAAGTTACGCGCA<br>TAAAAGTGTTCGATGCAGATGAAATAGGTTCTG<br>ATAATTGGCTGGCAAATTTTACATTTGCATCAG<br>GAAATGA<br>AGGAGGTTATTTCCACATAGAAACAGATGCTC<br>AAACTAACGAAGGAATTGTGACCCTTATTAAG<br>GAAGTAGATTATGAAGAAATGAAGAATCTTGA<br>CTTCAGTGTTATTGTCGCTAATAAAGCAGCTTT<br>TCACAAGTCGATTAGGAGTAAATACAAGCCTA<br>CACCCATTCCCATCAAGGTCAAAGTGAAAAAT<br>GTGAAAGAAGGCATTCATTTTAAAAGCAGCGT<br>CATCTCAATTTATGTTAGCGAGAGCATGGATAG<br>ATCAAGCAAAGGCCAAATAATTGGAAATTTTC<br>AAGCTTTTGATGAGGACCTGGACTACCAGCCC<br>ATGCAAGATATGTAAAATTAGAAGATAGAGAT<br>AATTGGATCTCTGTGGATTCTGTCACATCTGAA<br>ATTAAACTTGCAAAACTTCCTGATTTTGAATCT<br>AGATATGTTCAAAATGGCACATACACTGTAAA<br>GATTGTGGCCATATCAGAAGATTATCCTAGAAA<br>AACCATCACTGGCACAGTCCTTATCAATGTTGA<br>AGACATCAACGACAACTGTCCCACACTGATAG<br>AGCCTGTGCAGACAATCTGTCACGATGCAGAG<br>TATGTGAATGTTACTGCAGAGGACCTGGATGG<br>ACACCCAAACAGTGGCCCTTTCAGTTTCTCCGT<br>CATTGACAAACCACCTGGCATGGCAGAAAAAT<br>GGAAAATAGCACGCCAAGAAAGTACCAGTGTG<br>CTGCTGCAACAAAGTGAGAAAAAGCTTGGGAG |

TABLE 2b-continued

Illustrative Gene product Sequences

| Transgene | Polypeptide | Nucleotide (Open Reading Frame) |
|---|---|---|
| | | AAGTGAAATTCAGTTCCTGATTTCAGACAATCA
GGGTTTTAGTTGTCCTGAAAAGCAGGTCCTTAC
ACTCACAGTTTGTGAGTGTCTGCATGGCAGCGG
CTGCAGGGAAGCACAGCATGACTCCTATGTGG
GCCTGGGACCCGCAGCAATTGCGCTCATGATTT
TGGCCTTTCTGCTCCTGCTATTGGTACCACTTTT
ACTGCTGA
TGTGCCATTGCGGAAAGGGCGCCAAAGGCTTT
ACCCCCATACCTGGCACCATAGAGATGCTGCAT
CCTTGGAATAATGAAGGAGCACCACCTGAAGA
CAAGGTGGTGCCATCATTTCTGCCAGTGGATCA
AGGGGGCAGTCTAGTAGGAAGAAATGGAGTAG
GAGGTATGGCCAAGGAAGCCACGATGAAAGGA
AGTAGCTCTGCTTCCATTGTCAAAGGGCAACAT
GAGATGTCCGAGATGGATGGAAGGTGGGAAGA
ACACAGAAGCCTGCTTTCTGGTAGAGCTACCCA
GTTTACAGGGGCCACAGGCGCTATCATGACCA
CTGAAACCACGAAGACCGCAAGGGCCACAGGG
GCTTCCAGAGACATGGCCGGAGCTCAGGCAGC
TGCTGTTGCACTGAACGAAGAATTCTTAAGAAA
TTATTTCACTGATAAAGCGGCCTCTTACACTGA
GGAAGATGAAAATCACACAGCCAAAGATTGCC
TTCTGGTTTATTCTCAGGAAGAAACTGAATCGC
TGAATGCTTCTATTGGTTGTTGCAGTTTTATTGA
AGGAGAGCTAGATGACCGCTTCTTAGATGATTT
GGGACTTAAATTCAAGACACTAGCTGAAGTTTG
CCTGGGTCAAAAAATAGATATAAATAAGGAAA
TTGAGCAGAGACAAAAACCTGCCACAGAAACA
AGTATGAACACAGCTTC
ACATTCACTCTGTGAGCAAACTATGGTTAATTC
AGAGAATACCTACTCCTCTGGCAGTAGCTTCCC
AGTTCCAAAATCTTTGCAAGAAGCCAATGCAG
AGAAAGTAACTCAGGAAATAGTCACTGAAAGA
TCTGTGTCTTCTAGGCAGGCGCAAAAGGTAGCT
ACACCTCTTCCTGACCCAATGGCTTCTAGAAAT
GTGATAGCAACAGAAACTTCCTATGTCACAGG
GTCCACTATGCCACCAACCACTGTGATCCTGGG
TCCTAGCCAGCCACAGAGCCTTATTGTGACAGA
GAGGGTGTATGCTCCAGCTTCTACCTTGGTAGA
TCAGCCTTATGCTAATGAAGGTACAGTTGTGGT
CACTGAAAGAGTAATACAGCCTCATGGGGGTG
GATCGAATCCTCTGGAAGGCACTCAGCATCTTC
AAGATGTACCTTACGTCATGGTGAGGGAAAGA
GAGAGCTTCCTTGCCCCCAGCTCAGGTGTGCAG
CCTACTCTGGCCATGCCTAATATAGCAGTAGGA
CAGAATGTGACAGTGACAGAAAGAGTTCTAGC
ACCTGCTTCCACTCTGCAATCCAGTTACCAGAT
TCCCACTGAAAATTCTATGACGGCTAGGAACAC
CACGGTGTCTGGAGCTGGAGTCCCTGGCC
CTCTGCCAGATTTTGGTTTAGAGGAATCTGGTC
ATTCTAATTCTACCATAACCACATCTTCCACCA
GAGTTACCAAGCATAGCACTGTACAGCATTCTT
ACTCCTAA (SEQ ID NO: 223) |
| Human JUP | MEVMNLMEQPIKVTEWQQTYTY
DSGIHSGANTCVPSVSSKGIMEED
EACGRQYTLKKTTTYTQGVPPSQ
GDLEYQMSTTARAKRVREAMCP
GVSGEDSSLLLATQVEGQATNLQ
RLAEPSQLLKSAIVHLINYQDDAE
LATRALPELTKLLNDEDPVVVTK
AAMIVNQLSKKEASRRALMGSPQ
LVAAVVRTMQNTSDLDTARCTTS
ILHNLSHHREGLLAIFKSGGIPALV
RMLSSPVESVLFYAITTLHNLLLY
QEGAKMAVRLADGLQKMVPLLN
KNNPKFLAITTDCLQLLAYGNQE
SKLIILANGGPQALVQIMRNYSYE
KLLWTTSRVLKVLSVCPSNKPAIV
EAGGMQALGKHLTSNSPRLVQN
CLWTLRNLSDVATKQEGLESVLK
ILVNQLSVDDVNVLTCATGTLSN
LTCNNSKNKTLVTQNSGVEALIH
AILRAGDKDDITEPAVCALRHLTS
RHPEAEMAQNSVRLNY
GIPAIVKLLNQPNQWPLVKATIGL | ATGGAGGTGATGAACCTGATGGAGCAGCCTAT
CAAGGTGACTGAGTGGCAGCAGACATACACCT
ACGACTCGGGTATCCACTCGGGCGCCAACACCT
GCGTGCCCTCCGTCAGCAGCAAGGGCATCATG
GAGGAGGATGAGGCCTGCGGGCGCCAGTACAC
GCTCAAGAAAACCACCACTTACACCCAGGGGG
TGCCCCCCAGCCAAGGTGATCTGGAGTACCAG
ATGTCCACAACAGCCAGGGCCAAACGGGTGCG
GGAGGCCATGTGCCCTGGTGTGTCAGGCGAGG
ACAGCTCGCTTCTGCTGGCCACCCAGGTGGAGG
GGCAGGCCACCAACCTGCAGCGACTGGCCGAG
CCGTCCCAGCTGCTCAAGTCGGCCATTGTGCAT
CTCATCAACTACC
AGGACGATGCCGAGCTGGCCACTCGCGCCCTG
CCCGAGCTCACCAAACTGCTCAACGACGAGGA
CCCGGTGGTGGTGACCAAGGCGGCCATGATTG
TGAACCAGCTGTCGAAGAAGGAGGCGTCGCGG
CGGGCCCTGATGGGCTCGCCCCAGCTGGTGGCC
GCTGTCGTGCGTACCATGCAGAATACCAGCGA
CCTGGACACAGCCCGCTGCACCACCAGCATCCT
GCACAACCTCTCCCACCACCGGGAGGGGCTGC
TCGCCATCTTCAAGTCGGGTGGCATCCCTGCTC |

TABLE 2b-continued

Illustrative Gene product Sequences

| Transgene | Polypeptide | Nucleotide (Open Reading Frame) |
|---|---|---|
| | IRNLALCPANHAPLQEAAVIPRLV QLLVKAHQDAQRHVAAGTQQPY TDGVRMEEIVEGCTGALHILARD PMNRMEIFRLNTIPLFVQLLYSSV ENIQRVAAGVLCELAQDKEAADA IDAEGASAPLMELLHSRNEGTAT YAAAVLFRISEDKNPDYRKRVSV ELTNSLFKHDPAAWEAAQSMIPIN EPYGDDMDATYRPMYSSDVPLDP LEMHMDMDGDYPIDTYSDGLRPP YPTADHMLA (SEQ ID NO: 226) | TGGTCCGCATGCTCAGCTCCCCTGTGGAGTCGG TCCTGTTCTATGCCATCACCACGCTGCACAACC TGCTCCTGTACCAGGAGGGCGCCAAGATGGCC GTGCGCCTGGACGGCTGCAAAAGATGGT GCCCCTGCTCAACAAGAACAACCCCAAGTTCCT GGCCATCACCACCGACTGCCTGCAGCTCCTGGC CTACGGCAACCAGGAGAGCAAGCTGATCATCC TGGCCAATGGTGGGCCCCAGGCCCTCGTGCAG ATCATGCGTAACTACAGTTATGAAAAGCTGCTC TGGACCACCAGTCGTGTGCTCAAGGTGCTATCC GTGTGTCCCAGCAATAAGCCTGCCATTGTGGAG GCTGGTGGGATGCAGGCCCTGGGCAAGCACCT GACCAGCAACAGCCCCCGCCTGGTGCAGAACT GCCTGTGGACCCTGCGCAACCTCTCAGATGTGG CCACCAAGCAGGAGGGCCTGGAGAGTGTGCTG AAGATTCTGGTGAATCAGCTGAGTGTGGATGA CGTCAACGTCCTCACCTGTGCCACGGGCACACT CTCCAACCTGACATGCAACAACAGCAAGAACA AGACGCTGGTGACACAGAACAGCGGTGTGGAG GCTCTCATCCATGCCATCCTGCGTGCTGGTGAC AAGGACGACATCACGGAGCCTGCCGTCTGCGC TCTGCGCCACCTCACTAGCCGCCACCCTGAGGC CGAGATGGCCCAGAACTCTGTGCGTCTCAACTA TGGCATCCCAGCCATCGTGAAGCTGCTCAACCA GCCCAACCAGTGGCCACTGGTCAAGGCAACCA TCGGCTTGATCAGGAATCTGGCCCTGTGCCCAG CCAACCATGCCCCGCTGCAGGAGGCAGCGGTC ATCCCCCGCCTCGTCCAACTGCTGGTGAAGGCC CACCAGGATGCCCAGCGCCACGTAGCTGCAGG CACACAGCAGCCCTACACGGATGGTGTGAGGA TGGAGGAGATTGTGGAGGGCTGCACCGGAGCA CTGCACATCCTCGCCCGGGACCCCATGAACCGC ATGGAGATCTTCCGGCTCAACACCATTCCCCTG TTTGTGCAGCTCCTGTACTCGTCGGTGGAGAAC ATCCAGCGCGTGGCTGCCGGGGTGCTGTGTGA GCTGGCCCAGGACAAGGAGGCGGCCGACGCCA TTGATGCAGAGGGGGCCTCGGCCCCACTCATG GAGTTGCTGCACTCCCGCAACGAGGGCACTGC CACCTACGCTGCTGCCGTCCTGTTCCGCATCTC CGAGGACAAGAACCCAGACTACCGGAAGCGCG TGTCCGTGGAGCTCACCAACTCCCTCTTCAAGC ATGACCCGGCTGCTGGGAGGCTGCCCAGAGC ATGATTCCCATCAATGAGCCCTATGGAGATGAC ATGGATGCCACCTACCGCCCCATGTACTCCAGC GATGTGCCCCTTGACCCGCTGGGAGATGCACATG GACATGGATGGAGACTACCCCATCGACACCTA CAGCGACGGCCTCAGGCCCCCGTACCCCACTGC AGACCACATGCTGGCCTAG (SEQ ID NO: 225) |
| Human JPH2 N-terminal fragment | MSGGRFDFDDGGAYCGGWEGGK AHGHGLCTGPKGQGEYSGSWNF GFEVAGVYTWPSGNTFEGYWSQ GKRHGLGIETKGRWLYKGEWTH GFKGRYGIRQSSSSGAKYEGTWN NGLQDGYGTETYADGGTYQGQF TNGMRHGYGVRQSVPYGMAVV VRSPLRTSLSSLRSEHSNGTVAPD SPASPASDGPALPSPAIPRGGFALS LLANAEAAARAPKGGGLFQRGA LLGKLRRAESRTSVGSQRSRVSFL KSDLSSGASDAASTASLGEAAEG ADEAAPFEADIDATTTETYMGEW KNDKRSGFGVSERSSGLRYEGEW LDNLRHGYGCTTLPDGHREEGKY RHNVLVKDTKRRMLQLKSNKVR QKVEHSVEGAQRAAAIARQKAEI AASRTSHAKAKAEAAEQAALAA NQESNIARTLARELAPDFYQPGPE YQKRRLLQEILENSESLLEPPDRG AGAAGLPQPPRESPQLHERETPRP EGGSPSPAGTPPQPKRPRPGVSKD GLLSPGAWNGEPSGEGSRSVTPSE GAGRRSPARPATERMAIEALQAP PAPSREPEVALYQGYHSYAVR (SEQ ID NO: 228) | ATGAGTGGGGGCCGCTTCGACTTTGATGATGGA GGGGCGTACTGCGGGGGCTGGGAGGGGGGAAA GGGCCCATGGGCATGGACTGTGCACAGGCCCCA AGGGCCAGGGCGAATACTCTGGCTCCTGGAAC TTTGGCTTTGAGGTGGCAGGTGTCTACACCTGG CCCAGCGGAAACACCTTTGAGGGATACTGGAG CCAGGGCAAACGGCATGGGCTGGGCATAGAGA CCAAGGGGCGCTGGCTCTACAAGGGCGAGTGG ACACATGGCTTCAAGGGACGCTACGGAATCCG GCAGAGCTCAAGCAGCGGTGCCAAGTATGAGG GCACCTGGAACAATGGCCTGCAAGACGGCTAT GGCACCGAGACCTATGCTGATGGAGGGACGTA CCAAGGCCAGTTCACCAACGGCATGCGCCATG GCTACGGAGTACGCCAGTCGGTGCCCTACGGG ATGGCCGTGGTGGTGCGCTCGCCGCTGCGCACG TCGCTGTCGTCCCTGCGCAGCGAGCACAGCAAC GGCACGGTGGCCCCGGACTCTCCCGCCTCGCCG GCCTCCGACGGCCCCGCACTGCCCTCGCCCGCC ATCCCGCGTGGCGGCTTCGCGCTCAGCCTCCTG GCCAATGCCGAGGCGGCCGCGCGGGCGCCCAA GGGCGGCGGCCTCTTCCAGCGGGGCGCGCTGC TGGGCAAGCTGCGGCGCGCAGAGTCGCGCACG TCCGTGGGTAGCCAGCGCAGCCGTGTCAGCTTC CTTAAGAGCGACCTCAGCTCGGGCGCCAGCGA CGCCGCGTCCACCGCCAGCCTGGGAGAGGCCG CCGAGGGCGCCGACGAGGCCGCACCCTTCGAG GCCGATATCGACGCCACCACCACCGAGACCTA |

TABLE 2b-continued

Illustrative Gene product Sequences

| Transgene | Polypeptide | Nucleotide (Open Reading Frame) |
|---|---|---|
| | | CATGGGCGAGTGGAAGAACGACAAACGCTCGG<br>GCTTCGGCGTGAGCGAACGCTCCAGTGGCCTCC<br>GCTACGAGGGCGAGTGGCTGGACAACCTGCGC<br>CACGGCTATGGCTGCACCACGCTGCCCGACGG<br>CCACCGCGAGGAGGGCAAGTACCGCCACAACG<br>TGCTGGTCAAGGACACCAAGCGCCGCATGCTG<br>CAGCTCAAGAGCAACAAGGTCCGCCAGAAAGT<br>GGAGCACAGTGTGGAGGGTGCCCAGCGCGCCG<br>CTGCTATCGCGCGCCAGAAGGCCGAGATTGCC<br>GCCTCCAGGACAAGCCACGCCAAGGCCAAAGC<br>TGAGGCAGCGGAACAGGCCGCCCTGGCTGCCA<br>ACCAGGAGTCCAACATTGCTCGCACTTTGGCCA<br>GGGAGCTGGCTCCGGACTTCTACCAGCCAGGTC<br>CGGAATATCAGAAGCGCCGGCTGCTGCAGGAG<br>ATCCTGGAGAACTCGGAGAGCCTGCTGGAGCC<br>CCCCGACCGGGGCGCCGGCGCAGCGGGCCTCC<br>CACAGCCGCCCCGCGAGAGCCCGCAGCTGCAC<br>GAGCGTGAGACCCCTCGGCCCGAGGGTGGCTC<br>CCCGTCACCGGCCGGGACGCCCCCGCAGCCCA<br>AGCGGCCCAGGCCCGGGGTGTCCAAGGACGGC<br>CTGCTGAGCCCAGGCGCCTGGAACGGCGAGCC<br>CAGCGGTGAGGGCAGCCGGTCAGTCACTCCGT<br>CCGAGGGCGCGGGCCGCCGCAGCCCCGCGCGT<br>CCAGCCACCGAGCGCATGGCCATCGAGGCTCT<br>GCAGGCACCGCCTGCGCCGTCGCGGGAGCCGG<br>AGGTGGCGCTTTACCAGGGCTACCACAGCTATG<br>CTGTGCGC (SEQ ID NO: 227) |
| Human PLN | MEKVQYLTRSAIRRASTIEMPQQ<br>ARQKLQNLFINFCLILICLLLICIIV<br>MLL (SEQ ID NO: 230) | ATGGAGAAAGTCCAATACCTCACTCGCTCAGCT<br>ATAAGAAGAGCCTCAACCATTGAAATGCCTCA<br>ACAAGCACGTCAAAAGCTACAGAATCTATTTAT<br>CAATTTCTGTCTCATCTTAATATGTCTCTTGCTG<br>ATCTGTATCATCGTGATGCTTCTCTGA<br>(SEQ ID NO: 229) |

Promoters and Enhancers

In some embodiments, the expression cassette of the disclosure comprises a promoter. The term "promoter" as used herein refers to a DNA sequence that directs the binding of RNA polymerase and thereby promotes RNA synthesis. Promoters and corresponding protein or polypeptide expression may be ubiquitous, meaning strongly active in a wide range of cells, tissues and species or cell-type specific, tissue-specific, or species specific. Examples of ubiquitous promoters include the CAG promoter and CMB promoter (Yue et al. *BioTechniques* 33:672-678 (2002)). Promoters may be "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

Various promoters may be used. The promoter may be cell-type specific. Constitutive promoters are used in expression cassettes and can be, for example, the cytomegalovirus enhancer fused to the chicken β-actin promoter (CAG), simian virus 40 (SV40) promoter, and the herpes simplex virus thymidine kinase (HSV-TK) promoter (Damdindorj et al. *PLoS One.* 9:e106472 (2014)). Other cell-type specific promoters may also be used. Cardiac cell specific promoters can be, for example, the MLC2v promoter (Phillips et al. *Hypertension* 39:651-5 (2002)) and the cardiac Troponin-T (cTnT) promoter (Konkalmatt et al. *Circ Cardiovasc Imaging.* 6:478-486 (2013)). The transgene polynucleotide sequence in an expression cassette can be, for example, an open reading frame encoding a protein. The ITRs in an expression cassette serve as markers used for viral packaging of the expression cassette (Clark et al. *Hum Gene Ther.* 6:1329-41 (1995)).

Advantageously, the promoter, optionally in conjunction with an enhancer, enables expression of the polynucleotide encoding a polypeptide (e.g., a DWORF polypeptide), or functional variant thereof, in a target cell.

In some embodiments, the expression cassette comprises a single promoter. In some embodiments, the expression cassette comprises at least one promoter. In some embodiments, the expression cassette comprises two promoters. In some embodiments, the expression cassette comprises a ubiquitous promoter. In some embodiments, the expression cassette comprises an inducible promoter. In some embodiments, the expression cassette comprises a cell-type specific promoter. In some embodiments, the promoter specifically promotes expression of the polynucleotide encoding a polypeptide, or functional variant thereof, in a cardiac cell (e.g., a cardiomyocyte). In some embodiments, the promoter specifically promotes expression of the polynucleotide encoding the DWORF polypeptide, or functional variant thereof, in a cardiac cell. In some embodiments, the promoter specifically promotes expression of the polynucleotide encoding the DWORF polypeptide, or functional variant thereof, in a cardiomyocyte. Illustrative promoter and enhancer sequences are provided in Table 3.

In some embodiments, the promoter is a chicken cardiac troponin-T (cTnT or ccTnT) promoter. In some embodiments, the chicken cTnT promoter comprises a polynucleotide sequence that shares at least 90%, 95%, 96%, 97%, 98%, 99%, or 100% identity to SEQ ID NO: 11. In some embodiments, the chicken cTnT promoter comprises SEQ ID NO: 11.

In some embodiments, the promoter is a human cTnT promoter. In some embodiments, the promoter is a short human cTnT promoter. In some embodiments, the short human cTnT promoter comprises a polynucleotide sequence that shares at least 90%, 95%, 96%, 97%, 98%, 99%, or 100% identity to SEQ ID NO: 12. In some embodiments, the short human cTnT promoter comprises SEQ ID NO: 12. In some embodiments, the promoter is a long human cTnT promoter. In some embodiments, the long human cTnT promoter comprises a polynucleotide sequence that shares at least 90%, 95%, 96%, 97%, 98%, 99%, or 100% identity to SEQ ID NO: 13. In some embodiments, the long human cTnT promoter comprises SEQ ID NO: 13.

The expression cassette can include one or more enhancers. The term "enhancer" as used herein refers to a DNA sequence that directs the binding of transcriptional regulatory proteins (e.g., transcriptional machinery) and RNA polymerase, and thereby promotes RNA synthesis. The enhancer can be operably linked to a promoter and modulate the expression of a transgene operably linked to a promoter. The presence of an enhancer can modulate transgene expression by, for example, increasing expression or decreasing expression. An enhancer can modulate transgene expression by, for example, increasing expression levels in a desired cell type, for example, a cardiac cell. An enhancer can modulate transgene expression by, for example, decreasing expression levels in an "off-target" cell type, or a cell type in which expression is not desired.

In some embodiments, the expression cassette comprises a single enhancer. In some embodiments, the expression cassette comprises at least one enhancer. In some embodiments, the expression cassette comprises two enhancers. In some embodiments, the expression cassette comprises three enhancers. In some embodiments, the expression cassette comprises four enhancers. In some embodiments, the expression cassette comprises an enhancer that is operably linked to a promoter. For example, a ACTC1 cardiac enhancer can be linked to a human cTnT promoter. In some embodiments, the expression cassette comprises an enhancer that is operably linked to another enhancer. For example, a ACTC1 cardiac enhancer can be operably linked to an αMHC enhancer. In some embodiments, the expression cassette comprises an enhancer that is operably linked to a promoter and operably linked to another enhancer.

In some embodiments, the enhancer comprises an ACTC1 cardiac enhancer (ACTC1e). In some embodiments, the ACTC1 cardiac enhancer shares at least 90%, 95%, 96%, 97%, 98%, 99%, or 100% identity to SEQ ID NO: 78. In some embodiments, the ACTC1 cardiac enhancer comprises SEQ ID NO: 78. In some embodiments, the enhancer comprises an αMHC enhancer (αMHCe). In some embodiments, the αMHC enhancer shares at least 90%, 95%, 96%, 97%, 98%, 99%, or 100% identity to SEQ ID NO: 79. In some embodiments, the αMHC enhancer comprises SEQ ID NO: 79.

TABLE 3

Illustrative Promoter and Enhancer Sequences

| Promoter/<br>Enhancer<br>Name | Sequences |
|---|---|
| Chicken cTnT | GGGATAAAAGCAGTCTGGGCTTTCACATGA<br>CAGCATCTGGGGCTGCGGCAGAGGGTCGGG<br>TCCGAAGCGCTGCCTTATCAGCGTCCCCAG<br>CCCTGGGAGGTGACAGCTGGCTGGCTTGTG<br>TCAGCCCCTCGGGCACTCACGTATCTCCGT<br>CCGACGGGTTTAAAATAGCAAAACTCTGAG<br>GCCACACAATAGCTTGGGCTTATATGGGCT<br>CCTGTGGGGGAAGGGGGAGCACGGAGGGGG<br>CCGGGGCCGCTGCTGCCAAAATAGCAGCTC<br>ACAAGTGTTGCATTCCTCTCTGGGCGCCGG<br>GCACATTCCTGCTGGCTCTGCCCGCCCCGG<br>GGTGGGCGCCGGGGGGACCTTAAAGCCTCT<br>GCCCCCCAAGGAGCCCTTCCCAGACAGCCG<br>CCGGCACCCACCGCTCCGTGGGA<br>(SEQ ID NO: 11) |
| Short Human<br>cTnT | GTCATGGAGAAGACCCACCTTGCAGATGTC<br>CTCACTGGGGCTGGCAGAGCCGGCAACCTG<br>CCTAAGGCTGCTCAGTCCATTAGGAGCCAG<br>TAGCCTGGAAGATGTCTTTACCCCCAGCAT<br>CAGTTCAAGTGGAGCAGCACATAACTCTTG<br>CCCTCTGCCTTCCAAGATTCTGGTGCTGAG<br>ACTTATGGAGTGTCTTGGAGGTTGCCTTCT<br>GCCCCCCAACCCTGCTCCCAGCTGGCCCTC<br>CCAGGCCTGGGTTGCTGGCCTCTGCTTTAT<br>CAGGATTCTCAAGAGGGACAGCTGGTTTAT<br>GTTGCATGACTGTTCCCTGCATATCTGCTC<br>TGGTTTTAAATAGCTTATCTGAGCAGCTGG<br>AGGACCACATGGGCTTATATGGCGTGGGGT<br>ACATGTTCCTGTAGCCTTGTCCCTGGCACC<br>TGCCAAAATAGCAGCCAACACCCCCCACCC<br>CCACCGCCATCCCCCTGCCCCACCCGTCCC<br>CTGTCGCACATTCCTCCCTCCGCAGGGCTG<br>GCTCACCAGGCCCCAGCCCACATGCCTGCT<br>TAAAGCCCTCTCCATCCTCTGCCTCACCCA<br>GTCCCCGCTGAGACTGAGCAGACGCCTCCA<br>(SEQ ID NO: 12) |
| Long Human<br>cTnT | AGAGGACCCTTTCAAGGACATTAGTGGTGG<br>AGGCAGCATAGTAGCTCCCAAGGCAGGAGG<br>ATTGAGAGAAGAGTTTGAGGACTGGGAAGG<br>CGGGACACATGATTGGGTGATGGGAGAAGG<br>GGGCAGAGAATAGCGAGATTGCTTTCTTTG<br>CCCACGGAGAAACAGAGGAGTGTGGATCAT<br>GAATGGGCAAGATCTTTAAGTGCCAGGGGG<br>GGTCATGGAGGAGGGGAGGGCCTGCTCCAG<br>AGGAGGACCATTCCTGCTTCAGAGCCAAGC<br>AGGACCTAGGCTGTGAAGATTCGGAGAAAG<br>AGATGGAGGGGAGAGTCAGCTCAGCTGCTT<br>ACTGGCTTGCTTTCCTCCTGTCTCTTTCAT<br>TTTCATAATCTACCAAACCCTGCAATGGGC<br>CAGCCTTGAACATACAAGTGCATGTGCATG<br>GTCAGACACAGGCAAGCAAGCAAGACCCCT<br>AGGCCTGACCTATGCATCTGCAATCTAGTA<br>GGTTTAGCAGATCATAGCCCCGCACTGCTT<br>GATTTTAAAGCCGTTAGGGGATGACCTTTG<br>ACAGTCCGCATCACCCCTCTCACACAACGA<br>GCGCCTGTTCAAGGTTCTTGACTGGAAGTT<br>CTACCTTGTATCTGGCCTCCTGTAGCAGTT<br>TCAGTCCATTCCCTGTGAGGAGGGTGTGCC<br>ACATGGCTTTGGGGGTCATGGAGAAGACCC<br>ACCTTGCAGATGTCCTCACTGGGGCTGGCA<br>GAGCCGGCAACCTGCCTAAGGCTGCTCAGT<br>CCATTAGGAGCCAGTAGCCTGGAAGATGTC<br>TTTACCCCCAGCATCAGTTCAAGTGGAGCA<br>GCACATAACTCTTGCCCTCTGCCTTCCAAG<br>ATTCTGGTGCTGAGACTTATGGAGTGTCTT<br>GGAGGTTGCCTTCTGCCCCCCAACCCTGCT<br>CCCAGCTGGCCCTCCCAGGCCTGGGTTGCT<br>GGCCTCTGCTTTATCAGGATTCTCAAGAGG<br>GACAGCTGGTTTATGTTGCATGACTGTTCC<br>CTGCATATCTGCTCTGGTTTTAAATAGCTT<br>ATCTGAGCAGCTGGAGGACCACATGGGCTT<br>ATATGGCGTGGGGTACATGTTCCTGTAGCC |

TABLE 3-continued

Illustrative Promoter and Enhancer Sequences

| Promoter/<br>Enhancer<br>Name | Sequences |
|---|---|
| | TTGTCCCTGGCACCTGCCAAAATAGCAGCC<br>AACACCCCCCACCCCCACCGCCATCCCCCT<br>GCCCCACCCGTCCCCTGTCGCACATTCCTC<br>CCTCCGCAGGGCTGGCTCACCAGGCCCCAG<br>CCCACATGCCTGCTTAAAGCCCTCTCCATC<br>CTCTGCCTCACCCAGTCCCCGCTGAGACTG<br>AGCAGACGCCTCCAGGATCTGTCGGCAGCT<br>GCTGTTCTGAGGTAAGGCTCGGGCAGGGCT<br>CTGGGGAAGAGGAGAGCAGAGAATGGACGG<br>GGAGATGTGAGGGTCTTGGGCCCTGGCATA<br>TTTACCCAGAGTCTGCCTGTGTCCGCAGAA<br>GTCCATGGCCCCTCCTGGTGGAGGCCACAC<br>TTCAGAGGACAGGTTGCCAGGTCTGGGCTC<br>CAAGATTGGTACAATAGAGCAGAGAGA<br>(SEQ ID NO: 13) |
| ACTC1 cardiac<br>enhancer<br>(ACTC1e) | AACTGGCCTGCCCGAGACCAAACGTGCGGA<br>ACGTAGTTAAGTGTTAGAGGTAGGATTTGA<br>AGCCTGTCGATCATTCTGATTCTCCTTTTC<br>TCTACGTCTGCTTCCTGTCAATGGGCATCC<br>TCACTGTCAAATGCAGATGGTACAGCAGGG<br>CTTGGTCTCAGCCAGGCAGGCCTCTCCCCA<br>GTCTCCATGGCTCAGCTGTCCAGCAGTTTC<br>ATCCCTAGACCATCCCAAACATGGTTGAGA<br>AGCTCTGAGGGGAGGACCCAGCACTGCCCG<br>GCCCCTGAAGATAATCAGCAGTCCTGCTCA<br>GCATATCAATCCAAGCCCACTCTAGACAGA<br>GATGCCGGTGCCCAGTTTTCTATTTTTAAC<br>TGGTGTGAACTGAAGGAAAAGCACAGCATT<br>AGAAGTCCAAGCA<br>(SEQ ID NO: 78) |
| αMHC cardiac<br>enhancer<br>(αMHCe) | CCTTCAGATTAAAAATAACTAAGGTAAGGG<br>CCATGTGGGTAGGGGAGGTGGTGTGAGACG<br>GTCCTGTCTCTCCTCTATCTGCCCATCGGC<br>CCTTTGGGGAGGAGGAATGTGCCCAAGGAC<br>TAAAAAAAGGCCCTGGAGCCAGAGGGGCGA<br>GGGCAGCAGACCTTTCATGGGCAAACCTCA<br>GGGCTGCTGTC<br>(SEQ ID NO: 79) |

Introns

The expression cassette can include an intron sequence, for example, a synthetic or chimeric intron sequence. The intron sequence can be used to adjust the length (i.e., size) of the expression cassette for improving recombinant AAV packaging. The intron sequence can be used to improve the efficiency of transgene expression (i.e., mRNA production or transcription) in a host cell containing the expression cassette. In some embodiments, the expression cassette comprises an intron. In some embodiments, the intron comprises the CMV intron (CMVint). In some embodiments, the CMV intron shares at least 90%, 95%, 96%, 97%, 98%, 99%, or 100% identity to SEQ ID NO: 80. In some embodiments, the CMV intron comprises SEQ ID NO: 80. In some embodiments, the intron comprises a chimeric intron. In some embodiments, the chimeric intron shares at least 90%, 95%, 96%, 97%, 98%, 99%, or 100% identity to SEQ ID NO: 81. In some embodiments, the chimeric intron comprises SEQ ID NO: 81.

TABLE 9

Illustrative Intron Sequences

| Intron | Intron Sequence |
|---|---|
| CMV intron | GTAAGTACCGCCTATAGACT<br>CTATAGGCACACCCCTTTGG<br>CTCTTATGCATGCTGACAGA<br>CTAACAGACTGTTCCTTTCC<br>TGGGTCTTTTCTGCAG<br>(SEQ ID NO: 80) |
| Chimeric Intron<br>(Chimint) | GTAAGTATCAAGGTTACAAG<br>ACAGGTTTAAGGAGACCAAT<br>AGAAACTGGGCTTGTCGAGA<br>CAGAGAAGACTCTTGCGTTT<br>CTGATAGGCACCTATTGGTC<br>TTACTGACATCCACTTTGCC<br>TTTCTCTCCACAG<br>(SEQ ID NO: 81) |

WPRE Sequences and Other Post-Transcriptional Elements

In some embodiments, the expression cassette comprises a posttranscriptional regulatory element.

In some embodiments, the expression cassette comprises a woodchuck hepatitis virus post-transcriptional element (WPRE). The WPRE sequence can be inserted, for example, proximal to on the 3' end of a transgene in a viral vector to, for example, optimize gene expression in a viral vector (Lee et al. *Exp Physiol*. 90:33-37 (2005)). In some embodiments, the WPRE comprises a polynucleotide sequence that shares at least 90%, 95%, 96%, 97%, 98%, 99%, or 100% identity to SEQ ID NO: 26. In some embodiments, the WPRE comprises SEQ ID NO: 26.

TABLE 4

Illustrative WPRE Sequence
WPRE Sequence

TCAACCTCTGGATTACAAAATTTGTGAAAGATTGACTGGTATTCT
TAACTATGTTGCTCCTTTTACGCTATGTGGATACGCTGCTTTAAT
GCCTTTGTATCATGCTATTGCTTCCCGTATGGCTTTCATTTTCTC
CTCCTTGTATAAATCCTGGTTGCTGTCTCTTTATGAGGAGTTGTG
GCCCGTTGTCAGGCAACGTGGCGTGGTGTGCACTGTGTTTGCTGA
CGCAACCCCCACTGGTTGGGGCATTGCCACCACCTGTCAGCTCCT
TTCCGGGACTTTCGCTTTCCCCCTCCCTATTGCCACGGCGGAACT
CATCGCCGCCTGCCTTGCCCGCTGCTGGACAGGGGCTCGGCTGTT
GGGCACTGACAATTCCGTGGTGTTGTCGGGGAAATCATCGTCCTT
TCCTTGGCTGCTCGCCTGTGTTGCCACCTGGATTCTGCGCGGGAC
GTCCTTCTGCTACGTCCCTTCGGCCCTCAATCCAGCGGACCTTCC
TTCCCGCGGCCTGCTGCCGGCTCTGCGGCCTCTTCCGCGTCTTCG
(SEQ ID NO: 26)

Poly Adenylation Sequences

In some embodiments, the expression cassette comprises a poly(A) signal sequence. In some embodiments, the poly(A) signal is a BGH poly(A) sequence. In some embodiments, the BGH poly(A) signal sequence comprises the polynucleotide sequence that shares at least 90%, 95%, 96%, 97%, 98%, 99%, or 100% identity to SEQ ID NO: 27. In some embodiments, the poly(A) signal is an SV40 poly(A) signal. In some embodiments, the SV40 poly(A) signal sequence comprises the polynucleotide sequence that shares at least 90%, 95%, 96%, 97%, 98%, 99%, or 100% identity to SEQ ID NO: 28.

TABLE 5

Illustrative Poly(A) Sequences

| Poly(A) Sequence | Sequence |
|---|---|
| BGH | GCCTCGACTGTGCCTTCTAG TTGCCAGCCATCTGTTGTTT GCCCCTCCCCCGTGCCTTCC TTGACCCTGGAAGGTGCCAC TCCCACTGTCCTTTCCTAAT AAAATGAGGAAATTGCATCG CATTGTCTGAGTAGGTGTCA TTCTATTCTGGGGGGTGGGG TGGGGCAGGACAGCAAGGGG GAGGATTGGGAAGACAATAG CAGGCATGCTGGGGA (SEQ ID NO: 27) |
| SV40 | GATCCAGACATGATAAGATA CATTGATGAGTTTGGACAAA CCACAACTAGAATGCAGTGA AAAAAATGCTTTATTTGTGA AATTTGTGATGCTATTGCTT TATTTGTAACCATTATAAGC TGCAATAAACAAGT (SEQ ID NO: 28) |

Inverted Terminal Repeat Sequences

In some embodiments, the expression cassette is flanked by AAV inverted terminal repeats (ITRs). In some embodiments, the ITRs comprise the polynucleotide sequence that shares at least 90%, 95%, 96%, 97%, 98%, 99%, or 100% identity to SEQ ID NO: 14 and/or SEQ ID NO: 15.

TABLE 6

Illustrative ITR Sequences
ITR Sequences

CTGCGCGCTCGCTCGCTCAC
TGAGGCCGCCCGGGCAAAGC
CCGGGCGTCGGGCGACCTTT
GGTCGCCCGGCCTCAGTGAG
CGAGCGAGCGCGCAGAGAGG
GAGTGGCCAACTCCATCACT
AGGGGTTCCT
(SEQ ID NO: 14)

AGGAACCCCTAGTGATGGAG
TTGGCCACTCCCTCTCTGCG
CGCTCGCTCGCTCACTGAGG
CCGGGCGACCAAAGGTCGCC
CGACGCCCGGGCTTTGCCCG
GGCGGCCTCAGTGAGCGAGC
GAGCGCGCAG
(SEQ ID NO: 15)

Illustrative Expression Cassettes

The disclosure provides expression cassettes comprising a polynucleotide comprising a 5' to 3' arrangement (sometimes referred to as an orientation) of elements. In some embodiments, the elements comprise one or more promoters; optionally one or more enhancers; optionally one or more introns; one or more transgenes; optionally one or more WPRE sequences; and optionally one or more polyadenylation sequences (p(A)). Illustrative order of the elements in the polynucleotide are shown in FIG. 1, FIG. 7A, FIG. 7B, FIG. 7C and Table 1. Illustrative orientations of the elements on the polynucleotide are also shown in FIG. 1, FIG. 7A, FIG. 7B, FIG. 7C and Table 1. In some embodiments, the 5' to 3' arrangement of elements is selected from:

5'-promoter-transgene-WPRE-p(A)-3';
5'-promoter-intron-transgene-WPRE-p(A)-3';
5'-promoter-transgene-WPRE-p(A)-promoter-transgene-WPRE-p(A);
5'-enhancer-promoter-transgene-WPRE-p(A)-3';
5'-enhancer-promoter-intron-transgene-WPRE-p(A)-3';
5'-enhancer-enhancer-promoter-transgene-WPRE-p(A)-3';
5'-enhancer-enhancer-promoter-intron-transgene-WPRE-p(A)-3';
5'-enhancer-promoter-intron-transgene-WPRE-p(A)-p(A)-transgene-intron-promoter-enhancer-3';
5'-enhancer-promoter-intron-transgene-WPRE-p(A)-enhancer-promoter-intron-transgene-p(A)-3';
5'-p(A)-WPRE-transgene-intron-promoter-enhancer-enhancer-promoter-intron-transgene-p(A)-3';
5'-promoter-intron-transgene-WPRE-p(A)-p(A)-transgene-intron-promoter-3';
5'-promoter-intron-transgene-WPRE-p(A)-promoter-intron-transgene-p(A)-3'; and
5'-p(A)-WPRE-transgene-intron-promoter-promoter-intron-transgene-p(A)-3'.

In some embodiments, the expression cassettes described herein achieve an increased expression level of the transgene compared to a second expression cassette comprising a polynucleotide having an arrangement of elements from 5' to 3' comprising: 5'-promoter-transgene-WPRE-p(A)-3'. In some embodiments, the expression level is increased between about 1.5-fold and about 150-fold compared the second expression cassette.

In some embodiments, the expression cassettes provided herein comprise the following elements (where the elements can be those described herein, e.g., the sequences of which are provided herein):

5'-promoter-transgene-WPRE-p(A)-3';
5'-promoter-intron-transgene-WPRE-p(A)-3';
5'-promoter-transgene-WPRE-p(A)-promoter-transgene-WPRE-p(A);
5'-enhancer-promoter-transgene-WPRE-p(A)-3';
5'-enhancer-promoter-intron-transgene-WPRE-p(A)-3';
5'-enhancer-enhancer-promoter-transgene-WPRE-p(A)-3';
5'-enhancer-enhancer-promoter-intron-transgene-WPRE-p(A)-3';
5'-enhancer-promoter-intron-transgene-WPRE-p(A)-p(A)-transgene-intron-promoter-enhancer-3';
5'-enhancer-promoter-intron-transgene-WPRE-p(A)-enhancer-promoter-intron-transgene-p(A)-3';
5'-p(A)-WPRE-transgene-intron-promoter-enhancer-enhancer-promoter-intron-transgene-p(A)-3';
5'-promoter-intron-transgene-WPRE-p(A)-p(A)-transgene-intron-promoter-3';
5'-promoter-intron-transgene-WPRE-p(A)-promoter-intron-transgene-p(A)-3'; or
5'-p(A)-WPRE-transgene-intron-promoter-promoter-intron-transgene-p(A)-3'.

In the expression cassettes described herein (such as those listed above), the orientation of the promoter, enhancer, transgene and poly(A) elements can be forward or reverse (e.g., in cases where there are more than one promoters, one promoter, optionally enhancer, and operably linked transgene can be oriented in a forward direction, and another promoter, optionally enhancer, and operably linked transgene can be oriented in a reverse direction).

In some embodiments, the expression cassettes provided herein comprise the following elements:

5'-cardiac-specific promoter-transgene-WPRE-p(A)-3';
5'-cardiac-specific promoter-intron (e.g., chimeric intron)-transgene-WPRE-p(A)-3';

5'-cardiac-specific promoter-transgene-WPRE-p(A)-promoter-transgene-WPRE-p(A), where both promoters and transgene sequences are in the same, forward orientation;

5'-cardiac-specific promoter-transgene-WPRE-p(A) (e.g., bGHpA)-3';

5'-cardiac-specific promoter-intron (e.g., CMV intron)-transgene-WPRE-p(A) (e.g., bGHpA)-3';

5'-enhancer (e.g., ACTC1e)-cardiac-specific promoter-transgene-WPRE-p(A) (e.g., bGHpA)-3';

5'-enhancer (e.g., αMHCe)-cardiac-specific promoter-transgene-WPRE-p(A) (e.g., bGHpA)-3';

5'-enhancer (e.g., ACTC1e)-cardiac-specific promoter-intron (e.g., CMV intron)-transgene-WPRE-p(A) (e.g., bGHpA)-3';

5'-enhancer (e.g., αMHCe)-cardiac-specific promoter-intron (e.g., CMV intron)-transgene-WPRE-p(A) (e.g., bGHpA)-3';

5'-enhancer (e.g., ACTC1e)-enhancer (e.g., αMHCe)-cardiac-specific promoter-transgene-WPRE-p(A) (e.g., bGHpA)-3';

5'-enhancer (e.g., αMHCe)-enhancer (e.g., ACTC1e)-cardiac-specific promoter-transgene-WPRE-p(A) (e.g., bGHpA)-3';

5'-enhancer (e.g., ACTC1e)-enhancer (e.g., αMHCe)-cardiac-specific promoter-intron (e.g., CMV intron)-transgene-WPRE-p(A) (e.g., bGHpA)-3';

5'-enhancer (e.g., αMHCe)-enhancer (e.g., ACTC1e)-cardiac-specific promoter-intron (e.g., CMV intron)-transgene-WPRE-p(A) (e.g., bGHpA)-3';

5'-cardiac-specific promoter-transgene with a codon-optimized polynucleotide sequence-WPRE-p(A) (e.g., bGHpA)-3';

5'-enhancer (e.g., αMHCe)-cardiac-specific promoter-intron (e.g., CMV intron)-transgene-WPRE-p(A) (e.g., bGHpA)-p(A) (e.g., SV40pA)-transgene (e.g., with a codon-optimized polynucleotide sequence)-intron (e.g., chimeric intron)-cardiac-specific promoter-enhancer (e.g., ACTC1e)-3', optionally wherein the first in order transgene and the promoter/enhancer sequences operably linked thereto are in a forward orientation, and the second in order transgene and the promoter/enhancer sequences operably linked thereto are in a reverse orientation;

5'-enhancer (e.g., αMHCe)-cardiac-specific promoter-intron (e.g., CMV intron)-transgene-WPRE-p(A) (e.g., bGHpA)-enhancer (e.g., ACTC1e)-cardiac-specific promoter-intron (e.g., chimeric intron)-transgene (e.g., with a codon-optimized polynucleotide sequence)-p(A) (e.g., SV40pA)-3', optionally wherein both the first and the second in order transgenes and the promoter/enhancer sequences operably linked thereto are in a forward orientation;

5'-p(A) (e.g., bGHpA)-WPRE-transgene-intron (e.g., CMV intron)-cardiac-specific promoter-enhancer (e.g., αMHCe)-enhancer (e.g., ACTC1e)-cardiac-specific promoter-intron (e.g., chimeric intron)-transgene (e.g., with a codon-optimized polynucleotide sequence)-p(A) (e.g., SV40pA)-3', optionally wherein the first in order transgene and the promoter/enhancer sequences operably linked thereto are in a reverse orientation, and the second in order transgene and the promoter/enhancer sequences operably linked thereto are in a forward orientation;

5'-cardiac-specific promoter-intron (e.g., CMV intron)-transgene-WPRE-p(A) (e.g., bGHpA)-p(A) (e.g., SV40pA)-transgene (e.g., with a codon-optimized polynucleotide sequence)-intron (e.g., chimeric intron)-cardiac-specific promoter-3', optionally wherein the first in order transgene and the promoter/enhancer sequences operably linked thereto are in a forward orientation, and the second in order transgene and the promoter/enhancer sequences operably linked thereto are in a reverse orientation;

5'-cardiac-specific promoter-intron (e.g., CMV intron)-transgene-WPRE-p(A) (e.g., bGHpA)-cardiac-specific promoter-intron (e.g., chimeric intron)-transgene (e.g., with a codon-optimized polynucleotide sequence)-p(A) (e.g., SV40pA)-3', optionally wherein both the first and the second in order transgenes and the promoter/enhancer sequences operably linked thereto are in a forward orientation; or 5'-p(A) (e.g., bGHpA)-WPRE-transgene-intron (e.g., CMV intron)-cardiac-specific promoter-cardiac-specific promoter-intron (e.g., chimeric intron)-transgene (e.g., with a codon-optimized polynucleotide sequence)-p(A) (e.g., SV40pA)-3', optionally wherein the first in order transgene and the promoter/enhancer sequences operably linked thereto are in a reverse orientation, and the second in order transgene and the promoter/enhancer sequences operably linked thereto are in a forward orientation.

In the expression cassettes described herein (such as those listed above), the cardiac-specific promoter can be a short human cTnT promoter (such as hcTnTp) or chicken cTnT promoter (such as ccTnTp). The more specific examples of the expression cassettes described above can be found in, e.g., FIG. 1, FIG. 7A, FIG. 7B, FIG. 7C and Table 1.

In some embodiments, the expression cassettes described herein enable an increased expression level of the transgene compared to a second expression cassette comprising a polynucleotide having an arrangement of elements from 5' to 3' comprising: 5'-promoter-transgene-WPRE-p(A)-3'. In some embodiments, the expression level is increased between about 1.5-fold and about 150-fold compared the second expression cassette.

In some embodiments, one or more (e.g., one, two, three or four) elements of the expression cassettes described herein can be omitted.

In some embodiments, one or more (e.g., one, two, three or four) elements of the expression cassettes described herein can be replaced by other elements, such as functionally equivalent elements.

In some embodiments of the expression cassettes provided herein, the WPRE element is replaced by any other post-transcriptional regulatory element known in the art. In some embodiments, the expression cassettes provided herein comprise any post-transcriptional regulatory element known in the art. In some embodiments, the expression cassettes provided herein do not comprise a post-transcriptional regulatory element (e.g., do not comprise the WPRE element). In some embodiments, the expression cassettes provided herein comprise WPRE.

In some embodiments of the expression cassettes provided herein, the bGHpA and/or SV40pA poly(A) element is replaced by any other poly(A) element known in the art. In some embodiments, the expression cassettes provided herein comprise any poly(A) element known in the art. In some embodiments, the expression cassettes provided herein do not comprise a poly(A) element. In some embodiments, the expression cassettes provided herein do not comprise bGHpA. In some embodiments, the expression cassettes provided herein do not comprise SV40pA. In some embodiments, the expression cassettes provided herein do not comprise bGHpA or SV40pA. In some embodiments, the expression cassettes provided herein comprise one or both of bGHpA and SV40pA.

In some embodiments of the expression cassettes provided herein, the CMV intron and/or chimeric intron element is replaced by any other intron element known in the art. In some embodiments, the expression cassettes provided herein comprise any intron element known in the art. In some embodiments, the expression cassettes provided herein do not comprise an intron. In some embodiments, the expression cassettes provided herein do not comprise a CMV intron. In some embodiments, the expression cassettes provided herein do not comprise a chimeric intron (e.g., do not comprise Chim int). In some embodiments, the expression cassettes provided herein do not comprise CMV intron or Chim int. In some embodiments, the expression cassettes provided herein comprise one or both of CMV intron and Chim int.

It should be understood that the illustrative orientations of the expression cassette can include flanking inverted terminal repeat (ITR) sequences on the 5' and 3' ends of the expression cassette. It should be understood that the ITR sequences can be optional. In some embodiments, the expression cassettes described herein do not include the ITR sequences (e.g., non-AAV, such as DNA plasmid-based, expression cassettes).

Operably linked elements, such as those in the illustrative orientations above, can be on one or both strands of the polynucleotide.

In some embodiments, the expression cassette comprises one copy of a sequence encoding a polypeptide (i.e., one copy of a transgene). In some embodiments, the expression cassette comprises two copies of a sequence encoding a polypeptide (i.e., two copies of a transgene). In some embodiments, where the expression cassette comprises two copies of a sequence encoding a polypeptide, the two "copies" are not identical. While not being bound by any theory, using two sequences encoding a polypeptide that are not identical may prevent DNA recombination within the vector. In some embodiments, the expression cassette comprises one copy that has the original DNA sequence encoding a polypeptide and one copy that has a codon optimized DNA sequence encoding the polypeptide. In some embodiments, where the expression cassette comprises two copies of a sequence encoding a polypeptide, the two copies are identical.

In some embodiments, the expression cassette comprises one or more promoters described herein (with or without one or more enhancers described herein) driving one or more copies of a transgene (such as any transgene described herein). In some embodiments, the expression cassette does not comprise an enhancer (e.g., αMHCe and/or ACTC1e). In some embodiments, the expression cassette comprises one or more enhancers such as cardiac-specific enhancers (e.g., αMHCe and/or ACTC1e). In some embodiments, the expression cassette comprises αMHCe enhancer (and, optionally, does not comprise ACTC1e enhancer). In some embodiments, the expression cassette comprises ACTC1e enhancer (and, optionally, does not comprise αMHCe enhancer). In some embodiments, the expression cassette comprises at least two enhancers in the order of first αMHCe and then ACTC1e. In some embodiments, the expression cassette comprises at least two enhancers in the order of first ACTC1e and then αMHCe. In some embodiments, the expression cassette comprises an intron element, e.g., a CMV intron element and/or a chimeric intron (such as Chim int described herein). In some embodiments, the expression cassette comprises an intron element but does not comprise an enhancer. In some embodiments, the expression cassette comprises an intron element (e.g., CMV intron and/or a chimeric intron) and further comprises an enhancer (e.g., αMHCe and/or ACTC1e). In some embodiments, the expression cassette comprises a transgene with a codon-optimized polynucleotide sequence. In some embodiments, the expression cassette comprises a transgene with a codon-optimized polynucleotide sequence but does not comprise an enhancer. In some embodiments, the expression cassette comprises a transgene with a codon-optimized polynucleotide sequence and further comprises an enhancer (e.g., αMHCe and/or ACTC1e). In some embodiments, the expression cassette comprises one or more promoters described herein and one, two or more enhancers described herein (e.g., comprises an αMHCe and/or ACTC1e enhancer) driving the expression of one or more copies of a transgene (without or without CMV intron or chimeric intron elements). In some embodiments, the promoter is a cardiac-specific promoter, e.g., a human cTnT promoter (such as a short human promoter, hcTnTp) and/or a chicken cTnT promoter (such as ccTnTp). In some of the embodiments, the enhancer is a cardiac-specific enhancer, e.g., αMHCe and/or ACTC1e. In some embodiments, two or more cardiac-specific enhancers are used, where the two or more of the enhancers can be the same or different (e.g., both or all αMHCe, both or all ACTC1e, or at least one αMHCe and at least one ACTC1e). In some embodiments, two cardiac-specific enhancers are used, where the two enhancers can be the same or different (e.g., both αMHCe, both ACTC1e, or one αMHCe and one ACTC1e). In some embodiments, the transgene comprises a non-codon-optimized polynucleotide sequence encoding a gene product. In some embodiments, the order of the elements is as shown in any of the expression cassettes depicted in FIG. 1, FIG. 7A, FIG. 7B, FIG. 7C and Table 1. For example, (i) the order of the promoter and transgene elements can be as shown in FIG. 1, FIG. 7A, FIG. 7B, FIG. 7C or Table 1, (ii) the order of promoter, enhancer and transgene elements can be as shown in FIG. 1, FIG. 7A, FIG. 7B, FIG. 7C or Table 1, (iii) the order of promoter, transgene, WPRE and poly(A) elements can be as shown in FIG. 1, FIG. 7A, FIG. 7B, FIG. 7C or Table 1, optionally with or without enhancer elements being in the same order as shown in FIG. 1, FIG. 7A, FIG. 7B, FIG. 7C or Table 1, or (iv) the order of promoter, transgene, WPRE, poly(A), CMV intron (such as CMVint) elements can be as shown in FIG. 1, FIG. 7A, FIG. 7B, FIG. 7C or Table 1, optionally with or without enhancer elements being in the same order as shown in FIG. 1, FIG. 7A, FIG. 7B, FIG. 7C or Table 1. In some embodiments, the orientation of any of the elements is as shown in any of the expression cassettes depicted in FIG. 1, FIG. 7A, FIG. 7B, FIG. 7C and Table 1. The sequences of individual expression cassette elements discussed herein (such as promoters, enhancers, transgenes, WPRE, poly(A), CMV intron and chimeric intron) can be any of the sequences of such elements provided herein or any sequences with at least, e.g., 75%, 80%, 85%, 90%, 95%, 97%, 98%, 99% or 100% sequence identity thereto.

Figure 7A:
FIG. 7A shows a diagram of an illustrative expression cassette orientation comprising a polynucleotide encoding a promoter, a DWORF polypeptide, a WPRE sequence, and a poly(A) signal sequence flanked by AAV inverted terminal repeats.
Figure 7B:
FIG. 7B shows a diagram of illustrative expression cassette orientations comprising a polynucleotide encoding a promoter, one or more enhancers, an intron, a DWORF polypeptide, a WPRE sequence, and a poly(A) signal sequence flanked by AAV inverted terminal repeats.

In some embodiments, the expression cassette comprises one promoter described herein (with or without one or more enhancers described herein) driving one copy of a transgene (such as any transgene described herein). In some embodiments, the expression cassette comprises one promoter described herein, without any enhancer (e.g., without any enhancer described herein, e.g., without αMHCe and/or without ACTC1e) driving one copy of a transgene, optionally, such an expression cassette comprises an intron element, e.g., a CMV intron element and/or a chimeric intron (such as Chim int described herein), and/or comprises a transgene with a codon-optimized polynucleotide sequence. In some embodiments, the expression cassette comprises one promoter described herein, without any enhancer (e.g., without any enhancer described herein, e.g., without αMHCe and/or without ACTC1e) driving one copy of a transgene, and further comprises a CMV intron and/or a chimeric intron (such as Chim int). In some embodiments, the expression cassette comprises one promoter described herein, without any enhancer (e.g., without any enhancer described herein, e.g., without αMHCe and/or without ACTC1e) driving one copy of a transgene, and further comprises a CMV intron. In some embodiments, the expression cassette comprises one promoter described herein, without any enhancer (e.g., without any enhancer described herein, e.g., without αMHCe and/or without ACTC1e) driving one copy of a transgene, wherein the transgene comprises a codon-optimized polynucleotide sequence. In some embodiments, the expression cassette comprises one promoter described herein and one, two or more enhancers described herein (e.g., comprises an αMHCe and/or ACTC1e enhancer) driving the expression of one copy of a transgene. In some embodiments, the expression cassette comprises one promoter described herein and one enhancer described herein (e.g., αMHCe or ACTC1e enhancer) driving the expression of one copy of a transgene. In some embodiments, the expression cassette comprises one promoter described herein and two enhancers described herein (e.g., both αMHCe, both ACTC1e, or one αMHCe and one ACTC1e) operably linked to one copy of a transgene. In some embodiments, the promoter is a cardiac-specific promoter, e.g., a human cTnT promoter (such as a short human promoter, hcTnTp) and/or a chicken cTnT promoter (such as ccTnTp). In some of the embodiments where one or more enhancers are used, the enhancer is a cardiac-specific enhancer, e.g., αMHCe and/or ACTC1e. In some embodiments, two or more cardiac-specific enhancers are used, where the two or more of the enhancers can be the same or different (e.g., both or all αMHCe, both or all ACTC1e, or at least one αMHCe and at least one ACTC1e). In some embodiments, two cardiac-specific enhancers are used, where the two enhancers can be the same or different (e.g., both αMHCe, both ACTC1e, or one αMHCe and one ACTC1e). In some embodiments, the expression cassette comprises at least two enhancers in the order of first αMHCe and then ACTC1e. In some embodiments, the expression cassette comprises at least two enhancers in the order of first ACTC1e and then αMHCe. In some embodiments, the transgene comprises a non-codon-optimized polynucleotide sequence encoding a gene product. In some embodiments, the transgene comprises a codon-optimized polynucleotide sequence encoding the gene product. In some embodiments, one or more intron elements are also used in addition to promoter and enhancer elements. In some embodiments, a CMV intron element is used. In some embodiments, a chimeric intron element (Chim int) is used. In some embodiments, both a CMV intron and a chimeric intron (Chim int) are used. In some embodiments where one promoter is used, the order of the elements is as shown in any of the expression cassettes depicted in FIG. 7B. For example, (i) the order of the promoter and transgene elements can be as shown in FIG. 7B, (ii) the order of promoter, enhancer and transgene elements can be as shown in FIG. 7B, (iii) the order of promoter, transgene, WPRE and poly(A) elements can be as shown in FIG. 7B, optionally with or without enhancer elements being in the same order as shown in FIG. 7B, or (iv) the order of promoter, transgene, WPRE, poly(A), CMV intron (such as CMVint) elements can be as shown in FIG. 7B, optionally with or without enhancer elements being in the same order as shown in FIG. 7B. In some embodiments where one promoter is used, the orientation of any of the elements is as shown in any of the expression cassettes depicted in FIG. 7B. In some embodiments, the orientation of the elements is forward orientation. In some embodiments, the orientation of the elements is reverse orientation. The sequences of individual expression cassette elements discussed herein (such as promoters, enhancers, transgenes, WPRE, poly(A), CMV intron and chimeric intron) can be any of the sequences of such elements provided herein or any sequences with at least, e.g., 75%, 80%, 85%, 90%, 95%, 97%, 98%, 99% or 100% sequence identity thereto.

Figure 7C:
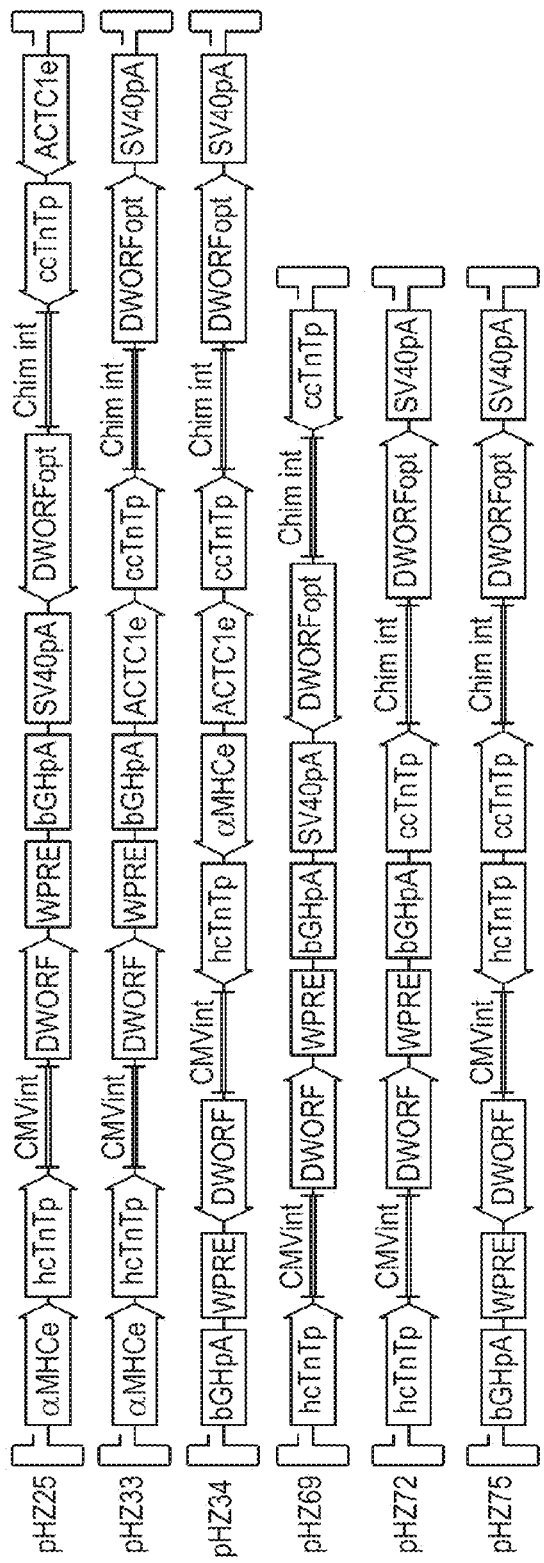
FIG. 7C shows a diagram of illustrative expression cassette orientations comprising a polynucleotide encoding a promoter, one or more enhancers, an intron, a DWORF polypeptide, a WPRE sequence, and a poly(A) signal sequence flanked by AAV inverted terminal repeats.

In some embodiments, the expression cassette comprises two promoters described herein (with or without one or more enhancers described herein) driving the expression of two copies of a transgene (such as any transgene described herein). In some embodiments, the expression cassette comprises two promoters described herein (with or without one or more enhancers described herein) each promoter operably linked to one copy of a transgene (such as any transgene described herein). In some embodiments, the expression cassette comprises two promoters described herein, without any enhancer (e.g., without any enhancer described herein, e.g., without αMHCe and/or without ACTC1e) driving the expression of two copies of a transgene. In some embodiments, the expression cassette comprises two promoters described herein and one, two or more enhancers described herein (e.g., comprising an αMHCe and/or ACTC1e enhancer) driving the expression of two copies of a transgene. In some embodiments, the expression cassette comprises two promoters described herein and two enhancers described herein (e.g., comprising an αMHCe and/or ACTC1e enhancer) operably linked to two copies of a transgene, where each transgene is operably linked to one promoter and one enhancer. In some embodiments, the promoter is a cardiac-specific promoter, e.g., a human cTnT promoter (such as a short human promoter, hcTnTp) and/or a chicken cTnT promoter (such as ccTnTp). In the embodiments where two promoters are used, the two promoters can be the same or different. In some embodiments, where the two promoters drive the expression of two copies of a transgene (each promoter driving expression of one copy of the transgene), both promoters can be cardiac-specific promoters, either the same cardiac-specific promoters or different from each other. In some embodiments, both promoters can be human cTnT promoters (e.g., both can be a short human promoter, hcTnTp). In some embodiments, both promoters can be chicken cTnT promoters (such as ccTnT). In some embodiments, the two promoters are different, e.g., one is a human cTnT promoter (such as a short human cTnT promoter, hcTnTp) and one is a chicken cTnT promoter (such as ccTnT). In some embodiments where two promoters and two transgenes are used, the two transgenes can be the same or different (such as the same or different variants of the same transgene). For example, the first copy of the transgene can be a non-codon-optimized polynucleotide sequence encoding a gene product, and the second copy of the transgene can be a codon-optimized polynucleotide sequence encoding the gene product. In some embodiments, both copies of the transgene used in an expression cassette are the same. In some of the embodiments where one or more enhancers are used, the enhancer is a cardiac-specific enhancer, e.g., αMHCe and/or ACTC1e. In some embodiments, two or more cardiac-specific enhancers are used, where the two or more of the enhancers can be the same or different (e.g., both or all αMHCe, both or all ACTC1e, or at least one αMHCe and at least one ACTC1e). In some embodiments, two cardiac-specific enhancers are used, where the two enhancers can be the same or different (e.g., both αMHCe, both ACTC1e, or one αMHCe and one ACTC1e). In some embodiments where two promoters are used, two cardiac-specific enhancers operably linked to the transgene are used as well, optionally wherein one enhancer is αMHCe and another is ACTC1e. In some embodiments, the expression cassette comprises at least two enhancers in the order of first αMHCe and then ACTC1e. In some embodiments, the expression cassette comprises at least two enhancers in the order of first ACTC1e and then αMHCe. In some embodiments where two promoters are used, one or more intron elements are also used. In some embodiments where two promoters are used, a CMV intron element is also used. In some embodiments where two promoters are used, a chimeric intron element (Chim int) is also used. In some embodiments where two promoters are used, a CMV intron and a chimeric intron (Chim int) are used. In some embodiments where two promoters are used, the order of the elements is as shown in any of the expression cassettes depicted in FIG. 7C. For example, (i) the order of the promoter and transgene elements can be as shown in FIG. 7C, (ii) the order of promoter, enhancer and transgene elements can be as shown in FIG. 7C, (iii) the order of promoter, transgene, WPRE and poly(A) elements can be as shown in FIG. 7C, optionally with or without enhancer elements being in the same order as shown in FIG. 7C, or (iv) the order of promoter, transgene, WPRE, poly(A), CMV intron (such as CMVint) and chimeric intron (such as Chim int) elements can be as shown in FIG. 7C, optionally with or without enhancer elements being in the same order as shown in FIG. 7C. In some embodiments where two promoters are used, the first promoter and the associated transgene (and, optionally an enhancer) are oriented in a forward 5' to 3' direction, and the second promoter and the associated transgene (and, optionally an enhancer) are oriented in a reverse direction. In some embodiments where two promoters are used, the first promoter and the associated transgene (and, optionally an enhancer) are oriented in reverse relative to 5' to 3' direction, and the second promoter and the associated transgene (and, optionally an enhancer) are oriented in a forward direction. In some embodiments where two promoters are used, both promoters and the associated transgenes (and, optionally an enhancer) are oriented in a forward 5' to 3' direction. In some embodiments where two promoters are used, both promoters and the associated transgenes (and, optionally an enhancer) are oriented in reverse relative to the 5' to 3' direction. In some embodiments where two promoters are used, the orientation of any of the elements (such forward or reverse orientation in 5' to 3' direction) is as shown in any of the expression cassettes depicted in FIG. 7C. In some embodiments where two promoters are used, the orientation of promoters, enhancers if any, transgenes, WPRE, poly(A), CMV intron and chimeric intron elements (such forward or reverse orientation in 5' to 3' direction) is as shown in any of the expression cassettes depicted in FIG. 7C. The sequences of individual expression cassette elements discussed herein (such as promoters, enhancers, transgenes, WPRE, poly(A), CMV intron and chimeric intron) can be any of the sequences of such elements provided herein or any sequences with at least, e.g., 75%, 80%, 85%, 90%, 95%, 97%, 98%, 99% or 100% sequence identity thereto.

Expression cassette sequences of the disclosure can be found, without limitation, in Table 1. In some embodiments, the expression cassette comprises about 3.2 kilobases (kb), 3.3 kb, 3.4 kb, 3.5 kb, 3.6 kb, 3.7 kb, or less. In some embodiments, the expression cassette comprises about 1.9 kb, 2.1 kb, 2.2 kb, 2.3 kb, 2.4 kb, 2.5 kb, 2.6 kb, 2.7 kb, 2.8 kb, 2.9 kb, 3.0 kb, 3.1 kb, 3.2 kb, or more.

In some embodiments, the expression cassette comprises a polynucleotide sequence that shares at least 75%, 80%, 90%, 95%, 96%, 97%, 98%, 99%, or 100% identity to SEQ ID NOs: 20-24 and SEQ ID NOs: 45-63. In some embodiments, the expression cassette comprises a polynucleotide sequence that shares at least 75%, 80%, 90%, 95%, 96%, 97%, 98%, 99%, or 100% identity to SEQ ID NOs: 64-75. In some embodiments, the expression cassette comprises a polynucleotide sequence that shares at least 75%, 80%, 90%, 95%, 96%, 97%, 98%, 99%, or 100% identity to SEQ ID NO: 61. In some embodiments, the expression cassette comprises SEQ ID NO: 61. In some embodiments, the expression cassette comprises a polynucleotide sequence that shares at least 75%, 80%, 90%, 95%, 96%, 97%, 98%, 99%, or 100% identity to SEQ ID NO: 62. In some embodiments, the expression cassette comprises SEQ ID NO: 62. In some embodiments, the expression cassette comprises a polynucleotide sequence that shares at least 75%, 80%, 90%, 95%, 96%, 97%, 98%, 99%, or 100% identity to SEQ ID NO: 63. In some embodiments, the expression cassette comprises SEQ ID NO: 63. In some embodiments, the expression cassette comprises a polynucleotide sequence that shares at least 75%, 80%, 90%, 95%, 96%, 97%, 98%, 99%, or 100% identity to SEQ ID NO: 49. In some embodiments, the expression cassette comprises a polynucleotide sequence that shares at least 75%, 80%, 90%, 95%, 96%, 97%, 98%, 99%, or 100% identity to SEQ ID NO: 51. In some embodiments, the expression cassette comprises a polynucleotide sequence that shares at least 75%, 80%, 90%, 95%, 96%, 97%, 98%, 99%, or 100% identity to SEQ ID NO: 55. In some embodiments, the expression cassette comprises a polynucleotide sequence that shares at least 75%, 80%, 90%, 95%, 96%, 97%, 98%, 99%, or 100% identity to SEQ ID NO: 56. In some embodiments, the expression cassette comprises a polynucleotide sequence that shares at least 75%, 80%, 90%, 95%, 96%, 97%, 98%, 99%, or 100% identity to SEQ ID NO: 57. In some embodiments, the expression cassette comprises a polynucleotide sequence that shares at least 75%, 80%, 90%, 95%, 96%, 97%, 98%, 99%, or 100% identity to SEQ ID NO: 58. In some embodiments, the expression cassette comprises a polynucleotide sequence that shares at least 75%, 80%, 90%, 95%, 96%, 97%, 98%, 99%, or 100% identity to SEQ ID NO: 59. In some embodiments, the expression cassette comprises a polynucleotide sequence that shares at least 75%, 80%, 90%, 95%, 96%, 97%, 98%, 99%, or 100% identity to SEQ ID NO: 60. In some embodiments, the expression cassette comprises a polynucleotide sequence that shares at least 75%, 80%, 90%, 95%, 96%, 97%, 98%, 99%, or 100% identity to SEQ ID NO: 67. In some embodiments, the expression cassette comprises a polynucleotide sequence that shares at least 75%, 80%, 90%, 95%, 96%, 97%, 98%, 99%, or 100% identity to SEQ ID NO: 69. In some embodiments, the expression cassette comprises a polynucleotide sequence that shares at least 75%, 80%, 90%, 95%, 96%, 97%, 98%, 99%, or 100% identity to SEQ ID NO: 74. In some embodiments, the expression cassette comprises a polynucleotide sequence that shares at least 75%, 80%, 90%, 95%, 96%, 97%, 98%, 99%, or 100% identity to SEQ ID NO: 75. In some of these embodiments, the sequence encoding DWORF (the DWORF open reading frame) can be replaced by a sequence encoding another polypeptide described herein, and the sequence identity referenced above does not take into account the part of the polynucleotide sequence encoding DWORF (the DWORF open reading frame).

In some embodiments, the transgene in the expression cassette encodes a polypeptide for use in treating or preventing a heart disease or disorder. In some embodiments, the transgene in the expression cassette encodes a polypeptide selected from: DWORF, junctophilin (e.g., JPH2), BAG family molecular chaperone regulator 3 (BAG3), alpha-crystallin B chain (CRYAB), LMNA (such as Lamin A and Lamin C isoforms), troponin I type 3 (TNNI3), phospholamban (PLN), lysosomal-associated membrane protein 2 (LAMP2, such as LAMP2a, LAMP2b and LAMP2c isoforms), desmoplakin (DSP, such as DPI and DPII isoforms), desmoglein 2 (DSG2), and junction plakoglobin (JUP), or a variant of any of these polypeptides (e.g., having at least 75%, at least 85%, at least 95%, at least 97% or at least 99% sequence identity thereto). In some embodiments, the transgene in the expression cassette encodes DWORF (or a variant thereof). In some embodiments, the transgene in the expression cassette encodes JPH2 (e.g., a full-length JPH2 or an N-terminal fragment of JPH2) (or a variant thereof). In some embodiments, the transgene in the expression cassette encodes BAG3 (or a variant thereof). In some embodiments, the transgene in the expression cassette encodes CRYAB (or a variant thereof). In some embodiments, the transgene in the expression cassette encodes LMNA Lamin A isoform (or a variant thereof). In some embodiments, the transgene in the expression cassette encodes LMNA Lamin C isoform (or a variant thereof). In some embodiments, the transgene in the expression cassette encodes TNNI3 (or a variant thereof). In some embodiments, the transgene in the expression cassette encodes PLN (or a variant thereof). In some embodiments, the transgene in the expression cassette encodes LAMP2a (or a variant thereof). In some embodiments, the transgene in the expression cassette encodes LAMP2b (or a variant thereof). In some embodiments, the transgene in the expression cassette encodes LAMP2c (or a variant thereof). In some embodiments, the transgene in the expression cassette encodes DSP DPI isoform (or a variant thereof). In some embodiments, the transgene in the expression cassette encodes DSP DPII isoform (or a variant thereof). In some embodiments, the transgene in the expression cassette encodes DSG2 (or a variant thereof). In some embodiments, the transgene in the expression cassette encodes JUP (or a variant thereof). In some embodiments, the transgene in the expression cassette encodes a human polypeptide (such as any human polypeptide described herein).

In some embodiments, the expression cassettes described herein lead to cardiac cell-specific expression of a transgene. In some embodiments, the expression cassettes described herein lead to cardiomyocyte-specific expression of a transgene. In some embodiments, the expression cassettes described herein allow high expression of a transgene in a cardiac cell (e.g., a cardiomyocyte) and low or no expression in other cells (e.g., low or no expression in liver cells, low or no expression in muscle cells except for muscle cells of the heart, low or no expression in cardiac fibroblasts). In some embodiments, the expression cassettes described herein allow high expression of a transgene in heart tissue of a subject (e.g., in human heart). In some embodiments, the expression cassettes described herein allow no or low expression of a transgene in tissues of a subject other than the heart (e.g., in liver or in muscles except those of the heart). "High" and "low" can be relative to each other, for example, the expression of a transgene in cardiac cells (e.g., cardiomyocytes) and/or heart tissue can be at least 2 fold, 5 fold, 10 fold, 15 fold, 20 fold, 50 fold, 100 fold, 150 fold, or 200 fold higher than its expression in other cells and tissues (e.g., liver, muscle except for the heart).

TABLE 1

Illustrative Expression Cassette Sequences

| Expression Cassette | Sequence |
| --- | --- |
| pCR-MD1<br>distinct sequence elements are indicated in bold, starting with ITR, hcTnTp, DWORF (which is also underlined), WPRE, polyA (hGHpA), ITR | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCT*TGTAGTTAATGATTAACCCGCCATGCTACT*<br>*TATCTACGTAGCCATGCTCTAGGAAGATCGGAATTCGCCC*<br>*TTAAG*GTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCACCCCCACCGCCATCCCCCTGCCCCACCC<br>GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCGAGACGC<br>CTCCA*GCGGCCGCCCGCCA*CCATGGCTGAGAAAGAGTCAA<br>CATCACCACACCTCATGGTTCCCATTCTTCTCCTGGTTGG<br>ATGGATTGTAGGCTGCATCATCGTTATTTACATTGTCTTC<br>TTCTAA*AAGCTTT*GGATCCAATCAACCTCTGGATTACAAA<br>ATTTGTGAAAGATTGACTGGTATTCTTAACTATGTTGCTC<br>CTTTTACGCTATGTGGATACGCTGCTTTAATGCCTTTGTA<br>TCATGCTATTGCTTCCCGTATGGCTTTCATTTTCTCCTCC<br>TTGTATAAATCCTGGTTGCTGTCTCTTTATGAGGAGTTGT<br>GGCCCGTTGTCAGGCAACGTGGCGTGGTGTGCACTGTGTT |

TABLE 1-continued

Illustrative Expression Cassette Sequences

| Expression Cassette | Sequence |
|---|---|
| | TGCTGACGCAACCCCCACTGGTTGGGGCATTGCCACCACC<br>TGTCAGCTCCTTTCCGGGACTTTCGCTTTCCCCCTCCCTA<br>TTGCCACGGCGGAACTCATCGCCGCCTGCCTTGCCCGCTG<br>CTGGACAGGGGCTCGGCTGTTGGGCACTGACAATTCCGTG<br>GTGTTGTCGGGGAAATCATCGTCCTTTCCTTGGCTGCTCG<br>CCTGTGTTGCCACCTGGATTCTGCGCGGGACGTCCTTCTG<br>CTACGTCCCTTCGGCCCTCAATCCAGCGGACCTTCCTTCC<br>CGCGGCCTGCTGCCGGCTCTGCGGCCTCTTCCGCGTCTTC<br>GAGATCTGCCTCGACTGTGCCTTCTAGTTGCCAGCCATCT<br>GTTGTTTGCCCCTCCCCCGTGCCTTCCTTGACCCTGGAAG<br>GTGCCACTCCCACTGTCCTTTCCTAATAAAATGAGGAAAT<br>TGCATCGCATTGTCTGAGTAGGTGTCATTCTATTCTGGGG<br>GGTGGGGTGGGGCAGGACAGCAAGGGGGAGGATTGGGAAG<br>ACAATAGCAGGCATGCTGGGGA*CTCGAGTTAAGGGCGAAT<br>TCCCGATTAGGATCTTCCTAGAGCATGGCTACGTAGATAA<br>GTAGCATGGCGGGTTAATCATTAACTACA*AGGAACCCCTA<br>GTGATGGAGTTGGCCACTCCCTCTCTGCGCGCTCGCTCGC<br>TCACTGAGGCCGGGCGACCAAAGGTCGCCCGACGCCCGGG<br>CTTTGCCCGGGCGGCCTCAGTGAGCGAGCGAGCGCGCAG<br>(SEQ ID NO: 20) |
| pCR-MD2 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGAGAGGACCCTTTCAAGGACATTAGTGGTGGAGGCA<br>GCATAGTAGCTCCCAAGGCAGAGGGATTGAGAGAAGAGTT<br>TGAGGACTGGGAAGGCGGGACACATGATTGGGTGATGGGA<br>GAAGGGGGCAGAGAATAGCGAGATTGCTTTCTTTGCCCAC<br>GGAGAAACAGAGGAGTGTGGATCATGAATGGGCAAGATCT<br>TTAAGTGCCAGGGGGGTCATGGAGGAGGGAGGGCCTGC<br>TCCAGAGGAGGACCATTCCTGCTTCAGAGCCAAGCAGGAC<br>CTAGGCTGTGAAGATTCGGAGAAAGAGATGGAGGGGAGAG<br>TCAGCTCAGCTGCTTACTGGCTTGCTTTCCTCCTGTCTCT<br>TTCATTTTCATAATCTACCAAACCCTGCAATGGGCCAGCC<br>TTGAACATACAAGTGCATGTGCATGGTCAGACACAGGCAA<br>GCAAGCAAGACCCCTAGGCCTGACCTATGCATCTGCAATC<br>TAGTAGGTTTAGCAGATCATAGCCCCGCACTGCTTGATTT<br>TAAAGCCGTTAGGGGATGACCTTTGACAGTCCGCATCACC<br>CCTCTCACACAACGAGCGCCTGTTCAAGGTTCTTGACTGG<br>AAGTTCTACCTTGTATCTGGCCTCCTGTAGCAGTTTCAGT<br>CCATTCCCTGTGAGGAGGGTGTGCCACATGGCTTTGGGGG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGTACATGTTCCTG<br>TAGCCTTGTCCCTGGCACCTGCCAAAATAGCAGCCAACAC<br>CCCCCACCCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAG<br>GATCTGTCGGCAGCTGCTGTTCTGAGGTAAGGCTCGGGCA<br>GGGCTCTGGGAAGAGGAGAGCAGAGAATGGACGGGGAGA<br>TGTGAGGGTCTTGGGCCCTGGCATATTTACCCAGAGTCTG<br>CCTGTGTCCGCAGAAGTCCATGGCCCCTCCTGGTGGAGGC<br>CACACTTCAGAGGACAGGTTGCCAGGTCTGGGCTCCAAGA<br>TTGGTACAATAGAGCAGAGAGAGGAGTCGCTGCGACGCTG<br>CCTTCGCCCCGTGCCCCGCTCCGCCGCCGCCTCGCGCCGC<br>CCGCCCCGGCTCTGACTGACCGCGTTACTCCCACAGGTGA<br>GCGGGCGGGACGGCCCTTCTCCTCCGGGCTGTAATTAGCG<br>CTTGGTTTAATGACGGCTTGTTTCTTTTCTGTGGCTGCGT<br>GAAAGCCTTGAGGGGCTCCGGGAGCTAGAGCCTCTGCTAA<br>CCATGTTCATGCCTTCTTCTTTTTCCTACAGCTCCTGGGC<br>AACGTGCTGGTTATTGTGCTGTCTCATCATTTTGGCAAAG<br>AATTCCCAATCGATACCCAATCGATACAGATCTAGCGGCC<br>GCGCCGCCACCATGGCTGAGAAAGAGTCAACATCACCACA<br>CCTCATGGTTCCCATTCTTCTCCTGGTTGGATGGATTGTA<br>GGCTGCATCATCGTTATTTACATTGTCTTCTTCTAACCAG<br>AGGTTGATTGGATCCAAGCTTTGGATCCAATGGATCCAAT |

TABLE 1-continued

Illustrative Expression Cassette Sequences

| Expression Cassette | Sequence |
|---|---|
| | CAACCTCTGGATTACAAAATTTGTGAAAGATTGACTGGTA<br>TTCTTAACTATGTTGCTCCTTTTACGCTATGTGGATACGC<br>TGCTTTAATGCCTTTGTATCATGCTATTGCTTCCCGTATG<br>GCTTTCATTTTCTCCTCCTTGTATAAATCCTGGTTGCTGT<br>CTCTTTATGAGGAGTTGTGGCCCGTTGTCAGGCAACGTGG<br>CGTGGTGTGCACTGTGTTTGCTGACGCAACCCCCACTGGT<br>TGGGGCATTGCCACCACCTGTCAGCTCCTTTCCGGGACTT<br>TCGCTTTCCCCCTCCCTATTGCCACGGCGGAACTCATCGC<br>CGCCTGCCTTGCCCGCTGCTGGACAGGGGCTCGGCTGTTG<br>GGCACTGACAATTCCGTGGTGTTGTCGGGGAAATCATCGT<br>CCTTTCCTTGGCTGCTCGCCTGTGTTGCCACCTGGATTCT<br>GCGCGGGACGTCCTTCTGCTACGTCCCTTCGGCCCTCAAT<br>CCAGCGGACCTTCCTTCCCGCGGCCTGCTGCCGGCTCTGC<br>GGCCTCTTCCGCGTCTTCGAGATCTGCCTCGACTGTGCCT<br>TCTAGTTGCCAGCCATCTGTTGTTTGCCCCTCCCCCGTGC<br>CTTCCTTGACCCTGGAAGGTGCCACTCCCACTGTCCTTTC<br>CTAATAAAATGAGGAAATTGCATCGCATTGTCTGAGTAGG<br>TGTCATTCTATTCTGGGGGGTGGGGTGGGGCAGGACAGCA<br>AGGGGGAGGATTGGGAAGACAATAGCAGGCATGCTGGGGA<br>CTCGAGTTAAGGGCGAATTCCCGATTAGGATCTTCCTAGA<br>GCATGGCTACGTAGATAAGTAGCATGGCGGGTTAATCATT<br>AACTACAAGGAACCCCTAGTGATGGAGTTGGCCACTCCCT<br>CTCTGCGCGCTCGCTCGCTCACTGAGGCCGGGCGACCAAA<br>GGTCGCCCGACGCCCGGGCTTTGCCCGGGCGGCCTCAGTG<br>AGCGAGCGAGCGCGCAG (SEQ ID NO: 21) |
| pCR-HD1 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGGTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCACCCCCACCGCCATCCCCCTGCCCCACCC<br>GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCAGACGC<br>CTCCAGCGGCCGCCCGCCACCATGGCAGAGAAGGCTGGAA<br>GCACTTTCTCTCACCTGCTCGTGCCGATTTTGCTTTTGAT<br>TGGGTGGATAGTTGGCTGTATCATAATGATCTACGTTGTC<br>TTTTCATAGAAGCTTTGGATCCAATCAACCTCTGGATTAC<br>AAAATTTGTGAAAGATTGACTGGTATTCTTAACTATGTTG<br>CTCCTTTTACGCTATGTGGATACGCTGCTTTAATGCCTTT<br>GTATCATGCTATTGCTTCCCGTATGGCTTTCATTTTCTCC<br>TCCTTGTATAAATCCTGGTTGCTGTCTCTTTATGAGGAGT<br>TGTGGCCCGTTGTCAGGCAACGTGGCGTGGTGTGCACTGT<br>GTTTGCTGACGCAACCCCCACTGGTTGGGGCATTGCCACC<br>ACCTGTCAGCTCCTTTCCGGGACTTTCGCTTTCCCCCTCC<br>CTATTGCCACGGCGGAACTCATCGCCGCCTGCCTTGCCCG<br>CTGCTGGACAGGGGCTCGGCTGTTGGGCACTGACAATTCC<br>GTGGTGTTGTCGGGGAAATCATCGTCCTTTCCTTGGCTGC<br>TCGCCTGTGTTGCCACCTGGATTCTGCGCGGGACGTCCTT<br>CTGCTACGTCCCTTCGGCCCTCAATCCAGCGGACCTTCCT<br>TCCCGCGGCCTGCTGCCGGCTCTGCGGCCTCTTCCGCGTC<br>TTCGAGATCTGCCTCGACTGTGCCTTCTAGTTGCCAGCCA<br>TCTGTTGTTTGCCCCTCCCCCGTGCCTTCCTTGACCCTGG<br>AAGGTGCCACTCCCACTGTCCTTTCCTAATAAAATGAGGA<br>AATTGCATCGCATTGTCTGAGTAGGTGTCATTCTATTCTG<br>GGGGGTGGGGTGGGGCAGGACAGCAAGGGGGAGGATTGGG<br>AAGACAATAGCAGGCATGCTGGGGACTGAGTTAAGGGCG<br>AATTCCCGATTAGGATCTTCCTAGAGCATGGCTACGTAGA<br>TAAGTAGCATGGCGGGTTAATCATTAACTACAAGGAACCC<br>CTAGTGATGGAGTTGGCCACTCCCTCTCTGCGCGCTCGCT<br>CGCTCACTGAGGCCGGGCGACCAAAGGTCGCCCGACGCCC<br>GGGCTTTGCCCGGGCGGCCTCAGTGAGCGAGCGAGCGCGC<br>AG (SEQ ID NO: 22) |

TABLE 1-continued

Illustrative Expression Cassette Sequences

| Expression Cassette | Sequence |
| --- | --- |
| pCR-HD2 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGAGAGGACCCTTTCAAGGACATTAGTGGTGGAGGCA<br>GCATAGTAGCTCCCAAGGCAGAGGGATTGAGAGAAGAGTT<br>TGAGGACTGGGAAGGCGGGACACATGATTGGGTGATGGGA<br>GAAGGGGGCAGAGAATAGCGAGATTGCTTTCTTTGCCCAC<br>GGAGAAACAGAGGAGTGTGGATCATGAATGGGCAAGATCT<br>TTAAGTGCCAGGGGGGTCATGGAGGAGGGGAGGGCCTGC<br>TCCAGAGGAGGACCATTCCTGCTTCAGAGCCAAGCAGGAC<br>CTAGGCTGTGAAGATTCGGAGAAAGAGATGGAGGGGAGAG<br>TCAGCTCAGCTGCTTACTGGCTTGCTTTCCTCCTGTCTCT<br>TTCATTTTCATAATCTACCAAACCCTGCAATGGGCCAGCC<br>TTGAACATACAAGTGCATGTGCATGGTCAGACACAGGCAA<br>GCAAGCAAGACCCCTAGGCCTGACCTATGCATCTGCAATC<br>TAGTAGGTTTAGCAGATCATAGCCCCGCACTGCTTGATTT<br>TAAAGCCGTTAGGGGATGACCTTTGACAGTCCGCATCACC<br>CCTCTCACACAACGAGCGCCTGTTCAAGGTTCTTGACTGG<br>AAGTTCTACCTTGTATCTGGCCTCCTGTAGCAGTTTCAGT<br>CCATTCCCTGTGAGGAGGGTGTGCCACATGGCTTTGGGGG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAG<br>GATCTGTCGGCAGCTGCTGTTCTGAGGTAAGGCTCGGGCA<br>GGGCTCTGGGGAAGAGGAGAGCAGAGAATGGACGGGGAGA<br>TGTGAGGGTCTTGGGCCCTGGCATATTTACCCAGAGTCTG<br>CCTGTGTCCGCAGAAGTCCATGGCCCCTCCTGGTGGAGGC<br>CACACTTCAGAGGACAGGTTGCCAGGTCTGGGCTCCAAGA<br>TTGGTACAATAGAGCAGAGAGAGGAGTCGCTGCGACGCTG<br>CCTTCGCCCCGTGCCCCGCTCCGCCGCCGCCTCGCGCCGC<br>CCGCCCCGGCTCTGACTGACCGCGTTACTCCCACAGGTGA<br>GCGGGCGGGACGGCCCTTCTCCTCCGGGCTGTAATTAGCG<br>CTTGGTTTAATGACGGCTTGTTTCTTTTCTGTGGCTGCGT<br>GAAAGCCTTGAGGGGCTCCGGGAGCTAGAGCCTCTGCTAA<br>CCATGTTCATGCCTTCTTCTTTTTCCTACAGCTCCTGGGC<br>AACGTGCTGGTTATTGTGCTGTCTCATCATTTTGGCAAAG<br>AATTCCCAATCGATACCCAATCGATACAGATCTAGCGGCC<br>GCGCCGCCACCATGGCAGAGAAGGCTGGAAGCACTTTCTC<br>TCACCTGCTCGTGCCGATTTTGCTTTTGATTGGGTGGATA<br>GTTGGCTGTATCATAATGATCTACGTTGTCTTTTCATAGC<br>CAGAGGTTGATTGGATCCAAGCTTTGGATCCAATGGATCC<br>AATCAACCTCTGGATTACAAAATTTGTGAAAGATTGACTG<br>GTATTCTTAACTATGTTGCTCCTTTTACGCTATGTGGATA<br>CGCTGCTTTAATGCCTTTGTATCATGCTATTGCTTCCCGT<br>ATGGCTTTCATTTTCTCCTCCTTGTATAAATCCTGGTTGC<br>TGTCTCTTTATGAGGAGTTGTGGCCCGTTGTCAGGCAACG<br>TGGCGTGGTGTGCACTGTGTTTGCTGACGCAACCCCCACT<br>GGTTGGGGCATTGCCACCACCTGTCAGCTCCTTTCCGGGA<br>CTTTCGCTTTCCCCCTCCCTATTGCCACGGCGGAACTCAT<br>CGCCGCCTGCCTTGCCCGCTGCTGGACAGGGGCTCGGCTG<br>TTGGGCACTGACAATTCCGTGGTGTTGTCGGGGAAATCAT<br>CGTCCTTTCCTTGGCTGCTCGCCTGTGTTGCCACCTGGAT<br>TCTGCGCGGGACGTCCTTCTGCTACGTCCCTTCGGCCCTC<br>AATCCAGCGGACCTTCCTTCCCGCGGCCTGCTGCCGGCTC<br>TGCGGCCTCTTCCGCGTCTTCGAGATCTGCCTCGACTGTG<br>CCTTCTAGTTGCCAGCCATCTGTTGTTTGCCCCTCCCCCG<br>TGCCTTCCTTGACCCTGGAAGGTGCCACTCCCACTGTCCT<br>TTCCTAATAAAATGAGGAAATTGCATCGCATTGTCTGAGT<br>AGGTGTCATTCTATTCTGGGGGGTGGGGTGGGGCAGGACA<br>GCAAGGGGGAGGATTGGGAAGACAATAGCAGGCATGCTGG<br>GGACTCGAGTTAAGGGCGAATTCCCGATTAGGATCTTCCT<br>AGAGCATGGCTACGTAGATAAGTAGCATGGCGGGTTAATC |

TABLE 1-continued

Illustrative Expression Cassette Sequences

| Expression Cassette | Sequence |
|---|---|
| | ATTAACTACAAGGAACCCCTAGTGATGGAGTTGGCCACTC<br>CCTCTCTGCGCGCTCGCTCGCTCACTGAGGCCGGGCGACC<br>AAAGGTCGCCCGACGCCCGGGCTTTGCCCGGGCGGCCTCA<br>GTGAGCGAGCGAGCGCGCAG (SEQ ID NO: 23) |
| | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACCAGGGTAATGGGGATCCTCTAGAACTATAGCTA<br>GAATTCGCCCTTACGGGCCCCCCCTCGAGGTCGGGATAAA<br>AGCAGTCTGGGCTTTCACATGACAGCATCTGGGGCTGCGG<br>CAGAGGGTCGGGTCCGAAGCGCTGCCTTATCAGCGTCCCC<br>AGCCCTGGGAGGTGACAGCTGGCTGGCTTGTGTCAGCCCC<br>TCGGGCACTCACGTATCTCCGTCCGACGGGTTTAAAATAG<br>CAAAACTCTGAGGCCACACAATAGCTTGGGCTTATATGGG<br>CTCCTGTGGGGAAGGGGGAGCACGGAGGGGGCCGGGGCC<br>GCTGCTGCCAAAATAGCAGCTCACAAGTGTTGCATTCCTC<br>TCTGGGCGCCGGGCACATTCCTGCTGGCTCTGCCCGCCCC<br>GGGGTGGGCGCCGGGGGGACCTTAAAGCCTCTGCCCCCCA<br>AGGAGCCCTTCCCAGACAGCCGCCGGCACCCACCGCTCCG<br>TGGGACGATCCCCGAAGCTCTAGAGCTTTATTGCGGTAGT<br>TTATCACAGTTAAATTGCTAACGCAGTCAGTGCTTCTGAC<br>ACAACAGTCTCGAACTTAAGCTGCAGAAGTTGGTCGTGAG<br>GCACTGGGCAGGTAAGTATCAAGGTTACAAGACAGGTTTA<br>AGGAGACCAATAGAAACTGGGCTTGTCGAGACAGAGAAGA<br>CTCTTGCGTTTCTGATAGGCACCTATTGGTCTTACTGACA<br>TCCACTTTGCCTTTCTCTCCACAGGTGTCCACTCCCAGTT<br>CAATTACAGCTCTTAAGGCTAGAGTACTTAATACGACTCA<br>CTATAGGCTAGCCGCCACCATGGCTGAGAAAGAGTCAACA<br>TCACCACACCTCATGGTTCCCATTCTTCTCCTGGTTGGAT<br>GGATTGTAGGCTGCATCATCGTTATTTACATTGTCTTCTT<br>CTAACGGCCGCGCGGATCCAGACATGATAAGATACATTGA<br>TGAGTTTGGACAAACCACAACTAGAATGCAGTGAAAAAAA<br>TGCTTTATTTGTGAAATTTGTGATGCTATTGCTTTATTTG<br>TAACCATTATAAGCTGCAATAAACAAGTTAACAACAACAA<br>TTGCATTCATTTTATGTTTCAGGTTCAGGGGGAGGTGTGG<br>GAGGTTTTTTAGTCGACCCGGGCGGCCTCGAGGACGGGGT<br>GAACTACGCCTGAGGATCCGATCTTTTTCCCTCTGCCAAA<br>AATTATGGGGACATCATGAAGCCCCTTGAGCATCTGACTT<br>CTGGCTAATAAAGGAAATTTATTTTCATTGCAATAGTGTG<br>TTGGAATTTTTTGTGTCTCTCACTCGGAAGCAATTCGTTG<br>ATCTGAATTTCGACCACCCATAATACCCATTACCCTGGTA<br>GATAAGTAGCATGGCGGGTTAATCATTAACTACAAGGAAC<br>CCCTAGTGATGGAGTTGGCCACTCCCTCTCTGCGCGCTCG<br>CTCGCTCACTGAGGCCGGGCGACCAAAGGTCGCCCGACGC<br>CCGGGCTTTGCCCGGGCGGCCTCAGTGAGCGAGCGAGCGC<br>GCAG (SEQ ID NO: 24) |
| pHZ15 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGAACTGGCCTGCCCGAGACCAAACGTGCGGAACGTA<br>GTTAAGTGTTAGAGGTAGGATTTGAAGCCTGTCGATCATT<br>CTGATTCTCCTTTTCTCTACGTCTGCTTCCTGTCAATGGG<br>CATCCTCACTGTCAAATGCAGATGGTACAGCAGGGCTTGG<br>TCTCAGCCAGGCAGGCCTCTCCCCAGTCTCCATGGCTCAG<br>CTGTCCAGCAGTTTCATCCCTAGACCATCCCAAACATGGT<br>TGAGAAGCTCTGAGGGGAGGACCCAGCACTGCCCGGCCCC<br>TGAAGATAATCAGCAGTCCTGCTCAGCATATCAATCCAAG<br>CCCACTCTAGACAGAGATGCCGGTGCCCAGTTTTCTATTT<br>TTAACTGGTGTGAACTGAAGGAAAAGCACAGCATTAGAAG<br>TCCAAGCAGTCATGGAGAAGACCCACCTTGCAGATGTCCT<br>CACTGGGGCTGGCAGAGCCGGCAACCTGCCTAAGGCTGCT<br>CAGTCCATTAGGAGCCAGTAGCCTGGAAGATGTCTTTACC<br>CCCAGCATCAGTTCAAGTGGAGCAGCACATAACTCTTGCC<br>CTCTGCCTTCCAAGATTCTGGTGCTGAGACTTATGGAGTG<br>TCTTGGAGGTTGCCTTCTGCCCCCCAACCCTGCTCCCAGC<br>TGGCCCTCCCAGGCCTGGGTTGCTGGCCTCTGCTTTATCA<br>GGATTCTCAAGAGGGACAGCTGGTTTATGTTGCATGACTG<br>TTCCCTGCATATCTGCTCTGGTTTTAAATAGCTTATCTGA<br>GCAGCTGGAGGACCACATGGGCTTATATGGCGTGGGGTAC<br>ATGTTCCTGTAGCCTTGTCCCTGGCACCTGCCAAAATAGC<br>AGCCAACACCCCCACCCCCACCGCCATCCCCCTGCCCCA |

TABLE 1-continued

Illustrative Expression Cassette Sequences

| Expression Cassette | Sequence |
|---|---|
| | CCCGTCCCCTGTCGCACATTCCTCCCTCCGCAGGGCTGGC
TCACCAGGCCCCAGCCCACATGCCTGCTTAAAGCCCTCTC
CATCCTCTGCCTCACCCAGTCCCCGCTGAGACTGAGCAGA
CGCCTCCAGCGGCCGCCCGCCACCATGGCTGAGAAAGAGT
CAACATCACCACACCTCATGGTTCCCATTCTTCTCCTGGT
TGGATGGATTGTAGGCTGCATCATCGTTATTTACATTGTC
TTCTTCTAAAAGCTTTGGATCCAATCAACCTCTGGATTAC
AAAATTTGTGAAAGATTGACTGGTATTCTTAACTATGTTG
CTCCTTTTACGCTATGTGGATACGCTGCTTTAATGCCTTT
GTATCATGCTATTGCTTCCCGTATGGCTTTCATTTTCTCC
TCCTTGTATAAATCCTGGTTGCTGTCTCTTTATGAGGAGT
TGTGGCCCGTTGTCAGGCAACGTGGCGTGGTGTGCACTGT
GTTTGCTGACGCAACCCCCACTGGTTGGGGCATTGCCACC
ACCTGTCAGCTCCTTTCCGGGACTTTCGCTTTCCCCCTCC
CTATTGCCACGGCGGAACTCATCGCCGCCTGCCTTGCCCG
CTGCTGGACAGGGGCTCGGCTGTTGGGCACTGACAATTCC
GTGGTGTTGTCGGGGAAATCATCGTCCTTTCCTTGGCTGC
TCGCCTGTGTTGCCACCTGGATTCTGCGCGGGACGTCCTT
CTGCTACGTCCCTTCGGCCCTCAATCCAGCGGACCTTCCT
TCCCGCGGCCTGCTGCCGGCTCTGCGGCCTCTTCCGCGTC
TTCGAGATCTGCCTCGACTGTGCCTTCTAGTTGCCAGCCA
TCTGTTGTTTGCCCCTCCCCCGTGCCTTCCTTGACCCTGG
AAGGTGCCACTCCCACTGTCCTTTCCTAATAAAATGAGGA
AATTGCATCGCATTGTCTGAGTAGGTGTCATTCTATTCTG
GGGGGTGGGGTGGGGCAGGACAGCAAGGGGGAGGATTGGG
AAGACAATAGCAGGCATGCTGGGGACTCGAGTTAAGGGCG
AATTCCCGATTAGGATCTTCCTAGAGCATGGCTACGTAGA
TAAGTAGCATGGCGGGTTAATCATTAACTACAAGGAACCC
CTAGTGATGGAGTTGGCCACTCCCTCTCTGCGCGCTCGCT
CGCTCACTGAGGCCGGGCGACCAAAGGTCGCCCGACGCCC
GGGCTTTGCCCGGGCGGCCTCAGTGAGCGAGCGAGCGCGC
AG (SEQ ID NO: 45) |
| pHZ16 | CTGCGCGCTCGCTCGCTCACTGAGGCCGCCCGGGCAAAGC
CCGGGCGTCGGGCGACCTTTGGTCGCCCGGCCTCAGTGAG
CGAGCGAGCGCGCAGAGAGGGAGTGGCCAACTCCATCACT
AGGGGTTCCTTGTAGTTAATGATTAACCCGCCATGCTACT
TATCTACGTAGCCATGCTCTAGGAAGATCGGAATTCGCCC
TTAAGAACTGGCCTGCCCGAGACCAAACGTGCGGAACGTA
GTTAAGTGTTAGAGGTAGGATTTGAAGCCTGTCGATCATT
CTGATTCTCCTTTTCTCTACGTCTGCTTCCTGTCAATGGG
CATCCTCACTGTCAAATGCAGATGGTACAGCAGGGCTTGG
TCTCAGCCAGGCAGGCCTCTCCCCAGTCTCCATGGCTCAG
CTGTCCAGCAGTTTCATCCCTAGACCATCCCAAACATGGT
TGAGAAGCTCTGAGGGGAGGACCCAGCACTGCCCGGCCCC
TGAAGATAATCAGCAGTCCTGCTCAGCATATCAATCCAAG
CCCACTCTAGACAGAGATGCCGGTGCCCAGTTTTCTATTT
TTAACTGGTGTGAACTGAAGGAAAAGCACAGCATTAGAAG
TCCAAGCACCTTCAGATTAAAAATAACTAAGGTAAGGGCC
ATGTGGGTAGGGGAGGTGGTGTGAGACGGTCCTGTCTCTC
CTCTATCTGCCCATCGGCCCTTTGGGGAGGAGGAATGTGC
CCAAGGACTAAAAAAAGGCCCTGGAGCCAGAGGGGCGAGG
GCAGCAGACCTTTCATGGGCAAACCTCAGGGCTGCTGTCG
TCATGGAGAAGACCCACCTTGCAGATGTCCTCACTGGGGC
TGGCAGAGCGGCAACCTGCCTAAGGCTGCTCAGTCCATT
AGGAGCCAGTAGCCTGGAAGATGTCTTTACCCCCAGCATC
AGTTCAAGTGGAGCAGCACATAACTCTTGCCCTCTGCCTT
CCAAGATTCTGGTGCTGAGACTTATGGAGTGTCTTGGAGG
TTGCCTTCTGCCCCCCAACCCTGCTCCCAGCTGGCCCTCC
CAGGCCTGGGTTGCTGGCCTCTGCTTTATCAGGATTCTCA
AGAGGGACAGCTGGTTTATGTTGCATGACTGTTCCCTGCA
TATCTGCTCTGGTTTTAAATAGCTTATCTGAGCAGCTGGA
GGACCACATGGGCTTATATGGCGTGGGTACATGTTCCTG
TAGCCTTGTCCCTGGCACCTGCCAAAATAGCAGCCAACAC
CCCCCACCCCACCGCCATCCCCCTGCCCCACCCGTCCCC
TGTCGCACATTCCTCCCTCCGCAGGGCTGGCTCACCAGGC
CCCAGCCCACATGCCTGCTTAAAGCCCTCTCCATCCTCTG
CCTCACCCAGTCCCCGCTGAGACTGAGCAGACGCCTCCAG
CGGCCGCCCGCCACCATGGCTGAGAAAGAGTCAACATCAC
CACACCTCATGGTTCCCATTCTTCTCCTGGTTGGATGGAT
TGTAGGCTGCATCATCGTTATTTACATTGTCTTCTTCTAA
AAGCTTTGGATCCAATCAACCTCTGGATTACAAAATTTGT
GAAAGATTGACTGGTATTCTTAACTATGTTGCTCCTTTTA
CGCTATGTGGATACGCTGCTTTAATGCCTTTGTATCATGC
TATTGCTTCCCGTATGGCTTTCATTTTCTCCTCCTTGTAT
AAATCCTGGTTGCTGTCTCTTTATGAGGAGTTGTGGCCCG |

TABLE 1-continued

Illustrative Expression Cassette Sequences

| Expression Cassette | Sequence |
|---|---|
| | TTGTCAGGCAACGTGGCGTGGTGTGCACTGTGTTTGCTGA<br>CGCAACCCCCACTGGTTGGGGCATTGCCACCACCTGTCAG<br>CTCCTTTCCGGGACTTTCGCTTTCCCCCTCCCTATTGCCA<br>CGGCGGAACTCATCGCCGCCTGCCTTGCCCGCTGCTGGAC<br>AGGGGCTCGGCTGTTGGGCACTGACAATTCCGTGGTGTTG<br>TCGGGGAAATCATCGTCCTTTCCTTGGCTGCTCGCCTGTG<br>TTGCCACCTGGATTCTGCGCGGGACGTCCTTCTGCTACGT<br>CCCTTCGGCCCTCAATCCAGCGGACCTTCCTTCCCGCGGC<br>CTGCTGCCGGCTCTGCGGCCTCTTCCGCGTCTTCGAGATC<br>TGCCTCGACTGTGCCTTCTAGTTGCCAGCCATCTGTTGTT<br>TGCCCCTCCCCCGTGCCTTCCTTGACCCTGGAAGGTGCCA<br>CTCCCACTGTCCTTTCCTAATAAAATGAGGAAATTGCATC<br>GCATTGTCTGAGTAGGTGTCATTCTATTCTGGGGGGTGGG<br>GTGGGGCAGGACAGCAAGGGGGAGGATTGGGAAGACAATA<br>GCAGGCATGCTGGGGACTCGAGTTAAGGGCGAATTCCCGA<br>TTAGGATCTTCCTAGAGCATGGCTACGTAGATAAGTAGCA<br>TGGCGGGTTAATCATTAACTACAAGGAACCCCTAGTGATG<br>GAGTTGGCCACTCCCTCTCTGCGCGCTCGCTCGCTCACTG<br>AGGCCGGGCGACCAAAGGTCGCCCGACGCCCGGGCTTTGC<br>CCGGGCGGCCTCAGTGAGCGAGCGAGCGCGCAG<br>(SEQ ID NO: 46) |
| pHZ17 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCGTCA<br>TGGAGAAGACCCACCTTGCAGATGTCCTCACTGGGGCTGG<br>CAGAGCCGGCAACCTGCCTAAGGCTGCTCAGTCCATTAGG<br>AGCCAGTAGCCTGGAAGATGTCTTTACCCCCAGCATCAGT<br>TCAAGTGGAGCAGCACATAACTCTTGCCCTCTGCCTTCCA<br>AGATTCTGGTGCTGAGACTTATGGAGTGTCTTGGAGGTTG<br>CCTTCTGCCCCCCAACCCTGCTCCCAGCTGGCCCTCCCAG<br>GCCTGGGTTGCTGGCCTCTGCTTTATCAGGATTCTCAAGA<br>GGGACAGCTGGTTTATGTTGCATGACTGTTCCCTGCATAT<br>CTGCTCTGGTTTTAAATAGCTTATCTGAGCAGCTGGAGGA<br>CCACATGGGCTTATATGGCGTGGGTACATGTTCCTGTAG<br>CCTTGTCCCTGGCACCTGCCAAAATAGCAGCCAACACCCC<br>CCACCCCCACCGCCATCCCCCTGCCCCACCCGTCCCCTGT<br>CGCACATTCCTCCCTCCGCAGGGCTGGCTCACCAGGCCCC<br>AGCCCACATGCCTGCTTAAAGCCCTCTCCATCCTCTGCCT<br>CACCCAGTCCCCGCTGAGACTGAGCAGACGCCTCCAGCGG<br>CCGCCCGCCACCATGGCTGAGAAAGAGTCAACATCACCAC<br>ACCTCATGGTTCCCATTCTTCTCCTGGTTGGATGGATTGT<br>AGGCTGCATCATCGTTATTTACATTGTCTTCTTCTAAAAG<br>CTTTGGATCCAATCAACCTCTGGATTACAAAATTTGTGAA<br>AGATTGACTGGTATTCTTAACTATGTTGCTCCTTTTACGC<br>TATGTGGATACGCTGCTTTAATGCCTTTGTATCATGCTAT<br>TGCTTCCCGTATGGCTTTCATTTTCTCCTCCTTGTATAAA<br>TCCTGGTTGCTGTCTCTTTATGAGGAGTTGTGGCCCGTTG<br>TCAGGCAACGTGGCGTGGTGTGCACTGTGTTTGCTGACGC<br>AACCCCCACTGGTTGGGGCATTGCCACCACCTGTCAGCTC<br>CTTTCCGGGACTTTCGCTTTCCCCCTCCCTATTGCCACGG<br>CGGAACTCATCGCCGCCTGCCTTGCCCGCTGCTGGACAGG<br>GGCTCGGCTGTTGGGCACTGACAATTCCGTGGTGTTGTCG<br>GGGAAATCATCGTCCTTTCCTTGGCTGCTCGCCTGTGTTG<br>CCACCTGGATTCTGCGCGGGACGTCCTTCTGCTACGTCCC<br>TTCGGCCCTCAATCCAGCGGACCTTCCTTCCCGCGGCCTG<br>CTGCCGGCTCTGCGGCCTCTTCCGCGTCTTCGAGATCTGC<br>CTCGACTGTGCCTTCTAGTTGCCAGCCATCTGTTGTTTGC<br>CCCTCCCCCGTGCCTTCCTTGACCCTGGAAGGTGCCACTC<br>CCACTGTCCTTTCCTAATAAAATGAGGAAATTGCATCGCA<br>TTGTCTGAGTAGGTGTCATTCTATTCTGGGGGGTGGGGTG<br>GGGCAGGACAGCAAGGGGGAGGATTGGGAAGACAATAGCA<br>GGCATGCTGGGGACTCGAGTTAAGGGCGAATTCCCGATTA<br>GGATCTTCCTAGAGCATGGCTACGTAGATAAGTAGCATGG<br>CGGGTTAATCATTAACTACAAGGAACCCCTAGTGATGGAG<br>TTGGCCACTCCCTCTCTGCGCGCTCGCTCGCTCACTGAGG<br>CCGGGCGACCAAAGGTCGCCCGACGCCCGGGCTTTGCCCG<br>GGCGGCCTCAGTGAGCGAGCGAGCGCGCAG<br>(SEQ ID NO: 47) |

TABLE 1-continued

Illustrative Expression Cassette Sequences

| Expression Cassette | Sequence |
| --- | --- |
| pHZ18 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCAACT<br>GGCCTGCCCGAGACCAAACGTGCGGAACGTAGTTAAGTGT<br>TAGAGGTAGGATTTGAAGCCTGTCGATCATTCTGATTCTC<br>CTTTTCTCTACGTCTGCTTCCTGTCAATGGGCATCCTCAC<br>TGTCAAATGCAGATGGTACAGCAGGGCTTGGTCTCAGCCA<br>GGCAGGCCTCTCCCCAGTCTCCATGGCTCAGCTGTCCAGC<br>AGTTTCATCCCTAGACCATCCCAAACATGGTTGAGAAGCT<br>CTGAGGGGAGGACCCAGCACTGCCCGGCCCCTGAAGATAA<br>TCAGCAGTCCTGCTCAGCATATCAATCCAAGCCCACTCTA<br>GACAGAGATGCCGGTGCCCAGTTTTCTATTTTTAACTGGT<br>GTGAACTGAAGGAAAAGCACAGCATTAGAAGTCCAAGCAG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCCACCGCCATCCCCCTGCCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAG<br>CGGCCGCCCGCCACCATGGCTGAGAAAGAGTCAACATCAC<br>CACACCTCATGGTTCCCATTCTTCTCCTGGTTGGATGGAT<br>TGTAGGCTGCATCATCGTTATTTACATTGTCTTCTTCTAA<br>AAGCTTTGGATCCAATCAACCTCTGGATTACAAAATTTGT<br>GAAAGATTGACTGGTATTCTTAACTATGTTGCTCCTTTTA<br>CGCTATGTGGATACGCTGCTTTAATGCCTTTGTATCATGC<br>TATTGCTTCCCGTATGGCTTTCATTTTCTCCTCCTTGTAT<br>AAATCCTGGTTGCTGTCTCTTTATGAGGAGTTGTGGCCCG<br>TTGTCAGGCAACGTGGCGTGGTGTGCACTGTGTTTGCTGA<br>CGCAACCCCCACTGGTTGGGGCATTGCCACCACCTGTCAG<br>CTCCTTTCCGGGACTTTCGCTTTCCCCCTCCCTATTGCCA<br>CGGCGGAACTCATCGCCGCCTGCCTTGCCCGCTGCTGGAC<br>AGGGGCTCGGCTGTTGGGCACTGACAATTCCGTGGTGTTG<br>TCGGGGAAATCATCGTCCTTTCCTTGGCTGCTCGCCTGTG<br>TTGCCACCTGGATTCTGCGCGGGACGTCCTTCTGCTACGT<br>CCCTTCGGCCCTCAATCCAGCGGACCTTCCTTCCCGCGGC<br>CTGCTGCCGGCTCTGCGGCCTCTTCCGCGTCTTCGAGATC<br>TGCCTCGACTGTGCCTTCTAGTTGCCAGCCATCTGTTGTT<br>TGCCCCTCCCCCGTGCCTTCCTTGACCCTGGAAGGTGCCA<br>CTCCCACTGTCCTTTCCTAATAAAATGAGGAAATTGCATC<br>GCATTGTCTGAGTAGGTGTCATTCTATTCTGGGGGGTGGG<br>GTGGGGCAGGACAGCAAGGGGGAGGATTGGGAAGACAATA<br>GCAGGCATGCTGGGGACTCGAGTTAAGGGCGAATTCCCGA<br>TTAGGATCTTCCTAGAGCATGGCTACGTAGATAAGTAGCA<br>TGGCGGGTTAATCATTAACTACAAGGAACCCCTAGTGATG<br>GAGTTGGCCACTCCCTCTCTGCGCGCTCGCTCGCTCACTG<br>AGGCCGGGCGACCAAAGGTCGCCCGACGCCCGGGCTTTGC<br>CCGGGCGCCTCAGTGAGCGAGCGAGCGCGCAG<br>(SEQ ID NO: 48) |
| pHZ19<br>distinct sequence elements<br>are indicated in bold,<br>starting with ITR,<br>enhancer/promoter combo<br>(αMHCe, followed by<br>ACTC1e, followed by<br>hcTnTp), DWORF (which<br>is also underlined), WPRE,<br>polyA (hGHpA), ITR | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCAACT |

TABLE 1-continued

Illustrative Expression Cassette Sequences

| Expression Cassette | Sequence |
|---|---|
| | GGCCTGCCCGAGACCAAACGTGCGGAACGTAGTTAAGTGT<br>TAGAGGTAGGATTTGAAGCCTGTCGATCATTCTGATTCTC<br>CTTTTCTCTACGTCTGCTTCCTGTCAATGGGCATCCTCAC<br>TGTCAAATGCAGATGGTACAGCAGGGCTTGGTCTCAGCCA<br>GGCAGGCCTCTCCCCAGTCTCCATGGCTCAGCTGTCCAGC<br>AGTTTCATCCCTAGACCATCCCAAACATGGTTGAGAAGCT<br>CTGAGGGGAGGACCCAGCACTGCCCGGCCCCTGAAGATAA<br>TCAGCAGTCCTGCTCAGCATATCAATCCAAGCCCACTCTA<br>GACAGAGATGCCGGTGCCCAGTTTTCTATTTTTAACTGGT<br>GTGAACTGAAGGAAAAGCACAGCATTAGAAGTCCAAGCAG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAT<br>AACTGGTAAGTACCGCCTATAGACTCTATAGGCACACCCC<br>TTTGGCTCTTATGCATGCTGACAGACTAACAGACTGTTCC<br>TTTCCTGGGTCTTTTCTGCAGGCCTGTACGGAAGTGTTAC<br>TTCTGCTCTAAAAGCTGCGGAATTGTACCCGCGGCCGATC<br>CAATCGATACAGATCTAGCGGCC*GCCCGCCACC*ATGGCTG<br>AGAAAGAGTCAACATCACCACACCTCATGGTTCCCATTCT<br>TCTCCTGGTTGGATGGATTGTAGGCTGCATCATCGTTATT<br>TACATTGTCTTCTTCTAA*AAGCTTTGGATCCA*ATCAACCT<br>CTGGATTACAAAATTTGTGAAAGATTGACTGGTATTCTTA<br>ACTATGTTGCTCCTTTTACGCTATGTGGATACGCTGCTTT<br>AATGCCTTTGTATCATGCTATTGCTTCCCGTATGGCTTTC<br>ATTTTCTCCTCCTTGTATAAATCCTGGTTGCTGTCTCTTT<br>ATGAGGAGTTGTGGCCCGTTGTCAGGCAACGTGGCGTGGT<br>GTGCACTGTGTTTGCTGACGCAACCCCCACTGGTTGGGGC<br>ATTGCCACCACCTGTCAGCTCCTTTCGGGACTTTCGCTT<br>TCCCCCTCCCTATTGCCACGGCGGAACTCATCGCCGCCTG<br>CCTTGCCCGCTGCTGGACAGGGGCTCGGCTGTTGGGCACT<br>GACAATTCCGTGGTGTTGTCGGGGAAATCATCGTCCTTTC<br>CTTGGCTGCTCGCCTGTGTTGCCACCTGGATTCTGCGCGG<br>GACGTCCTTCTGCTACGTCCCTTCGGCCCTCAATCCAGCG<br>GACCTTCCTTCCCGCGGCCTGCTGCCGGCTCTGCGGCCTC<br>TTCCGCGTCTTCG*AGATCT*GCCTCGACTGTGCCTTCTAGT<br>TGCCAGCCATCTGTTGTTTGCCCCTCCCCCGTGCCTTCCT<br>TGACCCTGGAAGGTGCCACTCCCACTGTCCTTTCCTAATA<br>AAATGAGGAAATTGCATCGCATTGTCTGAGTAGGTGTCAT<br>TCTATTCTGGGGGGTGGGTGGGCAGGACAGCAAGGGGG<br>AGGATTGGGAAGACAATAGCAGGCATGCTGGGGA*CTCGAG*<br>*TTAAGGGCGAATTCCCGATTAGGATCTTCCTAGAGCATGG*<br>*CTACGTAGATAAGTAGCATGGCGGGTTAATCATTAACTAC*<br>AAGGAACCCCTAGTGATGGAGTTGGCCACTCCCTCTCTGC<br>GCGCTCGCTCGCTCACTGAGGCCGGGCGACCAAAGGTCGC<br>CCGACGCCCGGGCTTTGCCCGGGCGGCCTCAGTGAGCGAG<br>CGAGCGCGCAG (SEQ ID NO: 49) |
| pHZ20 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGGTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCCACCCCCACCGCCATCCCCCTGCCCCACCC |

TABLE 1-continued

Illustrative Expression Cassette Sequences

| Expression Cassette | Sequence |
|---|---|
| | GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCAGACGC<br>CTCCATAACTGGTAAGTACCGCCTATAGACTCTATAGGCA<br>CACCCCTTTGGCTCTTATGCATGCTGACAGACTAACAGAC<br>TGTTCCTTTCCTGGGTCTTTTCTGCAGGCCTGTACGGAAG<br>TGTTACTTCTGCTCTAAAAGCTGCGGAATTGTACCCGCGG<br>CCGATCCAATCGATACAGATCTAGCGGCCGCCCGCCACCA<br>TGGCTGAGAAAGAGTCAACATCACCACACCTCATGGTTCC<br>CATTCTTCTCCTGGTTGGATGGATTGTAGGCTGCATCATC<br>GTTATTTACATTGTCTTCTTCTAAAAGCTTTGGATCCAAT<br>CAACCTCTGGATTACAAAATTTGTGAAAGATTGACTGGTA<br>TTCTTAACTATGTTGCTCCTTTTACGCTATGTGGATACGC<br>TGCTTTAATGCCTTTGTATCATGCTATTGCTTCCCGTATG<br>GCTTTCATTTTCTCCTCCTTGTATAAATCCTGGTTGCTGT<br>CTCTTTATGAGGAGTTGTGGCCCGTTGTCAGGCAACGTGG<br>CGTGGTGTGCACTGTGTTTGCTGACGCAACCCCCACTGGT<br>TGGGGCATTGCCACCACCTGTCAGCTCCTTTCCGGGACTT<br>TCGCTTTCCCCCTCCCTATTGCCACGGCGGAACTCATCGC<br>CGCCTGCCTTGCCCGCTGCTGGACAGGGGCTCGGCTGTTG<br>GGCACTGACAATTCCGTGGTGTTGTCGGGGAAATCATCGT<br>CCTTTCCTTGGCTGCTCGCCTGTGTTGCCACCTGGATTCT<br>GCGCGGGACGTCCTTCTGCTACGTCCCTTCGGCCCTCAAT<br>CCAGCGGACCTTCCTTCCCGCGGCCTGCTGCCGGCTCTGC<br>GGCCTCTTCCGCGTCTTCGAGATCTGCCTCGACTGTGCCT<br>TCTAGTTGCCAGCCATCTGTTGTTTGCCCCTCCCCCGTGC<br>CTTCCTTGACCCTGGAAGGTGCCACTCCCACTGTCCTTTC<br>CTAATAAAATGAGGAAATTGCATCGCATTGTCTGAGTAGG<br>TGTCATTCTATTCTGGGGGGTGGGGTGGGGCAGGACAGCA<br>AGGGGGAGGATTGGGAAGACAATAGCAGGCATGCTGGGGA<br>CTCGAGTTAAGGGCGAATTCCCGATTAGGATCTTCCTAGA<br>GCATGGCTACGTAGATAAGTAGCATGGCGGGTTAATCATT<br>AACTACAAGGAACCCCTAGTGATGGAGTTGGCCACTCCCT<br>CTCTGCGCGCTCGCTCGCTCACTGAGGCCGGGCGACCAAA<br>GGTCGCCCGACGCCCGGGCTTTGCCCGGGCGGCCTCAGTG<br>AGCGAGCGAGCGCGCAG (SEQ ID NO: 50) |
| pHZ21<br>distinct sequence elements<br>are indicated in bold,<br>starting with ITR,<br>enhancer/promoter combo<br>(ACTC1e, followed by<br>αMHCe, followed by<br>hcTnTp), DWORF (which<br>is also underlined), WPRE,<br>polyA (hGHpA), ITR | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCT *TGTAGTTAATGATTAACCCGCCATGCTACT<br>TATCTACGTAGCCATGCTCTAGGAAGATCGGAATTCGCCC<br>TTAAG***AACTGGCCTGCCCGAGACCAAACGTGCGGAACGTA<br>GTTAAGTGTTAGAGGTAGGATTTGAAGCCTGTCGATCATT<br>CTGATTCTCCTTTTCTCTACGTCTGCTTCCTGTCAATGGG<br>CATCCTCACTGTCAAATGCAGATGGTACAGCAGGGCTTGG<br>TCTCAGCCAGGCAGGCCTCTCCCCAGTCTCCATGGCTCAG<br>CTGTCCAGCAGTTTCATCCCTAGACCATCCCAAACATGGT<br>TGAGAAGCTCTGAGGGGAGGACCCAGCACTGCCCGGCCCC<br>TGAAGATAATCAGCAGTCCTGCTCAGCATATCAATCCAAG<br>CCCACTCTAGACAGAGATGCCGGTGCCCAGTTTTCTATTT<br>TTAACTGGTGTGAACTGAAGGAAAAGCACAGCATTAGAAG<br>TCCAAGCACCTTCAGATTAAAAATAACTAAGGTAAGGGCC<br>ATGTGGGTAGGGGAGGTGGTGTGAGACGGTCCTGTCTCTC<br>CTCTATCTGCCCATCGGCCCTTTGGGGAGGAGGAATGTGC<br>CCAAGGACTAAAAAAAGGCCCTGGAGCCAGAGGGGCGAGG<br>GCAGCAGACCTTTCATGGGCAAACCTCAGGGCTGCTGTCG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAT<br>AACTGGTAAGTACCGCCTATAGACTCTATAGGCACACCCC<br>TTTGGCTCTTATGCATGCTGACAGACTAACAGACTGTTCC<br>TTTCCTGGGTCTTTTCTGCAGGCCTGTACGGAAGTGTTAC<br>TTCTGCTCTAAAAGCTGCGGAATTGTACCCGCGGCCGATC |

TABLE 1-continued

Illustrative Expression Cassette Sequences

| Expression Cassette | Sequence |
| --- | --- |
| | CAATCGATACAGATCTAGCGGCCGCCCGCCACCATGGCTG |
| | AGAAAGAGTCAACATCACCACACCTCATGGTTCCCATTCT |
| | TCTCCTGGTTGGATGGATTGTAGGCTGCATCATCGTTATT |
| | TACATTGTCTTCTTCTAAAAGCTTTGGATCCAATCAACCT |
| | CTGGATTACAAAATTTGTGAAAGATTGACTGGTATTCTTA |
| | ACTATGTTGCTCCTTTTACGCTATGTGGATACGCTGCTTT |
| | AATGCCTTTGTATCATGCTATTGCTTCCCGTATGGCTTTC |
| | ATTTTCTCCTCCTTGTATAAATCCTGGTTGCTGTCTCTTT |
| | ATGAGGAGTTGTGGCCCGTTGTCAGGCAACGTGGCGTGGT |
| | GTGCACTGTGTTTGCTGACGCAACCCCCACTGGTTGGGGC |
| | ATTGCCACCACCTGTCAGCTCCTTTCCGGGACTTTCGCTT |
| | TCCCCCTCCCTATTGCCACGGCGGAACTCATCGCCGCCTG |
| | CCTTGCCCGCTGCTGGACAGGGGCTCGGCTGTTGGGCACT |
| | GACAATTCCGTGGTGTTGTCGGGGAAATCATCGTCCTTTC |
| | CTTGGCTGCTCGCCTGTGTTGCCACCTGGATTCTGCGCGG |
| | GACGTCCTTCTGCTACGTCCCTTCGGCCCTCAATCCAGCG |
| | GACCTTCCTTCCCGCGGCCTGCTGCCGGCTCTGCGGCCTC |
| | TTCCGCGTCTTCGAGATCTGCCTCGACTGTGCCTTCTAGT |
| | TGCCAGCCATCTGTTGTTTGCCCCTCCCCCGTGCCTTCCT |
| | TGACCCTGGAAGGTGCCACTCCCACTGTCCTTTCCTAATA |
| | AAATGAGGAAATTGCATCGCATTGTCTGAGTAGGTGTCAT |
| | TCTATTCTGGGGGGTGGGGTGGGGCAGGACAGCAAGGGGG |
| | AGGATTGGGAAGACAATAGCAGGCATGCTGGGGACTCGAG |
| | TTAAGGGCGAATTCCCGATTAGGATCTTCCTAGAGCATGG |
| | CTACGTAGATAAGTAGCATGGCGGGTTAATCATTAACTAC |
| | AAGGAACCCCTAGTGATGGAGTTGGCCACTCCCTCTCTGC |
| | GCGCTCGCTCGCTCACTGAGGCCGGGCGACCAAAGGTCGC |
| | CCGACGCCCGGGCTTTGCCCGGGCGGCCTCAGTGAGCGAG |
| | CGAGCGCGCAG (SEQ ID NO: 51) |
| pHZ22 | CTGCGCGCTCGCTCGCTCACTGAGGCCGCCCGGGCAAAGC |
| | CCGGGCGTCGGGCGACCTTTGGTCGCCCGGCCTCAGTGAG |
| | CGAGCGAGCGCGCAGAGAGGGAGTGGCCAACTCCATCACT |
| | AGGGGTTCCTTGTAGTTAATGATTAACCCGCCATGCTACT |
| | TATCTACGTAGCCATGCTCTAGGAAGATCGGAATTCGCCC |
| | TTAAGAACTGGCCTGCCCGAGACCAAACGTGCGGAACGTA |
| | GTTAAGTGTTAGAGGTAGGATTTGAAGCCTGTCGATCATT |
| | CTGATTCTCCTTTTCTCTACGTCTGCTTCCTGTCAATGGG |
| | CATCCTCACTGTCAAATGCAGATGGTACAGCAGGGCTTGG |
| | TCTCAGCCAGGCAGGCCTCTCCCCAGTCTCCATGGCTCAG |
| | CTGTCCAGCAGTTTCATCCCTAGACCATCCCAAACATGGT |
| | TGAGAAGCTCTGAGGGGAGGACCCAGCACTGCCCGGCCCC |
| | TGAAGATAATCAGCAGTCCTGCTCAGCATATCAATCCAAG |
| | CCCACTCTAGACAGAGATGCCGGTGCCCAGTTTTCTATTT |
| | TTAACTGGTGTGAACTGAAGGAAAAGCACAGCATTAGAAG |
| | TCCAAGCAGTCATGGAGAAGACCCACCTTGCAGATGTCCT |
| | CACTGGGGCTGGCAGAGCCGGCAACCTGCCTAAGGCTGCT |
| | CAGTCCATTAGGAGCCAGTAGCCTGGAAGATGTCTTTACC |
| | CCCAGCATCAGTTCAAGTGGAGCAGCACATAACTCTTGCC |
| | CTCTGCCTTCCAAGATTCTGGTGCTGAGACTTATGGAGTG |
| | TCTTGGAGGTTGCCTTCTGCCCCCCAACCCTGCTCCCAGC |
| | TGGCCCTCCCAGGCCTGGGTTGCTGGCCTCTGCTTTATCA |
| | GGATTCTCAAGAGGGACAGCTGGTTTATGTTGCATGACTG |
| | TTCCCTGCATATCTGCTCTGGTTTTAAATAGCTTATCTGA |
| | GCAGCTGGAGGACCACATGGGCTTATATGGCGTGGGGTAC |
| | ATGTTCCTGTAGCCTTGTCCCTGGCACCTGCCAAAATAGC |
| | AGCCAACACCCCCACCCCCACCGCCATCCCCCTGCCCCA |
| | CCCGTCCCCTGTCGCACATTCCTCCCTCCGCAGGGCTGGC |
| | TCACCAGGCCCCAGCCCACATGCCTGCTTAAAGCCCTCTC |
| | CATCCTCTGCCTCACCCAGTCCCCGCTGAGACTGAGCAGA |
| | CGCCTCCATAACTGGTAAGTACCGCCTATAGACTCTATAG |
| | GCACACCCCTTTGGCTCTTATGCATGCTGACAGACTAACA |
| | GACTGTTCCTTTCCTGGGTCTTTTCTGCAGGCCTGTACGG |
| | AAGTGTTACTTCTGCTCTAAAAGCTGCGGAATTGTACCCG |
| | CGGCCGATCCAATCGATACAGATCTAGCGGCCGCCCGCCA |
| | CCATGGCTGAGAAAGAGTCAACATCACCACACCTCATGGT |
| | TCCCATTCTTCTCCTGGTTGGATGGATTGTAGGCTGCATC |
| | ATCGTTATTTACATTGTCTTCTTCTAAAAGCTTTGGATCC |
| | AATCAACCTCTGGATTACAAAATTTGTGAAAGATTGACTG |
| | GTATTCTTAACTATGTTGCTCCTTTTACGCTATGTGGATA |
| | CGCTGCTTTAATGCCTTTGTATCATGCTATTGCTTCCCGT |
| | ATGGCTTTCATTTTCTCCTCCTTGTATAAATCCTGGTTGC |
| | TGTCTCTTTATGAGGAGTTGTGGCCCGTTGTCAGGCAACG |
| | TGGCGTGGTGTGCACTGTGTTTGCTGACGCAACCCCCACT |
| | GGTTGGGGCATTGCCACCACCTGTCAGCTCCTTTCCGGGA |
| | CTTTCGCTTTCCCCCTCCCTATTGCCACGGCGGAACTCAT |

TABLE 1-continued

Illustrative Expression Cassette Sequences

| Expression Cassette | Sequence |
|---|---|
| | CGCCGCCTGCCTTGCCCGCTGCTGGACAGGGGCTCGGCTG<br>TTGGGCACTGACAATTCCGTGGTGTTGTCGGGGAAATCAT<br>CGTCCTTTCCTTGGCTGCTCGCCTGTGTTGCCACCTGGAT<br>TCTGCGCGGGACGTCCTTCTGCTACGTCCCTTCGGCCCTC<br>AATCCAGCGGACCTTCCTTCCCGCGGCCTGCTGCCGGCTC<br>TGCGGCCTCTTCCGCGTCTTCGAGATCTGCCTCGACTGTG<br>CCTTCTAGTTGCCAGCCATCTGTTGTTTGCCCCTCCCCCG<br>TGCCTTCCTTGACCCTGGAAGGTGCCACTCCCACTGTCCT<br>TTCCTAATAAAATGAGGAAATTGCATCGCATTGTCTGAGT<br>AGGTGTCATTCTATTCTGGGGGTGGGGTGGGGCAGGACA<br>GCAAGGGGGAGGATTGGGAAGACAATAGCAGGCATGCTGG<br>GGACTCGAGTTAAGGGCGAATTCCCGATTAGGATCTTCCT<br>AGAGCATGGCTACGTAGATAAGTAGCATGGCGGGTTAATC<br>ATTAACTACAAGGAACCCCTAGTGATGGAGTTGGCCACTC<br>CCTCTCTGCGCGCTCGCTCGCTCACTGAGGCCGGGCGACC<br>AAAGGTCGCCCGACGCCCGGGCTTTGCCCGGGCGGCCTCA<br>GTGAGCGAGCGAGCGCGCAG (SEQ ID NO: 52) |
| pHZ23 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCGTCA<br>TGGAGAAGACCCACCTTGCAGATGTCCTCACTGGGGCTGG<br>CAGAGCCGGCAACCTGCCTAAGGCTGCTCAGTCCATTAGG<br>AGCCAGTAGCCTGGAAGATGTCTTTACCCCCAGCATCAGT<br>TCAAGTGGAGCAGCACATAACTCTTGCCCTCTGCCTTCCA<br>AGATTCTGGTGCTGAGACTTATGGAGTGTCTTGGAGGTTG<br>CCTTCTGCCCCCCAACCCTGCTCCCAGCTGGCCCTCCCAG<br>GCCTGGGTTGCTGGCCTCTGCTTTATCAGGATTCTCAAGA<br>GGGACAGCTGGTTTATGTTGCATGACTGTTCCCTGCATAT<br>CTGCTCTGGTTTTAAATAGCTTATCTGAGCAGCTGGAGGA<br>CCACATGGGCTTATATGGCGTGGGGTACATGTTCCTGTAG<br>CCTTGTCCCTGGCACCTGCCAAAATAGCAGCCAACACCCC<br>CCACCCCCACCGCCATCCCCCTGCCCCACCCGTCCCCTGT<br>CGCACATTCCTCCCTCCGCAGGGCTGGCTCACCAGGCCCC<br>AGCCCACATGCCTGCTTAAAGCCCTCTCCATCCTCTGCCT<br>CACCCAGTCCCCGCTGAGACTGAGCAGACGCCTCCATAAC<br>TGGTAAGTACCGCCTATAGACTCTATAGGCACACCCCTTT<br>GGCTCTTATGCATGCTGACAGACTAACAGACTGTTCCTTT<br>CCTGGGTCTTTTCTGCAGGCCTGTACGGAAGTGTTACTTC<br>TGCTCTAAAAGCTGCGGAATTGTACCCGCGGCCGATCCAA<br>TCGATACAGATCTAGCGGCCGCCCGCCACCATGGCTGAGA<br>AAGAGTCAACATCACCACACCTCATGGTTCCCATTCTTCT<br>CCTGGTTGGATGGATTGTAGGCTGCATCATCGTTATTTAC<br>ATTGTCTTCTTCTAAAAGCTTTGGATCCAATCAACCTCTG<br>GATTACAAAATTTGTGAAAGATTGACTGGTATTCTTAACT<br>ATGTTGCTCCTTTTACGCTATGTGGATACGCTGCTTTAAT<br>GCCTTTGTATCATGCTATTGCTTCCCGTATGGCTTTCATT<br>TTCTCCTCCTTGTATAAATCCTGGTTGCTGTCTCTTTATG<br>AGGAGTTGTGGCCCGTTGTCAGGCAACGTGGCGTGGTGTG<br>CACTGTGTTTGCTGACGCAACCCCCACTGGTTGGGGCATT<br>GCCACCACCTGTCAGCTCCTTTCCGGGACTTTCGCTTTCC<br>CCCTCCCTATTGCCACGGCGGAACTCATCGCCGCCTGCCT<br>TGCCCGCTGCTGGACAGGGGCTCGGCTGTTGGGCACTGAC<br>AATTCCGTGGTGTTGTCGGGGAAATCATCGTCCTTTCCTT<br>GGCTGCTCGCCTGTGTTGCCACCTGGATTCTGCGCGGGAC<br>GTCCTTCTGCTACGTCCCTTCGGCCCTCAATCCAGCGGAC<br>CTTCCTTCCCGCGGCCTGCTGCCGGCTCTGCGGCCTCTTC<br>CGCGTCTTCGAGATCTGCCTCGACTGTGCCTTCTAGTTGC<br>CAGCCATCTGTTGTTTGCCCCTCCCCCGTGCCTTCCTTGA<br>CCCTGGAAGGTGCCACTCCCACTGTCCTTTCCTAATAAAA<br>TGAGGAAATTGCATCGCATTGTCTGAGTAGGTGTCATTCT<br>ATTCTGGGGGTGGGGTGGGGCAGGACAGCAAGGGGGAGG<br>ATTGGGAAGACAATAGCAGGCATGCTGGGGACTCGAGTTA<br>AGGGCGAATTCCCGATTAGGATCTTCCTAGAGCATGGCTA<br>CGTAGATAAGTAGCATGGCGGGTTAATCATTAACTACAAG<br>GAACCCCTAGTGATGGAGTTGGCCACTCCCTCTCTGCGCG<br>CTCGCTCGCTCACTGAGGCCGGGCGACCAAAGGTCGCCCG<br>ACGCCCGGGCTTTGCCCGGGCGGCCTCAGTGAGCGAGCGA<br>GCGCGCAG (SEQ ID NO: 53) |

TABLE 1-continued

Illustrative Expression Cassette Sequences

| Expression Cassette | Sequence |
| --- | --- |
| pHZ24 | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGGTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCACCCCCACCGCCATCCCCCTGCCCCACCC<br>GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCAGACGC<br>CTCCAGCGGCCGCCCGCCACCATGGCCGAGAAGGAATCTA<br>CCAGCCCCCACCTGATGGTGCCTATTCTGCTGCTGGTGGG<br>CTGGATCGTCGGCTGCATCATCGTGATCTACATCGTGTTC<br>TTCTGAAAGCTTTGGATCCAATCAACCTCTGGATTACAAA<br>ATTTGTGAAAGATTGACTGGTATTCTTAACTATGTTGCTC<br>CTTTTACGCTATGTGGATACGCTGCTTTAATGCCTTTGTA<br>TCATGCTATTGCTTCCCGTATGGCTTTCATTTTCTCCTCC<br>TTGTATAAATCCTGGTTGCTGTCTCTTTATGAGGAGTTGT<br>GGCCCGTTGTCAGGCAACGTGGCGTGGTGTGCACTGTGTT<br>TGCTGACGCAACCCCACTGGTTGGGGCATTGCCACCACC<br>TGTCAGCTCCTTTCCGGGACTTTCGCTTTCCCCCTCCCTA<br>TTGCCACGGCGGAACTCATCGCCGCCTGCCTTGCCCGCTG<br>CTGGACAGGGGCTCGGCTGTTGGGCACTGACAATTCCGTG<br>GTGTTGTCGGGGAAATCATCGTCCTTTCCTTGGCTGCTCG<br>CCTGTGTTGCCACCTGGATTCTGCGCGGGACGTCCTTCTG<br>CTACGTCCCTTCGGCCCTCAATCCAGCGGACCTTCCTTCC<br>CGCGGCCTGCTGCCGGCTCTGCGGCCTCTTCCGCGTCTTC<br>GAGATCTGCCTCGACTGTGCCTTCTAGTTGCCAGCCATCT<br>GTTGTTTGCCCCTCCCCCGTGCCTTCCTTGACCCTGGAAG<br>GTGCCACTCCCACTGTCCTTTCCTAATAAAATGAGGAAAT<br>TGCATCGCATTGTCTGAGTAGGTGTCATTCTATTCTGGGG<br>GGTGGGGTGGGGCAGGACAGCAAGGGGGAGGATTGGGAAG<br>ACAATAGCAGGCATGCTGGGGACTCGAGTTAAGGGCGAAT<br>TCCCGATTAGGATCTTCCTAGAGCATGGCTACGTAGATAA<br>GTAGCATGGCGGGTTAATCATTAACTACAAGGAACCCCTA<br>GTGATGGAGTTGGCCACTCCCTCTCTGCGCGCTCGCTCGC<br>TCACTGAGGCCGGGCGACCAAAGGTCGCCCGACGCCCGGG<br>CTTTGCCCGGCGGCCTCAGTGAGCGAGCGAGCGCGCAG<br>(SEQ ID NO: 54) |
| pHZ25<br>distinct sequence elements<br>are indicated in bold,<br>starting with ITR,<br>promoter/enhancer combo<br>(αMHCe, followed by<br>hcTnTp), DWORF (which<br>is also underlined), WPRE,<br>polyA (hGHpA), SV40pA,<br>optimized DWORF (which<br>is also underlined),<br>promoter/enhancer combo<br>(ccTnTp, followed by<br>ACTC1e), ITR | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCAACTCCATCACT<br>AGGGGTTCCT_TGTAGTTAATGATTAACCCGCCATGCTACT_<br>_TATCTACGTAGCCATGCTCTAGGAAGATCGGAATTCGCCC_<br>_TTAAGC_CTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCGTCA<br>TGGAGAAGACCCACCTTGCAGATGTCCTCACTGGGGCTGG<br>CAGAGCCGGCAACCTGCCTAAGGCTGCTCAGTCCATTAGG<br>AGCCAGTAGCCTGGAAGATGTCTTTACCCCCAGCATCAGT<br>TCAAGTGGAGCAGCACATAACTCTTGCCCTCTGCCTTCCA<br>AGATTCTGGTGCTGAGACTTATGGAGTGTCTTGGAGGTTG<br>CCTTCTGCCCCCCAACCCTGCTCCCAGCTGGCCCTCCCAG<br>GCCTGGGTTGCTGGCCTCTGCTTTATCAGGATTCTCAAGA<br>GGGACAGCTGGTTTATGTTGCATGACTGTTCCCTGCATAT<br>CTGCTCTGGTTTTAAATAGCTTATCTGAGCAGCTGGAGGA<br>CCACATGGGCTTATATGGCGTGGGGTACATGTTCCTGTAG<br>CCTTGTCCCTGGCACCTGCCAAAATAGCAGCCAACACCCC<br>CCACCCCCACCGCCATCCCCCTGCCCCACCCGTCCCCTGT<br>CGCACATTCCTCCCTCCGCAGGGCTGGCTCACCAGGCCCC<br>AGCCCACATGCCTGCTTAAAGCCCTCTCCATCCTCTGCCT<br>CACCCAGTCCCCGCTGAGACTGAGCAGACGCCTCCATAAC |

TABLE 1-continued

Illustrative Expression Cassette Sequences

| Expression Cassette | Sequence |
|---|---|
| | TGGTAAGTACCGCCTATAGACTCTATAGGCACACCCCTTT |
| | GGCTCTTATGCATGCTGACAGACTAACAGACTGTTCCTTT |
| | CCTGGGTCTTTTCTGCAGGCCTGTACGGAAGTGTTACTTC |
| | TGCTCTAAAAGCTGCGGAATTGTACCCGCGGCCGATCCAA |
| | TCGATACAGATCTAGCGGCC*GCCCGCCACC*ATGGCTGAGA |
| | AAGAGTCAACATCACCACACCTCATGGTTCCCATTCTTCT |
| | CCTGGTTGGATGGATTGTAGGCTGCATCATCGTTATTTAC |
| | ATTGTCTTCTTCTAA*AAGCTTTGGATCC*AATCAACCTCTG |
| | GATTACAAAATTTGTGAAAGATTGACTGGTATTCTTAACT |
| | ATGTTGCTCCTTTTACGCTATGTGGATACGCTGCTTTAAT |
| | GCCTTTGTATCATGCTATTGCTTCCCGTATGGCTTTCATT |
| | TTCTCCTCCTTGTATAAATCCTGGTTGCTGTCTCTTTATG |
| | AGGAGTTGTGGCCCGTTGTCAGGCAACGTGGCGTGGTGTG |
| | CACTGTGTTTGCTGACGCAACCCCCACTGGTTGGGGCATT |
| | GCCACCACCTGTCAGCTCCTTTCCGGGACTTTCGCTTTCC |
| | CCCTCCCTATTGCCACGGCGGAACTCATCGCCGCCTGCCT |
| | TGCCCGCTGCTGGACAGGGGCTCGGCTGTTGGGCACTGAC |
| | AATTCCGTGGTGTTGTCGGGGAAATCATCGTCCTTTCCTT |
| | GGCTGCTCGCCTGTGTTGCCACCTGGATTCTGCGCGGGAC |
| | GTCCTTCTGCTACGTCCCTTCGGCCCTCAATCCAGCGGAC |
| | CTTCCTTCCCGCGGCCTGCTGCCGGCTCTGCGGCCTCTTC |
| | CGCGTCTTCGAGATCTGCCTCGACTGTGCCTTCTAGTTGC |
| | CAGCCATCTGTTGTTTGCCCCTCCCCGTGCCTTCCTTGA |
| | CCCTGGAAGGTGCCACTCCCACTGTCCTTTCCTAATAAAA |
| | TGAGGAAATTGCATCGCATTGTCTGAGTAGGTGTCATTCT |
| | ATTCTGGGGGGTGGGGTGGGGCAGGACAGCAAGGGGGAGG |
| | ATTGGGAAGACAATAGCAGGCATGCTGGGGA*CTCGAGTTA* |
| | *AGGGCAGCCAGAAGTCAGATGCTCAAGGGGCTTCATGATG* |
| | *TCCCCATAATTTTTGGCAGAGGGAAAAAGATCGGATCCTC* |
| | *AGGCGTAGTTCACCCCGTCCTCGAGGCCGCCCGGGTCGAC* |
| | *TAAAAAACCTCCCACACCTCCCCCTGAACCTGAAACATAA* |
| | *AATGAATGCAATTGTTGTTGTTAA*CTTGTTTATTGCAGCT |
| | TATAATGGTTACAAATAAAGCAATAGCATCACAAATTTCA |
| | CAAATAAAGCATTTTTTTCACTGCATTCTAGTTGTGGTTT |
| | GTCCAAACTCATCAATGTATCTTATCATGTCTGGATC*CGC* |
| | *GCGGCCG*TCAGAAGAACACGATGTAGATCACGATGATGCA |
| | GCCGACGATCCAGCCCACCAGCAGCAGAATAGGCACCATC |
| | AGGTGGGGGCTGGTAGATTCCTTCTCGGCCAT*GGTGGCGG* |
| | *CTAGCCTATAGTGAGTCGTATTA*AGTACTCTAGCCTTAAG |
| | AGCTGTAATTGAACTGGGAGTGGACACCTGTGGAGAGAAA |
| | GGCAAAGTGGATGTCAGTAAGACCAATAGGTGCCTATCAG |
| | AAACGCAAGAGTCTTCTCTGTCTCGACAAGCCCAGTTTCT |
| | ATTGGTCTCCTTAAACCTGTCTTGTAACCTTGATACTTAC |
| | CTGCCCAGTGCCTCACGACCAACTTCTGCAGCTTAAGTTC |
| | GAGACTGTTGTGTCAGAAGCACTGACTGCGTTAGCAATTT |
| | AACTGTGATAAACTACCGCAATAAAGCTCTAGAGCTTCGG |
| | GGATCGTCCCACGGAGCGGTGGGTGCCGGCGGCTGTCTGG |
| | GAAGGGCTCCTTGGGGGGCAGAGGCTTTAAGGTCCCCCCG |
| | GCGCCCACCCCGGGGGGGCAGAGCCAGCAGGAATGTGCC |
| | CGGCGCCCAGAGGAGGAATGCAACACTTGTGAGCTGCTATT |
| | TTGGCAGCAGCGGCCCCGGCCCCCTCCGTGCTCCCCCTTC |
| | CCCCACAGGAGCCCATATAAGCCCAAGCTATTGTGTGGCC |
| | TCAGAGTTTTGCTATTTTAAACCCGTCGGACGGAGATACG |
| | TGAGTGCCCGAGGGGCTGACACAAGCCAGCCAGCTGTCAC |
| | CTCCCAGGGCTGGGGACGCTGATAAGGCAGCGCTTCGGAC |
| | CCGACCCTCTGCCGCAGCCCCAGATGCTGTCATGTGAAAG |
| | CCCAGACTGCTTTTATCCCTGCTTGGACTTCTAATGCTGT |
| | GCTTTTCCTTCAGTTCACACCAGTTAAAAATAGAAAACTG |
| | GGCACCGGCATCTCTGTCTAGAGTGGGCTTGGATTGATAT |
| | GCTGAGCAGGACTGCTGATTATCTTCAGGGGCCGGGCAGT |
| | GCTGGGTCCTCCCCTCAGAGCTTCTCAACCATGTTTGGGA |
| | TGGTCTAGGGATGAAACTGCTGGACAGCTGAGCCATGGAG |
| | ACTGGGGAGAGGCCTGCCTGGCTGAGACCAAGCCCTGCTG |
| | TACCATCTGCATTTGACAGTGAGGATGCCCATTGACAGGA |
| | AGCAGACGTAGAGAAAGGAGAATCAGAATGATCGACAGG |
| | CTTCAAATCCTACCTCTAACACTTAACTACGTTCCGCACG |
| | TTTGGTCTCGGGCAGGCCAGTT*GAATTCCCGATTAGGATC* |
| | *TTCCTAGAGCATGGCTACGTAGATAAGTAGCATGGCGGGT* |
| | *TAATCATTAACTACAAGGAACCCCTAGTGATGGAGTTGGC* |
| | CACTCCCTCTCTGCGCGCTCGCTCGCTCACTGAGGCCGGG |
| | CGACCAAAGGTCGCCCGACGCCCGGGCTTTGCCCGGCGG |
| | CCTCAGTGAGCGAGCGAGCGCGCAG (SEQ ID NO: 55) |
| pHZ33 distinct sequence elements are indicated in bold, | CTGCGCGCTCGCTCGCTCACTGAGGCCGCCCGGGCAAAGC CCGGGCGTCGGGCGACCTTTGGTCGCCCGGCCTCAGTGAG CGAGCGAGCGCGCAGAGAGGGGAGTGGCCAACTCCATCACT |

TABLE 1-continued

Illustrative Expression Cassette Sequences

| Expression Cassette | Sequence |
| --- | --- |
| starting with ITR, promoter/enhancer combo (αMHCe, followed by hcTnTp), DWORF (which is also underlined), WPRE, polyA (hGHpA), promoter/enhancer combo (ACTC1e, followed by ccTnTp), optimized DWORF (which is also underlined), SV40pA, ITR | AGGGGTTCCT*TGTAGTTAATGATTAACCCGCCATGCTACT TATCTACGTAGCCATGCTCTAGGAAGATCGGAATTCGCCC TTAAG*CCTTCAGATTAAAAATAACTAAGGTAAGGGCCATG TGGGTAGGGGAGGTGGTGTGAGACGGTCCTGTCTCTCCTC TATCTGCCCATCCGGCCCTTTGGGGAGGAGGAATGTGCCCA AGGACTAAAAAAAGGCCCTGGAGCCAGAGGGGCGAGGGCA GCAGACCTTTCATGGGCAAACCTCAGGGCTGCTGTCGTCA TGGAGAAGACCCACCTTGCAGATGTCCTCACTGGGGCTGG CAGAGCCGGCAACCTGCCTAAGGCTGCTCAGTCCATTAGG AGCCAGTAGCCTGGAAGATGTCTTTACCCCCAGCATCAGT TCAAGTGGAGCAGCACATAACTCTTGCCCTCTGCCTTCCA AGATTCTGGTGCTGAGACTTATGGAGTGTCTTGGAGGTTG CCTTCTGCCCCCCAACCCTGCTCCCAGCTGGCCCTCCCAG GCCTGGGTTGCTGGCCTCTGCTTTATCAGGATTCTCAAGA GGGACAGCTGGTTTATGTTGCATGACTGTTCCCTGCATAT CTGCTCTGGTTTTAAATAGCTTATCTGAGCAGCTGGAGGA CCACATGGGCTTATATGGCGTGGGGTACATGTTCCTGTAG CCTTGTCCCTGGCACCTGCCAAAATAGCAGCCAACACCCC CCACCCCCACCGCCATCCCCCTGCCCCACCCGTCCCCTGT CGCACATTCCTCCCTCCGCAGGGCTGGCTCACCAGGCCCC AGCCCACATGCCTGCTTAAAGCCCTCTCCATCCTCTGCCT CACCCAGTCCCCGCTGAGACTGAGCAGACGCCTCCATAAC TGGTAAGTACCGCCTATAGACTCTATAGGCACACCCCTTT GGCTCTTATGCATGCTGACAGACTAACAGACTGTTCCTTT CCTGGGTCTTTTCTGCAGGCCTGTACGGAAGTGTTACTTC TGCTCTAAAAGCTGCGGAATTGTACCCGCGGCCGATCCAA TCGATACAGATCTAGC*GGCCGCCCGCCACC*<u>ATGGCTGAGA AAGAGTCAACATCACCACACCTCATGGTTCCCATTCTTCT CCTGGTTGGATGGATTGTAGGCTGCATCATCGTTATTTAC ATTGTCTTCTTCTAA</u>*AAGCTTTGGATCCA*ATCAACCTCTG GATTACAAATTTGTGAAAGATTGACTGGTATTCTTAACT ATGTTGCTCCTTTTACGCTATGTGGATACGCTGCTTTAAT GCCTTTGTATCATGCTATTGCTTCCCGTATGGCTTTCATT TTCTCCTCCTTGTATAAATCCTGGTTGCTGTCTCTTTATG AGGAGTTGTGGCCCGTTGTCAGGCAACGTGGCGTGGTGTG CACTGTGTTTGCTGACGCAACCCCCACTGGTTGGGGCATT GCCACCACCTGTCAGCTCCTTTCCGGGACTTTCGCTTTCC CCCTCCCTATTGCCACGGCGGAACTCATCGCCGCCTGCCT TGCCCGCTGCTGGACAGGGGCTCGGCTGTTGGGCACTGAC AATTCCGTGGTGTTGTCGGGGAAATCATCGTCCTTTCCTT GGCTGCTCGCCTGTGTTGCCACCTGGATTCTGCGCGGGAC GTCCTTCTGCTACGTCCCTTCGGCCCTCAATCCAGCGGAC CTTCCTTCCCGCGGCCTGCTGCCGGCTCTGCGGCCTCTTC CGCGTCTTCG*AGATC*TGCCTCGACTGTGCCTTCTAGTTGC CAGCCATCTGTTGTTTGCCCCTCCCCGTGCCTTCCTTGA CCCTGGAAGGTGCCACTCCCACTGTCCTTTCCTAATAAAA TGAGGAAATTGCATCGCATTGTCTGAGTAGGTGTCATTCT ATTCTGGGGGGTGGGGTGGGGCAGGACAGCAAGGGGGAGG ATTGGGAAGACAATAGCAGGCATGCTGGGGA*CTCGAGTTA AGGGCAGCCAGAAGTCAGATGCTCAAGGGGCTTCATGATG TCCCCATAATTTTTGGCAGAGGGAAAAAGATCGGATCCTC AGGCGTAGTTCACCCCGTCCTCGAGGCCGCCCGGGTCGAC TAAAAAACCTCCCACACCTCCCCCTGAACCTGAAACATAA AATGAATGCAATTGTTGTTGTTAAACTGGCCTGCCCGAGA CCAAACGTGCGGAACGTAGTTAAGTGTTA*GAGGTAGGATT TGAAGCCTGTCGATCATTCTGATTCTCCTTTTCTCTACGT CTGCTTCCTGTCAATGGGCATCCTCACTGTCAAATGCAGA TGGTACAGCAGGGCTTGGTCTCAGCCAGGCAGGCCTCTCC CCAGTCTCCATGGCTCAGCTGTCCAGCAGTTTCATCCCTA GACCATCCCAAACATGGTTGAGAAGCTCTGAGGGGAGGAC CCAGCACTGCCCGGCCCCTGAAGATAATCAGCAGTCCTGC TCAGCATATCAATCCAAGCCCACTCTAGACAGAGATGCCG GTGCCCAGTTTTCTATTTTTAACTGGTGTGAACTGAAGGA AAAGCACAGCATTAGAAGTCCAAGCAGGGATAAAAGCAGT CTGGGCTTTCACATGACAGCATCTGGGGCTGCGGCAGAGG GTCGGGTCCGAAGCGCTGCCTTATCAGCGTCCCCAGCCCT GGGAGGTGACAGCTGGCTGGCTTGTGTCAGCCCCTCGGGC ACTCACGTATCTCCGTCCGACGGGTTTAAAATAGCAAAAC TCTGAGGCCACACAATAGCTTGGGCTTATATGGGCTCCTG TGGGGAAGGGGAGCACGGAGGGGGCCGGGGCCGCTGCT GCCAAAATAGCAGCTCACAAGTGTTGCATTCCTCTCTGGG CGCCGGGCACATTCCTGCTGGCTCTGCCCGCCCCGGGGTG GGCGCCGGGGGACCTTAAAGCCTCTGCCCCCAAGGAGC CCTTCCCAGACAGCCGCCGGCACCCACCGCTCCGTGGGAC GATCCCCGAAGCTCTAGAGCTTTATTGCGGTAGTTTATCA CAGTTAAATTGCTAACGCAGTCAGTGCTTCTGACACAACA |

TABLE 1-continued

Illustrative Expression Cassette Sequences

| Expression Cassette | Sequence |
|---|---|
| | GTCTCGAACTTAAGCTGCAGAAGTTGGTCGTGAGGCACTG<br>GGCAGGTAAGTATCAAGGTTACAAGACAGGTTTAAGGAGA<br>CCAATAGAAACTGGGCTTGTCGAGACAGAGAAGACTCTTG<br>CGTTTCTGATAGGCACCTATTGGTCTTACTGACATCCACT<br>TTGCCTTTCTCTCCACAGGTGTCCACTCCCAGTTCAATTA<br>CAGCTCTTAAGGCTAGAGTACT*TAATACGACTCACTATAG*<br>*GCTAGCCGCCACC*ATGGCCGAGAAGGAATCTACCAGCCCC<br>CACCTGATGGTGCCTATTCTGCTGCTGGTGGGCTGGATCG<br>TCGGCTGCATCATCGTGATCTACATCGTGTTCTTCTGA*CG*<br>*GCCGCGCG*GATCCAGACATGATAAGATACATTGATGAGTT<br>TGGACAAACCACAACTAGAATGCAGTGAAAAAAATGCTTT<br>ATTTGTGAAATTTGTGATGCTATTGCTTTATTTGTAACCA<br>TTATAAGCTGCAATAAACAAGT*GAATTCCCGATTAGGATC*<br>*TTCCTAGAGCATGGCTACGTAGATAAGTAGCATGGCGGGT*<br>*TAATCATTAACTACAAGGAACCCCTAGTGATGGAGTTGGC*<br>*CACTCCCTCTCTGCGCGCTCGCTCGCTCACTGAGGCCGGG*<br>*CGACCAAAGGTCGCCCGACGCCCGGGCTTTGCCCGGGCGG*<br>*CCTCAGTGAGCGAGCGAGCGCGCAG* (SEQ ID NO: 56) |
| pHZ34<br>distinct sequence elements are indicated in bold, starting with ITR, polyA (hGHpA), WPRE, DWORF (which is also underlined), promoter/enhancer combo (hcTnTp, followed by αMHCe, followed by ACTC1e, followed by ccTnTp), optimized DWORF (which is also underlined), SV40pA, ITR | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCT*TGTAGTTAATGATTAACCCGCCATGCTACT*<br>*TATCTACGTAGCCATGCTCTAGGAAGATCGGAATTC*TCCC<br>CAGCATGCCTGCTATTGTCTTCCCAATCCTCCCCCTTGCT<br>GTCCTGCCCCACCCCACCCCCCAGAATAGAATGACACCTA<br>CTCAGACAATGCGATGCAATTTCCTCATTTTATTAGGAAA<br>GGACAGTGGGAGTGGCACCTTCCAGGGTCAAGGAAGGCAC<br>GGGGGAGGGGCAAACAACAGATGGCTGGCAACTAGAAGGC<br>ACAGTCGAGGC*AGATC*TCGAAGACGCGGAAGAGGCCGCAG<br>AGCCGGCAGCAGGCCGCGGGAAGGAAGGTCCGCTGGATTG<br>AGGGCCGAAGGGACGTAGCAGAAGGACGTCCCGCGCAGAA<br>TCCAGGTGGCAACACAGGCGAGCAGCCAAGGAAAGGACGA<br>TGATTTCCCCGACAACACCACGGAATTGTCAGTGCCCAAC<br>AGCCGAGCCCCTGTCCAGCAGCGGGCAAGGCAGGCGGCGA<br>TGAGTTCCGCCGTGGCAATAGGGAGGGGGAAAGCGAAAGT<br>CCCCGGAAAGGAGCTGACAGGTGGTGGCAATGCCCCAACCA<br>GTGGGGGTTGCGTCAGCAAACACAGTGCACACCACGCCAC<br>GTTGCCTGACAACGGGCCACAACTCCTCATAAAGAGACAG<br>CAACCAGGATTTATACAAGGAGGAGAAAATGAAAGCCATA<br>CGGGAAGCAATAGCATGATACAAAGGCATTAAAGCAGCGT<br>ATCCACATAGCGTAAAAGGAGCAACATAGTTAAGAATACC<br>AGTCAATCTTTCACAAATTTTGTAATCCAGAGGTTGA*TTG*<br>*GATCCAAAGCTT*TTAGAAGAAGACAATGTAAATAACGATG<br>ATGCAGCCTACAATCCATCCAACCAGGAGAAGAATGGGAA<br>CCATGAGGTGTGGTGATGTTGACTCTTTCTCAGCCATGGT<br>GGCGGGCGGCCGCTAGATCTGTATCGATTGGATCGGCCGC<br>GGGTACAATTCCGCAGCTTTTAGAGCAGAAGTAACACTTC<br>CGTACAGGCCTGCAGAAAAGACCCAGGAAAGGAACAGTCT<br>GTTAGTCTGTCAGCATGCATAAGAGCCAAAGGGGTGTGCC<br>TATAGAGTCTATAGGCGGTACTTACCAGTTATGGAGGCGT<br>CTGCTCAGTCTCAGCGGGGACTGGGTGAGGCAGAGGATGG<br>AGAGGGCTTTAAGCAGGCATGTGGGCTGGGGCCTGGTGAG<br>CCAGCCCTGCGGAGGGAGGAATGTGCGACAGGGGACGGGT<br>GGGGCAGGGGGATGGCGGTGGGGGTGGGGGGTGTTGGCTG<br>CTATTTTGGCAGGTGCCAGGGACAAGGCTACAGGAACATG<br>TACCCCACGCCATATAAGCCCATGTGGTCCTCCAGCTGCT<br>CAGATAAGCTATTTAAAACCAGAGCAGATATGCAGGGAAC<br>AGTCATGCAACATAAACCAGCTGTCCCTCTTGAGAATCCT<br>GATAAAGCAGAGGCCAGCAACCCAGGCCTGGGAGGGCCAG<br>CTGGGAGCAGGGTTGGGGGGCAGAAGGCAACCTCCAAGAC<br>ACTCCATAAGTCTCAGCACCAGAATCTTGGAAGGCAGAGG<br>GCAAGAGTTATGTGCTGCTCCACTTGAACTGATGCTGGGG<br>GTAAAGACATCTTCCAGGCTACTGGCTCCTAATGGACTGA<br>GCAGCCTTAGGCAGGTTGCCGGCTCTGCCAGCCCCAGTGA<br>GGACATCTGCAAGGTGGGTCTTCTCCATGACGACAGCAGC<br>CCTGAGGTTTGCCCATGAAAGGTCTGCTGCCCTCGCCCCT<br>CTGGCTCCAGGGCCTTTTTTTAGTCCTTGGGCACATTCCT<br>CCTCCCCAAAGGGCCGATGGGCAGATAGAGGAGAGACAGG<br>ACCGTCTCACACCACCTCCCCTACCCACATGGCCCTTACC<br>TTAGTTATTTTTAATCTGAAGG*CTCGAGTTAAGGGCAGCC*<br>*AGAAGTCAGATGCTCAAGGGGCTTCATGATGTCCCCATAA*<br>*TTTTTGGCAGAGGGAAAAAGATCGGATCCTCAGGCGTAGT*<br>*TCACCCCGTCCTCGAGGCCGCCCGGGTCGACTAAAAAACC*<br>*TCCCACACCTCCCCCTGAACCTGAAACATAAAATGAATGC*<br>*AATTGTTGTTGTTA*AACTGGCCTGCCCGAGACCAAACGTG |

TABLE 1-continued

Illustrative Expression Cassette Sequences

| Expression Cassette | Sequence |
|---|---|
| | CGGAACGTAGTTAAGTGTTAGAGGTAGGATTTGAAGCCTG<br>TCGATCATTCTGATTCTCCTTTTCTCTACGTCTGCTTCCT<br>GTCAATGGGCATCCTCACTGTCAAATGCAGATGGTACAGC<br>AGGGCTTGGTCTCAGCCAGGCAGGCCTCTCCCCAGTCTCC<br>ATGGCTCAGCTGTCCAGCAGTTTCATCCCTAGACCATCCC<br>AAACATGGTTGAGAAGCTCTGAGGGGAGGACCCAGCACTG<br>CCCGGCCCCTGAAGATAATCAGCAGTCCTGCTCAGCATAT<br>CAATCCAAGCCCACTCTAGACAGAGATGCCGGTGCCCAGT<br>TTTCTATTTTTAACTGGTGTGAACTGAAGGAAAAGCACAG<br>CATTAGAAGTCCAAGCAGGGATAAAAGCAGTCTGGGCTTT<br>CACATGACAGCATCTGGGGCTGCGGCAGAGGGTCGGGTCC<br>GAAGCGCTGCCTTATCAGCGTCCCCAGCCCTGGGAGGTGA<br>CAGCTGGCTGGCTTGTGTCAGCCCCTCGGGCACTCACGTA<br>TCTCCGTCCGACGGGTTTAAAATAGCAAAACTCTGAGGCC<br>ACACAATAGCTTGGGCTTATATGGGCTCCTGTGGGGGAAG<br>GGGGAGCACGGAGGGGGCCGGGGCCGCTGCTGCCAAAATA<br>GCAGCTCACAAGTGTTGCATTCCTCTCTGGGCGCCGGGCA<br>CATTCCTGCTGGCTCTGCCCGCCCCGGGTGGGCGCCGGG<br>GGGACCTTAAAGCCTCTGCCCCCCAAGGAGCCCTTCCCAG<br>ACAGCCGCCGGCACCCACCGCTCCGTGGGACGATCCCCGA<br>AGCTCTAGAGCTTTATTGCGGTAGTTTATCACAGTTAAAT<br>TGCTAACGCAGTCAGTGCTTCTGACACAACAGTCTCGAAC<br>TTAAGCTGCAGAAGTTGGTCGTGAGGCACTGGGCAGGTAA<br>GTATCAAGGTTACAAGACAGGTTTAAGGAGACCAATAGAA<br>ACTGGGCTTGTCGAGACAGAGAAGACTCTTGCGTTTCTGA<br>TAGGCACCTATTGGTCTTACTGACATCCACTTTGCCTTTC<br>TCTCCACAGGTGTCCACTCCCAGTTCAATTACAGCTCTTA<br>AGGCTAGAGTACT*TAATACGACTCACTATAGGCTAGCCGC*<br>*CACC*ATGGCCGAGAAGGAATCTACCAGCCCCCACCTGATG<br><u>GTGCCTATTCTGCTGCTGGTGGGCTGGATCGTCGGCTGCA</u><br><u>TCATCGTGATCTACATCGTGTTCTTCTGA</u>CGGCCGCGCGG<br>ATCCAGACATGATAAGATACATTGATGAGTTTGGACAAAC<br>CACAACTAGAATGCAGTGAAAAAAATGCTTTATTTGTGAA<br>ATTTGTGATGCTATTGCTTTATTTGTAACCATTATAAGCT<br>GCAATAAACAAGT*GAATTCCCGATTAGGATCTTCCTAGAG*<br>*CATGGCTACGTAGATAAGTAGCATGGCGGGTTAATCATTA*<br>*ACTACAAGGAACCCCTAGTGATGGAGTTGGCCACTCCCTC*<br>TCTGCGCGCTCGCTCGCTCACTGAGGCCGGGCGACCAAAG<br>GTCGCCCGACGCCCGGGCTTTGCCCGGGCGGCCTCAGTGA<br>GCGAGCGAGCGCGCAG (SEQ ID NO: 57) |
| pHZ69<br>distinct sequence elements<br>are indicated in bold,<br>starting with ITR, hcTnTp,<br>DWORF (which is also<br>underlined), WPRE, polyA<br>(hGHpA), SV40pA,<br>optimized DWORF (which<br>is also underlined), ccTnTp,<br>ITR | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCT*TGTAGTTAATGATTAACCCGCCATGCTACT*<br>*TATCTACGTAGCCATGCTCTAGGAAGATCGGAATTCGCCC*<br>*TTAAG*GTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCACCCCCACCGCCATCCCCCTGCCCCACCC<br>GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCAGACGC<br>CTCCATAACTGGTAAGTACCGCCTATAGACTCTATAGGCA<br>CACCCCTTTGGCTCTTATGCATGCTGACAGACTAACAGAC<br>TGTTCCTTTCCTGGGTCTTTTCTGCAGGCCTGTACGGAAG<br>TGTTACTTCTGCTCTAAAAGCTGCGGAATTGTACCCGCGG<br>CCGATCCAATCGATACAGATCTA*GCGGCCGCCCGCCACC*<u>A</u><br><u>TGGCTGAGAAAGAGTCAACATCACCACACCTCATGGTTCC</u><br><u>CATTCTTCTCCTGGTTGGATGGATTGTAGGCTGCATCATC</u><br><u>GTTATTTACATTGTCTTCTTCTA</u>*AAAGCTTTGGATCCAAT*<br>*CAACCTCTGGATTACAAAATTTGTGAAAGATTGACTGGTA*<br>*TTCTTAACTATGTTGCTCCTTTTACGCTATGTGGATACGC*<br>*TGCTTTAATGCCTTTGTATCATGCTATTGCTTCCCGTATG*<br>*GCTTTCATTTTCTCCTCTTGTATAAATCCTGGTTGCTGT*<br>*CTCTTTATGAGGAGTTGTGGCCCGTTGTCAGGCAACGTGG*<br>*CGTGGTGTGCACTGTGTTTGCTGACGCAACCCCCACTGGT*<br>*TGGGGCATTGCCACCACCTGTCAGCTCCTTTCCGGGACTT* |

TABLE 1-continued

Illustrative Expression Cassette Sequences

| Expression Cassette | Sequence |
|---|---|
| | TCGCTTTCCCCCTCCCTATTGCCACGGCGGAACTCATCGC<br>CGCCTGCCTTGCCCGCTGCTGGACAGGGGCTCGGCTGTTG<br>GGCACTGACAATTCCGTGGTGTTGTCGGGGAAATCATCGT<br>CCTTTCCTTGGCTGCTCGCCTGTGTTGCCACCTGGATTCT<br>GCGCGGGACGTCCTTCTGCTACGTCCCTTCGGCCCTCAAT<br>CCAGCGGACCTTCCTTCCCGCGGCCTGCTGCCGGCTCTGC<br>GGCCTCTTCCGCGTCTTCG*AGATCTGCCTCGACTGTGCCT<br>TCTAGTTGCCAGCCATCTGTTGTTTGCCCCTCCCCCGTGC<br>CTTCCTTGACCCTGGAAGGTGCCACTCCCACTGTCCTTTC<br>CTAATAAAATGAGGAAATTGCATCGCATTGTCTGAGTAGG<br>TGTCATTCTATTCTGGGGGGTGGGGTGGGGCAGGACAGCA<br>AGGGGGAGGATTGGGAAGACAATAGCAGGCATGCTGGGGA*<br>*CTCGAGTTAAGGGCAGCCAGAAGTCAGATGCTCAAGGGGC<br>TTCATGATGTCCCCATAATTTTTGGCAGAGGGAAAAAGAT<br>CGGATCCTCAGGCGTAGTTCACCCCGTCCTCGAGGCCGCC<br>CGGGTCGACTAAAAAACCTCCCACACCTCCCCCTGAACCT<br>GAAACATAAAATGAATGCAATTGTTGTTGTTAA*CTTGTTT<br>ATTGCAGCTTATAATGGTTACAAATAAAGCAATAGCATCA<br>CAAATTTCACAAATAAAGCATTTTTTTCACTGCATTCTAG<br>TTGTGGTTTGTCCAAACTCATCAATGTATCTTATCATGTC<br>TGGATC*CGCGCGGCCG*TCAGAAGAACACGATGTAGATCAC<br>GATGATGCAGCCGACGATCCAGCCCACCAGCAGCAGAATA<br>GGCACCATCAGGTGGGGGCTGGTAGATTCCTTCTCGGCCA<br>*T*GGTGGCGGCTAGCCTATAGTGAGTCGTATTA<u>AGTACTCT<br>AGCCTTAAGAGCTGTAATTGAACTGGGAGTGGACACCTGT<br>GGAGAGAAAGGCAAAGTGGATGTCAGTAAGACCAATAGGT<br>GCCTATCAGAAACGCAAGAGTCTTCTCTGTCTCGACAAGC<br>CCAGTTTCTATTGGTCTCCTTAAACCTGTCTTGTAACCTT<br>GATACTTACCTGCCCAGTGCCTCACGACCAACTTCTGCAG<br>CTTAAGTTCGAGACTGTTGTGTCAGAAGCACTGACTGCGT<br>TAGCAATTTAACTGTGATAAACTACCGCAATAAAGCTCTA<br>GAGCTTCGGGGATCGTCCCACGGAGCGGTGGGTGCCGGCG<br>GCTGTCTGGGAAGGGCTCCTTGGGGGGCAGAGGCTTTAAG<br>GTCCCCCCGGCGCCCACCCCGGGGGGGGCAGAGCCAGCAG<br>GAATGTGCCCGGCGCCCAGAGAGGAATGCAACACTTGTGA<br>GCTGCTATTTTGGCAGCAGCGGCCCCGGCCCCTCCGTGC<br>TCCCCCTTCCCCCACAGGAGCCCATATAAGCCCAAGCTAT<br>TGTGTGGCCTCAGAGTTTTGCTATTTTAAACCCGTCGGAC<br>GGAGATACGTGAGTGCCCGAGGGGCTGACACAAGCCAGCC<br>AGCTGTCACCTCCCAGGGCTGGGACGCTGATAAGGCAGC<br>GCTTCGGACCCGACCCTCTGCCGCAGCCCCAGATGCTGTC<br>ATGTGAAAGCCCAGACTGCTTTTATCCC</u>*GAATTCCCGATT<br>AGGATCTTCCTAGAGCATGGCTACGTAGATAAGTAGCATG<br>GCGGG*TTAATCATTAACTACA*AGGAACCCCTAGTGATGGA<br>GTTGGCCACTCCCTCTCTGCGCGCTCGCTCGCTCACTGAG<br>GCCGGGCGACCAAAGGTCGCCCGACGCCCGGGCTTTGCCC<br>GGGCGGCCTCAGTGAGCGAGCGAGCGCGCAG<br>(SEQ ID NO: 58) |
| pHZ72<br>distinct sequence elements<br>are indicated in bold,<br>starting with ITR, hcTnTp,<br>DWORF (which is also<br>underlined), WPRE, polyA<br>(hGHpA), ccTnTp,<br>optimized DWORF (which<br>is also underlined),<br>SV40pA, ITR | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCT*TGTAGTTAATGATTAACCCGCCATGCTACT<br>TATCTACGTAGCCATGCTCTAGGAAGATCGGAATTCGCCC<br>TTAAG*GTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCACCCCCACCGCCATCCCCCTGCCCCACCC<br>GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCAGACGC<br>CTCCATAACTGGTAAGTACCGCCTATAGACTCTATAGGCA<br>CACCCCTTTGGCTCTTATGCATGCTGACAGACTAACAGAC<br>TGTTCCTTTCCTGGGTCTTTTCTGCAGGCCTGTACGGAAG<br>TGTTACTTCTGCTCTAAAAGCTGCGGAATTGTACCCGCGG<br>CCGATCCAATCGATACAGATCTAGCGGCC*GCCCGCCACC<u>A<br>TGGCTGAGAAAGAGTCAACATCACCACACCTCATGGTTCC<br>CATTCTTCTCCTGGTTGGATGGATTGTAGGCTGCATCATC</u> |

TABLE 1-continued

Illustrative Expression Cassette Sequences

| Expression Cassette | Sequence |
|---|---|
| | GTTATTTACATTGTCTTCTTCTAA*AAGCTTTGGATCCAAT* |
| | *CAACCTCTGGATTACAAAATTTGTGAAAGATTGACTGGTA* |
| | TTCTTAACTATGTTGCTCCTTTTACGCTATGTGGATACGC |
| | TGCTTTAATGCCTTTGTATCATGCTATTGCTTCCCGTATG |
| | GCTTTCATTTTCTCCTCCTTGTATAAATCCTGGTTGCTGT |
| | CTCTTTATGAGGAGTTGTGGCCCGTTGTCAGGCAACGTGG |
| | CGTGGTGTGCACTGTGTTTGCTGACGCAACCCCCACTGGT |
| | TGGGGCATTGCCACCACCTGTCAGCTCCTTTCCGGGACTT |
| | TCGCTTTCCCCCTCCCTATTGCCACGGCGGAACTCATCGC |
| | CGCCTGCCTTGCCCGCTGCTGGACAGGGGCTCGGCTGTTG |
| | GGCACTGACAATTCCGTGGTGTTGTCGGGGAAATCATCGT |
| | CCTTTCCTTGGCTGCTCGCCTGTGTTGCCACCTGGATTCT |
| | GCGCGGGACGTCCTTCTGCTACGTCCCTTCGGCCCTCAAT |
| | CCAGCGGACCTTCCTTCCCGCGGCCTGCTGCCGGCTCTGC |
| | GGCCTCTTCCGCGTCTTCG*AGATCT*GCCTCGACTGTGCCT |
| | TCTAGTTGCCAGCCATCTGTTGTTTGCCCCTCCCCCGTGC |
| | CTTCCTTGACCCTGGAAGGTGCCACTCCCACTGTCCTTTC |
| | CTAATAAAATGAGGAAATTGCATCGCATTGTCTGAGTAGG |
| | TGTCATTCTATTCTGGGGGGTGGGGTGGGGCAGGACAGCA |
| | AGGGGGAGGATTGGGAAGACAATAGCAGGCATGCTGGGGA |
| | *CTCGAGTTAAGGGCAGCCAGAAGTCAGATGCTCAAGGGGC* |
| | *TTCATGATGTCCCCATAATTTTTGGCAGAGGGAAAAAGAT* |
| | *CGGATCCTCAGGCGTAGTTCACCCCGTCCTCGAGGCCGCC* |
| | *CGGGTCGACTAAAAAACCTCCCACACCTCCCCCTGAACCT* |
| | *GAAACATAAAATGAATGCAATTGTTGTTGTT*AGGGATAAA |
| | AGCAGTCTGGGCTTTCACATGACAGCATCTGGGGCTGCGG |
| | CAGAGGGTCGGGTCCGAAGCGCTGCCTTATCAGCGTCCCC |
| | AGCCCTGGGAGGTGACAGCTGGCTGGCTTGTGTCAGCCCC |
| | TCGGGCACTCACGTATCTCCGTCCGACGGGTTTAAAATAG |
| | CAAAACTCTGAGGCCACACAATAGCTTGGGCTTATATGGG |
| | CTCCTGTGGGGAAGGGGAGCACGGAGGGGGCCGGGGCC |
| | GCTGCTGCCAAAATAGCAGCTCACAAGTGTTGCATTCCTC |
| | TCTGGGCGCCGGGCACATTCCTGCTGGCTCTGCCCGCCCC |
| | GGGGTGGGCGCCGGGGGGACCTTAAAGCCTCTGCCCCCCA |
| | AGGAGCCCTTCCCAGACAGCCGCCGGCACCCACCGCTCCG |
| | TGGGACGATCCCCGAAGCTCTAGAGCTTTATTGCGGTAGT |
| | TTATCACAGTTAAATTGCTAACGCAGTCAGTGCTTCTGAC |
| | ACAACAGTCTCGAACTTAAGCTGCAGAAGTTGGTCGTGAG |
| | GCACTGGGCAGGTAAGTATCAAGGTTACAAGACAGGTTTA |
| | AGGAGACCAATAGAAACTGGGCTTGTCGAGACAGAGAAGA |
| | CTCTTGCGTTTCTGATAGGCACCTATTGGTCTTACTGACA |
| | TCCACTTTGCCTTTCTCTCCACAGGTGTCCACTCCCAGTT |
| | CAATTACAGCTCTTAAGGCTAGAGTACT*TAATACGACTCA* |
| | *CTATAGGCTAGCCGCCACC*ATGGCCGAGAAGGAATCTACC |
| | AGCCCCCACCTGATGGTGCCTATTCTGCTGCTGGTGGGCT |
| | GGATCGTCGGCTGCATCATCGTGATCTACATCGTGTTCTT |
| | CTGA*CGGCCGCGCG*GATCCAGACATGATAAGATACATTGA |
| | TGAGTTTGGACAAACCACAACTAGAATGCAGTGAAAAAAA |
| | TGCTTTATTTGTGAAATTTGTGATGCTATTGCTTTATTTG |
| | TAACCATTATAAGCTGCAATAAACAAGT*GAATTCCCGATT* |
| | *AGGATCTTCCTAGAGCATGGCTACGTAGATAAGTAGCATG* |
| | *GCGGGTTAATCATTAACTACA*AGGAACCCCTAGTGATGGA |
| | GTTGGCCACTCCCTCTGCGCGCTCGCTCGCTCACTGAG |
| | GCCGGGCGACCAAAGGTCGCCCGACGCCCGGGCTTTGCCC |
| | GGGCGGCCTCAGTGAGCGAGCGAGCGCGCAG |
| | (SEQ ID NO: 59) |
| pHZ75 distinct sequence elements are indicated in bold, starting with ITR, polyA (hGHpA), WPRE, DWORF(which is also underlined), hcTnTp/ccTnTp combo, optimized DWORF (which is also underlined), SV40pA, ITR | CTGCGCGCTCGCTCGCTCACTGAGGCCGCCCGGGCAAAGC CCGGGCGTCGGGCGACCTTTGGTCGCCCGGCCTCAGTGAG CGAGCGAGCGCGCAGAGAGGGAGTGGCCAACTCCATCACT AGGGGTTCCT*TGTAGTTAATGATTAACCCGCCATGCTACT* *TATCTACGTAGCCATGCTCTAGGAAGATCGGAATTC*TCCC CAGCATGCCTGCTATTGTCTTCCCAATCCTCCCCCTTGCT GTCCTGCCCCACCCCACCCCCCAGAATAGAATGACACCTA CTCAGACAATGCGATGCAATTTCCTCATTTTATTAGGAAA GGACAGTGGGAGTGGCACCTTCCAGGGTCAAGGAAGGCAC GGGGGAGGGGCAAACAACAGATGGCTGGCAACTAGAAGGC ACAGTCGAGGC*AGATCT*CGAAGACGCGGAAGAGGCCGCAG AGCCGGCAGCAGGCCGCGGGAAGGAAGGTCCGCTGGATTG AGGGCCGAAGGGACGTAGCAGAAGGACGTCCCGCGCAGAA TCCAGGTGGCAACACAGGCGAGCAGCCAAGGAAAGGACGA TGATTTCCCCGACAACACCACGGAATTGTCAGTGCCCAAC AGCCGAGCCCTGTCCAGCAGCGGGCAAGGCAGGCGGCGA TGAGTTCCGCCGTGGCAATAGGGAGGGGAAAGCGAAAGT CCCGGAAAGGAGCTGACAGGTGGTGGCAATGCCCCAACCA GTGGGGGTTGCGTCAGCAAACACAGTGCACACCACGCCAC |

TABLE 1-continued

Illustrative Expression Cassette Sequences

| Expression Cassette | Sequence |
|---|---|
| | GTTGCCTGACAACGGGCCACAACTCCTCATAAAGAGACAG<br>CAACCAGGATTTATACAAGGAGGAGAAAATGAAAGCCATA<br>CGGGAAGCAATAGCATGATACAAAGGCATTAAAGCAGCGT<br>ATCCACATAGCGTAAAAGGAGCAACATAGTTAAGAATACC<br>AGTCAATCTTTCACAAATTTTGTAATCCAGAGGTTGA*TTG<br>GATCCAAAGCTT*TTAGAAGAAGACAATGTAAATAACGATG<br>ATGCAGCCTACAATCCATCCAACCAGGAGAAGAATGGGAA<br>CCATGAGGTGTGGTGATGTTGACTCTTTCTCAGCCATGGT<br>GGCGG*GCGGCCGC*TAGATCTGTATCGATTGGATCGGCCGC<br>GGGTACAATTCCGCAGCTTTTAGAGCAGAAGTAACACTTC<br>CGTACAGGCCTGCAGAAAAGACCCAGGAAAGGAACAGTCT<br>GTTAGTCTGTCAGCATGCATAAGAGCCAAAGGGGTGTGCC<br>TATAGAGTCTATAGGCGGTACTTACCAGTTATGGAGGCGT<br>CTGCTCAGTCTCAGCGGGACTGGGTGAGGCAGAGGATGG<br>AGAGGGCTTTAAGCAGGCATGTGGGCTGGGGCCTGGTGAG<br>CCAGCCCTGCGGAGGGAGGAATGTGCGACAGGGGACGGGT<br>GGGGCAGGGGATGGCGGTGGGGGTGGGGGGTGTTGGCTG<br>CTATTTTGGCAGGTGCCAGGGACAAGGCTACAGGAACATG<br>TACCCCACGCCATATAAGCCCATGTGGTCCTCCAGCTGCT<br>CAGATAAGCTATTTAAAACCAGAGCAGATATGCAGGGAAC<br>AGTCATGCAACATAAACCAGCTGTCCCTCTTGAGAATCCT<br>GATAAAGCAGAGGCCAGCAACCCAGGCCTGGGAGGGCCAG<br>CTGGGAGCAGGGTTGGGGGGCAGAAGGCAACCTCCAAGAC<br>ACTCCATAAGTCTCAGCACCAGAATCTTGGAAGGCAGAGG<br>GCAAGAGTTATGTGCTGCTCCACTTGAACTGATGCTGGGG<br>GTAAAGACATCTTCCAGGCTACTGGCTCCTAATGGACTGA<br>GCAGCCTTAGGCAGGTTGCCGGCTCTGCCAGCCCCAGTGA<br>GGACATCT*GCAAGGTGGGTCTTCTCCATGAC*CTCGAGTTA<br>*AGGGCAGCCAGAAGTCAGATGCTCAAGGGGCTTCATGATG<br>TCCCCATAATTTTTGGCAGAGGGAAAAAGATCGGATCCTC<br>AGGCGTAGTTCACCCCGTCCTCGAGGCCGCCCGGGTCGAC<br>TAAAAAACCTCCCACACCTCCCCCTGAACCTGAAACATAA<br>AATGAATGCAATTGTTGTTGTTAGGGATAAAAGCAGTCTG<br>GGCTTTCACATGACAGCATCTGGGGCTGCGGCAGAGGGTC<br>GGGTCCGAAGCGCTGCCTTATCAGCGTCCCCAGCCCTGGG<br>AGGTGACAGCTGGCTGGCTTGTGTCAGCCCCTCGGGCACT<br>CACGTATCTCCGTCCGACGGGTTTAAAATAGCAAAACTCT<br>GAGGCCACACAATAGCTTGGGCTTATATGGGCTCCTGTGG<br>GGGAAGGGGGAGCACGGAGGGGGCCGGGGCCGCTGCTGCC<br>AAAATAGCAGCTCACAAGTGTTGCATTCCTCTCTGGGCGC<br>CGGGCACATTCCTGCTGGCTCTGCCCGCCCCGGGGTGGGC<br>GCCGGGGGGACCTTAAAGCCTCTGCCCCCCAAGGAGCCCT<br>TCCCAGACAGCCGCCGGCACCCACCGCTCCGTGGGA*CGAT<br>CCCCGAAGCTCTAGAGCTTTATTGCGGTAGTTTATCACAG<br>TTAAATTGCTAACGCAGTCAGTGCTTCTGACACAACAGTC<br>TCGAACTTAAGCTGCAGAAGTTGGTCGTGAGGCACTGGGC<br>AGGTAAGTATCAAGGTTACAAGACAGGTTTAAGGAGACCA<br>ATAGAAACTGGGCTTGTCGAGACAGAGAAGACTCTTGCGT<br>TTCTGATAGGCACCTATTGGTCTTACTGACATCCACTTTG<br>CCTTTCTCTCCACAGGTGTCCACTCCCAGTTCAATTACAG<br>CTCTTAAGGCTAGAGTACTTAATACGACTCACTATAGGCT<br>AGCCGCCACC*ATGGCCGAGAAGGAATCTACCAGCCCCCAC<br>CTGATGGTGCCTATTCTGCTGCTGGTGGGCTGGATCGTCG<br>GCTGCATCATCGTGATCTACATCGTGTTCTTCTGA*CGGCC<br>GCGCG*GATCCAGACATGATAAGATACATTGATGAGTTTGG<br>ACAAACCACAACTAGAATGCAGTGAAAAAAATGCTTTATT<br>TGTGAAATTTGTGATGCTATTGCTTTATTTGTAACCATTA<br>TAAGCTGCAATAAACAAGT*GAATTCCCGATTAGGATCTTC<br>CTAGAGCATGGCTACGTAGATAAGTAGCATGGCGGGTTAA<br>TCATTAACTACA*AGGAACCCCTAGTGATGGAGTTGGCCAC<br>TCCCTCTCTGCGCGCTCGCTCGCTCACTGAGGCCGGGCGA<br>CCAAAGGTCGCCCGACGCCCGGGCTTTGCCCGGGCGGCCT<br>CAGTGAGCGAGCGAGCGCGCAG (SEQ ID NO: 60) |
| pHZ51 (human DWORF version of pHZ15) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGAACTGGCCTGCCCGAGACCAAACGTGCGGAACGTA<br>GTTAAGTGTTAGAGGTAGGATTTGAAGCCTGTCGATCATT<br>CTGATTCTCCTTTTCTCTACGTCTGCTTCCTGTCAATGGG<br>CATCCTCACTGTCAAATGCAGATGGTACAGCAGGGCTTGG<br>TCTCAGCCAGGCAGGCCTCTCCCCAGTCTCCATGGCTCAG<br>CTGTCCAGCAGTTTCATCCCTAGACCATCCCAAACATGGT<br>TGAGAAGCTCTGAGGGGAGGACCCAGCACTGCCCGGCCCC |

TABLE 1-continued

Illustrative Expression Cassette Sequences

| Expression Cassette | Sequence |
|---|---|
| | TGAAGATAATCAGCAGTCCTGCTCAGCATATCAATCCAAG
CCCACTCTAGACAGAGATGCCGGTGCCCAGTTTTCTATTT
TTAACTGGTGTGAACTGAAGGAAAAGCACAGCATTAGAAG
TCCAAGCAGTCATGGAGAAGACCCACCTTGCAGATGTCCT
CACTGGGGCTGGCAGAGCCGGCAACCTGCCTAAGGCTGCT
CAGTCCATTAGGAGCCAGTAGCCTGGAAGATGTCTTTACC
CCCAGCATCAGTTCAAGTGGAGCAGCACATAACTCTTGCC
CTCTGCCTTCCAAGATTCTGGTGCTGAGACTTATGGAGTG
TCTTGGAGGTTGCCTTCTGCCCCCCAACCCTGCTCCCAGC
TGGCCCTCCCAGGCCTGGGTTGCTGGCCTCTGCTTTATCA
GGATTCTCAAGAGGGACAGCTGGTTTATGTTGCATGACTG
TTCCCTGCATATCTGCTCTGGTTTTAAATAGCTTATCTGA
GCAGCTGGAGGACCACATGGGCTTATATGGCGTGGGGTAC
ATGTTCCTGTAGCCTTGTCCCTGGCACCTGCCAAAATAGC
AGCCAACACCCCCACCCCCACCGCCATCCCCCTGCCCCA
CCCGTCCCTGTCGCACATTCCTCCCTCCGCAGGGCTGGC
TCACCAGGCCCCAGCCCACATGCCTGCTTAAAGCCCTCTC
CATCCTCTGCCTCACCCAGTCCCCGCTGAGACTGAGCAGA
CGCCTCCAGCGGCCGCCCGCCACCATGGCTGAAAAAGCGG
GGTCTACATTTTCACACCTTCTGGTTCCTATTCTTCTCCT
GATTGGCTGGATTGTGGGCTGCATCATAATGATTTATGTT
GTCTTCTCTTAGAAGCTTTGGATCCAATCAACCTCTGGAT
TACAAAATTTGTGAAAGATTGACTGGTATTCTTAACTATG
TTGCTCCTTTTACGCTATGTGGATACGCTGCTTTAATGCC
TTTGTATCATGCTATTGCTTCCCGTATGGCTTTCATTTTC
TCCTCCTTGTATAAATCCTGGTTGCTGTCTCTTTATGAGG
AGTTGTGGCCCGTTGTCAGGCAACGTGGCGTGGTGTGCAC
TGTGTTTGCTGACGCAACCCCCACTGGTTGGGGCATTGCC
ACCACCTGTCAGCTCCTTTCCGGGACTTTCGCTTTCCCCC
TCCCTATTGCCACGGCGGAACTCATCGCCGCCTGCCTTGC
CCGCTGCTGGACAGGGGCTCGGCTGTTGGGCACTGACAAT
TCCGTGGTGTTGTCGGGGAAATCATCGTCCTTTCCTTGGC
TGCTCGCCTGTGTTGCCACCTGGATTCTGCGCGGGACGTC
CTTCTGCTACGTCCCTTCGGCCCTCAATCCAGCGGACCTT
CCTTCCCGCGGCCTGCTGCCGGCTCTGCGGCCTCTTCCGC
GTCTTCGAGATCTGCCTCGACTGTGCCTTCTAGTTGCCAG
CCATCTGTTGTTTGCCCCTCCCCCGTGCCTTCCTTGACCC
TGGAAGGTGCCACTCCCACTGTCCTTTCCTAATAAAATGA
GGAAATTGCATCGCATTGTCTGAGTAGGTGTCATTCTATT
CTGGGGGGTGGGGTGGGGCAGGACAGCAAGGGGGAGGATT
GGGAAGACAATAGCAGGCATGCTGGGGACTCGAGTTAAGG
GCGAATTCCCGATTAGGATCTTCCTAGAGCATGGCTACGT
AGATAAGTAGCATGGCGGGTTAATCATTAACTACAAGGAA
CCCCTAGTGATGGAGTTGGCCACTCCCTCTCTGCGCGCTC
GCTCGCTCACTGAGGCCGGGCGACCAAAGGTCGCCCGACG
CCCGGGCTTTGCCCGGGCGGCCTCAGTGAGCGAGCGAGCG
CGCAG (SEQ ID NO: 61) |
| pHZ100 (human DWORF version of pHZ72) | CTGCGCGCTCGCTCGCTCACTGAGGCCGCCCGGGCAAAGC
CCGGGCGTCGGGCGACCTTTGGTCGCCCGGCCTCAGTGAG
CGAGCGAGCGCGCAGAGAGGGAGTGGCCAACTCCATCACT
AGGGGTTCCTTGTAGTTAATGATTAACCCGCCATGCTACT
TATCTACGTAGCCATGCTCTAGGAAGATCGGAATTCGCCC
TTAAGGTCATGGAGAAGACCCACCTTGCAGATGTCCTCAC
TGGGGCTGGCAGAGCCGGCAACCTGCCTAAGGCTGCTCAG
TCCATTAGGAGCCAGTAGCCTGGAAGATGTCTTTACCCCC
AGCATCAGTTCAAGTGGAGCAGCACATAACTCTTGCCCTC
TGCCTTCCAAGATTCTGGTGCTGAGACTTATGGAGTGTCT
TGGAGGTTGCCTTCTGCCCCCCAACCCTGCTCCCAGCTGG
CCCTCCCAGGCCTGGGTTGCTGGCCTCTGCTTTATCAGGA
TTCTCAAGAGGGACAGCTGGTTTATGTTGCATGACTGTTC
CCTGCATATCTGCTCTGGTTTTAAATAGCTTATCTGAGCA
GCTGGAGGACCACATGGGCTTATATGGCGTGGGGTACATG
TTCCTGTAGCCTTGTCCCTGGCACCTGCCAAAATAGCAGC
CAACACCCCCACCCCCACCGCCATCCCCCTGCCCCACCCC
GTCCCTGTCGCACATTCCTCCCTCCGCAGGGCTGGCTCA
CCAGGCCCCAGCCCACATGCCTGCTTAAAGCCCTCTCCAT
CCTCTGCCTCACCCAGTCCCCGCTGAGACTGAGCAGACGC
CTCCATAACTGGTAAGTACCGCCTATAGACTCTATAGGCA
CACCCCTTTGGCTCTTATGCATGCTGACAGACTAACAGAC
TGTTCCTTTCCTGGGTCTTTTCTGCAGGCCTGTACGGAAG
TGTTACTTCTGCTCTAAAAGCTGCGGAATTGTACCCGCGG
CCGATCCAATCGATACAGATCTAGCGGCCGCCCGCCACCA
TGGCTGAAAAAGCGGGGTCTACATTTTCACACCTTCTGGT
TCCTATTCTTCTCCTGATTGGCTGGATTGTGGGCTGCATC
ATAATGATTTATGTTGTCTTCTCTTAGAAGCTTTGGATCC |

TABLE 1-continued

Illustrative Expression Cassette Sequences

| Expression Cassette | Sequence |
|---|---|
| | AATCAACCTCTGGATTACAAAATTTGTGAAAGATTGACTG<br>GTATTCTTAACTATGTTGCTCCTTTTACGCTATGTGGATA<br>CGCTGCTTTAATGCCTTTGTATCATGCTATTGCTTCCCGT<br>ATGGCTTTCATTTTCTCCTCCTTGTATAAATCCTGGTTGC<br>TGTCTCTTTATGAGGAGTTGTGGCCCGTTGTCAGGCAACG<br>TGGCGTGGTGTGCACTGTGTTTGCTGACGCAACCCCCACT<br>GGTTGGGGCATTGCCACCACCTGTCAGCTCCTTTCCGGGA<br>CTTTCGCTTTCCCCCTCCCTATTGCCACGGCGGAACTCAT<br>CGCCGCCTGCCTTGCCCGCTGCTGGACAGGGGCTCGGCTG<br>TTGGGCACTGACAATTCCGTGGTGTTGTCGGGGAAATCAT<br>CGTCCTTTCCTTGGCTGCTCGCCTGTGTTGCCACCTGGAT<br>TCTGCGCGGGACGTCCTTCTGCTACGTCCCTTCGGCCCTC<br>AATCCAGCGGACCTTCCTTCCCGCGGCCTGCTGCCGGCTC<br>TGCGGCCTCTTCCGCGTCTTCGAGATCTGCCTCGACTGTG<br>CCTTCTAGTTGCCAGCCATCTGTTGTTTGCCCCTCCCCCG<br>TGCCTTCCTTGACCCTGGAAGGTGCCACTCCCACTGTCCT<br>TTCCTAATAAAATGAGGAAATTGCATCGCATTGTCTGAGT<br>AGGTGTCATTCTATTCTGGGGGGTGGGGTGGGGCAGGACA<br>GCAAGGGGGAGGATTGGGAAGACAATAGCAGGCATGCTGG<br>GGACTCGAGTTAAGGGCAGCCAGAAGTCAGATGCTCAAGG<br>GGCTTCATGATGTCCCCATAATTTTTGGCAGAGGGAAAAA<br>GATCGGATCCTCAGGCGTAGTTCACCCCGTCCTCGAGGCC<br>GCCCGGGTCGACTAAAAAACCTCCCACACCTCCCCCTGAA<br>CCTGAAACATAAAATGAATGCAATTGTTGTTGTTAGGGAT<br>AAAAGCAGTCTGGGCTTTCACATGACAGCATCTGGGGCTG<br>CGGCAGAGGGTCGGGTCCGAAGCGCTGCCTTATCAGCGTC<br>CCCAGCCCTGGGAGGTGACAGCTGGCTGGCTTGTGTCAGC<br>CCCTCGGGCACTCACGTATCTCCGTCCGACGGGTTTAAAA<br>TAGCAAAACTCTGAGGCCACACAATAGCTTGGGCTTATAT<br>GGGCTCCTGTGGGGGAAGGGGGAGCACGGAGGGGGCCGGG<br>GCCGCTGCTGCCAAAATAGCAGCTCACAAGTGTTGCATTC<br>CTCTCTGGGCGCCGGGCACATTCCTGCTGGCTCTGCCCGC<br>CCCGGGGTGGGCGCCGGGGGACCTTAAAGCCTCTGCCCC<br>CCAAGGAGCCCTTCCCAGACAGCCGCCGGCACCCACCGCT<br>CCGTGGGACGATCCCCGAAGCTCTAGAGCTTTATTGCGGT<br>AGTTTATCACAGTTAAATTGCTAACGCAGTCAGTGCTTCT<br>GACACAACAGTCTCGAACTTAAGCTGCAGAAGTTGGTCGT<br>GAGGCACTGGGCAGGTAAGTATCAAGGTTACAAGACAGGT<br>TTAAGGAGACCAATAGAAACTGGGCTTGTCGAGACAGAGA<br>AGACTCTTGCGTTTCTGATAGGCACCTATTGGTCTTACTG<br>ACATCCACTTTGCCTTTCTCTCCACAGGTGTCCACTCCCA<br>GTTCAATTACAGCTCTTAAGGCTAGAGTACTTAATACGAC<br>TCACTATAGGCTAGCCGCCACCATGGCCGAGAAGGCCGGA<br>TCTACCTTCAGCCACCTGCTGGTCCCTATTCTGCTGCTGA<br>TCGGCTGGATCGTGGGCTGCATCATCATGATCTACGTGGT<br>GTTCAGCTGACGGCCGCGCGGATCCAGACATGATAAGATA<br>CATTGATGAGTTTGGACAAACCACAACTAGAATGCAGTGA<br>AAAAAATGCTTTATTTGTGAAATTTGTGATGCTATTGCTT<br>TATTTGTAACCATTATAAGCTGCAATAAACAAGTGAATTC<br>CCGATTAGGATCTTCCTAGAGCATGGCTACGTAGATAAGT<br>AGCATGGCGGGTTAATCATTAACTACAAGGAACCCCTAGT<br>GATGGAGTTGGCCACTCCCTCTCTGCGCGCTCGCTCGCTC<br>ACTGAGGCCGGGCGACCAAAGGTCGCCCGACGCCCGGGCT<br>TTGCCCGGGCGGCCTCAGTGAGCGAGCGAGCGCGCAG<br>(SEQ ID NO: 62) |
| pHZ101 (human DWORF version of pHZ75) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCTCCC<br>CAGCATGCCTGCTATTGTCTTCCCAATCCTCCCCCTTGCT<br>GTCCTGCCCCACCCCACCCCCCAGAATAGAATGACACCTA<br>CTCAGACAATGCGATGCAATTTCCTCATTTTATTAGGAAA<br>GGACAGTGGGAGTGGCACCTTCCAGGGTCAAGGAAGGCAC<br>GGGGGAGGGGCAAACAACAGATGGCTGGCAACTAGAAGGC<br>ACAGTCGAGGCAGATCTCGAAGACGCGGAAGAGGCCGCAG<br>AGCCGGCAGCAGGCCGCGGGAAGGAAGGTCCGCTGGATTG<br>AGGGCCGAAGGGACGTAGCAGAAGGACGTCCCGCGCAGAA<br>TCCAGGTGGCAACACAGGCGAGCAGCCAAGGAAAGGACGA<br>TGATTTCCCCGACAACACCACGGAATTGTCAGTGCCCAAC<br>AGCCGAGCCCCTGTCCAGCAGCGGGCAAGGCAGGCGGCGA<br>TGAGTTCCGCCGTGGCAATAGGGAGGGGAAAGCGAAAGT<br>CCCGGAAAGGAGCTGACAGGTGGTGGCAATGCCCCAACCA<br>GTGGGGGTTGCGTCAGCAAACACAGTGCACACCACGCCAC<br>GTTGCCTGACAACGGGCCACAACTCCTCATAAAGAGACAG |

TABLE 1-continued

Illustrative Expression Cassette Sequences

| Expression Cassette | Sequence |
|---|---|
| | CAACCAGGATTTATACAAGGAGGAGAAAATGAAAGCCATA<br>CGGGAAGCAATAGCATGATACAAAGGCATTAAAGCAGCGT<br>ATCCACATAGCGTAAAAGGAGCAACATAGTTAAGAATACC<br>AGTCAATCTTTCACAAATTTTGTAATCCAGAGGTTGATTG<br>GATCCAAAGCTTCTAAGAGAAGACAACATAAATCATTATG<br>ATGCAGCCCACAATCCAGCCAATCAGGAGAAGAATAGGAA<br>CCAGAAGGTGTGAAAATGTAGACCCCGCTTTTTCAGCCAT<br>GGTGGCGGGCGGCCGCTAGATCTGTATCGATTGGATCGGC<br>CGCGGGTACAATTCCGCAGCTTTTAGAGCAGAAGTAACAC<br>TTCCGTACAGGCCTGCAGAAAAGACCCAGGAAAGGAACAG<br>TCTGTTAGTCTGTCAGCATGCATAAGAGCCAAAGGGGTGT<br>GCCTATAGAGTCTATAGGCGGTACTTACCAGTTATGGAGG<br>CGTCTGCTCAGTCTCAGCGGGGACTGGGTGAGGCAGAGGA<br>TGGAGAGGGCTTTAAGCAGGCATGTGGGCTGGGGCCTGGT<br>GAGCCAGCCCTGCGGAGGGAGGAATGTGCGACAGGGGACG<br>GGTGGGGCAGGGGATGGCGGTGGGGGTGGGGGTGTTGG<br>CTGCTATTTTGGCAGGTGCCAGGGACAAGGCTACAGGAAC<br>ATGTACCCCACGCCATATAAGCCCATGTGGTCCTCCAGCT<br>GCTCAGATAAGCTATTTAAAACCAGAGCAGATATGCAGGG<br>AACAGTCATGCAACATAAACCAGCTGTCCCTCTTGAGAAT<br>CCTGATAAAGCAGAGGCCAGCAACCCAGGCCTGGGAGGGC<br>CAGCTGGGAGCAGGGTTGGGGGGCAGAAGGCAACCTCCAA<br>GACACTCCATAAGTCTCAGCACCAGAATCTTGGAAGGCAG<br>AGGGCAAGAGTTATGTGCTGCTCCACTTGAACTGATGCTG<br>GGGGTAAAGACATCTTCCAGGCTACTGGCTCCTAATGGAC<br>TGAGCAGCCTTAGGCAGGTTGCCGGCTCTGCCAGCCCCAG<br>TGAGGACATCTGCAAGGTGGGTCTTCTCCATGACCTCGAG<br>TTAAGGGCAGCCAGAAGTCAGATGCTCAAGGGGCTTCATG<br>ATGTCCCCATAATTTTTGGCAGAGGGAAAAAGATCGGATC<br>CTCAGGCGTAGTTCACCCCGTCCTCGAGGCCGCCCGGGTC<br>GACTAAAAAACCTCCCACACCTCCCCCTGAACCTGAAACA<br>TAAAATGAATGCAATTGTTGTTGTTAGGGATAAAAGCAGT<br>CTGGGCTTTCACATGACAGCATCTGGGGCTGCGGCAGAGG<br>GTCGGGTCCGAAGCGCTGCCTTATCAGCGTCCCCAGCCCT<br>GGGAGGTGACAGCTGGCTGGCTTGTGTCAGCCCCTCGGGC<br>ACTCACGTATCTCCGTCCGACGGGTTTAAAATAGCAAAAC<br>TCTGAGGCCACACAATAGCTTGGGCTTATATGGGCTCCTG<br>TGGGGGAAGGGGGAGCACGGAGGGGGCCGGGGCCGCTGCT<br>GCCAAAATAGCAGCTCACAAGTGTTGCATTCCTCTCTGGG<br>CGCCGGGCACATTCCTGCTGGCTCTGCCCGCCCCGGGGTG<br>GGCGCCGGGGGGACCTTAAAGCCTCTGCCCCCCAAGGAGC<br>CCTTCCCAGACAGCCGCCGGCACCCACCGCTCCGTGGGAC<br>GATCCCCGAAGCTCTAGAGCTTTATTGCGGTAGTTTATCA<br>CAGTTAAATTGCTAACGCAGTCAGTGCTTCTGACACAACA<br>GTCTCGAACTTAAGCTGCAGAAGTTGGTCGTGAGGCACTG<br>GGCAGGTAAGTATCAAGGTTACAAGACAGGTTTAAGGAGA<br>CCAATAGAAACTGGGCTTGTCGAGACAGAGAAGACTCTTG<br>CGTTTCTGATAGGCACCTATTGGTCTTACTGACATCCACT<br>TTGCCTTTCTCTCCACAGGTGTCCACTCCCAGTTCAATTA<br>CAGCTCTTAAGGCTAGAGTACTTAATACGACTCACTATAG<br>GCTAGCCGCCACCATGGCCGAGAAGGCCGGATCTACCTTC<br>AGCCACCTGCTGGTCCCTATTCTGCTGCTGATCGGCTGGA<br>TCGTGGGCTGCATCATCATGATCTACGTGGTGTTCAGCTG<br>ACGGCCGCGCGGATCCAGACATGATAAGATACATTGATGA<br>GTTTGGACAAACCACAACTAGAATGCAGTGAAAAAAATGC<br>TTTATTTGTGAAATTTGTGATGCTATTGCTTTATTTGTAA<br>CCATTATAAGCTGCAATAAACAAGTGAATTCCCGATTAGG<br>ATCTTCCTAGAGCATGGCTACGTAGATAAGTAGCATGGCG<br>GGTTAATCATTAACTACAAGGAACCCCTAGTGATGGAGTT<br>GGCCACTCCCTCTCTGCGCGCTCGCTCGCTCACTGAGGCC<br>GGGCGACCAAAGGTCGCCCGACGCCCGGGCTTTGCCCGGG<br>CGGCCTCAGTGAGCGAGCGAGCGCGCAG<br>(SEQ ID NO: 63) |
| pHZ52 (human DWORF version of pHZ16) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGAACTGGCCTGCCCGAGACCAAACGTGCGGAACGTA<br>GTTAAGTGTTAGAGGTAGGATTTGAAGCCTGTCGATCATT<br>CTGATTCTCCTTTTCTCTACGTCTGCTTCCTGTCAATGGG<br>CATCCTCACTGTCAAATGCAGATGGTACAGCAGGGCTTGG<br>TCTCAGCCAGGCAGGCCTCTCCCCAGTCTCCATGGCTCAG<br>CTGTCCAGCAGTTTCATCCCTAGACCATCCCAAACATGGT<br>TGAGAAGCTCTGAGGGGAGGACCCAGCACTGCCCGGCCCC |

TABLE 1-continued

Illustrative Expression Cassette Sequences

| Expression Cassette | Sequence |
|---|---|
|  | TGAAGATAATCAGCAGTCCTGCTCAGCATATCAATCCAAG<br>CCCACTCTAGACAGAGATGCCGGTGCCCAGTTTTCTATTT<br>TTAACTGGTGTGAACTGAAGGAAAAGCACAGCATTAGAAG<br>TCCAAGCACCTTCAGATTAAAAATAACTAAGGTAAGGGCC<br>ATGTGGGTAGGGGAGGTGGTGTGAGACGGTCCTGTCTCTC<br>CTCTATCTGCCCATCGGCCCTTTGGGGAGGAGGAATGTGC<br>CCAAGGACTAAAAAAAGGCCCTGGAGCCAGAGGGGCGAGG<br>GCAGCAGACCTTTCATGGGCAAACCTCAGGGCTGCTGTCG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAG<br>CGGCCGCCCGCCACCATGGCTGAAAAAGCGGGGTCTACAT<br>TTTCACACCTTCTGGTTCCTATTCTTCTCCTGATTGGCTG<br>GATTGTGGGCTGCATCATAATGATTTATGTTGTCTTCTCT<br>TAGAAGCTTTGGATCCAATCAACCTCTGGATTACAAAATT<br>TGTGAAAGATTGACTGGTATTCTTAACTATGTTGCTCCTT<br>TTACGCTATGTGGATACGCTGCTTTAATGCCTTTGTATCA<br>TGCTATTGCTTCCCGTATGGCTTTCATTTTCTCCTCCTTG<br>TATAAATCCTGGTTGCTGTCTCTTTATGAGGAGTTGTGGC<br>CCGTTGTCAGGCAACGTGGCGTGGTGTGCACTGTGTTTGC<br>TGACGCAACCCCCACTGGTTGGGGCATTGCCACCACCTGT<br>CAGCTCCTTTCCGGGACTTTCGCTTTCCCCCTCCCTATTG<br>CCACGGCGGAACTCATCGCCGCCTGCCTTGCCCGCTGCTG<br>GACAGGGGCTCGGCTGTTGGGCACTGACAATTCCGTGGTG<br>TTGTCGGGGAAATCATCGTCCTTTCCTTGGCTGCTCGCCT<br>GTGTTGCCACCTGGATTCTGCGCGGGACGTCCTTCTGCTA<br>CGTCCCTTCGGCCCTCAATCCAGCGGACCTTCCTTCCCGC<br>GGCCTGCTGCCGGCTCTGCGGCCTCTTCCGCGTCTTCGAG<br>ATCTGCCTCGACTGTGCCTTCTAGTTGCCAGCCATCTGTT<br>GTTTGCCCCTCCCCCGTGCCTTCCTTGACCCTGGAAGGTG<br>CCACTCCCACTGTCCTTTCCTAATAAAATGAGGAAATTGC<br>ATCGCATTGTCTGAGTAGGTGTCATTCTATTCTGGGGGGT<br>GGGGTGGGGCAGGACAGCAAGGGGGAGGATTGGGAAGACA<br>ATAGCAGGCATGCTGGGGACTCGAGTTAAGGGCGAATTCC<br>CGATTAGGATCTTCCTAGAGCATGGCTACGTAGATAAGTA<br>GCATGGCGGGTTAATCATTAACTACAAGGAACCCCTAGTG<br>ATGGAGTTGGCCACTCCCTCTCTGCGCGCTCGCTCGCTCA<br>CTGAGGCCGGGCGACCAAAGGTCGCCCGACGCCCGGGCTT<br>TGCCCGGGCGGCCTCAGTGAGCGAGCGAGCGCGCAG<br>(SEQ ID NO: 64) |
| pHZ53 (human DWORF<br>version of pHZ17) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAGGCCCTGGAGCCAGAGGGGCGAGGGCA<br>GCAGACCTTTCATGGGCAAACCTCAGGGCTGCTGTCGTCA<br>TGGAGAAGACCCACCTTGCAGATGTCCTCACTGGGGCTGG<br>CAGAGCCGGCAACCTGCCTAAGGCTGCTCAGTCCATTAGG<br>AGCCAGTAGCCTGGAAGATGTCTTTACCCCCAGCATCAGT<br>TCAAGTGGAGCAGCACATAACTCTTGCCCTCTGCCTTCCA<br>AGATTCTGGTGCTGAGACTTATGGAGTGTCTTGGAGGTTG<br>CCTTCTGCCCCCAACCCTGCTCCCAGCTGGCCCTCCCAG<br>GCCTGGGTTGCTGGCCTCTGCTTTATCAGGATTCTCAAGA<br>GGGACAGCTGGTTTATGTTGCATGACTGTTCCCTGCATAT<br>CTGCTCTGGTTTTAAATAGCTTATCTGAGCAGCTGGAGGA<br>CCACATGGGCTTATATGGCGTGGGGTACATGTTCCTGTAG<br>CCTTGTCCCTGGCACCTGCCAAAATAGCAGCCAACACCCC<br>CCACCCCCACCGCCATCCCCCTGCCCCACCCGTCCCCTGT<br>CGCACATTCCTCCCTCCGCAGGGCTGGCTCACCAGGCCCC |

TABLE 1-continued

Illustrative Expression Cassette Sequences

| Expression Cassette | Sequence |
|---|---|
| | AGCCCACATGCCTGCTTAAAGCCCTCTCCATCCTCTGCCT<br>CACCCAGTCCCCGCTGAGACTGAGCAGACGCCTCCAGCGG<br>CCGCCCGCCACCATGGCTGAAAAAGCGGGGTCTACATTTT<br>CACACCTTCTGGTTCCTATTCTTCTCCTGATTGGCTGGAT<br>TGTGGGCTGCATCATAATGATTTATGTTGTCTTCTCTTAG<br>AAGCTTTGGATCCAATCAACCTCTGGATTACAAAATTTGT<br>GAAAGATTGACTGGTATTCTTAACTATGTTGCTCCTTTTA<br>CGCTATGTGGATACGCTGCTTTAATGCCTTTGTATCATGC<br>TATTGCTTCCCGTATGGCTTTCATTTTCTCCTCCTTGTAT<br>AAATCCTGGTTGCTGTCTCTTTATGAGGAGTTGTGGCCCG<br>TTGTCAGGCAACGTGGCGTGGTGTGCACTGTGTTTGCTGA<br>CGCAACCCCCACTGGTTGGGGCATTGCCACCACCTGTCAG<br>CTCCTTTCCGGGACTTTCGCTTTCCCCCTCCCTATTGCCA<br>CGGCGGAACTCATCGCCGCCTGCCTTGCCCGCTGCTGGAC<br>AGGGGCTCGGCTGTTGGGCACTGACAATTCCGTGGTGTTG<br>TCGGGGAAATCATCGTCCTTTCCTTGGCTGCTCGCCTGTG<br>TTGCCACCTGGATTCTGCGCGGGACGTCCTTCTGCTACGT<br>CCCTTCGGCCCTCAATCCAGCGGACCTTCCTTCCCGCGGC<br>CTGCTGCCGGTCTGCGGCCTCTTCCGCGTCTTCGAGATC<br>TGCCTCGACTGTGCCTTCTAGTTGCCAGCCATCTGTTGTT<br>TGCCCCTCCCCCGTGCCTTCCTTGACCCTGGAAGGTGCCA<br>CTCCCACTGTCCTTTCCTAATAAAATGAGGAAATTGCATC<br>GCATTGTCTGAGTAGGTGTCATTCTATTCTGGGGGTGGG<br>GTGGGGCAGGACAGCAAGGGGGAGGATTGGGAAGACAATA<br>GCAGGCATGCTGGGGACTCGAGTTAAGGGCGAATTCCCGA<br>TTAGGATCTTCCTAGAGCATGGCTACGTAGATAAGTAGCA<br>TGGCGGGTTAATCATTAACTACAAGGAACCCCTAGTGATG<br>GAGTTGGCCACTCCCTCTCTGCGCGCTCGCTCGCTCACTG<br>AGGCCGGGCGACCAAAGGTCGCCCGACGCCCGGGCTTTGC<br>CCGGGCGGCCTCAGTGAGCGAGCGAGCGCGCAG<br>(SEQ ID NO: 65) |
| pHZ54 (human DWORF<br>version of pHZ18) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCAACT<br>GGCCTGCCCGAGACCAAACGTGCGGAACGTAGTTAAGTGT<br>TAGAGGTAGGATTTGAAGCCTGTCGATCATTCTGATTCTC<br>CTTTTTCTCTACGTCTGCTTCCTGTCAATGGGCATCCTCAC<br>TGTCAAATGCAGATGGTACAGCAGGGCTTGGTCTCAGCCA<br>GGCAGGCCTCTCCCCAGTCTCCATGGCTCAGCTGTCCAGC<br>AGTTTCATCCCTAGACCATCCCAAACATGGTTGAGAAGCT<br>CTGAGGGGAGGACCCAGCACTGCCCGGCCCCTGAAGATAA<br>TCAGCAGTCCTGCTCAGCATATCAATCCAAGCCCACTCTA<br>GACAGAGATGCCGGTGCCCAGTTTTCTATTTTTAACTGGT<br>GTGAACTGAAGGAAAAGCACAGCATTAGAAGTCCAAGCAG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAG<br>CGGCCGCCCGCCACCATGGCTGAAAAAGCGGGGTCTACAT<br>TTTCACACCTTCTGGTTCCTATTCTTCTCCTGATTGGCTG<br>GATTGTGGGCTGCATCATAATGATTTATGTTGTCTTCTCT<br>TAGAAGCTTTGGATCCAATCAACCTCTGGATTACAAAATT<br>TGTGAAAGATTGACTGGTATTCTTAACTATGTTGCTCCTT<br>TTACGCTATGTGGATACGCTGCTTTAATGCCTTTGTATCA<br>TGCTATTGCTTCCCGTATGGCTTTCATTTTCTCCTCCTTG<br>TATAAATCCTGGTTGCTGTCTCTTTATGAGGAGTTGTGGC<br>CCGTTGTCAGGCAACGTGGCGTGGTGTGCACTGTGTTTGC |

TABLE 1-continued

Illustrative Expression Cassette Sequences

| Expression Cassette | Sequence |
|---|---|
| | TGACGCAACCCCCACTGGTTGGGGCATTGCCACCACCTGT<br>CAGCTCCTTTCCGGGACTTTCGCTTTCCCCCTCCCTATTG<br>CCACGGCGGAACTCATCGCCGCCTGCCTTGCCCGCTGCTG<br>GACAGGGGCTCGGCTGTTGGGCACTGACAATTCCGTGGTG<br>TTGTCGGGGAAATCATCGTCCTTTCCTTGGCTGCTCGCCT<br>GTGTTGCCACCTGGATTCTGCGCGGGACGTCCTTCTGCTA<br>CGTCCCTTCGGCCCTCAATCCAGCGGACCTTCCTTCCCGC<br>GGCCTGCTGCCGGCTCTGCGGCCTCTTCCGCGTCTTCGAG<br>ATCTGCCTCGACTGTGCCTTCTAGTTGCCAGCCATCTGTT<br>GTTTGCCCCTCCCCCGTGCCTTCCTTGACCCTGGAAGGTG<br>CCACTCCCACTGTCCTTTCCTAATAAAATGAGGAAATTGC<br>ATCGCATTGTCTGAGTAGGTGTCATTCTATTCTGGGGGGT<br>GGGGTGGGGCAGGACAGCAAGGGGGAGGATTGGGAAGACA<br>ATAGCAGGCATGCTGGGGACTCGAGTTAAGGGCGAATTCC<br>CGATTAGGATCTTCCTAGAGCATGGCTACGTAGATAAGTA<br>GCATGGCGGGTTAATCATTAACTACAAGGAACCCCTAGTG<br>ATGGAGTTGGCCACTCCCTCTCTGCGCGCTCGCTCGCTCA<br>CTGAGGCCGGGCGACCAAAGGTCGCCCGACGCCCGGGCTT<br>TGCCCGGGCGGCCTCAGTGAGCGAGCGAGCGCGCAG<br>(SEQ ID NO: 66) |
| pHZ55 (human DWORF<br>version of pHZ19) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCAACT<br>GGCCTGCCCGAGACCAAACGTGCGGAACGTAGTTAAGTGT<br>TAGAGGTAGGATTTGAAGCCTGTCGATCATTCTGATTCTC<br>CTTTTCTCTACGTCTGCTTCCTGTCAATGGGCATCCTCAC<br>TGTCAAATGCAGATGGTACAGCAGGGCTTGGTCTCAGCCA<br>GGCAGGCCTCTCCCCAGTCTCCATGGCTCAGCTGTCCAGC<br>AGTTTCATCCCTAGACCATCCCAAACATGGTTGAGAAGCT<br>CTGAGGGGAGGACCCAGCACTGCCCGGCCCCTGAAGATAA<br>TCAGCAGTCCTGCTCAGCATATCAATCCAAGCCCACTCTA<br>GACAGAGATGCCGGTGCCCAGTTTTCTATTTTTAACTGGT<br>GTGAACTGAAGGAAAAGCACAGCATTAGAAGTCCAAGCAG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAT<br>AACTGGTAAGTACCGCCTATAGACTCTATAGGCACACCCC<br>TTTGGCTCTTATGCATGCTGACAGACTAACAGACTGTTCC<br>TTTCCTGGGTCTTTTCTGCAGGCCTGTACGGAAGTGTTAC<br>TTCTGCTCTAAAAGCTGCGGAATTGTACCCGCGGCCGATC<br>CAATCGATACAGATCTAGCGGCCGCCCGCCACCATGGCTG<br>AAAAAGCGGGGTCTACATTTTCACACCTTCTGGTTCCTAT<br>TCTTCTCCTGATTGGCTGGATTGTGGGCTGCATCATAATG<br>ATTTATGTTGTCTTCTCTTAGAAGCTTTGGATCCAATCAA<br>CCTCTGGATTACAAAATTTGTGAAAGATTGACTGGTATTC<br>TTAACTATGTTGCTCCTTTTACGCTATGTGGATACGCTGC<br>TTTAATGCCTTTGTATCATGCTATTGCTTCCCGTATGGCT<br>TTCATTTTCTCCTCCTTGTATAAATCCTGGTTGCTGTCTC<br>TTTATGAGGAGTTGTGGCCCGTTGTCAGGCAACGTGGCGT<br>GGTGTGCACTGTGTTTGCTGACGCAACCCCCACTGGTTGG<br>GGCATTGCCACCACCTGTCAGCTCCTTTCCGGGACTTTCG<br>CTTTCCCCCTCCCTATTGCCACGGCGGAACTCATCGCCGC<br>CTGCCTTGCCCGCTGCTGGACAGGGGCTCGGCTGTTGGGC<br>ACTGACAATTCCGTGGTGTTGTCGGGGAAATCATCGTCCT<br>TTCCTTGGCTGCTCGCCTGTGTTGCCACCTGGATTCTGCG<br>CGGGACGTCCTTCTGCTACGTCCCTTCGGCCCTCAATCCA |

TABLE 1-continued

Illustrative Expression Cassette Sequences

| Expression Cassette | Sequence |
|---|---|
| | GCGGACCTTCCTTCCCGCGGCCTGCTGCCGGCTCTGCGGC<br>CTCTTCCGCGTCTTCGAGATCTGCCTCGACTGTGCCTTCT<br>AGTTGCCAGCCATCTGTTGTTTGCCCCTCCCCCGTGCCTT<br>CCTTGACCCTGGAAGGTGCCACTCCCACTGTCCTTTCCTA<br>ATAAAATGAGGAAATTGCATCGCATTGTCTGAGTAGGTGT<br>CATTCTATTCTGGGGGGTGGGGTGGGGCAGGACAGCAAGG<br>GGGAGGATTGGGAAGACAATAGCAGGCATGCTGGGGACTC<br>GAGTTAAGGGCGAATTCCCGATTAGGATCTTCCTAGAGCA<br>TGGCTACGTAGATAAGTAGCATGGCGGGTTAATCATTAAC<br>TACAAGGAACCCCTAGTGATGGAGTTGGCCACTCCCTCTC<br>TGCGCGCTCGCTCGCTCACTGAGGCCGGGCGACCAAAGGT<br>CGCCCGACGCCCGGGCTTTGCCCGGGCGGCCTCAGTGAGC<br>GAGCGAGCGCGCAG (SEQ ID NO: 67) |
| pHZ56 (human DWORF<br>version of pHZ20) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGGTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCACCCCCACCGCCATCCCCCTGCCCCACCC<br>GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCAGACGC<br>CTCCATAACTGGTAAGTACCGCCTATAGACTCTATAGGCA<br>CACCCCTTTGGCTCTTATGCATGCTGACAGACTAACAGAC<br>TGTTCCTTTCCTGGGTCTTTTCTGCAGGCCTGTACGGAAG<br>TGTTACTTCTGCTCTAAAAGCTGCGGAATTGTACCCGCGG<br>CCGATCCAATCGATACAGATCTAGCGGCCGCCCGCCACCA<br>TGGCTGAAAAAGCGGGGTCTACATTTTCACACCTTCTGGT<br>TCCTATTCTTCTCCTGATTGGCTGGATTGTGGGCTGCATC<br>ATAATGATTTATGTTGTCTTCTCTTAGAAGCTTTGGATCC<br>AATCAACCTCTGGATTACAAAATTTGTGAAAGATTGACTG<br>GTATTCTTAACTATGTTGCTCCTTTTACGCTATGTGGATA<br>CGCTGCTTTAATGCCTTTGTATCATGCTATTGCTTCCCGT<br>ATGGCTTTCATTTTCTCCTCCTTGTATAAATCCTGGTTGC<br>TGTCTCTTTATGAGGAGTTGTGGCCCGTTGTCAGGCAACG<br>TGGCGTGGTGTGCACTGTGTTTGCTGACGCAACCCCCACT<br>GGTTGGGGCATTGCCACCACCTGTCAGCTCCTTTCCGGGA<br>CTTTCGCTTTCCCCCTCCCTATTGCCACGGCGGAACTCAT<br>CGCCGCCTGCCTTGCCCGCTGCTGGACAGGGGCTCGGCTG<br>TTGGGCACTGACAATTCCGTGGTGTTGTCGGGGAAATCAT<br>CGTCCTTTCCTTGGCTGCTCGCCTGTGTTGCCACCTGGAT<br>TCTGCGCGGGACGTCCTTCTGCTACGTCCCTTCGGCCCTC<br>AATCCAGCGGACCTTCCTTCCCGCGGCCTGCTGCCGGCTC<br>TGCGGCCTCTTCCGCGTCTTCGAGATCTGCCTCGACTGTG<br>CCTTCTAGTTGCCAGCCATCTGTTGTTTGCCCCTCCCCCG<br>TGCCTTCCTTGACCCTGGAAGGTGCCACTCCCACTGTCCT<br>TTCCTAATAAAATGAGGAAATTGCATCGCATTGTCTGAGT<br>AGGTGTCATTCTATTCTGGGGGGTGGGGTGGGGCAGGACA<br>GCAAGGGGGAGGATTGGGAAGACAATAGCAGGCATGCTGG<br>GGACTCGAGTTAAGGGCGAATTCCCGATTAGGATCTTCCT<br>AGAGCATGGCTACGTAGATAAGTAGCATGGCGGGTTAATC<br>ATTAACTACAAGGAACCCCTAGTGATGGAGTTGGCCACTC<br>CCTCTCTGCGCGCTCGCTCGCTCACTGAGGCCGGGCGACC<br>AAAGGTCGCCCGACGCCCGGGCTTTGCCCGGGCGGCCTCA<br>GTGAGCGAGCGAGCGCGCAG (SEQ ID NO: 68) |
| pHZ57 (human DWORF<br>version of pHZ21) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGAACTGGCCTGCCCGAGACCAAACGTGCGGAACGTA<br>GTTAAGTGTTAGAGGTAGGATTTGAAGCCTGTCGATCATT<br>CTGATTCTCCTTTTCTCTACGTCTGCTTCCTGTCAATGGG |

TABLE 1-continued

Illustrative Expression Cassette Sequences

| Expression Cassette | Sequence |
|---|---|
| | CATCCTCACTGTCAAATGCAGATGGTACAGCAGGGCTTGG<br>TCTCAGCCAGGCAGGCCTCTCCCCAGTCTCCATGGCTCAG<br>CTGTCCAGCAGTTTCATCCCTAGACCATCCCAAACATGGT<br>TGAGAAGCTCTGAGGGGAGGACCCAGCACTGCCCGGCCCC<br>TGAAGATAATCAGCAGTCCTGCTCAGCATATCAATCCAAG<br>CCCACTCTAGACAGAGATGCCGGTGCCCAGTTTTCTATTT<br>TTAACTGGTGTGAACTGAAGGAAAAGCACAGCATTAGAAG<br>TCCAAGCACCTTCAGATTAAAAATAACTAAGGTAAGGGCC<br>ATGTGGGTAGGGGAGGTGGTGTGAGACGGTCCTGTCTCTC<br>CTCTATCTGCCCATCGGCCCTTTGGGGAGGAGGAATGTGC<br>CCAAGGACTAAAAAAAGGCCCTGGAGCCAGAGGGGCGAGG<br>GCAGCAGACCTTTCATGGGCAAACCTCAGGGCTGCTGTCG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAT<br>AACTGGTAAGTACCGCCTATAGACTCTATAGGCACACCCC<br>TTTGGCTCTTATGCATGCTGACAGACTAACAGACTGTTCC<br>TTTCCTGGGTCTTTTCTGCAGGCCTGTACGGAAGTGTTAC<br>TTCTGCTCTAAAAGCTGCGGAATTGTACCCGCGGCCGATC<br>CAATCGATACAGATCTAGCGGCCGCCCGCCACCATGGCTG<br>AAAAAGCGGGGTCTACATTTTCACACCTTCTGGTTCCTAT<br>TCTTCTCCTGATTGGCTGGATTGTGGGCTGCATCATAATG<br>ATTTATGTTGTCTTCTCTTAGAAGCTTTGGATCCAATCAA<br>CCTCTGGATTACAAAATTTGTGAAAGATTGACTGGTATTC<br>TTAACTATGTTGCTCCTTTTACGCTATGTGGATACGCTGC<br>TTTAATGCCTTTGTATCATGCTATTGCTTCCCGTATGGCT<br>TTCATTTTCTCCTCCTTGTATAAATCCTGGTTGCTGTCTC<br>TTTTATGAGGAGTTGTGGCCCGTTGTCAGGCAACGTGGCGT<br>GGTGTGCACTGTGTTTGCTGACGCAACCCCCACTGGTTGG<br>GGCATTGCCACCACCTGTCAGCTCCTTTCCGGGACTTTCG<br>CTTTCCCCCTCCCTATTGCCACGGCGGAACTCATCGCCGC<br>CTGCCTTGCCCGCTGCTGGACAGGGGCTCGGCTGTTGGGC<br>ACTGACAATTCCGTGGTGTTGTCGGGGAAATCATCGTCCT<br>TTCCTTGGCTGCTCGCCTGTGTTGCCACCTGGATTCTGCG<br>CGGGACGTCCTTCTGCTACGTCCCTTCGGCCCTCAATCCA<br>GCGGACCTTCCTTCCCGCGGCCTGCTGCCGGCTCTGCGGC<br>CTCTTCCGCGTCTTCGAGATCTGCCTCGACTGTGCCTTCT<br>AGTTGCCAGCCATCTGTTGTTTGCCCCTCCCCCGTGCCTT<br>CCTTGACCCTGGAAGGTGCCACTCCCACTGTCCTTTCCTA<br>ATAAAATGAGGAAATTGCATCGCATTGTCTGAGTAGGTGT<br>CATTCTATTCTGGGGGGTGGGTGGGGCAGGACAGCAAGG<br>GGGAGGATTGGGAAGACAATAGCAGGCATGCTGGGGACTC<br>GAGTTAAGGGCGAATTCCCGATTAGGATCTTCCTAGAGCA<br>TGGCTACGTAGATAAGTAGCATGGCGGGTTAATCATTAAC<br>TACAAGGAACCCCTAGTGATGGAGTTGGCCACTCCCTCTC<br>TGCGCGCTCGCTCGCTCACTGAGGCCGGGCGACCAAAGGT<br>CGCCCGACGCCCGGGCTTTGCCCGGGCGGCCTCAGTGAGC<br>GAGCGAGCGCGCAG (SEQ ID NO: 69) |
| pHZ58 (human DWORF<br>version of pHZ22) | CTGCGCGCTCGCTCGCTCACTGAGGCCGCCCGGGCAAAGC<br>CCGGGCGTCGGGCGACCTTTCGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGAACTGGCCTGCCCGAGACCAAACGTGCGGAACGTA<br>GTTAAGTGTTAGAGGTAGGATTTGAAGCCTGTCGATCATT<br>CTGATTCTCCTTTTCTCTACGTCTGCTTCCTGTCAATGGG<br>CATCCTCACTGTCAAATGCAGATGGTACAGCAGGGCTTGG<br>TCTCAGCCAGGCAGGCCTCTCCCCAGTCTCCATGGCTCAG<br>CTGTCCAGCAGTTTCATCCCTAGACCATCCCAAACATGGT<br>TGAGAAGCTCTGAGGGGAGGACCCAGCACTGCCCGGCCCC<br>TGAAGATAATCAGCAGTCCTGCTCAGCATATCAATCCAAG<br>CCCACTCTAGACAGAGATGCCGGTGCCCAGTTTTCTATTT<br>TTAACTGGTGTGAACTGAAGGAAAAGCACAGCATTAGAAG |

TABLE 1-continued

Illustrative Expression Cassette Sequences

| Expression Cassette | Sequence |
|---|---|
|  | TCCAAGCACCTTCAGATTAAAAATAACTAAGGTAAGGGCC<br>ATGTGGGTAGGGGAGGTGGTGTGAGACGGTCCTGTCTCTC<br>CTCTATCTGCCCATCGGCCCTTTGGGGAGGAGGAATGTGC<br>CCAAGGACTAAAAAAAGGCCCTGGAGCCAGAGGGGCGAGG<br>GCAGCAGACCTTTCATGGGCAAACCTCAGGGCTGCTGTCG<br>TCATGGAGAAGACCCACCTTGCAGATGTCCTCACTGGGGC<br>TGGCAGAGCCGGCAACCTGCCTAAGGCTGCTCAGTCCATT<br>AGGAGCCAGTAGCCTGGAAGATGTCTTTACCCCCAGCATC<br>AGTTCAAGTGGAGCAGCACATAACTCTTGCCCTCTGCCTT<br>CCAAGATTCTGGTGCTGAGACTTATGGAGTGTCTTGGAGG<br>TTGCCTTCTGCCCCCCAACCCTGCTCCCAGCTGGCCCTCC<br>CAGGCCTGGGTTGCTGGCCTCTGCTTTATCAGGATTCTCA<br>AGAGGGACAGCTGGTTTATGTTGCATGACTGTTCCCTGCA<br>TATCTGCTCTGGTTTTAAATAGCTTATCTGAGCAGCTGGA<br>GGACCACATGGGCTTATATGGCGTGGGGTACATGTTCCTG<br>TAGCCTTGTCCCTGGCACCTGCCAAAATAGCAGCCAACAC<br>CCCCCACCCCCACCGCCATCCCCCTGCCCCACCCGTCCCC<br>TGTCGCACATTCCTCCCTCCGCAGGGCTGGCTCACCAGGC<br>CCCAGCCCACATGCCTGCTTAAAGCCCTCTCCATCCTCTG<br>CCTCACCCAGTCCCCGCTGAGACTGAGCAGACGCCTCCAT<br>AACTGGTAAGTACCGCCTATAGACTCTATAGGCACACCCC<br>TTTGGCTCTTATGCATGCTGACAGACTAACAGACTGTTCC<br>TTTCCTGGGTCTTTTCTGCAGGCCTGTACGGAAGTGTTAC<br>TTCTGCTCTAAAAGCTGCGGAATTGTACCCGCGGCCGATC<br>CAATCGATACAGATCTAGCGGCCGCCCGCCACCATGGCTG<br>AAAAAGCGGGGTCTACATTTTCACACCTTCTGGTTCCTAT<br>TCTTCTCCTGATTGGCTGGATTGTGGGCTGCATCATAATG<br>ATTTATGTTGTCTTCTCTTAGAAGCTTTGGATCCAATCAA<br>CCTCTGGATTACAAAATTTGTGAAAGATTGACTGGTATTC<br>TTAACTATGTTGCTCCTTTTACGCTATGTGGATACGCTGC<br>TTTAATGCCTTTGTATCATGCTATTGCTTCCCGTATGGCT<br>TTCATTTTCTCCTCCTTGTATAAATCCTGGTTGCTGTCTC<br>TTTATGAGGAGTTGTGGCCCGTTGTCAGGCAACGTGGCGT<br>GGTGTGCACTGTGTTTGCTGACGCAACCCCCACTGGTTGG<br>GGCATTGCCACCACCTGTCAGCTCCTTTCCGGGACTTTCG<br>CTTTCCCCCTCCCTATTGCCACGGCGGAACTCATCGCCGC<br>CTGCCTTGCCCGCTGCTGGACAGGGGCTCGGCTGTTGGGC<br>ACTGACAATTCCGTGGTGTTGTCGGGGAAATCATCGTCCT<br>TTCCTTGGCTGCTCGCCTGTGTTGCCACCTGGATTCTGCG<br>CGGGACGTCCTTCTGCTACGTCCCTTCGGCCCTCAATCCA<br>GCGGACCTTCCTTCCCGCGGCCTGCTGCCGGCTCTGCGGC<br>CTCTTCCGCGTCTTCGAGATCTGCCTCGACTGTGCCTTCT<br>AGTTGCCAGCCATCTGTTGTTTGCCCCTCCCCCGTGCCTT<br>CCTTGACCCTGGAAGGTGCCACTCCCACTGTCCTTTCCTA<br>ATAAAATGAGGAAATTGCATCGCATTGTCTGAGTAGGTGT<br>CATTCTATTCTGGGGGGTGGGGTGGGGCAGGACAGCAAGG<br>GGGAGGATTGGGAAGACAATAGCAGGCATGCTGGGGACTC<br>GAGTTAAGGGCGAATTCCCGATTAGGATCTTCCTAGAGCA<br>TGGCTACGTAGATAAGTAGCATGGCGGGTTAATCATTAAC<br>TACAAGGAACCCCTAGTGATGGAGTTGGCCACTCCCTCTC<br>TGCGCGCTCGCTCGCTCACTGAGGCCGGGCGACCAAAGGT<br>CGCCCGACGCCCGGGCTTTGCCCGGGCGGCCTCAGTGAGC<br>GAGCGAGCGCGCAG (SEQ ID NO: 70) |
| pHZ59 (human DWORF version of pHZ23) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAGGCCCTGGAGCCAGAGGGGCGAGGGCA<br>GCAGACCTTTCATGGGCAAACCTCAGGGCTGCTGTCGTCA<br>TGGAGAAGACCCACCTTGCAGATGTCCTCACTGGGGCTGG<br>CAGAGCCGGCAACCTGCCTAAGGCTGCTCAGTCCATTAGG<br>AGCCAGTAGCCTGGAAGATGTCTTTACCCCCAGCATCAGT<br>TCAAGTGGAGCAGCACATAACTCTTGCCCTCTGCCTTCCA<br>AGATTCTGGTGCTGAGACTTATGGAGTGTCTTGGAGGTTG<br>CCTTCTGCCCCCAACCCTGCTCCCAGCTGGCCCTCCCAG<br>GCCTGGGTTGCTGGCCTCTGCTTTATCAGGATTCTCAAGA<br>GGGACAGCTGGTTTATGTTGCATGACTGTTCCCTGCATAT<br>CTGCTCTGGTTTTAAATAGCTTATCTGAGCAGCTGGAGGA<br>CCACATGGGCTTATATGGCGTGGGGTACATGTTCCTGTAG<br>CCTTGTCCCTGGCACCTGCCAAAATAGCAGCCAACACCCC<br>CCACCCCCACCGCCATCCCCCTGCCCCACCCGTCCCCTGT |

TABLE 1-continued

Illustrative Expression Cassette Sequences

| Expression Cassette | Sequence |
|---|---|
| | CGCACATTCCTCCCTCCGCAGGGCTGGCTCACCAGGCCCC<br>AGCCCACATGCCTGCTTAAAGCCCTCTCCATCCTCTGCCT<br>CACCCAGTCCCCGCTGAGACTGAGCAGACGCCTCCATAAC<br>TGGTAAGTACCGCCTATAGACTCTATAGGCACACCCCTTT<br>GGCTCTTATGCATGCTGACAGACTAACAGACTGTTCCTTT<br>CCTGGGTCTTTTCTGCAGGCCTGTACGGAAGTGTTACTTC<br>TGCTCTAAAAGCTGCGGAATTGTACCCGCGGCCGATCCAA<br>TCGATACAGATCTAGCGGCCGCCCGCCACCATGGCTGAAA<br>AAGCGGGGTCTACATTTTCACACCTTCTGGTTCCTATTCT<br>TCTCCTGATTGGCTGGATTGTGGGCTGCATCATAATGATT<br>TATGTTGTCTTCTCTTAGAAGCTTTGGATCCAATCAACCT<br>CTGGATTACAAAATTTGTGAAAGATTGACTGGTATTCTTA<br>ACTATGTTGCTCCTTTTACGCTATGTGGATACGCTGCTTT<br>AATGCCTTTGTATCATGCTATTGCTTCCCGTATGGCTTTC<br>ATTTTCTCCTCCTTGTATAAATCCTGGTTGCTGTCTCTTT<br>ATGAGGAGTTGTGGCCCGTTGTCAGGCAACGTGGCGTGGT<br>GTGCACTGTGTTTGCTGACGCAACCCCCACTGGTTGGGGC<br>ATTGCCACCACCTGTCAGCTCCTTTCCGGGACTTTCGCTT<br>TCCCCCTCCCTATTGCCACGGCGGAACTCATCGCCGCCTG<br>CCTTGCCCGCTGCTGGACAGGGGCTCGGCTGTTGGGCACT<br>GACAATTCCGTGGTGTTGTCGGGGAAATCATCGTCCTTTC<br>CTTGGCTGCTCGCCTGTGTTGCCACCTGGATTCTGCGCGG<br>GACGTCCTTCTGCTACGTCCCTTCGGCCCTCAATCCAGCG<br>GACCTTCCTTCCCGCGGCCTGCTGCCGGCTCTGCGGCCTC<br>TTCCGCGTCTTCGAGATCTGCCTCGACTGTGCCTTCTAGT<br>TGCCAGCCATCTGTTGTTTGCCCCTCCCCCGTGCCTTCCT<br>TGACCCTGGAAGGTGCCACTCCCACTGTCCTTTCCTAATA<br>AAATGAGGAAATTGCATCGCATTGTCTGAGTAGGTGTCAT<br>TCTATTCTGGGGGGTGGGGTGGGGCAGGACAGCAAGGGGG<br>AGGATTGGGAAGACAATAGCAGGCATGCTGGGGACTCGAG<br>TTAAGGGCGAATTCCCGATTAGGATCTTCCTAGAGCATGG<br>CTACGTAGATAAGTAGCATGGCGGGTTAATCATTAACTAC<br>AAGGAACCCCTAGTGATGGAGTTGGCCACTCCCTCTCTGC<br>GCGCTCGCTCGCTCACTGAGGCCGGGCGACCAAAGGTCGC<br>CCGACGCCCGGGCTTTGCCCGGGCGGCCTCAGTGAGCGAG<br>CGAGCGCGCAG (SEQ ID NO: 71) |
| pHZ60 (human DWORF version of pHZ24) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGGTCATGGAGAAGACCCACCTTGCAGATGTCCTCAC<br>TGGGGCTGGCAGAGCCGGCAACCTGCCTAAGGCTGCTCAG<br>TCCATTAGGAGCCAGTAGCCTGGAAGATGTCTTTACCCCC<br>AGCATCAGTTCAAGTGGAGCAGCACATAACTCTTGCCCTC<br>TGCCTTCCAAGATTCTGGTGCTGAGACTTATGGAGTGTCT<br>TGGAGGTTGCCTTCTGCCCCCCAACCCTGCTCCCAGCTGG<br>CCCTCCCAGGCCTGGGTTGCTGGCCTCTGCTTTATCAGGA<br>TTCTCAAGAGGGACAGCTGGTTTATGTTGCATGACTGTTC<br>CCTGCATATCTGCTCTGGTTTTAAATAGCTTATCTGAGCA<br>GCTGGAGGACCACATGGGCTTATATGGCGTGGGGTACATG<br>TTCCTGTAGCCTTGTCCCTGGCACCTGCCAAAATAGCAGC<br>CAACACCCCCACCCCCACCGCCATCCCCCTGCCCCACCC<br>GTCCCCTGTCGCACATTCCTCCCTCCGCAGGGCTGGCTCA<br>CCAGGCCCCAGCCCACATGCCTGCTTAAAGCCCTCTCCAT<br>CCTCTGCCTCACCCAGTCCCCGCTGAGACTGAGCAGACGC<br>CTCCAGCGGCCGCCCGCCACCATGGCCGAGAAGGCCGGAT<br>CTACCTTCAGCCACCTGCTGGTCCCTATTCTGCTGCTGAT<br>CGGCTGGATCGTGGGCTGCATCATCATGATCTACGTGGTG<br>TTCAGCTGAAAGCTTTGGATCCAATCAACCTCTGGATTAC<br>AAAATTTGTGAAAGATTGACTGGTATTCTTAACTATGTTG<br>CTCCTTTTACGCTATGTGGATACGCTGCTTTAATGCCTTT<br>GTATCATGCTATTGCTTCCCGTATGGCTTTCATTTTCTCC<br>TCCTTGTATAAATCCTGGTTGCTGTCTCTTTATGAGGAGT<br>TGTGGCCCGTTGTCAGGCAACGTGGCGTGGTGTGCACTGT<br>GTTTGCTGACGCAACCCCCACTGGTTGGGGCATTGCCACC<br>ACCTGTCAGCTCCTTTCCGGGACTTTCGCTTTCCCCCTCC<br>CTATTGCCACGGCGGAACTCATCGCCGCCTGCCTTGCCCG<br>CTGCTGGACAGGGGCTCGGCTGTTGGGCACTGACAATTCC<br>GTGGTGTTGTCGGGGAAATCATCGTCCTTTCCTTGGCTGC<br>TCGCCTGTGTTGCCACCTGGATTCTGCGCGGGACGTCCTT<br>CTGCTACGTCCCTTCGGCCCTCAATCCAGCGGACCTTCCT<br>TCCCGCGGCCTGCTGCCGGCTCTGCGGCCTCTTCCGCGTC<br>TTCGAGATCTGCCTCGACTGTGCCTTCTAGTTGCCAGCCA<br>TCTGTTGTTTGCCCCTCCCCCGTGCCTTCCTTGACCCTGG |

TABLE 1-continued

Illustrative Expression Cassette Sequences

| Expression Cassette | Sequence |
|---|---|
| | AAGGTGCCACTCCCACTGTCCTTTCCTAATAAAATGAGGA<br>AATTGCATCGCATTGTCTGAGTAGGTGTCATTCTATTCTG<br>GGGGGTGGGGTGGGGCAGGACAGCAAGGGGGAGGATTGGG<br>AAGACAATAGCAGGCATGCTGGGGACTCGAGTTAAGGGCG<br>AATTCCCGATTAGGATCTTCCTAGAGCATGGCTACGTAGA<br>TAAGTAGCATGGCGGGTTAATCATTAACTACAAGGAACCC<br>CTAGTGATGGAGTTGGCCACTCCCTCTCTGCGCGCTCGCT<br>CGCTCACTGAGGCCGGGCGACCAAAGGTCGCCCGACGCCC<br>GGGCTTTGCCCGGGCGGCCTCAGTGAGCGAGCGAGCGCGC<br>AG (SEQ ID NO: 72) |
| pHZ61 (human DWORF version of pHZ25) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCGTCA<br>TGGAGAAGACCCACCTTGCAGATGTCCTCACTGGGGCTGG<br>CAGAGCCGGCAACCTGCCTAAGGCTGCTCAGTCCATTAGG<br>AGCCAGTAGCCTGGAAGATGTCTTTACCCCCAGCATCAGT<br>TCAAGTGGAGCAGCACATAACTCTTGCCCTCTGCCTTCCA<br>AGATTCTGGTGCTGAGACTTATGGAGTGTCTTGGAGGTTG<br>CCTTCTGCCCCCCAACCCTGCTCCCAGCTGGCCCTCCCAG<br>GCCTGGGTTGCTGGCCTCTGCTTTATCAGGATTCTCAAGA<br>GGGACAGCTGGTTTATGTTGCATGACTGTTCCCTGCATAT<br>CTGCTCTGGTTTTAAATAGCTTATCTGAGCAGCTGGAGGA<br>CCACATGGGCTTATATGGCGTGGGTACATGTTCCTGTAG<br>CCTTGTCCCTGGCACCTGCCAAAATAGCAGCCAACACCCC<br>CCACCCCCACCGCCATCCCCCTGCCCCACCCGTCCCCTGT<br>CGCACATTCCTCCCTCCGCAGGGCTGGCTCACCAGGCCCC<br>AGCCCACATGCCTGCTTAAAGCCCTCTCCATCCTCTGCCT<br>CACCCAGTCCCCGCTGAGACTGAGCAGACGCCTCCATAAC<br>TGGTAAGTACCGCCTATAGACTCTATAGGCACACCCCTTT<br>GGCTCTTATGCATGCTGACAGATAACAGACTGTTCCTTT<br>CCTGGGTCTTTTCTGCAGGCCTGTACGGAAGTGTTACTTC<br>TGCTCTAAAAGCTGCGGAATTGTACCCGCGGCCGATCCAA<br>TCGATACAGATCTAGCGGCCGCCCGCCACCATGGCTGAAA<br>AAGCGGGGTCTACATTTTCACACCTTCTGGTTCCTATTCT<br>TCTCCTGATTGGCTGGATTGTGGGCTGCATCATAATGATT<br>TATGTTGCTTCTCTTAGAAGCTTTGGATCCAATCAACCT<br>CTGGATTACAAAATTTGTGAAAGATTGACTGGTATTCTTA<br>ACTATGTTGCTCCTTTTACGCTATGTGGATACGCTGCTTT<br>AATGCCTTTGTATCATGCTATTGCTTCCCGTATGGCTTTC<br>ATTTTCTCCTCCTTGTATAAATCCTGGTTGCTGTCTCTTT<br>ATGAGGAGTTGTGGCCCGTTGTCAGGCAACGTGGCGTGGT<br>GTGCACTGTGTTTGCTGACGCAACCCCCACTGGTTGGGGC<br>ATTGCCACCACCTGTCAGCTCCTTTCCGGGACTTTCGCTT<br>TCCCCCTCCCTATTGCCACGGCGGAACTCATCGCCGCCTG<br>CCTTGCCCGCTGCTGGACAGGGGCTCGGCTGTTGGGCACT<br>GACAATTCCGTGGTGTTGTCGGGGAAATCATCGTCCTTTC<br>CTTGGCTGCTCGCCTGTGTTGCCACCTGGATTCTGCGCGG<br>GACGTCCTTCTGCTACGTCCCTTCGGCCCTCAATCCAGCG<br>GACCTTCCTTCCCGCGGCCTGCTGCCGGCTCTGCGGCCTC<br>TTCCGCGTCTTCGAGATCTGCCTCGACTGTGCCTTCTAGT<br>TGCCAGCCATCTGTTGTTTGCCCCTCCCCCGTGCCTTCCT<br>TGACCCTGGAAGGTGCCACTCCCACTGTCCTTTCCTAATA<br>AAATGAGGAAATTGCATCGCATTGTCTGAGTAGGTGTCAT<br>TCTATTCTGGGGGGTGGGGTGGGGCAGGACAGCAAGGGGG<br>AGGATTGGGAAGACAATAGCAGGCATGCTGGGGACTCGAG<br>TTAAGGGCAGCCAGAAGTCAGATGCTCAAGGGGCTTCATG<br>ATGTCCCCATAATTTTTGGCAGAGGGAAAAAGATCGGATC<br>CTCAGGCGTAGTTCACCCCGTCCTCGAGGCCGCCCGGGTC<br>GACTAAAAAACCTCCCACACCTCCCCCTGAACCTGAAACA<br>TAAAATGAATGCAATTGTTGTTGTTAACTTGTTTATTGCA<br>GCTTATAATGGTTACAAATAAAGCAATAGCATCACAAATT<br>TCACAAATAAAGCATTTTTTCACTGCATTCTAGTTGTGG<br>TTTGTCCAAACTCATCAATGTATCTTATCATGTCTGGATC<br>CGCGCGGCCGTCAGCTGAACACCACGTAGATCATGATGAT<br>GCAGCCCACGATCCAGCCGATCAGCAGCAGAATAGGGACC<br>AGCAGGTGGCTGAAGGTAGATCCGGCCTTCTCGGCCATGG<br>TGGCGGCTAGCCTATAGTGAGTCGTATTAAGTACTCTAGC<br>CTTAAGAGCTGTAATTGAACTGGGAGTGGACACCTGTGGA |

TABLE 1-continued

Illustrative Expression Cassette Sequences

| Expression Cassette | Sequence |
|---|---|
| | GAGAAAGGCAAAGTGGATGTCAGTAAGACCAATAGGTGCC<br>TATCAGAAACGCAAGAGTCTTCTCTGTCTCGACAAGCCCA<br>GTTTCTATTGGTCTCCTTAAACCTGTCTTGTAACCTTGAT<br>ACTTACCTGCCCAGTGCCTCACGACCAACTTCTGCAGCTT<br>AAGTTCGAGACTGTTGTGTCAGAAGCACTGACTGCGTTAG<br>CAATTTAACTGTGATAAACTACCGCAATAAAGCTCTAGAG<br>CTTCGGGGATCGTCCCACGGAGCGGTGGGTGCCGGCGGCT<br>GTCTGGGAAGGGCTCCTTGGGGGGCAGAGGCTTTAAGGTC<br>CCCCCGGCGCCCACCCCGGGGGGGGCAGAGCCAGCAGGAA<br>TGTGCCCGGCGCCCAGAGAGGAATGCAACACTTGTGAGCT<br>GCTATTTTGGCAGCAGCGGCCCCGGCCCCCTCCGTGCTCC<br>CCCTTCCCCCACAGGAGCCCATATAAGCCCAAGCTATTGT<br>GTGGCCTCAGAGTTTTGCTATTTTAAACCCGTCGGACGGA<br>GATACGTGAGTGCCCGAGGGGCTGACACAAGCCAGCCAGC<br>TGTCACCTCCCAGGGCTGGGGACGCTGATAAGGCAGCGCT<br>TCGGACCCGACCCTCTGCCGCAGCCCCAGATGCTGTCATG<br>TGAAAGCCCAGACTGCTTTTATCCCTGCTTGGACTTCTAA<br>TGCTGTGCTTTTCCTTCAGTTCACACCAGTTAAAAATAGA<br>AAACTGGGCACCGGCATCTCTGTCTAGAGTGGGCTTGGAT<br>TGATATGCTGAGCAGGACTGCTGATTATCTTCAGGGGCCG<br>GGCAGTGCTGGGTCCTCCCCTCAGAGCTTCTCAACCATGT<br>TTGGGATGGTCTAGGGATGAAACTGCTGGACAGCTGAGCC<br>ATGGAGACTGGGGAGAGGCCTGCCTGGCTGAGACCAAGCC<br>CTGCTGTACCATCTGCATTTGACAGTGAGGATGCCCATTG<br>ACAGGAAGCAGACGTAGAGAAAAGGAGAATCAGAATGATC<br>GACAGGCTTCAAATCCTACCTCTAACACTTAACTACGTTC<br>CGCACGTTTGGTCTCGGGCAGGCCAGTTGAATTCCCGATT<br>AGGATCTTCCTAGAGCATGGCTACGTAGATAAGTAGCATG<br>GCGGGTTAATCATTAACTACAAGGAACCCCTAGTGATGGA<br>GTTGGCCACTCCCTCTCTGCGCGCTCGCTCGCTCACTGAG<br>GCCGGGCGACCAAAGGTCGCCCGACGCCCGGGCTTTGCCC<br>GGGCGGCCTCAGTGAGCGAGCGAGCGCGCAG<br>(SEQ ID NO: 73) |
| pHZ62 (human DWORF<br>version of pHZ33) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCGCCC<br>TTAAGCCTTCAGATTAAAAATAACTAAGGTAAGGGCCATG<br>TGGGTAGGGGAGGTGGTGTGAGACGGTCCTGTCTCTCCTC<br>TATCTGCCCATCGGCCCTTTGGGGAGGAGGAATGTGCCCA<br>AGGACTAAAAAAAGGCCCTGGAGCCAGAGGGGCGAGGGCA<br>GCAGACCTTTCATGGGCAAACCTCAGGGCTGCTGTCGTCA<br>TGGAGAAGACCCACCTTGCAGATGTCCTCACTGGGGCTGG<br>CAGAGCCGGCAACCTGCCTAAGGCTGCTCAGTCCATTAGG<br>AGCCAGTAGCCTGGAAGATGTCTTTACCCCCAGCATCAGT<br>TCAAGTGGAGCAGCACATAACTCTTGCCCTCTGCCTTCCA<br>AGATTCTGGTGCTGAGACTTATGGAGTGTCTTGGAGGTTG<br>CCTTCTGCCCCCCAACCCTGCTCCCAGCTGGCCCTCCCAG<br>GCCTGGGTTGCTGGCCTCTGCTTTATCAGGATTCTCAAGA<br>GGGACAGCTGGTTTATGTTGCATGACTGTTCCCTGCATAT<br>CTGCTCTGGTTTTAAATAGCTTATCTGAGCAGCTGGAGGA<br>CCACATGGGCTTATATGGCGTGGGTACATGTTCCTGTAG<br>CCTTGTCCCTGGCACCTGCCAAAATAGCAGCCAACACCCC<br>CCACCCCCACCGCCATCCCCCTGCCCCACCCGTCCCCTGT<br>CGCACATTCCTCCCTCCGCAGGGCTGGCTCACCAGGCCCC<br>AGCCCACATGCCTGCTTAAAGCCCTCTCCATCCTCTGCCT<br>CACCCAGTCCCCGCTGAGACTGAGCAGACGCCTCCATAAC<br>TGGTAAGTACCGCCTATAGACTCTATAGGCACACCCCTTT<br>GGCTCTTATGCATGCTGACAGACTAACAGACTGTTCCTTT<br>CCTGGGTCTTTTCTGCAGGCCTGTACGGAAGTGTTACTTC<br>TGCTCTAAAAGCTGCGGAATTGTACCCGCGGCCGATCCAA<br>TCGATACAGATCTAGCGGCCGCCCGCCACCATGGCTGAAA<br>AAGCGGGGTCTACATTTTCACACCTTCTGGTTCCTATTCT<br>TCTCCTGATTGGCTGGATTGTGGGCTGCATCATAATGATT<br>TATGTTGTCTTCTCTTAGAAGCTTTGGATCCAATCAACCT<br>CTGGATTACAAAATTTGTGAAAGATTGACTGGTATTCTTA<br>ACTATGTTGCTCCTTTTACGCTATGTGGATACGCTGCTTT<br>AATGCCTTTGTATCATGCTATTGCTTCCCGTATGGCTTTC<br>ATTTTCTCCTCCTTGTATAAATCCTGGTTGCTGTCTCTTT<br>ATGAGGAGTTGTGGCCCGTTGTCAGGCAACGTGGCGTGGT<br>GTGCACTGTGTTTGCTGACGCAACCCCCACTGGTTGGGGC<br>ATTGCCACCACCTGTCAGCTCCTTTCCGGGACTTTCGCTT<br>TCCCCCCTCCCTATTGCCACGGCGGAACTCATCGCCGCTG<br>CCTTGCCCGCTGCTGGACAGGGGCTCGGCTGTTGGGCACT |

TABLE 1-continued

Illustrative Expression Cassette Sequences

| Expression Cassette | Sequence |
| --- | --- |
| | GACAATTCCGTGGTGTTGTCGGGGAAATCATCGTCCTTTC<br>CTTGGCTGCTCGCCTGTGTTGCCACCTGGATTCTGCGCGG<br>GACGTCCTTCTGCTACGTCCCTTCGGCCCTCAATCCAGCG<br>GACCTTCCTTCCCGCGGCCTGCTGCCGGCTCTGCGGCCTC<br>TTCCGCGTCTTCGAGATCTGCCTCGACTGTGCCTTCTAGT<br>TGCCAGCCATCTGTTGTTTGCCCCTCCCCCGTGCCTTCCT<br>TGACCCTGGAAGGTGCCACTCCCACTGTCCTTTCCTAATA<br>AAATGAGGAAATTGCATCGCATTGTCTGAGTAGGTGTCAT<br>TCTATTCTGGGGGGTGGGGTGGGGCAGGACAGCAAGGGGG<br>AGGATTGGGAAGACAATAGCAGGCATGCTGGGGACTCGAG<br>TTAAGGGCAGCCAGAAGTCAGATGCTCAAGGGGCTTCATG<br>ATGTCCCCATAATTTTTGGCAGAGGGAAAAAGATCGGATC<br>CTCAGGCGTAGTTCACCCCGTCCTCGAGGCCGCCCGGGTC<br>GACTAAAAAACCTCCCACACCTCCCCCTGAACCTGAAACA<br>TAAAATGAATGCAATTGTTGTTGTTAAACTGGCCTGCCCG<br>AGACCAAACGTGCGGAACGTAGTTAAGTGTTAGAGGTAGG<br>ATTTGAAGCCTGTCGATCATTCTGATTCTCCTTTTCTCTA<br>CGTCTGCTTCCTGTCAATGGGCATCCTCACTGTCAAATGC<br>AGATGGTACAGCAGGGCTTGGTCTCAGCCAGGCAGGCCTC<br>TCCCCAGTCTCCATGGCTCAGCTGTCCAGCAGTTTCATCC<br>CTAGACCATCCCAAACATGGTTGAGAAGCTCTGAGGGGAG<br>GACCCAGCACTGCCCGGCCCTGAAGATAATCAGCAGTCC<br>TGCTCAGCATATCAATCCAAGCCCACTCTAGACAGAGATG<br>CCGGTGCCCAGTTTTCTATTTTTAACTGGTGTGAACTGAA<br>GGAAAAGCACAGCATTAGAAGTCCAAGCAGGGATAAAAGC<br>AGTCTGGGCTTTCACATGACAGCATCTGGGGCTGCGGCAG<br>AGGGTCGGGTCCGAAGCGCTGCCTTATCAGCGTCCCCAGC<br>CCTGGGAGGTGACAGCTGGCTGGCTTGTGTCAGCCCCTCG<br>GGCACTCACGTATCTCCGTCCGACGGGTTTAAAATAGCAA<br>AACTCTGAGGCCACACAATAGCTTGGGCTTATATGGGCTC<br>CTGTGGGGAAGGGGAGCACGGAGGGGGCCGGGGCCGCT<br>GCTGCCAAAATAGCAGCTCACAAGTGTTGCATTCCTCTCT<br>GGGCGCCGGGCACATTCCTGCTGGCTCTGCCCGCCCCGGG<br>GTGGGCGCCGGGGGGACCTTAAAGCCTCTGCCCCCCAAGG<br>AGCCCTTCCCAGACAGCCGCCGGCACCCACCGCTCCGTGG<br>GACGATCCCCGAAGCTCTAGAGCTTTATTGCGGTAGTTTA<br>TCACAGTTAAATTGCTAACGCAGTCAGTGCTTCTGACACA<br>ACAGTCTCGAACTTAAGCTGCAGAAGTTGGTCGTGAGGCA<br>CTGGGCAGGTAAGTATCAAGGTTACAAGACAGGTTTAAGG<br>AGACCAATAGAAACTGGGCTTGTCGAGACAGAGAAGACTC<br>TTGCGTTTCTGATAGGCACCTATTGGTCTTACTGACATCC<br>ACTTTGCCTTTCTCTCCACAGGTGTCCACTCCCAGTTCAA<br>TTACAGCTCTTAAGGCTAGAGTACTTAATACGACTCACTA<br>TAGGCTAGCCGCCACCATGGCCGAGAAGGCCGGATCTACC<br>TTCAGCCACCTGCTGGTCCCTATTCTGCTGCTGATCGGCT<br>GGATCGTGGGCTGCATCATCATGATCTACGTGGTGTTCAG<br>CTGACGGCCGCGCGGATCCAGACATGATAAGATACATTGA<br>TGAGTTTGGACAAACCACAACTAGAATGCAGTGAAAAAAA<br>TGCTTTATTTGTGAAATTTGTGATGCTATTGCTTTATTTG<br>TAACCATTATAAGCTGCAATAAACAAGTGAATTCCCGATT<br>AGGATCTTCCTAGAGCATGGCTACGTAGATAAGTAGCATG<br>GCGGGTTAATCATTAACTACAAGGAACCCCTAGTGATGGA<br>GTTGGCCACTCCCTCTGCGCGCTCGCTCGCTCACTGAG<br>GCCGGGCGACCAAAGGTCGCCCGACGCCCGGGCTTTGCCC<br>GGGCGGCCTCAGTGAGCGAGCGAGCGCGCAG<br>(SEQ ID NO: 74) |
| pHZ63 (human DWORF version of pHZ34) | CTGCGCGCTCGCTCGCTCACTGAGGCCGCCCGGGCAAAGC<br>CCGGGCGTCGGGCGACCTTTGGTCGCCCGGCCTCAGTGAG<br>CGAGCGAGCGCGCAGAGAGGGAGTGGCCAACTCCATCACT<br>AGGGGTTCCTTGTAGTTAATGATTAACCCGCCATGCTACT<br>TATCTACGTAGCCATGCTCTAGGAAGATCGGAATTCTCCC<br>CAGCATGCCTGCTATTGTCTTCCCAATCCTCCCCCTTGCT<br>GTCCTGCCCCACCCCACCCCCCAGAATAGAATGACACCTA<br>CTCAGACAATGCGATGCAATTTCCTCATTTTATTAGGAAA<br>GGACAGTGGGAGTGGCACCTTCCAGGGTCAAGGAAGGCAC<br>GGGGGAGGGGCAAACAACAGATGGCTGGCAACTAGAAGGC<br>ACAGTCGAGGCAGATCTCGAAGACGCGGAAGAGGCCGCAG<br>AGCCGGCAGCAGGCCGCGGGAAGGAAGGTCCGCTGGATTG<br>AGGGCCGAAGGGACGTAGCAGAAGGACGTCCCGCGCAGAA<br>TCCAGGTGGCAACACAGGCGAGCAGCCAAGGAAAGGACGA<br>TGATTTCCCCGACAACACCACGGAATTGTCAGTGCCCAAC<br>AGCCGAGCCCTGTCCAGCAGCGGGCAAGGCAGGCGGCGA<br>TGAGTTCCGCCGTGGCAATAGGGAGGGGAAAGCGAAAGT<br>CCCGGAAAGGAGCTGACAGGTGGTGGCAATGCCCCAACCA<br>GTGGGGGTTGCGTCAGCAAACACAGTGCACACCACGCCAC |

TABLE 1-continued

Illustrative Expression Cassette Sequences

| Expression Cassette | Sequence |
|---|---|
| | GTTGCCTGACAACGGGCCACAACTCCTCATAAAGAGACAG |
| | CAACCAGGATTTATACAAGGAGGAGAAAATGAAAGCCATA |
| | CGGGAAGCAATAGCATGATACAAAGGCATTAAAGCAGCGT |
| | ATCCACATAGCGTAAAAGGAGCAACATAGTTAAGAATACC |
| | AGTCAATCTTTCACAAATTTTGTAATCCAGAGGTTGATTG |
| | GATCCAAAGCTTCTAAGAGAAGACAACATAAATCATTATG |
| | ATGCAGCCCACAATCCAGCCAATCAGGAGAAGAATAGGAA |
| | CCAGAAGGTGTGAAAATGTAGACCCCGCTTTTTCAGCCAT |
| | GGTGGCGGGCGGCCGCTAGATCTGTATCGATTGGATCGGC |
| | CGCGGGTACAATTCCGCAGCTTTTAGAGCAGAAGTAACAC |
| | TTCCGTACAGGCCTGCAGAAAAGACCCAGGAAAGGAACAG |
| | TCTGTTAGTCTGTCAGCATGCATAAGAGCCAAAGGGGTGT |
| | GCCTATAGAGTCTATAGGCGGTACTTACCAGTTATGGAGG |
| | CGTCTGCTCAGTCTCAGCGGGGACTGGGTGAGGCAGAGGA |
| | TGGAGAGGGCTTTAAGCAGGCATGTGGGCTGGGGCCTGGT |
| | GAGCCAGCCCTGCGGAGGGAGGAATGTGCGACAGGGGACG |
| | GGTGGGGCAGGGGGATGGCGGTGGGGGTGGGGGGTGTTGG |
| | CTGCTATTTTGGCAGGTGCCAGGGACAAGGCTACAGGAAC |
| | ATGTACCCCACGCCATATAAGCCCATGTGGTCCTCCAGCT |
| | GCTCAGATAAGCTATTTAAAACCAGAGCAGATATGCAGGG |
| | AACAGTCATGCAACATAAACCAGCTGTCCCTCTTGAGAAT |
| | CCTGATAAAGCAGAGGCCAGCAACCCAGGCCTGGGAGGGC |
| | CAGCTGGGAGCAGGGTTGGGGGGCAGAAGGCAACCTCCAA |
| | GACACTCCATAAGTCTCAGCACCAGAATCTTGGAAGGCAG |
| | AGGGCAAGAGTTATGTGCTGCTCCACTTGAACTGATGCTG |
| | GGGGTAAAGACATCTTCCAGGCTACTGGCTCCTAATGGAC |
| | TGAGCAGCCTTAGGCAGGTTGCCGGCTCTGCCAGCCCCAG |
| | TGAGGACATCTGCAAGGTGGGTCTTCTCCATGACGACAGC |
| | AGCCCTGAGGTTTGCCCATGAAAGGTCTGCTGCCCTCGCC |
| | CCTCTGGCTCCAGGGCCTTTTTTTAGTCCTTGGGCACATT |
| | CCTCCTCCCCAAAGGGCCGATGGGCAGATAGAGGAGAGAC |
| | AGGACCGTCTCACACCACCTCCCCTACCCACATGGCCCTT |
| | ACCTTAGTTATTTTTAATCTGAAGGCTCGAGTTAAGGGCA |
| | GCCAGAAGTCAGATGCTCAAGGGGCTTCATGATGTCCCCA |
| | TAATTTTTGGCAGAGGGAAAAAGATCGGATCCTCAGGCGT |
| | AGTTCACCCCGTCCTCGAGGCCGCCCGGGTCGACTAAAAA |
| | ACCTCCCACACCTCCCCCTGAACCTGAAACATAAAATGAA |
| | TGCAATTGTTGTTGTTAAACTGGCCTGCCCGAGACCAAAC |
| | GTGCGGAACGTAGTTAAGTGTTAGAGGTAGGATTTGAAGC |
| | CTGTCGATCATTCTGATTCTCCTTTTCTCTACGTCTGCTT |
| | CCTGTCAATGGGCATCCTCACTGTCAAATGCAGATGGTAC |
| | AGCAGGGCTTGGTCTCAGCCAGGCAGGCCTCTCCCCAGTC |
| | TCCATGGCTCAGCTGTCCAGCAGTTTCATCCCTAGACCAT |
| | CCCAAACATGGTTGAGAAGCTCTGAGGGGAGGACCCAGCA |
| | CTGCCCGGCCCCTGAAGATAATCAGCAGTCCTGCTCAGCA |
| | TATCAATCCAAGCCCACTCTAGACAGAGATGCCGGTGCCC |
| | AGTTTTCTATTTTTAACTGGTGTGAACTGAAGGAAAAGCA |
| | CAGCATTAGAAGTCCAAGCAGGGATAAAAGCAGTCTGGGC |
| | TTTCACATGACAGCATCTGGGGCTGCGGCAGAGGGTCGGG |
| | TCCGAAGCGCTGCCTTATCAGCGTCCCCAGCCCTGGGAGG |
| | TGACAGCTGGCTGGCTTGTGTCAGCCCCTCGGGCACTCAC |
| | GTATCTCCGTCCGACGGGTTTAAAATAGCAAAACTCTGAG |
| | GCCACACAATAGCTTGGGCTTATATGGGCTCCTGTGGGGG |
| | AAGGGGGAGCACGGAGGGGGCCGGGGCCGCTGCTGCCAAA |
| | ATAGCAGCTCACAAGTGTTGCATTCCTCTCTGGGCGCCGG |
| | GCACATTCCTGCTGGCTCTGCCCGCCCCGGGGTGGGCGCC |
| | GGGGGGACCTTAAAGCCTCTGCCCCCCAAGGAGCCCTTCC |
| | CAGACAGCCGCCGGCACCCACCGCTCCGTGGGACGATCCC |
| | CGAAGCTCTAGAGCTTTATTGCGGTAGTTTATCACAGTTA |
| | AATTGCTAACGCAGTCAGTGCTTCTGACACAACAGTCTCG |
| | AACTTAAGCTGCAGAAGTTGGTCGTGAGGCACTGGGCAGG |
| | TAAGTATCAAGGTTACAAGACAGGTTTAAGGAGACCAATA |
| | GAAACTGGGCTTGTCGAGACAGAGAAGACTCTTGCGTTTC |
| | TGATAGGCACCTATTGGTCTTACTGACATCCACTTTGCCT |
| | TTCTCTCCACAGGTGTCCACTCCCAGTTCAATTACAGCTC |
| | TTAAGGCTAGAGTACTTAATACGACTCACTATAGGCTAGC |
| | CGCCACCATGGCCGAGAAGGCCGGATCTACCTTCAGCCAC |
| | CTGCTGGTCCCTATTCTGCTGCTGATCGGCTGGATCGTGG |
| | GCTGCATCATCATGATCTACGTGGTGTTCAGCTGACGGCC |
| | GCGCGGATCCAGACATGATAAGATACATTGATGAGTTTGG |
| | ACAAACCACAACTAGAATGCAGTGAAAAAAATGCTTTATT |
| | TGTGAAATTTGTGATGCTATTGCTTTATTTGTAACCATTA |
| | TAAGCTGCAATAAACAAGTGAATTCCCGATTAGGATCTTC |
| | CTAGAGCATGGCTACGTAGATAAGTAGCATGGCGGGTTAA |

TABLE 1-continued

Illustrative Expression Cassette Sequences

| Expression Cassette | Sequence |
|---|---|
| | TCATTAACTACAAGGAACCCCTAGTGATGGAGTTGGCCAC<br>TCCCTCTCTGCGCGCTCGCTCGCTCACTGAGGCCGGGCGA<br>CCAAAGGTCGCCCGACGCCCGGGCTTTGCCCGGGCGGCCT<br>CAGTGAGCGAGCGAGCGCGCAG (SEQ ID NO: 75) |

Vectors

In some aspects, the disclosure provides vectors comprising the expression cassettes provided herein. The vector can be any viral vector or any non-viral vector known in the art or described herein.

In some embodiments, the vector is a viral vector. In some embodiments the viral vector is an adeno-associated virus vector (AAV), an adenoviral vector (AV), a lentiviral vector (LV), a retroviral vector (RV), a herpes simplex virus vector (HSV), or a poxvirus vector.

In some embodiments, provided herein is an AAV comprising any expression cassette described herein. In some embodiments, provided herein is an AV comprising any expression cassette described herein. In some embodiments, provided herein is an LV comprising any expression cassette described herein. In some embodiments, provided herein is an RV comprising any expression cassette described herein. In some embodiments, provided herein is an HSV comprising any expression cassette described herein. In some embodiments, provided herein is a poxvirus-based vector comprising any expression cassette described herein.

In some embodiments, the vector is a non-viral vector. In some embodiments, the non-viral vector is a naked DNA (e.g., a DNA plasmid). In some embodiments, the non-viral vector is a plasmid. In some embodiments, the non-viral vector is a liposome or lipid vector comprising plasmid DNA and a lipid solution.

For example, viral and non-viral vectors and delivery systems are described in Sung & Kim 2019, Biomaterials Research 23:8; Mali, 2013, Indian Journal of Human Genetics, 19(1):3-8; Hardee et al., 2017, Genes 8:65; Bulcha et al., 2020, Signal Transduction and Targeted Therapy; Ghosh et al., 2020, Applied Biosafety: Journal of ABSA International 25(1):7-18, the disclosures of each of which are hereby incorporated by reference herein in their entireties.

In some embodiments, the vectors are recombinant vectors.

In some embodiments, the vectors described herein comprise an expression cassette comprising a polynucleotide encoding any gene product described herein. In some embodiments, the expression cassette comprises a sequence that shares at least 75%, 80%, 90%, 95%, 96%, 97%, 98%, 99%, or 100% identity to SEQ ID NOS: 201, 203, 205, 207, 209, 211, 213, 215, 217, 219, 221, 223, 225, In some embodiments, the vectors described herein comprise an expression cassette comprises a polynucleotide encoding DWORF. In some embodiments, the expression cassette comprises a polynucleotide sequence that shares at least 75%, 80%, 90%, 95%, 96%, 97%, 98%, 99%, or 100% identity to SEQ ID NOs: 20-24 and SEQ ID NOs: 45-75.

In some aspects of the disclosure, a vector is used to deliver the expression cassettes described herein to cardiac cells of a subject, e.g., to treat cardiomyopathy. In some embodiments, the disclosure provides a viral vector comprising an expression cassette comprising a polynucleotide encoding a gene product (such as any gene product described herein, e.g., a DWORF polypeptide) operatively linked to a promoter and a pharmaceutically acceptable carrier. In some embodiments, the disclosure provides a virion comprising a capsid and an expression cassette comprising a polynucleotide encoding a gene product (such as any gene product described herein, e.g., a DWORF polypeptide) operatively linked to a promoter and a pharmaceutically acceptable carrier. In some embodiments, the disclosure provides a plasmid comprising an expression cassette comprising a polynucleotide encoding a gene product (such as any gene product described herein, e.g., a DWORF polypeptide) operatively linked to a promoter and a pharmaceutically acceptable carrier.

In some embodiments, the viral vectors described herein are replication incompetent, in that it cannot independently further replicate and package its genome. For example, when a cardiac cell is targeted with a virion, the transgene is expressed in the targeted cardiac cell, however, due to the fact that the targeted cardiac cell lacks packaging and accessory function genes, the virion is not able to replicate. In some embodiments, the viral vectors described herein are replication-competent.

In some embodiments, the vectors described herein are capable of being delivered to both dividing and non-dividing cells. In some embodiments, the vectors described herein are capable of being delivered to non-dividing cells. In some embodiments, the vectors described herein are capable of being delivered to dividing cells.

In some embodiments, the vectors comprising the expression cassettes described herein lead to cardiac cell-specific expression of a transgene. In some embodiments, the vectors comprising the expression cassettes described herein lead to cardiomyocyte-specific expression of a transgene. In some embodiments, the vectors comprising the expression cassettes described herein allow high expression of a transgene in a cardiac cell (e.g., a cardiomyocyte) and low or no expression in other cells (e.g., low or no expression in liver cells, low or no expression in muscle cells except for muscle cells of the heart, low or no expression in cardiac fibroblasts). In some embodiments, the vectors comprising the expression cassettes described herein allow high expression of a transgene in heart tissue of a subject (e.g., in human heart). In some embodiments, the vectors comprising the expression cassettes described herein allow no or low expression of a transgene in tissues of a subject other than the heart (e.g., in liver or in muscles except those of the heart). "High" and "low" can be relative to each other, for example, the expression of a transgene in cardiac cells (e.g., cardiomyocytes) and/or heart tissue can be at least 2 fold, 5 fold, 10 fold, 15 fold, 20 fold, 50 fold, 100 fold, 150 fold, or 200 fold higher than its expression in other cells and tissues (e.g., liver, muscle except for the heart).

Recombinant AAV Virions

In some aspects, the disclosure provides recombinant AAV (rAAV) virions comprising the expression cassettes provided herein. In some embodiments, the rAAV virion comprises a capsid protein and an expression cassette. In some embodiments, the expression cassette comprises a polynucleotide encoding any gene product described herein.

In some embodiments, the expression cassette comprises a polynucleotide encoding DWORF. In some embodiments, the expression cassette comprises a polynucleotide sequence that shares at least 75%, 80%, 90%, 95%, 96%, 97%, 98%, 99%, or 100% identity to SEQ ID NOs: 20-24 and SEQ ID NOs: 45-63. In some embodiments, the expression cassette comprises a polynucleotide sequence that shares at least 75%, 80%, 90%, 95%, 96%, 97%, 98%, 99%, or 100% identity to SEQ ID NO: 61. In some embodiments, the expression cassette comprises SEQ ID NO: 61. In some embodiments, the expression cassette comprises a polynucleotide sequence that shares at least 75%, 80%, 90%, 95%, 96%, 97%, 98%, 99%, or 100% identity to SEQ ID NO: 62. In some embodiments, the expression cassette comprises SEQ ID NO: 62. In some embodiments, the expression cassette comprises a polynucleotide sequence that shares at least 75%, 80%, 90%, 95%, 96%, 97%, 98%, 99%, or 100% identity to SEQ ID NO: 63. In some embodiments, the expression cassette comprises SEQ ID NO: 63.

In some aspects of the disclosure, an rAAV virion is used to deliver the expression cassettes described herein to cardiac cells of a subject, e.g., to treat cardiomyopathy. Accordingly, the disclosure provides an rAAV virion, the rAAV virion comprising an AAV capsid and an expression cassette comprising a polynucleotide encoding a DWORF polypeptide operatively linked to a promoter and a pharmaceutically acceptable carrier.

The rAAV virions of the disclosure comprise a capsid protein. Capsid proteins are structural proteins that make up the assembled icosahedral packaging of the rAAV virion that contains the expression cassette. Capsid proteins are classified by the serotype. Wild type capsid serotypes in rAAV virions can be, for example, AAV1, AAV2, AAV3, AAV4, AAV5, AAV6, AAV7, AAV8, AAV9, AAV10, AAV11, or AAV12 (Naso et al. *BioDrugs* 31:317-334 (2017)). Engineered capsid types include chimeric capsids and mosaic capsids (Choi et al. *Curr Gene Ther.* 5: 299-310 (2005)). Capsids are selected for rAAV virions based on their ability to transduce specific tissue or cell types (Liu et al. *Curr Pharm Des.* 21:3248-56 (2015)).

Any capsid protein that can facilitate rAAV virion transduction into cardiac cells for delivery of a transgene, as described herein, can be used. Capsid proteins used in rAAV virions for transgene delivery to cardiac cells that result in high expression can be, for example, AAV4, AAV6, AAV7, AAV8, and AAV9 (Zincarelli et al. *Mol. Ther.* 16:P1073-1080 (2008)). Artificial capsids, such as chimeric capsids generated through combinatorial libraries, can also be used for transgene delivery to cardiac cells that results in high expression (see U.S. 63/012,703, the contents of which are herein incorporated by reference). Other capsid proteins with various features can also be used in the rAAV virions of the disclosure. AAV vectors and capsids are provided in U.S. Pat. Nos. 10,011,640B2; 7,892,809B2, 8,632,764B2, 8,889,641B2, 9,475,845B2, 10,889,833B2, 10,480,011B2, and 10,894,949B2, the contents of which are herein incorporated by reference; and Int'l Pat. Pub. Nos. WO2020198737A1, WO2019028306A2, WO2016054554A1, WO2018152333A1, WO2017106236A1, WO2008124724A1, WO2017212019A1, WO2020117898A1, WO2017192750A1, WO2020191300A1, and WO2017100671A1, the contents of which are herein incorporated by reference.

In some embodiments, the rAAV virions of the disclosure comprise an engineered capsid protein. Engineered capsid proteins can be derived from a parental, e.g., wild type, capsid and include, for example, variant polypeptide sequence with respect to a parental capsid sequence at one or more sites. For example, variant sites of the parental capsid can occur at the VR-IV site, VR-V site, VR-VII site and/or VR-VIII site (see, e.g., Buning and Srivastava. *Mol Ther Methods Clin Dev.* 12:248-265 (2019)).

In some embodiments, the capsid protein is an AAV5/AAV9 chimeric capsid protein. In some embodiments, the chimeric capsid protein comprises at least 1, 2, 3, 4, 5 or more polypeptide segments that are derived from AAV5 capsid protein (SEQ ID NO. 144). In some embodiments, the chimeric capsid protein comprises at least 1, 2, 3, 4, 5 or more polypeptide segments that are derived from AAV9 capsid protein (SEQ ID NO: 143). In some embodiments, at least one polypeptide segment is derived from the AAV5 capsid protein and at least one polypeptide segment is derived from the AAV9 capsid protein.

In some embodiments, the capsid protein is a combinatory capsid proteins. As used herein, "combinatory capsid protein" refers to a AAV5/AAV9 chimeric capsid protein, which further comprises amino acid variations with respect to the chimeric parental sequence at one or more sites. In some embodiments, the one or more sites of the chimeric parental sequence are selected from those equivalent to the VR-IV site, the VR-V site, the VR-VII site and the VR-VIII site of the AAV9 capsid protein.

In some embodiments, the rAAV virions comprise an engineered capsid protein selected from Table 7.

TABLE 7

| Engineered Capsid Proteins | |
| --- | --- |
| Engineered Capsid | SEQ ID NO: |
| CR9-01 | 145 |
| CR9-07 | 146 |
| CR9-08 | 147 |
| CR9-09 | 148 |
| CR9-10 | 149 |
| CR9-11 | 150 |
| CR9-13 | 151 |
| CR9-14 | 152 |
| CR9-15 | 153 |
| CR9-16 | 154 |
| CR9-17 | 155 |
| CR9-20 | 156 |
| CR9-21 | 157 |
| CR9-22 | 158 |
| ZC23 | 159 |
| ZC24 | 160 |
| ZC25 | 161 |
| ZC26 | 162 |
| ZC27 | 163 |
| ZC28 | 164 |
| ZC29 | 165 |
| ZC30 | 166 |
| ZC31 | 167 |
| ZC32 | 168 |
| ZC33 | 169 |
| ZC34 | 170 |
| ZC35 | 171 |
| ZC40 | 172 |
| ZC41 | 173 |
| ZC42 | 174 |
| ZC43 | 175 |
| ZC44 | 176 |
| ZC45 | 177 |
| ZC46 | 178 |
| ZC47 | 179 |
| ZC48 | 180 |

TABLE 7-continued

Engineered Capsid Proteins

| Engineered Capsid | SEQ ID NO: |
|---|---|
| ZC49 | 181 |
| ZC50 | 182 |
| TN47-07 | 183 |
| TN47-10 | 184 |
| TN47-13 | 185 |
| TN47-14 | 186 |
| TN47-17 | 187 |
| TN47-22 | 188 |
| TN40-07 | 189 |
| TN40-10 | 190 |
| TN40-13 | 191 |
| TN40-14 | 192 |
| TN40-17 | 193 |
| TN40-22 | 194 |
| TN44-07 | 195 |
| TN44-10 | 196 |
| TN44-13 | 197 |
| TN44-14 | 198 |
| TN44-17 | 199 |
| TN44-22 | 200 |

In some embodiments, the rAAV is replication defective, in that the rAAV virion cannot independently further replicate and package its genome. For example, when a cardiac cell is targeted with rAAV virions, the transgene is expressed in the targeted cardiac cell, however, due to the fact that the targeted cardiac cell lacks AAV rep and cap genes and accessory function genes, the rAAV is not able to replicate.

In some embodiments, rAAV virions of the present disclosure encapsulating the expression cassettes as described herein, can be produced using helper-free production. rAAVs are replication-deficient viruses and normally require components from a live helper virus, such as adenovirus, in a host cell for packaging of infectious rAAV virions. rAAV helper-free production systems allow the production of infectious rAAV virions without the use of a live helper virus. In the helper-free system, a host packaging cell line is co-transfected with three plasmids. A first plasmid may contain adenovirus gene products (e.g., E2A, E4, and VA RNA genes) needed for the packaging of rAAV virions. A second plasmid may contain required AAV genes (e.g., REP and CAP genes). A third plasmid contains the polynucleotide sequence encoding the transgene of interest and a promoter flanked by ITRs. A host packaging cell line can be, for example, AAV-293 host cells. Suitable host cells contain additional components required for packaging infectious rAAV virions that are not supplied by the plasmids. In some embodiments, the CAP genes can encode, for example, AAV capsid proteins as described herein.

In some embodiments, the CAP genes can encode, for example, AAV capsid proteins as described herein. In some embodiments, the promoter is a promoter sequence as described herein. In some embodiments, the promoter sequence is a cTnT promoter sequence. In some embodiments, the polypeptide of interest is a DWORF polypeptide.

The expression cassettes, enhancers and/or promoters described herein with respect to AAV virions need not be limited to their use in AAV virions and can be incorporated in essentially any other construct where expression of a polynucleotide encoding a gene product is desired.

rAAV virions can deliver transgenes to cells in a subject that are, in turn, expressed in the cell. A transgene delivered by an rAAV virion may be incorporated into the genome of the targeted cell, allowing for potential long-term expression of the transgene product. Compared to other viral transgene delivery systems, such as adenoviruses, rAAV virions have the advantage of low immunogenicity. rAAV virions can be used to transduce and deliver transgenes to many cells types, including eye, blood, liver, heart, joint tissue, muscle, brain kidney or lung cells (U.S. Pat. Nos. 10,308,957; 9,803,218). rAAV virions can contain genomes up to about 5.2 kilobases (kb), limiting the size of the polynucleotide that can be integrated into the host cell to about 4.4 kb (Choi et al. *Mol Brain.* 7:1 (2014)).

Methods of Use

Methods of Increasing Polypeptide Expression

The disclosure provides methods of increasing polypeptide expression in a cell comprising contacting the cell with any vector or virion (e.g., rAAV virion) described herein. In some embodiments, the cell is a cardiac cell. In some embodiments, the cell is a cardiomyocyte. In some embodiments, the contacting is in vitro. In some embodiments, the contacting is in vivo. In some embodiments, the polypeptide is any polypeptide for use in treating or preventing a heart disease. In some embodiments, the polypeptide is any polypeptide described herein. In some embodiments, the polypeptide is encoded by any transgene described herein.

The disclosure provides methods of increasing polypeptide expression in a tissue comprising contacting the tissue with any vector or virion (e.g., rAAV virion) described herein. In some embodiments, the tissue is cardiac tissue. In some embodiments, the contacting is in vitro. In some embodiments, the contacting is in vivo.

The disclosure provides methods of increasing polypeptide expression in an organ comprising contacting the organ with any vector or virion (e.g., rAAV virion) described herein. In some embodiments, the organ is a heart. In some embodiments, the heart is diseased or at risk of disease. In some embodiments, the heart has borderline or reduced ejection fraction. In some embodiments, the heart has a normal ejection fraction. In some embodiments, the heart comprises a genetic mutation associated with a heart disease. In some embodiments, the genetic mutation is a PLN mutation. In some embodiments, the heart has low or undetectable polypeptide expression compared to a healthy heart. In some embodiments, the contacting is in vitro. In some embodiments, the contacting is in vivo.

The disclosure provides methods of increasing polypeptide expression in a subject comprising administering to the subject any vector or virion (e.g., rAAV virion) described herein. In some embodiments the subject is an animal. An animal can be, without limitation, a mouse, rat, dog, or non-human primate. In some embodiments, the subject is a human. In some embodiments, the increased polypeptide expression is in the heart of the subject. In some embodiments, the subject has a heart disease or is at risk of a heart disease. In some embodiments, the subject has borderline or reduced ejection fraction. In some embodiments, the subject has a normal ejection fraction. In some embodiments, the subject has a genetic mutation associated with a heart disease. In some embodiments, the genetic mutation is a PLN mutation. In some embodiments, the subject has low or undetectable level of DWORF expression compared to a healthy subject.

In some embodiments, the polypeptide is expressed in a cell, tissue, organ, or subject at a desired level of expression. A "desired level of expression" can be selected such that the level of expression is relative to the polypeptide expression in a healthy or diseased cell, tissue, organ, or subject. For example, an increased level in polypeptide expression relative to a diseased cardiac cell, cardiac tissue, heart, or subject with a heart disease or disorder can be a desired level of expression. The desired level of expression can be expressed relative to the difference in expression achieved between different vector or virions (e.g., rAAV virions) containing different expression cassettes. For example, a vector or virion (e.g., rAAV virion) comprising an expression cassette comprising a promoter and an enhancer may achieve a desired level of expression compared to a vector or virion (e.g., rAAV virion) comprising only a promoter.

The polypeptide expression level achieved by any vector or virion (e.g., rAAV virion) comprising an expression cassette can be described as a "fold" change (i.e., increase or decrease) compared to basal polypeptide expression. The polypeptide expression level achieved by a vector or virion (e.g., rAAV virion) comprising an expression cassette can be described as a "fold change" compared to polypeptide expression achieved by an expression cassette comprising a single promoter, no enhancers, and a sequence encoding the polypeptide. Fold change is a relative quantity, such that the levels of expression between the expression level achieved by an expression cassette and reference expression level are expressed as a ratio. It is understood that when describing fold change of polypeptide expression, "about" refers to ±0.5-fold. Polypeptide expression levels can be categorized as "low expression", "medium expression", or "high expression." "Low expression" is meant to include expression levels between about 1.5-fold and 20-fold increase in polypeptide expression. "Medium expression" is meant to include expression levels between about 20-fold increase and about 60-fold increase in polypeptide expression. "High expression" is meant to include expression levels between about 60-fold and 140-fold increase in polypeptide expression.

In some embodiments, the polypeptide expression level is between about a 1.5-fold and 150-fold increase. In some embodiments, the polypeptide expression level is increased at least about 1.5-fold, about 3.5-fold, about 5.5-fold, about 7.5-fold, about 9.5-fold, about 11.5-fold, about 13.5-fold, about 15.5-fold, about 17.5-fold, about 19.5-fold, about 21.5-fold, about 23.5-fold, about 25.5-fold, about 27.5-fold, about 29.5-fold, about 31.5-fold, about 33.5-fold, about 35.5-fold, about 37.5-fold, about 39.5-fold, about 41.5-fold, about 43.5-fold, about 45.5-fold, about 47.5-fold, about 49.5-fold, about 51.5-fold, about 53.5-fold, about 55.5-fold, about 57.5-fold, about 59.5-fold, about 61.5-fold, about 63.5-fold, about 65.5-fold, about 67.5-fold, about 69.5-fold, about 71.5-fold, about 73.5-fold, about 75.5-fold, about 77.5-fold, about 79.5-fold, about 81.5-fold, about 83.5-fold, about 85.5-fold, about 87.5-fold, about 89.5-fold, about 91.5-fold, about 93.5-fold, about 95.5-fold, about 97.5-fold, about 99.5-fold, about 101.5-fold, about 103.5-fold, about 105.5-fold, about 107.5-fold, about 109.5-fold, about 111.5-fold, about 113.5-fold, about 115.5-fold, about 117.5-fold, about 119.5-fold, about 121.5-fold, about 123.5-fold, about 125.5-fold, about 127.5-fold, about 129.5-fold, about 131.5-fold, about 133.5-fold, about 135.5-fold, about 137.5-fold, about 139.5-fold, about 141.5-fold, about 143.5-fold, about 145.5-fold, about 147.5-fold, or about 149.5-fold.

In some embodiments, the polypeptide expression level is increased at least or more than about 5-fold. In some embodiments, the polypeptide expression level is increased at least or more than about 10-fold. In some embodiments, the polypeptide expression level is increased at least or more than about 15-fold. In some embodiments, the polypeptide expression level is increased at least or more than about 25-fold. In some embodiments, the polypeptide expression level is increased at least or more than about 35-fold. In some embodiments, the polypeptide expression level is increased at least or more than about 50-fold. In some embodiments, the polypeptide expression level is increased at least or more than about 60-fold. In some embodiments, the polypeptide expression level is increased at least or more than about 75-fold. In some embodiments, the polypeptide expression level is increased at least or more than about 85-fold. In some embodiments, the polypeptide expression level is increased at least or more than about 100-fold. In some embodiments, the polypeptide expression level is increased at least or more than about 110-fold. In some embodiments, the polypeptide expression level is increased at least or more than about 125-fold.

In some embodiments, the fold increase is relative to an expression cassette comprising a single promoter, no enhancers, and a sequence encoding the polypeptide. In some embodiments, the fold increase is relative to a healthy cell, tissue, organ, or subject. In some embodiments, the fold increase is relative to a diseased cell, tissue, organ, or subject.

Methods of Increasing DWORF Expression

The disclosure provides methods of increasing DWORF expression in a cell comprising contacting the cell with the rAAV virions described herein. In some embodiments, the cell is a cardiac cell. In some embodiments, the cell is a cardiomyocyte. In some embodiments, the contacting is in vitro. In some embodiments, the contacting is in vivo.

The disclosure provides methods of increasing DWORF expression in a tissue comprising contacting the tissue with the rAAV virions described herein. In some embodiments, the tissue is cardiac tissue. In some embodiments, the contacting is in vitro. In some embodiments, the contacting is in vivo.

The disclosure provides methods of increasing DWORF expression in an organ comprising contacting the organ with the rAAV virions described herein. In some embodiments, the organ is a heart. In some embodiments, the heart is diseased or at risk of disease. In some embodiments, the heart has borderline or reduced ejection fraction. In some embodiments, the heart has a normal ejection fraction. In some embodiments, the heart comprises a genetic mutation associated with a heart disease. In some embodiments, the genetic mutation is a PLN mutation. In some embodiments, the heart has low or undetectable DWORF expression compared to a healthy heart. In some embodiments, the contacting is in vitro. In some embodiments, the contacting is in vivo.

The disclosure provides methods of increasing DWORF expression in a subject comprising administering to the subject the rAAV virions described herein. In some embodiments the subject is an animal. An animal can be, without limitation, a mouse, rat, dog, or non-human primate. In some embodiments, the subject is a human. In some embodiments, the increased DWORF expression is in the heart of the subject. In some embodiments, the subject has a heart disease or is at risk of a heart disease. In some embodiments, the subject has borderline or reduced ejection fraction. In some embodiments, the subject has a normal ejection fraction. In some embodiments, the subject has a genetic mutation associated with a heart disease. In some embodiments, the genetic mutation is a PLN mutation. In some embodiments, the subject has low or undetectable level of DWORF expression compared to a healthy subject.

In some embodiments, DWORF is expressed in a cell, tissue, organ, or subject at a desired level of expression. A "desired level of expression" can be selected such that the level of expression is relative to DWORF expression in a healthy or diseased cell, tissue, organ, or subject. For example, an increased level in DWORF expression relative to a diseased cardiac cell, cardiac tissue, heart, or subject with a heart disease or disorder can be a desired level of expression. The desired level of expression can be expressed relative to the difference in expression achieved between different rAAV virions containing different expression cassettes. For example, an rAAV virion comprising an expression cassette comprising a promoter and an enhancer may achieve a desired level of expression compared to an rAAV virion comprising only a promoter.

The DWORF expression level achieved by an rAAV virion comprising an expression cassette can be described as a "fold" change (i.e., increase or decrease) compared to basal DWORF expression. The DWORF expression level achieved by an rAAV virion comprising an expression cassette can be described as a "fold change" compared to DWORF expression achieved by an expression cassette comprising a single promoter, no enhancers, and a sequence encoding DWORF. Fold change is a relative quantity, such that the levels of expression between the expression level achieved by an expression cassette and reference expression level are expressed as a ratio. It is understood that when describing fold change of DWORF expression, "about" refers to ±0.5-fold. DWORF expression levels can be categorized as "low expression", "medium expression", or "high expression." "Low expression" is meant to include expression levels between about 1.5-fold and 20-fold increase in DWORF expression. "Medium expression" is meant to include expression levels between about 20-fold increase and about 60-fold increase in DWORF expression. "High expression" is meant to include expression levels between about 60-fold and 140-fold increase in DWORF expression.

In some embodiments, the DWORF expression level is between about a 1.5-fold and 150-fold increase. In some embodiments, the DWORF expression level is increased about 1.5-fold, about 3.5-fold, about 5.5-fold, about 7.5-fold, about 9.5-fold, about 11.5-fold, about 13.5-fold, about 15.5-fold, about 17.5-fold, about 19.5-fold, about 21.5-fold, about 23.5-fold, about 25.5-fold, about 27.5-fold, about 29.5-fold, about 31.5-fold, about 33.5-fold, about 35.5-fold, about 37.5-fold, about 39.5-fold, about 41.5-fold, about 43.5-fold, about 45.5-fold, about 47.5-fold, about 49.5-fold, about 51.5-fold, about 53.5-fold, about 55.5-fold, about 57.5-fold, about 59.5-fold, about 61.5-fold, about 63.5-fold, about 65.5-fold, about 67.5-fold, about 69.5-fold, about 71.5-fold, about 73.5-fold, about 75.5-fold, about 77.5-fold, about 79.5-fold, about 81.5-fold, about 83.5-fold, about 85.5-fold, about 87.5-fold, about 89.5-fold, about 91.5-fold, about 93.5-fold, about 95.5-fold, about 97.5-fold, about 99.5-fold, about 101.5-fold, about 103.5-fold, about 105.5-fold, about 107.5-fold, about 109.5-fold, about 111.5-fold, about 113.5-fold, about 115.5-fold, about 117.5-fold, about 119.5-fold, about 121.5-fold, about 123.5-fold, about 125.5-fold, about 127.5-fold, about 129.5-fold, about 131.5-fold, about 133.5-fold, about 135.5-fold, about 137.5-fold, about 139.5-fold, about 141.5-fold, about 143.5-fold, about 145.5-fold, about 147.5-fold, or about 149.5-fold.

In some embodiments, the DWORF expression level is increased at least or more than about 5-fold. In some embodiments, the DWORF expression level is increased at least or more than about 10-fold. In some embodiments, the DWORF expression level is increased at least or more than about 15-fold. In some embodiments, the DWORF expression level is increased at least or more than about 25-fold. In some embodiments, the DWORF expression level is increased at least or more than about 35-fold. In some embodiments, the DWORF expression level is increased at least or more than about 50-fold. In some embodiments, the DWORF expression level is increased at least or more than about 60-fold. In some embodiments, the DWORF expression level is increased at least or more than about 75-fold. In some embodiments, the DWORF expression level is increased at least or more than about 85-fold. In some embodiments, the DWORF expression level is increased at least or more than about 100-fold. In some embodiments, the DWORF expression level is increased at least or more than about 110-fold. In some embodiments, the DWORF expression level is increased at least or more than about 125-fold.

In some embodiments, the fold increase is relative to an expression cassette comprising a single promoter, no enhancers, and a sequence encoding DWORF. In some embodiments, the fold increase is relative to a healthy cell, tissue, organ, or subject. In some embodiments, the fold increase is relative to a diseased cell, tissue, organ, or subject.

Methods of Treatment

In an aspect, any vector comprising an expression cassette described herein may be used for treating disease, such as heart disease.

In an aspect, rAAV virions comprising an expression cassette described herein may be used for treating disease (Wang et al. *Nat Rev Drug Discov.* 18:358-378 (2019)). For treatment, rAAV virions have been used to deliver transgenes encoding polypeptides such as microdystrophin (Chamberlain et al. *Mol Ther.* 25:1125-1131 (2017)), glial cell line-derived neurotrophic factor (McFarthing et al. *J Parkinsons Dis.* 9:251-264 (2019)), and Factor IX (Nathwani et al. *N Engl J Med.* 371:1994-2004 (2014)).

A variety of strategies for treating heart failure using rAAV-based delivery of a transgene have been pursued in vivo. In a pig model of heart failure, β-adrenergic receptor, a regulator of contractility, has been targeted by delivery of a small polypeptide, βARKct that indirectly prevents disruption of β-adrenergic receptor signaling (Raake et al. *Eur Heart J.* 34:1437-47 (2013)). In a canine model, cardiomyocyte viability was enhanced by rAAV-based delivery of a vascular endothelial growth factor (VEGF) isoform. In human clinical trials, rAAV-based delivery of an isoform of the SERCA calcium pump, SERCA2a, to the heart was tested as a treatment for heart failure. SERCA, or sarco/endoplasmic reticulum $Ca^{2+}$-ATPase, or SR $Ca^{2+}$-ATPase, is a calcium ATPase-type P-ATPase. SERCA resides in the sarcoplasmic reticulum (SR) within muscle cells. It is a $Ca^{2+}$ ATPase that transfers $Ca^{2+}$ from the cytosol of the cell to the lumen of the SR at the expense of ATP hydrolysis during muscle relaxation. SERCA activity is necessary for proper contractile function of the heart. However, direct replacement of SERCA activity by rAAV-based delivery of the SERCA2a isoform failed to show a significant effect in clinical trials (Bass-Stringer et al. *Heart, Lung and Circulation.* 27:1285-1300 (2018)). Enhancing SERCA activity using alternative strategies is desired for treating diseases of the heart, e.g., heart failure and cardiomyopathy.

There are three major domains on the cytoplasmic face of SERCA: the phosphorylation and nucleotide-binding domains, which form the catalytic site, and the actuator domain, which is involved in the transmission of major conformational changes. The rate at which SERCA moves $Ca^{2+}$ across the SR membrane can be controlled by the regulatory protein phospholamban (PLN). SERCA is normally inhibited by PLN, with which it is closely associated. Increased β-adrenergic stimulation reduces the association between SERCA and PLN by the phosphorylation of PLN by PKA. When PLN is associated with SERCA, the rate of Ca$^{2+}$ movement is reduced; upon dissociation of PLN, Ca$^{2+}$ movement increases.

An alternative strategy to enhancing SERCA activity by delivering a SERCA2a isoform is to enhance activity of natively expressed SERCA by displacing PLN. Contacting SERCA with the DWORF polypeptide, described in detail above, can displace PLN and enhance SERCA activity.

In some embodiments, the disclosure provides a method of treating a heart disease or disorder in a subject in need thereof, the method comprising administering an effective amount of a vector comprising an expression cassette comprising a polynucleotide encoding a therapeutic polypeptide operatively linked to a promoter, wherein the therapeutic polypeptide can be any polypeptide useful for treating heart disease. As described herein, the vector can be any viral or non-viral vector.

In some embodiments, the disclosure provides a method of treating a heart disease or disorder in a subject in need thereof, the method comprising administering an effective amount of a recombinant adeno-associated virus (rAAV) virion, the rAAV virion comprising an AAV capsid and an expression cassette comprising a polynucleotide encoding a DWORF polypeptide operatively linked to a promoter.

In a method of treating a subject as described herein, "treating" or "treatment of a condition or subject in need thereof" refers to (1) taking steps to obtain beneficial or desired results, including clinical results such as the reduction of symptoms; (2) inhibiting the disease, for example, arresting or reducing the development of the disease or its clinical symptoms; (3) relieving the disease, for example, causing regression of the disease or its clinical symptoms; or (4) delaying the disease. For purposes of the methods described herein, beneficial or desired clinical results include, but are not limited to, reduction of symptoms associated with heart failure, cardiomyopathy, dilated cardiomyopathy, myocardial infarction, acute myocardial infarction, and chronic myocardial infarction.

In other aspects, the disclosure provides a method of preventing a heart disease or disorder in a subject in need thereof, the method comprising administering an effective amount of a vector comprising an expression cassette comprising a polynucleotide encoding a therapeutic polypeptide operatively linked to a promoter, wherein the therapeutic polypeptide can be any polypeptide useful for preventing heart disease. As described herein, the vector can be any viral or non-viral vector. In some embodiments, prevention of a disease causes the clinical symptoms of the disease not to develop in a patient that may be predisposed to the disease, but does not yet experience or display symptoms of the disease.

Subjects in need of treatment using the compositions and methods of the present disclosure include, but are not limited to, a subject suffering from or being at risk of heart failure. A subject "suffering from" heart failure is considered to have symptoms associated with or a confirmed diagnosis of any of the heart diseases described herein. A subject "at risk of" heart failure is considered to have one or more risk factors associated with any of the heart diseases described herein.

In some embodiments, the methods described herein are useful to treat heart disease or disorder with reduced ejection fraction (HFrEF). In some embodiments, the methods described herein are useful to treat heart disease or disorder with preserved ejection fraction (HFpEF).

In some embodiments, the methods described herein are useful to treat cardiomyopathy. In some embodiments, a method described herein is useful to treat dilated cardiomyopathy. In some embodiments, the subject suffers from or is at risk for cardiomyopathy. In some embodiments, the cardiomyopathy is dilated cardiomyopathy (DCM). In some embodiments, the DCM is genetic DCM (e.g., DCM associated with a PLN mutation in a subject to be treated). In some embodiments, the methods described herein are useful to treat PLN mutation-associated cardiomyopathy. In some embodiments, the DCM is non-genetic DCM. In some embodiments, subject suffers from or is at risk for myocardial infarction. In some embodiments, the myocardial infarction is chronic myocardial infarction. In some embodiments, the myocardial infarction is acute myocardial infarction.

Cardiomyopathy phenotypes can manifest in a subject through a multitude of molecular mechanisms. Transgenic animals have been developed to investigate the molecular pathophysiology of specific mechanisms and the efficacy of potential therapeutic and prevention strategies for cardiomyopathy phenotypes (Law et al. *J Clin Med.* 9:520 (2020)). These animal models can be used to evaluate aspects of the rAAV viral genomes, rAAV virions, and compositions thereof described herein. The MLP$^{-/-}$ transgenic mouse model, for example, recapitulates the phenotype of dilated cardiomyopathy by knocking out the muscle LIM protein, a positive regulator of myogenic differentiation associated with the actin-based cytoskeleton. The absence of LIM protein results in a disruption of cytoskeletal architecture and decreased Ca$^{2+}$ cycling (Minamisawa et al. *Cell.* 99:313-22 (1999)). Artificial replacement with a phosphomimetic PLN transgene delivered by rAAV reduced DCM symptoms in the animals, including improved ejection fraction (Iwanaga Y et al. *J Clin Invest.* 113:727-736 (2004). While the MLP$^{-/-}$ model recapitulates DCM phenotype in a general way, other transgenic mouse models of DCM are more appropriate for specific DCM phenotypes, such as those driven by a mutation to the PLN gene. For example, a transgenic mouse model to recapitulate the clinically observed PLN-R14Del mutation has been developed (Haghighi et al. *Proc. Natl. Acad. Sci. U.S.A* 103:1388-1393 (2006)). It is expected that mouse models with different transgenic modifications to induce a DCM phenotype are not interchangeable for the purpose of evaluating the efficacy of a given therapeutic or prevention strategy, and that each model provides different information about the translation of a therapy.

In some embodiments, the subject in need of treatment has an inherited risk allele (i.e., mutation) for a heart disease or disorder. A risk allele can be, for example, a mutation to the PLN gene. Mutations to the PLN gene can cause a dysfunctional inhibitory effect on SERCA activity. Clinically observable mutations in the PLN gene and protein include a mutation in the PLN promoter, a truncation resulting in a PLN$^{L39stop}$ mutant, aberrant R9C, R9L, and R9H mutations, PLN gene duplications, and deletion of arginine 14 (R14del) in the regulatory domain of PLN. Each of these mutations have been directly linked to dilated cardiomyopathy, hypertrophic cardiomyopathy, or arrhythmic right ventricular cardiomyopathy (Table 8.) (Landstrom et al. *Am Heart J.* 161:165-171 (2011), Lee et al. *Cardiol Young.* 24:953-954 (2014); Haghighi et al. *J. Clin. Invest.* 111:869-876 (2003); Schmitt et al. *Science* 299:1410-1413 (2003); Haghighi et al. *Proc. Natl. Acad. Sci. U.S.A* 103:1388-1393 (2006); Medeiros A et al. Am. Heart J. 162:1088-1095 (2011)).

TABLE 8

PLN mutations and associated heart diseases

| PLN Mutation | Associated Heart Disease |
|---|---|
| PLN promoter mutation | Dilated Cardiomyopathy; Hypertrophic Cardiomyopathy |
| PLN$^{L39stop}$ | Dilated Cardiomyopathy; Hypertrophic Cardiomyopathy |
| R9C | Dilated Cardiomyopathy |
| R9L | Dilated Cardiomyopathy |
| R9H | Dilated Cardiomyopathy |
| PLN gene duplication | Dilated Cardiomyopathy |
| R14del | Dilated Cardiomyopathy; Arrhythmic Right Ventricular Cardiomyopathy |

The various mutations in PLN have different mechanisms of inducing a cardiomyopathy phenotype. For example, the R9C mutation indirectly blocks the phosphorylation of PLN by PKA and prevents the formation of monomeric PLN that can bind to SERCA. In some embodiments, the subject in need of treatment has a PLN promoter mutation. In some embodiments, the subject in need of treatment has a PLN$^{L39stop}$ mutation. In some embodiments, the subject in need of treatment has a R9C mutation. In some embodiments, the subject in need of treatment has a R9L mutation. In some embodiments, the subject in need of treatment has a R9H mutation. In some embodiments, the subject in need of treatment has a PLN gene duplication. In some embodiments, the subject in need of treatment has a R14del mutation.

Mutations can be detected by many types of genetic analysis known in the art. Genetic analysis can be, for example, direct sequencing, fluorescent in situ hybridization assays, polymerase chain reaction-based assays, nucleotide microarray assays, or any other technique known in the art to determine the sequence characteristics of polynucleotides sampled from a subject. For example, DNA was isolated from the peripheral blood samples patients diagnosed with either dilated cardiomyopathy (DCM) or arrhythmic right ventricular cardiomyopathy (ARVC). The coding region of the PLN gene in the isolated DNA was sequenced using a BigDye Terminator DNA sequencing kit (version 2.0) on a 3730 Genetic Analyzer (Applied Biosystems, Foster City, CA, USA). Patients diagnosed with either DCM or ARVC both carried the PLN R14del mutation (van der Zwaag et al. *Eur J Heart Fail.* 14:1199-1207 (2012)).

Methods of Reducing, Improving, and Preventing Symptoms

In some embodiments, the disclosure provides a method of reducing one or more symptoms of a heart disease or disorder in a subject comprising administration of any vector comprising an expression cassette described herein. In some embodiments, the symptoms are reduced compared to the symptoms of the heart disease or disorder prior to administration of the vector comprising an expression cassette described herein to the subject. In some embodiments, the disclosure provides a method of reducing one or more symptoms of a heart disease or disorder in a subject comprising administration of an rAAV virion described herein. In some embodiments, the symptoms are reduced compared to the symptoms of the heart disease or disorder prior to administration of the rAAV virion to the subject. In some embodiments, the heart disease or disorder is heart failure. In some embodiments, the heart disease or disorder is cardiomyopathy. In some embodiments, the heart disease or disorder is dilated cardiomyopathy. In some embodiments, the heart disease or disorder is myocardial infarction. In some embodiments, the heart disease or disorder is chronic myocardial infarction. In some embodiments, the heart disease or disorder is acute myocardial infarction.

In some embodiments, the disclosure provides a method of improving one or more symptoms of a heart disease or disorder in a subject comprising administration of a vector comprising an expression cassette described herein. In some embodiments, the symptoms are improved compared to the symptoms of the heart disease or disorder prior to administration of the vector to the subject. In some embodiments, the disclosure provides a method of improving one or more symptoms of a heart disease or disorder in a subject comprising administration of an rAAV virion described herein. In some embodiments, the symptoms are improved compared to the symptoms of the heart disease or disorder prior to administration of the rAAV virion to the subject. In some embodiments, the heart disease or disorder is heart failure. In some embodiments, the heart disease or disorder is cardiomyopathy. In some embodiments, the heart disease or disorder is dilated cardiomyopathy. In some embodiments, the heart disease or disorder is myocardial infarction. In some embodiments, the heart disease or disorder is chronic myocardial infarction. In some embodiments, the heart disease or disorder is acute myocardial infarction.

In some embodiments, the disclosure provides a method of preventing one or more symptoms of a heart disease or disorder in a subject comprising administration of a vector comprising an expression cassette described herein. In some embodiments, the disclosure provides a method of preventing one or more symptoms of a heart disease or disorder in a subject comprising administration of the rAAV virion described herein. In some embodiments, the symptoms are prevented in a subject considered to be at-risk of the heart disease or disorder. In some embodiments, the heart disease or disorder is heart failure. In some embodiments, the heart disease or disorder is cardiomyopathy. In some embodiments, the heart disease or disorder is dilated cardiomyopathy. In some embodiments, the heart disease or disorder is myocardial infarction. In some embodiments, the heart disease or disorder is chronic myocardial infarction. In some embodiments, the heart disease or disorder is acute myocardial infarction.

In some embodiments, the symptoms are reduced compared to the symptoms of the heart disease or disorder prior to administration of the vector to the subject. In some embodiments, the symptoms are reduced compared to the symptoms of the heart disease or disorder prior to administration of the rAAV virion to the subject. In some embodiments, the heart disease or disorder is heart failure. In some embodiments, the heart disease or disorder is cardiomyopathy. In some embodiments, the heart disease or disorder is dilated cardiomyopathy. In some embodiments, the heart disease or disorder is myocardial infarction. In some embodiments, the heart disease or disorder is chronic myocardial infarction. In some embodiments, the heart disease or disorder is acute myocardial infarction.

As used herein, "symptoms" include any of the diagnostic criteria or symptoms associated with, e.g., heart diseases described herein. Severity and changes of symptoms and diagnostic results are determined by a medical professional qualified to deliver assessments and analyze the results of such assessments.

Common symptoms in subjects with or at risk of developing heart disease are fatigue, dyspnea, edema, chest pain, arrhythmias, blood clots, impaired heart valve function, and heart murmur. In some embodiments, the subject experiences reduced symptoms associated with the heart diseases described herein following administration of the vector, an rAAV virion or compositions of the disclosure. In some embodiments, the improved symptoms are one or more of enhanced contractility; reduced fatigue; reduced dyspnea; reduced edema; reduced chest pain; reduced arrhythmias; reduced blood clots; improved heart valve function; and reduced heart murmur. In some embodiments, the symptom is a change in 6 minute walk distance. In some embodiments, symptoms are determined by the Minnesota Living with Heart Failure Questionnaire. In some embodiments, the symptom is an abnormal level of B-type natriuretic peptide (i.e., BNP, NT-proBNP). In some embodiments, the severity of symptoms are determined by measuring LV remodeling. In some embodiments of the method described herein improves one or more measures of cardiac function. In some embodiments, the measures of cardiac function comprise fractional shortening and/or left ventricular internal dimension (LVID). In some embodiments, the measures of cardiac function comprises left ventricular end-systolic volume (LVESV). In some embodiments, the improvement in cardiac function is ejection fraction. In some embodiments, improvement in cardiac function is observed at weeks 2 through 12. In some embodiments, the method reduces cardiac remodeling. In some embodiments, the method counteracts a decrease in DWORF expression in subjects suffering from myocardial infarction.

Ejection fraction is a measurement of the percentage of blood leaving the heart each time it contracts. The ejection fraction is determined using the stroke volume (SV) and the end-diastolic volume (EDV), calculated as: EF (%)=(SV/EDV)×100. Ejection fraction can be measured in a subject with imaging tests, including echocardiogram, cardiac catheterization, magnetic resonance imaging (MRI), computerized tomography (CT), and/or nuclear medicine scan. A normal ejection fraction is between about 50% and about 75%. A "borderline" ejection fraction can range between about 41% and about 50%. A reduced ejection fraction is less than about 41%. A borderline or reduced ejection fraction can be used as a symptom in diagnosing a heart disease or disorder. It is understood that the cutoff values between normal, borderline, and reduced ejection fraction are approximate and one skilled in the art, e.g., a cardiologist, will ultimately make the determination.

In some embodiments of the methods provided herein, it may be desirable to improve ejection fraction. Ejection fraction can be considered to be improved if the ejection fraction percentage increases. In some embodiments, the ejection fraction In some embodiments of the methods provided herein, it may be desirable to preserve ejection fraction. Preserving ejection fraction can be used to prevent the onset of a heart disease or disorder in a subject at risk thereof, prevent the progression of a heart disease or disorder, or prevent worsening of symptoms associated with a heart disease or disorder in a subject at risk of or suffering therefrom.

The disclosure provides methods of improving ejection fraction in a subject at risk or suffering from a heart disease or disorder. In some embodiments, ejection fraction is improved (i.e., increased) in the subject following administration of a vector comprising an expression cassette described herein. In some embodiments, ejection fraction is improved (i.e., increased) in the subject following administration of a vector or an rAAV virion described herein. In some embodiments, ejection fraction is improved about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 22 weeks or about 24 weeks following administration of the vector or the rAAV virion to the subject. In some embodiments, ejection fraction is improved about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% following administration of the vector or the rAAV virion to the subject.

The disclosure provides methods of preserving ejection fraction in a subject at risk or suffering from a heart disease or disorder. For example, the subject may maintain an ejection fraction that would otherwise be expected to reduce in the absence of administration of the vector or the rAAV virion or pharmaceutical composition of the disclosure. In some embodiments, ejection fraction is preserved in the subject following administration of the vector or the rAAV virion of the disclosure. In some embodiments, ejection fraction is preserved about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 22 weeks or about 24 weeks following administration of the vector or rAAV virion to the subject. In some embodiments, ejection fraction is preserved by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% following administration of the vector or rAAV virion to the subject.

Assessment of heart contractility can be used to assess acute and chronic forms of heart failure. Heart contractility may be monitored by using invasive hemodynamic monitoring, continuous ECG monitoring, central venous pressure, kidney function, pulse oximetry, arterial pressure monitoring, pulmonary artery catheter, and/or transeophageal echocardiography (Kuhn C, Werdan K. *Surgical Treatment: Evidence-Based and Problem-Oriented*. Munich: Zuckschwerdt; 2001. Available from: https://www.ncbi.nlm.nih.gov/books/NBK6895/).

Dyspnea and fatigue associated with heart disease described herein can be measured using questionnaires. The Modified Pulmonary Functional Status and Dyspnea Questionnaire (PFSDQ-M) 10 (Huang et al. *Am J Crit Care*. 17:436-442 (2008)) and Minnesota Living with Heart Failure Questionnaire (MLHFQ) 11 (Bilbao et al. *Health Qual Life Outcomes*. 14:23 (2016)), for example, can be used to measure subjects with a heart disease as described herein. The questionnaires are self-administered and allow a score to be derived that is used to assess symptom severity for dyspnea, fatigue, and other heart-health related symptoms.

Cardiomyopathy, myocardial infarction and heart valve function may be assessed using one or more of an exercise stress test, electrocardiogram, echocardiogram, chest X-ray, cardiac CT scan, or angiogram with cardiac catheterization, cardiac MRI, B-type natriuretic peptide (BNP) levels in the blood, and/or genetic screening. Further testing is required to diagnose specific types of cardiomyopathy, myocardial infarction, or heart valve dysfunction.

In some aspects, administration of a vector comprising an expression cassette described herein to a subject results in an improvement in exercise capacity of the subject (e.g., improvement in running distance and/or time to exhaustion). In some aspects, administration of an rAAV comprising an expression cassette described herein encoding DWORF to a subject results in an improvement in exercise capacity of the subject (e.g., improvement in running distance and/or time to exhaustion).

Dilated cardiomyopathy (DCM) is a progressive disease of heart muscle characterized by chamber enlargement and contractile dysfunction of the left ventricle in the absence of chronic pressure and/or volume overload. DCM is diagnosed primarily using echocardiography.

Echocardiography with a PLAX view in 2D/M-mode is used to measure several parameters, including ejection fraction, LVIDd/s, IVSd, LVPWd, and fractional shortening. These parameters are used to assess the left ventricle cavity size, wall thickness, and radial function. Diagnostic criterion for DCM includes LVIDd/s greater than 112% (2 S.D) corrected for age and body surface area (BSA). Fractional shortening less than 25% is a criterion for the diagnosis of DCM in the presence of a dilated ventricle (Mathew et al. *Echo Res Pract.* 4:G1-G13 (2017)).

Qualitative assessment of left and right ventricular structure and function with special reference to radial and longitudinal function and regional wall motion abnormalities are assessed by echocardiography in the apical four-chamber (A4C) view in 2D mode. Ejection fraction (EF) can be estimated using, for example, biplane Simpsons method. EF of less than 45% is a diagnostic criterion for DCM in the presence of dilated ventricle (Mathew et al. *Echo Res Pract.* 4: G1-G13 (2017)).

Administration

In some embodiments, the vectors and compositions of the present disclosure can be administered to a subject in need thereof by systemic application, e.g., by intravenous, intra-arterial or intraperitoneal delivery. In some embodiments, the rAAV virion and compositions of the present disclosure can be administered to a subject in need thereof by systemic application, e.g., by intravenous, intra-arterial or intraperitoneal delivery of a vector in analogy to what has been shown in animal models (Katz et al., *Gene Ther* 19:659-669 (2012)). In some embodiments, the vectors, rAAV virions and compositions of the present disclosure treat or prevent heart failure. In some embodiments, the cardiomyopathy, wherein the vector is administered systemically. In some embodiments, the rAAV virion is administered by intravenous or intracoronary injection.

The disclosure provides methods for expressing a polypeptide in a cell in vitro, ex vivo, or in vivo. In some embodiments, the disclosure provides methods for expressing a DWORF polypeptide in a cell in vitro, ex vivo, or in vivo. The method comprises, for example, exposing a target cell to the vectors, rAAV virions or pharmaceutical compositions described herein. A target cell can be, for example and without limitation, a cardiac cell, a muscle cell, an induced pluripotent stem cell-derived cardiomyocyte (iPSC-CM), and/or a cardiomyocyte. In some embodiments, a method of expressing a polypeptide (e.g., DWORF polypeptide) in a cell comprises transfecting or transducing (alternating referred to as "infecting") a target cell or population of target cells with a vector described herein. In some embodiments, a method of expressing a polypeptide (e.g., DWORF polypeptide) in a cell comprises transducing (alternating referred to as "infecting") a target cell or population of target cells with an rAAV virion or pharmaceutical compositions described herein. In some embodiments, the rAAV transduces cardiac cells. In some embodiments, the rAAV transduces cardiomyocytes. In some embodiments, the rAAV transduces induced pluripotent stem cell-derived cardiomyocytes (iPSC-CM).

In some embodiments, the vector transfection or transduction increases polypeptide expression in the heart of the subject. In some embodiments, the rAAV transduction increases DWORF polypeptide expression in the heart of the subject. "Increased polypeptide expression" typically refers to expression at least 5%, 10%, 15%, 20% or more compared to a control subject or tissue not treated with the vector. "Increased DWORF polypeptide expression" typically refers to expression at least 5%, 10%, 15%, 20% or more compared to a control subject or tissue not treated with the vector. In some embodiments, detectable expression means expression at 1.5-fold, 2-fold, 2.5-fold, or 3-fold greater than a no-vector control. Expression can be assessed by Western blot, as described in the example that follows, or enzyme-linked immunosorbent assay (ELISA), or other methods known in the art. In some cases, expression is measured quantitatively using a standard curve. Standard curves can be generated using purified protein, e.g., purified DWORF polypeptide, by methods described in the examples or known in the art. Alternatively, expression of the therapeutic gene product can be assessed by quantification of the corresponding mRNA. In some embodiments, the method causes the expression of the polypeptide (e.g., DWORF polypeptide) in the heart of the subject.

In some embodiments, the method causes no detectable expression of the polypeptide in the muscles of the subject except the heart, in the liver of the subject, and/or in cardiac fibroblasts. In some embodiments, the method causes expression of the polypeptide in cardiomyocytes.

In some embodiments, the method causes no detectable expression of the DWORF polypeptide in the muscles of the subject except the heart. In some embodiments, the method causes no detectable expression of the DWORF polypeptide in the liver of the subject. In some embodiments, the method causes expression of the DWORF polypeptide in cardiomyocytes. In some embodiments, the method causes no detectable expression of the DWORF polypeptide in cardiac fibroblasts.

In some embodiments, the increased polypeptide expression in heart tissue occurs at doses, in vector genomes (vg) per kilogram weight of subject (kg), of $3 \times 10^{14}$ vg/kg or less, $2 \times 10^{14}$ vg/kg or less, $1 \times 10^{14}$ vg/kg or less, $9 \times 10^{13}$ vg/kg or less, $8 \times 10^{13}$ vg/kg or less, $7 \times 10^{13}$ vg/kg or less, $6 \times 10^{13}$ vg/kg or less, $5 \times 10^{13}$ vg/kg or less, $4 \times 10^{13}$ vg/kg or less, $3 \times 10^{13}$ vg/kg or less, $2 \times 10^{13}$ vg/kg or less, or $1 \times 10^{13}$ vg/kg or less.

In some embodiments, the increased DWORF expression in heart tissue occurs at doses, in vector genomes (vg) per kilogram weight of subject (kg), of $3 \times 10^{14}$ vg/kg or less, $2 \times 10^{14}$ vg/kg or less, $1 \times 10^{14}$ vg/kg or less, $9 \times 10^{13}$ vg/kg or less, $8 \times 10^{13}$ vg/kg or less, $7 \times 10^{13}$ vg/kg or less, $6 \times 10^{13}$ vg/kg or less, $5 \times 10^{13}$ vg/kg or less, $4 \times 10^{13}$ vg/kg or less, $3 \times 10^{13}$ vg/kg or less, $2 \times 10^{13}$ vg/kg or less, or $1 \times 10^{13}$ vg/kg or less.

Pharmaceutical Compositions and Kits

The vectors of the disclosure are generally delivered to the subject as a pharmaceutical composition. In some embodiments, the rAAV virion of the disclosure is delivered to the subject as a pharmaceutical composition. Pharmaceutical compositions comprise a pharmaceutically acceptable solvent (e.g., water, etc.) and one or more excipients. In some embodiments, the pharmaceutical compositions comprise a buffer at about neutral pH (pH 5, 6, 7, 8, or 9). In some embodiments, the pharmaceutical composition comprises phosphate buffered saline (e.g., PBS at pH of about 7). The pharmaceutical compositions may comprise a pharmaceutically acceptable salt. The concentration of the salt may be selected to ensure that the pharmaceutical composition is isotonic to, or nearly isotonic to, the target tissue.

In various embodiments, the compositions described herein contain vehicles (e.g., carriers, diluents and excipients) that are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Illustrative pharmaceutical forms suitable for injectable use include, e.g., sterile aqueous solutions or dispersions; formulations including sesame oil, peanut oil or aqueous propylene glycol; and sterile powders for the extemporaneous preparation of sterile injectable solutions or dispersions.

In various embodiments, the pharmaceutical compositions of the disclosure comprise about $1\times10^8$ genome copies per milliliter (GC/mL), about $5\times10^8$ GC/mL, about $1\times10^9$ GC/mL, about $5\times10^9$ GC/mL, about $1\times10^{10}$ GC/mL, about $5\times10^{10}$ GC/mL, about $1\times10^{11}$ GC/mL, about $5\times10^{11}$ GC/mL, about $1\times10^{12}$ GC/mL, about $5\times10^{12}$ GC/mL, about $5\times10^{13}$ GC/mL, about $1\times10^{14}$ GC/mL, or about $5\times10^{14}$ GC/mL of the viral vector (e.g., rAAV virion).

In various embodiments, the pharmaceutical compositions of the disclosure comprise about $1\times10^8$ viral genomes per milliliter (vg/mL), about $5\times10^8$ vg/mL, about $1\times10^9$ vg/mL, about $5\times10^9$ vg/mL, about $1\times10^{10}$ vg/mL, about $5\times10^{10}$ vg/mL, about $1\times10^{11}$ vg/mL, about $5\times10^{11}$ vg/mL, about $1\times10^{12}$ vg/mL, about $5\times10^{12}$ vg/mL, about $5\times10^{13}$ vg/mL, about $1\times10^{14}$ vg/mL, or about $5\times10^{14}$ vg/mL of the viral vector (e.g., rAAV virion).

In some embodiments, the pharmaceutical compositions of the disclosure are administered in a total volume of about 1 mL, 5 mL, 10 mL, about 20 mL, about 25 mL, about 30 mL, about 35 mL, about 40 mL, about 45 mL, about 50 mL, about 55 mL, about 60 mL, 65 mL, about 70 mL, about 75 mL, about 80 mL, about 85 mL, about 90 mL, about 95 mL, about 100 mL, about 105 mL, about 110 mL, about 115 mL, about 120 mL, about 125 mL, about 130 mL, about 135 mL, about 140 mL, about 145 mL, about 150 mL, about 155 mL, about 160 mL, about 165 mL, about 170 mL, about 175 mL, about 180 mL, about 185 mL, about 190 mL, about 200 mL, about 205 mL, about 210 mL, about 215 mL, or about 220 mL.

Genome copies per milliliter can be determined by quantitative polymerase change reaction (qPCR) using a standard curve generated with a reference sample having a known concentration of the polynucleotide genome of the virus. For AAV, the reference sample used is often the transfer plasmid used in generation of the rAAV virion but other reference samples may be used.

Alternatively or in addition, the concentration of a viral vector can be determined by measuring the titer of the vector on a cell line. Viral titer is typically expressed as viral particles (vp) per unit volume (e.g., vp/mL). In various embodiments, the pharmaceutical compositions of the disclosure comprise about $1\times10^8$ viral particles per milliliter (vp/mL), about $5\times10^8$ vp/mL, about $1\times10^9$ vp/mL, about $5\times10^9$ vp/mL, about $1\times10^{10}$ vp/mL, about $5\times10^{10}$ vp/mL, about $1\times10^{11}$ vp/mL, about $5\times10^{11}$ vp/mL, about $1\times10^{12}$ vp/mL, about $5\times10^{12}$ vp/mL, about $5\times10^{13}$ vp/mL, or about $1\times10^{14}$ vp/mL, or about $5\times10^{14}$ of the viral vector (e.g., rAAV virion).

In some embodiments, the present disclosure provides a kit comprising a container housing a pharmaceutical composition as described herein.

NUMBERED EMBODIMENTS OF THE INVENTION I

Embodiment 1: A recombinant adeno-associated virus (rAAV) virion, comprising a capsid protein and a viral genome comprising an expression cassette comprising a polynucleotide sequence encoding a dwarf open reading frame (DWORF) polypeptide operatively linked to a promoter, the expression cassette flanked by inverted terminal repeats.

Embodiment 2: The rAAV virion of embodiment 1, wherein the DWORF polypeptide shares at least 90%, 95%, 96%, 97%, 98%, or 99% identity to a sequence selected from SEQ ID NOs: 1, 3, 4, 7, 9, 23, and 43.

Embodiment 3: The rAAV virion of embodiment 1, wherein the DWORF polypeptide is selected from SEQ ID NOs: 1, 3, 4, 7, 9, 23, and 43.

Embodiment 4: The rAAV virion of embodiment 1 or 2, wherein the promoter is a chicken cTnT promoter.

Embodiment 5: The rAAV virion of embodiment 4, wherein the chicken cTnT promoter shares at least 90%, 95%, 96%, 97%, 98%, or 99% identity to SEQ ID NO: 11.

Embodiment 6: The rAAV virion of embodiment 4, wherein the chicken cTnT promoter comprises SEQ ID NO: 11.

Embodiment 7: The rAAV virion of embodiment 1 or 2, wherein the promoter is a human cTnT promoter.

Embodiment 8: The rAAV virion of embodiment 7, wherein the human cTnT promoter shares at least 90%, 95%, 96%, 97%, 98%, or 99% identity to SEQ ID NO: 12 or SEQ ID NO: 13.

Embodiment 9: The rAAV virion of embodiment 7, wherein the human cTnT promoter comprises SEQ ID NO: 12 or SEQ ID NO: 13.

Embodiment 10: The rAAV virion of any one of embodiments 1 to 9, wherein the expression cassette further comprises one or more enhancers.

Embodiment 11: The rAAV virion of embodiment 10, wherein the enhancer the one or more enhancers are selected from a ACTC1 cardiac enhancer and a αMHC enhancer.

Embodiment 12: The rAAV virion of embodiment 11, wherein the ACTC1 cardiac enhancer shares at least 90%, 95%, 96%, 97%, 98%, or 99% identity to SEQ ID NO: 78.

Embodiment 13: The rAAV virion of embodiment 11, wherein the ACTC1 cardiac enhancer comprises SEQ ID NO: 78.

Embodiment 14: The rAAV virion of embodiment 11, wherein the αMHC enhancer shares at least 90%, 95%, 96%, 97%, 98%, or 99% identity to SEQ ID NO: 79.

Embodiment 15: The rAAV virion of embodiment 11, wherein the αMHC enhancer comprises SEQ ID NO: 79.

Embodiment 16: The rAAV virion of any one of embodiments 1 to 15, wherein the expression cassette further comprises an intron.

Embodiment 17: The rAAV virion of embodiment 16, wherein the intron is selected from a CMV intron and a chimeric intron.

Embodiment 18: The rAAV virion of embodiment 17, wherein the CMV intron shares at least 90%, 95%, 96%, 97%, 98%, or 99% identity to SEQ ID NO: 80.

Embodiment 19: The rAAV virion of embodiment 17, wherein the CMV intron comprises SEQ ID NO: 80.

Embodiment 20: The rAAV virion of embodiment 17, wherein the chimeric intron shares at least 90%, 95%, 96%, 97%, 98%, or 99% identity to SEQ ID NO: 81.

Embodiment 21: The rAAV virion of embodiment 17, wherein the chimeric intron comprises SEQ ID NO: 81.

Embodiment 22: The rAAV virion of any one of embodiments 1 to 21, wherein the expression cassette further comprises a WPRE sequence.

Embodiment 23: The rAAV virion of embodiment 22, wherein the WPRE sequence shares at least 90%, 95%, 96%, 97%, 98%, or 99% identity to SEQ ID NO: 26.

Embodiment 24: The rAAV virion of embodiment 22, wherein the WPRE sequence comprises SEQ ID NO: 26.

Embodiment 25: The rAAV virion of any one of embodiments 1 to 24, wherein the expression cassette further comprises a polyadenylation sequence.

Embodiment 26: The rAAV virion of embodiment 25, wherein the polyadenylation sequence is selected from a BGH polyadenylation sequence and a SV40 polyadenylation sequence.

Embodiment 27: The rAAV virion of embodiment 26, wherein the BGH polyadenylation sequence shares at least 90%, 95%, 96%, 97%, 98%, or 99% identity to SEQ ID NO: 27.

Embodiment 28: The rAAV virion of embodiment 26, wherein the BGH polyadenylation sequence comprises SEQ ID NO: 27.

Embodiment 29: The rAAV virion of embodiment 26, wherein the SV40 polyadenylation sequence shares at least 90%, 95%, 96%, 97%, 98%, or 99% identity to SEQ ID NO: 28.

Embodiment 30: The rAAV virion of embodiment 26, wherein the SV40 polyadenylation sequence comprises SEQ ID NO: 28.

Embodiment 31: The rAAV virion of any one of embodiments 1 to 30, wherein the expression cassette is flanked by ITRs.

Embodiment 32: The rAAV virion of embodiment 31, wherein the ITRs share at least 90%, 95%, 96%, 97%, 98%, or 99% identity to one or more of SEQ ID NO: 14 and SEQ ID NO: 15.

Embodiment 33: The rAAV virion of embodiment 31, wherein the ITRs comprise one or more of SEQ ID NO: 14 and SEQ ID NO: 15.

Embodiment 34: The rAAV virion of any one of embodiments 1 to 33, wherein the expression cassette comprises a single promoter.

Embodiment 35: The rAAV virion of any one of embodiments 1 to 33, wherein the expression cassette comprises two promoters.

Embodiment 36: The rAAV virion of any one of embodiments 1 to 35 wherein the expression cassette comprises a single copy a sequence encoding the DWORF polypeptide.

Embodiment 37: The rAAV virion of any one of embodiments 1 to 35 wherein the expression cassette comprises two copies of a sequence encoding the DWORF polypeptide.

Embodiment 38: The rAAV virion of any one of embodiments 1 to 37 wherein the expression cassette comprises one, two, three, or four enhancers.

Embodiment 39: The rAAV virion of any one of embodiments 1 to 38 wherein the expression cassette comprises one or two introns.

Embodiment 40: The rAAV virion of any one of embodiments 1 to 39 wherein the expression cassette comprises one or two WPRE sequences.

Embodiment 41: The rAAV virion of any one of embodiments 1 to 40 wherein the expression cassette comprises one or two polyadenylation sequences.

Embodiment 42: The rAAV virion of any one of embodiments 1 to 41 wherein the expression cassette comprises about 3.2 kb, about, about 3.3 kb, about 3.4 kb, about 3.5 kb, about 3.6 kb, about 3.7 kb, or less.

Embodiment 43: The rAAV virion of any one of embodiments 1 to 41 wherein the expression cassette comprises about 1.9 kb, about 2.1 kb, about 2.2 kb, about 2.3 kb, about 2.4 kb, about 2.5 kb, about 2.6 kb, about 2.7 kb, about 2.8 kb, about 2.9 kb, about 3.0 kb, about 3.1 kb, about 3.2 kb, or more.

Embodiment 44: The rAAV virion of embodiment 1, wherein the expression cassette comprises a polynucleotide sequence that shares at least 75%, 80%, 90%, 95%, 96%, 97%, 98%, 99%, or 100% identity to any one of SEQ ID NOs: 20-24 or SEQ ID NOs: 45-75.

Embodiment 45: The rAAV virion of embodiment 1, wherein the expression cassette comprises any one of SEQ ID NOs: 20-24 or SEQ ID NOs: 45-75.

Embodiment 46: The rAAV virion of embodiment 1, wherein the expression cassette comprises a polynucleotide sequence that shares at least 75%, 80%, 90%, 95%, 96%, 97%, 98%, or 99% identity to SEQ ID NO: 61.

Embodiment 47: The rAAV virion of embodiment 1, wherein the expression cassette comprises SEQ ID NO: 61.

Embodiment 48: The rAAV virion of embodiment 1, wherein the expression cassette comprises a polynucleotide sequence that shares at least 75%, 80%, 90%, 95%, 96%, 97%, 98%, or 99% identity to SEQ ID NO: 62.

Embodiment 49: The rAAV virion of embodiment 1, wherein the expression cassette comprises SEQ ID NO: 62.

Embodiment 50: The rAAV virion of embodiment 1, wherein the expression cassette comprises a polynucleotide sequence that shares at least 75%, 80%, 90%, 95%, 96%, 97%, 98%, or 99% identity to SEQ ID NO: 63.

Embodiment 51: The rAAV virion of embodiment 1, wherein the expression cassette comprises SEQ ID NO: 63.

Embodiment 52: The rAAV virion of any one of embodiments 1 to 51, wherein the capsid protein shares at least 98%, at least 99%, or 100% identity to an AAV9 capsid protein (SEQ ID NO: 143).

Embodiment 53: The rAAV virion of any one of embodiments 1 to 51, wherein the capsid protein shares at least 98%, at least 99%, or 100% identity to an AAV5 capsid protein (SEQ ID NO: 144).

Embodiment 54: The rAAV virion of any one of embodiments 1 to 51, wherein the capsid protein is a chimeric capsid protein.

Embodiment 55: The rAAV virion of any one of embodiments 1 to 51, wherein the capsid protein is an AAV5/AAV9 chimeric capsid protein.

Embodiment 56: The rAAV virion of any one of embodiments 1 to 51, wherein the capsid protein is selected from any one of SEQ ID NOs: 145-200.

Embodiment 57: An expression cassette comprising polynucleotide sequence encoding a dwarf open reading frame (DWORF) polypeptide operatively linked to a promoter.

Embodiment 58: The expression cassette of embodiment 57, wherein the DWORF polypeptide is selected from SEQ ID NOs: 1, 3, 4, 7, 9, 23, and 43.

Embodiment 59: The expression cassette of embodiment 57 or 58, wherein the promoter is a chicken cTnT promoter.

Embodiment 60: The expression cassette of embodiment 59, wherein the chicken cTnT promoter shares at least 90%, 95%, 96%, 97%, 98%, or 99% identity to SEQ ID NO: 11.

Embodiment 61: The expression cassette of embodiment 59, wherein the chicken cTnT promoter comprises SEQ ID NO: 11.

Embodiment 62: The expression cassette of embodiment 57 or 58, wherein the promoter is a human cTnT promoter.

Embodiment 63: The expression cassette of embodiment 62, wherein the human cTnT promoter shares at least 90%, 95%, 96%, 97%, 98%, or 99% identity to SEQ ID NO: 12 or SEQ ID NO: 13.

Embodiment 64: The expression cassette of embodiment 62, wherein the human cTnT promoter comprises SEQ ID NO: 12 or SEQ ID NO: 13.

Embodiment 65: The expression cassette of any one of embodiments 57 to 64, wherein the expression cassette further comprises one or more enhancers.

Embodiment 66: The expression cassette of embodiment 65, wherein the enhancer the one or more enhancers are selected from a ACTC1 cardiac enhancer and a αMHC enhancer.

Embodiment 67: The expression cassette of embodiment 66, wherein the ACTC1 cardiac enhancer shares at least 90%, 95%, 96%, 97%, 98%, or 99% identity to SEQ ID NO: 78.

Embodiment 68: The expression cassette of embodiment 66, wherein the ACTC1 cardiac enhancer comprises SEQ ID NO: 78.

Embodiment 69: The expression cassette of embodiment 66, wherein the αMHC enhancer shares at least 90%, 95%, 96%, 97%, 98%, or 99% identity to SEQ ID NO: 79.

Embodiment 70: The expression cassette of embodiment 66, wherein the αMHC enhancer comprises SEQ ID NO: 79.

Embodiment 71: The expression cassette of any one of embodiments 57 to 70, wherein the expression cassette further comprises an intron.

Embodiment 72: The expression cassette of any one of embodiments 57 to 70, wherein the intron is selected from a CMV intron and a chimeric intron.

Embodiment 73: The expression cassette of embodiment 72, wherein the CMV intron shares at least 90%, 95%, 96%, 97%, 98%, or 99% identity to SEQ ID NO: 80.

Embodiment 74: The expression cassette of embodiment 72, wherein the CMV intron comprises SEQ ID NO: 80.

Embodiment 75: The expression cassette of embodiment 72, wherein the chimeric intron shares at least 90%, 95%, 96%, 97%, 98%, or 99% identity to SEQ ID NO: 81.

Embodiment 76: The expression cassette of embodiment 72, wherein the chimeric intron comprises SEQ ID NO: 81.

Embodiment 77: The expression cassette of any one of embodiments 57 to 76, wherein the expression cassette further comprises a WPRE sequence.

Embodiment 78: The expression cassette of embodiment 77, wherein the WPRE sequence shares at least 90%, 95%, 96%, 97%, 98%, or 99% identity to SEQ ID NO: 26.

Embodiment 79: The expression cassette of embodiment 77, wherein the WPRE sequence comprises SEQ ID NO: 26.

Embodiment 80: The expression cassette of any one of embodiments 57 to 79, wherein the expression cassette further comprises a polyadenylation sequence.

Embodiment 81: The expression cassette of embodiment 80, wherein the polyadenylation sequence is selected from a BGH polyadenylation sequence and a SV40 polyadenylation sequence.

Embodiment 82: The expression cassette of embodiment 81, wherein the BGH polyadenylation sequence shares at least 90%, 95%, 96%, 97%, 98%, or 99% identity to SEQ ID NO: 27.

Embodiment 83: The expression cassette of embodiment 81, wherein the BGH polyadenylation sequence comprises SEQ ID NO: 27.

Embodiment 84: The expression cassette of embodiment 81, wherein the SV40 polyadenylation sequence shares at least 90%, 95%, 96%, 97%, 98%, or 99% identity to SEQ ID NO: 28.

Embodiment 85: The expression cassette of embodiment 81, wherein the SV40 polyadenylation sequence comprises SEQ ID NO: 28.

Embodiment 86: The expression cassette of any one of embodiments 57 to 85, wherein the expression cassette is flanked by ITRs.

Embodiment 87: The expression cassette of embodiment 86, wherein the ITRs share at least 90%, 95%, 96%, 97%, 98%, or 99% identity to one or more of SEQ ID NO: 14 and SEQ ID NO: 15.

Embodiment 88: The expression cassette of embodiment 86, wherein the ITRs comprise one or more of SEQ ID NO: 14 and SEQ ID NO: 15.

Embodiment 89: The expression cassette of any one of embodiments 57 to 88 comprising a single promoter.

Embodiment 90: The expression cassette of any one of embodiments 57 to 88 comprising two promoters.

Embodiment 91: The expression cassette of any one of embodiments 57 to 90 comprising a single copy a sequence encoding the DWORF polypeptide.

Embodiment 92: The expression cassette of any one of embodiments 57 to 90 comprising two copies of a sequence encoding the DWORF polypeptide.

Embodiment 93: The expression cassette of any one of embodiments 57 to 92 comprising one, two, three, or four enhancers.

Embodiment 94: The expression cassette of any one of embodiments 57 to 93 comprising one or two introns.

Embodiment 95: The expression cassette of any one of embodiments 57 to 94 comprising one or two WPRE sequences.

Embodiment 96: The expression cassette of any one of embodiments 57 to 95 comprising one or two polyadenylation sequences.

Embodiment 97: The expression cassette of any one of embodiments 57 to 96 comprising about 3.2 kb, about, about 3.3 kb, about 3.4 kb, about 3.5 kb, about 3.6 kb, about 3.7 kb, or less.

Embodiment 98: The expression cassette of any one of embodiments 57 to 96 comprising about 1.9 kb, about 2.1 kb, about 2.2 kb, about 2.3 kb, about 2.4 kb, about 2.5 kb, about 2.6 kb, about 2.7 kb, about 2.8 kb, about 2.9 kb, about 3.0 kb, about 3.1 kb, about 3.2 kb, or more.

Embodiment 99: The expression cassette of embodiment 1, comprising a polynucleotide sequence that shares at least 75%, 80%, 90%, 95%, 96%, 97%, 98%, 99%, or 100% identity to any one of SEQ ID NOs: 20-24 or SEQ ID NOs: 45-75.

Embodiment 100: The expression cassette of embodiment 57, comprising any one of SEQ ID NOs: 20-24 or SEQ ID NOs: 45-75.

Embodiment 101: The expression cassette of embodiment 57, comprising a polynucleotide sequence that shares at least 75%, 80%, 90%, 95%, 96%, 97%, 98%, or 99% identity to SEQ ID NO: 61.

Embodiment 102: The expression cassette of embodiment 57, comprising SEQ ID NO: 61.

Embodiment 103: The expression cassette of embodiment 57, comprising a polynucleotide sequence that shares at least 75%, 80%, 90%, 95%, 96%, 97%, 98%, or 99% identity to SEQ ID NO: 62.

Embodiment 104: The expression cassette of embodiment 57, comprising SEQ ID NO: 62.

Embodiment 105: The expression cassette of embodiment 57, comprising a polynucleotide sequence that shares at least 75%, 80%, 90%, 95%, 96%, 97%, 98%, or 99% identity to SEQ ID NO: 63.

Embodiment 106: The expression cassette of embodiment 57, comprising SEQ ID NO: 63.

Embodiment 107: The expression cassette of any one of embodiments 57 to 98, further comprising a 5' inverted terminal repeat and a 3' inverted terminal repeat.

Embodiment 108: A pharmaceutical composition comprising the rAAV virion of any one of embodiments 1 to 56 and an pharmaceutically acceptable diluent.

Embodiment 109: A kit comprising the pharmaceutical composition of embodiment 108.

Embodiment 110: A method of increasing DWORF expression in a cell comprising contacting a cell with the rAAV virion of any one of embodiments 1 to 56 or the composition of embodiment 108.

Embodiment 111: The method of embodiment 110, wherein the cell is a cardiac cell.

Embodiment 112: The method of embodiment 111, wherein the cardiac cell is a cardiomyocyte.

Embodiment 113: The method of any one of embodiments 110 to 112, wherein DWORF expression is increased between about 1.5-fold and 150-fold.

Embodiment 114: The method of any one of embodiments 110 to 113, wherein the contacting is in vitro.

Embodiment 115: The method of any one of embodiments 110 to 113, wherein the contacting is in vivo.

Embodiment 116: A method of increasing DWORF expression in a tissue comprising contacting the tissue with the rAAV virion of any one of embodiments 1 to 56 or the composition of embodiment 108.

Embodiment 117: The method of embodiment 116, wherein the tissue is cardiac tissue.

Embodiment 118: The method of embodiment 116 or 117, wherein DWORF expression is increased between about 1.5-fold and 150-fold.

Embodiment 119: The method of any one of embodiments 116 to 118, wherein the contacting is in vitro.

Embodiment 120: The method of embodiment 116 or 118, wherein the contacting is in vivo.

Embodiment 121: A method of increasing DWORF expression in an organ comprising contacting the organ with the rAAV virion of any one of embodiments 1 to 56 or the composition of embodiment 108.

Embodiment 122: The method of embodiment 121, wherein the organ is a heart.

Embodiment 123: The method of embodiment 122, wherein the heart is diseased or is at risk of disease.

Embodiment 124: The method of embodiment 122 or embodiment 123, wherein the heart has reduced or borderline ejection fraction.

Embodiment 125: The method of embodiment 122 or embodiment 123, wherein the heart has a normal ejection fraction.

Embodiment 126: The method of any one of embodiments 122 to 125, wherein the heart comprises a genetic mutation associated with a heart disease.

Embodiment 127: The method of embodiment 126, wherein the genetic mutation is a PLN mutation.

Embodiment 128: The method of any one of embodiments 121 to 127, wherein the heart has low or undetectable DWORF expression compared to a healthy heart.

Embodiment 129: The method of any one of embodiments 121 to 128, wherein DWORF expression is increased between about 1.5-fold and 150-fold.

Embodiment 130: The method of any one of embodiments 121 to 129, wherein the contacting is in vitro.

Embodiment 131: The method of any one of embodiments 121 to 129, wherein the contacting is in vivo.

Embodiment 132: A method of increasing DWORF expression in an subject comprising administering to the subject the rAAV virion of any one of embodiments 1 to 56 or the composition of embodiment 108.

Embodiment 133: The method of embodiment 132, wherein the subject is an animal.

Embodiment 134: The method of embodiment 132, wherein the subject is a human.

Embodiment 135: The method of any one of embodiments 132 to 134, wherein DWORF expression is increased in the heart of the subject.

Embodiment 136: The method of any one of embodiments 132 to 135, wherein subject has a heart disease or is at risk of a heart disease.

Embodiment 137: The method of any one of embodiments 132 to 136, wherein subject has borderline or reduced ejection fraction.

Embodiment 138: The method of any one of embodiments 132 to 136, wherein the subject has normal ejection fraction.

Embodiment 139: The method of any one of embodiments 132 to 138, wherein the subject has a genetic mutation associated with a heart disease.

Embodiment 140: The method of embodiment 139, wherein the genetic mutation is a PLN mutation.

Embodiment 141: The method of any one of embodiments 132 to 140, wherein the subject has a low or undetectable level of DWORF expression compared to a healthy subject.

Embodiment 142: A method of treating a heart disease or disorder in a subject in need thereof comprising administering to the subject the rAAV virion of any one of embodiments 1 to 56 or the composition of embodiment 108.

Embodiment 143: The method of embodiment 142, wherein the subject has a heart disease or disorder.

Embodiment 144: The method of embodiment 142, wherein the subject is a risk of developing a heart disease or disorder.

Embodiment 145: The method or any one of embodiments 142 to 144, wherein the heart disease or disorder is cardiomyopathy.

Embodiment 146: The method of any one of embodiments 142 to 144, wherein the heart disease or disorder is dilated cardiomyopathy.

Embodiment 147: The method of any one of embodiments 142 to 144, wherein the heart disease or disorder is myocardial infarction.

Embodiment 148: The method of any one of embodiments 142 to 144, wherein the heart disease or disorder is chronic myocardial infarction.

Embodiment 149: The method of any one of embodiments 142 to 144, wherein the heart disease or disorder is acute myocardial infarction.

Embodiment 150: The method of any one of embodiments 142 to 149, wherein the subject has an inherited risk allele for a heart disease or disorder.

Embodiment 151: The method of any one of embodiments 142 to 150, wherein the inherited risk allele comprises a mutation to the PLN gene.

Embodiment 152: The method of embodiment 151, wherein the mutation to the PLN gene is a PLN promoter mutation.

Embodiment 153: The method of embodiment 151, wherein the mutation to the PLN gene is a PLN$^{L39stop}$ mutation.

Embodiment 154: The method of embodiment 151, wherein the mutation to the PLN gene is a RC9 mutation.

Embodiment 155: The method of embodiment 151, wherein the mutation to the PLN gene is a R9L mutation.

Embodiment 156: The method of embodiment 151, wherein the mutation to the PLN gene is a PLN gene duplication.

Embodiment 157: The method of embodiment 151, wherein the mutation to the PLN gene is a R14del mutation.

Embodiment 158: The method of any one of embodiments 142 to 157, wherein the heart disease or disorder is with reduced ejection fraction (HFrEF).

Embodiment 159: The method of any one of embodiments 142 to 157, wherein the heart disease of disorder is with preserved ejection fraction (HFpEF).

Embodiment 160: The method of any one of embodiments 142 to 159, wherein the method causes expression of the DWORF polypeptide in the heart of the subject.

Embodiment 161: The method of any one of embodiments 142 to 160, wherein the method causes expression of the DWORF polypeptide in cardiomyocytes.

Embodiment 162: The method of any one of embodiments 142 to 161, wherein the method causes no detectable expression of the DWORF polypeptide in the muscles of the subject except the heart.

Embodiment 163: The method of any one of embodiments 142 to 162, wherein the method causes no detectable expression of the DWORF polypeptide in the liver of the subject.

Embodiment 164: The method of any one of embodiments 142 to 163, wherein the method causes no detectable expression of the DWORF polypeptide in cardiac fibroblasts.

Embodiment 165: The method of any one of embodiments 142 to 164, wherein the method improves one or more measures of cardiac function, optionally fraction shortening and/or left ventricular internal dimension (LVID).

Embodiment 166: The method of any one of embodiments 142 to 165, wherein the improvement in cardiac function is observed at weeks 2 through week 16.

Embodiment 167: The method of any one of embodiments 142 to 166, wherein the method reduces cardiac remodeling.

Embodiment 168: The method of any one of embodiments 142 to 166, wherein the method counteracts a decrease in DWORF expression in subjects suffering from or at risk of a heart disease.

Embodiment 169: The method of any one of embodiments 142 to 168, wherein the rAAV virion is administered by systemic administration.

Embodiment 170: The method of embodiment 169, wherein the systemic administration is selected from intravenous or intracoronary injection.

Embodiment 171: The method of embodiment 169 or 170, wherein the rAAV is administered as a unit dose.

Embodiment 172: The method of embodiment 171, wherein the unit dose comprises about $3\times10^{14}$ vg/kg or less, about $2\times10^{14}$ vg/kg or less, about $1\times10^{14}$ vg/kg or less, about $9\times10^{13}$ vg/kg or less, about $8\times10^{13}$ vg/kg or less, about $7\times10^{13}$ vg/kg or less, about $6\times10^{13}$ vg/kg or less, about $5\times10^{13}$ vg/kg or less, about $4\times10^{13}$ vg/kg or less, about $3\times10^{13}$ vg/kg or less, about $2\times10^{13}$ vg/kg or less, or about $1\times10^{13}$ vg/kg or less.

Embodiment 173: A method of alleviating one or more symptoms of a heart disease or disorder in a subject in need thereof comprising administering the rAAV virion of any one of embodiments 1 to 56 or the composition of embodiment 108.

Embodiment 174: A method of improving one or more symptoms of a heart disease or disorder in a subject in need thereof comprising administering the rAAV virion of any one of embodiments 1 to 56 or the composition of embodiment 108.

Embodiment 175: A method of preventing one or more symptoms of a heart disease or disorder in a subject in need thereof comprising administering the rAAV virion of any one of embodiments 1 to 56 or the composition of embodiment 108.

Embodiment 176: An expression cassette comprising a polynucleotide comprising a 5' to 3' arrangement of elements, wherein the elements comprise:
 i. one or more promoters;
 ii. optionally one or more enhancers;
 iii. optionally one or more introns;
 iv. one or more transgenes;
 v. optionally one or more WPRE sequences; and
 vi. optionally one or more polyadenylation sequences, p(A).

Embodiment 177: The expression cassette of embodiment 176, wherein the 5' to 3' arrangement of elements is selected from:
 i. 5'-promoter-intron-transgene-WPRE-p(A)-3';
 ii. 5'-enhancer-promoter-transgene-WPRE-p(A)-3';
 iii. 5'-enhancer-enhancer-promoter-transgene-WPRE-p(A)-3';
 iv. 5'-enhancer-enhancer-promoter-intron-transgene-WPRE-p(A)-3';
 v. 5'-enhancer-promoter-intron-transgene-WPRE-p(A)-3';
 vi. 5'-enhancer-promoter-intron-transgene-WPRE-p(A)-p(A)-transgene-intron-promoter-enhancer-3';
 vii. 5'-enhancer-promoter-intron-transgene-WPRE-p(A)-enhancer-promoter-intron-transgene-p(A)-3';
 viii. 5'-p(A)-WPRE-transgene-intron-promoter-enhancer-enhancer-promoter-intron-transgene-p(A)-3';
 ix. 5'-promoter-intron-transgene-WPRE-p(A)-p(A)-transgene-intron-promoter-3';
 x. 5'-promoter-intron-transgene-WPRE-p(A)-promoter-intron-transgene-p(A)-3'; and
 xi. 5'-p(A)-WPRE-transgene-intron-promoter-promoter-intron-transgene-p(A)-3'.

Embodiment 178: The expression cassette of embodiment 176 or embodiment 177, wherein the transgene has an increased expression level compared to a second expression cassette comprising a polynucleotide having an arrangement of elements from 5' to 3' comprising: 5'-promoter-transgene-WPRE-p(A)-3'.

Embodiment 179: The expression cassette of embodiment 178, wherein the increased expression level is between about 1.5-fold and about 150-fold compared to the second expression cassette.

Embodiment 180: A recombinant adeno-associated virus (rAAV) virion, comprising a capsid protein and a viral genome comprising an expression cassette of any one of embodiments 176 to 179, the expression cassette flanked by inverted terminal repeats.

Embodiment 181: The rAAV of embodiment 180, wherein the expression cassette comprises a transgene, wherein the transgene encodes a polypeptide use for treating or a preventing a heart disease, or alleviating symptoms associated with a heart disease.

Embodiment 182: The rAAV of embodiment 180 or embodiment 181, wherein the capsid protein is selected from any one of SEQ ID NOs: 145-200.

NUMBERED EMBODIMENTS OF THE INVENTION H

Embodiment 1: A recombinant adeno-associated virus (rAAV) virion, comprising a capsid protein and a viral genome comprising an expression cassette comprising a polynucleotide sequence encoding a polypeptide operatively linked to a promoter, the expression cassette flanked by inverted terminal repeats, optionally wherein the polypeptide is for expression in a cardiac cell or tissue and/or for use in treating or a preventing a heart disease.

Embodiment 2: The rAAV virion of embodiment 1, wherein the polypeptide is selected from DWORF, JPH2, BAG3, CRYAB, Lamin A isoform of LMNA, Lamin C isoform of LMNA, TNNI3, PLN, LAMP2a, LAMP2b, LAMP2c, DPI isoform of DSP, DPII isoform of DSP, DSG2, and JUP.

Embodiment 3: The rAAV virion of embodiment 1 or 2, wherein the polypeptide shares at least 90%, 95%, 96%, 97%, 98%, 99% or 100% sequence identity to a sequence selected from polypeptide sequences in Tables 2a and 2b.

Embodiment 4: The rAAV virion of any one of embodiments 1-3, wherein the promoter is a chicken cTnT promoter.

Embodiment 5: The rAAV virion of embodiment 4, wherein the chicken cTnT promoter shares at least 90%, 95%, 96%, 97%, 98%, or 99% identity to SEQ ID NO: 11.

Embodiment 6: The rAAV virion of embodiment 4, wherein the chicken cTnT promoter comprises SEQ ID NO: 11.

Embodiment 7: The rAAV virion of any one of embodiments 1-3, wherein the promoter is a human cTnT promoter.

Embodiment 8: The rAAV virion of embodiment 7, wherein the human cTnT promoter shares at least 90%, 95%, 96%, 97%, 98%, or 99% identity to SEQ ID NO: 12 or SEQ ID NO: 13.

Embodiment 9: The rAAV virion of embodiment 7, wherein the human cTnT promoter comprises SEQ ID NO: 12 or SEQ ID NO: 13.

Embodiment 10: The rAAV virion of any one of embodiments 1 to 9, wherein the expression cassette further comprises one or more enhancers.

Embodiment 11: The rAAV virion of embodiment 10, wherein the enhancer the one or more enhancers are selected from a ACTC1 cardiac enhancer and a αMHC enhancer.

Embodiment 12: The rAAV virion of embodiment 11, wherein the ACTC1 cardiac enhancer shares at least 90%, 95%, 96%, 97%, 98%, or 99% identity to SEQ ID NO: 78.

Embodiment 13: The rAAV virion of embodiment 11, wherein the ACTC1 cardiac enhancer comprises SEQ ID NO: 78.

Embodiment 14: The rAAV virion of embodiment 11, wherein the αMHC enhancer shares at least 90%, 95%, 96%, 97%, 98%, or 99% identity to SEQ ID NO: 79.

Embodiment 15: The rAAV virion of embodiment 11, wherein the αMHC enhancer comprises SEQ ID NO: 79.

Embodiment 16: The rAAV virion of any one of embodiments 1 to 15, wherein the expression cassette further comprises an intron.

Embodiment 17: The rAAV virion of embodiment 16, wherein the intron is selected from a CMV intron and a chimeric intron.

Embodiment 18: The rAAV virion of embodiment 17, wherein the CMV intron shares at least 90%, 95%, 96%, 97%, 98%, or 99% identity to SEQ ID NO: 80.

Embodiment 19: The rAAV virion of embodiment 17, wherein the CMV intron comprises SEQ ID NO: 80.

Embodiment 20: The rAAV virion of embodiment 17, wherein the chimeric intron shares at least 90%, 95%, 96%, 97%, 98%, or 99% identity to SEQ ID NO: 81.

Embodiment 21: The rAAV virion of embodiment 17, wherein the chimeric intron comprises SEQ ID NO: 81.

Embodiment 22: The rAAV virion of any one of embodiments 1 to 21, wherein the expression cassette further comprises a WPRE sequence.

Embodiment 23: The rAAV virion of embodiment 22, wherein the WPRE sequence shares at least 90%, 95%, 96%, 97%, 98%, or 99% identity to SEQ ID NO: 26.

Embodiment 24: The rAAV virion of embodiment 22, wherein the WPRE sequence comprises SEQ ID NO: 26.

Embodiment 25: The rAAV virion of any one of embodiments 1 to 24, wherein the expression cassette further comprises a polyadenylation sequence.

Embodiment 26: The rAAV virion of embodiment 25, wherein the polyadenylation sequence is selected from a BGH polyadenylation sequence and a SV40 polyadenylation sequence.

Embodiment 27: The rAAV virion of embodiment 26, wherein the BGH polyadenylation sequence shares at least 90%, 95%, 96%, 97%, 98%, or 99% identity to SEQ ID NO: 27.

Embodiment 28: The rAAV virion of embodiment 26, wherein the BGH polyadenylation sequence comprises SEQ ID NO: 27.

Embodiment 29: The rAAV virion of embodiment 26, wherein the SV40 polyadenylation sequence shares at least 90%, 95%, 96%, 97%, 98%, or 99% identity to SEQ ID NO: 28.

Embodiment 30: The rAAV virion of embodiment 26, wherein the SV40 polyadenylation sequence comprises SEQ ID NO: 28.

Embodiment 31: The rAAV virion of any one of embodiments 1 to 30, wherein the expression cassette is flanked by ITRs.

Embodiment 32: The rAAV virion of embodiment 31, wherein the ITRs share at least 90%, 95%, 96%, 97%, 98%, or 99% identity to one or more of SEQ ID NO: 14 and SEQ ID NO: 15.

Embodiment 33: The rAAV virion of embodiment 31, wherein the ITRs comprise one or more of SEQ ID NO: 14 and SEQ ID NO: 15.

Embodiment 34: The rAAV virion of any one of embodiments 1 to 33, wherein the expression cassette comprises a single promoter.

Embodiment 35: The rAAV virion of any one of embodiments 1 to 33, wherein the expression cassette comprises two promoters.

Embodiment 36: The rAAV virion of any one of embodiments 1 to 35, wherein the expression cassette comprises a single copy a sequence encoding the polypeptide.

Embodiment 37: The rAAV virion of any one of embodiments 1 to 35, wherein the expression cassette comprises two copies of a sequence encoding the polypeptide.

Embodiment 38: The rAAV virion of any one of embodiments 1 to 37, wherein the expression cassette comprises one, two, three, or four enhancers.

Embodiment 39: The rAAV virion of any one of embodiments 1 to 38, wherein the expression cassette comprises one or two introns.

Embodiment 40: The rAAV virion of any one of embodiments 1 to 39, wherein the expression cassette comprises one or two WPRE sequences.

Embodiment 41: The rAAV virion of any one of embodiments 1 to 40, wherein the expression cassette comprises one or two polyadenylation sequences.

Embodiment 42: The rAAV virion of any one of embodiments 1 to 41, wherein the expression cassette comprises about 3.2 kb, about, about 3.3 kb, about 3.4 kb, about 3.5 kb, about 3.6 kb, about 3.7 kb, or less.

Embodiment 43: The rAAV virion of any one of embodiments 1 to 42, wherein the expression cassette comprises about 1.9 kb, about 2.1 kb, about 2.2 kb, about 2.3 kb, about 2.4 kb, about 2.5 kb, about 2.6 kb, about 2.7 kb, about 2.8 kb, about 2.9 kb, about 3.0 kb, about 3.1 kb, about 3.2 kb, or more.

Embodiment 44: The rAAV virion of any one of embodiments 1-3, wherein the expression cassette comprises a polynucleotide sequence that shares at least 75%, 80%, 90%, 95%, 96%, 97%, 98%, 99%, or 100% sequence identity to any one of SEQ ID NOs: 20-24 or SEQ ID NOs: 45-75, optionally without the sequence or sequences encoding DWORF (open reading frame or open reading frames encoding DWORF). In some embodiments, where the expression cassette is for expression of a polypeptide other than DWORF, the polynucleotide sequence shares at least 75%, 80%, 90%, 95%, 96%, 97%, 98%, 99%, or 100% identity to a sequence within any one of SEQ ID NOs: 20-24 or SEQ ID NOs: 45-75 where the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 45: The rAAV virion of any one of embodiments 1-3, wherein the expression cassette comprises any one of SEQ ID NOs: 20-24 or SEQ ID NOs: 45-75, optionally without the sequence or sequences encoding DWORF (open reading frame or open reading frames encoding DWORF). In some embodiments, where the expression cassette is for expression of a polypeptide other than DWORF, the polynucleotide sequence comprises a sequence within any one of SEQ ID NOs: 20-24 or SEQ ID NOs: 45-75 where the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 46: The rAAV virion of any one of embodiments 1-3, wherein the expression cassette comprises a polynucleotide sequence that shares at least 75%, 80%, 90%, 95%, 96%, 97%, 98%, or 99% identity to any one of SEQ ID NO: 49, SEQ ID NO: 51, SEQ ID NO: 55, SEQ ID NO: 56, SEQ ID NO: 57, SEQ ID NO: 58, SEQ ID NO: 59 and SEQ ID NO: 60, optionally without the sequence or sequences encoding DWORF (open reading frame or open reading frames encoding DWORF). In some embodiments, where the expression cassette is for expression of a polypeptide other than DWORF, the polynucleotide sequence comprises a sequence sharing at least 75%, 80%, 90%, 95%, 96%, 97%, 98%, or 99% identity to SEQ ID NO: 49, SEQ ID NO: 51, SEQ ID NO: 55, SEQ ID NO: 56, SEQ ID NO: 57, SEQ ID NO: 58, SEQ ID NO: 59 and SEQ ID NO: 60 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 47: The rAAV virion of any one of embodiments 1-3, wherein the expression cassette comprises any one of SEQ ID NO: 49, SEQ ID NO: 51, SEQ ID NO: 55, SEQ ID NO: 56, SEQ ID NO: 57, SEQ ID NO: 58, SEQ ID NO: 59 and SEQ ID NO: 60, optionally without the sequence or sequences encoding DWORF (open reading frame or open reading frames encoding DWORF). In some embodiments, where the expression cassette is for expression of a polypeptide other than DWORF, the polynucleotide sequence comprises a sequence of SEQ ID NO: 49, SEQ ID NO: 51, SEQ ID NO: 55, SEQ ID NO: 56, SEQ ID NO: 57, SEQ ID NO: 58, SEQ ID NO: 59 and SEQ ID NO: 60 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 48: The rAAV virion of any one of embodiments 1-3, wherein the expression cassette comprises a polynucleotide sequence that shares at least 75%, 80%, 90%, 95%, 96%, 97%, 98%, or 99% identity to any one of SEQ ID NO: 55, SEQ ID NO: 56, SEQ ID NO: 57, and SEQ ID NO: 58, optionally without the sequence or sequences encoding DWORF (open reading frame or open reading frames encoding DWORF). In some embodiments, where the expression cassette is for expression of a polypeptide other than DWORF, the polynucleotide sequence comprises a sequence sharing at least 75%, 80%, 90%, 95%, 96%, 97%, 98%, or 99% identity to any one of SEQ ID NO: 55, SEQ ID NO: 56, SEQ ID NO: 57, and SEQ ID NO: 58 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 49: The rAAV virion of any one of embodiments 1-3, wherein the expression cassette comprises any one of SEQ ID NO: 55, SEQ ID NO: 56, SEQ ID NO: 57, and SEQ ID NO: 58, optionally without the sequence or sequences encoding DWORF (open reading frame or open reading frames encoding DWORF). In some embodiments, where the expression cassette is for expression of a polypeptide other than DWORF, the polynucleotide sequence comprises a sequence of any one of SEQ ID NO: 55, SEQ ID NO: 56, SEQ ID NO: 57, and SEQ ID NO: 58 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 50: The rAAV virion of any one of embodiments 1-3, wherein the expression cassette comprises a polynucleotide sequence that shares at least 75%, 80%, 90%, 95%, 96%, 97%, 98%, or 99% identity to any one of SEQ ID NO: 62, SEQ ID NO: 63, SEQ ID NO: 67, SEQ ID NO: 69, SEQ ID NO: 74, and SEQ ID NO: 75, optionally without the sequence or sequences encoding DWORF (open reading frame or open reading frames encoding DWORF). In some embodiments, where the expression cassette is for expression of a polypeptide other than DWORF, the polynucleotide sequence comprises a sequence sharing at least 75%, 80%, 90%, 95%, 96%, 97%, 98%, or 99% identity to any one of SEQ ID NO: 62, SEQ ID NO: 63, SEQ ID NO: 67, SEQ ID NO: 69, SEQ ID NO: 74, and SEQ ID NO: 75 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 51: The rAAV virion of any one of embodiments 1-3, wherein the expression cassette comprises any one of SEQ ID NO: 62, SEQ ID NO: 63, SEQ ID NO: 67, SEQ ID NO: 69, SEQ ID NO: 74, and SEQ ID NO: 75, optionally without the sequence or sequences encoding DWORF (open reading frame or open reading frames encoding DWORF). In some embodiments, where the expression cassette is for expression of a polypeptide other than DWORF, the polynucleotide sequence comprises a sequence of any one of SEQ ID NO: 62, SEQ ID NO: 63, SEQ ID NO: 67, SEQ ID NO: 69, SEQ ID NO: 74, and SEQ ID NO: 75 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 52: The rAAV virion of any one of embodiments 1 to 51, wherein the capsid protein shares at least 98%, at least 99%, or 100% identity to an AAV9 capsid protein (SEQ ID NO: 143).

Embodiment 53: The rAAV virion of any one of embodiments 1 to 51, wherein the capsid protein shares at least 98%, at least 99%, or 100% identity to an AAV5 capsid protein (SEQ ID NO: 144).

Embodiment 54: The rAAV virion of any one of embodiments 1 to 51, wherein the capsid protein is a chimeric capsid protein.

Embodiment 55: The rAAV virion of any one of embodiments 1 to 51, wherein the capsid protein is an AAV5/AAV9 chimeric capsid protein.

Embodiment 56: The rAAV virion of any one of embodiments 1 to 51, wherein the capsid protein is selected from any one of SEQ ID NOs: 145-200.

Embodiment 57: An expression cassette comprising a polynucleotide sequence encoding a polypeptide operatively linked to a promoter, optionally wherein the polypeptide is for expression in a cardiac cell or tissue and/or for use in treating or a preventing a heart disease.

Embodiment 58: The expression cassette of embodiment 57, wherein the polypeptide is selected from DWORF, JPH2, BAG3, CRYAB, Lamin A isoform of LMNA, Lamin C isoform of LMNA, TNNI3, PLN, LAMP2a, LAMP2b, LAMP2c, DPI isoform of DSP, DPII isoform of DSP, DSG2, and JUP, optionally wherein the polypeptide shares at least 90%, 95%, 96%, 97%, 98%, 99% or 100% sequence identity to a sequence selected from polypeptide sequences in Tables 2a and 2b.

Embodiment 59: The expression cassette of embodiment 57 or 58, wherein the promoter is a chicken cTnT promoter.

Embodiment 60: The expression cassette of embodiment 59, wherein the chicken cTnT promoter shares at least 90%, 95%, 96%, 97%, 98%, or 99% identity to SEQ ID NO: 11.

Embodiment 61: The expression cassette of embodiment 59, wherein the chicken cTnT promoter comprises SEQ ID NO: 11.

Embodiment 62: The expression cassette of embodiment 57 or 58, wherein the promoter is a human cTnT promoter.

Embodiment 63: The expression cassette of embodiment 62, wherein the human cTnT promoter shares at least 90%, 95%, 96%, 97%, 98%, or 99% identity to SEQ ID NO: 12 or SEQ ID NO: 13.

Embodiment 64: The expression cassette of embodiment 62, wherein the human cTnT promoter comprises SEQ ID NO: 12 or SEQ ID NO: 13.

Embodiment 65: The expression cassette of any one of embodiments 57 to 64, wherein the expression cassette further comprises one or more enhancers.

Embodiment 66: The expression cassette of embodiment 65, wherein the enhancer the one or more enhancers are selected from a ACTC1 cardiac enhancer and a αMHC enhancer.

Embodiment 67: The expression cassette of embodiment 66, wherein the ACTC1 cardiac enhancer shares at least 90%, 95%, 96%, 97%, 98%, or 99% identity to SEQ ID NO: 78.

Embodiment 68: The expression cassette of embodiment 66, wherein the ACTC1 cardiac enhancer comprises SEQ ID NO: 78.

Embodiment 69: The expression cassette of embodiment 66, wherein the αMHC enhancer shares at least 90%, 95%, 96%, 97%, 98%, or 99% identity to SEQ ID NO: 79.

Embodiment 70: The expression cassette of embodiment 66, wherein the αMHC enhancer comprises SEQ ID NO: 79.

Embodiment 71: The expression cassette of any one of embodiments 57 to 70, wherein the expression cassette further comprises an intron.

Embodiment 72: The expression cassette of any one of embodiments 57 to 70, wherein the intron is selected from a CMV intron and a chimeric intron.

Embodiment 73: The expression cassette of embodiment 72, wherein the CMV intron shares at least 90%, 95%, 96%, 97%, 98%, or 99% identity to SEQ ID NO: 80.

Embodiment 74: The expression cassette of embodiment 72, wherein the CMV intron comprises SEQ ID NO: 80.

Embodiment 75: The expression cassette of embodiment 72, wherein the chimeric intron shares at least 90%, 95%, 96%, 97%, 98%, or 99% identity to SEQ ID NO: 81.

Embodiment 76: The expression cassette of embodiment 72, wherein the chimeric intron comprises SEQ ID NO: 81.

Embodiment 77: The expression cassette of any one of embodiments 57 to 76, wherein the expression cassette further comprises a WPRE sequence.

Embodiment 78: The expression cassette of embodiment 77, wherein the WPRE sequence shares at least 90%, 95%, 96%, 97%, 98%, or 99% identity to SEQ ID NO: 26.

Embodiment 79: The expression cassette of embodiment 77, wherein the WPRE sequence comprises SEQ ID NO: 26.

Embodiment 80: The expression cassette of any one of embodiments 57 to 79, wherein the expression cassette further comprises a polyadenylation sequence.

Embodiment 81: The expression cassette of embodiment 80, wherein the polyadenylation sequence is selected from a BGH polyadenylation sequence and a SV40 polyadenylation sequence.

Embodiment 82: The expression cassette of embodiment 81, wherein the BGH polyadenylation sequence shares at least 90%, 95%, 96%, 97%, 98%, or 99% identity to SEQ ID NO: 27.

Embodiment 83: The expression cassette of embodiment 81, wherein the BGH polyadenylation sequence comprises SEQ ID NO: 27.

Embodiment 84: The expression cassette of embodiment 81, wherein the SV40 polyadenylation sequence shares at least 90%, 95%, 96%, 97%, 98%, or 99% identity to SEQ ID NO: 28.

Embodiment 85: The expression cassette of embodiment 81, wherein the SV40 polyadenylation sequence comprises SEQ ID NO: 28.

Embodiment 86: The expression cassette of any one of embodiments 57 to 85, wherein the expression cassette is flanked by ITRs.

Embodiment 87: The expression cassette of embodiment 86, wherein the ITRs share at least 90%, 95%, 96%, 97%, 98%, or 99% identity to one or more of SEQ ID NO: 14 and SEQ ID NO: 15.

Embodiment 88: The expression cassette of embodiment 86, wherein the ITRs comprise one or more of SEQ ID NO: 14 and SEQ ID NO: 15.

Embodiment 89: The expression cassette of any one of embodiments 57 to 88 comprising a single promoter.

Embodiment 90: The expression cassette of any one of embodiments 57 to 88 comprising two promoters.

Embodiment 91: The expression cassette of any one of embodiments 57 to 90 comprising a single copy aسlauequence encoding the polypeptide.

Embodiment 92: The expression cassette of any one of embodiments 57 to 90 comprising two copies of a sequence encoding the polypeptide.

Embodiment 93: The expression cassette of any one of embodiments 57 to 92 comprising one, two, three, or four enhancers.

Embodiment 94: The expression cassette of any one of embodiments 57 to 93 comprising one or two introns.

Embodiment 95: The expression cassette of any one of embodiments 57 to 94 comprising one or two WPRE sequences.

Embodiment 96: The expression cassette of any one of embodiments 57 to 95 comprising one or two polyadenylation sequences.

Embodiment 97: The expression cassette of any one of embodiments 57 to 96 comprising about 3.2 kb, about, about 3.3 kb, about 3.4 kb, about 3.5 kb, about 3.6 kb, about 3.7 kb, or less.

Embodiment 98: The expression cassette of any one of embodiments 57 to 97 comprising about 1.9 kb, about 2.1 kb, about 2.2 kb, about 2.3 kb, about 2.4 kb, about 2.5 kb, about 2.6 kb, about 2.7 kb, about 2.8 kb, about 2.9 kb, about 3.0 kb, about 3.1 kb, about 3.2 kb, or more.

Embodiment 99: The expression cassette of embodiment 57 or 58, comprising a polynucleotide sequence that shares at least 75%, 80%, 90%, 95%, 96%, 97%, 98%, 99%, or 100% identity to any one of SEQ ID NOs: 20-24 or SEQ ID NOs: 45-75, optionally without the sequence or sequences encoding DWORF (open reading frame or open reading frames encoding DWORF). In some embodiments, where the expression cassette is for expression of a polypeptide other than DWORF, the polynucleotide sequence shares at least 75%, 80%, 90%, 95%, 96%, 97%, 98%, 99%, or 100% identity to a sequence of any one of SEQ ID NOs: 20-24 or SEQ ID NOs: 45-75 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 100: The expression cassette of embodiment 57 or 58, comprising a polynucleotide sequence of any one of SEQ ID NOs: 20-24 or SEQ ID NOs: 45-75, optionally without the sequence or sequences encoding DWORF (open reading frame or open reading frames encoding DWORF). In some embodiments, where the expression cassette is for expression of a polypeptide other than DWORF, the polynucleotide sequence comprises any one of SEQ ID NOs: 20-24 or SEQ ID NOs: 45-75 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 101: The expression cassette of embodiment 57 or 58, comprising a polynucleotide sequence that shares at least 75%, 80%, 90%, 95%, 96%, 97%, 98%, or 99% identity to any one of SEQ ID NO: 49, SEQ ID NO: 51, SEQ ID NO: 55, SEQ ID NO: 56, SEQ ID NO: 57, SEQ ID NO: 58, SEQ ID NO: 59, and SEQ ID NO: 60, optionally without the sequence or sequences encoding DWORF (open reading frame or open reading frames encoding DWORF). In some embodiments, where the expression cassette is for expression of a polypeptide other than DWORF, the polynucleotide sequence shares at least 75%, 80%, 90%, 95%, 96%, 97%, 98%, or 99% identity to any one of SEQ ID NO: 49, SEQ ID NO: 51, SEQ ID NO: 55, SEQ ID NO: 56, SEQ ID NO: 57, SEQ ID NO: 58, SEQ ID NO: 59, and SEQ ID NO: 60 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 102: The expression cassette of embodiment 57 or 58, comprising a polynucleotide sequence of any one of SEQ ID NO: 49, SEQ ID NO: 51, SEQ ID NO: 55, SEQ ID NO: 56, SEQ ID NO: 57, SEQ ID NO: 58, SEQ ID NO: 59, and SEQ ID NO: 60, optionally without the sequence or sequences encoding DWORF (open reading frame or open reading frames encoding DWORF). In some embodiments, where the expression cassette is for expression of a polypeptide other than DWORF, the polynucleotide sequence comprises a sequence of any one of SEQ ID NO: 49, SEQ ID NO: 51, SEQ ID NO: 55, SEQ ID NO: 56, SEQ ID NO: 57, SEQ ID NO: 58, SEQ ID NO: 59, and SEQ ID NO: 60 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 103: The expression cassette of embodiment 57 or 58, comprising a polynucleotide sequence that shares at least 75%, 80%, 90%, 95%, 96%, 97%, 98%, or 99% identity to any one of SEQ ID NO: 55, SEQ ID NO: 56, SEQ ID NO: 57, and SEQ ID NO: 58, optionally without the sequence or sequences encoding DWORF (open reading frame or open reading frames encoding DWORF). In some embodiments, where the expression cassette is for expression of a polypeptide other than DWORF, the polynucleotide sequence shares at least 75%, 80%, 90%, 95%, 96%, 97%, 98%, or 99% identity to any one of SEQ ID NO: 55, SEQ ID NO: 56, SEQ ID NO: 57, and SEQ ID NO: 58 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 104: The expression cassette of embodiment 57, comprising any one of SEQ ID NO: 55, SEQ ID NO: 56, SEQ ID NO: 57, and SEQ ID NO: 58, optionally without the sequence or sequences encoding DWORF (open reading frame or open reading frames encoding DWORF). In some embodiments, where the expression cassette is for expression of a polypeptide other than DWORF, the polynucleotide sequence comprises a sequence of any one of SEQ ID NO: 55, SEQ ID NO: 56, SEQ ID NO: 57, and SEQ ID NO: 58 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 105: The expression cassette of embodiment 57 or 58, comprising a polynucleotide sequence that shares at least 75%, 80%, 90%, 95%, 96%, 97%, 98%, or 99% identity to any one of SEQ ID NO: 62, SEQ ID NO: 63, SEQ ID NO: 67, SEQ ID NO: 69, SEQ ID NO: 74, and SEQ ID NO: 75, optionally without the sequence or sequences encoding DWORF (open reading frame or open reading frames encoding DWORF). In some embodiments, where the expression cassette is for expression of a polypeptide other than DWORF, the polynucleotide sequence comprises a sequence that shares at least 75%, 80%, 90%, 95%, 96%, 97%, 98%, or 99% identity to any one of SEQ ID NO: 62, SEQ ID NO: 63, SEQ ID NO: 67, SEQ ID NO: 69, SEQ ID NO: 74, and SEQ ID NO: 75 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 106: The expression cassette of embodiment 57 or 58, comprising any one of SEQ ID NO: 62, SEQ ID NO: 63, SEQ ID NO: 67, SEQ ID NO: 69, SEQ ID NO: 74, and SEQ ID NO: 75, optionally without the sequence or sequences encoding DWORF (open reading frame or open reading frames encoding DWORF). In some embodiments, where the expression cassette is for expression of a polypeptide other than DWORF, the polynucleotide sequence comprises a sequence of any one of SEQ ID NO: 62, SEQ ID NO: 63, SEQ ID NO: 67, SEQ ID NO: 69, SEQ ID NO: 74, and SEQ ID NO: 75 in which the sequence or sequences encoding DWORF (open reading frame or open reading frames encoding DWORF) are replaced by a sequence or sequences encoding the polypeptide other than DWORF (e.g., any polypeptide described herein, such as any polypeptide listed in Table 2b which also provide sequences of such polypeptides).

Embodiment 107: The expression cassette of any one of embodiments 99 to 106, wherein the expression cassette does not comprise a 5' inverted terminal repeat and a 3' inverted terminal repeat of the polynucleotide sequence.

Embodiment 108: A pharmaceutical composition comprising the rAAV virion of any one of embodiments 1 to 56 and a pharmaceutically acceptable carrier, or a pharmaceutical composition comprising a vector comprising the expression cassette of any of embodiments 57 to 107 and a pharmaceutically acceptable carrier.

Embodiment 109: A kit comprising the pharmaceutical composition of embodiment 108.

Embodiment 110: A method of increasing a polypeptide expression in a cell comprising contacting a cell with the rAAV virion of any one of embodiments 1 to 56, a vector comprising the expression cassette of any one of embodiments 57-107, or the composition of embodiment 108.

Embodiment 111: The method of embodiment 110, wherein the cell is a cardiac cell.

Embodiment 112: The method of embodiment 111, wherein the cardiac cell is a cardiomyocyte.

Embodiment 113: The method of any one of embodiments 110 to 112, wherein the polypeptide expression is increased between about 1.5-fold and 150-fold.

Embodiment 114: The method of any one of embodiments 110 to 113, wherein the contacting is in vitro.

Embodiment 115: The method of any one of embodiments 110 to 113, wherein the contacting is in vivo.

Embodiment 116: A method of increasing a polypeptide expression in a tissue comprising contacting the tissue with the rAAV virion of any one of embodiments 1 to 56, a vector comprising the expression cassette of any one of embodiments 57-107, or the composition of embodiment 108.

Embodiment 117: The method of embodiment 116, wherein the tissue is cardiac tissue.

Embodiment 118: The method of embodiment 116 or 117, wherein polypeptide expression is increased between about 1.5-fold and 150-fold.

Embodiment 119: The method of any one of embodiments 116 to 118, wherein the contacting is in vitro.

Embodiment 120: The method of embodiment 116 or 118, wherein the contacting is in vivo.

Embodiment 121: A method of increasing a polypeptide expression in an organ comprising contacting the organ with the rAAV virion of any one of embodiments 1 to 56, a vector comprising the expression cassette of any one of embodiments 57-107, or the composition of embodiment 108.

Embodiment 122: The method of embodiment 121, wherein the organ is a heart.

Embodiment 123: The method of embodiment 122, wherein the heart is diseased or is at risk of disease.

Embodiment 124: The method of embodiment 122 or embodiment 123, wherein the heart has reduced or borderline ejection fraction.

Embodiment 125: The method of embodiment 122 or embodiment 123, wherein the heart has a normal ejection fraction.

Embodiment 126: The method of any one of embodiments 122 to 125, wherein the heart comprises a genetic mutation associated with a heart disease.

Embodiment 127: The method of embodiment 126, wherein the genetic mutation is a PLN mutation.

Embodiment 128: The method of any one of embodiments 121 to 127, wherein the heart has low or undetectable polypeptide expression compared to a healthy heart.

Embodiment 129: The method of any one of embodiments 121 to 128, wherein the polypeptide expression is increased between about 1.5-fold and 150-fold.

Embodiment 130: The method of any one of embodiments 121 to 129, wherein the contacting is in vitro.

Embodiment 131: The method of any one of embodiments 121 to 129, wherein the contacting is in vivo.

Embodiment 132: A method of increasing a polypeptide expression in an subject comprising administering to the subject the rAAV virion of any one of embodiments 1 to 56, a vector comprising the expression cassette of any one of embodiments 57-107, or the composition of embodiment 108.

Embodiment 133: The method of embodiment 132, wherein the subject is an animal.

Embodiment 134: The method of embodiment 132, wherein the subject is a human.

Embodiment 135: The method of any one of embodiments 132 to 134, wherein the polypeptide expression is increased in the heart of the subject.

Embodiment 136: The method of any one of embodiments 132 to 135, wherein subject has a heart disease or is at risk of a heart disease.

Embodiment 137: The method of any one of embodiments 132 to 136, wherein subject has borderline or reduced ejection fraction.

Embodiment 138: The method of any one of embodiments 132 to 136, wherein the subject has normal ejection fraction.

Embodiment 139: The method of any one of embodiments 132 to 138, wherein the subject has a genetic mutation associated with a heart disease.

Embodiment 140: The method of embodiment 139, wherein the genetic mutation is a PLN mutation.

Embodiment 141: The method of any one of embodiments 132 to 140, wherein the subject has a low or undetectable level of the polypeptide expression compared to a healthy subject.

Embodiment 142: A method of treating a heart disease or disorder in a subject in need thereof comprising administering to the subject the rAAV virion of any one of embodiments 1 to 56, a vector comprising the expression cassette of any one of embodiments 57-107, or the composition of embodiment 108.

Embodiment 143: The method of embodiment 142, wherein the subject has a heart disease or disorder.

Embodiment 144: The method of embodiment 142, wherein the subject is a risk of developing a heart disease or disorder.

Embodiment 145: The method or any one of embodiments 142 to 144, wherein the heart disease or disorder is cardiomyopathy.

Embodiment 146: The method of any one of embodiments 142 to 144, wherein the heart disease or disorder is dilated cardiomyopathy.

Embodiment 147: The method of any one of embodiments 142 to 144, wherein the heart disease or disorder is myocardial infarction.

Embodiment 148: The method of any one of embodiments 142 to 144, wherein the heart disease or disorder is chronic myocardial infarction.

Embodiment 149: The method of any one of embodiments 142 to 144, wherein the heart disease or disorder is acute myocardial infarction.

Embodiment 150: The method of any one of embodiments 142 to 149, wherein the subject has an inherited risk allele for a heart disease or disorder.

Embodiment 151: The method of any one of embodiments 142 to 150, wherein the inherited risk allele comprises a mutation to the PLN gene.

Embodiment 152: The method of embodiment 151, wherein the mutation to the PLN gene is a PLN promoter mutation.

Embodiment 153: The method of embodiment 151, wherein the mutation to the PLN gene is a $PLN^{L39stop}$ mutation.

Embodiment 154: The method of embodiment 151, wherein the mutation to the PLN gene is a RC9 mutation.

Embodiment 155: The method of embodiment 151, wherein the mutation to the PLN gene is a R9L mutation.

Embodiment 156: The method of embodiment 151, wherein the mutation to the PLN gene is a PLN gene duplication.

Embodiment 157: The method of embodiment 151, wherein the mutation to the PLN gene is a R14del mutation.

Embodiment 158: The method of any one of embodiments 142 to 157, wherein the heart disease or disorder is with reduced ejection fraction (HFrEF).

Embodiment 159: The method of any one of embodiments 142 to 157, wherein the heart disease of disorder is with preserved ejection fraction (HFpEF).

Embodiment 160: The method of any one of embodiments 142 to 159, wherein the method causes expression of the polypeptide in the heart of the subject.

Embodiment 161: The method of any one of embodiments 142 to 160, wherein the method causes expression of the polypeptide in cardiomyocytes.

Embodiment 162: The method of any one of embodiments 142 to 161, wherein the method causes no detectable expression of the polypeptide in the muscles of the subject except the heart.

Embodiment 163: The method of any one of embodiments 142 to 162, wherein the method causes no detectable expression of the polypeptide in the liver of the subject.

Embodiment 164: The method of any one of embodiments 142 to 163, wherein the method causes no detectable expression of the polypeptide in cardiac fibroblasts.

Embodiment 165: The method of any one of embodiments 142 to 164, wherein the method improves one or more measures of cardiac function, optionally fraction shortening and/or left ventricular internal dimension (LVID).

Embodiment 166: The method of any one of embodiments 142 to 165, wherein the improvement in cardiac function is observed at weeks 2 through week 24.

Embodiment 167: The method of any one of embodiments 142 to 166, wherein the method reduces cardiac remodeling.

Embodiment 168: The method of any one of embodiments 142 to 166, wherein the method counteracts a decrease in the polypeptide expression in subjects suffering from or at risk of a heart disease.

Embodiment 169: The method of any one of embodiments 142 to 168, wherein the administering is by systemic administration.

Embodiment 170: The method of embodiment 169, wherein the systemic administration is selected from intravenous or intracoronary injection.

Embodiment 171: The method of embodiment 169 or 170, wherein the rAAV is administered as a unit dose.

Embodiment 172: The method of embodiment 171, wherein the unit dose comprises about $3\times10^{14}$ vg/kg or less, about $2\times10^{14}$ vg/kg or less, about $1\times10^{14}$ vg/kg or less, about $9\times10^{13}$ vg/kg or less, about $8\times10^{13}$ vg/kg or less, about $7\times10^{13}$ vg/kg or less, about $6\times10^{13}$ vg/kg or less, about $5\times10^{13}$ vg/kg or less, about $4\times10^{13}$ vg/kg or less, about $3\times10^{13}$ vg/kg or less, about $2\times10^{13}$ vg/kg or less, or about $1\times10^{13}$ vg/kg or less.

Embodiment 173: A method of alleviating one or more symptoms of a heart disease or disorder in a subject in need thereof comprising administering the rAAV virion of any one of embodiments 1 to 56, a vector comprising the expression cassette of any one of embodiments 57-107, or the composition of embodiment 108.

Embodiment 174: A method of improving one or more symptoms of a heart disease or disorder in a subject in need thereof comprising administering the rAAV virion of any one of embodiments 1 to 56, a vector comprising the expression cassette of any one of embodiments 57-107, or the composition of embodiment 108.

Embodiment 175: A method of preventing one or more symptoms of a heart disease or disorder in a subject in need thereof comprising administering the rAAV virion of any one of embodiments 1 to 56, a vector comprising the expression cassette of any one of embodiments 57-107, or the composition of embodiment 108.

Embodiment 176: An expression cassette comprising a polynucleotide comprising:
 i. one or more promoters;
 ii. optionally one or more enhancers;
 iii. optionally one or more introns;
 iv. one or more transgenes, optionally wherein the one or more transgenes encode one or more polypeptides for use in treating or a preventing a heart disease;
 v. optionally one or more WPRE sequences; and
 vi. optionally one or more polyadenylation sequences, p(A).

Embodiment 177: The expression cassette of embodiment 176, wherein the 5' to 3' arrangement of elements is selected from:
 (i) 5'-promoter-transgene-WPRE-p(A)-3';
 (ii) 5'-promoter-intron-transgene-WPRE-p(A)-3';
 (iii) 5'-promoter-transgene-WPRE-p(A)-promoter-transgene-WPRE-p(A);
 (iv) 5'-enhancer-promoter-transgene-WPRE-p(A)-3';
 (v) 5'-enhancer-promoter-intron-transgene-WPRE-p(A)-3';
 (vi) 5'-enhancer-enhancer-promoter-transgene-WPRE-p(A)-3';
 (vii) 5'-enhancer-enhancer-promoter-intron-transgene-WPRE-p(A)-3';
 (viii) 5'-enhancer-promoter-intron-transgene-WPRE-p(A)-p(A)-transgene-intron-promoter-enhancer-3';
 (ix) 5'-enhancer-promoter-intron-transgene-WPRE-p(A)-enhancer-promoter-intron-transgene-p(A)-3';
 (x) 5'-p(A)-WPRE-transgene-intron-promoter-enhancer-enhancer-promoter-intron-transgene-p(A)-3';
 (xi) 5'-promoter-intron-transgene-WPRE-p(A)-p(A)-transgene-intron-promoter-3';
 (xii) 5'-promoter-intron-transgene-WPRE-p(A)-promoter-intron-transgene-p(A)-3'; and
 (xiii) 5'-p(A)-WPRE-transgene-intron-promoter-promoter-intron-transgene-p(A)-3';
 wherein optionally the transgene encodes a polypeptide for use in treating or a preventing a heart disease.

Embodiment 178: The expression cassette of embodiment 176 or embodiment 177, wherein the transgene has an increased expression level compared to a second expression cassette comprising a polynucleotide having an arrangement of elements from 5' to 3' comprising: 5'-promoter-transgene-WPRE-p(A)-3'.

Embodiment 179: The expression cassette of embodiment 178, wherein the increased expression level is between about 1.5-fold and about 150-fold compared to the second expression cassette.

Embodiment 180: A recombinant adeno-associated virus (rAAV) virion, comprising a capsid protein and a viral genome comprising an expression cassette of any one of embodiments 176 to 179, the expression cassette flanked by inverted terminal repeats.

Embodiment 181: The rAAV of embodiment 180, wherein the expression cassette comprises a transgene, wherein the transgene encodes a polypeptide for use in treating or a preventing a heart disease, or alleviating symptoms associated with a heart disease.

Embodiment 182: The rAAV of embodiment 180 or embodiment 181 wherein the capsid protein is selected from any one of SEQ ID NOs: 145-200.

EXAMPLES

Example 1: Novel Expression Cassettes

The purpose of this study was to evaluate several engineered expression cassettes for their ability to express a transgene in human induced pluripotent stem cell derived cardiomyocytes (hiPSC-CM) and a mouse model.

Figure 1:
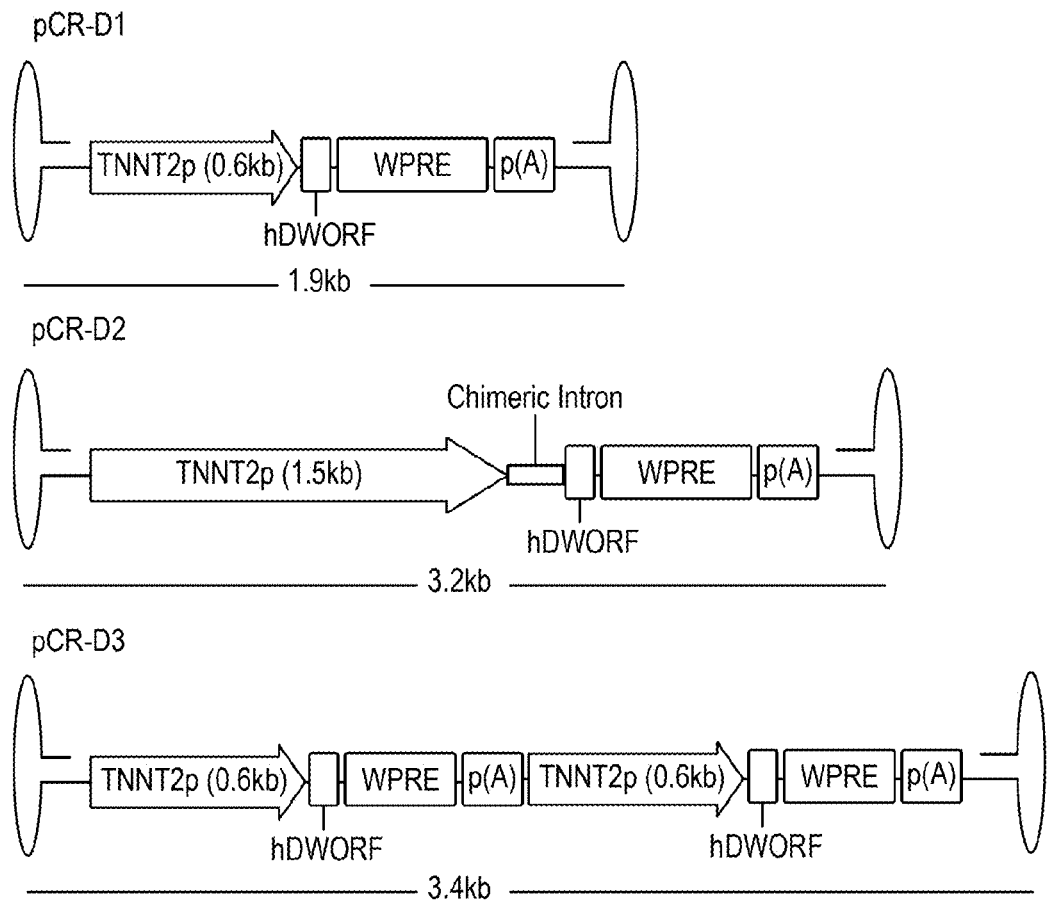
FIG. 1 shows a diagram of illustrative embodiments of expression cassettes comprising a polynucleotide encoding a promoter, a DWORF polypeptide, a WPRE sequence, and a poly(A) signal sequence flanked by AAV inverted terminal repeats.
Figure 2:
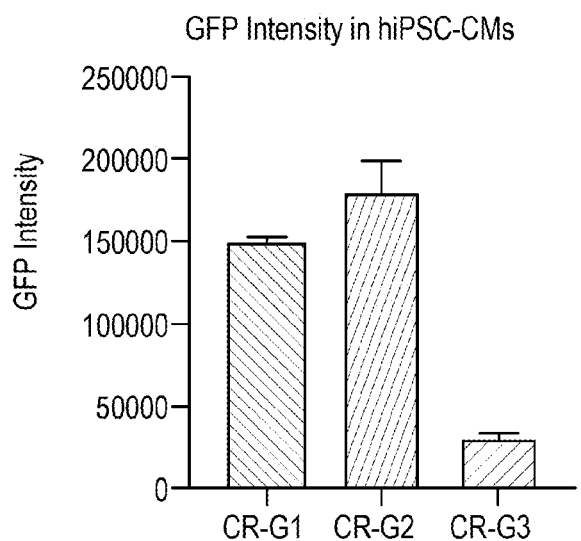
FIG. 2 is a graph showing expression of GFP delivered to human induced pluripotent stem cell derived cardiomyocytes in vitro using an embodiment of an expression cassette packaged into an rAAV virion.
Figure 3:
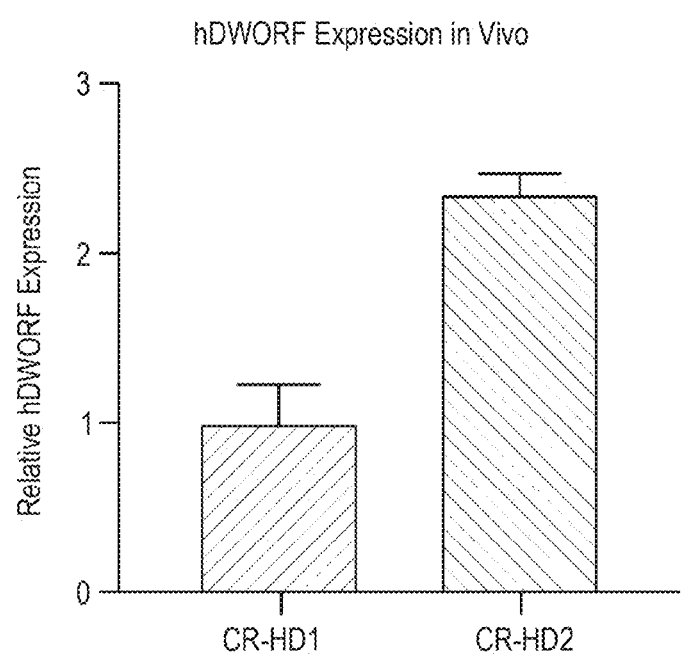
FIG. 3 is a graph showing expression of human DWORF polypeptide delivered in vivo in a murine model using an embodiment of an expression cassette packed into an rAAV virion using an AAV9 capsid protein.

The human DWORF (hDWORF) polynucleotide (SEQ ID NO: 33) was inserted into expression cassettes designed to induce strong cardiomyocyte-specific expression while maintaining a total size of 3-4.7 kbp in length. Three unique expression cassettes were generated, pCR-HD1 (SEQ ID NO: 22), pCR-HD2 (SEQ ID NO: 23), and pCR-HD3. FIG. 1 shows an illustrative embodiment of each expression cassette, which contained iterations of a cardiac Troponin T promoter (see Table 3), WPRE (SEQ ID NO: 26) and BGH poly(A) signal (SEQ ID NO: 27). To evaluate expression of a transgene encoded by each expression cassette in hiPSC-CMs, the DWORF transgene was replaced with GFP in each expression cassettes, designated CR-G1, CR-G2, and CR-G3 corresponding to pCR-HD1, pCR-HD2, and pCR-HD3, respectively. The CR-G1, CR-G2, and CR-G3 expression cassettes were packaged into rAAV virions using an AAV6 capsid (SEQ ID NO: 39) protein. Cells were infected with each rAAV virion containing the expression cassette variants at an MOI of 50,000, and GFP expression was quantified by flow cytometry. FIG. 2 shows the pCR-G1, pCR-G2, and pCR-G3 expression cassettes showed high levels of expression in hiPSC-CMs. Surprisingly, the double transgene construct exhibited lower expression, likely due to the homologous recombination between the tandem repeat sequences. Next, the expression cassettes containing hDWORF, pCR-HD1 and pCR-HD2 were evaluated in a wild type CD1 mouse model. Each cassette was packaged into rAAV virions using an AAV9 capsid protein. The rAAV virions ($5 \times 10^{11}$ vg) were administered systemically by retro-orbital injection into wild type CD1 mice (N=2). Two weeks following injection, animals were sacrificed and hDWORF expression was assessed in hearts. FIG. 3 shows the pCR-HD2 expression cassette results in about a 2-fold increase in hDWORF expression. It was concluded that increasing the length of the canonical hTNNT2 promoter from 600 bp to 1.5 kb, increasing total vector size from 1.9 kb to 3.2 kb, and/or inserting an intron surprisingly doubles gene expression.

Example 2: Evaluation in hiPSC-CMs

The purpose of this study was to evaluate the ability of chimeric capsid proteins to facilitate infection of hiPSC- CMs with an rAAV virion containing an expression cassette encoding an HA-tagged hDWORF protein and the chimeric capsid protein.

Figure 4A:
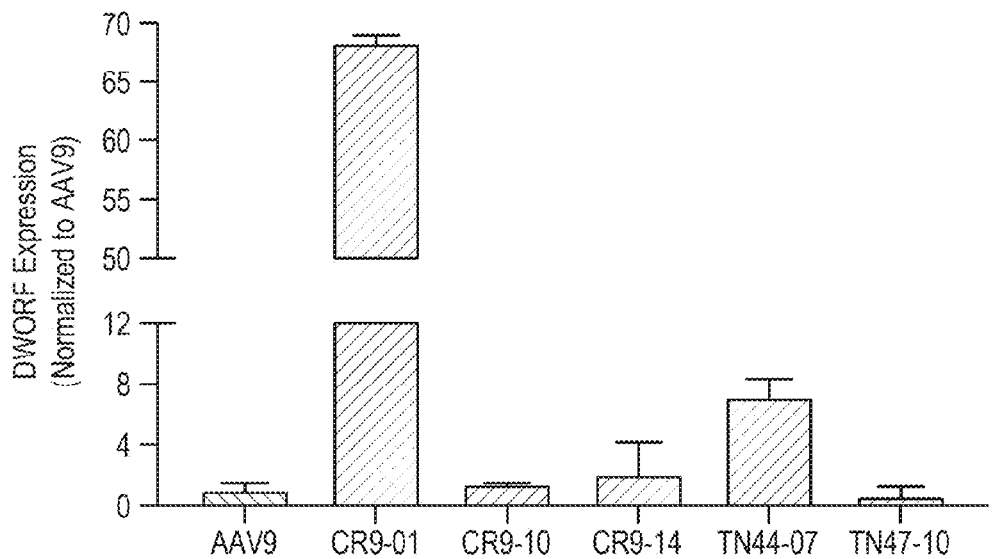
FIG. 4A is a graph showing expression of human DWORF in induced pluripotent stem cell derived cardiomyocytes using an embodiment of an expression cassette packaged into an rAAV virion one of several AAV protein capsid proteins described herein.
Figure 4B:
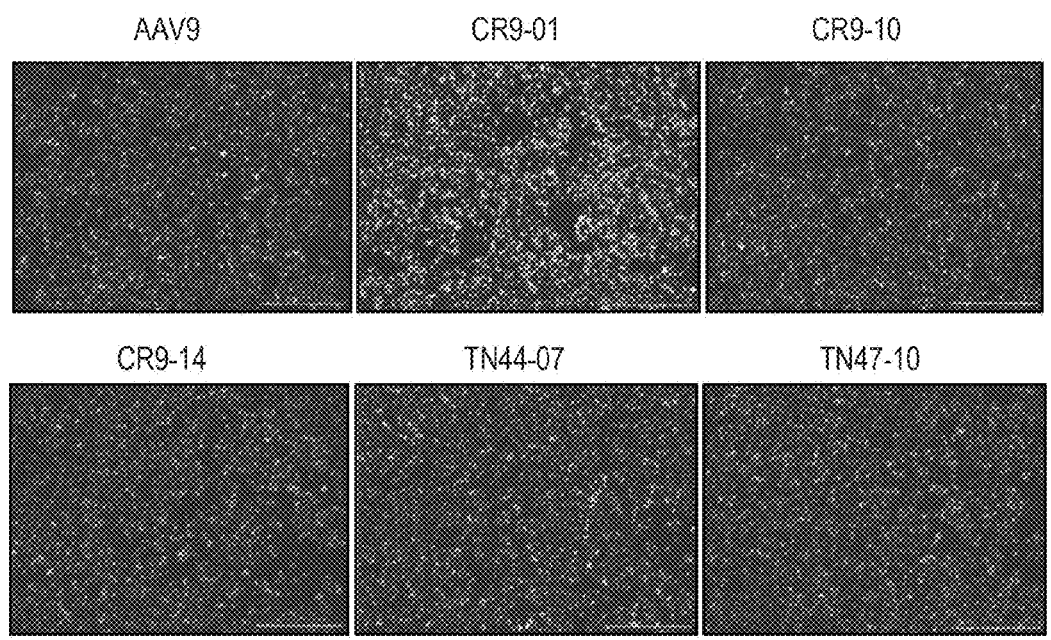
FIG. 4B is a series of images showing expression of GFP using an embodiment of an expression cassette described herein packaged into an rAAV virion one of several AAV protein capsid proteins described herein.

Expression cassettes encoding an HA-tagged hDWORF protein were packaged into rAAV virions with using a one of five chimeric capsid proteins. The chimeric capsid proteins tested include CR9-01 (SEQ ID NO: 29), CR9-10 (SEQ ID NO: 19), CR9-14 (SEQ ID NO: 30), TN44-07 (SEQ ID NO: 31), or TN47-10 (SEQ ID NO: 18), and the AAV9 capsid protein (SEQ ID NO: 16) was used as a control. Wild type hiPSC-CMs were infected at a MOI of 3,900. Five days following infection, cells were fixed and stained for SERCA2a and HA-tagged hDWORF. Stained cells were imaged (FIG. 4B) and quantified (FIG. 4A) using a cytation imager, and expression was normalized to AAV9. FIG. 4A shows HA-tagged hDWORF expression in hiPSC-CM cell cultures infected with rAAV virions containing the CR9-01, CR9-10, CR9-14, or TN44-07 chimeric capsid proteins. Each of these capsids performed as well or better than the AAV9 capsid protein in delivering a functional expression cassette.

Example 3: Evaluation in a Murine Model

The purpose of this study was to evaluate the ability of chimeric capsid proteins to facilitate infection of heart tissue in wildtype mice with an rAAV virion containing an expression cassette encoding an HA-tagged hDWORF protein and the chimeric capsid protein.

Figure 5A:
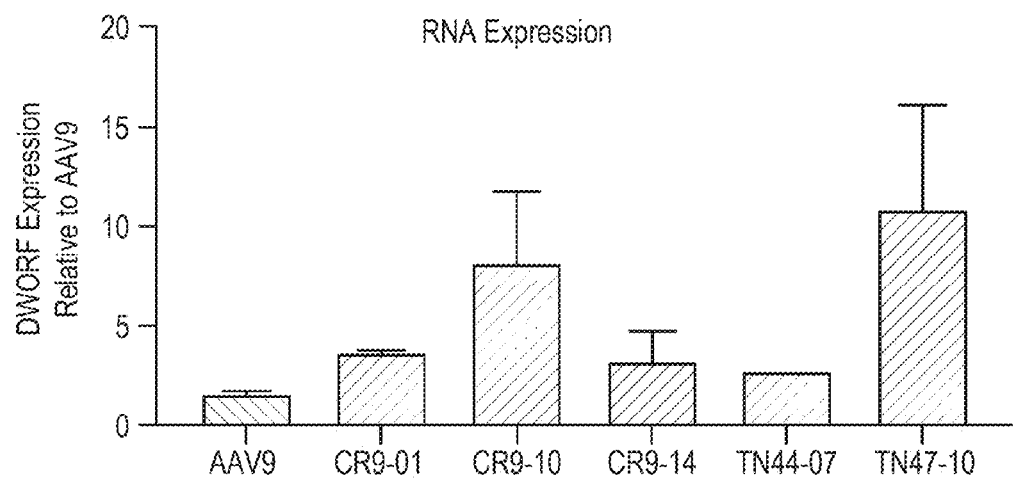
FIG. 5A is a graph showing DWORF RNA expression in heart tissue from animals treated with rAAV virions containing an embodiment of an expression cassette packaged with one of five chimeric capsid proteins or the AAV9 capsid protein.
Figure 5B:
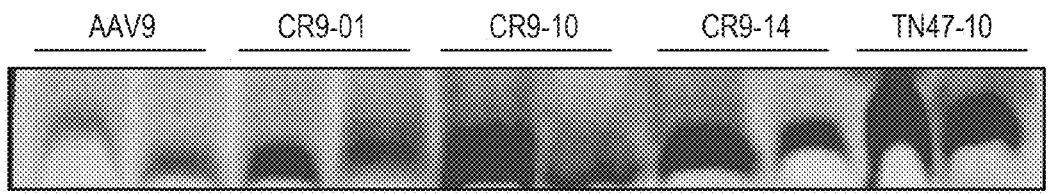
FIG. 5B is an immunoblot showing DWORF protein levels in heart tissue from animals treated with rAAV virions containing an embodiment of an expression cassette packaged with one of four chimeric capsid proteins or the AAV9 capsid protein.

Expression cassettes encoding an HA-tagged hDWORF protein were packaged into rAAV virions with using one of five chimeric capsid proteins. The chimeric capsid proteins tested include CR9-01 (SEQ ID NO: 29), CR9-10 (SEQ ID NO: 19), CR9-14 (SEQ ID NO: 30), TN44-07 (SEQ ID NO: 31), or TN47-10 (SEQ ID NO: 18), and the AAV9 capsid protein (SEQ ID NO: 16) was used as a control. The rAAV virions were delivered by retro-orbital injection into wild-type mice at a dose of $5\times10^{11}$ vg/mouse (N=3). Fourteen days following injection, animals were sacrificed, and heart tissue was collected for RNA and protein analysis. FIG. 5A shows hDWORF RNA expression in heart tissue infected with the indicated capsid. All expression levels were normalized to the expression levels in the AAV9 group. The results indicate that in vivo delivery of rAAV virions packaged with the CR9-01, CR9-10, CR9-14, TN44-07, and TN47-10 each showed increased hDWORF expression compared to parental AAV9. The rAAV virions containing the CR9-10 and TN47-10 capsids showed the highest levels of expression compared to the other tested capsids (~9-fold and -11-fold increased, respectively). FIG. 5B shows that hDWORF protein expression confirmed the RNA expression levels in the heart tissue, indicating that hDWORF RNA was translated to protein in the infected cells and that the modified capsids dramatically increased protein expression.

Example 4: DWORF Gene Therapy in a PLN-R14$^{\Delta/\Delta}$ Model

The purpose of this study was to evaluate the ability of rAAV virions containing an expression cassette encoding an mDWORF protein to reduce symptoms associated with cardiomyopathy in mice harboring the PLN-R14 deletion mutation.

Transgenic mice expressing a homozygous PLN gene harboring the arginine 14 deletion (PLN-R14$^{\Delta/\Delta}$) recapitulates human cardiomyopathy, exhibiting similar histopathologic abnormalities and premature death (Haghighi K et al. Proc. Natl. Acad. Sci. U.S.A 103:1388-1393 (2006)). In particular, the transgenic mice can be used as a model of dilated cardiomyopathy. The model is significantly more severe than a MLP$^{-/-}$ knockout and clinically relevant, as there are no known MLP knockout cardiomyopathy patients.

Figure 6A:
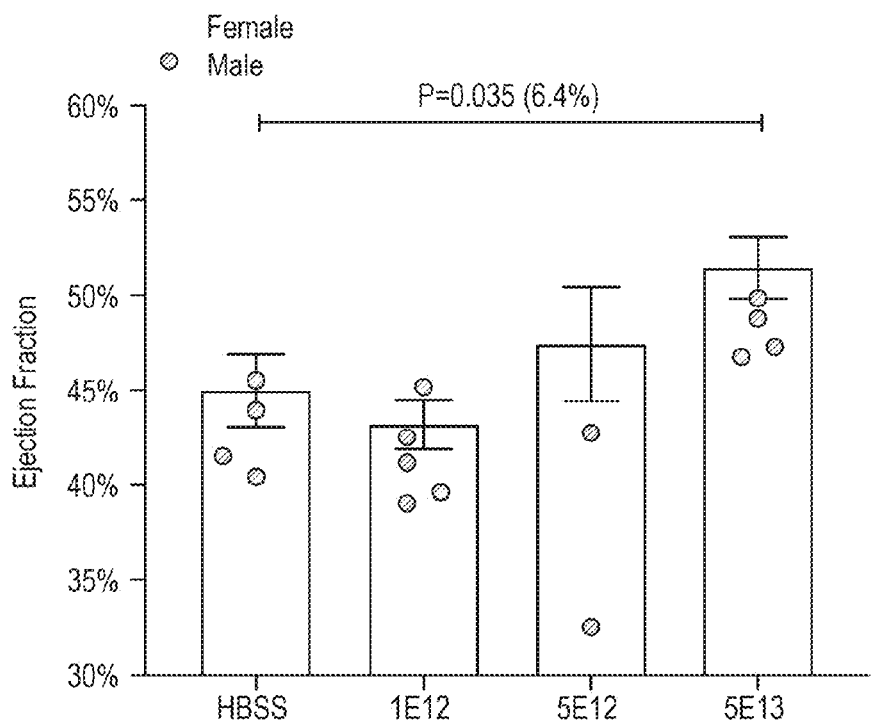
FIG. 6A is a graph showing improved ejection fraction in a PLN-R14$^{\Delta/\Delta}$ mouse model following treatment with an embodiment of an expression cassette packaged into an rAAV virion using AAV9 protein capsid.
Figure 6B:
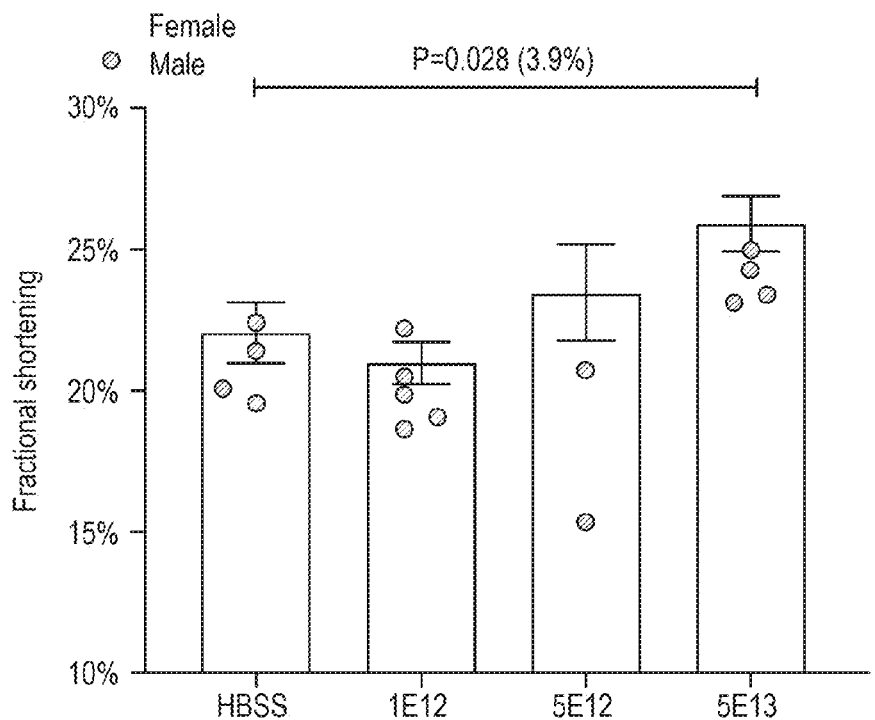
FIG. 6B is a graph showing improved fractional shortening in a PLN-R14$^{\Delta/\Delta}$ mouse model following treatment with an embodiment of an expression cassette packaged into an rAAV virion using AAV9 protein capsid.

In this study, three-week-old homozygous PLN-R14del animals were injected with either Hank's Balanced Salt Solution (HBSS) as sham control or rAAV virions comprised of the pCR-MD1 expression cassette (SEQ ID NO: 20) and the AAV9 capsid protein. PLN-R14$^{\Delta/\Delta}$ mice were administered rAAV virions by retro-orbital injection with a dose ranging from $5\times10^{12}$ vg/kg to $5\times10^{13}$ vg/kg (N=7-8/group). Ejection fraction and fractional shortening were assessed by echocardiography as markers of cardiac function at 6.5 weeks of age. FIG. 6A show a dose-dependent improvement in ejection fraction compared to sham control (p=0.035). FIG. 6B shows a dose-dependent improvement in fractional shortening compared to sham control (p=0.028).

Together these results indicate systemic administration of rAAV virions expressing DWORF improves cardiac function in an animal model of cardiomyopathy. Observation of this effect in mice treated at three weeks of age demonstrates that this gene therapy can both treat and prevent development of hypertrophic cardiomyopathy (HCM).

Example 5: rAAV-Mediated DWORF Expression

Expression cassettes were packaged with AAV9 capsid into rAAV virions and injected into 4 week old wildtype C57B16 mice at a dose of $5\times10^{13}$ vg/kg (N=4). Mouse hearts were harvested at 3 weeks following injection. DWORF protein expression was determined by Western blots and quantified (FIG. 8C, Table 10). A transgenic mouse (Tg-dworf) with a high DWORF expression level was used as a positive control.

The results show that combinations of specific promoters and enhancers and their orientation in the expression cassette lead to different levels of DWORF expression. The specific expression cassettes used in this example and the associated elements and their orientation are shown in FIG. 7A-7C. DWORF expression was increased with added elements compared to promoter alone, but the extent of increased DWORF expression was not predictable based on elements and orientation alone.

Figure 8A:
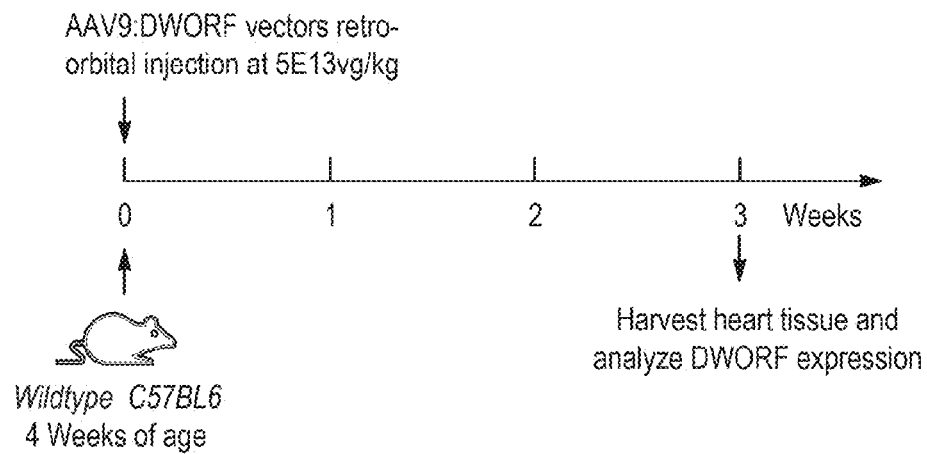
FIG. 8A is a schematic diagram which outlines the strategy for assessing the expression of DWORF in cardiomyocytes mice retro-orbitally injected with AAV9:DWORF constructs containing various regulatory elements and arrangements in vivo.
Figure 8B:
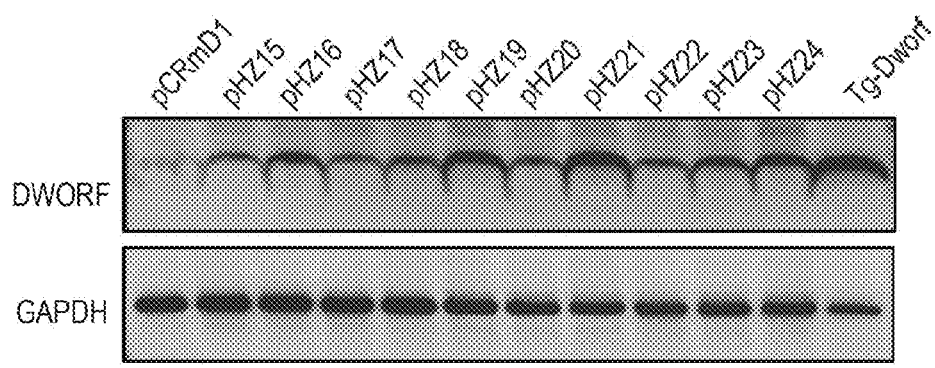
FIG. 8B is a western blot which demonstrates the expression of DWORF and GAPDH in cardiomyocytes mice retro-orbitally injected with AAV9:DWORF constructs containing various regulatory elements and arrangements in vivo.
Figure 8B:
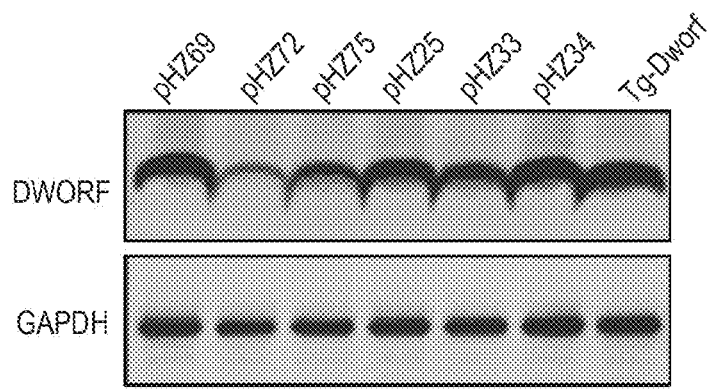
Figure 8C:
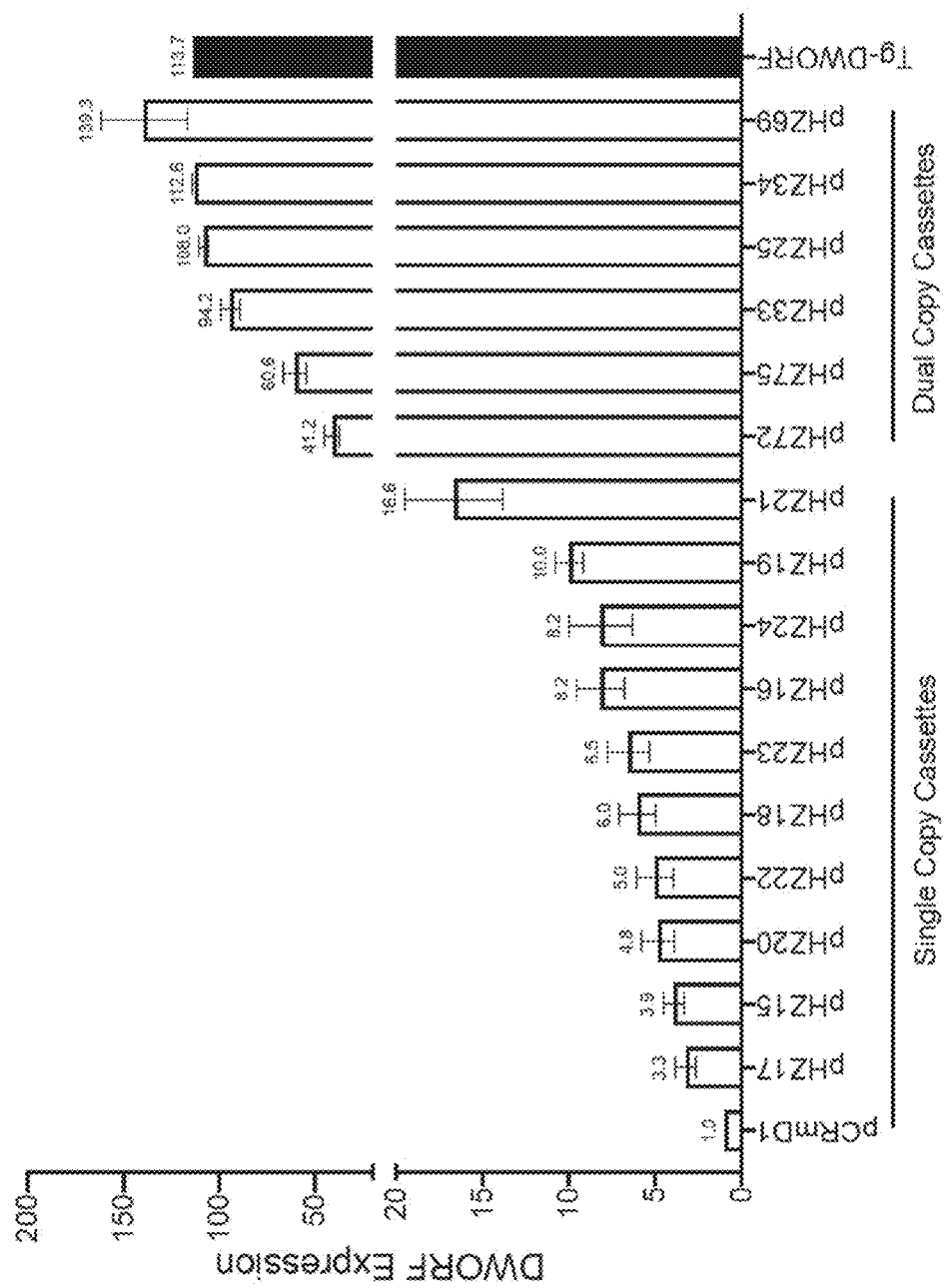
FIG. 8C is a chart showing the DWORF expression level in an animal model achieved using a panel of rAAV virions comprising expression cassettes encoding a DWORF polypeptide.

FIG. 8A shows the strategy for evaluating the expression of transgene (DWORF) in cardiomyocytes of naïve mice. Three weeks post-injection, animals were sacrificed and DWORF expression was assessed in hearts. FIG. 8B shows expression analysis results for 16 AAV constructs with various regulatory elements and arrangements to increase CM-selective expression of transgene (DWORF). In particular, FIG. 8B shows the expression of DWORF in wild type C57BL6 mouse cardiomyocytes harvested three weeks after retro-orbital inject with AAV9:DWORF vectors as assessed by western blot; the lower western blot panels display the expression of GAPDH as a positive control. Quantification of these data in FIG. 8C revealed that combinations of specific promoters and enhancers and their orientation in the expression cassette result in different levels of transgene expression. A transgenic mouse (Tg-dworf) with a high DWORF expression level was used as a positive control in this example.

For each expression cassette, DWORF expression was normalized to the observed level for the pCRmD1 expression cassette, which has only the human cTnT promoter without added enhancer elements. Adding the ACTC1 enhancer (pHZ15) or αMHC enhancer (pHZ17) increased DWORF expression about 3-fold to about 4-fold relative to pCRmD1. Adding the CMV intron (pHZ20) was observed to increase DWORF expression about 5-fold. Combining the promoter, a single enhancer, and an intron (pH22 and pH23) did not significantly increase DWORF expression compared to any element alone. Combining both enhancers with the promoter only marginally increased DWORF expression to about 6- to 8-fold compared to promoter alone. Surprising, the combination of both enhancers, a promoter, and an intron increased DWORF expression about 10- to 16-fold. Interestingly, the 5' to 3' order of enhancers plays a fine-tune role in regulating protein expression. Orienting the ACTC1 enhancer 5' to the second enhancer (pHZ16 or pHZ21) appears to increase DWORF expression compared to orienting the ACTC1 enhancer 3' to the second enhancer (pHZ18 or pHZ19). Including a codon optimized DWORF transgene (pHZ24) also increased expression.

TABLE 10

DWORF Expression

| Expression Cassette | DWORF Expression Fold Increase over Promoter Only |
|---|---|
| pCRmD1 | 1.0 |
| pHZ15 | 3.9 |
| pHZ16 | 8.2 |
| pHZ17 | 3.3 |
| pHZ18 | 6.0 |
| pHZ19 | 10.0 |
| pHZ20 | 4.8 |
| pHZ21 | 16.6 |
| pHZ22 | 5.0 |
| pHZ23 | 6.5 |
| pHZ24 | 8.2 |
| pHZ25 | 108.0 |
| pHZ33 | 94.2 |
| pHZ34 | 112.6 |
| pHZ69 | 139.3 |
| pHZ72 | 41.2 |
| pHZ75 | 60.6 |
| Tg-DWORF (Positive Control) | 113.7 |

Although adding various regulatory elements greatly increased DWORF expression, adding more copies of the transgene (pHZ25, pHZ33, pHZ34, pHZ69, pHZ72 and pHZ75) has an unexpected synergistic impact on DWORF levels. We used different enhancers, promoters, introns, and codon-optimized DWORF in each copy to avoid the homologous recombination between the tandem repeat sequences. The dual copies vectors have about 40- to 140-fold more expression than DWORF under transcriptional control of the promoter alone. Surprisingly, the orientation of the two copies has an unexpected role in regulating gene expression. For example, a tail-to-tail orientation shows the best expression, followed by head-to-head and head-to-tail arrangements. The results also suggest that different arrangements of the two copies of the transgene can be used to fine-tune the transgene expression.

Example 6: Effect of DWORF Expression on Ejection Fraction

Figure 9:
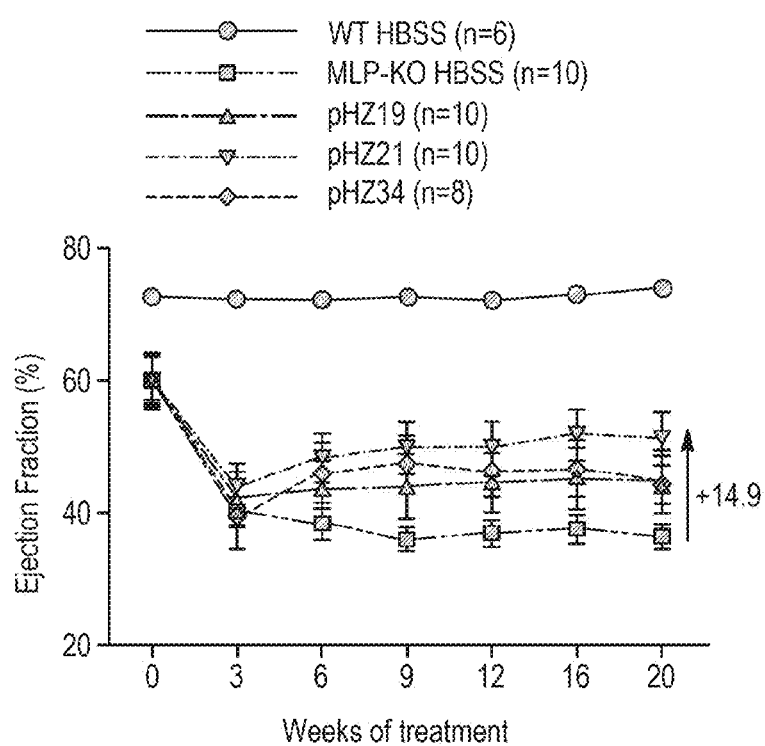
FIG. 9 is a plot showing improved ejection fraction in an animal model of cardiomyopathy treated with a panel of rAAV virions comprising expression cassettes encoding a DWORF polypeptide.

The effect of rAAV mediated DWORF expression on ejection fraction was determined in an MLP knockout (MLP-KO) dilated cardiomyopathy (DCM) model. Three of the rAAV virions were tested, including those with vector genomes having a single copy expression cassettes pHZ19 and pHZ21, and one having a dual copy expression cassette pHZ34. MLP-KO mice were dosed with either pHZ19 at $5\times10^{13}$ vg/kg, pHZ21 at $5\times10^{13}$ vg/kg, or pHZ34 at $1\times10^{13}$ vg/kg. Virions were delivered by retro-orbital injection at 6 weeks of age, at which time the mice were presenting with moderate heart failure. Cardiac functions were accessed by echocardiography at 3, 6, 9, 12, 16 and 20 weeks post-treatment. As shown in FIG. 9, pHZ21 at a $5\times10^{13}$ vg/kg dose significantly improved ejection fraction (14.4%) by 16 weeks post-virus injection compared to the HBSS group. Although pHZ21 only has a 1.6 fold more DWORF expression than the pHZ19, this modest improvement in expression seems to have a very profound effect on improving cardiac function. The dose of pHZ34 is five times lower than the pHZ19 and pHZ21, but it achieved similar improvement as the pHZ21 and better improvement than pHZ19, highlight the importance of DWORF expression.

Figure 10:
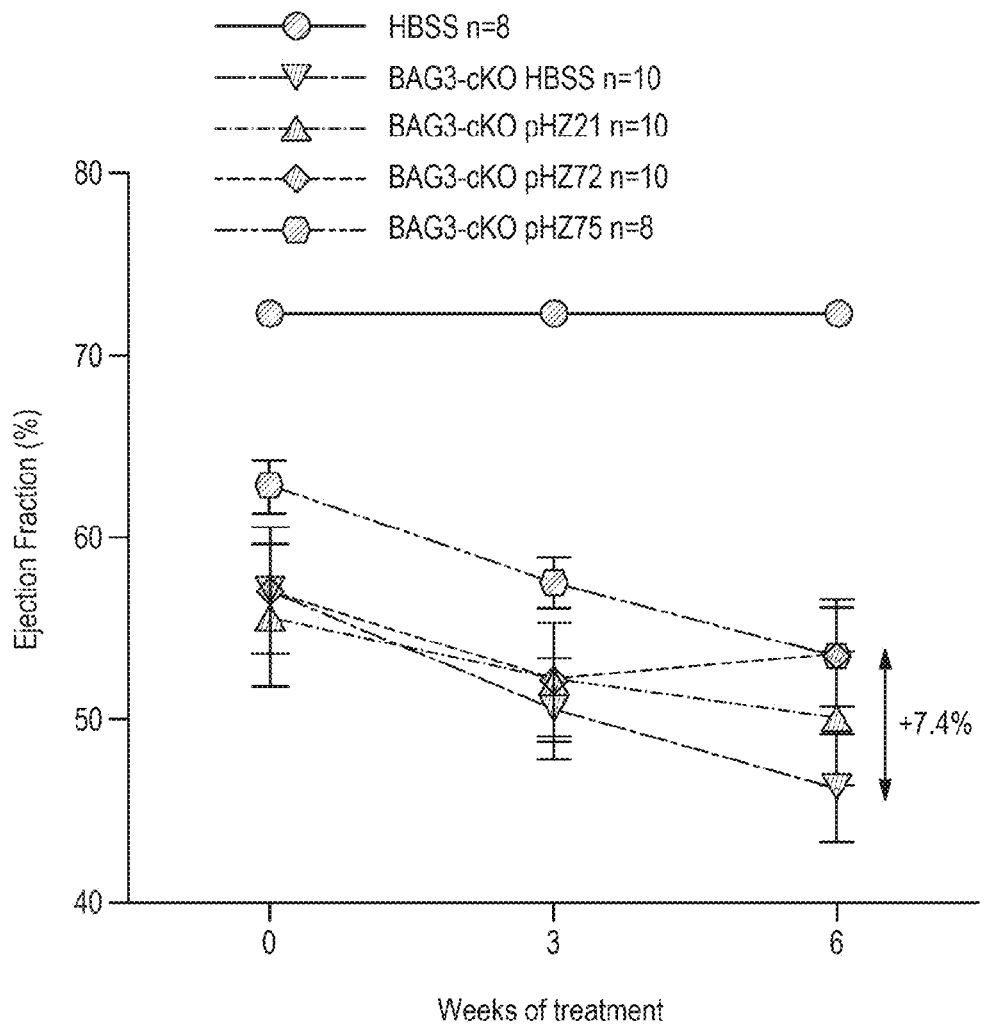
FIG. 10 is a plot showing preserved ejection fraction in an animal model of cardiomyopathy treated with a panel of rAAV virions comprising expression cassettes encoding a DWORF polypeptide.

Three of the DWORF expression cassettes were tested in another well characterized DCM model, the BAG3 cardiac conditional knock-out (BAG3-cKO) model. DWORF expression cassettes were tested in this model included one single copy vector, the pHZ21, and two dual-copy vectors, pHZ72 and pHZ75. BAG3-cKO mice were dosed with either $5\times10^{13}$ vg/kg AAV9-pHZ21, AAV9-pHZ72 and AAV9-pHZ75. Virions were delivered by retro-orbital injection at 8 weeks of age when the mice have already developed moderate heart failure. Cardiac functions were accessed by echocardiography at 3 and 6 weeks post-treatment. As shown in FIG. 10, pHZ72 at a $5\times10^{13}$ vg/kg dose substantially improved ejection fraction (7.4%) by 6 weeks post-virus injection compared to the HBSS group, suggesting that such optimized DWORF gene therapy can improve cardiac function in this model.

Example 7: Effect of DWORF Constructs in a Severe MLP-KO DCM Mouse Model

The purpose of this study was to test how optimized DWORF vectors can improve heart function and exercise capacity in a well-characterized MLP knockout (MLP-KO) dilated cardiomyopathy model.

FIG. 11A is the schematic diagram of the study design. Three of the rAAV virions were tested, including those with vector genomes having a single copy expression cassettes pHZ19 and pHZ21, and one having a dual copy expression cassette pHZ34. MLP-KO mice were dosed with either pHZ19 at $5\times10^{13}$ vg/kg, pHZ21 at $5\times10^{13}$ vg/kg, or pHZ34 at $1\times10^{13}$ vg/kg. Virions were delivered by retro-orbital injection at 6 weeks of age, at which time the mice were presenting with moderate heart failure. Cardiac functions were accessed by echocardiography 3-4 weeks and up to 24 weeks post-treatment. MLP-KO mice have limited exercise capacity compared to their wild-type littermates. To assess how much DWORF gene therapy can improve exercise capacity in MLP-KO mice, mice were allowed to run on a rodent treadmill and their running duration was monitored at 26 weeks.

As shown in FIG. 11B and FIG. 11C, pHZ21 at a $5\times10^{13}$ vg/kg dose significantly improved ejection fraction (14.3%) by 24 weeks post-virus injection compared to the HBSS group. Although pHZ21 only has a 1.6 fold more DWORF expression than the pHZ19, this modest improvement in expression seems to have a very profound effect on improving cardiac function. The dose of pHZ34 is five times lower than the pHZ19 and pHZ21, but it achieved similar improvement as the pHZ21 and better improvement than pHZ19, highlighting the importance of DWORF expression. FIG. 11D and FIG. 11E show that MLP-KO mice have limited exercise capacity compared to their wild-type littermates. pHZ21, the best DWORF vector to improve ejection fraction, also significantly improved exercise capacity, including running distance and time to exhaustion, in the MLP KO DCM mouse model 26 weeks post-treatment relative to the saline control.

Overall, this study shows that AAV-delivered DWORF mitigated the contractile dysfunction and improved exercise capacity in this MLP-KO DCM model. AAV:DWORF cassettes expressed higher levels of DWORF, supporting the most significant degree of efficacy that was durable out to 24 weeks. These results show that DWORF gene therapy can be used for normalizing calcium homeostasis and limiting disease progression.

Example 8: Tolerability of DWORF Gene Therapy in Naïve Mice

The purpose of this study was to evaluate the tolerability of DWORF gene therapy in naïve mice. FIG. 12A is the schematic diagram of the study design. Naïve mice were dosed with either HBSS saline control or AAV9:pHZ21 vector at two doses: $5 \times 10^{13}$ vg/kg and $2 \times 10^{14}$ vg/kg. Viruses were delivered via intraperitoneal (IP) injection at postnatal day 3 (P3). Cardiac functions were evaluated by echocardiography 4 weeks after viral injection.

FIG. 12B shows that AAV9:pHZ21 is well tolerated in wild-type mice up to $2 \times 10^{14}$ vg/kg. Compared with the saline control group, there are no differences in body weight, ejection fraction, heart rate, and left ventricular mass (LV mass) for those groups that were dosed with AAV9:pHZ21.

INCORPORATION BY REFERENCE

Various references such as patents, patent applications, and publications are cited herein, the disclosures of which are hereby incorporated herein by reference in their entireties. Also, all references mentioned herein are specifically incorporated by reference to disclose and describe the methods and/or materials in connection with which the publications are cited.

What is claimed is:

1. An expression cassette comprising a polynucleotide sequence encoding a dwarf open reading frame (DWORF) polypeptide operatively linked to a cardiac troponin T (cTnT) promoter, an actin, alpha cardiac muscle 1 (ACTC1) cardiac enhancer, and an alpha-myosin heavy chain (αMHC) enhancer, wherein the expression cassette further comprises a polyadenylation sequence, and wherein the ACTC1 cardiac enhancer comprises a polynucleotide sequence that is at least 95% identical to SEQ ID NO: 78.

2. The expression cassette of claim 1, wherein the DWORF polypeptide is a human DWORF polypeptide or a functional variant thereof sharing at least 80% or 90% sequence identity to SEQ ID NO: 3.

3. The expression cassette of claim 2, wherein the human DWORF polypeptide comprises the amino acid sequence of SEQ ID NO:3.

4. The expression cassette of claim 1, wherein the cTnT promoter is a human cTnT promoter.

5. The expression cassette of claim 4, wherein the human cTnT promoter comprises a polynucleotide sequence that shares at least 90%, 95%, 96%, 97%, 98%, 99%, or 100% identity to SEQ ID NO: 12.

6. The expression cassette of claim 4, wherein the human cTnT promoter comprises the polynucleotide sequence of SEQ ID NO: 12.

7. The expression cassette of claim 1, wherein the αMHC enhancer comprises a polynucleotide sequence that shares at least 90%, 95%, 96%, 97%, 98%, or 99% identity to SEQ ID NO: 79.

8. The expression cassette of claim 1, wherein the ACTC1 cardiac enhancer comprises the polynucleotide sequence of SEQ ID NO: 78.

9. The expression cassette of claim 1, wherein the αMHC enhancer comprises the polynucleotide sequence of SEQ ID NO: 79.

10. The expression cassette of claim 1, wherein the expression cassette further comprises an intron.

11. The expression cassette of claim 10, wherein the intron is selected from a CMV intron and a chimeric intron.

12. The expression cassette of claim 11, wherein the CMV intron comprises a polynucleotide sequence that shares at least 90%, 95%, 96%, 97%, 98%, 99%, or 100% identity to SEQ ID NO: 80, and wherein the chimeric intron comprises a polynucleotide sequence that shares at least 90%, 95%, 96%, 97%, 98%, 99%, or 100% identity to SEQ ID NO: 81.

13. The expression cassette of claim 1, wherein the expression cassette further comprises a woodchuck hepatitis virus post-transcriptional element (WPRE) sequence, wherein the WPRE sequence comprises a polynucleotide sequence that shares at least 90%, 95%, 96%, 97%, 98%, 99%, or 100% identity to SEQ ID NO: 26.

14. The expression cassette of claim 1, wherein the polyadenylation sequence is selected from a BGH polyadenylation sequence and an SV40 polyadenylation sequence.

15. The expression cassette of claim 14, wherein the BGH polyadenylation sequence comprises a polynucleotide sequence that shares at least 90%, 95%, 96%, 97%, 98%, 99%, or 100% identity to SEQ ID NO: 27, and wherein the SV40 polyadenylation sequence comprises a polynucleotide sequence that shares at least 90%, 95%, 96%, 97%, 98%, 99%, or 100% identity to SEQ ID NO: 28.

16. The expression cassette of claim 1, comprising a single copy of the polynucleotide sequence encoding the DWORF polypeptide.

17. The expression cassette of claim 1, wherein the expression cassette comprises a single copy of the polynucleotide sequence encoding the DWORF polypeptide, wherein the DWORF polypeptide is a human DWORF polypeptide, wherein the cTnT promoter is a human cTnT promoter, and an αMHC enhancer, and wherein the expression cassette further comprises a CMV intron and a BGH polyadenylation sequence.

18. The expression cassette of claim 17, wherein the expression cassette has a 5' to 3' arrangement of: the ACTC1 cardiac enhancer, the αMHC enhancer, the human cTnT promoter, the CMV intron, the polynucleotide sequence encoding the human DWORF polypeptide, and the BGH polyadenylation sequence; and wherein the ACTC1 cardiac enhancer, the αMHC enhancer, the human cInT promoter, and the polynucleotide sequence encoding the human DWORF polypeptide are in the same orientation.

19. The expression cassette of claim 18, wherein the expression cassette further comprises a WPRE sequence between the polynucleotide sequence encoding the human DWORF polypeptide and the BGH polyadenylation sequence.

20. The expression cassette of claim 18, wherein the expression cassette is flanked by inverted terminal repeats (ITRs), and wherein the ITRs comprise a polynucleotide sequence that shares at least 90%, 95%, 96%, 97%, 98%, 99%, or 100% identity to SEQ ID NO: 14 or SEQ ID NO: 15.

21. The expression cassette of claim 17, wherein the expression cassette comprises a polynucleotide sequence that shares at least 75%, 80%, 90%, 95%, 96%, 97%, 98%, or 99% sequence identity to SEQ ID NO: 69.

22. The expression cassette of claim 17, wherein the expression cassette comprises polynucleotide sequence of SEQ ID NO: 69.

23. A recombinant adeno-associated virus (rAAV) virion, comprising a capsid protein and a viral genome comprising the expression cassette of claim 1.

24. The rAAV virion of claim 23, wherein the capsid protein is a wild type AAV9 capsid protein or a variant thereof.

25. The rAAV virion of claim 24, wherein the capsid protein shares at least 98% sequence identity to SEQ ID NO: 143.

26. A pharmaceutical composition comprising the rAAV virion of claim 23 and a pharmaceutically acceptable diluent.

* * * * *

UNITED STATES PATENT AND TRADEMARK OFFICE
CERTIFICATE OF CORRECTION

Page 1 of 1

PATENT NO. : 12,151,001 B2
APPLICATION NO. : 18/468594
DATED : November 26, 2024
INVENTOR(S) : Huanyu Zhou et al.

It is certified that error appears in the above-identified patent and that said Letters Patent is hereby corrected as shown below:

In the Claims

At Column 333, Claim number 17, Line number 40-41, reads:
"wherein the cTnT promoter is a human cTnT promoter, and an αMHC enhancer,"
Should read:
--wherein the cTnT promoter is a human cTnT promoter--

At Column 334, Claim number 18, Line number 7, reads:
"cardiac enhancer, the αMHC enhancer, the human cInT promoter,"
Should read:
--cardiac enhancer, the αMHC enhancer, the human cTnT promoter,--

Signed and Sealed this
Nineteenth Day of August, 2025

Coke Morgan Stewart
*Acting Director of the United States Patent and Trademark Office*